US012435322B2

(12) United States Patent
Ledbetter et al.

(10) Patent No.: US 12,435,322 B2
(45) Date of Patent: *Oct. 7, 2025

(54) THERAPEUTIC NUCLEASE COMPOSITIONS AND METHODS

(71) Applicant: University Of Washington Through Its Center For Commercialization, Seattle, WA (US)

(72) Inventors: Jeffrey A. Ledbetter, Seattle, WA (US); Martha Hayden-Ledbetter, Seattle, WA (US); Keith Elkon, Seattle, WA (US); Xizhang Sun, Seattle, WA (US)

(73) Assignee: University Of Washington, Seattle, WA (US)

( * ) Notice: Subject to any disclaimer, the term of this patent is extended or adjusted under 35 U.S.C. 154(b) by 554 days.

This patent is subject to a terminal disclaimer.

(21) Appl. No.: 17/696,364

(22) Filed: Mar. 16, 2022

(65) Prior Publication Data

US 2023/0057085 A1 Feb. 23, 2023

Related U.S. Application Data

(60) Continuation of application No. 15/679,746, filed on Aug. 17, 2017, now Pat. No. 11,306,297, which is a continuation of application No. 14/516,161, filed on Oct. 16, 2014, now Pat. No. 9,790,479, which is a division of application No. 13/799,843, filed on Mar. 13, 2013, now abandoned, which is a division of application No. 13/197,731, filed on Aug. 3, 2011, now Pat. No. 8,841,416, which is a continuation of application No. PCT/US2010/055131, filed on Nov. 2, 2010.

(60) Provisional application No. 61/370,752, filed on Aug. 4, 2010, provisional application No. 61/257,458, filed on Nov. 2, 2009.

(51) Int. Cl.

| | |
|---|---|
| ***A61K 39/40*** | (2006.01) |
| ***C07K 16/18*** | (2006.01) |
| ***C12N 9/22*** | (2006.01) |
| ***C12N 9/96*** | (2006.01) |
| ***C12N 11/06*** | (2006.01) |
| *A61K 38/00* | (2006.01) |
| *C07K 1/00* | (2006.01) |

(52) U.S. Cl.

CPC ................ *C12N 9/22* (2013.01); *C07K 16/18* (2013.01); *C12N 9/96* (2013.01); *C12N 11/06* (2013.01); *A61K 38/00* (2013.01); *C07K 2319/30* (2013.01); *C12Y 301/27005* (2013.01); *Y02P 20/582* (2015.11)

(58) Field of Classification Search

None

See application file for complete search history.

(56) References Cited

U.S. PATENT DOCUMENTS

| | | | |
|---|---|---|---|
| 3,773,919 | A | 11/1973 | Boswell et al. |
| 3,941,763 | A | 3/1976 | Sarantakis |
| 4,683,195 | A | 7/1987 | Mullis et al. |
| 4,683,202 | A | 7/1987 | Mullis |
| 4,800,159 | A | 1/1989 | Mullis et al. |
| 4,965,188 | A | 10/1990 | Mullis et al. |
| 5,428,130 | A | 6/1995 | Capon et al. |
| 5,453,269 | A | 9/1995 | Haber et al. |
| 5,559,212 | A | 9/1996 | Ardelt |
| 5,637,481 | A | 6/1997 | Ledbetter et al. |
| 5,648,260 | A | 7/1997 | Winter et al. |
| 5,658,570 | A | 8/1997 | Newman et al. |
| 5,739,277 | A | 4/1998 | Presta et al. |
| 5,834,250 | A | 11/1998 | Wells et al. |
| 5,840,296 | A | 11/1998 | Raines et al. |
| 5,840,840 | A | 11/1998 | Rybak et al. |
| 5,869,046 | A | 2/1999 | Presta et al. |
| 5,955,073 | A | 9/1999 | Rybak et al. |
| 5,973,116 | A | 10/1999 | Epenetos et al. |
| 5,989,830 | A | 11/1999 | Davis et al. |
| 6,096,871 | A | 8/2000 | Presta et al. |
| 6,121,022 | A | 9/2000 | Presta et al. |
| 6,175,003 | B1 | 1/2001 | Saxena |
| 6,194,551 | B1 | 2/2001 | Idusogie et al. |
| 6,239,257 | B1 | 5/2001 | Ardelt |
| 6,242,195 | B1 | 6/2001 | Idusogie et al. |
| 6,277,375 | B1 | 8/2001 | Ward |
| 6,280,991 | B1 | 8/2001 | Raines |
| 6,348,343 | B2 | 2/2002 | Lazarus et al. |
| 6,391,607 | B1 | 5/2002 | Lazarus et al. |
| 6,475,983 | B1 | 11/2002 | Eid et al. |
| 6,482,626 | B2 | 11/2002 | Baker et al. |

(Continued)

FOREIGN PATENT DOCUMENTS

| | | |
|---|---|---|
| BR | 112012010202 | 9/2015 |
| CL | 2438-2013 | 8/2013 |

(Continued)

OTHER PUBLICATIONS

Chinese Second Office Action, Chinese Application No. 201280032451.2, Nov. 10, 2015, 17 pages.

(Continued)

*Primary Examiner* — Chun W Dahle

(74) *Attorney, Agent, or Firm* — McDonnell Boehnen Hulbert & Berghoff

(57) ABSTRACT

Hybrid nuclease molecules and methods for treating an immune-related disease or disorder in a mammal, and a pharmaceutical composition for treating an immune-related disease in a mammal.

22 Claims, 26 Drawing Sheets

Specification includes a Sequence Listing.

(56) References Cited

U.S. PATENT DOCUMENTS

| | | | | |
|---|---|---|---|---|
| 6,528,624 | B1 | 3/2003 | Idusogie et al. | |
| 6,538,124 | B1 | 3/2003 | Idusogie et al. | |
| 6,653,104 | B2 | 11/2003 | Goldenberg | |
| 6,660,843 | B1 | 12/2003 | Feige et al. | |
| 6,716,974 | B1 | 4/2004 | Maciag et al. | |
| 6,737,056 | B1 | 5/2004 | Presta | |
| 6,821,505 | B2 | 11/2004 | Ward | |
| 6,998,253 | B1 | 2/2006 | Presta et al. | |
| 7,033,572 | B2 | 4/2006 | Goldenberg | |
| 7,067,298 | B2 | 6/2006 | Atham et al. | |
| 7,074,592 | B2 | 7/2006 | Ashkenazi et al. | |
| 7,083,784 | B2 | 8/2006 | Dall'Acqua et al. | |
| 7,098,016 | B2 | 8/2006 | Raines et al. | |
| 7,118,751 | B1 | 10/2006 | Ledbetter et al. | |
| 7,247,302 | B1 | 7/2007 | Rosok et al. | |
| 7,317,091 | B2 | 1/2008 | Lazar et al. | |
| 7,364,731 | B2 | 4/2008 | Idusogie et al. | |
| 7,407,785 | B2 | 8/2008 | Lazarus et al. | |
| 7,416,875 | B2 | 8/2008 | Raines et al. | |
| 7,544,487 | B2 | 6/2009 | Goldenberg et al. | |
| 7,655,757 | B2 | 2/2010 | Raines et al. | |
| 7,662,925 | B2 | 2/2010 | Lazar et al. | |
| 7,754,208 | B2 | 7/2010 | Ledbetter et al. | |
| 7,754,209 | B2 | 7/2010 | Ledbetter et al. | |
| 7,807,409 | B2 | 10/2010 | Kopetzki | |
| 7,829,084 | B2 | 11/2010 | Ledbetter et al. | |
| 8,029,782 | B2 | 10/2011 | Klink et al. | |
| 8,067,548 | B2 | 11/2011 | Wang et al. | |
| 8,642,752 | B2 | 2/2014 | Swayze et al. | |
| 8,697,065 | B2 | 4/2014 | Strong et al. | |
| 8,841,416 | B2 | 9/2014 | Ledbetter et al. | |
| 8,937,157 | B2 | 1/2015 | Ledbetter et al. | |
| 9,790,479 | B2 | 10/2017 | Ledbetter et al. | |
| 10,000,745 | B2 | 6/2018 | Ledbetter et al. | |
| 10,202,588 | B2 | 2/2019 | Ledbetter et al. | |
| 10,988,745 | B2 | 4/2021 | Posada et al. | |
| 11,306,295 | B2 | 4/2022 | Ledbetter et al. | |
| 11,306,297 | B2 * | 4/2022 | Ledbetter ................. | C12N 9/96 |
| 2002/0103125 | A1 | 8/2002 | Ashkenazi et al. | |
| 2003/0108548 | A1 | 6/2003 | Bluestone et al. | |
| 2004/0132101 | A1 | 7/2004 | Azar et al. | |
| 2005/0054832 | A1 | 3/2005 | Lazar et al. | |
| 2005/0136049 | A1 | 6/2005 | Ledbetter et al. | |
| 2005/0158307 | A1 | 7/2005 | Spies et al. | |
| 2005/0175614 | A1 | 8/2005 | Ledbetter et al. | |
| 2005/0180970 | A1 | 8/2005 | Ledbetter et al. | |
| 2005/0186216 | A1 | 8/2005 | Ledbetter et al. | |
| 2005/0202012 | A1 | 9/2005 | Ledbetter et al. | |
| 2005/0202023 | A1 | 9/2005 | Ledbetter et al. | |
| 2005/0202028 | A1 | 9/2005 | Ledbetter et al. | |
| 2005/0202534 | A1 | 9/2005 | Ledbetter et al. | |
| 2005/0238646 | A1 | 10/2005 | Ledbetter et al. | |
| 2006/0040262 | A1 | 2/2006 | Morris et al. | |
| 2006/0235208 | A1 | 10/2006 | Lazar et al. | |
| 2006/0263774 | A1 | 11/2006 | Clark et al. | |
| 2007/0025982 | A1 | 2/2007 | Ledbetter et al. | |
| 2007/0059306 | A1 | 3/2007 | Grosmaire et al. | |
| 2007/0111281 | A1 | 5/2007 | Sondermann et al. | |
| 2007/0231329 | A1 | 10/2007 | Lazar et al. | |
| 2007/0237765 | A1 | 10/2007 | Lazar et al. | |
| 2007/0237766 | A1 | 10/2007 | Lazar et al. | |
| 2007/0237767 | A1 | 10/2007 | Lazar et al. | |
| 2007/0237779 | A1 | 10/2007 | Ledbetter et al. | |
| 2007/0243188 | A1 | 10/2007 | Lazar et al. | |
| 2007/0248603 | A1 | 10/2007 | Lazar et al. | |
| 2007/0286859 | A1 | 12/2007 | Lazar et al. | |
| 2008/0057056 | A1 | 3/2008 | Lazar et al. | |
| 2008/0181892 | A1 | 7/2008 | Ledbetter et al. | |
| 2008/0227958 | A1 | 9/2008 | Thompson et al. | |
| 2008/0242845 | A1 | 10/2008 | Lazar et al. | |
| 2008/0279850 | A1 | 11/2008 | Brady et al. | |
| 2008/0293121 | A1 | 11/2008 | Lazarus et al. | |
| 2009/0148447 | A1 | 6/2009 | Ledbetter et al. | |
| 2009/0175867 | A1 | 7/2009 | Thompson et al. | |
| 2009/0196870 | A1 | 8/2009 | Ledbetter et al. | |
| 2009/0214539 | A1 | 8/2009 | Grosmaire et al. | |
| 2009/0258005 | A1 | 10/2009 | Gill et al. | |
| 2009/0274692 | A1 | 11/2009 | Tan et al. | |
| 2010/0015661 | A1 | 1/2010 | Dubel et al. | |
| 2010/0034820 | A1 | 2/2010 | Ledbetter et al. | |
| 2010/0099101 | A1 | 4/2010 | Behrens et al. | |
| 2010/0203052 | A1 | 8/2010 | Ledbetter et al. | |
| 2010/0279932 | A1 | 11/2010 | Ledbetter et al. | |
| 2010/0330089 | A1 | 12/2010 | Damle et al. | |
| 2011/0033483 | A1 | 2/2011 | Thompson et al. | |
| 2011/0081345 | A1 | 4/2011 | Moore et al. | |
| 2011/0091461 | A1 | 4/2011 | Ledbetter et al. | |
| 2011/0105729 | A1 | 5/2011 | Ledbetter et al. | |
| 2011/0123440 | A1 | 5/2011 | Hansen et al. | |
| 2011/0151515 | A1 | 6/2011 | Heifetz et al. | |
| 2011/0171208 | A1 | 7/2011 | Tan et al. | |
| 2012/0225066 | A1 | 9/2012 | Ledbetter et al. | |
| 2013/0089546 | A1 | 4/2013 | Ledbetter et al. | |
| 2013/0177561 | A1 | 7/2013 | Ledbetter et al. | |
| 2013/0183308 | A1 | 7/2013 | Ledbetter et al. | |
| 2013/0184334 | A1 | 7/2013 | Ledbetter et al. | |
| 2014/0044711 | A1 | 2/2014 | Ledbetter et al. | |
| 2014/0178379 | A1 | 6/2014 | Ledbetter et al. | |
| 2014/0178479 | A1 | 6/2014 | Bakhru et al. | |
| 2014/0227269 | A1 | 8/2014 | Ledbetter et al. | |
| 2015/0037871 | A1 | 2/2015 | Ledbetter et al. | |
| 2015/0152399 | A1 | 6/2015 | Ledbetter et al. | |
| 2018/0187174 | A1 | 7/2018 | Ledbetter et al. | |
| 2019/0119660 | A1 | 4/2019 | Ledbetter et al. | |
| 2019/0241878 | A1 | 8/2019 | Posada et al. | |
| 2021/0395711 | A1 | 12/2021 | Ledbetter et al. | |

FOREIGN PATENT DOCUMENTS

| | | |
|---|---|---|
| CL | 2013-02428 | 8/2014 |
| CN | 1852976 | 10/2006 |
| CN | 101990439 | 3/2011 |
| CN | 102770533 | 11/2012 |
| CN | 103930127 | 7/2014 |
| DE | 102005009219 | 8/2006 |
| EP | 0036676 | 9/1981 |
| EP | 0058481 | 8/1982 |
| EP | 0088046 | 9/1983 |
| EP | 0133988 | 3/1985 |
| EP | 0143949 | 6/1985 |
| EP | 1277716 | 1/2003 |
| EP | 2496691 | 2/2017 |
| EP | 2704737 | 1/2018 |
| JP | 2004-525630 | 8/2004 |
| JP | 2006-512407 | 4/2006 |
| JP | 2007-524686 | 8/2007 |
| JP | 2007-525443 | 9/2007 |
| JP | 2008-502590 | 1/2009 |
| JP | 2012-537194 | 3/2013 |
| JP | 2014-508143 | 8/2014 |
| JP | 2014-519809 | 8/2014 |
| JP | 2018-087224 | 6/2018 |
| WO | 1988/07089 | 9/1988 |
| WO | 1993/15722 | 8/1993 |
| WO | 1996/14339 | 5/1996 |
| WO | 1998/05787 | 2/1998 |
| WO | 1998/23289 | 6/1998 |
| WO | 1999/25044 | 5/1999 |
| WO | 1999/51642 | 10/1999 |
| WO | 1999/58572 | 11/1999 |
| WO | 2000/009560 | 2/2000 |
| WO | 2000/032767 | 6/2000 |
| WO | 2000/042072 | 7/2000 |
| WO | 2001/02440 | 1/2001 |
| WO | 2002/044215 | 6/2002 |
| WO | 2002/060919 | 8/2002 |
| WO | 2002/060955 | 8/2002 |
| WO | 2002/072605 | 9/2002 |
| WO | 2002/096948 | 12/2002 |
| WO | 2003/074569 | 9/2003 |
| WO | 2004/016750 | 2/2004 |
| WO | 2004/029207 | 4/2004 |
| WO | 2004/035752 | 4/2004 |
| WO | 2004/063351 | 7/2004 |

(56) References Cited

FOREIGN PATENT DOCUMENTS

| | | |
|---|---|---|
| WO | 2004/074455 | 9/2004 |
| WO | 2004/099249 | 11/2004 |
| WO | 2005/018572 | 3/2005 |
| WO | 2005/040217 | 5/2005 |
| WO | 2005/047327 | 5/2005 |
| WO | 2005044859 A2 | 5/2005 |
| WO | 2005/063808 | 7/2005 |
| WO | 2005/063815 | 7/2005 |
| WO | 2005/070963 | 8/2005 |
| WO | 2005/077981 | 8/2005 |
| WO | 2005/080586 | 9/2005 |
| WO | 2005/092925 | 10/2005 |
| WO | 2005/123780 | 12/2005 |
| WO | 2006/019447 | 2/2006 |
| WO | 2006/047350 | 5/2006 |
| WO | 2006/085967 | 8/2006 |
| WO | 2007/122511 | 11/2007 |
| WO | 2007/141580 | 12/2007 |
| WO | 2008/037311 | 4/2008 |
| WO | 2009/015345 | 1/2009 |
| WO | 2009023386 A2 | 2/2009 |
| WO | 2009/064 777 | 5/2009 |
| WO | 2011/053982 | 5/2011 |
| WO | 2012/149440 | 11/2012 |

OTHER PUBLICATIONS

Chinese Third Office Action, Chinese Application No. 201280032451. 2, Aug. 5, 2016, 11 pages.

Chinese Fourth Office Action, Chinese Application No. 201280032451. 2, Feb. 28, 2017, 4 pages (with concise explanation of relevance).

Clark, E.A. et al., "CD16-Mediated Antibody Dependent Cellular Cytotoxicity is Required for B Cell Depletion by a Small Modular Immunopharmaceutical Specific for CD20," Blood, 2003, p. 646a, vol. 102, No. 11.

Colombian First Office Action, Colombian Application No. 13 279038, May 29, 2015, 13 pages (with concise explanation of relevance).

Colombian Office Action, Colombian Application No. 15 234237, May 12, 2016, 12 pages (with concise explanation of relevance).

Davis, Jr., J.C. et al., "Recombinant Human Dnase I (rhDNase) in Patients with Lupus Nephritis," Lupus, 1999, pp. 68-76, vol. 8.

Dübel, S., "Novel Recombinant Antibody Constructs and Fusion Proteins for Therapy and Research," Department of Biotechnology, Technical University of Braunschweig, Germany, Jun. 17, 2008, 15 pages.

Dwyer, M.A. et al., "Expression and Characterization of a DNase I—Fe Fusion Enzyme," The Journal of Biological Chemistry, Apr. 2, 1999, pp. 9738-9743, vol. 274, No. 14.

Egyptian Office Action, Egyptian Application No. PCT1666/2013, May 24, 2014, 2 pages.

Eurasian Office Action, Eurasian Application No. 201391585/28, Jun. 25, 2015, 4 pages.

European Extended Search Report, European Application No. 12777116. 0, Jun. 3, 2015, 7 pages.

European Examination Report, European Application No. 10827655. 1, Feb. 12, 2016, 4 pages.

European Examination Report, European Application No. 12777116. 0, Oct. 25, 2016, 4 pages.

Extended European Search Report, European Patent Application No. 10827655.1, Jun. 24, 2013, 12 pages.

European Extended Search Report, European Application No. 16198956. 1, May 4, 2017, 8 pages.

Fenton et al., "Anti-dsDNA Antibodies Promote Initiation, and Acquired Loss of Renal Dnase1 Promotes Progression of Lupus Nephritis in Autoimmune (NZBxNZW)F1 Mice," PloS One, 2009 (published online Dec. 2009), p. e8474, vol. 4, No. 12.

Fujihara, J. et al., "Comparative Biochemical Properties of Vertebrate Deoxyribonuclease I," Comparative Biochemistry and Physiology, Part B, 2012, pp. 263-273, vol. 163.

Gavalchin, J. et al.,"The NZB X SWR Model of Lupus Nephritis. I. Cross-Reactive Idiotypes of Monoclonal Anti-DNA Antibodies in Relation to Antigenic Specificity, Charge, and Allotype. Identification of Interconnected Idiotype Families Inherited from the Normal SWR and the Autoimmune NZB Parents," The Journal of Immunology, Jan. 1, 1987, pp. 128-137, vol. 138.

Gen Bank Accession No. CAA 11830, Nov. 20, 1998, 2 pages, [Online] Retrieved from the Internet<URL:http://www.ncbi.nlm.nih.gov/protein/CAA 11830>.

Georgian Office Action, Georgian Application No. AP 2012 013299, May 13, 2014, 2 pages, (with English summary).

Georgian Office Action, Georgian Application No. AP 2012 013299, Oct. 27, 2015, 3 pages (with concise explanation of relevance).

Gillies, S.D. et al., "Improving the Efficacy of Antibody-Interleukin 2 Fusion Proteins by Reducing Their Interaction with Fe Receptros", Cancer Res. (1999) vol. 59, p. 2159-2166).

Guo, J. et al., "Clinical Applications of DNaseq," International Journal of Pathology and Clinical Medicine, Apr. 2009, pp. 125-129, vol. 29, No. 2 (with English abstract).

Indian First Examination Report, Indian Application No. 4709/CHENP/2012, Feb. 21, 2017, 9 pages.

Indonesian Office Action, Indonesian Application No. W00201305523, Sep. 20, 2016, 4 pages.

Invitation to Pay Additional Fees, And, Where Applicable, Protest Fee, PCT Application No. PCT/US10/55131, Feb. 9, 2011, 2 pages.

Israel Office Action, Israel Application No. 2194 75, Jun. 19, 2014, pages.

Israel First Office Action, Israel Application No. 219475, Jun. 19, 2014, 4 pages (with concise explanation of relevance).

Israel Second Office Action, Israel Application No. 2194 75, May 14, 2015, 6 pages (with concise explanation of relevance).

Israel First Office Action, Israel Application No. 229074, Nov. 11, 2015, 5 pages (with concise explanation of relevance).

Israel Office Action, Israel Application No. 2194 75, Aug. 22, 2016, 7 pages (with concise explanation of relevance).

Israel Office Action, Israel Application No. 22907 4, Sep. 6, 2017, 8 pages (with concise explanation of relevance).

Japanese First Office Action, Japanese Application No. 2012-537194, Nov. 27, 2014, 28 pages.

Japanese Second Office Action, Japanese Application No. 2012-537194, Nov. 9, 2015, 15 pages (with concise explanation of relevance).

Japanese Office Action, Japanese Application No. 2014-508143, Mar. 23, 2016, 10 pages.

Japanese Office Action, Japanese Application No. 2016-045546, Jan. 18, 2016, 6 pages (with concise explanation of relevance).

Japanese Office Action, Japanese Application No. 2016-243950, Sep. 28, 2017, 4 pages.

Japanese Office Action, Japanese Application No. 2016-045546, Oct. 16, 2017, 2 pages.

Jefferis, R. et al., "Interaction Sites on Human IgG—Fc for FcyR: Current Models," Immunology Letters, Jun. 3, 2002, pp. 57-65, vol. 82, No. 1-2.

Johnson, R.J. et al., "Inhibition of Human Pancreatic Ribonuclease by the Human Ribonuclease Inhibitor Protein," J. Mol. Biol., 2007, pp. 434-449, vol. 368.

Karasinska, J.M., "Searching for the Aircardi-Goutieres Syndrome Genes: TREX1 and Ribonuclease H2 Make the Cut," Clin. Genet., 2006, pp. 457-461, vol. 70.

Kenyan Office Action, Kenyan Application No. KE/P/2013/1931, Sep. 14, 2015, 5 pages.

Korean Office Action, Korean Application No. 10-2012-7014363, Nov. 21, 2016, 4 pages (with concise explanation of relevance).

Korean Office Action, Korean Application No. 10-2012-7014363, Jul. 27, 2017, 8 pages (with concise explanation of relevance).

Ledbetter, J.A., "Discovery of Biological Drugs: Seattle at the Leading Edge," Grand Rounds, Department of Medicine, University of Washington, Feb. 4, 2010, 36 pages.

Linsley, P.S. et al., "CTLA-4 Is a Second Receptor for the B Cell Activation Antigen B7," J. Exp. Med., Sep. 1991, pp. 561-569, vol. 174.

Lovgren, T., et al., "Induction of Interferon-a by Immune Complexes or Liposomes Containing Systemic Lupus Erythematosus

(56) References Cited

OTHER PUBLICATIONS

Autoantigen and Sjogren's Syndrom Autoantigen-Associated RNA", Arthritis and Rheumatism (2006) vol. 54, No. 6, p. 1917-1927.
Macanovic, M. et al., "The treatment of systemic lupus erythematosus (SLE) in NZB/W F1 hybrid mice; studies with recombinant murine DNase and with dexamethasone," Clin Exp Immunol, 1996, pp. 243-252, vol. 106.
Martinez-Valle, F. et al., "DNase 1 Activity in Patients with Systemic Lupus Erythematosus: Relationship with Epimediological, Clinical Immunological and Therapeutical Features," Lupus, 2009, pp. 418-423, vol. 18, No. 5.
Menzel, et al., "Human Antibody RNase Fusion Protein Targeting CD30+ Lymphomas," Blood, Apr. 2008, pp. 3830-3837, vol. 111, No. 7.
Mexican First Office Action, Mexican Application No. 12/005062, Jun. 9, 2014, 6 pages.
Mexican Second Office Action, Mexican Application No. 12/005062, Feb. 9, 2015, 13 pages.
Mexican Third Office Action, Mexican Application No. 12/005062, Oct. 2, 2015, 9 pages.
Mexican First Office Action, Mexican Application No. 13/012612, Jun. 26, 2015, 7 pages.
Mexican Office Action, Mexican Application No. 13/012612, Feb. 9, 2016, 8 pages.
Mexican Third Office Action, Mexican Application No. 13/012612, Feb. 14, 2016, 12 pages.
New Zealand Application No. 599842, Filed Nov. 2, 2010, Not yet published.
New Zealand Application No. 628189, Filed Nov. 2, 2010, Not yet published.
New Zealand Examination Report, New Zealand Application No. 599842, Feb. 11, 2013, 3 pages.
New Zealand Further Examination Report, New Zealand Application No. 599842, Aug. 21, 2014, 3 pages.
New Zealand First Examination Report, New Zealand Application No. 628189, Aug. 21, 2014, 3 pages.
New Zealand First Examination Report, New Zealand Application No. 616989, Aug. 25, 2014, 2 pages.
New Zealand Examination Report, New Zealand Application No. 599842, Dec. 12, 2014, 3 pages.
New Zealand First Examination Report, New Zealand Application No. 717205, Mar. 9, 2016, 3 pages.
New Zealand First Examination Report, New Zealand Application No. 717398, Mar. 15, 2016, 2 pages.
New Zealand Second Examination Report, New Zealand Application No. 717398, Nov. 14, 2017, 2 pages.
New Zealand First Examination Report, New Zealand Application No. 735554, Nov. 14, 2017, 2 pages.
New Zealand Second Examination Report, New Zealand Application No. 717205, Nov. 20, 2017, 3 pages.
New Zealand First Examination Report, New Zealand Application No. 735379, Nov. 20, 2017, 5 pages.
Ni, Y. et al., "Research Progress of DNaseq," International Journal of Pathology and Clinical Medicine, Dec. 2006, pp. 531-535, vol. 26, No. 6.
"Nuclease (biology)," Brittanica Online Encyclopedia, 1 page, [Online] [Retrieved on Feb. 20, 2013], Retrieved from the Internet<URL:http://www.britannica.com/EBchecked/topic/421887/nuclease?sections=421887main&vie . . . >.
Pan, C.Q. et al., "Ca2+-Dependent Activity of Human DNase I and Its Hyperactive Variants," Protein Science, 1999, pp. 1780-1788, vol. 8.
Pan, C.Q. et al., "Improved Potency of Hyperactive and Actin-Resistant Human DNase I Variants for Treatment of Cystic Fibrosis and Systemic Lupus Erythematosus," The Journal of Biological Chemistry, Jul. 17, 1998, pp. 18374-18381, vol. 273, No. 29.
PCT International Search Report and Written Opinion, PCT Application No. PCT/US10/55131, Apr. 29, 2011, 18 pages.
PCT International Search Report and Written Opinion, PCT Application No. PCT/US12/35614, Sep. 4, 2012, 17 pages.
Peruvian Office Action, Peruvian Application No. 2425, Sep. 25, 2017, 18 pages.
Philippines Office Action, Philippines Application No. 1 /2013/502441, Aug. 8, 2017, 3 pages.
Prince, W.S. et al., "Pharmacodynamics of Recombinant Human DNase I in Serum," Clin. Exp. Immunol., 1998, pp. 289-296, vol. 113.
Rodriguez, A.M. et al., "Identification, Localization and Expression of Two Novel Human Genes Similar to Deoxyribonuclease I," Genomics, 1997, pp. 507-513, vol. 42.
Shak, S. et al., "Recombinant Human DNase I Reduces the Viscosity of Cystic Fibrosis Sputum," Proc. Natl. Acad. Sci., Dec. 1990, pp. 9188-9192, vol. 87.
Skolnick, J. et al., "From Genes to Protein Structure and Function: Novel Applications of Computational Approaches in the Genomic Era," TIBTECH, Jan. 2000, pp. 34-39, vol. 18.
Sondermann, P. et al., "The 3.2 ANG Crystal Structure of the Human IgG1 Fe Frahment-FcYRIII Complex," Nature, Jul. 20, 2000, pp. 267-273, vol. 406, No. 6793.
Stavenhagen, J.B. et al., "Fe Optimization of Therapeutic Antibodies Enhances Their Ability to Kill Tumor Cells in Vitro and Controls Tumor Expansion in Vivo Via Lof Affinity Activating Fey Receptors," Cancer Research, 2007, pp. 8882-8890, vol. 67.
Strohl, W.R., "Optimization of Fe-mediated effector functions of monoclonal antibodies," Curr. Opin. Biotechnol., (Nov. 11, 2009) vol. 20, p. 685-691.
Sun, X. et al., "Increased RNase Expression Reduces Inflammation and Prolongs Survival in TLR7 Transgenic Mice," The Journal of Immunology, Feb. 4, 2013, 9 pages.
Thai Office Action, Thai Application No. 1301006180, Apr. 23, 2015, 2 pages (with concise explanation of relevance).
Whisstock, J.C. et al., "Prediction of Protein Function from Protein Sequence and Structure," Quarterly Reviews of Biophysics, Cambridge University Press, 2003, pp. 307-340, vol. 36, No. 3.
Yasuda, T. et al., "A Biochemical and Genetic Study on All Non-Synonymous Single Nucleotide Polymorphisms of the Gene Encoding Human Deoxyribonuclease I Potentially Relevant to Autoimmunity," The International Journal of Biochemistry & Cell Biology, 2010, pp. 1216-1225, vol. 42.
Zeng, Z. et al., "Cloning and Characterization of a Novel Human DNase," Biochemical and Biophysical Research Communication, 1997, pp. 499-504, vol. 231.
Zhao, W.P. et al., "Relationship Between RNA Released from Mouse Apoptotic Murine Splenocytes and Autoimmune Disease," Chinese Journal of Biochemistry and Molecular Biology, 2003, pp. 662-666, vol. 19, No. 5 (with English abstract).
Canadian Office Action, Canadian Application No. 2,779,615, Sep. 25, 2013, 5 pages.
GenBank Accession No. CAA55817.1 (May 20, 1994), Filipenko, M.L. et al., NCBI Sequence Viewer v2.0, 3 pages, [online] [Retrieved on Dec. 12, 2013] Retrieved from the Internet at <URL:http://www.ncbi.nlm.nih.gov/protein/CAA55817 .1 >.
Ukrainian Office Action, Ukrainian Application No. A201312889, Jul. 13, 2016, 8 pages (with concise explanation of relevance).
United States Restriction Requirement, U.S. Appl. No. 13/197,731, filed Aug. 3, 2012, 11 pages.
United States Restriction Requirement, U.S. Appl. No. 13/197,731, filed Aug. 17, 2012, 11 pages.
United States Restriction Requirement, U.S. Appl. No. 13/197,731, filed Nov. 16, 2012, 7 pages.
United States Office Action, U.S. Appl. No. 13/197,731, filed Feb. 27, 2013, 17 pages.
United States Restriction Requirement, U.S. Appl. No. 13/505,421, filed Apr. 16, 2013, 8 pages.
United States Restriction Requirement, U.S. Appl. No. 13/505,421, filed Aug. 6, 2013, 8 pages.
Bowman et al., "Measurement of fatigue and discomfort in primary Sjögren's syndrome using a new questionnaire tool," Rheumatology 2004; 43:758-764.
Bowman et al., "Randomized Controlled Trial of Rituximab and Cost-Effectiveness Analysis in Treating Fatigue and Oral Dryness in Primary Sjögren's Syndrome," Arthritis & Rheumatology, vol. 69, No. 7, Jul. 2017, pp. 1440-1450.

(56) References Cited

OTHER PUBLICATIONS

Burge et al., "Evaluation of RNase therapy in systemic lupus erythematosus: a randomised phase 2a clinical trial of RSLV-132," Lupus Science & Medicine, 2024; 11; e001113.
Chiche et al., "Modular Transcriptional Repertoire Analyses of Adults With Systemic Lupus Erythematosus Reveal Distinct Type I and Type II Interferon Signatures," Arthritis & Rheumatology, vol. 66, No. 6, Jun. 2014, pp. 1583-1595.
Database UniProt [Online] "Deoxyribonuclease gamma, Dnase1L3", Accession No. Q13609 (Nov. 1, 1997), https://www.uniprot.org/uniprotkb/Q13609/entry, 9 pages.
Database UniProt [Online] "Deoxyribonuclease-1, DNase1", Accession No. P24855 (Mar. 1, 1992), https://www.uniprot.org/uniprotkb/P24855/entry, 10 pages.
Database UniProt [Online] "Interferon Regulatory factor 7", Accession No. P70434 (Feb. 1, 1997), https://www.uniprot.org/uniprotkb/P70434/entry, 8 pages.
Database UniProt [Online] "Interferon-induced GTP-binding protein Mx1", Accession No. P09922 (Jul. 1, 1989), https://www.uniprot.org/uniprotkb/P09922/entry, 6 pages.
Database UniProt [Online] "Interferon-induced protein with tetratricopeptide repeats 1", Accession No. Q64282 (Nov. 1, 1996), https://www.uniprot.org/uniprotkb/Q64282/entry, 7 pages.
Database UniProt [Online] "Ribonuclease Pancreatic, RNase", Accession No. P07998 (Feb. 1, 2005), https://www.uniprot.org/uniprotkb/P07998/entry, 9 pages.
Database UniProt [Online] "S-adenosylmethionine-dependent nucleotide dehydratase RSAD2", Accession No. Q8CBB9 (Mar. 1, 2003), https://www.uniprot.org/uniprotkb/Q8CBB9/entry, 8 pages.
Database UniProt [Online] "Three-prime repair exonuclease 1", Accession No. Q9NSU2 (Oct. 1, 2000), https://www.uniprot.org/uniprotkb/Q9NSU2/entry, 12 pages.
Dörner et al., "THU0313 Double-Blind, Randomized Study of VAY736 Single Dose Treatment in Patients with Primary Sjögren's Syndrome (PSS)," Annals of the Rheumatic Diseases, Jun. 9, 2016, pp. 300-301.
Extended European Search Report for EP Application No. 18167227.0 dated Feb. 4, 2019, 7 pages.
Extended European Search Report for EP Application No. 18190143.0 dated Dec. 12, 2018, 6 pages.
Fisher et al., "OP0202: Effect of RSLV-132 on Fatigue in Patients with Primary Sjögren's Syndrome—Results of a Phase II Randomised, Double-Blind, Placebo-Controlled, Proof of Concept Study", Scientific Abstracts, Oral Presentations, Jun. 13, 2019, p. 177.1-177.
Haldorsen et al., "A five-year prospective study of fatigue in primary Sjögren's syndrome," Arthritis Research & Therapy 2001, 13:R167.
Iyoda et al., "All-trans-retinoic acid aggravates cryoglobulin-associated membranoproliferative glomerulonephritis in mice," Nephrol Dial Transplant (2007) 22: 3451-3461.
Jaeger, "Digit Symbol Substitution Test: The Case for Sensitivity Over Specificity in Neuropsychological Testing," Journal of Clinical Psychopharmacology, vol. 38, No. 5, Oct. 2018, pp. 513-519.
Posada et al., "Improvement of Severe Fatigue Following Nuclease Therapy in Patients with Primary Sjögren's Syndrome: A Randomized Clinical Trial," Arthritis & Rheumatology, vol. 73, No. 1, Jan. 2021, pp. 143-150.
Segal et al., "Prevalence, Severity and Predictors of Fatigue in Primary Sjögren's Syndrome," Arthritis Rheum. Dec. 15, 2005; 59(12): 1780-1787.
Seror et al., "EULAR Sjögren's syndrome disease activity index (ESSDAI): a user guide," RMD Open 2015; 1:e000022.
Seror et al., "EULAR Sjögren's Syndrome Patient Reported Index (ESSPRI): development of a consensus patient index for primary Sjögren's syndrome," Ann Rheum Dis 2011; 70:968-972.
Strömbeck et al., "Assessment of fatigue in primary Sjögren's syndrome: the Swedish version of the Profile of Fatigue," Scandinavian Journal of Rheumatology 2005, 34:6, 455-459.
European Extended Search Report, European Application No. 10827655.1, Jun. 24, 2013, 11 pages.
United States Advisory Action, U.S. Appl. No. 14/174,167, filed Oct. 17, 2014, 4 pages.
United States Office Action, U.S. Appl. No. 13/505,421, filed Oct. 22, 2013, 13 pages.
United States Office Action, U.S. Appl. No. 13/505,421, filed Jun. 12, 2014, 13 pages.
United States Restriction Requirement, U.S. Appl. No. 14/174,167, filed Apr. 15, 2014, 6 pages.
United States Office Action, U.S. Appl. No. 14/174,167, filed May 8, 2014, 18 pages.
United States Office Action, U.S. Appl. No. 14/174,167, filed Aug. 25, 2014, 12 pages.
United States Restriction Requirement, U.S. Appl. No. 14/516,161, filed Jan. 26, 2017, 6 pages.
United States Restriction Requirement, U.S. Appl. No. 14/599,567, filed Apr. 6, 2017, 5 pages.
United States Office Action, U.S. Appl. No. 14/599,567, filed Jul. 21, 2017, 9 pages.
Video of Medicine Grand Rounds on Feb. 4, 2010 by Jeffrey Ledbetter, Research Professor of Medicine, Division of Rheumatology; Affiliate Associate Professor of Microbiology University of Washington School of Medicine, Can be Viewed at <http://depts.washington.edu/medweb/conferences/GRarchive.html#ledbetter>.
Bave et al., "Activation of the Type I Interferon System in Primary Sjögren's Syndrome," Arthritis & Rheumatism, Apr. 2005, pp. 1185-1195, vol. 52, No. 4.
U.S. Restriction Requirement in U.S. Appl. No. 13/822,215; mailed Jul. 21, 2017, 8 pages.
U.S. Office Action in U.S. Appl. No. 16/229,431; mailed Jun. 18, 2019, 6 pages.
U.S. Office Action in U.S. Appl. No. 16/229,431; mailed Feb. 24, 2020, 6 pages.
The International Preliminary Report on Patentability for International Application No. PCT/US2010/055131; issued May 8, 2012, 9 pages.
The International Preliminary Report on Patentability for International Application No. PCT/US2012/035614; issued Mar. 25, 2014, 8 pages.
Man & Zhong, "Advances in the pathogenesis and etiology of Sjogren's syndrome" Journal of Clinical Stomatology, vol. 24, Issue 4; pp. 251-253 (Apr. 2008). In Chinese—English translation of abstract provided.
Shields et al., "High resolution mapping of the binding site on human IgG1 for Fc gamma RI, Fc gamma RII, Fc gamma RIII, and FcRn and design of IgG1 variants with improved binding to the Fc gamma R" J Biol Chem 276(9):6591-604 (Mar. 2001).
Eisenman et al. Lupus 2017, 26:825-834. (Year: 2017).
A study of RSLV-132 in Subjects with Primary Sjogren's Syndrome. pp. 1-5, US National Library of Medicine. Feb. 23, 2018 (Year: 2018).
MedlinePlus. pp. 1-4, National Institutes of Health/US National Library of Medicine, Feb. 23, 2018 (Year: 2018).
Boix et al. Mol. Biosyst. 2007, 3:317-335. (Year: 2007).
Fujihara et al. Comparative Biochemistry and Physiology, Part B 163 (2012) 263-273. (Year: 2012).
Rutkoski, T.J. and Raines, RT., Curr. Pharm_ Biotechnol., (2008), vol. 9, pp. 185-199.
Tew, M.B et al., Arthritis and Reumatism, (2001), vol. 44, No. 10, pp. 2446-2447.
Mathew, et al., "Humanized immunotoxins:A new generation of immunotoxins for targeted cancer therapy," Cancer Sci (Aug. 2009) vol. 100(8): 1359-1365.
"Autoimmune Disorders," MedlinePlus, National Institutes of Health/U.S. National Library of Medicine, Review Date May 21, 2017, Last Updated Feb. 7, 2018, 4 pages, May Be Retrieved at https://medlineplus.gov/ency/article/000816.htm>.
Burge, D.J. et al., "Safety, Pharmacokinetics, and Pharmacodynamics of RSLV-132, an RNase-Fc Fusion Protein in Systemic Lupus Erythematosus: A Randomized, Double-Blind, Placebo-Controlled Study," Lupus, 2017, pp. 825-834, vol. 26.
Israel Office Action, Israel Application No. 219475, Jan. 22, 2018, 3 pages (with concise explanation of relevance).

(56) References Cited

OTHER PUBLICATIONS

Mexican First Office Action, Mexican Application No. 14/013439, Nov. 21, 2017, 6 pages.
"A Study of RSLV-132 in Subjects with Primary Sjogren's Syndrome (RSLV-132)," US National Library of Medicine, ClinicalTrials.gov, Feb. 23, 2018, 5 pages, May Be Retrieved at https://clinicaltrials.gov/ct2/show/study/NCT03247686>.
United States Office Action, U.S. Appl. No. 13/822,215, filed Feb. 28, 2018, 9 pages.
Australian First Office Action, Australian Application No. 2012249360, Mar. 7, 2014, 19 pages.
Australian First Office Action, Australian Application No. 2010313103, Mar. 14, 2014, 4 pages.
Australian First Office Action, Australian Application No. 2013203097, Mar. 14, 2014, 4 pages.
Australian Second Office Action, Australian Application No. 2012249360, Nov. 27, 2015, 3 pages.
Australian Second Examination Report, Australian Application No. 2016201790, Nov. 11, 2016, 3 pages.
Australian First Examination Report, Australian Application No. 2016202135, Nov. 11, 2016, 4 pages.
Beintema J.J. et al., "Differences in Glycosylation Pattern of Human Secretory Ribonucleases," Biochem. J., 1988, pp. 501-505, vol. 255.
Berland, R., et al., "Toll-like Receptor 7-Dependent Loss of B Cell Tolerance in Pathogenic Autoantibody Knockin Mice," Immunity, Sep. 2006, pp. 429-440, vol. 25.
Bitonti, A.J. et al., "Pulmonary Delivery of an Erythropoietin Fe Fusion Protein in Non-Human Primates Through an Immunolobulin Transport Pathway," PNAS, Jun. 29, 2004, pp. 9763-9768, vol. 101, No. 26.
Boix, E. et al., "Mammalian Antimicrobial Proteins and Peptides: Overview on the RNase A Superfamily Members Involved in Innate Host Defence," Molecular Biosystems, 2007, pp. 317-335, vol. 3.
Brekke, O.H. et al., "Human IgG Isotype-Specific Amino Acid Residues Affecting Complement-Mediated Cell Lysis and Phagocytosis," European Journal of Immunology, 1994, pp. 2542-2547, vol. 24.
Brekke, O.H. et al., "Therapeutic Antibodies for Human Diseases at the Dawn of the Twenty-First Century," Nature Reviews, Jan. 2003, pp. 52-62, vol. 2.
Canadian First Office Action, Canadian Application No. 2,834,626, Feb. 5, 2015, 6 pages.
Canadian Second Office Action, Canadian Application No. 2,834,626, Jan. 12, 2016, 3 pages.
Canadian Second Office Action, Canadian Application No. 2,779,612, Dec. 8, 2015, 7 pages.
Canadian Third Office Action, Canadian Application No. 2,779,615, Mar. 6, 2017, 8 pages.
Canadian Office Action, Canadian Application No. 2,834,626, Dec. 22, 2017, 3 pages.
Canfield, Stephen M. et al., "The Binding Affinity of Human IgG for its High Affinity Fe Receptor Is Determined by Multiple Amino Acids in the CH2 Domain and Is Modulated by the Hinge Region," J. Exp. Med., vol. 173:1483-1491 (1991).
Carsana, A. et al. "Structure of the Bovine Pancreatic Ribonuclease Gene: The Unique Intervening Sequence in the 5' Untranslated Region Contains a Promoter-Like Element," Nucleic Acids Research, Jun. 24, 1988, pp. 5491-5550, vol. 16, No. 12.
Chan, A.C. et al., "Therapeutic Antibodies for Autoimmunity and Inflammation," Nature Reviews Immunology, May 2010, pp. 301-316, vol. 10.
Chilean First Office Action, Chilean Application No. 03123-2013, Feb. 25, 2015, 13 pages (with concise explanation of relevance).
Chilean Second Office Action, Chilean Application No. 03123-2013, Nov. 13, 2015, 25 pages.
Chinese Office Action, Chinese Application No. 201080060471.1, Apr. 12, 2013, 20 pages.
Chinese Office Action, Chinese Application No. 2010800604 71 .1, Feb. 27, 2014, 15 pages.
Chinese Third Office Action, Chinese Application No. 201080060471.1, Aug. 26, 2014, 12 pages.
Chinese Fourth Office Action, Chinese Application No. 201080060471.1, May 14, 2015, 9 pages.
Chinese Fifth Office Action, Chinese Application No. 201080060471.1, Dec. 16, 2015, 4 pages.
Chinese First Office Action, Chinese Application No. 201280032451.2, Dec. 11, 2014, 21 paqes.
English Translation of "Reference A"—Definition of Antibody-dependent cell-mediated cytotoxicity (ADDC). Dictionary of Biology, 1st Ed. p. 434 (2010)—2 pages submitted.
U.S. Restriction Requirement in U.S. Appl. No. 15/679,746; mailed May 21, 2019, 5 pages.
U.S. Restriction Requirement in U.S. Appl. No. 15/679,746; mailed Jan. 23, 2020, 6 pages.
U.S. Office Action in U.S. Appl. No. 15/679,746; mailed Jul. 21, 2020, 13 pages.
U.S. Office Action in U.S. Appl. No. 15/679,746; mailed Mar. 25, 2021, 14 pages.
U.S. Appl. No. 13/197,731, filed Aug. 3, 2011, Ledbetter et al.
U.S. Appl. No. 14/516,161, filed Oct. 16, 2011, Ledbetter et al.
U.S. Appl. No. 13/822,215, filed Mar. 11, 2013, Ledbetter et al.
U.S. Appl. No. 14/174,167, filed Feb. 6, 2014, Ledbetter et al.
U.S. Appl. No. 14/599,567, filed Jan. 19, 2015, Ledbetter et al.
U.S. Appl. No. 16/229,431, filed Dec. 21, 2018, Ledbetter et al.
U.S. Appl. No. 13/799,854, filed Mar. 13, 2018, Ledbetter et al.
U.S. Appl. No. 13/799,843, filed Mar. 13, 2018, Ledbetter et al.
U.S. Appl. No. 13/505,421, filed Jul. 16, 2012, Ledbetter et al.
U.S. Appl. No. 13/796,730, filed Mar. 12, 2013, Ledbetter et al.
U.S. Appl. No. 14/258,319, filed Apr. 22, 2014, Ledbetter et al.
U.S. Appl. No. 17/324,641, filed May 19, 2021, Ledbetter et al.
Bennett et al. "Interferon and granulopoiesis signatures in systemic lupus erythematosus blood" J. Exp. Med. 197(6): 711-23 (2003).
Notice of Allowance for U.S. Appl. No. 17/324,641 dated Jan. 23, 202.

* cited by examiner

```
Predicted nucleotide and amino acid sequence encoded by MR1B1-NL-mIgG2a-TM Fusion
                                  Gene:
                                 HindIII     NcoI

                          MetGly LeuGluLys SerLeuIleLeu PheProLeu PhePheLeu
  1  GTTAAGCTTG CCACCATGGG TCTGGAGAAG TCCCTCATTC TGTTTCCATT GTTTTTCCTG
     CAATTCGAAC GGTGGTACCC AGACCTCTTC AGGGAGTAAG ACAAAGGTAA CAAAAAGGAC
                                                 SmaI

                                                 XmaI

                                             AvaI          PstI

     LeuLeuGlyTrp ValGlnPro SerProGly ArgGluSerAla AlaGlnLys PheGlnArg
 61  CTGCTTGGAT GGGTCCAGCC TTCCCCGGGC AGGGAATCTG CAGCACAGAA GTTTCAGCGG
     GACGAACCTA CCCAGGTCGG AAGGGGCCCG TCCCTTAGAC GTCGTGTCTT CAAAGTCGCC
                                         BamHI

     GlnHisMetAsp ProAspGly SerSerIle AsnSerProThr TyrCysAsn GlnMetMet
121  CAGCACATGG ATCCAGATGG TTCCTCCATC AACAGCCCCA CCTACTGCAA CCAAATGATG
     GTCGTGTACC TAGGTCTACC AAGGAGGTAG TTGTCGGGGT GGATGACGTT GGTTTACTAC

     LysArgArgAsp MetThrAsn GlySerCys LysProValAsn ThrPheVal HisGluPro
181  AAACGCCGGG ATATGACAAA TGGGTCATGC AAGCCCGTGA ACACCTTCGT GCATGAGCCC
     TTTGCGGCCC TATACTGTTT ACCCAGTACG TTCGGGCACT TGTGGAAGCA CGTACTCGGG

     LeuAlaAspVal GlnAlaVal CysSerGln GluAsnValThr CysLysAsn ArgLysSer
241  TTGGCAGATG TCCAGGCCGT CTGCTCCCAG GAAAATGTCA CCTGCAAGAA CAGGAAGAGC
     AACCGTCTAC AGGTCCGGCA GACGAGGGTC CTTTTACAGT GGACGTTCTT GTCCTTCTCG

     AsnCysTyrLys SerSerSer AlaLeuHis IleThrAspCys HisLeuLys GlyAsnSer
301  AACTGCTACA AGAGCAGCTC TGCCCTGCAC ATCACTGACT GCCACCTGAA GGGCAACTCC
     TTGACGATGT TCTCGTCGAG ACGGGACGTG TAGTGACTGA CGGTGGACTT CCCGTTGAGG

     LysTyrProAsn CysAspTyr LysThrThr GlnTyrGlnLys HisIleIle ValAlaCys
361  AAGTATCCCA ACTGTGACTA CAAGACCACT CAATACCAGA AGCACATCAT TGTGGCCTGT
     TTCATAGGGT TGACACTGAT GTTCTGGTGA GTTATGGTCT TCGTGTAGTA ACACCGGACA
                                                            XhoI

                                                            AvaI

     GluGlyAsnPro TyrValPro ValHisPhe AspAlaThrVal LeuGluPro ArgGlyLeu
421  GAAGGGAACC CCTACGTACC AGTCCACTTT GATGCTACTG TGCTCGAGCC CAGAGGTCTC
     CTTCCCTTGG GGATGCATGG TCAGGTGAAA CTACGATGAC ACGAGCTCGG GTCTCCAGAG
```

Figure 1

```
        ThrIleLysPro SerProPro CysLysCys ProAlaProAsn LeuLeuGly GlySerSer
481     ACAATCAAGC CCTCTCCTCC ATGCAAATGC CCAGCACCTA ACCTCTTGGG TGGATCATCC
        TGTTAGTTCG GGAGAGGAGG TACGTTTACG GGTCGTGGAT TGGAGAACCC ACCTAGTAGG

                                                                NcoI
        ValPheIlePhe ProProLys IleLysAsp ValLeuMetIle SerLeuSer ProMetVal
541     GTCTTCATCT TCCCTCCAAA GATCAAGGAT GTACTCATGA TCTCCCTGAG CCCCATGGTC
        CAGAAGTAGA AGGGAGGTTT CTAGTTCCTA CATGAGTACT AGAGGGACTC GGGGTACCAG

        ThrCysValVal ValAspVal SerGluAsp AspProAspVal GlnIleSer TrpPheVal
601     ACATGTGTGG TGGTGGATGT GAGCGAGGAT GACCCAGACG TCCAGATCAG CTGGTTTGTG
        TGTACACACC ACCACCTACA CTCGCTCCTA CTGGGTCTGC AGGTCTAGTC GACCAAACAC

        AsnAsnValGlu ValHisThr AlaGlnThr GlnThrHisArg GluAspTyr AsnSerThr
661     AACAACGTGG AAGTACACAC AGCTCAGACA CAAACCCATA GAGAGGATTA CAACAGTACT
        TTGTTGCACC TTCATGTGTG TCGAGTCTGT GTTTGGGTAT CTCTCCTAAT GTTGTCATGA

        LeuArgValVal SerAlaLeu ProIleGln HisGlnAspTrp MetSerGly LysGluPhe
721     CTCCGGGTGG TCAGTGCCCT CCCCATCCAG CACCAGGACT GGATGAGTGG CAAGGAGTTC
        GAGGCCCACC AGTCACGGGA GGGGTAGGTC GTGGTCCTGA CCTACTCACC GTTCCTCAAG

        LysCysSerVal AsnAsnLys AspLeuPro AlaSerIleGlu ArgThrIle SerLysPro
781     AAATGCTCGG TCAACAACAA AGACCTCCCA GCGTCCATCG AGAGAACCAT CTCAAAACCC
        TTTACGAGCC AGTTGTTGTT TCTGGAGGGT CGCAGGTAGC TCTCTTGGTA GAGTTTTGGG
```

Figure 1 (Con't)

```
SacI
                   ~~~~~~
          ArgGlyProVal ArgAlaPro GlnValTyr ValLeuProPro ProAlaGlu GluMetThr
          ~~~~~~~~~~~~~~~~~~~~~~~~~~~~~~~~~~~~~~~~~~~~~~~~~~~~~~~~~~~~~~~~~~~
841       AGAGGGCCAG TAAGAGCTCC ACAGGTATAT GTCTTGCCTC CACCAGCAGA AGAGATGACT
          TCTCCCGGTC ATTCTCGAGG TGTCCATATA CAGAACGGAG GTGGTCGTCT TCTCTACTGA
          ~~~~~~~~~~~~~~~~~~~~~~~~~~~~~~~~~~~~~~~~~~~~~~~~~~~~~~~~~~~~~~~~~~~
          LysLysGluPhe SerLeuThr CysMetIle ThrGlyPheLeu ProAlaGlu IleAlaVal
          ~~~~~~~~~~~~~~~~~~~~~~~~~~~~~~~~~~~~~~~~~~~~~~~~~~~~~~~~~~~~~~~~~~~
901       AAGAAAGAGT TCAGTCTGAC CTGCATGATC ACAGGCTTCT TACCTGCCGA AATTGCTGTG
          TTCTTTCTCA AGTCAGACTG GACGTACTAG TGTCCGAAGA ATGGACGGCT TTAACGACAC
          ~~~~~~~~~~~~~~~~~~~~~~~~~~~~~~~~~~~
          AspTrpThrSer AsnGlyArg ThrGluGln AsnTyrLysAsn ThrAlaThr ValLeuAsp
          ~~~~~~~~~~~~~~~~~~~~~~~~~~~~~~~~~~~~~~~~~~~~~~~~~~~~~~~~~~~~~~~~~~~
961       GACTGGACCA GCAATGGGCG TACAGAGCAA AACTACAAGA ACACCGCAAC AGTCCTGGAC
          CTGACCTGGT CGTTACCCGC ATGTCTCGTT TTGATGTTCT TGTGGCGTTG TCAGGACCTG
          SerAspGlySer TyrPheMet TyrSerLys LeuArgValGln LysSerThr TrpGluArg
          ~~~~~~~~~~~~~~~~~~~~~~~~~~~~~~~~~~~~~~~~~~~~~~~~~~~~~~~~~~~~~~~~~~~
1021      TCTGATGGTT CTTACTTCAT GTACAGCAAG CTCAGAGTAC AAAAGAGCAC TTGGGAAAGA
          AGACTACCAA GAATGAAGTA CATGTCGTTC GAGTCTCATG TTTTCTCGTG AACCCTTTCT
                                        BsaSI
                                        ~~~~~~
          GlySerLeuPhe AlaCysSer ValValHis GluGlyLeuHis AsnHisLeu ThrThrLys
          ~~~~~~~~~~~~~~~~~~~~~~~~~~~~~~~~~~~~~~~~~~~~~~~~~~~~~~~~~~~~~~~~~~~
1081      GGAAGTCTTT TCGCCTGCTC AGTGGTCCAC GAGGGTCTGC ACAATCACCT TACGACTAAG
          CCTTCAGAAA AGCGGACGAG TCACCAGGTG CTCCCAGACG TGTTAGTGGA ATGCTGATTC
                                            XbaI
                                           ~~~~~~
          SerPheSerArg ThrProGly Lys******
          ~~~~~~~~~~~~~~~~~~~~~~~~~~
1141      AGCTTCTCTC GGACTCCGGG TAAATGATAA TCTAGAA
          TCGAAGAGAG CCTGAGGCCC ATTTACTATT AGATCTT
```

Figure 1 (Con't)

Representative RNase and DNase Ig fusion genes.

TLR7.1-RnaseA:

| Fraction of alive mice TLR7.1 | Fraction of alive mice TLR7.1-RNaseA |
|---|---|
| 2 mo: 22/23 | 2 mo: 16/17 |
| 3 mo: 20/23 | 3 mo: 16/17 |
| 4 mo: 17/23 | 4 mo: 15/17 |
| 5 mo: 15/23 | 5 mo: 14/17 |
| 6 mo: 12/23 | 6 mo: 14/17 |
| 7 mo: 11/23 | 7 mo: 14/17 |
| 8 mo: 11/23 | 8 mo: 13/17 |
| 9 mo: 10/23 | 9 mo: 12/17 |
| 10 mo:9/23 | 10 mo: 12/17 |

As of 10.14.10
P value: 0.0065

Surival proportion
TLR7.1: 40%
TLR7.1-RnaseA: 70.5%

| Nuclease 1 or 2 | lnk 1 or 2 | IgGFc |
|---|---|---|
| hRNase-WT | (gly4ser)3 | SCCH-hIgG1WT |
| hRNase-G88D | (gly4ser)4 | hIgG1-P238S |
| hDNase1 WT | (gly4ser)5 | hIgG1-N297S |
| hDNAse1-A114F | NLG | hIgG1-P331S |
| hDNase1-G105R;A114F | none | mIgG2a-WT |
| hDNase1-G105R | (gly4ser)n | mIgG2c-WT |
| hTREX1-72AA | | mIgG2A-C WT or MT |
| hDNase1L3 | | |
| hTREX1-lnk-hTREX1 | | |

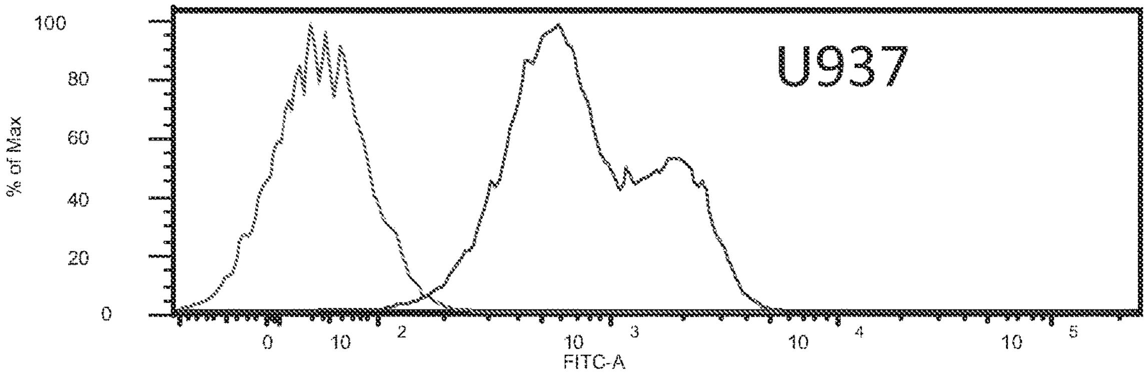
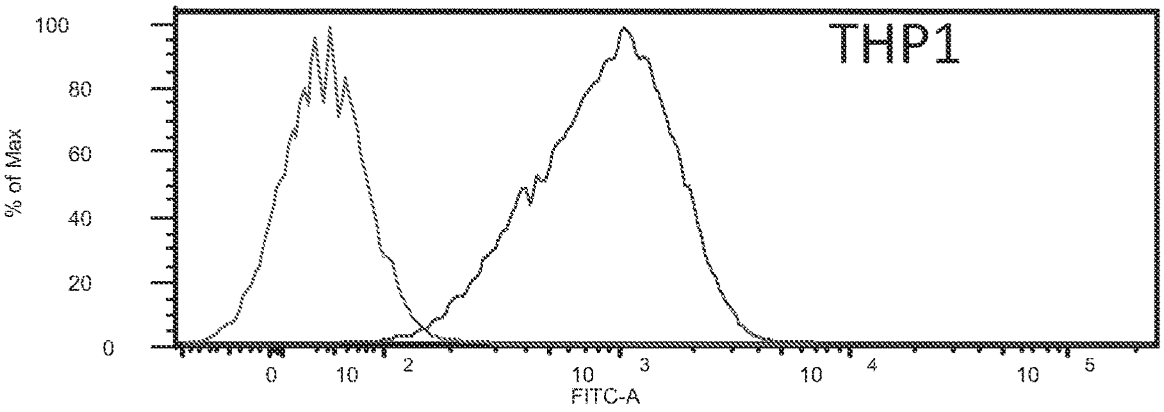
Figure 14

1: BDCA2 transfected COS sup
2: Control without enzyme
3: Mock transfected COS sup
4: Trex1-(Gly4S)4-Ig transfected COS sup
5: Trex1-(Gly4S)5-Ig transfected COS sup
6: human TREX1 positive control 1: BDCA2-Ig transfected COS sup (1ml) used as positive control
2: Mock COS sup (1ml) used as negative control
3: Trex1-(Gly4S)4-Ig transfected COS sup (1ml)
4: Trex1-(Gly4S)5-Ig transfected COS sup (1ml)

1.control
2.2A3(600nM MTX)
3.2A3(800nM MTX)
4.3A5(300nM MTX)
5.3A5(400nM MTX)
6.8H8(600nM MTX)
7.bulk CHO sup 1,2,3,4,5: mDNase1l3-L-Ig transfected COS sup 2ul, 5ul, 10ul, 15ul and 20ul
6: mDNase1l3-NL-Ig transfected COS sup 20ul
7: mRNase-Ig transfected COS sup 20ul
8: COS sup 20ul Mock
090210-8=DNaseWTIg
090210-9=DNase105/114Ig
091210-8=Rnase-Ig-DNase105/114
091210-14=Rnase-Ig-DNase114

0.22 purified mRNaseA-WT-mIgG2c-WT fusion protein
0.47 purified mRNaseA-WT-hmIgG2c-WT fusion protein A. Gel analysis of Plasmid DNA Digestion
1 2 3 4 5 6 7
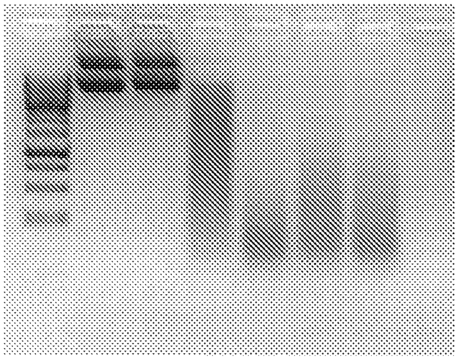
1: plasmid DNA mix
2: mock sup
3: 090210-8
4: 090210-9
5: 091210-8
6: 091210-14
7: DNAseI
B. DNase Alert Substrate digestion/UV visualization
1 2 3 4
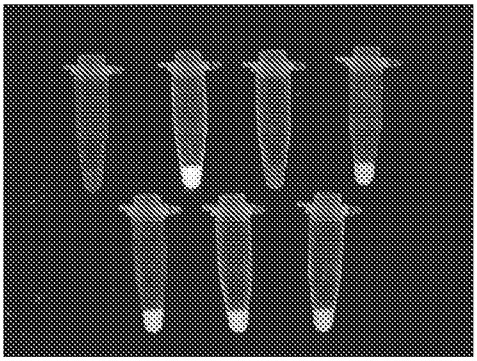
5 6 7
1: neg. control ddH2O
2:DNase 1 (2 U)
3: mock transfected sup.
4: 090210-8
5: 090210-9
6: 091210-8
7: 091210-14
Figure 22

THERAPEUTIC NUCLEASE COMPOSITIONS AND METHODS

CROSS REFERENCE TO RELATED APPLICATIONS

This application is a continuation of U.S. patent application Ser. No. 15/679,746, filed Aug. 17, 2017now U.S. Pat. No. 11,306,297 issued Apr. 19, 2022, which is a continuation of U.S. patent application Ser. No. 14/516,161, filed Oct. 16, 2014 now U.S. Pat. No. 9,790,479 issued Oct. 17, 2017, which is a division of U.S. patent application Ser. No. 13/799,843, filed Mar. 13, 2013, which is a division of U.S. patent application Ser. No. 13/197,731 filed Aug. 3, 2011 now U.S. Pat. No. 8,841,416 issued Sep. 23, 2014, which is a continuation of International Application No. PCT/US2010/055131, filed Nov. 2, 2010, which claims priority to U.S. Provisional Application No. 61/370,752, filed Aug. 4, 2010 and U.S. Provisional Application No. 61/257,458, filed Nov. 2, 2009, the entire disclosures of which are hereby incorporated by reference in their entireties.

STATEMENT REGARDING FEDERALLY SPONSORED RESEARCH OR DEVELOPMENT

This invention was made with support from the National Institutes of Health (Grants AI44257, NS065933, and AR048796), the Alliance for Lupus Research, and the Washington State Life Science Discovery Fund (2087750). The government has certain rights in the invention.

REFERENCE TO A SEQUENCE LISTING

This application includes a Sequence Listing submitted electronically as a text file named 19-551-WO-USCDC2_SeqList_ST25.txt, created on Mar. 16, 2022, with a size of 373.886 bytes. The sequence listing is incorporated by reference.

BACKGROUND

Excessive release of (ribo)nucleoprotein particles from dead and dying cells can cause lupus pathology by two mechanisms: (i) Deposition or in situ formation of chromatin/anti-chromatin complexes causes nephritis and leads to loss of renal function; and (ii) nucleoproteins activate innate immunity through toll-like receptor (TLR) 7, 8, and 9 as well as TLR-independent pathway(s). Release of nucleoproteins can serve as a potent antigen for autoantibodies in SLE, providing amplification of B cell and DC activation through co-engagement of antigen receptors and TLRs. Thus, there exists a need for a means to remove inciting antigens and/or attenuate immune stimulation, immune amplification, and immune complex mediated disease in subjects in need thereof.

SUMMARY

Disclosed herein is a hybrid nuclease molecule comprising a first nuclease domain and an Fc domain, wherein the first nuclease domain is operatively coupled to the Fc domain. In some embodiments, the hybrid nuclease molecule further includes a first linker domain, and the first nuclease domain is operatively coupled to the Fc domain by the first linker domain.

In some embodiments, a hybrid nuclease molecule is a polypeptide, wherein the amino acid sequence of the first nuclease domain comprises a human, wild-type RNase amino acid sequence, wherein the first linker domain is (Gly4Ser)n, where n is 0, 1, 2, 3, 4 or 5, wherein the amino acid sequence of the Fc domain comprises a human, wild-type IgG1 Fc domain amino acid sequence, and wherein the first linker domain is coupled to the C-terminus of the first nuclease domain and the N-terminus of the Fc domain. In some embodiments, a hybrid nuclease molecule is a polypeptide comprising or consisting of a sequence shown in Table 2. In some embodiments, a hybrid nuclease molecule is a polypeptide comprising SEQ ID NO:149. In some embodiments, a hybrid nuclease molecule is a polypeptide comprising SEQ ID NO:145. In some embodiments, a hybrid nuclease molecule is a polypeptide comprising SEQ ID NO:161. In some embodiments, a hybrid nuclease molecule is a polypeptide comprising SEQ ID NO:162. In some embodiments, a hybrid nuclease molecule is a polypeptide comprising SEQ ID NO:163.

In some embodiments, a hybrid nuclease molecule comprises wild-type, human DNase1 linked to wild-type, human IgG1. In some embodiments, a hybrid nuclease molecule comprises human DNase1 G105R A114F linked to a wild-type, human IgG1 Fc domain by a (gly4ser)n linker domain where n=0, 1, 2, 3, 4, or 5. In some embodiments, a hybrid nuclease molecule comprises wild-type, human RNase1 linked to wild-type, human IgG1 linked to wild-type, human DNase1. In some embodiments, a hybrid nuclease molecule comprises wild-type, human RNase1 linked to wild-type, human IgG1 linked to human DNase1 G105R A114F. In some embodiments, a hybrid nuclease molecule is a polypeptide, wherein the amino acid sequence of the first nuclease domain comprises a RNase amino acid sequence, wherein the first linker domain is between 5 and 32 amino acids in length, wherein the amino acid sequence of the Fc domain comprises a human, Fc domain amino acid sequence, and wherein the first linker domain is coupled to the C-terminus of the first nuclease domain and the N-terminus of the Fc domain. In some embodiments, the linker domain includes (gly4ser)5 and restriction sites BglII, AgeI, and XhoI. In some embodiments, a hybrid nuclease molecule is a polypeptide, wherein the amino acid sequence of the first nuclease domain comprises a human RNase amino acid sequence, wherein the first linker domain is a NLG peptide between 5 and 32 amino acids in length, wherein the amino acid sequence of the Fc domain comprises a human, wild-type Fc domain amino acid sequence, and wherein the first linker domain is coupled to the C-terminus of the first nuclease domain and the N-terminus of the Fc domain.

In some embodiments, the Fc domain binds to an Fc receptor on a human cell. In some embodiments, the serum half-life of the molecule is significantly longer than the serum half-life of the first nuclease domain alone. In some embodiments, the nuclease activity of the first nuclease domain of the molecule is the same or greater than the nuclease domain alone. In some embodiments, administration of the molecule to a mouse increases the survival rate of the mouse as measured by a mouse Lupus model assay.

In some embodiments, a hybrid nuclease molecule includes a leader sequence. In some embodiments, the leader sequence is human VK3LP peptide from the human kappa light chain family, and the leader sequence is coupled to the N-terminus of the first nuclease domain.

In some embodiments, the molecule is a polypeptide. In some embodiments, the molecule is a polynucleotide.

In some embodiments, the first nuclease domain comprises an RNase. In some embodiments, the RNase is a human RNase. In some embodiments, the RNase is a polypeptide comprising an amino acid sequence at least 90% similar to an RNase amino acid sequence set forth in Table 2. In some embodiments, the RNase is a human RNase A family member. In some embodiments, the RNase is a human pancreatic RNase1.

In some embodiments, the first nuclease domain comprises a DNase. In some embodiments, the DNase is a human DNase. In some embodiments, the DNase is a polypeptide comprising an amino acid sequence at least 90% similar to a DNase amino acid sequence set forth in Table 2. In some embodiments, the DNase is selected from the group consisting of human DNase I, TREX1, and human DNase 1L3.

In some embodiments, the Fc domain is a human Fc domain. In some embodiments, the Fc domain is a wild-type Fc domain. In some embodiments, the Fc domain is a mutant Fc domain. In some embodiments, the Fc domain is a human IgG1 Fc domain. In some embodiments, the Fc domain is a polypeptide comprising an amino acid sequence at least 90% similar to an Fc domain amino acid sequence set forth in Table 2.

In some embodiments, the first linker domain has a length of about 1 to about 50 amino acids. In some embodiments, the first linker domain has a length of about 5 to about 31 amino acids. In some embodiments, the first linker domain has a length of about 15 to about 25 amino acids. In some embodiments, the first linker domain has a length of about 20 to about 32 amino acids. In some embodiments, the first linker domain has a length of about 20 amino acids. In some embodiments, the first linker domain has a length of about 25 amino acids. In some embodiments, the first linker domain has a length of about 18 amino acids. In some embodiments, the first linker domain comprises a gly/ser peptide. In some embodiments, the gly/ser peptide is of the formula $(Gly_4Ser)n$, wherein n is a positive integer selected from the group consisting of 1, 2, 3, 4, 5, 6, 7, 8, 9, and 10. In some embodiments, the gly/ser peptide includes $(Gly_4Ser)3$. In some embodiments, the gly/ser peptide includes $(Gly_4Ser)4$. In some embodiments, the gly/ser peptide includes $(Gly_4Ser)5$. In some embodiments, the first linker domain includes at least one restriction site. In some embodiments, the first linker domain includes about 12 or greater nucleotides including at least one restriction site. In some embodiments, the first linker domain includes two or more restriction sites. In some embodiments, the first linker domain includes a plurality of restriction sites. In some embodiments, the first linker domain comprises an NLG peptide. In some embodiments, the first linker domain comprises an N-linked glycosylation site.

In some embodiments, the first nuclease domain is linked to the N-terminus of the Fc domain. In some embodiments, the first nuclease domain is linked to the C-terminus of the Fc domain.

In some embodiments, the hybrid nuclease molecule further includes a second nuclease domain. In some embodiments, the first and second nuclease domains are distinct nuclease domains. In some embodiments, the first and second nuclease domains are the same nuclease domains. In some embodiments, the second nuclease domain is linked to the C-terminus of the Fc domain. In some embodiments, the second nuclease domain is linked to the N-terminus of the Fc domain. In some embodiments, the second nuclease domain is linked to the C-terminus of the first nuclease domain. In some embodiments, the second nuclease domain is linked to the N-terminus of the first nuclease domain.

Also disclosed herein is a dimeric polypeptide comprising a first polypeptide and a second polypeptide, wherein the first polypeptide comprises a first nuclease domain, and an Fc domain, wherein the first nuclease domain is operatively coupled to the Fc domain. In some embodiments, the second polypeptide is a second hybrid nuclease molecule comprising a second nuclease domain, and a second Fc domain, wherein the second nuclease domain is operatively coupled to the second Fc domain.

Also disclosed herein is a pharmaceutical composition comprising at least one hybrid nuclease molecule and/or at least one dimeric polypeptide as described herein, and a pharmaceutically acceptable excipient.

Also disclosed herein is a nucleic acid molecule encoding a hybrid nuclease molecule disclosed herein. Also disclosed herein is a recombinant expression vector comprising a nucleic acid molecule disclosed herein. Also disclosed herein is a host cell transformed with a recombinant expression vector disclosed herein.

Also disclosed herein is a method of making a hybrid nuclease disclosed herein, comprising: providing a host cell comprising a nucleic acid sequence that encodes the hybrid nuclease molecule; and maintaining the host cell under conditions in which the hybrid nuclease molecule is expressed.

Also disclosed herein is a method for treating or preventing a condition associated with an abnormal immune response, comprising administering to a patient in need thereof an effective amount of an isolated hybrid nuclease molecule disclosed herein. In some embodiments, the condition is an autoimmune disease. In some embodiments, the autoimmune disease is selected from the group consisting of insulin-dependent diabetes mellitus, multiple sclerosis, experimental autoimmune encephalomyelitis, rheumatoid arthritis, experimental autoimmune arthritis, myasthenia gravis, thyroiditis, an experimental form of uveoretinitis, Hashimoto's thyroiditis, primary myxoedema, thyrotoxicosis, pernicious anaemia, autoimmune atrophic gastritis, Addison's disease, premature menopause, male infertility, juvenile diabetes, Goodpasture's syndrome, pemphigus vulgaris, pemphigoid, sympathetic ophthalmia, phacogenic uveitis, autoimmune haemolytic anaemia, idiopathic leucopenia, primary biliary cirrhosis, active chronic hepatitis Hbs-ve, cryptogenic cirrhosis, ulcerative colitis, Sjogren's syndrome, scleroderma, Wegener's granulomatosis, polymyositis, dermatomyositis, discoid LE, systemic lupus erythematosus (SLE), and connective tissue disease. In some embodiments, the autoimmune disease is SLE.

BRIEF DESCRIPTION OF THE SEVERAL VIEWS OF THE DRAWINGS

These and other features, aspects, and advantages of the present invention will become better understood with regard to the following description, and accompanying drawings, where:

FIG. 1 shows the nucleotide and amino acid sequence of the mRNase-mIgG2a with mutations at P238S, K322S, and P331S. This sequence is listed in the sequence listing as huVK3LP+mrib1+mIgG2A-C-2S (SEQ ID NO:114).

FIG. 14 shows the binding of hRNase1-WT-hIgG1-WT to human monocytic cell lines U937 and THP1. The peak on the left in both plots is control and the peak on the right in both plots is hRNase1-WT-hIgG1-WT.

FIG. 22 shows a composite figure displaying results of DNase nuclease activity assays performed on COS supernatants from transfected cells. The description of the numbering (e.g., 090210-8 and 091210-8) from FIG. 21 applies to this figure as well.

DETAILED DESCRIPTION

Figure 2:
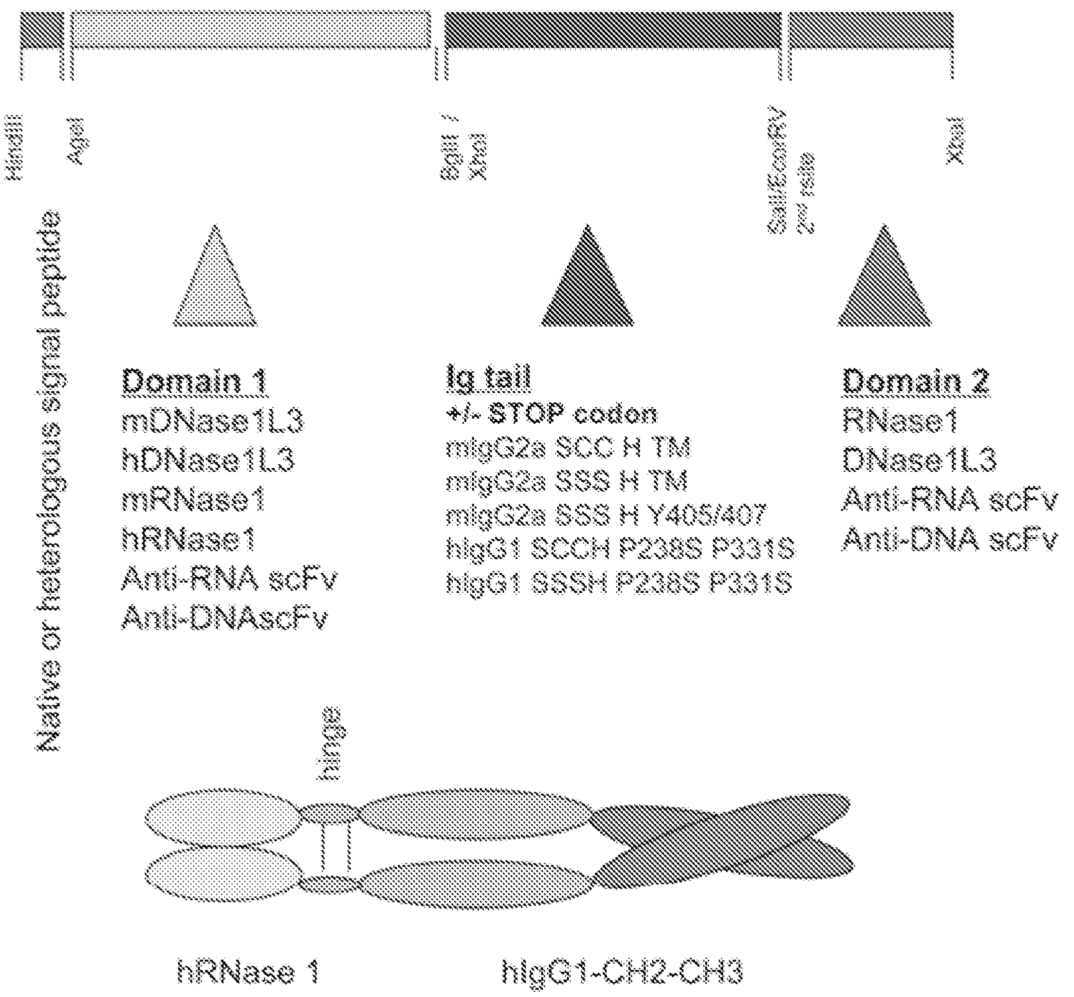
FIG. 2 shows a schematic diagram of some embodiments of hybrid nuclease molecules described herein.

Terms used in the claims and specification are defined as set forth below unless otherwise specified. In the case of direct conflict with a term used in a parent provisional patent application, the term used in the instant specification shall control.

"Amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

An "amino acid substitution" refers to the replacement of at least one existing amino acid residue in a predetermined amino acid sequence (an amino acid sequence of a starting polypeptide) with a second, different "replacement" amino acid residue. An "amino acid insertion" refers to the incorporation of at least one additional amino acid into a predetermined amino acid sequence. While the insertion will usually consist of the insertion of one or two amino acid residues, the present larger "peptide insertions," can be made, e.g. insertion of about three to about five or even up to about ten, fifteen, or twenty amino acid residues. The inserted residue(s) may be naturally occurring or non-naturally occurring as disclosed above. An "amino acid deletion" refers to the removal of at least one amino acid residue from a predetermined amino acid sequence.

"Polypeptide," "peptide", and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

"Nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer et al., *Nucleic Acid Res.* 19:5081, 1991; Ohtsuka et al., *J. Biol. Chem.* 260:2605-2608, 1985); and Cassol et al., 1992; Rossolini et al., *Mol. Cell. Probes* 8:91-98, 1994). For arginine and leucine, modifications at the second base can also be conservative. The term nucleic acid is used interchangeably with gene, cDNA, and mRNA encoded by a gene.

Polynucleotides of the present invention can be composed of any polyribonucleotide or polydeoxribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, the polynucleotide can be composed of triple-stranded regions comprising RNA or DNA or both RNA and DNA. A polynucleotide can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

As used herein, the term "hybrid nuclease molecule" refers to polynucleotides or polypeptides that comprise at least one nuclease domain and at least one Fc domain. Hybrid nuclease molecules are also referred to as fusion protein(s) and fusion gene(s). For example, in one embodiment, a hybrid nuclease molecule can be a polypeptide comprising at least one Fc domain linked to a nuclease domain such as DNase and/or RNase. As another example, a hybrid nuclease molecule can include an RNase nuclease domain, a linker domain, and an Fc domain. SEQ ID NO:161 is an example of a hybrid nuclease molecule. Other examples are described in more detail below. In one embodiment a hybrid nuclease molecule of the invention can include additional modifications. In another embodiment, a hybrid nuclease molecule may be modified to add a functional moiety (e.g., PEG, a drug, or a label).

In certain aspects, the hybrid nuclease molecules of the invention can employ one or more "linker domains," such as polypeptide linkers. As used herein, the term "linker domain" refers to a sequence which connects two or more domains in a linear sequence. As used herein, the term "polypeptide linker" refers to a peptide or polypeptide sequence (e.g., a synthetic peptide or polypeptide sequence) which connects two or more domains in a linear amino acid sequence of a polypeptide chain. For example, polypeptide linkers may be used to connect a nuclease domain to an Fc domain. Preferably, such polypeptide linkers can provide flexibility to the polypeptide molecule. In certain embodiments the polypeptide linker is used to connect (e.g., genetically fuse) one or more Fc domains and/or one or more nuclease domains. A hybrid nuclease molecule of the invention may comprise more than one linker domain or peptide linker.

As used herein, the term "gly-ser polypeptide linker" refers to a peptide that consists of glycine and serine residues. An exemplary gly/ser polypeptide linker comprises the amino acid sequence Ser$(Gly_4Ser)$n. In one embodiment, n=1. In one embodiment, n=2. In another embodiment, n=3, i.e., Ser$(Gly_4Ser)$3. In another embodiment, n=4, i.e., Ser $(Gly_4Ser)$4. In another embodiment, n=5. In yet another embodiment, n=6. In another embodiment, n=7. In yet another embodiment, n=8. In another embodiment, n=9. In yet another embodiment, n=10. Another exemplary gly/ser polypeptide linker comprises the amino acid sequence Ser $(Gly_4Ser)$n. In one embodiment, n=1. In one embodiment, n=2. In a preferred embodiment, n=3. In another embodiment, n=4. In another embodiment, n=5. In yet another embodiment, n=6.

As used herein, the terms "linked," "fused", or "fusion", are used interchangeably. These terms refer to the joining together of two more elements or components or domains, by whatever means including chemical conjugation or recombinant means. Methods of chemical conjugation (e.g., using heterobifunctional crosslinking agents) are known in the art.

As used herein, the term "Fc region" shall be defined as the portion of a native immunoglobulin formed by the respective Fc domains (or Fc moieties) of its two heavy chains.

As used herein, the term "Fc domain" refers to a portion of a single immunoglobulin (Ig) heavy chain. As such, Fc domain can also be referred to as "Ig" or "IgG." In some embodiments, an Fc domain begins in the hinge region just upstream of the papain cleavage site and ending at the C-terminus of the antibody. Accordingly, a complete Fc domain comprises at least a hinge domain, a CH2 domain, and a CH3 domain. In certain embodiments, an Fc domain comprises at least one of: a hinge (e.g., upper, middle, and/or lower hinge region) domain, a CH2 domain, a CH3 domain, a CH4 domain, or a variant, portion, or fragment thereof. In other embodiments, an Fc domain comprises a complete Fc domain (i.e., a hinge domain, a CH2 domain, and a CH3 domain). In one embodiment, an Fc domain comprises a hinge domain (or portion thereof) fused to a CH3 domain (or portion thereof). In another embodiment, an Fc domain comprises a CH2 domain (or portion thereof) fused to a CH3 domain (or portion thereof). In another embodiment, an Fc domain consists of a CH3 domain or portion thereof. In another embodiment, an Fc domain consists of a hinge domain (or portion thereof) and a CH3 domain (or portion thereof). In another embodiment, an Fc domain consists of a CH2 domain (or portion thereof) and a CH3 domain. In another embodiment, an Fc domain consists of a hinge domain (or portion thereof) and a CH2 domain (or portion thereof). In one embodiment, an Fc domain lacks at least a portion of a CH2 domain (e.g., all or part of a CH2 domain). In one embodiment, an Fc domain of the invention comprises at least the portion of an Fc molecule known in the art to be required for FcRn binding. In another embodiment, an Fc domain of the invention comprises at least the portion of an Fc molecule known in the art to be required for FcγR binding. In one embodiment, an Fc domain of the invention comprises at least the portion of an Fc molecule known in the art to be required for Protein A binding. In one embodiment, an Fc domain of the invention comprises at least the portion of an Fc molecule known in the art to be required for protein G binding. An Fc domain herein generally refers to a polypeptide comprising all or part of the Fc domain of an immunoglobulin heavy-chain. This includes, but is not limited to, polypeptides comprising the entire CH1, hinge, CH2, and/or CH3 domains as well as fragments of such peptides comprising only, e.g., the hinge, CH2, and CH3 domain. The Fc domain may be derived from an immunoglobulin of any species and/or any subtype, including, but not limited to, a human IgG1, IgG2, IgG3, IgG4, IgD, IgA, IgE, or IgM antibody. The Fc domain encompasses native Fc and Fc variant molecules. As with Fc variants and native Fe's, the term Fc domain includes molecules in monomeric or multimeric form, whether digested from whole antibody or produced by other means.

As set forth herein, it will be understood by one of ordinary skill in the art that any Fc domain may be modified such that it varies in amino acid sequence from the native Fc domain of a naturally occurring immunoglobulin molecule. In certain exemplary embodiments, the Fc domain retains an effector function (e.g., FcγR binding).

The Fc domains of a polypeptide of the invention may be derived from different immunoglobulin molecules. For example, an Fc domain of a polypeptide may comprise a CH2 and/or CH3 domain derived from an IgG1 molecule and a hinge region derived from an IgG3 molecule. In another example, an Fc domain can comprise a chimeric hinge region derived, in part, from an IgG1 molecule and, in part, from an IgG3 molecule. In another example, an Fc domain can comprise a chimeric hinge derived, in part, from an IgG1 molecule and, in part, from an IgG4 molecule.

A polypeptide or amino acid sequence "derived from" a designated polypeptide or protein refers to the origin of the polypeptide. Preferably, the polypeptide or amino acid sequence which is derived from a particular sequence has an amino acid sequence that is essentially identical to that sequence or a portion thereof, wherein the portion consists of at least 10-20 amino acids, preferably at least 20-30 amino acids, more preferably at least 30-50 amino acids, or which is otherwise identifiable to one of ordinary skill in the art as having its origin in the sequence.

Polypeptides derived from another peptide may have one or more mutations relative to the starting polypeptide, e.g., one or more amino acid residues which have been substituted with another amino acid residue or which has one or more amino acid residue insertions or deletions.

A polypeptide can comprise an amino acid sequence which is not naturally occurring. Such variants necessarily have less than 100% sequence identity or similarity with the starting hybrid nuclease molecules. In a preferred embodiment, the variant will have an amino acid sequence from about 75% to less than 100% amino acid sequence identity or similarity with the amino acid sequence of the starting polypeptide, more preferably from about 80% to less than 100%, more preferably from about 85% to less than 100%, more preferably from about 90% to less than 100% (e.g., 91%, 92%, 93%, 94%, 95%, 96%, 97%, 98%, 99%) and most preferably from about 95% to less than 100%, e.g., over the length of the variant molecule.

In one embodiment, there is one amino acid difference between a starting polypeptide sequence and the sequence derived therefrom. Identity or similarity with respect to this sequence is defined herein as the percentage of amino acid residues in the candidate sequence that are identical (i.e. same residue) with the starting amino acid residues, after aligning the sequences and introducing gaps, if necessary, to achieve the maximum percent sequence identity.

In one embodiment, a polypeptide of the invention consists of, consists essentially of, or comprises an amino acid sequence selected from Table 2 and functionally active variants thereof. In an embodiment, a polypeptide includes an amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth in Table 2. In an embodiment, a polypeptide includes a contiguous amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to a contiguous amino acid sequence set forth in Table 2. In an embodiment, a polypeptide includes an amino acid sequence having at least 10, 15, 20, 25, 30, 35, 40, 45, 50, 55, 60, 65, 70, 75, 80, 85, 90, 95, 100, 200, 300, 400, or 500 (or any integer within these numbers) contiguous amino acids of an amino acid sequence set forth in Table 2.

In an embodiment, the peptides of the invention are encoded by a nucleotide sequence. Nucleotide sequences of the invention can be useful for a number of applications, including: cloning, gene therapy, protein expression and purification, mutation introduction, DNA vaccination of a host in need thereof, antibody generation for, e.g., passive immunization, PCR, primer and probe generation, siRNA design and generation (see, e.g., the Dharmacon siDesign website), and the like. In an embodiment, the nucleotide sequence of the invention comprises, consists of, or consists essentially of, a nucleotide sequence selected from Table 2. In an embodiment, a nucleotide sequence includes a nucleotide sequence at least 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence set forth in Table 2. In an embodiment, a nucleotide sequence includes a contiguous nucleotide sequence at least 80%, 81%, 82%, 83%, 84%, 85%, 86%, 87%, 88%, 89%, 90%, 91%, 92%, 93%, 94%, 95%, 96%, 97%, 98%, or 99% identical to a contiguous nucleotide sequence set forth in Table 2. In an embodiment, a nucleotide sequence includes a nucleotide sequence having at least 10, 15, 20, 25, 30, 35, 40, 45, 50, 55, 60, 65, 70, 75, 80, 85, 90, 95, 100, 200, 300, 400, or 500 (or any integer within these numbers) contiguous nucleotides of a nucleotide sequence set forth in Table 2.

Preferred hybrid nuclease molecules of the invention comprise a sequence (e.g., at least one Fc domain) derived from a human immunoglobulin sequence. However, sequences may comprise one or more sequences from another mammalian species. For example, a primate Fc domain or nuclease domain may be included in the subject sequence. Alternatively, one or more murine amino acids may be present in a polypeptide. In some embodiments, polypeptide sequences of the invention are not immunogenic and/or have reduced immunogenicity.

It will also be understood by one of ordinary skill in the art that the hybrid nuclease molecules of the invention may be altered such that they vary in sequence from the naturally occurring or native sequences from which they were derived, while retaining the desirable activity of the native sequences. For example, nucleotide or amino acid substitutions leading to conservative substitutions or changes at "non-essential" amino acid residues may be made. An isolated nucleic acid molecule encoding a non-natural variant of a hybrid nuclease molecule derived from an immunoglobulin (e.g., an Fc domain) can be created by introducing one or more nucleotide substitutions, additions or deletions into the nucleotide sequence of the immunoglobulin such that one or more amino acid substitutions, additions or deletions are introduced into the encoded protein. Mutations may be introduced by standard techniques, such as site-directed mutagenesis and PCR-mediated mutagenesis.

The peptide hybrid nuclease molecules of the invention may comprise conservative amino acid substitutions at one or more amino acid residues, e.g., at essential or non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in a binding polypeptide is preferably replaced with another amino acid residue from the same side chain family. In another embodiment, a string of amino acids can be replaced with a structurally similar string that differs in order and/or composition of side chain family members. Alternatively, in another embodiment, mutations may be introduced randomly along all or part of a coding sequence, such as by saturation mutagenesis, and the resultant mutants can be incorporated into binding polypeptides of the invention and screened for their ability to bind to the desired target.

The term "ameliorating" refers to any therapeutically beneficial result in the treatment of a disease state, e.g., an autoimmune disease state (e.g., SLE), including prophylaxis, lessening in the severity or progression, remission, or cure thereof.

The term "in situ" refers to processes that occur in a living cell growing separate from a living organism, e.g., growing in tissue culture.

The term "in vivo" refers to processes that occur in a living organism.

The term "mammal" or "subject" or "patient" as used herein includes both humans and non-humans and include but is not limited to humans, non-human primates, canines, felines, murines, bovines, equines, and porcines.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website.

The term "sufficient amount" means an amount sufficient to produce a desired effect, e.g., an amount sufficient to modulate protein aggregation in a cell.

The term "therapeutically effective amount" is an amount that is effective to ameliorate a symptom of a disease. A therapeutically effective amount can be a "prophylactically effective amount" as prophylaxis can be considered therapy.

It must be noted that, as used in the specification and the appended claims, the singular forms "a," "an" and "the" include plural referents unless the context clearly dictates otherwise.

Compositions

Hybrid Nuclease Molecules

In some embodiments, a composition of the invention includes a hybrid nuclease molecule. In some embodiments, a hybrid nuclease molecule includes a nuclease domain operatively linked to an Fc domain. In some embodiments, a hybrid nuclease molecule includes a nuclease domain linked to an Fc domain. In some embodiments the hybrid nuclease molecule is a nuclease protein. In some embodiments, the hybrid nuclease molecule is a nuclease polynucleotide.

In some embodiments, the nuclease domain is linked to the Fc domain via a linker domain. In some embodiments, the linker domain is a linker peptide. In some embodiments, the linker domain is a linker nucleotide. In some embodiments, the hybrid nuclease molecule includes a leader molecule, e.g., a leader peptide. In some embodiments, the leader molecule is a leader peptide positioned at the N-terminus of the nuclease domain. In some embodiments, the hybrid nuclease molecule will include a stop codon. In some embodiments, the stop codon will be at the C-terminus of the Fc domain.

Figure 12:
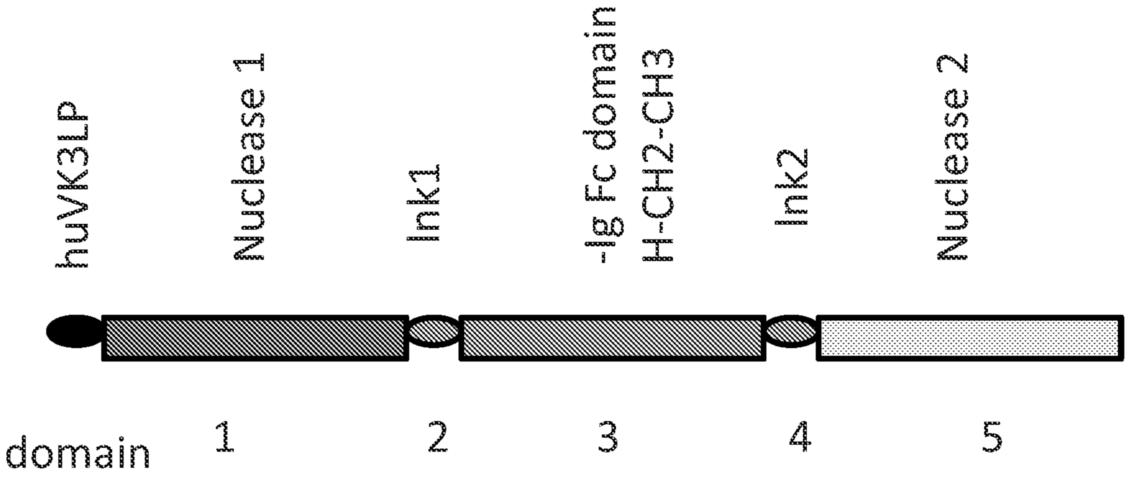
FIG. 12 shows a prototype structure for creating different embodiments of hybrid nuclease molecules.

In some embodiments, the hybrid nuclease molecule further includes a second nuclease domain. In some embodiments, the second nuclease domain is linked to the Fc domain via a second linker domain. In some embodiments, the second linker domain will be at the C-terminus of the Fc domain. FIG. 12 shows at least one embodiment of a hybrid nuclease molecule. In some embodiments, a hybrid nuclease molecule includes a sequence shown in Table 2.

In some embodiments, a hybrid nuclease molecule is an RNase molecule or DNase molecule or a multi-enzyme molecule (e.g., both RNase and DNase or two RNA or DNA nucleases with different specificity for substrate) attached to an Fc domain that specifically binds to extracellular immune complexes. In some embodiments, the Fc domain does not effectively bind Fcγ receptors. In one aspect, the hybrid nuclease molecule does not effectively bind C1q. In other aspects, the hybrid nuclease molecule comprises an in frame Fc domain from IgG1. In other aspects, the hybrid nuclease molecule further comprises mutations in the hinge, CH2, and/or CH3 domains. In other aspects, the mutations are P238S, P331S or N297S, and may include mutations in one or more of the three hinge cysteines. In some such aspects, the mutations in one or more of three hinge cysteines can be SCC or SSS. In other aspects, the molecules contain the SCC hinge, but are otherwise wild type for human IgG1 Fc CH2 and CH3 domains, and bind efficiently to Fc receptors, facilitating uptake of the hybrid nuclease molecule into the endocytic compartment of cells to which they are bound. In other aspects, the molecule has activity against single and/or double-stranded RNA substrates.

In some aspects, the activity of the hybrid nuclease molecule is detectable in vitro and/or in vivo. In some aspects, the hybrid nuclease molecule binds to a cell, a malignant cell, or a cancer cell and interferes with its biologic activity.

In another aspect, a multifunctional RNase molecule is provided that is attached to another enzyme or antibody having binding specificity, such as an scFv targeted to RNA or a second nuclease domain with the same or different specificities as the first domain.

In another aspect, a multifunctional DNase molecule is provided that is attached to another enzyme or antibody having binding specificity, such as an scFv targeted to DNA or a second nuclease domain with the same or different specificities as the first domain.

In another aspect, a hybrid nuclease molecule is adapted for preventing or treating a disease or disorder in a mammal by administering an hybrid nuclease molecule attached to an Fc region, in a therapeutically effective amount to the mammal in need thereof, wherein the disease is prevented or treated. In other aspects, the disease or disorder is an autoimmune disease or cancer. In some such aspects, the autoimmune disease is insulin-dependent diabetes mellitus, multiple sclerosis, experimental autoimmune encephalomyelitis, rheumatoid arthritis, experimental autoimmune arthritis, myasthenia gravis, thyroiditis, an experimental form of uveoretinitis, Hashimoto's thyroiditis, primary myxoedema, thyrotoxicosis, pernicious anaemia, autoimmune atrophic gastritis, Addison's disease, premature menopause, male infertility, juvenile diabetes, Goodpasture's syndrome, pemphigus vulgaris, pemphigoid, sympathetic ophthalmia, phacogenic uveitis, autoimmune haemolytic anaemia, idiopathic leucopenia, primary biliary cirrhosis, active chronic hepatitis Hbs-ve, cryptogenic cirrhosis, ulcerative colitis, Sjogren's syndrome, scleroderma, Wegener's granulomatosis, polymyositis, dermatomyositis, discoid LE, systemic lupus erythematosus, or connective tissue disease.

In some embodiments, the targets of the RNase enzyme activity of RNase hybrid nuclease molecules are primarily extracellular, consisting of, e.g., RNA contained in immune complexes with anti-RNP autoantibody and RNA expressed on the surface of cells undergoing apoptosis. In some embodiments, the RNase hybrid nuclease molecule is active in the acidic environment of the endocytic vesicles. In some embodiments, an RNase hybrid nuclease molecule includes a wild-type (wt) Fc domain in order to, e.g, allow the molecule to bind FcR and enter the endocytic compartment through the entry pathway used by immune complexes. In some embodiments, an RNase hybrid nuclease molecule including a wt Fc domain is adapted to be active both extracellularly and in the endocytic environment (where TLR7 can be expressed). In some aspects, this allows an RNase hybrid nuclease molecule including a wt Fc domain to stop TLR7 signaling through previously engulfed immune complexes or by RNAs that activate TLR7 after viral infection. In some embodiments, the wt RNase of an RNase hybrid nuclease molecule is not resistant to inhibition by an RNase cytoplasmic inhibitor. In some embodiments, the wt RNase of an RNase hybrid nuclease molecule is not active in the cytoplasm of a cell.

In some embodiments, a hybrid nuclease molecule including a wt Fc domain is used for therapy of an autoimmune disease, e.g., SLE.

In some embodiments, Fc domain binding to an Fc receptor (FcR) is increased, e.g., via alterations of glycosylation and/or changes in amino acid sequence. In some embodiments, a hybrid nuclease molecule has one or more Fc alterations that increase FcR binding.

Alternative ways to construct a hybrid nuclease molecule attached to an Fc domain are envisioned. In some embodiments, the domain orientation can be altered to construct an Ig-RNase molecule or an Ig-DNase molecule or an RNase-Ig molecule or an RNase-Ig molecule that retains FcR binding and has active nuclease domains.

In some embodiments, DNase hybrid nuclease molecules include a wt Fc domain that can allow, e.g., the molecules to undergo endocytosis after binding FcR. In some embodiments, the DNase hybrid nuclease molecules can be active towards extracellular immune complexes containing DNA, e.g., either in soluble form or deposited as insoluble complexes.

In some embodiments, hybrid nuclease molecules include both DNase and RNase. In some embodiments, these hybrid nuclease molecules can improve the therapy of SLE because they can, e.g., digest immune complexes containing RNA, DNA, or a combination of both RNA and DNA; and when they further include a wt Fc domain, they are active both extracellularly and in the endocytic compartment where TLR7 and TLR9 can be located.

In some embodiments, linker domains include (gly4ser) 3, 4 or 5 variants that alter the length of the linker by 5 amino acid progressions. In another embodiment, a linker domain is approximately 18 amino acids in length and includes an N-linked glycosylation site, which can be sensitive to protease cleavage in vivo. In some embodiments, an N-linked glycosylation site can protect the hybrid nuclease molecules from cleavage in the linker domain. In some embodiments, an N-linked glycosylation site can assist in separating the folding of independent functional domains separated by the linker domain.

In some embodiments, hybrid nuclease molecules can include both mutant and/or wild type human IgG1 Fc domains. In some embodiments, the hybrid nuclease molecules can be expressed from both COS transient and CHO stable transfections. In some embodiments, both the CD80/86 binding and the RNase activity are preserved in a hybrid nuclease molecule. In some embodiments, hybrid nuclease molecules include DNase1L3-Ig-linker-RNase constructs. In some embodiments, a hybrid nuclease molecule includes a DNase1-Ig-linker-RNase construct or an RNase-Ig-linker-DNase construct. In some embodiments, fusion junctions between enzyme domains and the other domains of the hybrid nuclease molecule is optimized.

In some embodiments, hybrid nuclease molecules include DNase-Ig hybrid nuclease molecules and/or hybrid DNase-RNase hybrid nuclease molecules.

In some embodiments, a hybrid nuclease molecule includes TREX1. In some embodiments, a TREX1 hybrid nuclease molecule can digest chromatin. In some embodiments, a TREX1 hybrid nuclease molecule is expressed by a cell. In some embodiments, the expressed hybrid nuclease molecule includes murine TREX-1 and a murine (wt or mutant) Fc domain. In some embodiments, a 20-25 amino acid (aa) linker domain between TREX1 and the IgG hinge can be required to allow DNase activity. In some embodiments, a hybrid nuclease molecule with a 15 aa linker domain is not active. In some embodiments, use of the 20 and 25 amino acid linker domains (plus 2 or more amino acids to incorporate restriction sites) results in functional activity as measured by chromatin digestion. In some embodiments, a hydrophobic region of approximately 72 aa can be removed from the COOH end of TREX-1 prior to fusion to the Fc domain via the linker domain. In some embodiments, a 20 amino acid linker domain version of the hybrid nuclease molecule exhibits high expression levels compared to controls and/or other hybrid nuclease molecules. In some embodiments, kinetic enzyme assays are used to compare the enzyme activity of hybrid nuclease molecules and controls in a quantitative manner.

In some embodiments, further optimization of the fusion junction chosen for truncation of a TREX1 enzyme can be used to improve expression of the hybrid nuclease molecules.

In some embodiments, the hybrid nuclease molecule includes a human TREX1-linker-Ig Fc domain hybrid nuclease molecule with 20 and/or 25 aa linker domains. In some embodiments, the linker domain(s) are variants of a (gly4ser)4 or (gly4ser)5 cassette with one or more restriction sites attached for incorporation into the hybrid nuclease molecules construct. In some embodiments, because of the head-to-tail dimerization useful for TREX1 enzyme activity; a flexible, longer linker domain can be used to facilitate proper folding.

In some embodiments, the hybrid nuclease molecule is a TREX1-tandem hybrid nuclease molecule. In some embodiments, an alternative method for facilitating head-to-tail folding of TREX1 is to generate a TREX1-TREX1-Ig hybrid nuclease molecule that incorporates two TREX1 domains in tandem, followed by a linker domain and an Ig Fc domain. In some embodiments, positioning of TREX1 cassettes in a head-to-tail manner can be corrected for head-to tail folding on either arm of the immunoenzyme and introduce a single TREX1 functional domain into each arm of the molecule. In some embodiments, each immunoenzyme of a hybrid nuclease molecule has two functional TREX1 enzymes attached to a single IgG Fc domain.

In some embodiments, the hybrid nuclease molecule includes TREX1-linker1-Ig-linker2-RNase.

In some embodiments, the hybrid nuclease molecule includes RNase-Ig-linker-TREX1. In some embodiments, cassettes are derived for both amino and carboxyl fusion of each enzyme for incorporation into hybrid nuclease molecules where the enzyme configuration is reversed. In some embodiments, the RNase enzyme exhibits comparable functional activity regardless of its position in the hybrid nuclease molecules. In some embodiments, alternative hybrid nuclease molecules can be designed to test whether a particular configuration demonstrates improved expression and/or function of the hybrid nuclease molecule components.

In some embodiments, the hybrid nuclease molecule includes 1L3-Ig. In some embodiments, the 1L3 DNase is constructed from a murine sequence and expressed. In some embodiments, the enzyme is active. In some embodiments, a murine 1L3 DNase-Ig-RNase hybrid nuclease is constructed and expressed. In some embodiments, the molecule includes human 1L3-Ig, human 1L3-Ig-RNase, and/or human RNase-Ig-1L3.

In some embodiments, the hybrid nuclease molecule includes DNase1-Ig. In some embodiments, a naturally occurring variant allele, A114F, which shows reduced sensitivity to actin is included in a DNase1-Ig hybrid nuclease molecule. In some embodiments, this mutation is introduced into a hybrid nuclease molecule to generate a more stable derivative of human DNase1. In some embodiments, a DNase1-linker-Ig containing a 20 or 25 aa linker domain is made. In some embodiments, hybrid nuclease molecules include RNase-Ig-linker-DNase1 where the DNase1 domain is located at the COOH side of the Ig Fc domain. In some embodiments, hybrid nuclease molecules are made that incorporate DNase1 and include: DNase1-linker-Ig-linker2-RNase, and/or RNase-Ig-linker-DNase1.

Another aspect of the present invention is to use gene therapy methods for treating or preventing disorders, diseases, and conditions with one or more hybrid nuclease molecules. The gene therapy methods relate to the introduction of hybrid nuclease molecule nucleic acid (DNA, RNA and antisense DNA or RNA) sequences into an animal to achieve expression of the polypeptide or polypeptides of the present invention. This method can include introduction of one or more polynucleotides encoding a hybrid nuclease molecule polypeptide of the present invention operatively linked to a promoter and any other genetic elements necessary for the expression of the polypeptide by the target tissue.

In gene therapy applications, hybrid nuclease molecule genes are introduced into cells in order to achieve in vivo synthesis of a therapeutically effective genetic product. "Gene therapy" includes both conventional gene therapies where a lasting effect is achieved by a single treatment, and the administration of gene therapeutic agents, which involves the one time or repeated administration of a therapeutically effective DNA or mRNA. The oligonucleotides can be modified to enhance their uptake, e.g., by substituting their negatively charged phosphodiester groups by uncharged groups.

Fc Domains

In some embodiments, a hybrid nuclease molecule includes an Fc domain. Fc domains useful for producing the hybrid nuclease molecules of the present invention may be obtained from a number of different sources. In preferred embodiments, an Fc domain of the hybrid nuclease molecule is derived from a human immunoglobulin. It is understood, however, that the Fc domain may be derived from an immunoglobulin of another mammalian species, including for example, a rodent (e.g. a mouse, rat, rabbit, guinea pig) or non-human primate (e.g. chimpanzee, macaque) species. Moreover, the hybrid nuclease molecule Fc domain or portion thereof may be derived from any immunoglobulin class, including IgM, IgG, IgD, IgA, and IgE, and any immunoglobulin isotype, including IgG1, IgG2, IgG3, and IgG4. In a preferred embodiment, the human isotype IgG1 is used.

A variety of Fc domain gene sequences (e.g. human constant region gene sequences) are available in the form of publicly accessible deposits. Constant region domains comprising an Fc domain sequence can be selected having a particular effector function (or lacking a particular effector function) or with a particular modification to reduce immunogenicity. Many sequences of antibodies and antibody-encoding genes have been published and suitable Fc domain sequences (e.g. hinge, CH2, and/or CH3 sequences, or portions thereof) can be derived from these sequences using art recognized techniques. The genetic material obtained using any of the foregoing methods may then be altered or synthesized to obtain polypeptides of the present invention. It will further be appreciated that the scope of this invention encompasses alleles, variants and mutations of constant region DNA sequences.

Fc domain sequences can be cloned, e.g., using the polymerase chain reaction and primers which are selected to amplify the domain of interest. To clone an Fc domain sequence from an antibody, mRNA can be isolated from hybridoma, spleen, or lymph cells, reverse transcribed into DNA, and antibody genes amplified by PCR. PCR amplification methods are described in detail in U.S. Pat. Nos. 4,683,195; 4,683,202; 4,800,159; 4,965,188; and in, e.g., "PCR Protocols: A Guide to Methods and Applications" Innis et al. eds., Academic Press, San Diego, Calif. (1990); Ho et al. 1989. Gene 77:51; Horton et al. 1993. Methods Enzymol. 217:270). PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes. Numerous primer sets suitable for amplification of antibody genes are known in the art (e.g., 5' primers based on the N-terminal sequence of purified antibodies (Benhar and Pastan. 1994. Protein Engineering 7:1509); rapid amplification of cDNA ends (Ruberti, F. et al. 1994. J. Immunol. Methods 173:33); antibody leader sequences (Larrick et al. 1989 Biochem. Biophys. Res. Commun. 160:1250). The cloning of antibody sequences is further described in Newman et al., U.S. Pat. No. 5,658,570, filed Jan. 25, 1995, which is incorporated by reference herein.

The hybrid nuclease molecules of the invention may comprise one or more Fc domains (e.g., 2, 3, 4, 5, 6, 7, 8, 9, 10, or more Fc domains). In one embodiment, the Fc domains may be of different types. In one embodiment, at least one Fc domain present in the hybrid nuclease molecule comprises a hinge domain or portion thereof. In another embodiment, the hybrid nuclease molecule of the invention comprises at least one Fc domain which comprises at least one CH2 domain or portion thereof. In another embodiment, the hybrid nuclease molecule of the invention comprises at least one Fc domain which comprises at least one CH3 domain or portion thereof. In another embodiment, the hybrid nuclease molecule of the invention comprises at least one Fc domain which comprises at least one CH4 domain or portion thereof. In another embodiment, the hybrid nuclease molecule of the invention comprises at least one Fc domain which comprises at least one hinge domain or portion thereof and at least one CH2 domain or portion thereof (e.g, in the hinge-CH2 orientation). In another embodiment, the hybrid nuclease molecule of the invention comprises at least one Fc domain which comprises at least one CH2 domain or portion thereof and at least one CH3 domain or portion thereof (e.g, in the CH2-CH3 orientation). In another embodiment, the hybrid nuclease molecule of the invention comprises at least one Fc domain comprising at least one hinge domain or portion thereof, at least one CH2 domain or portion thereof, and least one CH3 domain or portion thereof, for example in the orientation hinge-CH2-CH3, hinge-CH3-CH2, or CH2-CH3-hinge.

In certain embodiments, the hybrid nuclease molecule comprises at least one complete Fc region derived from one or more immunoglobulin heavy chains (e.g., an Fc domain including hinge, CH2, and CH3 domains, although these need not be derived from the same antibody). In other embodiments, the hybrid nuclease molecule comprises at least two complete Fc domains derived from one or more immunoglobulin heavy chains. In preferred embodiments, the complete Fc domain is derived from a human IgG immunoglobulin heavy chain (e.g., human IgG1).

In another embodiment, a hybrid nuclease molecule of the invention comprises at least one Fc domain comprising a complete CH3 domain. In another embodiment, a hybrid nuclease molecule of the invention comprises at least one Fc domain comprising a complete CH2 domain. In another embodiment, a hybrid nuclease molecule of the invention comprises at least one Fc domain comprising at least a CH3 domain, and at least one of a hinge region, and a CH2 domain. In one embodiment, a hybrid nuclease molecule of the invention comprises at least one Fc domain comprising a hinge and a CH3 domain. In another embodiment, a hybrid nuclease molecule of the invention comprises at least one Fc domain comprising a hinge, a CH2, and a CH3 domain. In preferred embodiments, the Fc domain is derived from a human IgG immunoglobulin heavy chain (e.g., human IgG1).

The constant region domains or portions thereof making up an Fc domain of a hybrid nuclease molecule of the invention may be derived from different immunoglobulin molecules. For example, a polypeptide of the invention may comprise a CH2 domain or portion thereof derived from an IgG1 molecule and a CH3 region or portion thereof derived from an IgG3 molecule. In another example, a hybrid nuclease molecule can comprise an Fc domain comprising a hinge domain derived, in part, from an IgG1 molecule and, in part, from an IgG3 molecule. As set forth herein, it will be understood by one of ordinary skill in the art that an Fc domain may be altered such that it varies in amino acid sequence from a naturally occurring antibody molecule.

In another embodiment, a hybrid nuclease molecule of the invention comprises one or more truncated Fc domains that are nonetheless sufficient to confer Fc receptor (FcR) binding properties to the Fc region. Thus, an Fc domain of a hybrid nuclease molecule of the invention may comprise or consist of an FcRn binding portion. FcRn binding portions may be derived from heavy chains of any isotype, including IgG1, IgG2, IgG3 and IgG4. In one embodiment, an FcRn binding portion from an antibody of the human isotype IgG1 is used. In another embodiment, an FcRn binding portion from an antibody of the human isotype IgG4 is used.

In one embodiment, a hybrid nuclease molecule of the invention lacks one or more constant region domains of a complete Fc region, i.e., they are partially or entirely deleted. In a certain embodiments hybrid nuclease molecules of the invention will lack an entire CH2 domain (ΔCH2 constructs). Those skilled in the art will appreciate that such constructs may be preferred due to the regulatory properties of the CH2 domain on the catabolic rate of the antibody. In certain embodiments, hybrid nuclease molecules of the invention comprise CH2 domain-deleted Fc regions derived from a vector (e.g., from IDEC Pharmaceuticals, San Diego) encoding an IgG1 human constant region domain (see, e.g., WO 02/060955A2 and WO02/096948A2). This exemplary vector is engineered to delete the CH2 domain and provide a synthetic vector expressing a domain-deleted IgG1 constant region. It will be noted that these exemplary constructs are preferably engineered to fuse a binding CH3 domain directly to a hinge region of the respective Fc domain.

In other constructs it may be desirable to provide a peptide spacer between one or more constituent Fc domains. For example, a peptide spacer may be placed between a hinge region and a CH2 domain and/or between a CH2 and a CH3 domain. For example, compatible constructs could be expressed wherein the CH2 domain has been deleted and the remaining CH3 domain (synthetic or unsynthetic) is joined to the hinge region with a 1-20, 1-10, or 1-5 amino acid peptide spacer. Such a peptide spacer may be added, for instance, to ensure that the regulatory elements of the constant region domain remain free and accessible or that the hinge region remains flexible. Preferably, any linker peptide compatible with the instant invention will be relatively non-immunogenic and not prevent proper folding of the Fc.

Changes to Fc Amino Acids

In certain embodiments, an Fc domain employed in a hybrid nuclease molecule of the invention is altered, e.g., by amino acid mutation (e.g., addition, deletion, or substitution). As used herein, the term "Fc domain variant" refers to an Fc domain having at least one amino acid substitution as compared to the wild-type Fc from which the Fc domain is derived. For example, wherein the Fc domain is derived from a human IgG1 antibody, a variant comprises at least one amino acid mutation (e.g., substitution) as compared to a wild type amino acid at the corresponding position of the human IgG1 Fc region.

The amino acid substitution(s) of an Fc variant may be located at a position within the Fc domain referred to as corresponding to the portion number that that residue would be given in an Fc region in an antibody.

In one embodiment, the Fc variant comprises a substitution at an amino acid position located in a hinge domain or portion thereof. In another embodiment, the Fc variant comprises a substitution at an amino acid position located in a CH2 domain or portion thereof. In another embodiment, the Fc variant comprises a substitution at an amino acid position located in a CH3 domain or portion thereof. In another embodiment, the Fc variant comprises a substitution at an amino acid position located in a CH4 domain or portion thereof.

In certain embodiments, the hybrid nuclease molecules of the invention comprise an Fc variant comprising more than one amino acid substitution. The hybrid nuclease molecules of the invention may comprise, for example, 2, 3, 4, 5, 6, 7, 8, 9, 10 or more amino acid substitutions. Preferably, the amino acid substitutions are spatially positioned from each other by an interval of at least 1 amino acid position or more, for example, at least 2, 3, 4, 5, 6, 7, 8, 9, or 10 amino acid positions or more. More preferably, the engineered amino acids are spatially positioned apart from each other by an interval of at least 5, 10, 15, 20, or 25 amino acid positions or more.

In certain embodiments, the Fc variant confers an improvement in at least one effector function imparted by an Fc domain comprising said wild-type Fc domain (e.g., an improvement in the ability of the Fc domain to bind to Fc receptors (e.g. FcγRI, FcγRII, or FcγRIII) or complement proteins (e.g. C1q), or to trigger antibody-dependent cytotoxicity (ADCC), phagocytosis, or complement-dependent cytotoxicity (CDCC)). In other embodiments, the Fc variant provides an engineered cysteine residue.

The hybrid nuclease molecules of the invention may employ art-recognized Fc variants which are known to impart an improvement in effector function and/or FcR binding. Specifically, a hybrid nuclease molecule of the invention may include, for example, a change (e.g., a substitution) at one or more of the amino acid positions disclosed in International PCT Publications WO88/07089A1, WO96/14339A1, WO98/05787A1, WO98/23289A1, WO99/51642A1, WO99/58572A1, WO00/09560A2, WO00/32767A1, WO00/42072A2, WO02/44215A2, WO02/060919A2, WO03/074569A2, WO04/016750A2, WO04/029207A2, WO04/035752A2, WO04/063351 A2, WO04/074455A2, WO04/099249A2, WO05/040217A2, WO04/044859, WO05/070963A1, WO05/077981A2, WO05/092925A2, WO05/123780A2, WO06/019447A1, WO06/047350A2, and WO06/085967A2; US Patent Publication Nos. US2007/0231329, US2007/0231329, US2007/0237765, US2007/0237766, US2007/0237767, US2007/0243188, US20070248603, US20070286859, US20080057056; or U.S. Pat. Nos. 5,648,260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; 7,083,784; and 7,317,091, each of which is incorporated by reference herein. In one embodiment, the specific change (e.g., the specific substitution of one or more amino acids disclosed in the art) may be made at one or more of the disclosed amino acid positions. In another embodiment, a different change at one or more of the disclosed amino acid positions (e.g., the different substitution of one or more amino acid position disclosed in the art) may be made.

In certain embodiments, a hybrid nuclease molecule of the invention comprises an amino acid substitution to an Fc domain which alters the antigen-independent effector functions of the antibody, in particular the circulating half-life of the antibody. Such hybrid nuclease molecules exhibit either increased or decreased binding to FcRn when compared to hybrid nuclease molecules lacking these substitutions and, therefore, have an increased or decreased half-life in serum, respectively. Fc variants with improved affinity for FcRn are anticipated to have longer serum half-lives, and such molecules have useful applications in methods of treating mammals where long half-life of the administered polypeptide is desired, e.g., to treat a chronic disease or disorder. In contrast, Fc variants with decreased FcRn binding affinity are expected to have shorter half-lives, and such molecules are also useful, for example, for administration to a mammal where a shortened circulation time may be advantageous, e.g. for in vivo diagnostic imaging or in situations where the starting polypeptide has toxic side effects when present in the circulation for prolonged periods. Fc variants with decreased FcRn binding affinity are also less likely to cross the placenta and, thus, are also useful in the treatment of diseases or disorders in pregnant women. In addition, other applications in which reduced FcRn binding affinity may be desired include those applications in which localization the brain, kidney, and/or liver is desired. In one exemplary embodiment, the hybrid nuclease molecules of the invention exhibit reduced transport across the epithelium of kidney glomeruli from the vasculature. In another embodiment, the hybrid nuclease molecules of the invention exhibit reduced transport across the blood brain barrier (BBB) from the brain, into the vascular space. In one embodiment, a hybrid nuclease molecule with altered FcRn binding comprises at least one Fc domain (e.g., one or two Fc domains) having one or more amino acid substitutions within the "FcRn binding loop" of an Fc domain. Exemplary amino acid substitutions which altered FcRn binding activity are disclosed in International PCT Publication No. WO05/047327 which is incorporated by reference herein.

In other embodiments, a hybrid nuclease molecule of the invention comprises an Fc variant comprising an amino acid substitution which alters the antigen-dependent effector functions of the polypeptide, in particular ADCC or complement activation, e.g., as compared to a wild type Fc region. In exemplary embodiment, said hybrid nuclease molecules exhibit altered binding to an Fc gamma receptor (e.g., CD16). Such hybrid nuclease molecules exhibit either increased or decreased binding to FcR gamma when compared to wild-type polypeptides and, therefore, mediate enhanced or reduced effector function, respectively. Fc variants with improved affinity for FcγRs are anticipated to enhance effector function, and such molecules have useful applications in methods of treating mammals where target molecule destruction is desired. In contrast, Fc variants with decreased FcγR binding affinity are expected to reduce effector function, and such molecules are also useful, for example, for treatment of conditions in which target cell destruction is undesirable, e.g., where normal cells may express target molecules, or where chronic administration of the polypeptide might result in unwanted immune system activation. In one embodiment, the polypeptide comprising an Fc exhibits at least one altered antigen-dependent effector function selected from the group consisting of opsonization, phagocytosis, complement dependent cytotoxicity, antigen-dependent cellular cytotoxicity (ADCC), or effector cell modulation as compared to a polypeptide comprising a wild type Fc region.

In one embodiment the hybrid nuclease molecule exhibits altered binding to an activating FcγR (e.g. FcγI, FcγIIa, or FcγRIIIa). In another embodiment, the hybrid nuclease molecule exhibits altered binding affinity to an inhibitory FcγR (e.g. FcγRIIb). Exemplary amino acid substitutions which altered FcR or complement binding activity are disclosed in International PCT Publication No. WO05/063815 which is incorporated by reference herein.

A hybrid nuclease molecule of the invention may also comprise an amino acid substitution which alters the glycosylation of the hybrid nuclease molecule. For example, the Fc domain of the hybrid nuclease molecule may comprise an Fc domain having a mutation leading to reduced glycosylation (e.g., N- or O-linked glycosylation) or may comprise an altered glycoform of the wild-type Fc domain (e.g., a low fucose or fucose-free glycan). In another embodiment, the hybrid nuclease molecule has an amino acid substitution near or within a glycosylation motif, for example, an N-linked glycosylation motif that contains the amino acid sequence NXT or NXS. Exemplary amino acid substitutions which reduce or alter glycosylation are disclosed in International PCT Publication No. WO05/018572 and US Patent Publication No. 2007/0111281, which are incorporated by reference herein.

In other embodiments, a hybrid nuclease molecule of the invention comprises at least one Fc domain having engineered cysteine residue or analog thereof which is located at the solvent-exposed surface. Preferably the engineered cysteine residue or analog thereof does not interfere with an effector function conferred by the Fc. More preferably, the alteration does not interfere with the ability of the Fc to bind to Fc receptors (e.g. FcγRI, FcγRII, or FcγRIII) or complement proteins (e.g. C1q), or to trigger immune effector function (e.g., antibody-dependent cytotoxicity (ADCC), phagocytosis, or complement-dependent cytotoxicity (CDCC)). In preferred embodiments, the hybrid nuclease molecules of the invention comprise an Fc domain comprising at least one engineered free cysteine residue or analog thereof that is substantially free of disulfide bonding with a second cysteine residue. Any of the above engineered cysteine residues or analogs thereof may subsequently be conjugated to a functional domain using art-recognized techniques (e.g., conjugated with a thiol-reactive heterobifunctional linker).

In one embodiment, the hybrid nuclease molecule of the invention may comprise a genetically fused Fc domain having two or more of its constituent Fc domains independently selected from the Fc domains described herein. In one embodiment, the Fc domains are the same. In another embodiment, at least two of the Fc domains are different. For example, the Fc domains of the hybrid nuclease molecules of the invention comprise the same number of amino acid residues or they may differ in length by one or more amino acid residues (e.g., by about 5 amino acid residues (e.g., 1, 2, 3, 4, or 5 amino acid residues), about 10 residues, about 15 residues, about 20 residues, about 30 residues, about 40 residues, or about 50 residues). In yet other embodiments, the Fc domains of the hybrid nuclease molecules of the invention may differ in sequence at one or more amino acid positions. For example, at least two of the Fc domains may differ at about 5 amino acid positions (e.g., 1, 2, 3, 4, or 5 amino acid positions), about 10 positions, about 15 positions, about 20 positions, about 30 positions, about 40 positions, or about 50 positions).

Linker Domains

In some embodiments, a hybrid nuclease molecule includes a linker domain. In some embodiments, a hybrid nuclease molecule includes a plurality of linker domains. In some embodiments, the linker domain is a polypeptide linker. In certain aspects, it is desirable to employ a polypeptide linker to fuse one or more Fc domains to one or more nuclease domains to form a hybrid nuclease molecule.

In one embodiment, the polypeptide linker is synthetic. As used herein the term "synthetic" with respect to a polypeptide linker includes peptides (or polypeptides) which comprise an amino acid sequence (which may or may not be naturally occurring) that is linked in a linear sequence of amino acids to a sequence (which may or may not be naturally occurring) (e.g., an Fc domain sequence) to which it is not naturally linked in nature. For example, the polypeptide linker may comprise non-naturally occurring polypeptides which are modified forms of naturally occurring polypeptides (e.g., comprising a mutation such as an addition, substitution or deletion) or which comprise a first amino acid sequence (which may or may not be naturally occurring). The polypeptide linkers of the invention may be employed, for instance, to ensure that Fc domains are juxtaposed to ensure proper folding and formation of a functional Fc domain. Preferably, a polypeptide linker compatible with the instant invention will be relatively non-immunogenic and not inhibit any non-covalent association among monomer subunits of a binding protein.

In certain embodiments, the hybrid nuclease molecules of the invention employ a polypeptide linker to join any two or more domains in frame in a single polypeptide chain. In one embodiment, the two or more domains may be independently selected from any of the Fc domains or nuclease domains discussed herein. For example, in certain embodiments, a polypeptide linker can be used to fuse identical Fc domains, thereby forming a homomeric Fc region. In other embodiments, a polypeptide linker can be used to fuse different Fc domains (e.g. a wild-type Fc domain and a Fc domain variant), thereby forming a heteromeric Fc region. In other embodiments, a polypeptide linker of the invention can be used to genetically fuse the C-terminus of a first Fc domain (e.g. a hinge domain or portion thereof, a CH2 domain or portion thereof, a complete CH3 domain or portion thereof, a FcRn binding portion, an FcγR binding portion, a complement binding portion, or portion thereof) to the N-terminus of a second Fc domain (e.g., a complete Fc domain).

In one embodiment, a polypeptide linker comprises a portion of an Fc domain. For example, in one embodiment, a polypeptide linker can comprise an immunoglobulin hinge domain of an IgG1, IgG2, IgG3, and/or IgG4 antibody. In another embodiment, a polypeptide linker can comprise a CH2 domain of an IgG1, IgG2, IgG3, and/or IgG4 antibody. In other embodiments, a polypeptide linker can comprise a CH3 domain of an IgG1, IgG2, IgG3, and/or IgG4 antibody. Other portions of an immunoglobulin (e.g. a human immunoglobulin) can be used as well. For example, a polypeptide linker can comprise a CH1 domain or portion thereof, a CL domain or portion thereof, a VH domain or portion thereof, or a VL domain or portion thereof. Said portions can be derived from any immunoglobulin, including, for example, an IgG1, IgG2, IgG3, and/or IgG4 antibody.

In exemplary embodiments, a polypeptide linker can comprise at least a portion of an immunoglobulin hinge region. In one embodiment, a polypeptide linker comprises an upper hinge domain (e.g., an IgG1, an IgG2, an IgG3, or IgG4 upper hinge domain). In another embodiment, a polypeptide linker comprises a middle hinge domain (e.g., an IgG1, an IgG2, an IgG3, or an IgG4 middle hinge domain). In another embodiment, a polypeptide linker comprises a lower hinge domain (e.g., an IgG1, an IgG2, an IgG3, or an IgG4 lower hinge domain).

In other embodiments, polypeptide linkers can be constructed which combine hinge elements derived from the same or different antibody isotypes. In one embodiment, the polypeptide linker comprises a chimeric hinge comprising at least a portion of an IgG1 hinge region and at least a portion of an IgG2 hinge region. In one embodiment, the polypeptide linker comprises a chimeric hinge comprising at least a portion of an IgG1 hinge region and at least a portion of an IgG3 hinge region. In another embodiment, a polypeptide linker comprises a chimeric hinge comprising at least a portion of an IgG1 hinge region and at least a portion of an IgG4 hinge region. In one embodiment, the polypeptide linker comprises a chimeric hinge comprising at least a portion of an IgG2 hinge region and at least a portion of an IgG3 hinge region. In one embodiment, the polypeptide linker comprises a chimeric hinge comprising at least a portion of an IgG2 hinge region and at least a portion of an IgG4 hinge region. In one embodiment, the polypeptide linker comprises a chimeric hinge comprising at least a portion of an IgG1 hinge region, at least a portion of an IgG2 hinge region, and at least a portion of an IgG4 hinge region. In another embodiment, a polypeptide linker can comprise an IgG1 upper and middle hinge and a single IgG3 middle hinge repeat motif. In another embodiment, a polypeptide linker can comprise an IgG4 upper hinge, an IgG1 middle hinge and a IgG2 lower hinge.

In another embodiment, a polypeptide linker comprises or consists of a gly-ser linker. As used herein, the term “gly-ser linker” refers to a peptide that consists of glycine and serine residues. An exemplary gly/ser linker comprises an amino acid sequence of the formula ($Gly_4Ser$)n, wherein n is a positive integer (e.g., 1, 2, 3, 4, or 5). A preferred gly/ser linker is ($Gly_4Ser$)4. Another preferred gly/ser linker is ($Gly_4Ser$)3. Another preferred gly/ser linker is ($Gly_4Ser$)5. In certain embodiments, the gly-ser linker may be inserted between two other sequences of the polypeptide linker (e.g., any of the polypeptide linker sequences described herein). In other embodiments, a gly-ser linker is attached at one or both ends of another sequence of the polypeptide linker (e.g., any of the polypeptide linker sequences described herein). In yet other embodiments, two or more gly-ser linker are incorporated in series in a polypeptide linker. In one embodiment, a polypeptide linker of the invention comprises at least a portion of an upper hinge region (e.g., derived from an IgG1, IgG2, IgG3, or IgG4 molecule), at least a portion of a middle hinge region (e.g., derived from an IgG1, IgG2, IgG3, or IgG4 molecule) and a series of gly/ser amino acid residues (e.g., a gly/ser linker such as ($Gly_4Ser$)n).

In one embodiment, a polypeptide linker of the invention comprises a non-naturally occurring immunoglobulin hinge region domain, e.g., a hinge region domain that is not naturally found in the polypeptide comprising the hinge region domain and/or a hinge region domain that has been altered so that it differs in amino acid sequence from a naturally occurring immunoglobulin hinge region domain. In one embodiment, mutations can be made to hinge region domains to make a polypeptide linker of the invention. In one embodiment, a polypeptide linker of the invention comprises a hinge domain which does not comprise a naturally occurring number of cysteines, i.e., the polypeptide linker comprises either fewer cysteines or a greater number of cysteines than a naturally occurring hinge molecule.

In other embodiments, a polypeptide linker of the invention comprises a biologically relevant peptide sequence or a sequence portion thereof. For example, a biologically relevant peptide sequence may include, but is not limited to, sequences derived from an anti-rejection or anti-inflammatory peptide. Said anti-rejection or anti-inflammatory peptides may be selected from the group consisting of a cytokine inhibitory peptide, a cell adhesion inhibitory peptide, a thrombin inhibitory peptide, and a platelet inhibitory peptide. In a one preferred embodiment, a polypeptide linker comprises a peptide sequence selected from the group consisting of an IL-1 inhibitory or antagonist peptide sequence, an erythropoietin (EPO)-mimetic peptide sequence, a thrombopoietin (TPO)-mimetic peptide sequence, G-CSF mimetic peptide sequence, a TNF-antagonist peptide sequence, an integrin-binding peptide sequence, a selectin antagonist peptide sequence, an anti-pathogenic peptide sequence, a vasoactive intestinal peptide (VIP) mimetic peptide sequence, a calmodulin antagonist peptide sequence, a mast cell antagonist, a SH3 antagonist peptide sequence, an urokinase receptor (UKR) antagonist peptide sequence, a somatostatin or cortistatin mimetic peptide sequence, and a macrophage and/or T-cell inhibiting peptide sequence. Exemplary peptide sequences, any one of which may be employed as a polypeptide linker, are disclosed in U.S. Pat. No. 6,660,843, which is incorporated by reference herein.

It will be understood that variant forms of these exemplary polypeptide linkers can be created by introducing one or more nucleotide substitutions, additions or deletions into the nucleotide sequence encoding a polypeptide linker such that one or more amino acid substitutions, additions or deletions are introduced into the polypeptide linker. For example, mutations may be introduced by standard techniques, such as site-directed mutagenesis and PCR-mediated mutagenesis.

Polypeptide linkers of the invention are at least one amino acid in length and can be of varying lengths. In one embodiment, a polypeptide linker of the invention is from about 1 to about 50 amino acids in length. As used in this context, the term “about” indicates+/−two amino acid residues. Since linker length must be a positive integer, the length of from about 1 to about 50 amino acids in length, means a length of from 1 to 48-52 amino acids in length. In another embodiment, a polypeptide linker of the invention is from about 10-20 amino acids in length. In another embodiment, a polypeptide linker of the invention is from about 15 to about 50 amino acids in length.

In another embodiment, a polypeptide linker of the invention is from about 20 to about 45 amino acids in length. In another embodiment, a polypeptide linker of the invention is from about 15 to about 25 amino acids in length. In another embodiment, a polypeptide linker of the invention is from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or more amino acids in length.

Polypeptide linkers can be introduced into polypeptide sequences using techniques known in the art. Modifications can be confirmed by DNA sequence analysis. Plasmid DNA can be used to transform host cells for stable production of the polypeptides produced.

Nuclease Domains

In certain aspects, a hybrid nuclease molecule includes a nuclease domain. Accordingly, the hybrid nuclease molecules of the invention typically comprise at least one nuclease domain and at least one linked Fc domain. In certain aspects, a hybrid nuclease molecule includes a plurality of nuclease domains.

In some embodiments, a nuclease domain is DNase. In some embodiments, the DNase is a Type I secreted DNase. In some embodiments, the DNase is DNase 1 and/or a DNase 1-like (DNaseL) enzyme, 1-3. In some embodiments, the DNase is TREX1.

In some embodiments, a nuclease domain is an RNase. In some embodiments, the RNase is an extracellular or secretory RNase of the RNase A superfamily, e.g., RNase A.

In one embodiment, the nuclease domain is operably linked (e.g., chemically conjugated or genetically fused (e.g., either directly or via a polypeptide linker)) to the N-terminus of an Fc domain. In another embodiment, the nuclease domain is operably linked (e.g., chemically conjugated or genetically fused (e.g., either directly or via a polypeptide linker)) to the C-terminus of an Fc domain. In other embodiments, a nuclease domain is operably linked (e.g., chemically conjugated or genetically fused (e.g., either directly or via a polypeptide linker)) via an amino acid side chain of an Fc domain. In certain exemplary embodiments, the nuclease domain is fused to an Fc domain via a human immunoglobulin hinge domain or portion thereof.

In certain embodiments, the hybrid nuclease molecules of the invention comprise two or more nuclease domains and at least one Fc domain. For example, nuclease domains may be operably linked to both the N-terminus and C-terminus of an Fc domain. In other exemplary embodiments, nuclease domains may be operably linked to both the N- and C-terminal ends of multiple Fc domains (e.g., two, three, four, five, or more Fc domains) which are linked together in series to form a tandem array of Fc domains.

In other embodiments, two or more nuclease domains are linked to each other (e.g., via a polypeptide linker) in series, and the tandem array of nuclease domains is operably linked (e.g., chemically conjugated or genetically fused (e.g., either directly or via a polypeptide linker)) to either the C-terminus or the N-terminus of a Fc domain or a tandem array of Fc domains. In other embodiments, the tandem array of nuclease domains is operably linked to both the C-terminus and the N-terminus of a Fc domain or a tandem array of Fc domains.

In other embodiments, one or more nuclease domains may be inserted between two Fc domains. For example, one or more nuclease domains may form all or part of a polypeptide linker of a hybrid nuclease molecule of the invention.

Preferred hybrid nuclease molecules of the invention comprise at least one nuclease domain (e.g., RNase or DNase), at least one linker domain, and at least one Fc domain.

In certain embodiments, the hybrid nuclease molecules of the invention have at least one nuclease domain specific for a target molecule which mediates a biological effect. In another embodiment, binding of the hybrid nuclease molecules of the invention to a target molecule (e.g. DNA or RNA) results in the reduction or elimination of the target molecule, e.g., from a cell, a tissue, or from circulation.

In certain embodiments, the hybrid nuclease molecules of the invention may comprise two or more nuclease domains. In one embodiment, the nuclease domains are identical, e.g., RNase and RNase, or TREX1 and TREX1. In another embodiment, the nuclease domains are different, e.g., DNase and RNase.

In other embodiments, the hybrid nuclease molecules of the invention may be assembled together or with other polypeptides to form binding proteins having two or more polypeptides ("multimers"), wherein at least one polypeptide of the multimer is a hybrid nuclease molecule of the invention. Exemplary multimeric forms include dimeric, trimeric, tetrameric, and hexameric altered binding proteins and the like. In one embodiment, the polypeptides of the multimer are the same (ie. homomeric altered binding proteins, e.g. homodimers, homotetramers). In another embodiment, the polypeptides of the multimer are different (e.g. heteromeric).

Methods of Making Hybrid Nuclease Molecules

The hybrid nuclease molecules of this invention largely may be made in transformed host cells using recombinant DNA techniques. To do so, a recombinant DNA molecule coding for the peptide is prepared. Methods of preparing such DNA molecules are well known in the art. For instance, sequences coding for the peptides could be excised from DNA using suitable restriction enzymes. Alternatively, the DNA molecule could be synthesized using chemical synthesis techniques, such as the phosphoramidate method. Also, a combination of these techniques could be used.

The invention also includes a vector capable of expressing the peptides in an appropriate host. The vector comprises the DNA molecule that codes for the peptides operatively linked to appropriate expression control sequences. Methods of affecting this operative linking, either before or after the DNA molecule is inserted into the vector, are well known. Expression control sequences include promoters, activators, enhancers, operators, ribosomal nuclease domains, start signals, stop signals, cap signals, polyadenylation signals, and other signals involved with the control of transcription or translation.

The resulting vector having the DNA molecule thereon is used to transform an appropriate host. This transformation may be performed using methods well known in the art.

Any of a large number of available and well-known host cells may be used in the practice of this invention. The selection of a particular host is dependent upon a number of factors recognized by the art. These include, for example, compatibility with the chosen expression vector, toxicity of the peptides encoded by the DNA molecule, rate of transformation, ease of recovery of the peptides, expression characteristics, bio-safety and costs. A balance of these factors must be struck with the understanding that not all hosts may be equally effective for the expression of a particular DNA sequence. Within these general guidelines, useful microbial hosts include bacteria (such as *E. coli* sp.), yeast (such as *Saccharomyces* sp.) and other fungi, insects, plants, mammalian (including human) cells in culture, or other hosts known in the art.

Next, the transformed host is cultured and purified. Host cells may be cultured under conventional fermentation conditions so that the desired compounds are expressed. Such fermentation conditions are well known in the art. Finally, the peptides are purified from culture by methods well known in the art.

The compounds may also be made by synthetic methods. For example, solid phase synthesis techniques may be used. Suitable techniques are well known in the art, and include those described in Merrifield (1973), Chem. Polypeptides, pp. 335-61 (Katsoyannis and Panayotis eds.); Merrifield (1963), J. Am. Chem. Soc. 85: 2149; Davis et al. (1985), Biochem. Intl. 10: 394-414; Stewart and Young (1969), Solid Phase Peptide Synthesis; U.S. Pat. No. 3,941,763; Finn et al. (1976), The Proteins (3rd ed.) 2: 105-253; and Erickson et al. (1976), The Proteins (3rd ed.) 2: 257-527. Solid phase synthesis is the preferred technique of making individual peptides since it is the most cost-effective method of making small peptides. Compounds that contain derivatized peptides or which contain non-peptide groups may be synthesized by well-known organic chemistry techniques.

Other methods are of molecule expression/synthesis are generally known in the art to one of ordinary skill.

Pharmaceutical Compositions and Therapeutic Methods of Use

In certain embodiments, a hybrid nuclease molecule is administered alone. In certain embodiments, a hybrid nuclease molecule is administered prior to the administration of at least one other therapeutic agent. In certain embodiments, a hybrid nuclease molecule is administered concurrent with the administration of at least one other therapeutic agent. In certain embodiments, a hybrid nuclease molecule is administered subsequent to the administration of at least one other therapeutic agent. In other embodiments, a hybrid nuclease molecule is administered prior to the administration of at least one other therapeutic agent. As will be appreciated by one of skill in the art, in some embodiments, the hybrid nuclease molecule is combined with the other agent/compound. In some embodiments, the hybrid nuclease molecule and other agent are administered concurrently. In some embodiments, the hybrid nuclease molecule and other agent are not administered simultaneously, with the hybrid nuclease molecule being administered before or after the agent is administered. In some embodiments, the subject receives both the hybrid nuclease molecule and the other agent during a same period of prevention, occurrence of a disorder, and/or period of treatment.

Pharmaceutical compositions of the invention can be administered in combination therapy, i.e., combined with other agents. In certain embodiments, the combination therapy comprises nuclease molecule, in combination with at least one other agent. Agents include, but are not limited to, in vitro synthetically prepared chemical compositions, antibodies, antigen binding regions, and combinations and conjugates thereof. In certain embodiments, an agent can act as an agonist, antagonist, allosteric modulator, or toxin.

In certain embodiments, the invention provides for pharmaceutical compositions comprising a hybrid nuclease molecule together with a pharmaceutically acceptable diluent, carrier, solubilizer, emulsifier, preservative and/or adjuvant.

In certain embodiments, the invention provides for pharmaceutical compositions comprising a hybrid nuclease molecule and a therapeutically effective amount of at least one additional therapeutic agent, together with a pharmaceutically acceptable diluent, carrier, solubilizer, emulsifier, preservative and/or adjuvant.

In certain embodiments, acceptable formulation materials preferably are nontoxic to recipients at the dosages and concentrations employed. In some embodiments, the formulation material(s) are for s.c. and/or I.V. administration. In certain embodiments, the pharmaceutical composition can contain formulation materials for modifying, maintaining or preserving, for example, the pH, osmolarity, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company (1995). In some embodiments, the formulation comprises PBS; 20 mM NaOAC, pH 5.2, 50 mM NaCl; and/or 10 mM NAOAC, pH 5.2, 9% Sucrose.

In certain embodiments, a hybrid nuclease molecule and/or a therapeutic molecule is linked to a half-life extending vehicle known in the art. Such vehicles include, but are not limited to, polyethylene glycol, glycogen (e.g., glycosylation of the hybrid nuclease molecule), and dextran. Such vehicles are described, e.g., in U.S. application Ser. No. 09/428,082, now U.S. Pat. No. 6,660,843 and published PCT Application No. WO 99/25044, which are hereby incorporated by reference for any purpose.

In certain embodiments, the optimal pharmaceutical composition will be determined by one skilled in the art depending upon, for example, the intended route of administration, delivery format and desired dosage. See, for example, Remington's Pharmaceutical Sciences, supra. In certain embodiments, such compositions may influence the physical state, stability, rate of in vivo release and rate of in vivo clearance of the antibodies of the invention.

In certain embodiments, the primary vehicle or carrier in a pharmaceutical composition can be either aqueous or non-aqueous in nature. For example, in certain embodiments, a suitable vehicle or carrier can be water for injection, physiological saline solution or artificial cerebrospinal fluid, possibly supplemented with other materials common in compositions for parenteral administration. In some embodiments, the saline comprises isotonic phosphate-buffered saline. In certain embodiments, neutral buffered saline or saline mixed with serum albumin are further exemplary vehicles. In certain embodiments, pharmaceutical compositions comprise Tris buffer of about pH 7.0-8.5, or acetate buffer of about pH 4.0-5.5, which can further include sorbitol or a suitable substitute therefore. In certain embodiments, a composition comprising a hybrid nuclease molecule, with or without at least one additional therapeutic agents, can be prepared for storage by mixing the selected composition having the desired degree of purity with optional formulation agents (Remington's Pharmaceutical Sciences, supra) in the form of a lyophilized cake or an aqueous solution. Further, in certain embodiments, a composition comprising a hybrid nuclease molecule, with or without at least one additional therapeutic agent, can be formulated as a lyophilizate using appropriate excipients such as sucrose.

In certain embodiments, the pharmaceutical composition can be selected for parenteral delivery. In certain embodiments, the compositions can be selected for inhalation or for delivery through the digestive tract, such as orally. The preparation of such pharmaceutically acceptable compositions is within the ability of one skilled in the art.

In certain embodiments, the formulation components are present in concentrations that are acceptable to the site of administration. In certain embodiments, buffers are used to maintain the composition at physiological pH or at a slightly lower pH, typically within a pH range of from about 5 to about 8.

In certain embodiments, when parenteral administration is contemplated, a therapeutic composition can be in the form of a pyrogen-free, parenterally acceptable aqueous solution comprising a desired hybrid nuclease molecule, with or without additional therapeutic agents, in a pharmaceutically acceptable vehicle. In certain embodiments, a vehicle for parenteral injection is sterile distilled water in which a hybrid nuclease molecule, with or without at least one additional therapeutic agent, is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that can provide for the controlled or sustained release of the product which can then be delivered via a depot injection. In certain embodiments, hyaluronic acid can also be used, and can have the effect of promoting sustained duration in the circulation. In certain embodiments, implantable drug delivery devices can be used to introduce the desired molecule.

In certain embodiments, a pharmaceutical composition can be formulated for inhalation. In certain embodiments, a hybrid nuclease molecule, with or without at least one additional therapeutic agent, can be formulated as a dry powder for inhalation. In certain embodiments, an inhalation solution comprising a hybrid nuclease molecule, with or without at least one additional therapeutic agent, can be formulated with a propellant for aerosol delivery. In certain embodiments, solutions can be nebulized. Pulmonary administration is further described in PCT application no. PCT/US94/001875, which describes pulmonary delivery of chemically modified proteins.

In certain embodiments, it is contemplated that formulations can be administered orally. In certain embodiments, a hybrid nuclease molecule, with or without at least one additional therapeutic agents, that is administered in this fashion can be formulated with or without those carriers customarily used in the compounding of solid dosage forms such as tablets and capsules. In certain embodiments, a capsule can be designed to release the active portion of the formulation at the point in the gastrointestinal tract when bioavailability is maximized and pre-systemic degradation is minimized. In certain embodiments, at least one additional agent can be included to facilitate absorption of a hybrid nuclease molecule and/or any additional therapeutic agents. In certain embodiments, diluents, flavorings, low melting point waxes, vegetable oils, lubricants, suspending agents, tablet disintegrating agents, and binders can also be employed.

In certain embodiments, a pharmaceutical composition can involve an effective quantity of a hybrid nuclease molecule, with or without at least one additional therapeutic agents, in a mixture with non-toxic excipients which are suitable for the manufacture of tablets. In certain embodiments, by dissolving the tablets in sterile water, or another appropriate vehicle, solutions can be prepared in unit-dose form. In certain embodiments, suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving a hybrid nuclease molecule, with or without at least one additional therapeutic agent(s), in sustained- or controlled-delivery formulations. In certain embodiments, techniques for formulating a variety of other sustained- or controlled-delivery means, such as liposome carriers, bio-erodible microparticles or porous beads and depot injections, are also known to those skilled in the art. See for example, PCT Application No. PCT/US93/00829 which describes the controlled release of porous polymeric microparticles for the delivery of pharmaceutical compositions. In certain embodiments, sustained-release preparations can include semipermeable polymer matrices in the form of shaped articles, e.g. films, or microcapsules. Sustained release matrices can include polyesters, hydrogels, polylactides (U.S. Pat. No. 3,773,919 and EP 058,481), copolymers of L-glutamic acid and gamma ethyl-L-glutamate (Sidman et al., Biopolymers, 22:547-556 (1983)), poly (2-hydroxyethyl-methacrylate) (Langer et al., J. Biomed. Mater. Res., 15:167-277 (1981) and Langer, Chem. Tech., 12:98-105 (1982)), ethylene vinyl acetate (Langer et al., supra) or poly-D(−)-3-hydroxybutyric acid (EP 133,988). In certain embodiments, sustained release compositions can also include liposomes, which can be prepared by any of several methods known in the art. See, e.g., Eppstein et al., Proc. Natl. Acad. Sci. USA, 82:3688-3692 (1985); EP 036,676; EP 088,046 and EP 143,949.

The pharmaceutical composition to be used for in vivo administration typically is sterile. In certain embodiments, this can be accomplished by filtration through sterile filtration membranes. In certain embodiments, where the composition is lyophilized, sterilization using this method can be conducted either prior to or following lyophilization and reconstitution. In certain embodiments, the composition for parenteral administration can be stored in lyophilized form or in a solution. In certain embodiments, parenteral compositions generally are placed into a container having a sterile access port, for example, an intravenous solution bag or vial having a stopper pierceable by a hypodermic injection needle.

In certain embodiments, once the pharmaceutical composition has been formulated, it can be stored in sterile vials as a solution, suspension, gel, emulsion, solid, or as a dehydrated or lyophilized powder. In certain embodiments, such formulations can be stored either in a ready-to-use form or in a form (e.g., lyophilized) that is reconstituted prior to administration.

In certain embodiments, kits are provided for producing a single-dose administration unit. In certain embodiments, the kit can contain both a first container having a dried protein and a second container having an aqueous formulation. In certain embodiments, kits containing single and multi-chambered pre-filled syringes (e.g., liquid syringes and lyosyringes) are included.

In certain embodiments, the effective amount of a pharmaceutical composition comprising a hybrid nuclease molecule, with or without at least one additional therapeutic agent, to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which a hybrid nuclease molecule, with or without at least one additional therapeutic agent, is being used, the route of administration, and the size (body weight, body surface or organ size) and/or condition (the age and general health) of the patient. In certain embodiments, the clinician can titer the dosage and modify the route of administration to obtain the optimal therapeutic effect. In certain embodiments, a typical dosage can range from about 0.1 μg/kg to up to about 100 mg/kg or more, depending on the factors mentioned above. In certain embodiments, the dosage can range from 0.1 μg/kg up to about 100 mg/kg; or 1 μg/kg up to about 100 mg/kg; or 5 μg/kg up to about 100 mg/kg.

In certain embodiments, the frequency of dosing will take into account the pharmacokinetic parameters of a hybrid nuclease molecule and/or any additional therapeutic agents in the formulation used. In certain embodiments, a clinician will administer the composition until a dosage is reached that achieves the desired effect. In certain embodiments, the composition can therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. In certain embodiments, appropriate dosages can be ascertained through use of appropriate dose-response data.

In certain embodiments, the route of administration of the pharmaceutical composition is in accord with known methods, e.g. orally, through injection by intravenous, intraperitoneal, intracerebral (intra-parenchymal), intracerebroventricular, intramuscular, subcutaneously, intra-ocular, intraarterial, intraportal, or intralesional routes; by sustained release systems or by implantation devices. In certain embodiments, the compositions can be administered by bolus injection or continuously by infusion, or by implantation device.

In certain embodiments, the composition can be administered locally via implantation of a membrane, sponge or another appropriate material onto which the desired molecule has been absorbed or encapsulated. In certain embodiments, where an implantation device is used, the device can be implanted into any suitable tissue or organ, and delivery of the desired molecule can be via diffusion, timed-release bolus, or continuous administration.

In certain embodiments, it can be desirable to use a pharmaceutical composition comprising a hybrid nuclease molecule, with or without at least one additional therapeutic agent, in an ex vivo manner. In such instances, cells, tissues and/or organs that have been removed from the patient are exposed to a pharmaceutical composition comprising a hybrid nuclease molecule, with or without at least one additional therapeutic agent, after which the cells, tissues and/or organs are subsequently implanted back into the patient.

In certain embodiments, a hybrid nuclease molecule and/or any additional therapeutic agents can be delivered by implanting certain cells that have been genetically engineered, using methods such as those described herein, to express and secrete the polypeptides. In certain embodiments, such cells can be animal or human cells, and can be autologous, heterologous, or xenogeneic. In certain embodiments, the cells can be immortalized. In certain embodiments, in order to decrease the chance of an immunological response, the cells can be encapsulated to avoid infiltration of surrounding tissues. In certain embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

The hybrid nuclease molecules of the instant invention are particularly effective in the treatment of autoimmune disorders or abnormal immune responses. In this regard, it will be appreciated that the hybrid nuclease molecules of the present invention may be used to control, suppress, modulate, treat, or eliminate unwanted immune responses to both external and autoantigens. In yet other embodiments the polypeptides of the present invention may be used to treat immune disorders that include, but are not limited to, insulin-dependent diabetes mellitus, multiple sclerosis, experimental autoimmune encephalomyelitis, rheumatoid arthritis, experimental autoimmune arthritis, myasthenia gravis, thyroiditis, an experimental form of uveoretinitis, Hashimoto's thyroiditis, primary myxoedema, thyrotoxicosis, pernicious anaemia, autoimmune atrophic gastritis, Addison's disease, premature menopause, male infertility, juvenile diabetes, Goodpasture's syndrome, pemphigus vulgaris, pemphigoid, sympathetic ophthalmia, phacogenic uveitis, autoimmune haemolytic anaemia, idiopathic leucopenia, primary biliary cirrhosis, active chronic hepatitis Hbs-ve, cryptogenic cirrhosis, ulcerative colitis, Sjogren's syndrome, scleroderma, Wegener's granulomatosis, polymyositis, dermatomyositis, discoid LE, systemic lupus erythematosus, or connective tissue disease.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W. H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pennsylvania: Mack Publishing Company, 1990); Carey and Sundberg *Advanced Organic Chemistry* 3rd *Ed.* (Plenum Press) Vols A and B (1992).

Example 1: Construction of RNase-Ig Fusion Genes

Murine RNase 1 was amplified as a full-length cDNA from an EST library (from Dr. C. Raine, Albert Einstein School of Medicine, Bronx, NY) who sent the clone to our laboratory without an MTA. Sequence specific 5' and 3' primers used were from the published sequences. The sequence of the clone was verified by sequencing analysis. The Genebank accession number is NCBI geneID 19752. Full length human RNase 1 was isolated from random primed and oligo dT primed cDNA derived from human pancreas total RNA (Ambion/Applied Biosystems, Austin, TX).

Once a full-length clone was isolated, primers were designed to create a fusion gene with the mouse IgG2a (SEQ ID NO:114) or human IgG1 (SEQ ID NO:110) Fc domains. Two different primers were designed for the 5' sequence fused at the amino terminus of the Fc tail; the first incorporated the native leader peptide from mouse (or human) RNase, while the second attached an AgeI site to the amino terminus of RNase at the predicted signal peptide cleavage site in order to fuse the RNase to a human VKIII leader peptide that we already had cloned and used for other expression studies. For the murine RNase, the sequence of the first primer is:

```
mribNL5'
30mer (RNase 5' with native leader and
HindIII + Kozak)
                                    (SEQ ID NO: 1)
gTT AAg CTT gCC ACC ATg ggT CTg gAg AAg TCC CTC

ATT CTg-3'
```

The second primer creates a gene fusion junction between an existing leader sequence and the mature sequence at the 5' end of the RNase, at or near the predicted leader peptide cleavage site.

```
27mer (RNase 5' mature sequence
(no leader, with AgeI site)
                                    (SEQ ID NO: 2)
5'-gAT ACC ACC ggT Agg gAA TCT gCA gCA CAg AAg

TTT CAg-3'
```

The sequence of the 3' primer for fusion to murine IgG2a at the carboxy end of RNase and the amino terminus of the Fc tail is as follows:

```
mrib3NH2
28mer (RNase 3' end with XhoI site for
fusion to mIgG2a).
                                    (SEQ ID NO: 3)
5'-ggC TCg AgC ACA gTA gCA TCA AAg tGG ACT ggT

ACg TAg g-3'
```

Two more oligos were designed to create an -Ig-RNase fusion gene, where the -Ig tail is amino terminal to the RNase enzyme domain.

```
mrib5X
36mer RNase 5' end with linker aa and
XbaI site for fusion to carboxy end of
Fc domain.
                                    (SEQ ID NO: 4)
5'-AAA TCT AgA CCT CAA CCA ggT Agg gAA TCT gCA

gCA CAg AAg TTT CAg-3'

mrib3X
31mer RNase 3' end with two stop codons
and XbaI site for fusion to carboxy end
of Fc domain.
                                    (SEQ ID NO: 5)
5'-TCT AgA CTA TCA CAC AgT AgC ATC AAA gTg gAC

Tgg TAC gTA g-3'
```

Example 2: Isolation of Anti-RNA or Anti-DNA scFvs from Monoclonal Antibody Expressing Hybridomas An anti-RNA hybridoma designated H564 was used to isolate V regions specific for RNA. Prior to harvesting, H564 anti-RNA hybridoma cells were kept in log phase growth for several days in RPMI 1640 media (Invitrogen/Life Technologies, Gaithersburg, Md.) supplemented with glutamine, pyruvate, DMEM non-essential amino acids, and penicillin-streptomycin. Cells were pelleted by centrifugation from the culture medium, and $2\times10^7$ cells were used to prepare RNA. RNA was isolated from the hybridoma cells using the QIAGEN RNAeasy kit (Valencia, Calif.) total RNA isolation kit and QIAGEN QIAshredder according to the manufacturer's instructions accompanying the kit. Four microgram (4 μg) of total RNA was used as template to prepare cDNA by reverse transcription. The RNA, 300 ng random primers, and 500 ng Oligo dT (12-18), and 1 μl 25 mM dNTPs were combined and denatured at 80° C. for 5 minutes prior to addition of enzyme. Superscript III reverse transcriptase (Invitrogen, Life Technologies) was added to the RNA plus primer mixture in a total volume of 25 μl in the presence of 5.times.second strand buffer and 0.1 M DTT provided with the enzyme. The reverse transcription reaction was allowed to proceed at 50° C. for one hour.

The cDNA generated in the reverse transcriptase reaction was purified by QIAquick PCR purification kits (QIAGEN, Valencia CA) and tailed with a poly-G sequence using terminal transferase (Invitrogen, Carlsbad, CA) according to manufacturer's instructions. Tailed cDNA was again purified by QIAquick PCR purification and eluted in 30 ul elution buffer (EB buffer) provided with the kits. Two microliters of tailed cDNA was used as template along with an anchor-tail 5' primer containing a poly-C domain, and constant region specific, degenerate 3' primers to amplify by PCR the variable regions for the light and heavy chain of the H564 antibody. The two variable chains were designed with restriction enzyme sites so that a scFv could be assembled by three way ligation of the two V regions to a linker sequence after amplification and restriction enzyme digestion.

A (gly4ser)4 peptide linker to be inserted between the two V regions was incorporated by amplification of this linker sequence by overlap extension PCR using overlapping primers encoding the two halves of the molecule. PCR fragments were isolated by agarose gel electrophoresis, fragments isolated by cutting the appropriate bands from the gel and purifying the amplified DNA using QIAquick gel extraction kits (QIAGEN, Valencia, CA). scFv derivatives from the H564 hybridoma were assembled as VH-linker-VL fusion genes that could be attached at either end of a larger -Ig fusion gene. The V.sub.H domain was amplified without a leader peptide, but included a 5' AgeI restriction site for fusion to the V.sub.L and a BglII restriction site at the 3' end for fusion to the linker domain.

The scFv-Ig was assembled by inserting the scFv HindIII-XhoI fragment into pDG containing the human IgG1 hinge, CH2, and CH3 regions, which was digested with restriction enzymes, HindIII and XhoI. After ligation, the ligation products were transformed into DH5-alpha bacteria. The scFv-Ig cDNA was subjected to cycle sequencing on a PE 9700 thermocycler using a 25-cycle program by denaturing at 96° C. for 10 seconds, annealing at 50° C. for 30 seconds, and extending at 72° C. for 4 minutes. The sequencing primers were pDG forward and reverse primers and an internal primer that annealed to the CH2 domain human in the IgG constant region portion. Sequencing reactions were performed using the Big Dye Terminator Ready Sequencing Mix v3.1 (PE-Applied Biosystems, Foster City, Calif.) according to the manufacturer's instructions. Samples were subsequently purified using Autoseq G25 columns (GE Healthcare) and the eluates dried in a Savant vacuum dryer, denatured in Template Suppression Reagent (PE-ABI), and analyzed on an ABI 310 Genetic Analyzer (PE-Applied Biosystems). The sequence was edited, translated, and analyzed using Vector Nti version 10.0 (Informax/Invitrogen, North Bethesda, Md.).

Construction of a Human RNaseI-hIgG1 (SEQ ID NO:125-127) Fusion Gene

Human RNase1 (SEQ ID NO:113) was isolated by PCR amplification from human pancreas total RNA obtained from Ambion/Applied Biosystems (Austin, TX). Four microgram (4 μg) of total RNA was used as template to prepare cDNA by reverse transcription. The RNA, 300 ng random primers, and 500 ng Oligo dT (12-18), and 1 ul 25 mM dNTPs were combined and denatured at 80° C. for 5 minutes prior to addition of enzyme. Superscript III reverse transcriptase (Invitrogen, Life Technologies) was added to the RNA plus primer mixture in a total volume of 25 μl in the presence of second strand buffer and 0.1 M DTT provided with the enzyme. The reverse transcription reaction was allowed to proceed at 50° C. for one hour. Reactions were further purified by QIAquick PCR purification columns, and cDNA eluted in 40 microliters EB buffer prior to use in PCR reactions. Two microliters cDNA eluate were added to PCR reactions containing 50 pmol 5' and 3' primers specific for human RNase1, and 45 microliters of PCR high fidelity supermix (Invitrogen, Carlsbad, CA) was added to 0.2 ml PCR reaction tubes. PCR reactions were performed using a C1000 thermal cycler (BioRad, Hercules CA). Reactions included an initial denaturation step at 95 C for 2 minutes, followed by 34 cycles with a 94° C., 30 sec denaturation, 50° C., 30 sec annealing, and 68° C., 1 minute extension step, followed by a final 4 minute extension at 72° C. Once wild type tails were isolated, the fragments were TOPO cloned into pCR2.1 vectors; DNA prepared using the QIAGEN spin plasmid miniprep kits according to manufacturer's instructions. Plasmid DNA was sequenced using ABI Dye Terminator v3.1 ready reaction mix according to manufacturer's instructions.

Example 3: Isolation of Human and Mouse -Fc Domains and Introduction of Mutations into the Coding Sequence For isolation of mouse (SEQ ID NO:114) and human -Fc domains (SEQ ID NO:110), RNA was derived from mouse or human tissue as follows. A single cell suspension was generated from mouse spleen in RPMI culture media. Alternatively, human PBMCs were isolated from fresh, whole blood using Lymphocyte Separation Media (LSM) Organon Teknika (Durham, NC), buffy coats harvested according to manufacturer's directions, and cells washed three times in PBS prior to use. Cells were pelleted by centrifugation from the culture medium, and $2\times10^7$ cells were used to prepare RNA. RNA was isolated from the cells using the QIAGEN RNAeasy kit (Valencia, Calif.) total RNA isolation kit and QIAGEN QIAshredder columns according to the manufacturer's instructions accompanying the kits. One microgram (4 μg) of total RNA was used as template to prepare cDNA by reverse transcription. The RNA, 300 ng random primers, and 500 ng Oligo dT (12-18), and 1 μl 25 mM dNTPs were combined and denatured at 80° C. for 5 minutes prior to addition of enzyme. Superscript III reverse transcriptase (Invitrogen, Life Technologies) was added to the RNA plus primer mixture in a total volume of 25 μl in the presence of .second strand buffer and 0.1 M DTT provided with the enzyme. The reverse transcription reaction was allowed to proceed at 50° C. for one hour. cDNA was purified using QIAquick (QIAGEN) PCR purification columns according to manufacturer's directions, and eluted in 40 microliters EB buffer prior to use in PCR reactions.

Wild type mouse and human -Fc domains were isolated by PCR amplification using the cDNA described above as template. The following primers were used for initial amplification of wild type sequences, but incorporated the desired mutational changes in the hinge domain:

```
mahIgG1CH2M: 47 mer
                                        (SEQ ID NO: 6)
5'-tgtccaccgtgtccagcacctgaactcctgggtggatcgtcagtctt

cc-3'

hIgG1-5scc: 49 mer
                                        (SEQ ID NO: 7)
5'-agatctcgagcccaaatcttctgacaaaactcacacatgtccaccgt

gt-3'

mahIgG1S: 51 mer
                                        (SEQ ID NO: 8)
5'-tctagattatcatttacccggagacagagagaggctcttctgcgtgt

agtg-3'

muIgG2aCH2: 58mer
                                        (SEQ ID NO: 9)
5'-cctccatgcaaatgcccagcacctaacctcttgggtggatcatccgt

cttcatcttcc-3'

mIgG2a-5scc: 47mer
                                       (SEQ ID NO: 10)
5'-gaagatctcgagcccagaggtcccacaatcaagccctctcctcc

a-3'

mIgG2a3S: 48mer
                                       (SEQ ID NO: 11)
5'-gtttctagattatcatttacccggagtccgagagaagctcttagtcg

t-3'
```

PCR reactions were performed using a C1000 thermal cycler (BioRad, Hercules CA) or an Eppendorf thermal cycler (ThermoFisher Scientific, Houston TX). Reactions included an initial denaturation step at 95° C. for 2 minutes, followed by 34 cycles with a 94° C., 30 sec denaturation, 50° C., 30 sec annealing, and 72° C., 1 minute extension step, followed by a final 4 minute extension at 72° C. Once wild type tails were isolated, the fragments were TOPO cloned into pCR2.1 vectors, DNA prepared using the QIAGEN spin plasmid miniprep kits according to manufacturer's instructions and clones sequenced using ABI Dye Terminator v3.1 sequencing reactions according to manufacturer's instructions.

DNA from the correct clones were used as templates in overlap extension PCRs to introduce mutations at the desired positions in the coding sequence for mouse IgG2a or human -IgG1. PCR reactions were set up using the full length wild type clones as template (1 microliter), 50 pmol 5' and 3' primers to PCR each portion of the -Fc domain up to and including the desired mutation site from each direction, and PCR hi fidelity Supermix (Invitrogen, Carlsbad CA), in 50 microliter reaction volumes using a short amplification cycle. As an example of the overlapping PCR mutagenesis, the primer combination used to introduce the P331S mutation into human -IgG1, was as follows:

A 5' subfragment was amplified using the full-length wild type clone as template, and the 5' primer was hIgG1-5scc: 5'-agatctcgagcccaaatcttctgacaaaactcacacatgtccaccgtgt-3' (SEQ ID NO:12), while the 3' primer was P331AS: 5'-gttttctcgatggaggctgggagggctttgttggagacc-3' (SEQ ID NO:13). A 3' subfragments was amplified using the full-length wild type clone as template and the 5' primer was P331S: 5'aaggtctccaacaaagccctcccagcctccatcgagaaaaca atctcc-3' (SEQ ID NO:14), while the 3' primer was mahIgG1S: 5'-tctagattatcatttacccggagacagagagaggctcttctg cgtgtagtg-3' (SEQ ID NO:15).

Once subfragments were amplified and isolated by agarose gel electrophoresis, they were purified by QIAquick gel purification columns and eluted in 30 microliters EB buffer according to manufacturer's instructions. Two rounds of PCR were then performed with the two subfragments as overlapping templates in new reactions. The cycler was paused and the 5' (hIgG1-5scc, see above) and 3' (mahIgG1S, see above) flanking primers were added to the reactions (50 pmol each). PCR amplifications were then carried out for 34 cycles at the conditions described for the wild type molecules above. Full length fragments were isolated by gel electrophoresis, and TOPO cloned into pCR2.1 vectors for sequence analysis. Fragments from clones with the correct sequence were then subcloned into expression vectors for creation of the different hybrid nuclease molecules described herein.

Example 4: Expression of RNAse-Ig (SEQ ID NO 124, 125, 126,127, 174 (Nucleotide) or 160, 161, 162,163, 175 (Amino Acid)), DNAse-Ig (SEQ ID NO: 118, 119,120,121,122,123, 186 (Nucleotide) or SEQ ID NO 154, 155, 156, 157, 158, 159, 187 (Amino Acid)), Multi-Subunit Ig Fusion Constructs (SEQ ID NO: 115, 116, 117, 172, 176, 178, 180 (Nucleotide) or SEQ ID NO 151 152, 153, 173, 177, 179, 181 (Amino Acid)), and H564 scFv-Ig Fusion Proteins in Stable CHO Cell Lines This example illustrates expression of the different -Ig fusion genes described herein in eukaryotic cell lines and characterization of the expressed fusion proteins by SDS-PAGE and by IgG sandwich ELISA.

The -Ig fusion gene fragments with correct sequence were inserted into the mammalian expression vector pDG, and DNA from positive clones was amplified using QIAGEN plasmid preparation kits (QIAGEN, Valencia, Calif.). The recombinant plasmid DNA (100 μg) was then linearized in a nonessential region by digestion with AscI, purified by phenol extraction, and resuspended in tissue culture media, Excell 302 (Catalog #14312-79P, JRH Biosciences, Lenexa, Kans./SAFC). Cells for transfection, CHO DG44 cells, were kept in logarithmic growth, and $10^7$ cells harvested for each transfection reaction. Linearized DNA was added to the CHO cells in a total volume of 0.8 ml for electroporation.

Stable production of the -Ig fusion protein was achieved by electroporation of a selectable, amplifiable plasmid, pDG, containing the RNase-Ig cDNA under the control of the CMV promoter, into Chinese Hamster Ovary (CHO) cells. The pDG vector is a modified version of pcDNA3 encoding the DHFR selectable marker with an attenuated promoter to increase selection pressure for the plasmid. Plasmid DNA was prepared using Qiagen maxiprep kits, and purified plasmid was linearized at a unique AscI site prior to phenol extraction and ethanol precipitation. Salmon sperm DNA (Sigma-Aldrich, St. Louis, Mo.) was added as carrier DNA, and 100 μg each of plasmid and carrier DNA was used to transfect $10^7$ CHO DG44 cells by electroporation. Cells were grown to logarithmic phase in Excell 302 media (JRH Biosciences) containing glutamine (4 mM), pyruvate, recombinant insulin, penicillin-streptomycin, and 2×DMEM nonessential amino acids (all from Life Technologies, Gaithersburg, Md.), hereafter referred to as "Excell 302 complete" media. Media for untransfected cells also contained HT (diluted from a 100× solution of hypoxanthine and thymidine) (Invitrogen/Life Technologies). Media for transfections under selection contained varying levels of methotrexate (Sigma-Aldrich) as selective agent, ranging from 50 nM to 1 μM. Electroporations were performed at 280 volts, 950 microFarads. Transfected cells were allowed to recover overnight in non-selective media prior to selective plating in 96 well flat bottom plates (Costar) at varying serial dilutions ranging from 125 cells/well to 2000 cells/well. Culture media for cell cloning was Excell 302 complete, containing 50 nM methotrexate. Once clonal outgrowth was sufficient, serial dilutions of culture supernatants from master wells were screened for expression of -Ig fusion protein by use of an -IgG sandwich ELISA. Briefly, NUNC immulon II plates were coated overnight at 4° C. with 7.5 microgram/ml F(ab'2) goat anti-mouse IgG (KPL Labs, Gaithersburg, MD) in PBS. Plates were blocked in PBS/3% BSA, and serial dilutions of culture supernatants incubated at room temperature for 2-3 hours. Plates were washed three times in PBS/0.05% Tween 20, and incubated with horseradish peroxidase conjugated F(ab'2) goat anti-mouse IgG2a (Southern Biotechnologies) and goat anti-mouse IgG (KPL) mixed together, each at 1:3500 in PBS/1.0% BSA, for 1-2 hours at room temperature. Plates were washed four times in PBS/0.05% Tween 20, and binding detected with SureBlue Reserve, TMB substrate (KPL Labs, Gaithersburg, MD). Reactions were stopped by addition of equal volume of 1N HCl, and plates read at 450 nM on a Spectramax Pro plate reader (Microdevices, Sunnyvale CA). The clones with the highest production of the fusion protein were expanded into T25 and then T75 flasks to provide adequate numbers of cells for freezing and for scaling up production of the fusion protein. Production levels were further increased in cultures from the four best clones by progressive amplification in methotrexate containing culture media. At each successive passage of cells, the Excell 302 complete media contained an increased concentration of methotrexate, such that only the cells that amplified the DHFR plasmid could survive. The production level of the top four unamplified master wells from the RNaseIg CHO transfectants ranged from 30-50 micrograms/ml culture. The amplified cultures are currently being assayed to determine production levels.

Supernatants were collected from CHO cells expressing the RNase-Ig, filtered through 0.2 μm PES express filters (Nalgene, Rochester, N.Y.) and were passed over a Protein A-agarose (IPA 300 crosslinked agarose) column (Repligen, Needham, Mass.). The column was washed with column wash buffer (90 mM Tris-Base, 150 mM NaCl, 0.05% sodium azide, pH 8.7), and bound protein was eluted using 0.1 M citrate buffer, pH 3.0. Fractions were collected and protein concentration was determined at 280 nM using a Nanodrop (Wilmington DE) microsample spectrophotometer, and blank determination using 0.1 M citrate buffer, pH 3.0. Fractions containing fusion protein were pooled, and buffer exchange performed by serial spins in PBS using centricon concentrators followed by filtration through 0.2 μm filter devices, to reduce the possibility of endotoxin contamination. An extinction coefficient of 1.05 was determined using the protein analysis tools in the Vector Nti Version 10.0 Software package (Informax, North Bethesda, Md.) and the predicted cleavage site from the online ExPasy protein analysis tools.

Example 5: SDS-PAGE Analysis of RNaseIg Fusion Protein

Purified RNase-Ig (SEQ ID NO:115) was analyzed by electrophoresis on SDS-Polyacrylamide gels. Fusion protein samples were boiled in SDS sample buffer with and without reduction of disulfide bonds and applied to SDS 10% Tris-BIS gels (Catalog #NP0301, Novex, Carlsbad, Calif.). Five micrograms of each purified protein was loaded on the gels. The proteins were visualized after electrophoresis by Coomassie Blue staining (Pierce Gel Code Blue Stain Reagent, Catalog #24590, Pierce, Rockford, Ill.), and destaining in distilled water. Molecular weight markers were included on the same gel (Kaleidoscope Prestained Standards, Catalog #161-0324, Bio-Rad, Hercules, Calif.). Other samples were run as follows: Rnase-Ig fusion protein in the sampling buffer (62.5 mM Tris-HCl, pH6.8, 2% SDS, 10% glycerol, 0.01% Bromophenol blue) with and without 5% 2-mercaptoethanol) was loaded onto the 4-12% pre-cast gel (Bio-RAD). The gel was running at 100 volts until the dye ran off the gel. The gel was stained in the GelCode Blue (Thermo scientific) at room temperature overnight and then washed with water.

Figure 3:
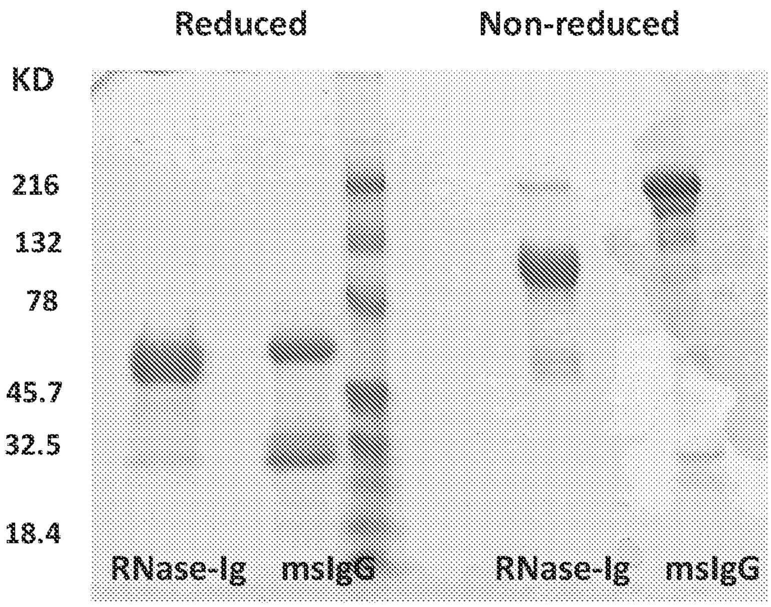
FIG. 3 shows the SDS-PAGE gel analysis of mRNase-mIgG2a-c under both reducing and non-reducing conditions.

FIG. 3 shows the RNase-Ig fusion protein compared to mouse IgG. Rnase-Ig was purified from supernatant transfected CHO cells by binding and elution from Protein A sepharose. The SDS-PAGE gel shows that Rnase-Ig is approximately 50 kDa when reduced and approximately 110 kDa when non-reduced.

Example 6: Detection of RNase-Ig in Mouse Sera

SRED Assay

The 2% agarose gel was prepared with distilled water. Poly-IC (Sigma) was dissolved in distilled water at 3 mg/ml and the gel plate was prepared as follows: 1.5 ml reaction buffer (0.2M Tris-HCl pH 7.0, 40 mM EDTA and 0.1 mg/ml ethidium bromide), 1 ml Poly-IC and 0.5 ml water were place in the tube and maintained at 50° C. for 5 min. 3 ml of the agarose (kept at 50° C.) was added to the tube. The mixture was immediately poured onto a glass plate. Sampling wells were punched in the gel. 2 μl of each serum sample was loaded into wells and the gel was incubated at 37° C. for 4 hours in the moist chamber. Then the gel was incubated in a buffer (20 mM sodium acetate pH5.2, 20 mg/ml ethidium bromide) on ice for 30 min. and read under UV.

Figure 4:
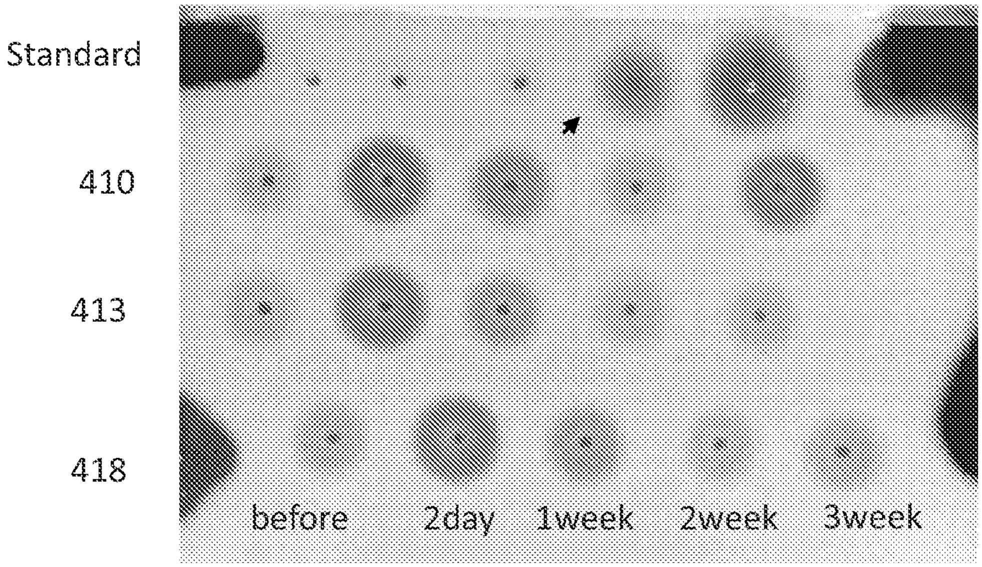
FIG. 4 shows gel immunoprecipitation analysis of mRNasemIg2a-c.

FIG. 4 shows RNase activity from three mice (410, 413, and 418) after intravenous injection of Rnase-Ig fusion protein (SEQ ID NO:150) (purified in this experiment from supernatant of transfected COS cells by binding and elution from protein A sepharose). A standard was used in the top row. Notice a second injection for mouse 410 (see arrow) after 2 weeks. 20 serum from each of three mice was loaded on 1% agarose gel containing 0.5 mg/ml poly-C. The gel was incubated for 4 hours in a moist chamber at 37° C., and then immersed in a buffer containing 20 mM sodium acetate and 20 ug/ml ethidium bromide for 30 min. The RNase activity is reflected by the size and intensity around the central well. This data shows that the RNase-Ig fusion protein has an extended half-life in mouse serum.

Example 7: Use of an Anti-RNA ELISA to Measure RNA Specific Antibodies in Mouse Sera A 96-well plate (Nunc, Thermal fisher scientific) was coated with 50 μg/ml of Poly-L-Lysine (Sigma) overnight. After washing five times with PBS containing 0.05% Tween, the plate was coated with 10 μg/ml of yeast RNA in PBS at 4° C. overnight. After washing five times, the plate was blocked with PBS containing 1% BSA at room temperature for 2 hours. Serum samples at 1:50 dilution were added to the plate and incubated at 4° C. overnight. Hybridoma H564 (anti-RNA) culture medium was used as standard, using two-fold serial dilutions starting at 1:300. Detection antibody was anti-mouse IgG conjugated with alkaline phosphatase (Jackson Lab), and was added to the plate at 1:5000 for 1 hour at room temperature. Phosphatase substrate (Sigma) was dissolved in developing buffer (ThermoFisher Scientific) and added to the plate at 50 μl/well. Samples were read at 405 nm using a Spectramax Plus plate reader (Microdevices, Sunnyvale, CA).

Figure 5:
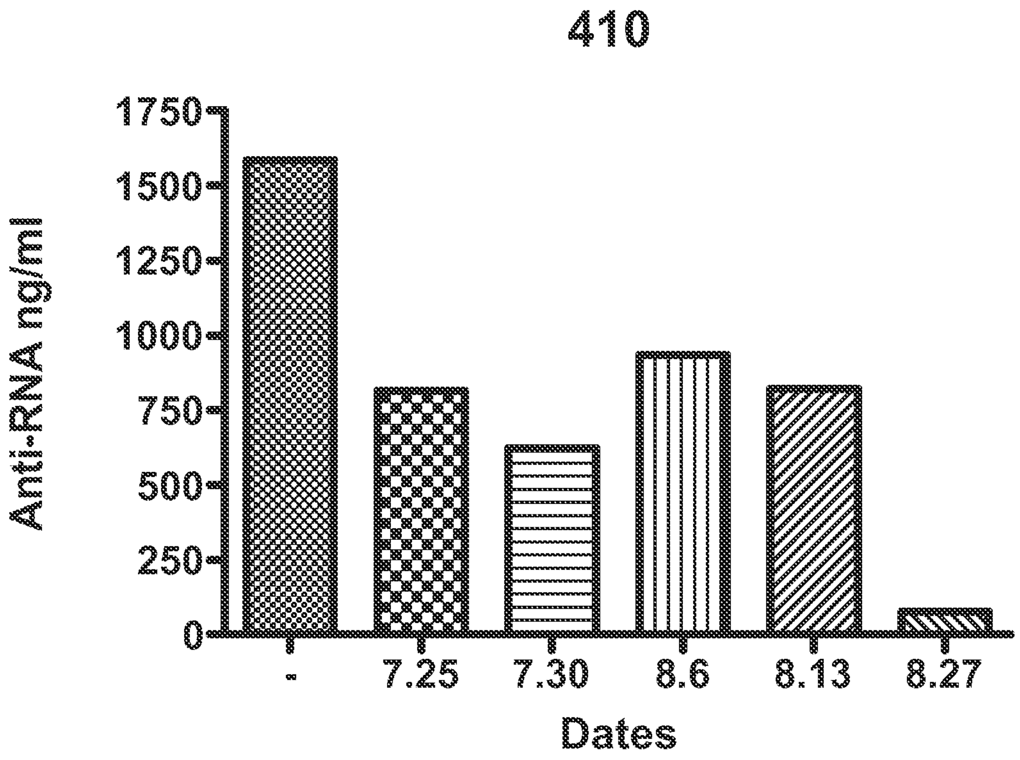
FIG. 5 shows an anti-RNA antibody ELISA titer before and after intravenous injection of RNase-Ig hybrid nuclease molecule from mouse 410. The data show that injection of RNase-Ig caused a reduction in titer of anti-RNA antibody that persisted for over 3 weeks.

FIG. 5 shows the results from the anti-RNA Antibody ELISA titer before and after intravenous injection of RNase-Ig fusion protein (SEQ ID NO:150) from mouse 410. The pre-coated Poly-L-lysine (50 m/ml) plate was coated with 10 ug/ml yeast RNA. Serum (1:50) was loaded on the plate and incubated overnight at 4° C. Detection antibody was anti-mouse IgG-alkaline phosphatase (Jackson Labs) at 1:5000 for 1 hour at room temperature, and then phosphatase substrate was added and read at 405 nm. The data show that injection of Rnase-Ig caused a reduction in titer of anti-RNA antibody that persisted for over 3 weeks.

Figure 6:
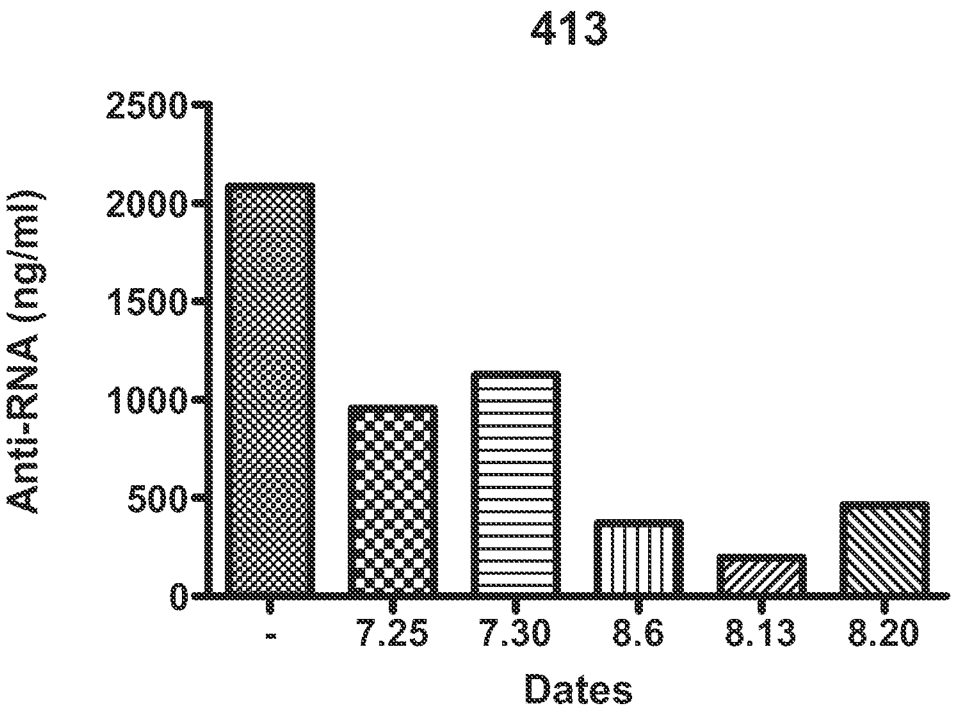
FIG. 6 shows that RNase-Ig addition abolished the induction of interferon-α from human peripheral blood mononuclear cells stimulated using immune complexes formed with serum from an SLE patient (J11) plus nuclear extract (NE). Titer of anti-RNA antibody was reduced after injection of RNase-Ig.

FIG. 6 shows the results from the anti-RNA Antibody ELISA titer before and after injection of RNase-Ig fusion protein (SEQ ID NO:150) within three weeks from mouse 413. The experiment was done as described for mouse 410. Titer of anti-RNA antibody was reduced after injection of Rnase-Ig.

Figure 7:
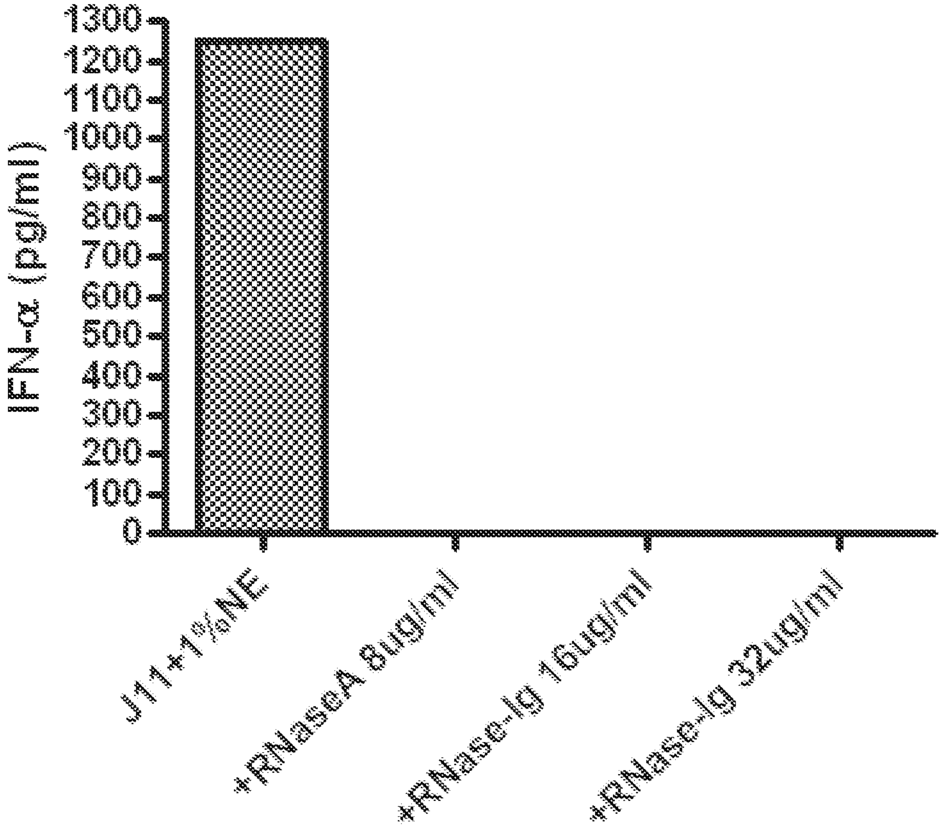
FIG. 7 shows that RNase-Ig addition abolished the induction of interferon-α from human peripheral blood mononuclear cells stimulated using immune complexes formed with serum from an SLE patient (J11) plus nuclear extract.

Example 8: IFN-Alpha Production by Human PBMCs is Inhibited by RNaseIg Addition to Cultures In Vitro RNase-Ig (SEQ ID NO:150) addition abolished the induction of interferon-α from human peripheral blood mononuclear cells stimulated using immune complexes formed with serum from an SLE patient (J11) plus nuclear extract (NE). Briefly, ELISA plates were coated with 50 microliters 1:2500 capture antibody (anti-IFN alpha, PBL 21112-1, Piscataway, NJ), and incubated overnight at 4° C. Plates were washed with PBS/0.05% Tween 20, blocked in PBS/1% BSA for 2 hours at room temperature, washed with PBS/0.05% Tween-20, and incubated with standard dilutions of IFN-alpha, or with serial dilutions of serum samples, and incubated 2 hours at room temperature. Plates were washed and incubated with 1:2000 detection antibody (PBL 31101-2, Piscataway, NJ) in PBS/1% BSA. Plates were washed in PBS/0.05% Tween-20, and incubated with 50 microliters donkey anti-rabbit HRP (Jackson Immunoresearch, Westgrove, PA) at 1:12,000 in PBS/1% BSA. Plates were washed five times prior to addition of TMB substrate. Reactions were stopped by addition of ½ volume 2N H2SO4, and samples read at 450 nm on a Spectramax Pro plate reader (MicroDevices, Sunnyvale, CA). The results are shown in FIG. 7, which shows RNase-Ig addition abolished the induction of interferon-α from human peripheral blood mononuclear cells stimulated using immune complexes formed with serum from an SLE patient (J11) plus nuclear extract.

Example 9: Phenotype of TLR7.1×RNaseA Double Transgenic Mice

Figure 8:
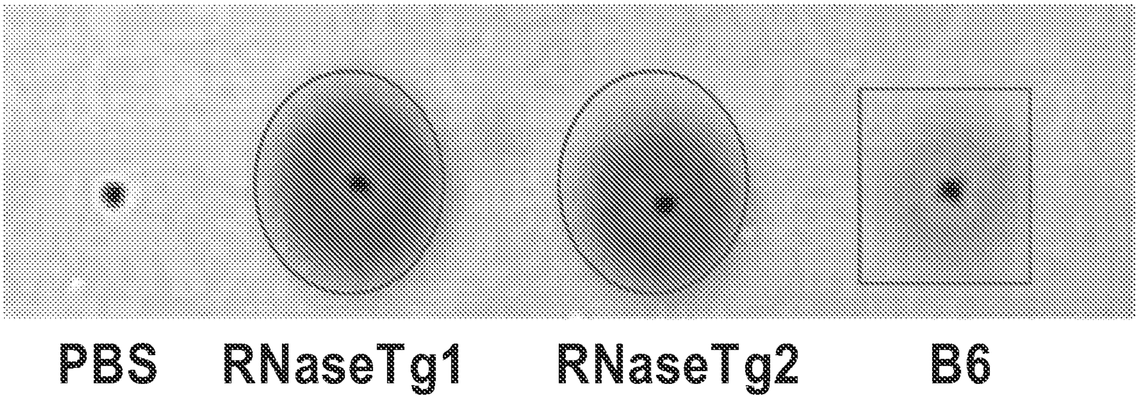
FIG. 8 shows single radial enzyme diffusion (SRED) analysis of serum from two RNase transgenic (Tg) mice compared to a normal B6 mouse.
Figure 9:
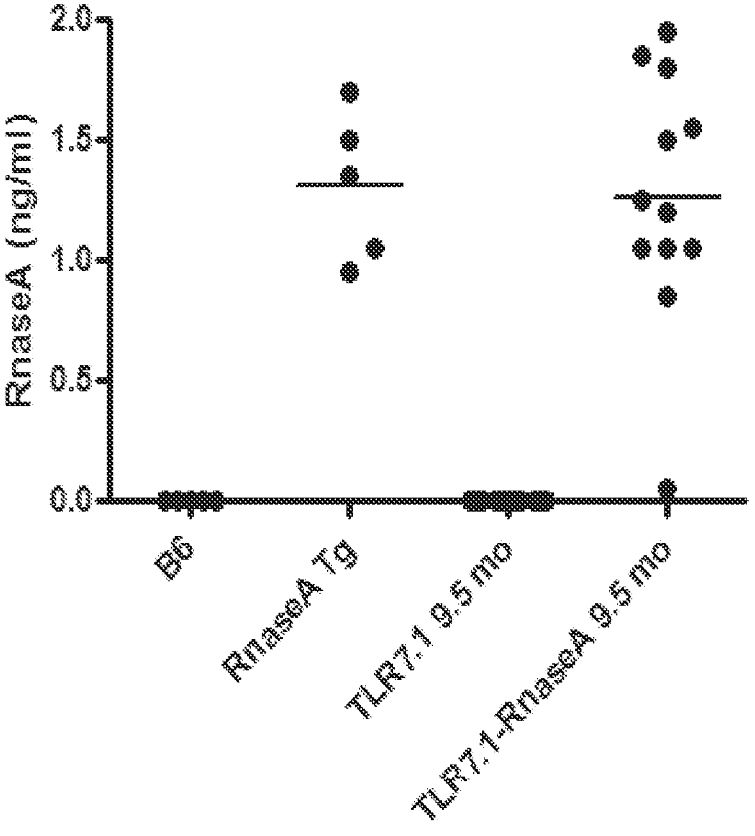
FIG. 9 shows the concentration of RNaseA in Tg and double Tg (DTg) mice measured by ELISA. Each dot represents the concentration measured in an individual mouse.

We have created mice that overexpress RNaseA (RNase Tg). This nuclease is expressed at high levels in RNase Tg mice (see FIG. 8). We have developed both a single radial diffusion (SRED) method (left panel) and a much more quantitative ELISA to quantify RNase in the serum (see FIG. 9). We crossed RNaseA Tg with TLR7.1 Tg mice to create the double Tg (DTg). TLR7.1 mice have 8-16 copies of TLR7 and develop a very aggressive, rapidly progressive lupus-like disease and start to die at 3 mo of age with a median survival of 6 mo. In a preliminary analysis, we bled DTg and littermate controls at 3 mo of age to see whether the DTg mice exhibited signs of improvement. As shown in FIG. 8, DTg mice had very high levels of RNase in their serum (equivalent to >13 U/ml RNase based on our standard with specific activity of 993 U/mg). RNaseA concentration in Tg and DTg mice was also measured by ELISA assay as shown in FIG. 9. The RNase A Tg and TLR7.1×RNaseA Dtg mice have RNase A serum concentrations between 1-2 ng/ml.

Detailed Method for Rnase a ELISA (Example 9, FIG. 9)

1. Coat plate with anti-RnaseA Abcam Ab(ab6610): 2.5-10 ug/ml 0/N in 4 C.
2. Wash plate 3 times with 0.05% Tween/1×PBS
3. Block with 1% BSA in PBS for at least 1 hour
4. Wash plate 3 times with 0.05% Tween/1×PBS
5. Load samples. Sample dilutions at 1:50
6. Incubate Rm Temp for 2 hours
7. Wash plate 3 times with 0.05% Tween/1×PBS
8. Prepare dilution of biotin labeled Anti Rnase Ab at dilution of 1:4500 (2.2 ug/ml). Leave RT for 1 hour (Rockland 200-4688: 10 mg/ml).
9. Wash plate 3 times
10. Dilute StrepAV HRP (Biolegend 405210) 1:2500. Cover with foil and leave at RT for 25-30 min.
11. Wash 6 times, let the liquid sit in wells for at least 30 seconds in between washes.
12. Add BD OptEIA substrate A+B 1:1. Wait until color changes 5-10 min max. Don't let the top well standard go over 1.0. Add 80 ul. (CatNos: 51-2606KC; ReagentA, 51-2607KC; ReagentB)
13. Add 40 ul of 1M sulfuric acid to stop reaction Product/Reagent Information:

RNaseA Ab: ab6610 (90 mg/ml)
ELISA buffer: 1% BSA in PBS

ELISA wash buffer: 0.05% Tween/1×PBS
Anti RNaseA biotin conjugated Ab: Rockland: 200-4688 (10 mg/ml)
Strep AV HRP: Biolegend 405210
BD OptEIA reagent A and B: 51-2606KC and 51-2607KC

Example 10: Survival Curves for TLR7.1 Transgenic Mouse Strains

Figure 10:
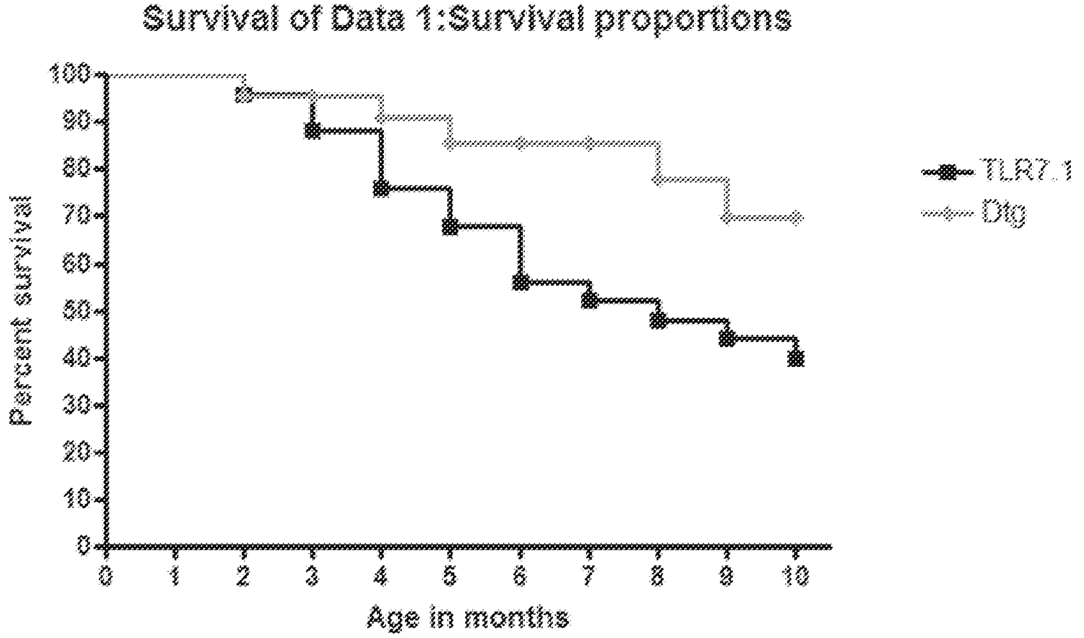
FIG. 10 shows survival of TLR7.1 Tg versus TLR7.1× RNaseA DTg mice

There was a highly significant difference between the DTg and the TLR7.1 littermate controls in survival. As shown in FIG. 10, at 10 months, 61% of TLR7.1 mice had died, whereas 31% of DTg mice had died. This data shows that overexpression of RNaseA exerted a strong therapeutic effect. The reasons why TLR7.1 mice die prematurely is not entirely clear, although severe anemia, thrombocytopenia, and glomerulonephritis could play a part. To determine whether red cell and platelet counts were positively impacted by RNaseA expression in the DTg mice, we performed blood counts but found no differences between the TLR7.1 and DTg mice. In contrast, there was a significant improvement in kidney histopathology in the DTg mice. We observed decreased deposition of IgG and C3 in DTg mice. PAS staining, which reflects inflammation in the mesangium was also reduced in DTg mice compared to TLR7.1 littermate controls. When we have now compared macrophage infiltration of the kidneys using anti-MAC-2 (galectin3) antibody (Lyoda et al. Nephrol Dial Transplat 22: 3451, 2007), there were many fewer mac-2 positive cells in the glomeruli of the DTg mice. The results of counting 20 glomeruli per mouse in 5 mice in each group revealed mean+/−SE of 3.8+/−1.1 and 1.4+/−0.2 for single versus DTg respectively, p=0.05. In addition, we quantified glomerular tuft size and observed a significant reduction in glomerular tuft size in the DTg mice (179+/−41 versus 128+/−16.8 um2 in single versus DTg respectively, p=0.037). In summary, TLR7.1×RNaseA DTg mice survive longer than their single Tg TLR7.1 littermates and have less inflammation and injury in their kidneys.

Example 11: Analysis of IRGs in Spleens of TLR Tg Mice

Figure 11:
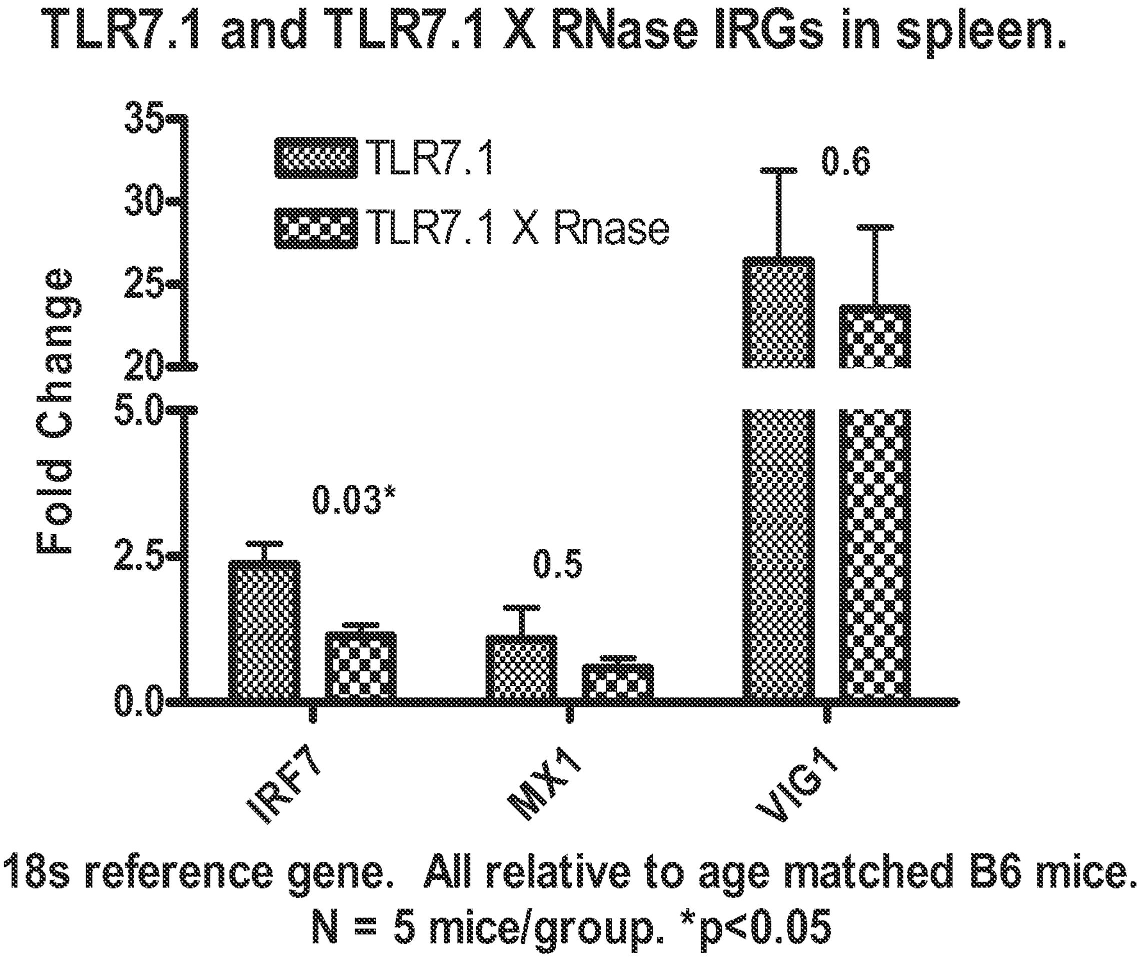
FIG. 11 shows quantitative PCR of IRGs in spleens of Tg versus DTg mice.

Analysis of interferon response genes (IRGs) in the spleens of TLR7.1 Tg and TLR7.1×RNaseA DTg mice showed that expression of the IRF7 gene was significantly lower in the DTg mice (p=0.03). Some other IRGs including MX1 and VIG1 were lower in DTg mice compared to Tg mice, but the differences were not significant. See FIG. 11. Quantitative PCR was performed as follows: total RNA was isolated from mouse spleens using the RNeasy mini kit (Qiagen, Valencia, CA, USA), DNase treated using Turbo DNA-free (Applied Biosystems, Foster City, CA, USA) and first-strand cDNA was produced with the RNA-to-cDNA kit (Applied Biosystems) using random primers. The 260/280 was between 1.7 and 2.0 for isolated RNA measured with a NanoDrop (Thermo Scientific, Waltham, MA, USA). cDNA was diluted to an equivalent of 1 ng/ul total RNA and 8 ul were used per reaction. Primers for the reference gene (18s) and genes of interest (GOI) were synthesized (IDT, Coralville, Iowa, USA) and diluted to the appropriate concentrations for qPCR using molecular grade water. BLAST results of the primers show specific sequence homology only to the reference gene or GOI. Reactions in duplicate (20 ul) were run on an ABI Fast 7500 system using a 1:1 mix of template and primer to SensiMix SYBR low-ROX master mix (Bioline, London, UK). Relative quantification was calculated using the $2^{-ddCT}$ method with age matched wild type B6 mice as baseline to determine fold changes for each GOI. The dissociation curves for the reactions show a single melt peak for each gene. The standard curve showed similar amplification efficiencies for each gene and that template concentrations were within the linear dynamic range for each of primer set.

Example 12: Structures for Generating Hybrid Nuclease Molecules

Hybrid nuclease molecules were designed to incorporate desired structures and functional activity of single enzyme or multi-enzyme structures as modular cassettes with compatible restriction enzyme sites for shuttling and domain exchange. The schematic structure of different embodiments of hybrid nuclease molecules is illustrated in FIG. 12. Primers are shown in Table 1. The nucleotide and amino acid sequences of representative hybrid nuclease molecules are shown in Table 2.

General Approach for Generation of Hybrid Nuclease Molecules

Human cDNAs were isolated from human pancreas RNA (Ambion) or human PBMC RNA from normal human peripheral blood lymphocytes (approximately 5×10 e6) using QIAgen RNAeasy kits (Valencia, CA) and QIAshredder kits to homogenize cell lysates (Qiagen, Valencia, CA). Human PBMCs were isolated from heparinized human blood diluted 1:1 in D-PBS and layered over LSM Lymphocyte Separation Medium (MP Biomedicals, Irvine, CA) Ficoll gradients.

Mouse spleen RNA was isolated using QIAgen RNAeasy kits (Valencia, CA) from approximately 5×10 e6 splenocytes. Cells were pelleted by centrifugation from the culture medium, and 5×10 e6 cells were used to prepare RNA. RNA was isolated from the cells using the QIAGEN RNAeasy kit (Valencia, Calif.) total RNA isolation kit and QIAGEN QIAshredder according to the manufacturer's instructions accompanying the kit. One to two microgram (1-2 μg) of total RNA was used as template to prepare cDNA by reverse transcription. The RNA, 300 ng random primers, and 500 ng Oligo dT (12-18), and 1 μl 25 mM dNTPs were combined and denatured at 80° C. for 5 minutes prior to addition of enzyme. Superscript III reverse transcriptase (Invitrogen, Life Technologies) was added to the RNA plus primer mixture in a total volume of 25 μl in the presence of 5 times second strand buffer and 0.1 M DTT provided with the enzyme. The reverse transcription reaction was allowed to proceed at 50° C. for one hour.

Between 10-100 ng cDNA was used in PCR amplification reactions using primers specific for the nuclease gene of interest (RNaseA, RNase1, DNase1, Trex1, DNase1L3, etc.) For initial cloning reactions, primers were designed to isolate the full length cDNA or truncation products encoding the gene of interest. Full length or shortened PCR fragments were isolated by agarose gel electrophoresis, and purified using Qiagen QIAquick columns to remove nucleotides, primers, and unwanted amplified products. Purified fragments were cloned into pCR2.1 TOPO cloning vectors (Invitrogen, Carlsbad, CA) and transformed into TOP10 competent bacteria. Isolated colonies were picked into Luria Broth media containing 50 ug/ml carbenicillin, and grown overnight to isolate plasmids. TOPO clones were screened for inserts of the correct size by digestion with EcoRI (NEB, Ipswich, MA) restriction enzyme and agarose gel electrophoresis of digested fragments. DNA sequence analysis of positive clones was performed with ABI Ready Reaction Mix v 3.1 and analyzed using an ABI 3730 XL DNA sequencer. Once correct clones were obtained, further sequence modifications were designed and PCR reactions performed to generate the desired alleles or expression cassettes. Truncation products and alleles were generated by PCR mutagenesis using overlapping primers for introduction of mutations at specific positions in the genes. Linkers were synthesized by overlapping PCR using internal overlapping primers and successive rounds of PCR to attach additional sequence to each terminus. Hybrid nuclease molecules were assembled as a string of several interchangeable cassettes. Molecules of the preferred embodiment contain a fixed leader peptide, a nuclease cassette, an optional cassette encoding a choice of several different polypeptide linkers, an -Ig Fc domain cassette with either a STOP codon or a linker at the carboxyl end of the CH3 domain, and for resolvICase type molecules, a second linker cassette, followed by a second nuclease cassette. FIG. 12 illustrate the cassette type structure of these hybrid nuclease molecules and examples of potential sequences inserted at each position. Once hybrid nuclease molecules were assembled, they were transferred to a mammalian expression plasmid pDG appropriate for transient expression in COS7 or other cells and stable expression in CHO DG44 cells using selection for DHFR with methotrexate.

Transient Expression of Hybrid Nuclease Molecules

COS-7 cells were transiently transfected with expression vector pDG containing hybrid nuclease molecule gene inserts. The day before transfection, cells were seeded at 4×10 e5 cells per 60 mm dish in 4 ml DMEM (ThermoFisher/Mediatech cell gro)+10% FBS tissue culture media. DMEM basal media was supplemented with 4.5 g/L glucose, sodium pyruvate, L-glutamine 4 mM, and non-essential amino acids. Fetal bovine serum (Hyclone, Logan, UT ThermoFisher Scientific) was added to media at 10% final volume. Cells were incubated at 37° C., 5% CO2 overnight and were approximately 40-80% confluent on the day of transfection. Plasmid DNA was prepared using Qiagen (Valencia, CA) QIAprep miniprep kits according to manufacturer's instructions, and eluted in 50 ul EB buffer. DNA concentrations were measured using a Nanodrop 1000 (Thermo Fisher Scientific, Wilmington DE) spectrophotometer. Plasmid DNA was transfected using Polyfect (Qiagen, Valencia, CA) transfection reagent according to manufacturer's instructions, using 2.5 ug plasmid DNA per 60 mm dish and 15 ul polyfect reagent in 150 ul serum free DMEM transfection cocktails. After complex formation, reactions were diluted into 1 ml cell growth media containing serum and all supplements, and added drop-wise to the plates containing 3 ml fresh DMEM complete culture media. Transient transfections were incubated for 48-72 hours prior to harvesting culture supernatants for further analysis.

Generation of Stable CHO DG44 Transfectants Expressing the Hybrid Nuclease Molecules of Interest Stable production of the hybrid nuclease molecules was achieved by electroporation of a selectable, amplifiable plasmid, pDG, containing the nuclease-Ig cDNA under the control of the CMV promoter, into Chinese Hamster Ovary (CHO) cells. The pDG vector is a modified version of pcDNA3 encoding the DHFR selectable marker with an attenuated promoter to increase selection pressure for the plasmid. Plasmid DNA was prepared using Qiagen maxiprep kits, and purified plasmid was linearized at a unique AscI site prior to phenol extraction and ethanol precipitation. Salmon sperm DNA (Sigma-Aldrich, St. Louis, Mo.) was added as carrier DNA, and 100 μg each of plasmid and carrier DNA was used to transfect $10^7$ CHO DG44 cells by electroporation. Cells were grown to logarithmic phase in Excell 302 media (JRH Biosciences) containing glutamine (4 mM), pyruvate, recombinant insulin, penicillin-streptomycin, and 2×DMEM nonessential amino acids (all from Life Technologies, Gaithersburg, Md.), hereafter referred to as "Excell 302 complete" media. Media for untransfected cells also contained HT (diluted from a 100× solution of hypoxanthine and thymidine) (Invitrogen/Life Technologies). Media for transfections under selection contained varying levels of methotrexate (Sigma-Aldrich) as selective agent, ranging from 50 nM to 1 μM. Electroporations were performed at 280 volts, 950 microFarads. Transfected cells were allowed to recover overnight in non-selective media prior to selective plating in 96 well flat bottom plates (Costar) at varying serial dilutions ranging from 125 cells/well to 2000 cells/well. Culture media for cell cloning was Excell 302 complete, containing 50 nM methotrexate. Once clonal outgrowth was sufficient, serial dilutions of culture supernatants from master wells were screened for expression of hybrid nuclease molecules by use of an -IgG sandwich ELISA. Briefly, NUNC immulon II plates were coated overnight at 4° C. with 7.5 microgram/ml F(ab'2) goat anti-mouse IgG (KPL Labs, Gaithersburg, MD) or 2 ug/ml goat anti-human or anti-mouse IgG (Jackson Immunoresearch, West Grove PA) in PBS. Plates were blocked in PBS/2-3% BSA, and serial dilutions of culture supernatants incubated at room temperature for 2-3 hours. Plates were washed three times in PBS/0.05% Tween 20, and incubated with horseradish peroxidase conjugated F(ab'2) goat anti-mouse IgG2a (Southern Biotechnologies) and goat anti-mouse IgG (KPL) mixed together, each at 1:3500 in PBS/1.0% BSA, or in horseradish peroxidase conjugated F(ab')2 goat anti-human IgG1 (Jackson Immunoresearch, West Grove, PA) at 1:2500 for 1-2 hours at room temperature. Plates were washed four times in PBS/0.05% Tween 20, and binding detected with SureBlue Reserve, TMB substrate (KPL Labs, Gaithersburg, MD). Reactions were stopped by addition of equal volume of 1N HCl, and plates read at 450 nM on a Spectramax Pro plate reader (Microdevices, Sunnyvale CA). The clones with the highest production of the hybrid nuclease molecule were expanded into T25 and then T75 flasks to provide adequate numbers of cells for freezing and for scaling up production of the fusion protein. Production levels were further increased in cultures from the four best clones by progressive amplification in methotrexate containing culture media. At each successive passage of cells, the Excell 302 complete media contained an increased concentration of methotrexate, such that only the cells that amplified the DHFR plasmid could survive.

Supernatants were collected from CHO cells expressing the hybrid nuclease molecule, filtered through 0.2 μm PES express filters (Nalgene, Rochester, N.Y.) and were passed over a Protein A-agarose (IPA 300 crosslinked agarose) column (Repligen, Needham, Mass.). The column was washed with column wash buffer (90 mM Tris-Base, 150 mM NaCl, 0.05% sodium azide, pH 8.7), and bound protein was eluted using 0.1 M citrate buffer, pH 3.0. Fractions were collected and protein concentration was determined at 280 nM using a Nanodrop (Wilmington DE) microsample spectrophotometer, and blank determination using 0.1 M citrate buffer, pH 3.0. Fractions containing hybrid nuclease molecules were pooled, and buffer exchange performed by serial spins in PBS using centricon concentrators followed by filtration through 0.2 μm filter devices, to reduce the possibility of endotoxin contamination.

Example 13: Analysis of Enzyme Kinetics for hRNase1-G88D-hIgG1 [SCCH-P238S-K322S-P331S]

The human RNase1 sequence was isolated from human pancreas RNA by random primed cDNA reverse transcription and PCR amplification as described in Example 12 for nuclease molecules. The following primers at 50 pmol per reaction were used from the primer set listed in the PCR primer table.

```
hRNase5'age:
                                   (SEQ ID NO: 16)
accggtaaggaatcccgggccaagaaattcc

hRNase3'bx:
                                   (SEQ ID NO: 17)
ctcgagatctgtagagtcctccacagaagcatcaaagtgg
```

The mutant form of human RNase G88D was created by using the following two primers in PCR and overlap PCR reactions to introduce a mutation at position 88 that alters the resistance of the enzyme to the cytoplasmic inhibitor.

```
hRNaseG88D-S:
                                   (SEQ ID NO: 18)
agactgccgcctgacaaacgactccaggtaccc

hRNAseG88D-AS:
                                   (SEQ ID NO: 19)
gggtacctggagtcgtttgtcaggcggcagtct
```

Both wild type and mutant versions of human RNase1 were isolated and cloned as described for hybrid nuclease molecules above. The wild type sequence was cloned using the first two primers listed above. Once the RNase fragments were TOPO cloned and sequenced, the AgeI-XhoI cassettes were transferred to the pDG expression vector already containing the human VK3LP insert and the human IgG1-WT cassette. Constructs were verified by digestion, and plasmid DNA prepared for transient transfections. Once function was confirmed from small scale transient transfections, the molecules were stably transfected into CHO DG44 in order to express sufficient quantities for further in vitro analysis. The wild type human RNase1 fusion protein is shown in Table 2, hVK3LP-hRNase1-WT-hIgG1-WT (SEQ ID NO:163). Similarly, wild type human RNase1 was also expressed as a fusion gene with a (gly4ser)4 (SEQ ID NO:125 or SEQ ID NO:161) or (gly4ser)5 (SEQ ID NO:126 or SEQ ID NO:162) linker domain inserted between the hRNase cassette and the hIgG1 Fc domain. The G88D mutant of human RNase1 was also expressed as a fusion gene designated hVK3LP-hRNase-G88D-hIgG1-WT (SEQ ID NO:124 or 160) or hIgG1-SCCH-P238S-K322S-P331S (SEQ ID NO:174 or 175), listed in Table 2.

Figure 13:
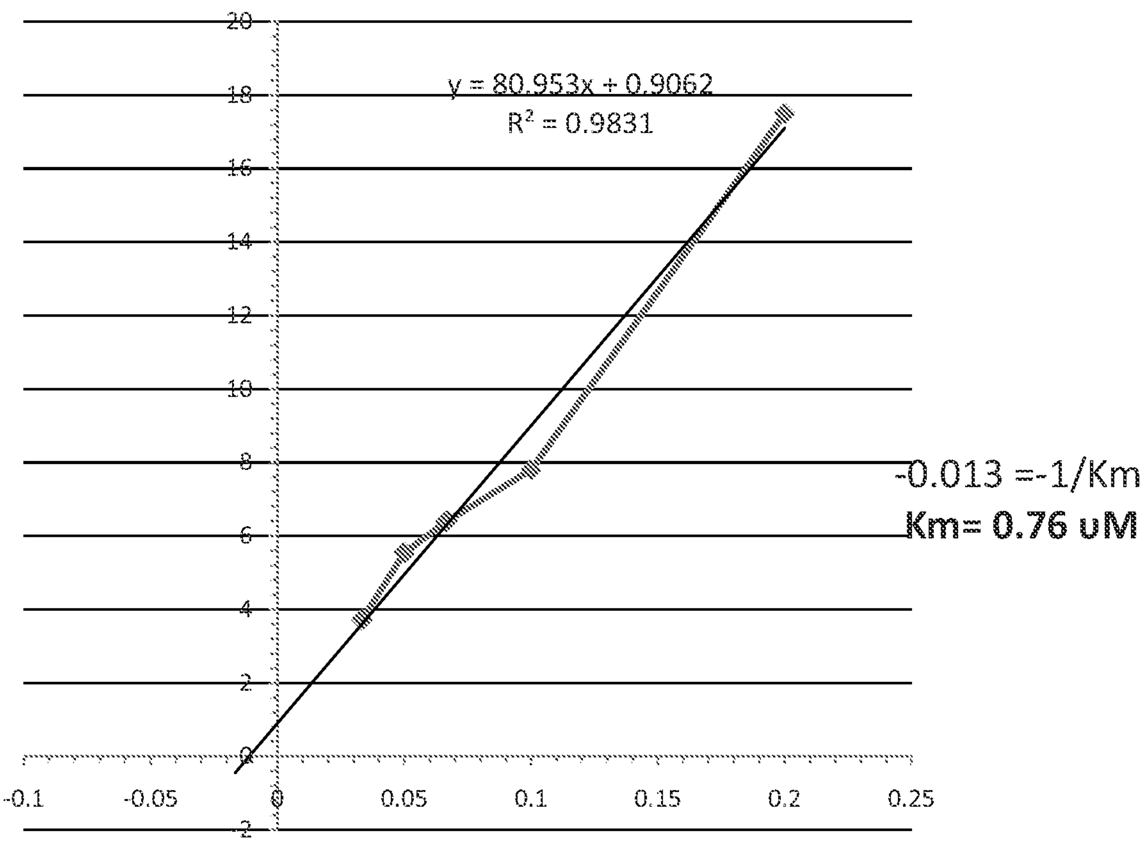
FIG. 13 shows the enzyme kinetics for hRNase1-G88D-hIgG1 SCCH-P238S-K322S-P331S hybrid nuclease molecules as measured using RNase Alert Substrate™.

The Lineweaver Burk plot of enzyme kinetics for the mutant hRNase1-G88D-hIgG1[SCCH-P238S-K322S-P331S] (SEQ ID NO:175) is shown in FIG. 13. To further define the functional characteristics of the bivalent RNase-Ig fusion protein, we performed preliminary determinations of the Michaelis constant, Km. Enzyme kinetics of purified human RNase1-Ig fusion protein was assayed using the RNase Alert Substrate (Ambion/IDT, San Diego, CA.) according to manufacturer's instructions and fluorescence assayed using a Spectramax M2 microplate reader (Molecular Devices, Sunnyvale, CA.). Fluorescence data was collected at 30 second intervals over the course of a 30 minute incubation, and analyzed using SoftmaxPro Software (Molecular Devices) Reaction rates at different substrate concentrations were measured and the data is shown in the form of a Lineweaver Burke plot.

Example 14: Analysis of Binding of hRNase1-hIgG to Human Monocytic Lines

Protein A purified hybrid nuclease molecules hRNase1-hIgG1-WT were incubated with human monocytic cell lines THP-1 or U937 to assess FcR mediated binding of the wild type or mutant Fc containing molecules. FIG. 14 shows the binding pattern of hRNase1-WT-hIgG1-WT (SEQ ID NO:161) to these two cell lines. Cells were incubated with 5 ug/ml purified fusion protein in PBS/2% FBS for 45 minutes on ice, washed three times in PBS/2% FBS, and incubated with FITC-goat anti-human IgG (Fc specific) (Jackson Immunoresearch, West Grove, PA) at 1:200 for 45 minutes on ice. Cells were washed two times in PBS/2% FBS and analyzed by flow cytometry using a FACS Canto (BD, Franklin Lakes, NJ) flow cytometer, and FlowJo software (TreeStar, Ashland, OR).

Example 15: IVIg Blocking of hRNase1-hIgG1 Binding to Human Monocytic Lines

Figure 15:
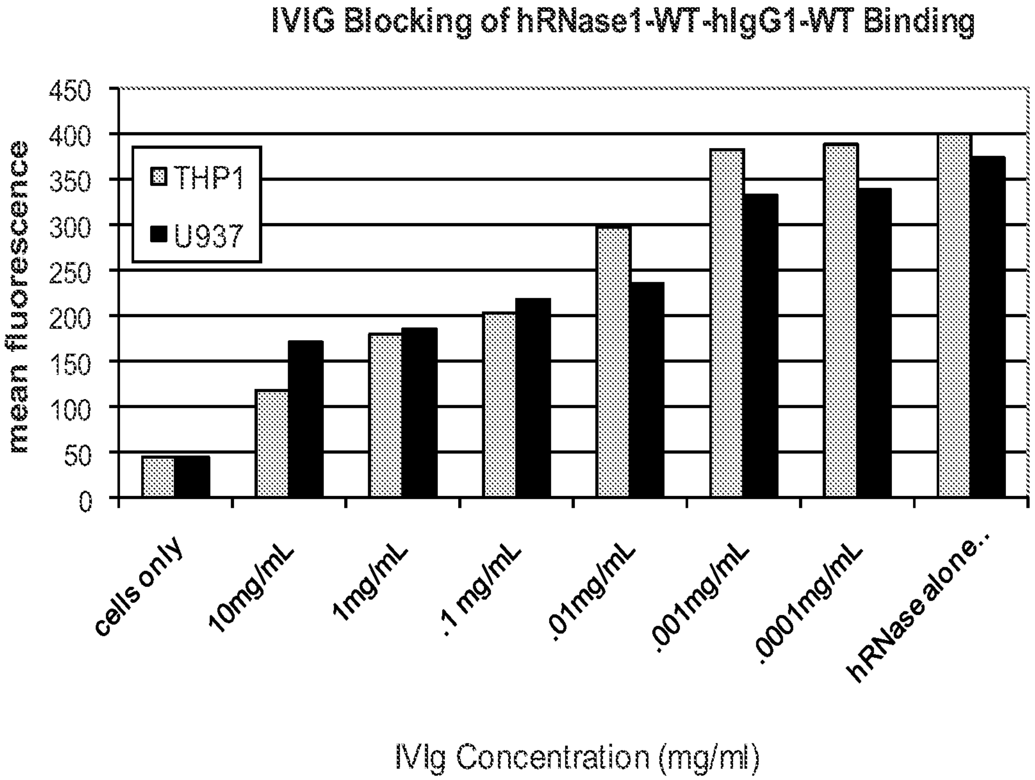
FIG. 15 shows the blocking activity of human IVIg for binding to U937 and THP-1 cells by hRNase1-WT-hIgG1-WT.

THP-1 or U937 cells were pre-incubated with IVIg starting at 10 mg/ml and performing 10-fold serial dilutions across the wells of a 96 well plate. Cells (approximately 1×10 e6 per well) were incubated on ice for 45 minutes. Pre-bound cells were washed twice and AF750 conjugated hRNase1-WT-hIgG1-WT (SEQ ID NO:161) at approximately 5 ug/ml was added to each well. Binding reactions were incubated 45 minutes on ice, washed twice in PBS/2% FBS, and analyzed by flow cytometry as described above. IVIg was able to partially block the binding of the labeled nuclease fusion protein, but even at 10 mg/ml, there was still residual binding detectable above background. FIG. 15 shows the blocking activity of human IVIg for binding to U937 and THP-1 cells by hRNase1-WT-hIgG1-WT (SEQ ID NO:161).

Example 16: Trex1-Ig Activity Assay

Murine Trex1 was cloned from mouse cDNA using the primers listed below:

```
mTrex1-5'age:
                                        (SEQ ID NO: 20)
accggtatgggctcacagaccctgccccatggtcaca

mTrex1-3'bx:
                                        (SEQ ID NO: 21)
ctcgagatctgttgttccagtggtagccggagtgccgtacatg
```

PCR reactions were performed using 50 pmol each primer in a total volume of 50 ul, under an amplification profile of 94 C 30 sec; 50 C 60 sec; 68 C 90 sec for 35 cycles of amplification. PCR products were cloned into the pCR2.1 vector and TOPO clones screened as previously described for prototype nuclease fusion gene cloning. Once sequence was verified, the cassettes were subcloned into the pDG expression vector fused to the mIgG tail or co-cloned with one of the (g4s)n linkers to construct Trex1-lnk molecules with different length linkers. Plasmid isolates were transiently transfected into COS cells as described and stable CHO transfectants generated as described for prototype nuclease fusion genes.

Fusion genes were constructed encoding Trex1Ig as follows: the genes incorporate the human VK3 leader peptide fused to murine Trex1 truncated at the COOH terminus by 72 amino acids (to remove the intracellular nuclear targeting sequences) fused to a (gly4ser)4 (SEQ ID NO:130) or (gly4ser)5 linker (SEQ ID NO:131), fused to the murine IgG2a/c allele that incorporates some changes from the IgGc sequence of the Balb/c IgG2a allele.

Figure 16:
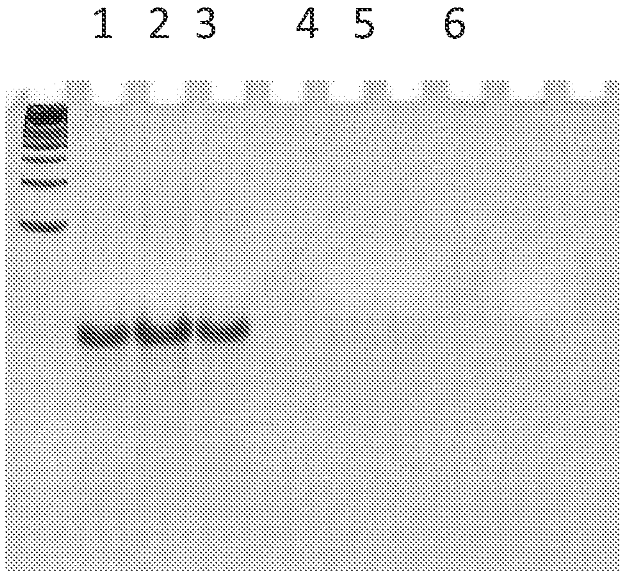
FIG. 16 shows the results of a DNA digestion assay by Trex1-(g4s)n-mIgG alternative forms.

The exonuclease activities of Trex1-Ig were measured in 30 ul reactions containing 20 mM Tris (pH7.5), 5 mM $MgCl_2$, 2 mM DTT, using a 36-mer oligonucleotide as substrate. Incubation reactions were allowed to proceed for 20-30 min at 37° C. Samples were subjected to electrophoresis on 23% polyacrylamide DNA gels overnight. Gels were incubated in TBE buffer containing 0.5 ug/ml ethidium bromide. The DNA was visualized by UV transilluminator, and photographed using a Kodak EDAS 290 digital camera equipped with ethidium bromide filters and analyzed using Kodak Molecular Imaging Software. The trex1 activity assay results for COS produced mTrex1-(g4s)4-mIgG2a-c (SEQ ID NO:166) and mTrex1-(g4s)5-mIgG2a-c (SEQ ID NO:167) are shown in FIG. 16.

Figure 17:
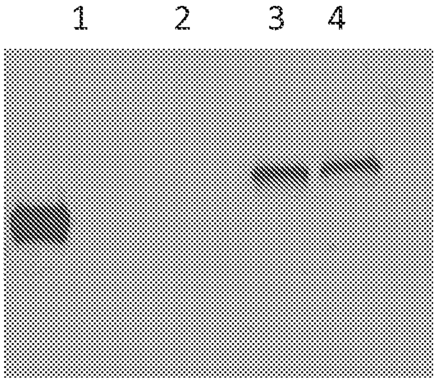
FIG. 17 shows the results of a Western Blot for trex1-$(Gly4S)_4$-Ig and trex1-(Gly4S)5-Ig culture supernatants from COS-7 transient transfections.

Example 17: Western Blot of mTrex1-Ig Single Hybrid Nuclease Molecules Produced by COS-7 Transient Transfection COS-7 cells were transiently transfected with plasmids containing hybrid nuclease molecules encoding Trex1-Ig as follows: the genes incorporate the human VK3 leader peptide fused to murine Trex1 truncated at the COOH terminus by 72 amino acids (to remove the nuclear envelope targeting sequences) fused to a (gly4ser)4 or (gly4ser)5 linker, fused to the murine IgG2a/c allele that incorporates some changes from the IgGc sequence from the Balb/c IgG2a allele. COS supernatants were harvested after 72 hours and 0.5-1.0 ml samples (depending on the experiment) were immunoprecipitated overnight at 4° C. with 100 ul protein A-agarose beads. Protein A beads were centrifuged and washed twice in PBS prior to resuspending in reducing SDS-PAGE loading buffer. Samples were heat treated at 100 C for 5 minutes, protein A beads centrifuged to pellet, and sample buffer loaded onto 10% SDS-PAGE gels. Samples were electrophoresed at 150 volts for 1.5-2 hours, and gels blotted to nitrocellulose membranes at 30 mAmp for 1 hour. Western blots were blocked in TBS/5% non-fat milk overnight. Blots were incubated with 1:2500 HRP (horseradish peroxidase) conjugated goat anti-mouse IgG2a/c (Fc specific, KPL) for 1.5 hours at room temperature, washed in PBS/0.5% Tween20 five or more times, and blots developed using ECL reagent. FIG. 17 shows a Western blot of immunoprecipitates from COS7 culture supernatants expressing mTrex1-(g4s)4 (SEQ ID NO:166) or (g4s)5-mIgG2a-c (SEQ ID NO:167) fusion proteins.

Example 18: Exonuclease Activity of DNase1L3Ig CHO Derived Fusion Protein

DNase1L3 was cloned from mouse spleen cDNA using the following primer pair to clone the mDNase1L3 including its native leader peptide sequence.

mdnase1L3-NL:

(SEQ ID NO: 22)

GTT AAG CTT GCC ACC ATG TCC CTG CAC CCA GCT TCC

CCA CGC CTG

Mdnase1L3-3bx:

(SEQ ID NO: 23)

CTC GAG ATC TGA GGA GCG ATT GCC TTT TTT TCT CTT

TTT GAG AG

Alternatively, PCR reactions were set up using the following primer pair to attach to the human VK3 leader peptide instead of the native leader.

mdnase1L3-age:

(SEQ ID NO: 24)

ACC GGT CTA AGG CTC TGC TCC TTC AAT GTG AGG TCC

TTT GGA

Mdnase1L3-3bx:

(SEQ ID NO: 25)

CTC GAG ATC TGA GGA GCG ATT GCC TTT TTT TCT CTT

TTT GAG AG

PCR reactions were performed using 50 pmol each primer in a total volume of 50 ul, under an amplification profile of 94 C 30 sec; 50 C 60 sec; 68 C 90 sec for 35 cycles of amplification. PCR products were cloned into the pCR2.1 vector and TOPO clones screened as previously described for prototype nuclease fusion gene cloning. Once sequence was verified, the cassettes were subcloned into the pDG expression vector fused to the mIgG tail. Plasmid isolates were transiently transfected into COS cells as described and stable CHO transfectants generated as described for prototype nuclease fusion genes.

Figure 18:
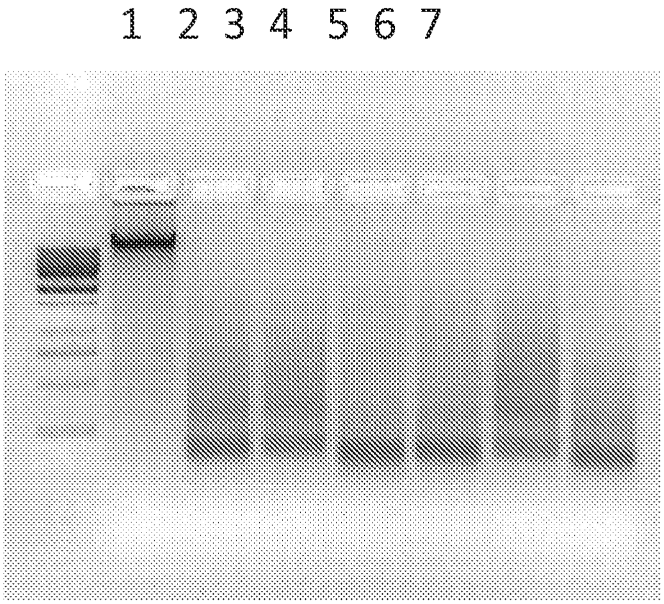
FIG. 18 shows DNA digestion patterns by different stably transfected CHO DG44 clones designated as 2A3, 3A5, and 8H8, expressing DNAse1L3-mIgG2a-c hybrid nuclease molecules.

The exonuclease activity in protein extracts from DNase1L3Ig (SEQ ID NO:185) CHO clones was measured in 30 ul reactions containing 20 mM Tris (pH7.5), 5 mM $MgCl_2$, 2 mM DTT, and a substrate. Incubation was 20-30 min at 37° C. Samples were then run on agarose DNA gel overnight. The gel was incubated in TBE buffer containing Ethidium bromide. The DNA was visualized under UV. The results of chromatin digestion analysis are shown in FIG. 18.

Figure 19:
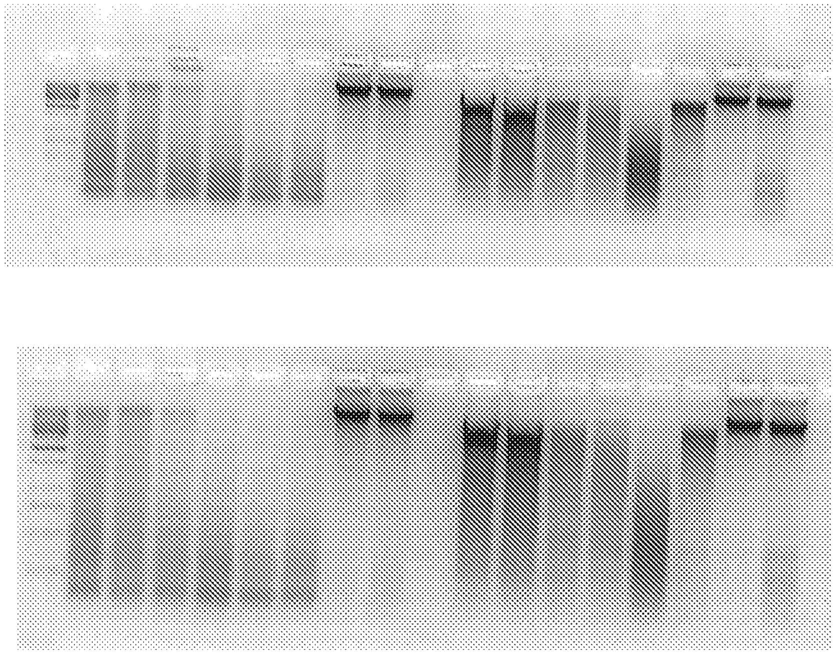
FIG. 19 shows DNA digestion patterns of decreasing amounts of DNase1L3-Ig hybrid nuclease molecules after various incubation times with and without heparin as an enzyme inhibitor.

Example 19: Dose Titration of Increasing Volumes of CHO Supernatant for Exonuclease Activity FIG. 19 shows titration analysis of the exonuclease digestion patterns obtained from COS supernatants expressing DNase1L3Ig fusion proteins (SEQ ID NO:183 or 185). Nuclear DNA Degradation assays were performed as follows: HeLa cells were cultured in DMEM media and nuclei from 10 e5 cells were isolated using NP-40 lysis. Nuclei were diluted into 200 ul reaction buffer containing 10 mM Hepes (pH 7.0), 50 mM NaCl, 2 mM $MgCl_2$, 2 mM $CaCl_2$, and 40 mM b-glycerophosphate. Nuclei were incubated for 3 hours at 37° C. in the volumes of culture supernatant indicated on the figure from DNase1L3 transfected COS cells. Nuclear DNA was isolated using QiAmp blood DNA minikit DNA was analyzed by 1.5% agarose gel electrophoresis. For control reactions, heparin was used at 250 i.u./ml, to inhibit nuclease activity.

Example 20: Construction and Expression of DNase1-Ig Single and Dual Enzyme Hybrid Nuclease Molecules Naturally occurring alleles of human DNase1 or DNase1 like molecules have been reported. The A114F mutation has been previously reported to occur in natural variants of human DNAse1 like enzymes, and to result in actin resistance of the enzymes containing this sequence change. See Pan, C Q, Dodge T H, Baker D L, Prince W E, Sinicropi D V, and Lazarus R A. J Biol Chem 273: 18374-18381, (1998); Zhen A, Parmelee D, Hyaw H, Coleman T A, Su K, Zhang J, Gentz R, Ruben S, Rosen C, and Li Y. Biochem and Biophys Res Comm 231: 499-504 (1997); and Rodriguez A M, Rodin D, Nomura H, Morton C C, Weremowicz S, and Schneider M C. Genomics 42: 507-513 (1997), all of which are herein incorporated by reference.

Similarly, the G105R mutation has been reported recently as a single nucleotide polymorphism in the gene encoding human DNAse 1 that is polymorphic in some or all populations, and that is relevant to autoimmunity. (See Yasuda T, Ueki M, Takeshita H, Fujihara J, Kimura-Kataoka K, Lida R, Tsubota E, Soejima M, Koda Y, Dato H, Panduro A. Int J Biochem Cell Biol 42(7): 1216-1225 (2010), herein incorporated by reference). Allelic variants at this position resulted in high activity harboring DNase 1 isoforms relative to wild type. Another naturally occurring, polymorphic mutation (R21S) has also been reported to confer higher activity. (See Yasuda, supra)

SLE patients have been reported to have significantly decreased levels of DNase1 activity (See Martinez-Valle F, Balada E, Ordi-Ros J, Bujan-Rivas S, Sellas-Fernandez A, Vilardell-Tarres M. Lupus 18(5): 418-423 (2009), herein incorporated by reference).

Naturally occurring enzyme variants may thus be less immunogenic when administered to patients, since these isoforms occur in the human population. We reasoned that the combination of the actin resistant properties of alleles similar to A114F with the increased enzymatic activity of alleles like G105R would generate novel allelic variants of human DNase1 that might show improved clinical activity in vitro and in vivo. To our knowledge, ours is the first report of this new mutant form of DNase1 generated from a combination of two naturally occurring variants G105R and A114F.

Human DNase 1 was isolated as described previously from human pancreas RNA (Ambion), by random primed cDNA and PCR using the following primer sets:

5'hDNase1-age:

(SEQ ID NO: 26)

GTT ACC GGT CTG AAG ATC GCA GCC TTC AAC ATC CAG

5'hDNase1-bx:

(SEQ ID NO: 27)

GTT CTC GAG ATC TTT CAG CAT CAC CTC CAC TGG ATA

GTG

Alternatively, the 3' DNase cassettes were amplified by PCR using the following primer pair.

3'hDNase1-RV:

(SEQ ID NO: 28)

GTT GAT ATC CTG AAG ATC GCA GCC TTC AAC ATC CAG

3'hDNase1-stop:

(SEQ ID NO: 29)

GTT TCT AGA TTA TCA CTT CAG CAT CAC CTC CAC TGG

ATA GTG

PCR reactions were performed using 50 pmol each primer, 2 ul cDNA, in a total volume of 50 ul using Platinum PCR Supermix as previously described. The amplification profile was 94 C 30 sec; 55 C 30 sec; 68 C 90 sec for 35 cycles.

Once the wild type gene was amplified by PCR, the fragments were subjected to gel electrophoresis and 850 bp fragments purified by QIAquick column purification. Fragments were cloned into pCR2.1, transformed by TOPO cloning according to manufacturer's instructions as described for the other constructs. Once sequence was verified, PCR primers were used to generate subfragments containing naturally occurring alleles for DNase1 that have been reported to improve specific activity and improve resistance to the inhibitory activity of actin. These subfragments contained overlapping sequence, permitting amplification of complete DNase1 subclones containing the desired allelic variations. COS 7 cells were transiently transfected in 60 mm dishes using Polyfect (Qiagen, Valencia, CA) transfection reagent. Plasmid DNA was prepared using the Qiagen QIAprep miniprep kits according to manufacturer's instructions. Plasmids were eluted in 50 ul EB buffer. DNA concentration was measured using the Nanodrop and an aliquot equivalent to 2.5 ug plasmid DNA used for each transfection reaction. Each DNaseIg (SEQ ID NOS.: 118, 119, 120, 121, 122 or 123) or RNase-Ig-DNase (SEQ ID NOS.: 115, 116, 117) expression cassette was inserted into the mammalian expression vector pDG, a derivative of pcDNA3.1. Transfected cells were incubated for 72 hours at 37° C., 5% CO2 prior to harvest of culture supernatants for further analysis. Culture supernatants were harvested, residual cells centrifuged from the solution, and the liquid transferred to new tubes.

Figure 20:
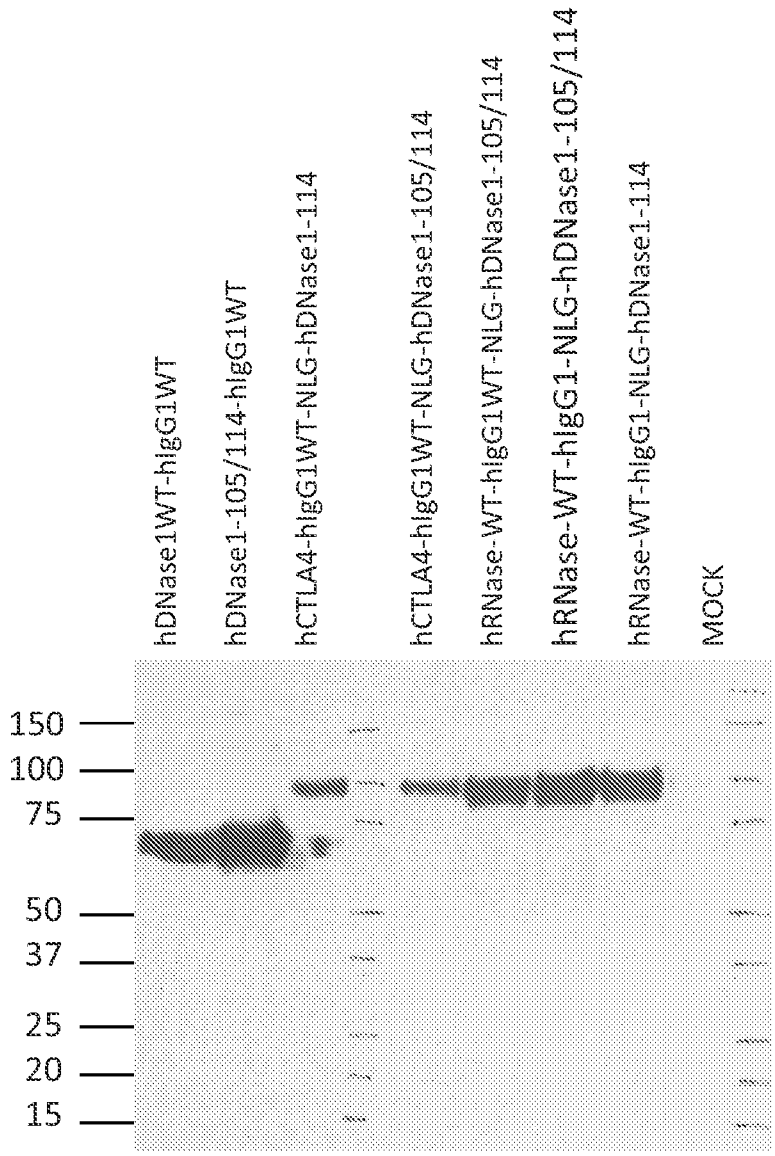
FIG. 20 shows a Western blot of immuneprecipitated fusion proteins from transiently transfected COS cells expressing different embodiments of hRNase1-Ig-hDNase1 or hDNase1-Ig hybrid nuclease molecules.

COS-7 cells were transiently transfected with plasmids containing human DNase1 wild type (SEQ ID NO:118) or naturally occurring DNase 1 mutant alleles (G105R and/or A114F) (SEQ ID NO:115, 116, or 117) fused to the wild type human IgG1 Fc domain. This hinge-CH2-CH3 cassette contains a single CS mutation in the hinge region to eliminate the first cysteine in this domain since it is unpaired due to absence of its pairing partner present in the light chain of the antibody. In addition, more complex multi-nuclease fusion proteins were also expressed from COS cell transient transfections. Western blot analysis was performed on supernatants from transient transfectants. The molecules shown in FIG. 20 contain human DNase1 fused to the human IgG1 wild type Fc domain (SEQ ID NO:154, 155, 156, or 159) or include human RNase1 (wild type) fused to the SCC hinge-CH2-CH3 Fc domain of human IgG1, followed by a novel linker containing an N-linked glycosylation site to protect the linker domain from protease cleavage, and the wild type (SEQ ID NO:153) or mutant allele (SEQ ID NO:151 or 152) forms of human DNase1 at the carboxy terminus of the molecule. COS supernatants were harvested after 72 hours and 0.5-1.0 ml samples (depending on the experiment) were immunoprecipitated overnight at 4° C. with 100 ul protein A-agarose beads. Protein A beads were centrifuged and washed twice in PBS prior to resuspending in SDS-PAGE loading buffer, for NuPAGE gels—reducing or nonreducing LDS sample buffer. Samples were heated according to manufacturer's instructions, protein A beads centrifuged to pellet, and sample buffer loaded onto 5-12% NuPAGE gradient gels. Samples were electrophoresed at 150 volts for 1.5-2 hours, and gels blotted to nitrocellulose membranes at 30 mAmp for 1 hour. Western blots were blocked in TBS/5% non-fat milk overnight. Blots were incubated with 1:2500 HRP (horseradish peroxidase) conjugated goat anti-human IgG (Fc specific, Jackson Immunoresearch) or goat anti-mouse IgG for 1.5 hours at room temperature, washed in PBS/0.5% Tween20 five or more times, and blots developed using ECL reagent.

Example 22: Screening COS Supernatants for Nuclease Enzyme Activity

Figure 21:
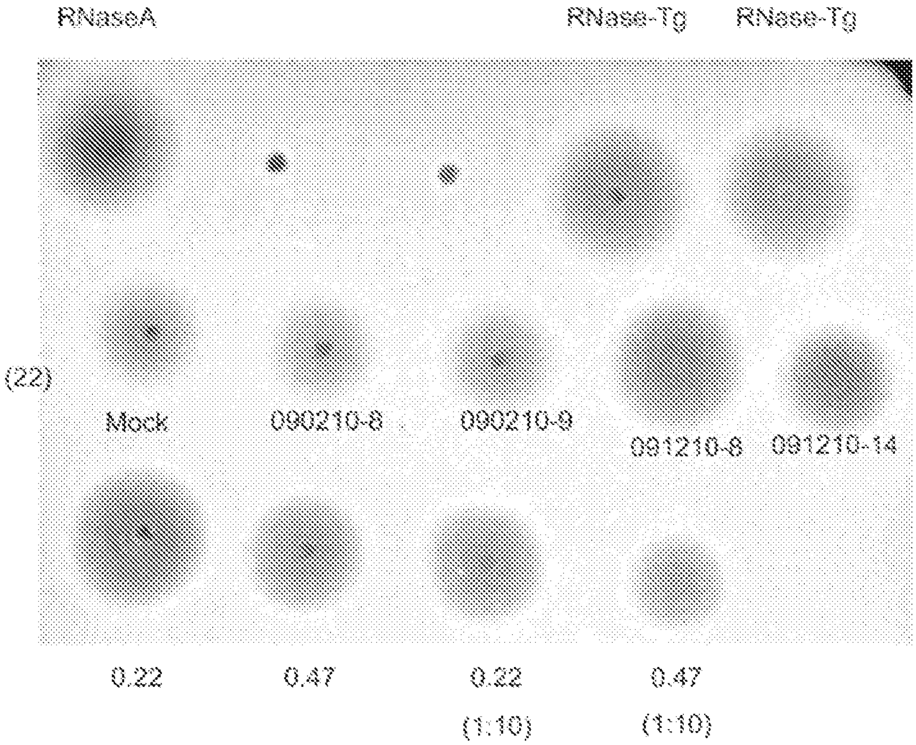
FIG. 21 shows SRED analysis to assess the presence of RNase activity in the COS supernatants expressing different embodiments of hRNase1-Ig-hDNase1 or hDNase1-Ig hybrid nuclease molecules.

FIG. 21 shows the results of RNase activity assays (SRED) analysis on harvested COS supernatants expressing hDNAse1Ig and hRNase1-Ig-hDNase1 fusion proteins by SRED.

COS supernatants from transient transfections of the hDNaseIg single or multispecific nucleases were assayed for nuclease activity as follows. A 2% agarose gel was prepared with distilled water. Poly-C(Sigma) was dissolved in distilled water at 3 mg/ml. the gel plate was prepared as follows: 1.5 ml reaction buffer (0.2M Tris-HCl pH7.0, 40 mM EDTA and 0.1 mg/ml Ethidium bromide), 1 ml Poly-C and 0.5 ml water were place in the tube and maintained at 50 C for 5 min. 3 ml of the agarose (kept at 50 C) was added to the tube. The mixture was immediately poured onto glass plate. Sampling wells were punched in the gel. Approximately 2 ul of each sample was loaded and the gel was incubated at 37 C for 4 hours in the moist chamber. Then the gel was incubated in a buffer (20 mM sodium acetate pH5.2, 20 mg/ml Ethidium bromide) on ice for 30 min. Gels were photographed on a UV transilluminator using a Kodak digital camera DC290 system equipped with ethidium bromide filters and analyzed using Kodak Molecular Imaging software.

FIG. 22 shows a composite figure displaying results of DNase nuclease activity assays performed on COS supernatants from transfected cells. Culture supernatants were harvested 72 hours after transfecting the following clones of DNase1 wild type and mutant-Ig fusion proteins: (1) 090210-8=hDNAse1-WT-hIgG1 WT (SEQ ID NO:154); (2) 090210-9=hDNase1-G105R; A114F-hIgG1 WT (SEQ ID NO:159); (3) 091210-8=hRNase1-WT-hIgG1-WT-DNase1-G105R; A114F (SEQ ID NO:151), and (4) 091210-14=hRNase-WT-hIgG1-WT-DNase1-A114F (SEQ ID NO:152).

Figure 23:
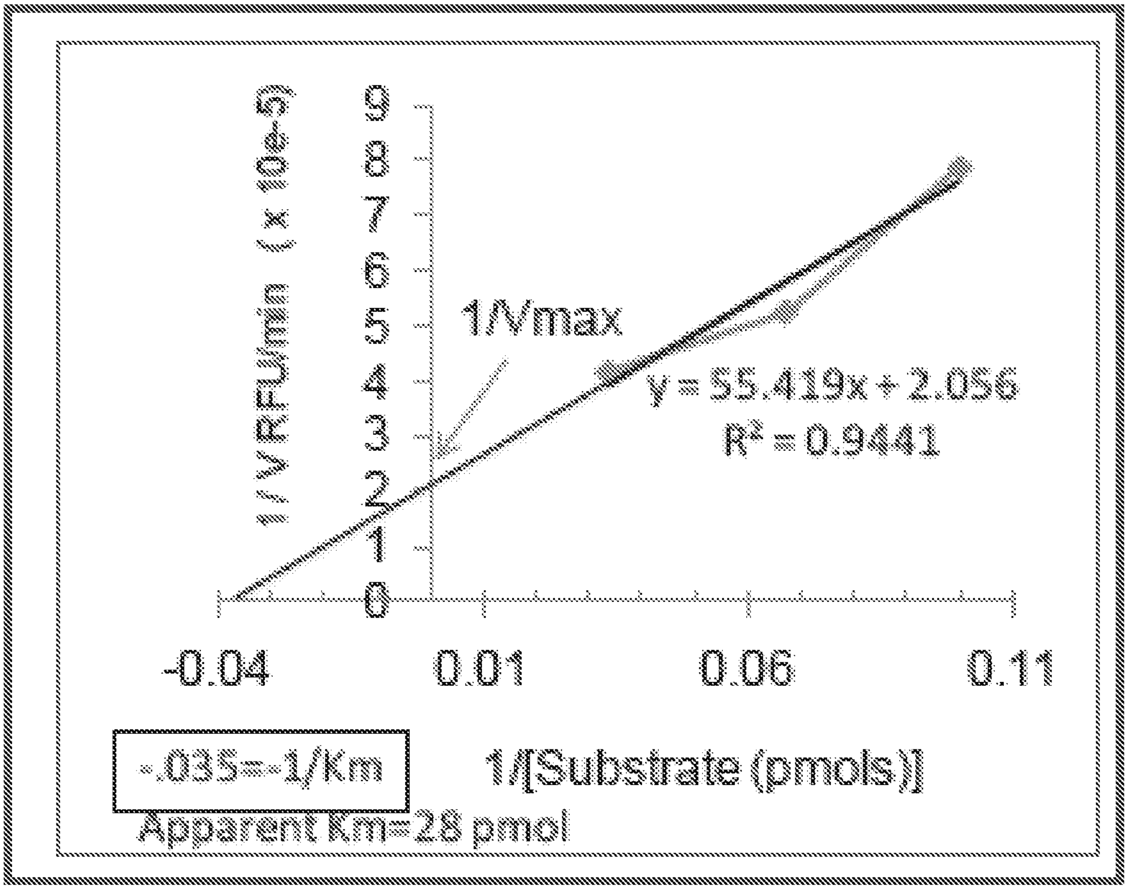
FIG. 23 shows enzyme kinetics assayed using the Rnase Alert Substrate (Ambion/IDT) and fluorescence quantified with a Spectramax M2 microplate Reader. Data was analyzed using Softmax Pro software (Molecular Devices). Reaction rates at different substrate concentrations were measured and the data shown as a Lineweaver-Burk plot. The apparent Km, corrected for volume is 280 nM.

The pH of the supernatants was adjusted to 0.0 with bicarbonate buffer to facilitate binding of expressed -Ig fusion proteins to protein A agarose beads. Panel A. of FIG. 23 shows gel electrophoresis analysis of plasmid DNA digestion: Protein A agarose slurry (50 ul per sample) was washed in PBS, and incubated overnight at 4° C. with 100 ul culture supernatant to immunoprecipitate -Ig fusion proteins. Immunoprecipitates were washed 4-5 times in 750 ul PBS, centrifuging at approximately 3500 rpm followed by aspiration of PBS. Final protein A precipitates were resuspended in 50 ul reaction buffer containing 20 mM Tris ph7.5. 2 mM CaCl2 and 2 mM MgCl2 containing 1.5 ug plasmid DNA (pDG expression vector). Reactions were incubated for 30 minutes at 37° C., heated at 65° C. for 5 min, and the DNA present in reactions analyzed by agarose gel electrophoresis on 1.5% TBE-agarose gels.

Panel B shows the results of a nuclease activity assay performed on the same culture supernatants using the DNase Alert Kit (IDT/Ambion). Reaction tubes containing lyophilized DNase Alert Substrate (50 pmoles) were resuspended with 5 ul nuclease free ddH2O supplied with the kit, 5 ul 10×DNase alert buffer, and 40 ul protein A slurry immunoprecipitated as follows: For these immunoprecipitations, 50 ul protein A agarose beads were incubated overnight with 50 ul culture supernatant. Samples were then washed 5 times with 0.75 ml PBS. Final protein A precipitates were resuspended in 80 ul nuclease free ddH2O, and 40 ul of the slurry (one half the precipitate) was transferred to the reaction tubes. Negative controls with mock transfected IP and ddH20 were also set up. A positive control was also set up containing DNase1 provided with the kit (2 units). Reactions were incubated 1 hour at 37° C., and exposed to short wave length UV transillumination to visualize fluorescence. Relative amounts of DNA digestion are indicated by degree of fluorescence.

Example 22: Examination of Mac-2 Positive Cells in DTg Mice

Early lupus mortality is usually due to nephritis or infection resulting from immunosuppression to treat nephritis. Therefore, an extremely important outcome for any new therapy is improvement in nephritis. While human studies are limited to quantitation of proteinuria and creatinine, in mice one can get an accurate assessment of inflammation and damage to the kidneys by histology and immunocytochemistry. We report that TLR7.1×RNase double transgenic (DTg) mice showed lower anti-RNA antibodies, less B cell activation, fewer immune deposits and less PAS positive staining glomeruli. We have further compared macrophage infiltration of the kidneys using the anti-Mac-2 (galectin3) antibody (Iyoda et al. Nephrol Dial Transplant 22: 3451, 2007). Frozen sections from kidneys obtained from single or double Tg were examined for numbers of Mac-2+ macrophages as well as glomerular size as described (Iyoda et al). Twenty randomly selected glomeruli (from the outer to inner side of the kidney) were counted for positive cells. There are many fewer mac-2 positive staining cells in the glomeruli of DTg as compared to single Tg mice (data not shown). The results of counting 20 glomeruli per mouse in a pilot study of n=4-5 in each group, revealed mean+/−SE of 3.8+/−1.1 and 1.4+/−0.2 for single versus DTg respectively, p=0.05. In addition, we quantified glomerular tuft size and observed a significant reduction in glomerular tuft size in the DTg mice (179.4+/−41 versus 128+/−16.8 um2 in single versus DTg respectively, p=0.037).

Example 23: Km of Purified Murine RNaseA-Ig Fusion Protein

To further define the functional characteristics of the bivalent RNase-Ig fusion protein (SEQ ID NO:150), we performed determinations of the Michaelis constant, Km. As shown in FIG. 23, the enzyme has a high affinity with a provisional Km of 280 nM (as a comparison, RNase A has a Km of 34 nM using polyC as substrate (delCardayre et al, Prot Eng 8:261, 1995)). FIG. 23 shows enzyme kinetics that were assayed using the Rnase Alert Substrate (Ambion/IDT) and fluorescence was quantified with a Spectramax M2 microplate Reader. Data was analyzed using Softmax Pro software (Molecular Devices). Reaction rates at different substrate concentrations were measured and the data shown as a Lineweaver-Burk plot. The apparent Km, corrected for volume is 280 nM.

Example 24: Analysis of 564Igi Tg Mice for Anti-RNA Antibodies

Figure 24:
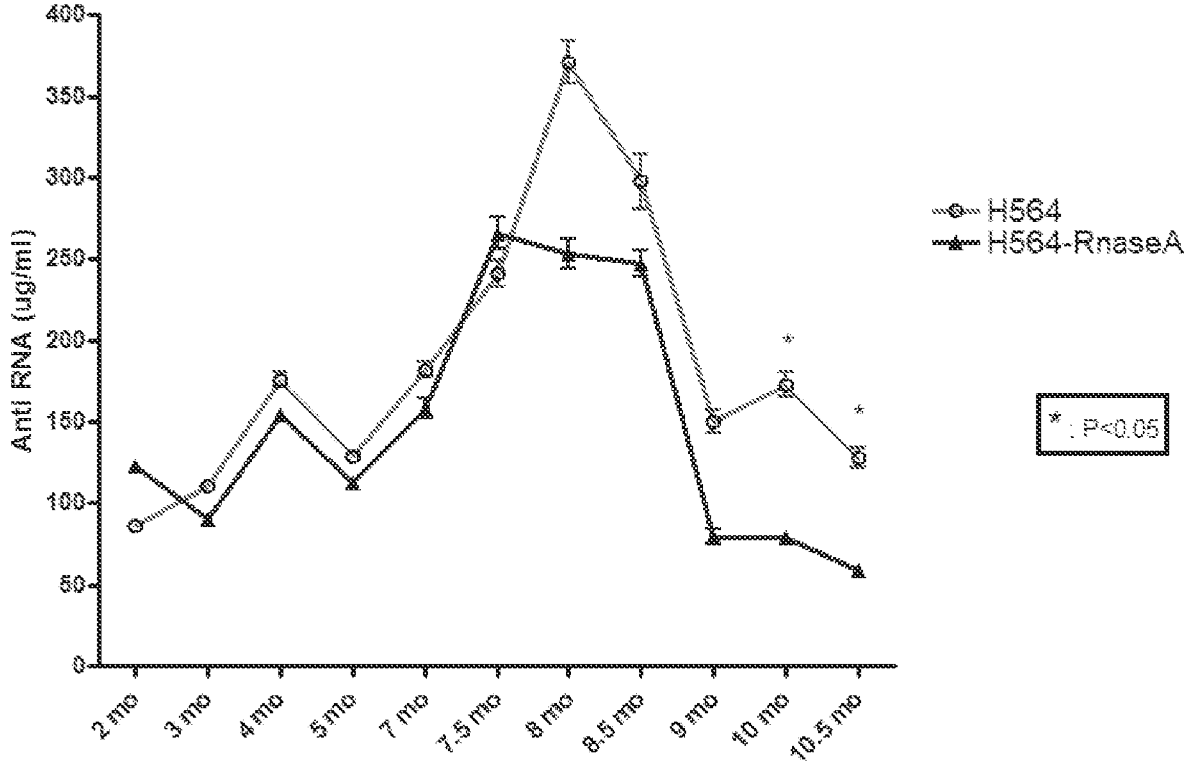
FIG. 24 shows the levels of anti-RNA antibodies in mouse sera from H564 and H564-RNaseA double transgenic mice at successive intervals as the transgenic mice aged.

564 Igi Tg mice: Dr. Imanishi-Kara inserted the rearranged VDJ genes from the H564 hybridoma into the endogenous Igh and Igk loci to create the 564Igi mouse on a B6 background. Sera from these mice stained the cytoplasm and nucleoli of fixed cells indicating a predominant anti-RNA specificity. Consistent with this finding and of special relevance to this patent application, antibody production was inhibited when these mice were made TRL7 deficient indicating that the stimulus for antibody production is indeed RNA. This mouse strain develops late onset glomerulonephritis. We analyzed the expression of anti-RNA antibodies in mice transgenic for H564 and also double transgenic mice coexpressing 564Ig and RNase transgenes. FIG. 24 compares the levels of anti-RNA antibodies in mouse sera at successive intervals as these transgenic mice aged.

See Gavalchin, J., R. A. Seder, and S. K. Datta. 1987. The NZB×SWR model of lupus nephritis. I. Cross-reactive idiotypes of monoclonal anti-DNA antibodies in relation to antigenic specificity, charge, and allotype. Identification of interconnected idiotype families inherited from the normal SWR and the autoimmune NZB parents. *J. Immunol.* 138: 128-137; and Berland, R., L. Fernandez, E. Kari, J. H. Han, I. Lomakin, S. Akira, H. H. Words, J. F. Kearney, A. A. Ucci, and T. Imanishi-Kari. 2006. Toll-like receptor 7-dependent loss of B cell tolerance in pathogenic autoantibody knockin mice. *Immunity* 25:429-440.

Example 25: In Vitro Assessment of Hybrid Nuclease Molecule Biological Activity

One or more hybrid nuclease molecules are purified, e.g., by affinity or ion exchange chromatography as previously described in the examples above. In some instances the hybrid nuclease molecule is a polypeptide. In some instances, the hybrid nuclease molecule includes one or more sequences from Table 2. In some instances the molecule is SEQ ID NO:161, 162, or 163. In some instances the molecule includes SEQ ID NO:145 and SEQ ID NO:149. In some instances the molecule is SEQ ID NO:151, 152, 153, 154, 155, 156, 157, 158, 159, 160, 161, 162, 163, 166, 167, 169, 170, 171, 173, 175, 177, 179, 181, 187, 189, 191, 193, 195, 197, 199, 201, 203, 205, or 207. The hybrid nuclease molecule can be any of those disclosed herein and any that can be constructed from the sequences disclosed herein (see Table 2), e.g., by taking a nuclease domain and linking it to an Fc domain; or, e.g., taking a nuclease domain and linking it to an Fc domain with a linker domain. Various linker domains (e.g., those described herein) can be used to link the Fc domains and/or nuclease domains. For example, linker domains 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more amino acids in length can be used. Molecules are assayed for the specific nuclease activity in vitro using qualitative assays to verify that they possess the desired nuclease function. Specific activities are generally then determined by fluorescence based kinetic assays utilizing substrates such as the RNase or DNase Alert Kit reagents, and a fluorescence plate reader set to take readings as a function of time. In addition, protein solutions are generally checked for endotoxin contamination using a commercially available kits, such as the Pyrotell Limulus Amebocyte Lysate (LAL) kit, 0.06 EU/ml detection limit from Cape Cod, Inc. (E. Palmouth, MA). Molecules are then assayed using a variety of in vitro assays for biological activity.

One series of in vitro assays will measure the effect of the molecules on cytokine production by human PBMC in response to various stimuli, in the presence or absence of the molecules in the cultures. Normal or patient human PBMC (approximately 1×10 e6 cells) are cultured for 24, 48, or 96 hours depending on the assay. PBMC are cultured in the presence of stimuli such as TLR ligands, costimulatory antibodies, immune complexes, and normal or autoimmune sera. The effects of the molecules on cytokine production is measured using commercially available reagents, such as the antibody pair kits from Biolegend (San Diego, CA) for IL-6, IL-8, IL-10, IL-4, IFN-gamma, TNF-alpha. Culture supernatants from in vitro cultures are harvested at 24, 48 hours or later time points to determine the effects of the molecules on cytokine production. IFN-alpha production is measured using, e.g., anti-human IFN-alpha antibodies and standard curve reagents available from PBL interferon source (Piscataway, NJ). A similar set of assays is performed using human lymphocyte subpopulations (isolated monocytes, B cells, pDCs, T cells, etc.); purified using, e.g., commercially available magnetic bead based isolation kits available from Miltenyi Biotech (Auburn, CA).

In addition, the effect of the molecules on expression of lymphocyte activation receptors such as CDS, CD23, CD69, CD80, CD86, and CD25 is assessed at various time points after stimulation. PBMC or isolated cell subpopulations are subjected to multi-color flow cytometry to determine how these molecules affect the expression of different receptors associated with immune cell activation.

Another set of assays will measure the effects of these molecules on the proliferation of different lymphocyte subpopulations in vitro. These assays will utilize, e.g., CFDA-SE staining (Invitrogen, Carlsbad, CA) of human PBMCs prior to stimulation. CFSE at 5 mM is diluted 1:3000 in PBS/0.5% BSA with 10 e7-10 e8 PBMCS or purified cell subsets and labeling reactions incubated for 3-4 minutes at 37 C prior to washing several times in RPMI/10% FBS to remove remaining CFSE. CFSE labeled cells are then incubated in co-culture reactions with various stimuli (TLR ligands, costimulatory antibodies, etc.) and the molecules for 4 days prior to analysis of cell proliferation by flow cytometry using dye-conjugated cell subpopulation specific antibodies.

The effect of these molecules on in vitro maturation of monocytes into DCs and macrophages is also assessed using both normal and patient PBMC samples.

The effectiveness of a hybrid nuclease molecule is demonstrated by comparing the results of an assay from cells treated with a hybrid nuclease molecule disclosed herein to the results of the assay from cells treated with control formulations. After treatment, the levels of the various markers (e.g., cytokines, cell-surface receptors, proliferation) described above are generally improved in an effective molecule-treated group relative to the marker levels existing prior to the treatment, or relative to the levels measured in a control group.

Example 26: Administration of a Hybrid Nuclease Molecule to a Mammal in Need Thereof Mammals (e.g., mice, rats, rodents, humans, guinea pigs) are used in the study. Mammals are administered (e.g., intravenously) one or more hybrid nuclease molecules comprising one or more sequences from Table 2 or a control. In some instances the molecule is SEQ ID NO:161, 162, or 163. In some instances the molecule includes SEQ ID NO:145 and SEQ ID NO:149. In some instances the molecule is SEQ ID NO:151, 152, 153, 154, 155, 156, 157, 158, 159, 160, 161, 162, 163, 166, 167, 169, 170, 171, 173, 175, 177, 179, 181, 187, 189, 191, 193, 195, 197, 199, 201, 203, 205, or 207. The hybrid nuclease molecule can be any of those disclosed herein and any that can be constructed from the sequences disclosed herein (see Table 2), e.g., by taking a nuclease domain and linking it to an Fc domain; or, e.g., taking a nuclease domain and linking it to an Fc domain with a linker domain. Various linker domains (e.g., those described herein) can be used to link the Fc domains and/or nuclease domains. For example, linker domains 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more amino acids in length can be used. In some instances the hybrid nuclease molecule is formulated a pharmaceutically acceptable carrier. In some instances the molecule is formulated as described in the pharmaceutical compositions section above. The hybrid nuclease molecule targets RNase and/or DNase.

Multiple rounds of doses are used where deemed useful. Effects on IFN-alpha levels, IFN-alpha response gene levels, autoantibody titers, kidney function and pathology, and/or circulating immune complex levels are monitored in the mammals. Similar studies are performed with different treatment protocols and administration routes (e.g., intramuscular administration, etc.). The effectiveness of a hybrid nuclease molecule is demonstrated by comparing the IFN-alpha levels, IFN-alpha response gene levels, autoantibody titers, kidney function and pathology, and/or circulating immune complex levels in mammals treated with a hybrid nuclease molecule disclosed herein to mammals treated with control formulations.

In an example, a human subject in need of treatment is selected or identified. The subject can be in need of, e.g., reducing a cause or symptom of SLE. The identification of the subject can occur in a clinical setting, or elsewhere, e.g., in the subject's home through the subject's own use of a self-testing kit.

At time zero, a suitable first dose of a hybrid nuclease molecule is administered to the subject. The hybrid nuclease molecule is formulated as described herein. After a period of time following the first dose, e.g., 7 days, 14 days, and 21 days, the subject's condition is evaluated, e.g., by measuring IFN-alpha levels, IFN-alpha response gene levels, autoantibody titers, kidney function and pathology, and/or circulating immune complex levels. Other relevant criteria can also be measured. The number and strength of doses are adjusted according to the subject's needs.

After treatment, the subject's IFN-alpha levels, IFN-alpha response gene levels, autoantibody titers, kidney function and pathology, and/or circulating immune complex levels are lowered and/or improved relative to the levels existing prior to the treatment, or relative to the levels measured in a similarly afflicted but untreated/control subject.

In another example, a rodent subject in need of treatment is selected or identified. The identification of the subject can occur in a laboratory setting or elsewhere.

At time zero, a suitable first dose of a hybrid nuclease molecule is administered to the subject. The hybrid nuclease molecule is formulated as described herein. After a period of time following the first dose, e.g., 7 days, 14 days, and 21 days, the subject's condition is evaluated, e.g., by measuring IFN-alpha levels, IFN-alpha response gene levels, autoantibody titers, kidney function and pathology, and/or circulating immune complex levels. Other relevant criteria can also be measured. The number and strength of doses are adjusted according to the subject's needs.

After treatment, the subject's IFN-alpha levels, IFN-alpha response gene levels, autoantibody titers, kidney function and pathology, and/or circulating immune complex levels are lowered and/or improved relative to the levels existing prior to the treatment, or relative to the levels measured in a similarly afflicted but untreated/control subject.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

Tables

TABLE 1

Primer Listing for RNase and DNase -Ig Fusion Gene Constructs

| SEQ ID NO: | Name | Sequence |
|---|---|---|
| | | human primers: |
| 30 | mahIgG1CH2M | tgtccaccgtgtccagcacctgaactcctgggtggatcgtcagtcttcc |
| 31 | huIgG1-H1 | agatctcgagcccaaatcttctgacaaaactcacacatgtccaccgtgt |
| 32 | hIgG1-5scc | gaagatctcgagcccaaatcttctgacaaaactcacacatgt |
| 33 | hIgG1SSSH | gttagatctcgagcccaaatcttctgacaaaactcacacatct |
| 34 | mah1gG1S | tctagattatcatttacccggagacagagagaggctcttctgcgtgtagtg |
| 35 | P331S | aaggtctccaacaaagccctcccagcctccatcgagaaaacaatctcc |
| 36 | P331AS | gttttctcgatggaggctgggagggctttgttggagacc |
| 37 | 5'hrnase | AAG CTT GCC ACC ATG GCT CTG GAG AAG TCT CTT GTC CGG CTC C |
| 38 | 3'hrnasebx | ctcgagatctgtagagtcctccacagaagcatcaaagtgg |
| 39 | 5'hrnaseage | accggtaaggaatcccgggccaagaaattcc |
| 40 | 3'hRNaseRV | gatatcccttccctgggcaaggaatcccgggccaagaaattccag |
| 41 | 3'hRNase-stop | gtttctagattattaggtagagtcctccacagaagcatcaaagtg |
| 42 | hdnase1L3-5NL | GGT AAG CTT GCC ACC ATG TCA CGG GAG CTG GCC CCA CTG CTG CTT |
| 43 | hdnase1L3-3bx | CTC GAG ATC TGA GGA GCG TTT GCT CTT TGT TTT CTT CCT TAG |
| 44 | hDNase1L3-5age | accggtatgaggatctgctccttcaacgtcaggtcctttgg |
| 45 | 5'hDNase1-age | GTT ACC GGT CTG AAG ATC GCA GCC TTC AAC ATC CAG |
| 46 | 5'hDNase1-bx | GTT CTC GAG ATC TTT CAG CAT CAC CTC CAC TGG ATA GTG |
| 47 | 3'hDNase1-RV | GTT GAT ATC CTG AAG ATC GCA GCC TTC AAC ATC CAG |
| 48 | 3'hDNase1-stop | GTT TCT AGA TTA TCA CTT CAG CAT CAC CTC CAC TGG ATA GTG |
| 49 | hDNase1 S105-114 | GAT GGC TGC GAG CCC TGC AGG AAC GAC ACC TTC AAC CGA GAG CCA TTC ATT GTC AGG TTC |
| 50 | hDNase1-as114-105 | GAA CCT GAC AAT GAA TGG CTC TCG GTT GAA GGT GTC GTT CCT GCA GGG CTC GCA GCC ATC |
| 51 | hDNase1-as114 | GGA GAA GAA CCT GAC AAT GAA TGG CTC TCG GTT GAA GGT |
| 52 | hDNase1-s114 | ACC TTC AAC CGA GAG CCA TTC ATT GTC AGG TTC TTC TCC |

TABLE 1-continued

Primer Listing for RNase and DNase -Ig Fusion Gene Constructs

| SEQ ID NO: | Name | Sequence |
|---|---|---|
| 53 | hTrex1-5'age | accggtatgggccctggagctcgcagacagggcag |
| 54 | hTrex1-3'bx | ctcgagatctttggtcctagcagaggctgtgacc |
| 55 | hTrex1-5' AX | accggtctcgagatgggccctggagctcgcagacagg |
| 56 | hTrex1-3'xho#2 | ctcgagtttggtcctagcagaggctgtgacc |
| | | Murine Primers: |
| 57 | mTrex1-5'age | accggtatgggctcacagaccctgccccatggtcaca |
| 58 | mTrex1-3'bx | ctcgagatctgttgttccagtggtagccggagtgccgtacatg |
| 59 | mdnase1L3-5NL | GTT AAG CTT GCC ACC ATG TCC CTG CAC CCA GCT TCC CCA CGC CTG |
| 60 | mdnase1L3-3bx | CTC GAG ATC TGA GGA GCG ATT GCC TTT TTT TCT CTT TTT GAG AG |
| 61 | mrib1-NL | gTT AAg CTT gCC ACC ATg ggT CTg gAg AAg TCC CTC ATT CTg |
| 62 | mrib3NH2 | ggC TCg AgC ACA gTA gCA TCA AAg tGG ACT ggT ACg TAg g |
| 63 | muIgG2aCH2 | cctccatgcaaatgcccagcacctaacctcttgggtggatcatccgtcttcatcttcc |
| 64 | mIgG2a-5 | agatctcgagcccagaggtcccacaatcaagccctctcctccatgcaaatgcc |
| 65 | mIgG2a-5scc | gaagatctcgagcccagaggtcccacaatcaagccctctcctcca |
| 66 | muIgG2aSSSH | atcaagccctctcctccatctaaatccccagcacctaac |
| 67 | mIgG2aKP5 | agtggcaaggagttcaaatgctcggtcaagaagaaagacctcccagcgtccatcgag |
| 68 | mIgG2aKP3 | ggttctctcgatggacgctgggaggtctttgttgttgaccgagcatttgaactcc |
| 69 | mIgG2a3S | gtttctagattatcatttacccggagtccgagagaagctcttagtcgt |
| | | Other Primers for different tail mutations and for multispecific fusion genes: |
| 70 | hIgG1-3ns-ns | gctagctccgtcgactttacccggagacagagagagg |
| 71 | K322S | gactggctgaatggcaaggagtacaagtgctcggtctccaacaaagccctc |
| 72 | K322AS | gagggctttgttggagaccgagcacttgtaagacttgccattcagccagtc |
| 73 | hIgG1N297S | ccgcgggaggagcagtacagcagcacgtaccgtgtggtcagcgtc |
| 74 | hIgG1N297S3 | gacgctgaccacacggtacgtgctgctgtactgctcctcccgcgg |
| 75 | mIgG2aNS | gatatctctagatttacccggagtccgagagaagctcttagtcgt |
| 76 | mIgG2a3ns-sal | gatatctccggagtcgactttacccggagtccgagagaagctcttag |

TABLE 1-continued

Primer Listing for RNase and DNase -Ig Fusion Gene Constructs

| SEQ ID NO: | Name | Sequence |
|---|---|---|
| 77 | mIgG2N297S5 | cacaaacccatagagaggattacagcagtactctccgggtggtc |
| 78 | mIgG2N297S3 | gaccacccggagagtactgctgtaatcctctctatgggtttgag |
| 79 | | |
| 80 | g4s4clnk3 | GAT ATC ACC GGT AGA ACC ACC TCC ACC ACT CCC ACC TCC TCC AGT GCC TCC |
| 81 | g4s4clnk5 | GTC GAC TCC GGA GGA GGT GGC TCA GGT GGT GGA GGC AGT GGA GGA GGT GG |
| 82 | Nlnkgly5 | aaagtcgacggagctagcagccccgtgaacgtgagcagccccagcgt g |
| 83 | Nlnkgly3 | cccatgatatcctgcacgctggggctgctc |
| 84 | hdnase1age | ACC GGT ATG AGG ATC TGC TCC TTC AAC GTC AGG TCC TTT GG |
| 85 | hdnase1L3-3S | AGA TCT TTA TCA GGA GCG TTT GCT CTT TGT TTT CTT CCT TAG |
| 86 | mdnase1L3-3S | TCT AGA TTA TCA GGA GCG ATT GCC TTT TTT TCT CTT TTT GAG AG |
| 87 | mdnase1L3-age | ACC GGT CTA AGG CTC TGC TCC TTC AAT GTG AGG TCC TTT GGA |
| 88 | mrib-L5' | gAT ACC ACC ggT Agg gAA TCT gCA gCA CAg AAg TTT CAg |
| 89 | mrib5X | AAA TCT AgA CCT CAA CCA ggT Agg gAA TCT gCA gCA CAg AAg TTT CAg |
| 90 | mrib3X | TCT AgA CTA TCA CAC AgT AgC ATC AAA gTg gAC Tgg TAC gTA |
| 91 | hRNaseG88D-S | agactgccgcctgacaaacgactccaggtaccc |
| 92 | hRNAseG88D-AS | gggtacctggagtcgtttgtcaggcggcagtct |
| 93 | g4s5-5-1 | GGC TCA GGT GGT GGA GGA TCT GGA GGA GGT GGC TCA GGT GGT GGA GGA TCT G |
| 94 | g4s5-2s | GTT AGA TCT CTC CGG AGG AGG TGG CTC AGG TGG TGG AGG ATC TGG A |
| 95 | g4s5-asxho | CTC GAG ACT CCC ACC TCC TCC AGA TCC TCC ACC ACC TGA GCC ACC T |
| 96 | g4s4-5' | AAA GAT CTC TCC GGA GGA GGT GGC TCA GGT GGT GGA GGA TCT GGA GGA GG |
| 97 | g4s4-3' | CTC GAG ACC GGT AGA ACC ACC TCC ACC ACT CCC ACC TCC TCC AGA TCC TC |
| 98 | g4s5-5 | GTT AGA TCT CTC CGG AGG AGG TGG CTC A |
| 99 | g4s5-3 | ACC GGT CTC GAG ACT CCC ACC TCC TCC AGA TC |

TABLE 2

| SEQ ID NO: | DESCRIPTION | SEQUENCE (NUCLEOTIDE SEQUENCES ARE 5'-3') |
|---|---|---|
| 100 | g4s4lnk | agatctctccggaggaggtggctcaggtggtggaggatctggaggaggtgggag tggtggaggtggttctaccggtctcgag |

TABLE 2-continued

| SEQ ID NO: | DESCRIPTION | SEQUENCE (NUCLEOTIDE SEQUENCES ARE 5'-3') |
|---|---|---|
| 101 | G4S5-1 | agatctctccggaggaggtggctcaggtggtggaggatctggaggaggtggctc aggtggtggaggatctggaggaggtgggagtaccggtctcgag |
| 102 | G4S5-2 | agatctctccggaggaggtggctcaggtggtggaggatctggaggaggtggctc aggtggtggaggatctggaggaggtgggagtctcgag |
| 103 | 3'hRNase G88D | gtcgacggagctagcagccccgtgaacgtgagcagccccagcgtgcaggatatc ccttccctgggcaaggaatcccgggccaagaaattccagcggcagcatatggac tcagacagttcccccagcagcagctccacctactgtaaccaaatgatgaggcgc cggaatatgacacaggggcggtgcaaaccagtgaacacctttgtgcacgagccc ctggtagatgtccagaatgtctgtttccaggaaaaggtcacctgcaagaacggg cagggcaactgctacaagagcaactccagcatgcacatcacagactgccgcctg acaaacgactccaggtaccccaactgtgcataccggaccagcccgaaggagaga cacatcattgtggcctgtgaagggagcccatatgtgccagtccactttgatgct tctgtggaggactctacctaataatctaga |
| 104 | hDNase1-3'-G105R; A114F | gatatcctgaagatcgcagccttcaacatccagacatttggggagaccaagatg tccaatgccaccctcgtcagctacattgtgcagatcctgagccgctatgacatc gccctggtccaggaggtcagagacagccacctgactgccgtggggaagctgctg gacaacctcaatcaggatgcaccagacacctatcactacgtggtcagtgagcca ctgggacggaacagctataaggagcgctacctgttcgtgtacaggcctgaccag gtgtctgcggtggacagctactactacgatgatggctgcgagccctgcaggaac gacaccttcaaccgagagccattcattgtcaggttcttctcccggttcacagag gtcagggagtttgccattgttcccctgcatgcggcccccggggacgcagtagcc gagatcgacgctctctatgacgtctacctggatgtccaagagaaatggggcttg gaggacgtcatgttgatgggcgacttcaatgcgggctgcagctatgtgagaccc tcccagtggtcatccatccgcctgtggacaagccccaccttccagtggctgatc cccgacagcgctgacaccacagctacacccacgcactgtgcctatgacaggatc gtggttgcagggatgctgctccgaggcgccgttgttcccgactcggctcttccc tttaacttccaggctgcctatggcctgagtgaccaactggcccaagccatcagt gaccactatccagtggaggtgatgctgaagtgataatctaga |
| 105 | hDNase1-3'-WT | gatatcctgaagatcgcagccttcaacatccagacatttggggagaccaagatg tccaatgccaccctcgtcagctacattgtgcagatcctgagccgctatgacatc gccctggtccaggaggtcagagacagccacctgactgccgtggggaagctgctg gacaacctcaatcaggatgcaccagacacctatcactacgtggtcagtgagcca ctgggacggaacagctataaggagcgctacctgttcgtgtacaggcctgaccag gtgtctgcggtggacagctactactacgatgatggctgcgagccctgcgggaac gacaccttcaaccgagagccagccattgtcaggttcttctcccggttcacagag gtcagggagtttgccattgttcccctgcatgcggcccccggggacgcagtagcc gagatcgacgctctctatgacgtctacctggatgtccaagagaaatggggcttg gaggacgtcatgttgatgggcgacttcaatgcgggctgcagctatgtgagaccc tcccagtggtcatccatccgcctgtggacaagccccaccttccagtggctgatc cccgacagcgctgacaccacagctacacccacgcactgtgcctatgacaggatc gtggttgcagggatgctgctccgaggcgccgttgttcccgactcggctcttccc tttaacttccaggctgcctatggcctgagtgaccaactggcccaagccatcagt gaccactatccagtggaggtgatgctgaaatgataatctaga |
| 106 | hDNase1-3'A114F | gatatcctgaagatcgcagccttcaacatccagacatttggggagaccaagatg tccaatgccaccctcgtcagctacattgtgcagatcctgagccgctatgacatc gccctggtccaggaggtcagagacagccacctgactgccgtggggaagctgctg gacaacctcaatcaggatgcaccagacacctatcactacgtggtcagtgagcca ctgggacggaacagctataaggagcgctacctgttcgtgtacaggcctgaccag gtgtctgcggtggacagctactactacgatgatggctgcgagccctgcgggaac gacaccttcaaccgagagccattcattgtcaggttcttctcccggttcacagag gtcagggagtttgccattgttcccctgcatgcggcccccggggacgcagtagcc gagatcgacgctctctatgacgtctacctggatgtccaagagaaatggggctta gaggacgtcatgttgatgggcgacttcaatgcgggctgcagctatgtgagaccc tcccagtggtcatccatccgcctgtggacaagccccaccttccagtggctgatc cccgacagcgctgacaccacagctacacccacgcactgtgcctatgacaggatc gtggttgcagggatgctgctccgaggcgccgttgttcccgactcggctcttccc tttaacttccaggctgcctatggcctgagtgaccaactggcccaagccatcagt gaccactatccagtggaggtgatgctgaagtgataatctaga |
| 107 | hDNase1-5'-G105R; A114F | accggtctgaagatcgcagccttcaacatccagacatttggggagaccaagatg tccaatgccaccctcgtcagctacattgtgcagatcctgagccgctatgacatc gccctggtccaggaggtcagagacagccacctgactgccgtggggaagctgctg gacaacctcaatcaggatgcaccagacacctatcactacgtggtcagtgagcca ctgggacggaacagctataaggagcgctacctgttcgtgtacaggcctgaccag gtgtctgcggtggacagctactactacgatgatggctgcgagccctgcaggaac gacaccttcaaccgagagccattcattgtcaggttcttctcccggttcacagag gtcagggagtttgccattgttcccctgcatgcggcccccggggacgcagtagcc gagatcgacgctctctatgacgtctacctggatgtccaagagaaatggggcttg gaggacgtcatgttgatgggcgacttcaatgcgggctgcagctatgtgagaccc tcccagtggtcatccatccgcctgtggacaagccccaccttccagtggctgatc cccgacagcgctgacaccacagctacacccacgcactgtgcctatgacaggatc gtggttgcagggatgctgctccgaggcgccgttgttcccgactcggctcttccc |

TABLE 2-continued

| SEQ ID NO: | DESCRIPTION | SEQUENCE (NUCLEOTIDE SEQUENCES ARE 5'-3') |
|---|---|---|
| | | tttaacttccaggctgcctatggcctgagtgaccaactggcccaagccatcagt<br>gaccactatccagtggaggtgatgctgaaagatctcgag |
| 108 | hDNase1-5'-WT | accggtctgaagatcgcagccttcaacatccagacatttggggagaccaagatg<br>tccaatgccaccctcgtcagctacattgtgcagatcctgagccgctatgacatc<br>gccctggtccaggaggtcagagacagccacctgactgccgtggggaagctgctg<br>gacaacctcaatcaggatgcaccagacacctatcactacgtggtcagtgagcca<br>ctgggacggaacagctataaggagcgctacctgttcgtgtacaggcctgaccag<br>gtgtctgcggtggacagctactactacgatgatggctgcgagccctgcgggaac<br>gacaccttcaaccgagagccagccattgtcaggttcttctcccggttcacagag<br>gtcagggagtttgccattgttcccctgcatgcggcccgggggacgcagtagcc<br>gagatcgacgctctctatgacgtctacctggatgtccaagagaaatggggcttg<br>gaggacgtcatgttgatgggcgacttcaatgcgggctgcagctatgtgagaccc<br>tcccagtggtcatccatccgcctgtggacaagccccaccttccagtggctgatc<br>cccgacagcgctgacaccacagctacacccacgcactgtgcctatgacaggatc<br>gtggttgcagggatgctgctccgaggcgccgttgttcccgactcggctcttccc<br>tttaacttccaggctgcctatggcctgagtgaccaactggcccaagccatcagt<br>gaccactatccagtggaggtgatgctgaaagatctcgag |
| 109 | hDNase1-5'-A114F | accggtctgaagatcgcagccttcaacatccagacatttggggagaccaagatg<br>tccaatgccaccctcgtcagctacattgtgcagatcctgagccgctatgacatc<br>gccctggtccaggaggtcagagacagccacctgactgccgtggggaagctgctg<br>gacaacctcaatcaggatgcaccagacacctatcactacgtggtcagtgagcca<br>ctgggacggaacagctataaggagcgctacctgttcgtgtacaggcctgaccag<br>gtgtctgcggtggacagctactactacgatgatggctgcgagccctgcgggaac<br>gacaccttcaaccgagagccattcattgtcaggttcttctcccggttcacagag<br>gtcagggagtttgccattgttcccctgcatgcggcccgggggacgcagtagcc<br>gagatcgacgctctctatgacgtctacctggatgtccaagagaaatggggctta<br>gaggacgtcatgttgatgggcgacttcaatgcgggctgcagctatgtgagaccc<br>tcccagtggtcatccatccgcctgtggacaagccccaccttccagtggctgatc<br>cccgacagcgctgacaccacagctacacccacgcactgtgcctatgacaggatc<br>gtggttgcagggatgctgctccgaggcgccgttgttcccgactcggctcttccc<br>tttaacttccaggctgcctatggcctgagtgaccaactggcccaagccatcagt<br>gaccactatccagtggaggtgatgctgaaagatctcgag |
| 110 | hIgG1WT | agatctcgagcccaaatcttctgacaaaactcacacatgtccaccgtgcccagc<br>acctgaactcctggggggaccgtcagtcttcctcttccccccaaaacccaagga<br>caccctcatgatctcccggacccctgaggtcacatgcgtggtggtggacgtgag<br>ccacgaagaccctgaggtcaagttcaactggtacgtggacggcgtggaggtgca<br>taatgccaagacaaagccgcgggaggagcagtacaacagcacgtaccgtgtggt<br>cagcgtcctcaccgtcctgcaccaggactggctgaatggcaaggagtacaagtg<br>caaggtctccaacaaagccctcccagcccccatcgagaaaaccatctccaaagc<br>caaagggcagccccgagaaccacaggtgtacaccctgcccccatcccgggatga<br>gctgaccaagaaccaggtcagcctgacctgcctggtcaaaggcttctatcccag<br>cgacatcgccgtggagtgggagagcaatgggcagccggagaacaactacaagac<br>cacgcctcccgtgctggactccgacggctccttcttcctctacagcaagctcac<br>cgtggacaagagcaggtggcagcaggggaacgtcttctcatgctccgtgatgca<br>tgaggctctgcacaaccactacacgcagaagagcctctctctgtctccgggtaa<br>atgataatctaga |
| 111 | hDNase1 + VK3LP | gttaagcttgccaccatggaaaccccagcgcagcttctcttcctcctgctactc<br>tggctcccagataccaccggtctgaagatcgcagccttcaacatccagacattt<br>ggggagaccaagatgtccaatgccaccctcgtcagctacattgtgcagatcctg<br>agccgctatgacatcgccctggtccaggaggtcagagacagccacctgactgcc<br>gtggggaagctgctggacaacctcaatcaggatgcaccagacacctatcactac<br>gtggtcagtgagccactgggacggaacagctataaggagcgctacctgttcgtg<br>tacaggcctgaccaggtgtctgcggtggacagctactactacgatgatggctgc<br>gagccctgcgggaacgacaccttcaaccgagagccagccattgtcaggttcttc<br>tcccggttcacagaggtcagggagtttgccattgttcccctgcatgcggccccg<br>ggggacgcagtagccgagatcgacgctctctatgacgtctacctggatgtccaa<br>gagaaatggggcttggaggacgtcatgttgatgggcgacttcaatgcgggctgc<br>agctatgtgagaccctcccagtggtcatccatccgcctgtggacaagccccacc<br>ttccagtggctgatccccgacagcgctgacaccacagctacacccacgcactgt<br>gcctatgacaggatcgtggttgcagggatgctgctccgaggcgccgttgttccc<br>gactcggctcttccctttaacttccaggctgcctatggcctgagtgaccaactg<br>gcccaagccatcagtgaccactatccagtggaggtgatgctgaagtga |
| 112 | hDNase1L3 | atgtcacgggagctggccccactgctgcttctcctcctctccatccacagcgcc<br>ctggccatgaggatctgctccttcaacgtcaggtcctttggggaaagcaagcag<br>gaagacaagaatgccatggatgtcattgtgaaggtcatcaaacgctgtgacatc<br>atactcgtgatggaaatcaaggacagcaacaacaggatctgccccatactgatg<br>gagaagctgaacagaaattcaaggagaggcataacatacaactatgtgattagc<br>tctcggcttggaagaaacacatataaagaacaatatgcctttctctacaaggaa<br>aagctggtgtctgtgaagaggagttatcactaccatgactatcaggatggagac<br>gcagatgtgttttccagggagccctttgtggtctggttccaatctccccacact<br>gctgtcaaagacttcgtgattatcccctgcacaccaccccagagacatccgtt<br>aaggagatcgatgagttggttgaggtctacacggacgtgaaacaccgctggaag |

TABLE 2-continued

| SEQ ID NO: | DESCRIPTION | SEQUENCE (NUCLEOTIDE SEQUENCES ARE 5'-3') |
|---|---|---|
| | | gcggagaatttcattttcatgggtgacttcaatgccggctgcagctacgtcccc |
| | | aagaaggcctggaagaacatccgcttgaggactgaccccaggtttgtttggctg |
| | | atcggggaccaagaggacaccacggtgaagaagagcaccaactgtgcatatgac |
| | | aggattgtgcttagaggacaagaaatcgtcagttctgttgttcccaagtcaaac |
| | | agtgtttttgacttccagaaagcttacaagctgactgaagaggaggccctggat |
| | | gtcagcgaccactttccagttgaatttaaactacagtcttcaagggccttcacc |
| | | aacagcaaaaaatctgtcactctaaggaagaaaacaaagagcaaacgctcctag |
| 113 | human | atgggtctggagaagtctcttgtccggctccttctgcttgtcctgatactgctg |
| | pancreatic | gtgctgggctgggtccagccttccctgggcaaggaatcccgggccaagaaattc |
| | ribo- | cagcggcagcatatggactcagacagttcccccagcagcagctccacctactgt |
| | nuclease | aaccaaatgatgaggcgccggaatatgacacaggggcggtgcaaaccagtgaac |
| | | acctttgtgcacgagcccctggtagatgtccagaatgtctgtttccaggaaaag |
| | | gtcacctgcaagaacgggcagggcaactgctacaagagcaactccagcatgcac |
| | | atcacagactgccgcctgacaaacggctccaggtaccccaactgtgcataccgg |
| | | accagcccgaaggagagacacatcattgtggcctgtgaagggagcccatatgtg |
| | | ccagtccactttgatgctactgtgtag |
| 114 | huVK3LP + | gttaagcttgccaccatggaaaccccagcgcagcttctcttcctcctgctactc |
| | mrib1 + | tggctcccagataccaccggtagggaatctgcagcacagaagtttcagcggcag |
| | mIgG2A-C- | cacatggatccagatggttcctccatcaacagccccacctactgcaaccaaatg |
| | 2S | atgaaacgccgggatatgacaaatgggtcatgcaagcccgtgaacaccttcgtg |
| | | catgagcccttggcagatgtccaggccgtctgctcccaggaaaatgtcacctgc |
| | | aagaacaggaagagcaactgctacaagagcagctctgccctgcacatcactgac |
| | | tgccacctgaagggcaactccaagtatcccaactgtgactacaagaccactcaa |
| | | taccagaagcacatcattgtggcctgtgaagggaacccctacgtaccagtccac |
| | | tttgatgctactgtgctcgagcccagaggtctcacaatcaagccctctcctcca |
| | | tgcaaatgcccagcacctaacctcttgggtggatcatccgtcttcatcttccct |
| | | ccaaagatcaaggatgtactcatgatctccctgagccccatggtcacatgtgtg |
| | | gtggtggatgtgagcgaggatgacccagacgtccagatcagctggtttgtgaac |
| | | aacgtggaagtacacacagctcagacacaaacccatagagaggattacaacagt |
| | | actctccgggtggtcagtgccctccccatccagcaccaggactggatgagtggc |
| | | aaggagttcaaatgctcggtcaacaacaaagacctcccagcgtccatcgagaga |
| | | accatctcaaaacccagagggccagtaagagctccacaggtatatgtcttgcct |
| | | ccaccagcagaagagatgactaagaaagagttcagtctgacctgcatgatcaca |
| | | ggcttcttacctgccgaaattgctgtggactggaccagcaatgggcgtacagag |
| | | caaaactacaagaacaccgcaacagtcctggactctgatggttcttacttcatg |
| | | tacagcaagctcagagtacaaaagagcacttgggaaagaggaagtcttttcgcc |
| | | tgctcagtggtccacgagggtctgcacaatcaccttacgactaagagcttctct |
| | | cggactccgggtaaatgataatctagaa |
| 115 | huVK3LP- | aagcttgccgccatggaaaccccagcgcagcttctcttcctcctgctactctgg |
| | hRNaseWT- | ctcccagataccaccggtaaggaatcccgggccaagaaattccagcggcagcat |
| | hIgGWt- | atggactcagacagttcccccagcagcagctccacctactgtaaccaaatgatg |
| | NLG- | aggcgccggaatatgacacaggggcggtgcaaaccagtgaacacctttgtgcac |
| | hDNAse1- | gagcccctggtagatgtccagaatgtctgtttccaggaaaaggtcacctgcaag |
| | 105-114 | aacgggcagggcaactgctacaagagcaactccagcatgcacatcacagactgc |
| | | cgcctgacaaacggctccaggtaccccaactgtgcataccggaccagcccgaag |
| | | gagagacacatcattgtggcctgtgaagggagcccatatgtgccagtccacttt |
| | | gatgcttctgtggaggactctacagatctcgagcccaaatcttctgacaaaact |
| | | cacacatgtccaccgtgcccagcacctgaactcctggggggaccgtcagtcttc |
| | | ctcttccccccaaaacccaaggacaccctcatgatctcccggacccctgaggtc |
| | | acatgcgtggtggtggacgtgagccacgaagaccctgaggtcaagttcaactgg |
| | | tacgtggacggcgtggaggtgcataatgccaagacaaagccgcgggaggagcag |
| | | tacaacagcacgtaccgtgtggtcagcgtcctcaccgtcctgcaccaggactgg |
| | | ctgaatggcaaggagtacaagtgcaaggtctccaacaaagccctcccagccccc |
| | | atcgagaaaaccatctccaaagccaaagggcagccccgagaaccacaggtgtac |
| | | accctgcccccatcccgggatgagctgaccaagaaccaggtcagcctgacctgc |
| | | ctggtcaaaggcttctatcccagcgacatcgccgtggagtgggagagcaatggg |
| | | cagccggagaacaactacaagaccacgcctcccgtgctggactccgacggctcc |
| | | ttcttcctctacagcaagctcaccgtggacaagagcaggtggcagcaggggaac |
| | | gtcttctcatgctccgtgatgcatgagggtctgcacaaccactacacgcagaag |
| | | agcctctctctgtctccgggtaaagtcgacggtgctagcagccatgtgaatgtg |
| | | agcagccctagcgtgcaggatatcctgaagatcgcagccttcaacatccagaca |
| | | tttggggagaccaagatgtccaatgccaccctcgtcagctacattgtgcagatc |
| | | ctgagccgctatgacatcgccctggtccaggaggtcagagacagccacctgact |
| | | gccgtggggaagctgctggacaacctcaatcaggatgcaccagacacctatcac |
| | | tacgtggtcagtgagccactgggacggaacagctataaggagcgctacctgttc |
| | | gtgtacaggcctgaccaggtgtctgcggtggacagctactactacgatgatggc |
| | | tgcgagccctgcgggaacgacaccttcaaccgagagccagccattgtcaggttc |
| | | ttctcccggttcacagaggtcagggagtttgccattgttcccctgcatgcggcc |
| | | ccgggggacgcagtagccgagatcgacgctctctatgacgtctacctggatgtc |
| | | caagagaaatggggctcggaggacgtcatgttgatgggcgacttcaatgcgggc |
| | | tgcagctatgtgagaccctcccagtggtcatccatccgcctgtggacaagcccc |
| | | accttccagtggctgatccccgacagcgctgacaccacagctacacccacgcac |
| | | tgtgcctatgacaggatcgtggttgcagggatgctgctccgaggcgccgttgtt |
| | | cccgactcggctcttccctttaacttccagnctgcctatggcctgagtgaccaa |

TABLE 2-continued

| SEQ ID NO: | DESCRIPTION | SEQUENCE (NUCLEOTIDE SEQUENCES ARE 5'-3') |
|---|---|---|
| | | ctggcccaagccatcagtgaccactatccagtggaggtgatgctgaagtgataa<br>tctaga |
| 116 | huVK3LP-<br>hRNaseWT-<br>hIgGWT-<br>NLG-<br>hDNase1-<br>114F | aagcttgccgccatggaaaccccagcgcagcttctcttcctcctgctactctgg<br>ctcccagataccaccggtaaggaatcccgggccaagaaattccagcggcagcat<br>atggactcagacagttcccccagcagcagctccacctactgtaaccaaatgatg<br>aggcgccggaatatgacacaggggcggtgcaaaccagtgaacacctttgtgcac<br>gagcccctggtagatgtccagaatgtctgtttccaggaaaaggtcacctgcaag<br>aacgggcagggcaactgctacaagagcaactccagcatgcacatcacagactgc<br>cgcctgacaaacggctccaggtaccccaactgtgcataccggaccagcccgaag<br>gagagacacatcattgtggcctgtgaagggagcccatatgtgccagtccacttt<br>gatgcttctgtggaggactctacagatctcgagcccaaatcttctgacaaaact<br>cacacatgtccaccgtgcccagcacctgaactcctggggggaccgtcagtcttc<br>ctcttccccccaaaacccaaggacaccctcatgatctcccggacccctgaggtc<br>acatgcgtggtggtggacgtgagccacgaagaccctgaggtcaagttcaactgg<br>tacgtggacggcgtggaggtgcataatgccaagacaaagccgcgggaggagcag<br>tacaacagcacgtaccgtgtggtcagcgtcctcaccgtcctgcaccaggactgg<br>ctgaatggcaaggagtacaagtgcaaggtctccaacaaagccctcccagccccc<br>atcgagaaaaccatctccaaagccaaagggcagccccgagaaccacaggtgtac<br>accctgcccccatcccgggatgagctgaccaagaaccaggtcagcctgacctgc<br>ctggtcaaaggcttctatcccagcgacatcgccgtggagtgggagagcaatggg<br>cagccggagaacaactacaagaccacgcctcccgtgctggactccgacggctcc<br>ttcttcctctacagcaagctcaccgtggacaagagcaggtggcagcaggggaac<br>gtcttctcatgctccgtgatgcatgagggtctgcacaaccactacacgcagaag<br>agcctctctctgtctccgggtaaagtcgacggtgctagcagccatgtgaatgtg<br>agcagccctagcgtgcaggatatcctgaagatcgcagccttcaacatccagaca<br>tttggggagaccaagatgtccaatgccaccctcgtcagctacattgtgcagatc<br>ctgagccgctatgacatcgccctggtccaggaggtcagagacagccacctgact<br>gccgtggggaagctgctggacaacctcaatcaggatgcaccagacacctatcac<br>tacgtggtcagtgagccactgggacggaacagctataaggagcgctacctgttc<br>gtgtacaggcctgaccaggtgtctgcggtggacagctactactacgatgatggc<br>tgcgagccctgcgggaacgacaccttcaaccgagagccattcattgtcaggttc<br>ttctcccggttcacagaggtcagggagtttgccattgttcccctgcatgcggcc<br>ccgggggacgcagtagccgagatcgacgctctctatgacgtctacctggatgtc<br>caagagaaatggggcttagaggacgtcatgttgatgggcgacttcaatgcgggc<br>tgcagctatgtgagaccctcccagtggtcatccatccgcctgtggacaagcccc<br>accttccagtggctgatccccgacagcgctgacaccacagctacacccacgcac<br>tgtgcctatgacaggatcgtggttgcagggatgctgctccgaggcgccgttgtt<br>cccgactcggctcttccctttaacttccaggctgcctatggcctgagtgaccaa<br>ctggcccaagccatcagtgaccactatccagtggaggtgatgctgaagtgataa<br>tctaga |
| 117 | huVK3LP-<br>hRNaseWT-<br>hIgGWT-<br>NLG-<br>hDNase1-<br>WT | aagcttgccgccatggaaaccccagcgcagcttctcttcctcctgctactctgg<br>ctcccagataccaccggtaaggaatcccgggccaagaaattccagcggcagcat<br>atggactcagacagttcccccagcagcagctccacctactgtaaccaaatgatg<br>aggcgccggaatatgacacaggggcggtgcaaaccagtgaacacctttgtgcac<br>gagcccctggtagatgtccagaatgtctgtttccaggaaaaggtcacctgcaag<br>aacgggcagggcaactgctacaagagcaactccagcatgcacatcacagactgc<br>cgcctgacaaacggctccaggtaccccaactgtgcataccggaccagcccgaag<br>gagagacacatcattgtggcctgtgaagggagcccatatgtgccagtccacttt<br>gatgcttctgtggaggactctacagatctcgagcccaaatcttctgacaaaact<br>cacacatgtccaccgtgcccagcacctgaactcctggggggaccgtcagtcttc<br>ctcttccccccaaaacccaaggacaccctcatgatctcccggacccctgaggtc<br>acatgcgtggtggtggacgtgagccacgaagaccctgaggtcaagttcaactgg<br>tacgtggacggcgtggaggtgcataatgccaagacaaagccgcgggaggagcag<br>tacaacagcacgtaccgtgtggtcagcgtcctcaccgtcctgcaccaggactgg<br>ctgaatggcaaggagtacaagtgcaaggtctccaacaaagccctcccagccccc<br>atcgagaaaaccatctccaaagccaaagggcagccccgagaaccacaggtgtac<br>accctgcccccatcccgggatgagctgaccaagaaccaggtcagcctgacctgc<br>ctggtcaaaggcttctatcccagcgacatcgccgtggagtgggagagcaatggg<br>cagccggagaacaactacaagaccacgcctcccgtgctggactccgacggctcc<br>ttcttcctctacagcaagctcaccgtggacaagagcaggtggcagcaggggaac<br>gtcttctcatgctccgtgatgcatgagggtctgcacaaccactacacgcagaag<br>agcctctctctgtctccgggtaaagtcgacggtgctagcagccatgtgaatgtg<br>agcagccctagcgtgcaggatatcctgaagatcgcagccttcaacatccagaca<br>tttggggagaccaagatgtccaatgccaccctcgtcagctacattgtgcagatc<br>ctgagccgctatgacatcgccctggtccaggaggtcagagacagccacctgact<br>gccgtggggaagctgctggacaacctcaatcaggatgcaccagacacctatcac<br>tacgtggtcagtgagccactgggacggaacagctataaggagcgctacctgttc<br>gtgtacaggcctgaccaggtgtctgcggtggacagctactactacgatgatggc<br>tgcgagccctgcgggaacgacaccttcaaccgagagccagccattgtcaggttc<br>ttctcccggttcacagaggtcagggagtttgccattgttcccctgcatgcggcc<br>ccgggggacgcagtagccgagatcgacgctctctatgacgtctacctggatgtc<br>caagagaaatggggcttggaggacgtcatgttgatgggcgacttcaatgcgggc<br>tgcagctatgtgagaccctcccagtggtcatccatccgcctgtggacaagcccc<br>accttccagtggctgatccccgacagcgctgacaccacagctacacccacgcac<br>tgtgcctatgacaggatcgtggttgcagggatgctgctccgaggcgccgttgtt |

TABLE 2-continued

| SEQ ID NO: | DESCRIPTION | SEQUENCE (NUCLEOTIDE SEQUENCES ARE 5'-3') |
|---|---|---|
| | | cccgactcggctcttccctttaacttccaggctgcctatggcctgagtgaccaa<br>ctggcccaagccatcagtgaccactatccagtggaggtgatgctgaaatgataa<br>tctaga |
| 118 | hVK3LP-hDNase1 (WT)-hIgG1WT | gttaagcttgccaccatggaaaccccagcgcagcttctcttcctcctgctactc<br>tggctcccagataccaccggtctgaagatcgcagccttcaacatccagacattt<br>ggggagaccaagatgtccaatgccaccctcgtcagctacattgtgcagatcctg<br>agccgctatgacatcgccctggtccaggaggtcagagacagccacctgactgcc<br>gtggggaagctgctggacaacctcaatcaggatgcaccagacacctatcactac<br>gtggtcagtgagccactgggacggaacagctataaggagcgctacctgttcgtg<br>tacaggcctgaccaggtgtctgcggtggacagctactactacgatgatggctgc<br>gagccctgcgggaacgacaccttcaaccgagagccagccattgtcaggttcttc<br>tcccggttcacagaggtcagggagtttgccattgttcccctgcatgcggccccg<br>ggggacgcagtagccgagatcgacgctctctatgacgtctacctggatgtccaa<br>gagaaatggggcttggaggacgtcatgttgatgggcgacttcaatgcgggctgc<br>agctatgtgagaccctcccagtggtcatccatccgcctgtggacaagccccacc<br>ttccagtggctgatccccgacagcgctgacaccacagctacacccacgcactgt<br>gcctatgacaggatcgtggttgcagggatgctgctccgaggcgccgttgttccc<br>gactcggctcttccctttaacttccaggctgcctatggcctgagtgaccaactg<br>gcccaagccatcagtgaccactatccagtggaggtgatgctgaaagatctcgag<br>cccaaatcttctgacaaaactcacacatgtccaccgtgcccagcacctgaactc<br>ctggggggaccgtcagtcttcctcttccccccaaaacccaaggacaccctcatg<br>atctcccggacccctgaggtcacatgcgtggtggtggacgtgagccacgaagac<br>cctgaggtcaagttcaactggtacgtggacggcgtggaggtgcataatgccaag<br>acaaagccgcgggaggagcagtacaacagcacgtaccgtgtggtcagcgtcctc<br>accgtcctgcaccaggactggctgaatggcaaggagtacaagtgcaaggtctcc<br>aacaaagccctcccagcccccatcgagaaaaccatctccaaagccaaagggcag<br>ccccgagaaccacaggtgtacaccctgcccccatcccgggatgagctgaccaag<br>aaccaggtcagcctgacctgcctggtcaaaggcttctatcccagcgacatcgcc<br>gtggagtgggagagcaatgggcagccggagaacaactacaagaccacgcctccc<br>gtgctggactccgacggctccttcttcctctacagcaagctcaccgtggacaag<br>agcaggtggcagcaggggaacgtcttctcatgctccgtgatgcatgaggctctg<br>cacaaccactacacgcagaagagcctctctctgtctccgggtaaatgataatct<br>aga |
| 119 | hVK3LP-hDNase1-A114F-hIgG1WT | gttaagcttgccaccatggaaaccccagcgcagcttctcttcctcctgctactc<br>tggctcccagataccaccggtctgaagatcgcagccttcaacatccagacattt<br>ggggagaccaagatgtccaatgccaccctcgtcagctacattgtgcagatcctg<br>agccgctatgacatcgccctggtccaggaggtcagagacagccacctgactgcc<br>gtggggaagctgctggacaacctcaatcaggatgcaccagacacctatcactac<br>gtggtcagtgagccactgggacggaacagctataaggagcgctacctgttcgtg<br>tacaggcctgaccaggtgtctgcggtggacagctactactacgatgatggctgc<br>gagccctgcgggaacgacaccttcaaccgagagccattcattgtcaggttcttc<br>tcccggttcacagaggtcagggagtttgccattgttcccctgcatgcggccccg<br>ggggacgcagtagccgagatcgacgctctctatgacgtctacctggatgtccaa<br>gagaaatggggcttagaggacgtcatgttgatgggcgacttcaatgcgggctgc<br>agctatgtgagaccctcccagtggtcatccatccgcctgtggacaagccccacc<br>ttccagtggctgatccccgacagcgctgacaccacagctacacccacgcactgt<br>gcctatgacaggatcgtggttgcagggatgctgctccgaggcgccgttgttccc<br>gactcggctcttccctttaacttccaggctgcctatggcctgagtgaccaactg<br>gcccaagccatcagtgaccactatccagtggaggtgatgctgaaagatctcgag<br>cccaaatcttctgacaaaactcacacatgtccaccgtgcccagcacctgaactc<br>ctggggggaccgtcagtcttcctcttccccccaaaacccaaggacaccctcatg<br>atctcccggacccctgaggtcacatgcgtggtggtggacgtgagccacgaagac<br>cctgaggtcaagttcaactggtacgtggacggcgtggaggtgcataatgccaag<br>acaaagccgcgggaggagcagtacaacagcacgtaccgtgtggtcagcgtcctc<br>accgtcctgcaccaggactggctgaatggcaaggagtacaagtgcaaggtctcc<br>aacaaagccctcccagcccccatcgagaaaaccatctccaaagccaaagggcag<br>ccccgagaaccacaggtgtacaccctgcccccatcccgggatgagctgaccaag<br>aaccaggtcagcctgacctgcctggtcaaaggcttctatcccagcgacatcgcc<br>gtggagtgggagagcaatgggcagccggagaacaactacaagaccacgcctccc<br>gtgctggactccgacggctccttcttcctctacagcaagctcaccgtggacaag<br>agcaggtggcagcaggggaacgtcttctcatgctccgtgatgcatgaggctctg<br>cacaaccactacacgcagaagagcctctctctgtctccgggtaaatgataatct<br>aga |
| 120 | hVK3LP-hDNase1-G105R; A114F-(G4S)4-hIgG1WT | gttaagcttgccaccatggaaaccccagcgcagcttctcttcctcctgctactc<br>tggctcccagataccaccggtctgaagatcgcagccttcaacatccagacattt<br>ggggagaccaagatgtccaatgccaccctcgtcagctacattgtgcagatcctg<br>agccgctatgacatcgccctggtccaggaggtcagagacagccacctgactgcc<br>gtggggaagctgctggacaacctcaatcaggatgcaccagacacctatcactac<br>gtggtcagtgagccactgggacggaacagctataaggagcgctacctgttcgtg<br>tacaggcctgaccaggtgtctgcggtggacagctactactacgatgatggctgc<br>gagccctgcaggaacgacaccttcaaccgagagccattcattgtcaggttcttc<br>tcccggttcacagaggtcagggagtttgccattgttcccctgcatgcggccccg<br>ggggacgcagtagccgagatcgacgctctctatgacgtctacctggatgtccaa<br>gagaaatggggcttggaggacgtcatgttgatgggcgacttcaatgcgggctgc |

TABLE 2-continued

| SEQ ID NO: | DESCRIP-TION | SEQUENCE (NUCLEOTIDE SEQUENCES ARE 5'-3') |
|---|---|---|
| | | agctatgtgagaccctcccagtggtcatccatccgcctgtggacaagccccacc<br>ttccagtggctgatccccgacagcgctgacaccacagctacacccacgcactgt<br>gcctatgacaggatcgtggttgcagggatgctgctccgaggcgccgttgttccc<br>gactcggctcttccctttaacttccaggctgcctatggcctgagtgaccaactg<br>gcccaagccatcagtgaccactatccagtggaggtgatgctgaaagatctctcc<br>ggaggaggtggctcaggtggtggaggatctggaggaggtgggagtggtggaggt<br>ggttctaccggtctcgagcccaaatcttctgacaaaactcacacatgtccaccg<br>tgcccagcacctgaactcctggggggaccgtcagtcttcctcttccccccaaaa<br>cccaaggacaccctcatgatctcccggacccctgaggtcacatgcgtggtggtg<br>gacgtgagccacgaagaccctgaggtcaagttcaactggtacgtggacggcgtg<br>gaggtgcataatgccaagacaaagccgcgggaggagcagtacaacagcacgtac<br>cgtgtggtcagcgtcctcaccgtcctgcaccaggactggctgaatggcaaggag<br>tacaagtgcaaggtctccaacaaagccctcccagcccccatcgagaaaaccatc<br>tccaaagccaaagggcagccccgagaaccacaggtgtacaccctgcccccatcc<br>cgggatgagctgaccaagaaccaggtcagcctgacctgcctggtcaaaggcttc<br>tatcccagcgacatcgccgtggagtgggagagcaatgggcagccggagaacaac<br>tacaagaccacgcctcccgtgctggactccgacggctccttcttcctctacagc<br>aagctcaccgtggacaagagcaggtggcagcaggggaacgtcttctcatgctcc<br>gtgatgcatgaggctctgcacaaccactacacgcagaagagcctctctctgtct<br>ccgggtaaatgataatctaga |
| 121 | hVK3LP-<br>hDNase1-<br>G105R;<br>A114F-<br>(G4S)5-1-<br>hIgG1WT | gttaagcttgccaccatggaaaccccagcgcagcttctcttcctcctgctactc<br>tggctcccagataccaccggtctgaagatcgcagccttcaacatccagacattt<br>ggggagaccaagatgtccaatgccaccctcgtcagctacattgtgcagatcctg<br>agccgctatgacatcgccctggtccaggaggtcagagacagccacctgactgcc<br>gtggggaagctgctggacaacctcaatcaggatgcaccagacacctatcactac<br>gtggtcagtgagccactgggacggaacagctataaggagcgctacctgttcgtg<br>tacaggcctgaccaggtgtctgcggtggacagctactactacgatgatggctgc<br>gagccctgcaggaacgacaccttcaaccgagagccattcattgtcaggttcttc<br>tcccggttcacagaggtcagggagtttgccattgttcccctgcatgcggccccg<br>ggggacgcagtagccgagatcgacgctctctatgacgtctacctggatgtccaa<br>gagaaatggggcttggaggacgtcatgttgatgggcgacttcaatgcgggctgc<br>agctatgtgagaccctcccagtggtcatccatccgcctgtggacaagccccacc<br>ttccagtggctgatccccgacagcgctgacaccacagctacacccacgcactgt<br>gcctatgacaggatcgtggttgcagggatgctgctccgaggcgccgttgttccc<br>gactcggctcttccctttaacttccaggctgcctatggcctgagtgaccaactg<br>gcccaagccatcagtgaccactatccagtggaggtgatgctgaaagatctctcc<br>ggaggaggtggctcaggtggtggaggatctggaggaggtggctcaggtggtgga<br>ggatctggaggaggtgggagtaccggtctcgagcccaaatcttctgacaaaact<br>cacacatgtccaccgtgcccagcacctgaactcctggggggaccgtcagtcttc<br>ctcttccccccaaaacccaaggacaccctcatgatctcccggacccctgaggtc<br>acatgcgtggtggtggacgtgagccacgaagaccctgaggtcaagttcaactgg<br>tacgtggacggcgtggaggtgcataatgccaagacaaagccgcgggaggagcag<br>tacaacagcacgtaccgtgtggtcagcgtcctcaccgtcctgcaccaggactgg<br>ctgaatggcaaggagtacaagtgcaaggtctccaacaaagccctcccagccccc<br>atcgagaaaaccatctccaaagccaaagggcagccccgagaaccacaggtgtac<br>accctgcccccatcccgggatgagctgaccaagaaccaggtcagcctgacctgc<br>ctggtcaaaggcttctatcccagcgacatcgccgtggagtgggagagcaatggg<br>cagccggagaacaactacaagaccacgcctcccgtgctggactccgacggctcc<br>ttcttcctctacagcaagctcaccgtggacaagagcaggtggcagcaggggaac<br>gtcttctcatgctccgtgatgcatgaggctctgcacaaccactacacgcagaag<br>agcctctctctgtctccgggtaaatgataatctaga |
| 122 | hVK3LP-<br>hDNAse1-<br>G105R;<br>A114F-<br>(G4S)5-2-<br>hIgG1-WT | gttaagcttgccaccatggaaaccccagcgcagcttctcttcctcctgctactc<br>tggctcccagataccaccggtctgaagatcgcagccttcaacatccagacattt<br>ggggagaccaagatgtccaatgccaccctcgtcagctacattgtgcagatcctg<br>agccgctatgacatcgccctggtccaggaggtcagagacagccacctgactgcc<br>gtggggaagctgctggacaacctcaatcaggatgcaccagacacctatcactac<br>gtggtcagtgagccactgggacggaacagctataaggagcgctacctgttcgtg<br>tacaggcctgaccaggtgtctgcggtggacagctactactacgatgatggctgc<br>gagccctgcaggaacgacaccttcaaccgagagccattcattgtcaggttcttc<br>tcccggttcacagaggtcagggagtttgccattgttcccctgcatgcggccccg<br>ggggacgcagtagccgagatcgacgctctctatgacgtctacctggatgtccaa<br>gagaaatggggcttggaggacgtcatgttgatgggcgacttcaatgcgggctgc<br>agctatgtgagaccctcccagtggtcatccatccgcctgtggacaagccccacc<br>ttccagtggctgatccccgacagcgctgacaccacagctacacccacgcactgt<br>gcctatgacaggatcgtggttgcagggatgctgctccgaggcgccgttgttccc<br>gactcggctcttccctttaacttccaggctgcctatggcctgagtgaccaactg<br>gcccaagccatcagtgaccactatccagtggaggtgatgctgaaagatctctcc<br>ggaggaggtggctcaggtggtggaggatctggaggaggtggctcaggtggtgga<br>ggatctggaggaggtgggagtctcgagcccaaatcttctgacaaaactcacaca<br>tgtccaccgtgcccagcacctgaactcctggggggaccgtcagtcttcctcttc<br>cccccaaaacccaaggacaccctcatgatctcccggacccctgaggtcacatgc<br>gtggtggtggacgtgagccacgaagaccctgaggtcaagttcaactggtacgtg<br>gacggcgtggaggtgcataatgccaagacaaagccgcgggaggagcagtacaac<br>agcacgtaccgtgtggtcagcgtcctcaccgtcctgcaccaggactggctgaat<br>ggcaaggagtacaagtgcaaggtctccaacaaagccctcccagcccccatcgag |

TABLE 2-continued

| SEQ ID NO: | DESCRIPTION | SEQUENCE (NUCLEOTIDE SEQUENCES ARE 5'-3') |
|---|---|---|
| | | aaaaccatctccaaagccaaagggcagccccgagaaccacaggtgtacaccctg<br>cccccatcccgggatgagctgaccaagaaccaggtcagcctgacctgcctggtc<br>aaaggcttctatcccagcgacatcgccgtggagtgggagagcaatgggcagccg<br>gagaacaactacaagaccacgcctcccgtgctggactccgacggctccttcttc<br>ctctacagcaagctcaccgtggacaagagcaggtggcagcaggggaacgtcttc<br>tcatgctccgtgatgcatgaggctctgcacaaccactacacgcagaagagcctc<br>tctctgtctccgggtaaatgataatctaga |
| 123 | hVK3LP-hDNase1-G105R; A114F-hIgG1WT | gttaagcttgccaccatggaaaccccagcgcagcttctcttcctcctgctactc<br>tggctcccagataccaccggtctgaagatcgcagccttcaacatccagacattt<br>ggggagaccaagatgtccaatgccaccctcgtcagctacattgtgcagatcctg<br>agccgctatgacatcgccctggtccaggaggtcagagacagccacctgactgcc<br>gtggggaagctgctggacaacctcaatcaggatgcaccagacacctatcactac<br>gtggtcagtgagccactgggacggaacagctataaggagcgctacctgttcgtg<br>tacaggcctgaccaggtgtctgcggtggacagctactactacgatgatggctgc<br>gagccctgcaggaacgacaccttcaaccgagagccattcattgtcaggttcttc<br>tcccggttcacagaggtcagggagtttgccattgttcccctgcatgcggccccg<br>ggggacgcagtagccgagatcgacgctctctatgacgtctacctggatgtccaa<br>gagaaatggggcttggaggacgtcatgttgatgggcgacttcaatgcgggctgc<br>agctatgtgagaccctcccagtggtcatccatccgcctgtggacaagccccacc<br>ttccagtggctgatccccgacagcgctgacaccacagctacacccacgcactgt<br>gcctatgacaggatcgtggttgcagggatgctgctccgaggcgccgttgttccc<br>gactcggctcttccctttaacttccaggctgcctatggcctgagtgaccaactg<br>gcccaagccatcagtgaccactatccagtggaggtgatgctgaaagatctcgag<br>cccaaatcttctgacaaaactcacacatgtccaccgtgcccagcacctgaactc<br>ctggggggaccgtcagtcttcctcttccccccaaaacccaaggacaccctcatg<br>atctcccggacccctgaggtcacatgcgtggtggtggacgtgagccacgaagac<br>cctgaggtcaagttcaactggtacgtggacggcgtggaggtgcataatgccaag<br>acaaagccgcgggaggagcagtacaacagcacgtaccgtgtggtcagcgtcctc<br>accgtcctgcaccaggactggctgaatggcaaggagtacaagtgcaaggtctcc<br>aacaaagccctcccagcccccatcgagaaaaccatctccaaagccaaagggcag<br>ccccgagaaccacaggtgtacaccctgcccccatcccgggatgagctgaccaag<br>aaccaggtcagcctgacctgcctggtcaaaggcttctatcccagcgacatcgcc<br>gtggagtgggagagcaatgggcagccggagaacaactacaagaccacgcctccc<br>gtgctggactccgacggctccttcttcctctacagcaagctcaccgtggacaag<br>agcaggtggcagcaggggaacgtcttctcatgctccgtgatgcatgaggctctg<br>cacaaccactacacgcagaagagcctctctctgtctccgggtaaatgataatct<br>aga |
| 124 | hVK3LP-hRNase (MT)-hIgG1WT | gttaagcttgccaccatggaaaccccagcgcagcttctcttcctcctgctactc<br>tggctcccagataccaccggtaaggaatcccgggccaagaaattccagcggcag<br>catatggactcagacagttcccccagcagcagctccacctactgtaaccaaatg<br>atgaggcgccggaatatgacacaggggcggtgcaaaccagtgaacacctttgtg<br>cacgagcccctggtagatgtccagaatgtctgtttccaggaaaaggtcacctgc<br>aagaacgggcagggcaactgctacaagagcaactccagcatgcacatcacagac<br>tgccgcctgacaaacgactccaggtaccccaactgtgcataccggaccagcccg<br>aaggagagacacatcattgtggcctgtgaagggagcccatatgtgccagtccac<br>tttgatgcttctgtggaggactctacagatctcgagcccaaatcttctgacaaa<br>actcacacatgtccaccgtgcccagcacctgaactcctggggggaccgtcagtc<br>ttcctcttccccccaaaacccaaggacaccctcatgatctcccggacccctgag<br>gtcacatgcgtggtggtggacgtgagccacgaagaccctgaggtcaagttcaac<br>tggtacgtggacggcgtggaggtgcataatgccaagacaaagccgcgggaggag<br>cagtacaacagcacgtaccgtgtggtcagcgtcctcaccgtcctgcaccaggac<br>tggctgaatggcaaggagtacaagtgcaaggtctccaacaaagccctcccagcc<br>cccatcgagaaaaccatctccaaagccaaagggcagccccgagaaccacaggtg<br>tacaccctgcccccatcccgggatgagctgaccaagaaccaggtcagcctgacc<br>tgcctggtcaaaggcttctatcccagcgacatcgccgtggagtgggagagcaat<br>gggcagccggagaacaactacaagaccacgcctcccgtgctggactccgacggc<br>tccttcttcctctacagcaagctcaccgtggacaagagcaggtggcagcagggg<br>aacgtcttctcatgctccgtgatgcatgaggctctgcacaaccactacacgcag<br>aagagcctctctctgtctccgggtaaatgataatctaga |
| 125 | hVK3LP-hRNase (WT)-(G4S)4lnk-hIgG1WT | gttaagcttgccaccatggaaaccccagcgcagcttctcttcctcctgctactc<br>tggctcccagataccaccggtaaggaatcccgggccaagaaattccagcggcag<br>catatggactcagacagttcccccagcagcagctccacctactgtaaccaaatg<br>atgaggcgccggaatatgacacaggggcggtgcaaaccagtgaacacctttgtg<br>cacgagcccctggtagatgtccagaatgtctgtttccaggaaaaggtcacctgc<br>aagaacgggcagggcaactgctacaagagcaactccagcatgcacatcacagac<br>tgccgcctgacaaacggctccaggtaccccaactgtgcataccggaccagcccg<br>aaggagagacacatcattgtggcctgtgaagggagcccatatgtgccagtccac<br>tttgatgcttctgtggaggactctacagatctctccggaggaggtggctcaggt<br>ggtggaggatctggaggaggtgggagtggtggaggtggttctaccggtctcgag<br>cccaaatcttctgacaaaactcacacatgtccaccgtgcccagcacctgaactc<br>ctggggggaccgtcagtcttcctcttccccccaaaacccaaggacaccctcatg<br>atctcccggacccctgaggtcacatgcgtggtggtggacgtgagccacgaagac<br>cctgaggtcaagttcaactggtacgtggacggcgtggaggtgcataatgccaag<br>acaaagccgcgggaggagcagtacaacagcacgtaccgtgtggtcagcgtcctc |

TABLE 2-continued

| SEQ ID NO: | DESCRIP-TION | SEQUENCE (NUCLEOTIDE SEQUENCES ARE 5'-3') |
|---|---|---|
| | | accgtcctgcaccaggactggctgaatggcaaggagtacaagtgcaaggtctcc<br>aacaaagccctcccagcccccatcgagaaaaccatctccaaagccaaagggcag<br>ccccgagaaccacaggtgtacaccctgcccccatcccgggatgagctgaccaag<br>aaccaggtcagcctgacctgcctggtcaaaggcttctatcccagcgacatcgcc<br>gtggagtgggagagcaatgggcagccggagaacaactacaagaccacgcctccc<br>gtgctggactccgacggctccttcttcctctacagcaagctcaccgtggacaag<br>agcaggtggcagcaggggaacgtcttctcatgctccgtgatgcatgaggctctg<br>cacaaccactacacgcagaagagcctctctctgtctccgggtaaatgataatct<br>aga |
| 126 | hVK3LP-hRNase (WT)-(G4S)5-2-lnk-hIgG1WT | gttaagcttgccaccatggaaaccccagcgcagcttctcttcctcctgctactc<br>tggctcccagataccaccggtaaggaatcccgggccaagaaattccagcggcag<br>catatggactcagacagttcccccagcagcagctccacctactgtaaccaaatg<br>atgaggcgccggaatatgacacaggggcggtgcaaaccagtgaacacctttgtg<br>cacgagcccctggtagatgtccagaatgtctgtttccaggaaaaggtcacctgc<br>aagaacgggcagggcaactgctacaagagcaactccagcatgcacatcacagac<br>tgccgcctgacaaacggctccaggtaccccaactgtgcataccggaccagcccg<br>aaggagagacacatcattgtggcctgtgaagggagcccatatgtgccagtccac<br>tttgatgcttctgtggaggactctacagatctctccggaggaggtggctcaggt<br>ggtggaggatctggaggaggtggctcaggtggtggaggatctggaggaggtggg<br>agtctcgagcccaaatcttctgacaaaactcacacatgtccaccgtgcccagca<br>cctgaactcctggggggaccgtcagtcttcctcttccccccaaaacccaaggac<br>accctcatgatctcccggacccctgaggtcacatgcgtggtggtggacgtgagc<br>cacgaagaccctgaggtcaagttcaactggtacgtggacggcgtggaggtgcat<br>aatgccaagacaaagccgcgggaggagcagtacaacagcacgtaccgtgtggtc<br>agcgtcctcaccgtcctgcaccaggactggctgaatggcaaggagtacaagtgc<br>aaggtctccaacaaagccctcccagcccccatcgagaaaaccatctccaaagcc<br>aaagggcagccccgagaaccacaggtgtacaccctgcccccatcccgggatgag<br>ctgaccaagaaccaggtcagcctgacctgcctggtcaaaggcttctatcccagc<br>gacatcgccgtggagtgggagagcaatgggcagccggagaacaactacaagacc<br>acgcctcccgtgctggactccgacggctccttcttcctctacagcaagctcacc<br>gtggacaagagcaggtggcagcaggggaacgtcttctcatgctccgtgatgcat<br>gaggctctgcacaaccactacacgcagaagagcctctctctgtctccgggtaaa<br>tgataatctaga |
| 127 | hVK3LP-hRNase (WT)-hIgG1WT | gttaagcttgccaccatggaaaccccagcgcagcttctcttcctcctgctactc<br>tggctcccagataccaccggtaaggaatcccgggccaagaaattccagcggcag<br>catatggactcagacagttcccccagcagcagctccacctactgtaaccaaatg<br>atgaggcgccggaatatgacacaggggcggtgcaaaccagtgaacacctttgtg<br>cacgagcccctggtagatgtccagaatgtctgtttccaggaaaaggtcacctgc<br>aagaacgggcagggcaactgctacaagagcaactccagcatgcacatcacagac<br>tgccgcctgacaaacggctccaggtaccccaactgtgcataccggaccagcccg<br>aaggagagacacatcattgtggcctgtgaagggagcccatatgtgccagtccac<br>tttgatgcttctgtggaggactctacagatctcgagcccaaatcttctgacaaa<br>actcacacatgtccaccgtgcccagcacctgaactcctggggggaccgtcagtc<br>ttcctcttccccccaaaacccaaggacaccctcatgatctcccggacccctgag<br>gtcacatgcgtggtggtggacgtgagccacgaagaccctgaggtcaagttcaac<br>tggtacgtggacggcgtggaggtgcataatgccaagacaaagccgcgggaggag<br>cagtacaacagcacgtaccgtgtggtcagcgtcctcaccgtcctgcaccaggac<br>tggctgaatggcaaggagtacaagtgcaaggtctccaacaaagccctcccagcc<br>cccatcgagaaaaccatctccaaagccaaagggcagccccgagaaccacaggtg<br>tacaccctgcccccatcccgggatgagctgaccaagaaccaggtcagcctgacc<br>tgcctggtcaaaggcttctatcccagcgacatcgccgtggagtgggagagcaat<br>gggcagccggagaacaactacaagaccacgcctcccgtgctggactccgacggc<br>tccttcttcctctacagcaagctcaccgtggacaagagcaggtggcagcagggg<br>aacgtcttctcatgctccgtgatgcatgaggctctgcacaaccactacacgcag<br>aagagcctctctctgtctccgggtaaatgataatctaga |
| 128 | murine Trex1 (FL) transcript variant 1 | atgggctcacagaccctgccccatggtcacatgcagaccctcatcttcttagac<br>ctggaagccactggcctgccttcgtctcggcccgaagtcacagagctgtgcctg<br>ctggctgtccacagacgtgctctggagaacacttccatttctcagggacatcca<br>cctccagtgcccagaccgccccgtgtggtggacaagctctctctgtgcattgct<br>ccagggaaagcctgtagccctggggccagtgagatcacaggtctgagcaaagct<br>gagctggaagtacaggggcgtcaacgcttcgatgacaacctggccatcctgctc<br>cgagccttcctgcagcgccagccacagccttgctgccttgtggcacacaacggt<br>gaccgctatgactttcctctgctccagacagagcttgctaggctgagcactccc<br>agtcccctagatggtaccttctgtgtggacagcatcgctgccctaaaggccttg<br>gaacaagctagcagcccctcagggaatggttcgaggaaaagctacagcctgggc<br>agcatctacacccgcctgtactggcaagcaccgacagactcacatactgctgaa<br>ggtgatgttctaaccctgctcagcatctgtcagtggaagccacaggccctactg<br>cagtgggtggacgaacatgcccggccctttagcaccgtcaagcccatgtacggc<br>actccggctaccactggaacaaccaacctaaggccacatgctgccacagctact<br>acaccccctggccacagccaatggaagtcccagcaatggcaggagcaggcgacct<br>aagagtcctcctccagagaaggtcccagaagccccatcacaggaggggctgctg<br>gccccactgagcctgctgaccctcctgaccttggcaatagccactctgtatgga<br>ctcttcctggcctcacctgggcagtaa |

TABLE 2-continued

| SEQ ID NO: | DESCRIPTION | SEQUENCE (NUCLEOTIDE SEQUENCES ARE 5'-3') |
|---|---|---|
| 129 | mTREX1-minec | atgggctcacagaccctgccccatggtcacatgcagaccctcatcttcttagac<br>ctggaagccactggcctgccttcgtctcggcccgaagtcacagagctgtgcctg<br>ctggctgtccacagacgtgctctggagaacacttccatttctcagggacatcca<br>cctccagtgcccagaccgccccgtgtggtggacaagctctctctgtgcattgct<br>ccagggaaagcctgtagccctggggccagtgagatcacaggtctgagcaaagct<br>gagctggaagtacaggggcgtcaacgcttcgatgacaacctggccatcctgctc<br>cgagccttcctgcagcgccagccacagccttgctgccttgtggcacacaacggt<br>gaccgctatgactttcctctgctccagacagagcttgctaggctgagcactccc<br>agtcccctagatggtaccttctgtgtggacagcatcgctgccctaaaggccttg<br>gaacaagctagcagcccctcagggaatggttcgaggaaaagctacagcctgggc<br>agcatctacacccgcctgtactggcaagcaccgacagactcacatactgctgaa<br>ggtgatgttctaaccctgctcagcatctgtcagtggaagccacaggccctactg<br>cagtgggtggacgaacatgcccggccctttagcaccgtcaagcccatgtacggc<br>actccggctaccactggaacaacagatctcgag |
| 130 | murine Trex1-(G4S)4-mIgG2a-c | aagcttgccaccatggaaaccccagcgcagcttctcttcctcctgctactctgg<br>ctcccagataccaccggtatgggctcacagaccctgccccatggtcacatgcag<br>accctcatcttcttagacctggaagccactggcctgccttcgtctcggcccgaa<br>gtcacagagctgtgcctgctggctgtccacagacgtgctctggagaacacttcc<br>atttctcagggacatccacctccagtgcccagaccgccccgtgtggtggacaag<br>ctctctctgtgcattgctccagggaaagcctgtagccctggggccagtgagatc<br>acaggtctgagcaaagctgagctggaagtacaggggcgtcaacgcttcgatgac<br>aacctggccatcctgctccgagccttcctgcagcgccagccacagccttgctgc<br>cttgtggcacacaacggtgaccgctatgactttcctctgctccagacagagctt<br>gctaggctgagcactcccagtcccctagatggtaccttctgtgtggacagcatc<br>gctgccctaaaggccttggaacaagctagcagcccctcagggaatggttcgagg<br>aaaagctacagcctgggcagcatctacacccgcctgtactggcaagcaccgaca<br>gactcacatactgctgaaggtgatgttctaaccctgctcagcatctgtcagtgg<br>aagccacaggccctactgcagtgggtggacgaacatgcccggccctttagcacc<br>gtcaagcccatgtacggcactccggctaccactggaacaacagatctctccgga<br>ggaggtggctcaggtggtggaggatctggaggaggtggctcagggagtggtgga<br>ggtggttctaccggtctcgagcccagaggtcccacaatcaagccctctcctcca<br>tgcaaatgcccagcacctaacctcttgggtggatcatccgtcttcatcttccct<br>ccaaagatcaaggatgtactcatgatctccctgagccccatggtcacatgtgtg<br>gtggtggatgtgagcgaggatgacccagacgtccagatcagctggtttgtgaac<br>aacgtggaagtacacacagctcagacacaaacccatagagaggattacaacagt<br>actctccgggtggtcagtgccctccccatccagcaccaggactggatgagtggc<br>aaggagttcaaatgctcggtcaacaacaaagacctcccagcgtccatcgagaga<br>accatctcaaaacccagagggccagtaagagctccacaggtatatgtcttgcct<br>ccaccagcagaagagatgactaagaaagagttcagtctgacctgcatgatcaca<br>ggcttcttacctgccgaaattgctgtggactggaccagcaatgggcgtacagag<br>caaaactacaagaacaccgcaacagtcctggactctgatggttcttacttcatg<br>tacagcaagctcagagtacaaaagagcacttgggaaagaggaagtcttttcgcc<br>tgctcagtggtccacgagggtctgcacaatcaccttacgactaagagcttctct<br>cggactccgggtaaatgataatctaga |
| 131 | murine Trex1-(G4S)5-mIgG2a-c | aagcttgccaccatggaaaccccagcgcagcttctcttcctcctgctactctgg<br>ctcccagataccaccggtatgggctcacagaccctgccccatggtcacatgcag<br>accctcatcttcttagacctggaagccactggcctgccttcgtctcggcccgaa<br>gtcacagagctgtgcctgctggctgtccacagacgtgctctggagaacacttcc<br>atttctcagggacatccacctccagtgcccagaccgccccgtgtggtggacaag<br>ctctctctgtgcattgctccagggaaagcctgtagccctggggccagtgagatc<br>acaggtctgagcaaagctgagctggaagtacaggggcgtcaacgcttcgatgac<br>aacctggccatcctgctccgagccttcctgcagcgccagccacagccttgctgc<br>cttgtggcacacaacggtgaccgctatgactttcctctgctccagacagagctt<br>gctaggctgagcactcccagtcccctagatggtaccttctgtgtggacagcatc<br>gctgccctaaaggccttggaacaagctagcagcccctcagggaatggttcgagg<br>aaaagctacagcctgggcagcatctacacccgcctgtactggcaagcaccgaca<br>gactcacatactgctgaaggtgatgttctaaccctgctcagcatctgtcagtgg<br>aagccacaggccctactgcagtgggtggacgaacatgcccggccctttagcacc<br>gtcaagcccatgtacggcactccggctaccactggaacaacagatctctccgga<br>ggaggtggctcaggtggtggaggatctggaggaggtggctcaggtggtggagga<br>tctggaggaggtgggagtctcgagcccagaggtcccacaatcaagccctctcct<br>ccatgcaaatgcccagcacctaacctcttgggtggatcatccgtcttcatcttc<br>cctccaaagatcaaggatgtactcatgatctccctgagccccatggtcacatgt<br>gtggtggtggatgtgagcgaggatgacccagacgtccagatcagctggtttgtg<br>aacaacgtggaagtacacacagctcagacacaaacccatagagaggattacaac<br>agtactctccgggtggtcagtgccctccccatccagcaccaggactggatgagt<br>ggcaaggagttcaaatgctcggtcaacaacaaagacctcccagcgtccatcgag<br>agaaccatctcaaaacccagagggccagtaagagctccacaggtatatgtcttg<br>cctccaccagcagaagagatgactaagaaagagttcagtctgacctgcatgatc<br>acaggcttcttacctgccgaaattgctgtggactggaccagcaatgggcgtaca<br>gagcaaaactacaagaacaccgcaacagtcctggactctgatggttcttacttc<br>atgtacagcaagctcagagtacaaaagagcacttgggaaagaggaagtcttttc<br>gcctgctcagtggtccacgagggtctgcacaatcaccttacgactaagagcttc<br>tctcggactccgggtaaatgataatctaga |

TABLE 2-continued

| SEQ ID NO: | DESCRIPTION | SEQUENCE (NUCLEOTIDE SEQUENCES ARE 5'-3') |
|---|---|---|
| 132 | NLG linker | gtcgacggcgcggccgccagccccgtgaacgtgagcagccccagcgtgcaggat<br>atc |
| 133 | murine Trex1-Trex1-(G4S)5-mIgG2a-c | aagcttgccaccatggaaaccccagcgcagcttctcttcctcctgctactctgg<br>ctcccagataccaccggtatgggctcacagaccctgccccatggtcacatgcag<br>accctcatcttcttagacctggaagccactggcctgccttcgtctcggcccgaa<br>gtcacagagctgtgcctgctggctgtccacagacgtgctctggagaacacttcc<br>atttctcagggacatccacctccagtgcccagaccgccccgtgtggtggacaag<br>ctctctctgtgcattgctccagggaaagcctgtagccctggggccagtgagatc<br>acaggtctgagcaaagctgagctggaagtacaggggcgtcaacgcttcgatgac<br>aacctggccatcctgctccgagccttcctgcagcgccagccacagccttgctgc<br>cttgtggcacacaacggtgaccgctatgactttcctctgctccagacagagctt<br>gctaggctgagcactcccagtcccctagatggtaccttctgtgtggacagcatc<br>gctgccctaaaggccttggaacaagctagcagcccctcagggaatggttcgagg<br>aaaagctacagcctgggcagcatctacacccgcctgtactggcaagcaccgaca<br>gactcacatactgctgaaggtgatgttctaaccctgctcagcatctgtcagtgg<br>aagccacaggccctactgcagtgggtggacgaacatgcccggccctttagcacc<br>gtcaagcccatgtacggcactccggctaccactggaacaacagatctcatgggc<br>tcacagaccctgccccatggtcacatgcagaccctcatcttcttagacctggaa<br>gccactggcctgccttcgtctcggcccgaagtcacagagctgtgcctgctggct<br>gtccacagacgtgctctggagaacacttccatttctcagggacatccacctcca<br>gtgcccagaccgccccgtgtggtggacaagctctctctgtgcattgctccaggg<br>aaagcctgtagccctggggccagtgagatcacaggtctgagcaaagctgagctg<br>gaagtacaggggcgtcaacgcttcgatgacaacctggccatcctgctccgagcc<br>ttcctgcagcgccagccacagccttgctgccttgtggcacacaacggtgaccgc<br>tatgactttcctctgctccagacagagcttgctaggctgagcactcccagtccc<br>ctagatggtaccttctgtgtggacagcatcgctgccctaaaggccttggaacaa<br>gctagcagcccctcagggaatggttcgaggaaaagctacagcctgggcagcatc<br>tacacccgcctgtactggcaagcaccgacagactcacatactgctgaaggtgat<br>gttctaaccctgctcagcatctgtcagtggaagccacaggccctactgcagtgg<br>gtggacgaacatgcccggccctttagcaccgtcaagcccatgtacggcactccg<br>gctaccactggaacaacagatctctccggaggaggtggctcaggtggtggagga<br>tctggaggaggtggctcaggtggtggaggatctggaggaggtgggagtctcgag<br>cccagaggtcccacaatcaagccctctcctccatgcaaatgcccagcacctaac<br>ctcttgggtggatcatccgtcttcatcttccctccaaagatcaaggatgtactc<br>atgatctccctgagccccatggtcacatgtgtggtggtggatgtgagcgaggat<br>gacccagacgtccagatcagctggtttgtgaacaacgtggaagtacacacagct<br>cagacacaaacccatagagaggattacaacagtactctccgggtggtcagtgcc<br>ctccccatccagcaccaggactggatgagtggcaaggagttcaaatgctcggtc<br>aacaacaaagacctcccagcgtccatcgagagaaccatctcaaaacccagaggg<br>ccagtaagagctccacaggtatatgtcttgcctccaccagcagaagagatgact<br>aagaaagagttcagtctgacctgcatgatcacaggcttcttacctgccgaaatt<br>gctgtggactggaccagcaatgggcgtacagagcaaaactacaagaacaccgca<br>acagtcctggactctgatggttcttacttcatgtacagcaagctcagagtacaa<br>aagagcacttgggaaagaggaagtcttttcgcctgctcagtggtccacgagggt<br>ctgcacaatcaccttacgactaagagcttctctcggactccgggtaaatgataa<br>tctaga |
| 134 | huVK3LP-huTREX1-72aa-(g4s)4-hIgG1-WT | aagcttgccaccatggaaaccccagcgcagcttctcttcctcctgctactctgg<br>ctcccagataccaccggtatgggccctggagctcgcagacagggcaggattgtg<br>cagggaaggcctgagatgtgcttctgcccacccctaccccactccctcccctt<br>cggatcttaacactgggcactcacacacccaccccatgctcctctccaggctca<br>gcagcaggtacgtacccaaccatgggctcgcaggccctgcccccggggcccatg<br>cagaccctcatctttttcgacatggaggccactggcttgcccttctcccagccc<br>aaggtcacggagctgtgcctgctggctgtccacagatgtgccctggagagcccc<br>cccacctctcaggggccacctcccacagttcctccaccaccgcgtgtggtagac<br>aagctctccctgtgtgtggctccggggaaggcctgcagccctgcagccagcgag<br>atcacaggtctgagcacagctgtgctggcagcgcatgggcgtcaatgttttgat<br>gacaacctggccaacctgctcctagccttcctgcggcgccagccacagccctgg<br>tgcctggtggcacacaatggtgaccgctacgacttcccctgctccaagcagag<br>ctggctatgctgggcctcaccagtgctctggatggtgccttctgtgtggatagc<br>atcactgcgctgaaggccctggagcgagcaagcagcccctcagaacacggccca<br>aggaagagctacagcctaggcagcatctacactcgcctgtatgggcagtcccct<br>ccagactcgcacacggctgagggtgatgtcctggccctgctcagcatctgtcag<br>tggagaccacaggccctgctgcggtgggtggatgctcacgccaggcctttcggc<br>accatcaggcccatgtatggggtcacagcctctgctaggaccaaagatctctcc<br>ggaggaggtggctcaggtggtggaggatctggaggaggtgggagtggtggaggt<br>ggttctaccggtctcgagcccaaatcttctgacaaaactcacacatgtccaccg<br>tgcccagcacctgaactcctggggggaccgtcagtcttcctcttccccccaaaa<br>cccaaggacaccctcatgatctcccggacccctgaggtcacatgcgtggtggtg<br>gacgtgagccacgaagaccctgaggtcaagttcaactggtacgtggacggcgtg<br>gaggtgcataatgccaagacaaagccgcgggaggagcagtacaacagcacgtac<br>cgtgtggtcagcgtcctcaccgtcctgcaccaggactggctgaatggcaaggag<br>tacaagtgcaaggtctccaacaaagccctcccagcccccatcgagaaaaccatc<br>tccaaagccaaagggcagccccgagaaccacaggtgtacaccctgcccccatcc<br>cgggatgagctgaccaagaaccaggtcagcctgacctgcctggtcaaaggcttc<br>tatcccagcgacatcgccgtggagtgggagagcaatgggcagccggagaacaac |

TABLE 2-continued

| SEQ ID NO: | DESCRIPTION | SEQUENCE (NUCLEOTIDE SEQUENCES ARE 5'-3') |
|---|---|---|
| | | tacaagaccacgcctcccgtgctggactccgacggctccttcttcctctacagc<br>aagctcaccgtggacaagagcaggtggcagcaggggaacgtcttctcatgctcc<br>gtgatgcatgaggctctgcacaaccactacacgcagaagagcctctctctgtct<br>ccgggtaaatgataatctaga |
| 135 | huVK3LP-huTREX1-72aa-(g4s)5-hIgG1-WT | aagcttgccaccatggaaaccccagcgcagcttctcttcctcctgctactctgg<br>ctcccagataccaccggtatgggccctggagctcgcagacagggcaggattgtg<br>cagggaaggcctgagatgtgcttctgcccacccctaccccactccctcccctt<br>cggatcttaacactgggcactcacacacccaccccatgctcctctccaggctca<br>gcagcaggtacgtacccaaccatgggctcgcaggccctgcccccggggcccatg<br>cagaccctcatctttttcgacatggaggccactggcttgcccttctcccagccc<br>aaggtcacggagctgtgcctgctggctgtccacagatgtgccctggagagcccc<br>cccacctctcaggggccacctcccacagttcctccaccaccgcgtgtggtagac<br>aagctctccctgtgtgtggctccggggaaggcctgcagccctgcagccagcgag<br>atcacaggtctgagcacagctgtgctggcagcgcatgggcgtcaatgttttgat<br>gacaacctggccaacctgctcctagccttcctgcggcgccagccacagccctgg<br>tgcctggtggcacacaatggtgaccgctacgacttcccccctgctccaagcagag<br>ctggctatgctgggcctcaccagtgctctggatggtgccttctgtgtggatagc<br>atcactgcgctgaaggccctggagcgagcaagcagcccctcagaacacggccca<br>aggaagagctacagcctaggcagcatctacactcgcctgtatgggcagtcccct<br>ccagactcgcacacggctgagggtgatgtcctggccctgctcagcatctgtcag<br>tggagaccacaggccctgctgcggtgggtggatgctcacgccaggcctttcggc<br>accatcaggcccatgtatggggtcacagcctctgctaggaccaaagatctctcc<br>ggaggaggtggctcaggtggtggaggatctggaggaggtggctcaggtggtgga<br>ggatctggaggaggtgggagtctcgagcccaaatcttctgacaaaactcacaca<br>tgtccaccgtgcccagcacctgaactcctggggggaccgtcagtcttcctcttc<br>cccccaaaacccaaggacaccctcatgatctcccggacccctgaggtcacatgc<br>gtggtggtggacgtgagccacgaagaccctgaggtcaagttcaactggtacgtg<br>gacggcgtggaggtgcataatgccaagacaaagccgcgggaggagcagtacaac<br>agcacgtaccgtgtggtcagcgtcctcaccgtcctgcaccaggactggctgaat<br>ggcaaggagtacaagtgcaaggtctccaacaaagccctcccagcccccatcgag<br>aaaaccatctccaaagccaaagggcagccccgagaaccacaggtgtacaccctg<br>cccccatcccgggatgagctgaccaagaaccaggtcagcctgacctgcctggtc<br>aaaggcttctatcccagcgacatcgccgtggagtgggagagcaatgggcagccg<br>gagaacaactacaagaccacgcctcccgtgctggactccgacggctccttcttc<br>ctctacagcaagctcaccgtggacaagagcaggtggcagcaggggaacgtcttc<br>tcatgctccgtgatgcatgaggctctgcacaaccactacacgcagaagagcctc<br>tctctgtctccgggtaaatgataatctaga |
| 136 | g4s41nk | dlsggggsggggsggggsggggstgle |
| 137 | G4S5-1 | dlsggggsggggsggggsggggsggggstgle |
| 138 | G4S5-2 | dlsggggsggggsggggsggggsggggsle |
| 139 | hDNase1-3' -G105R; A114F | dilkiaafniqtfgetkmsnatlvsyivqilsrydialvqevrdshltavgkll<br>dnlnqdapdtyhyvvseplgrnsykerylfvyrpdqvsavdsyyyddgcepcrn<br>dtfnrepfivrffsrftevrefaivplhaapgdavaeidalydvyldvqekwgl<br>edvmlmgdfnagcsyvrpsqwssirlwtsptfqwlipdsadttatpthcaydri<br>vvagmllrgavvpdsalpfnfqaayglsdqlaqaisdhypvevmlk* |
| 140 | hDNase1-3'-WT | dilkiaafniqtfgetkmsnatlvsyivqilsrydialvqevrdshltavgkll<br>dnlnqdapdtyhyvvseplgrnsykerylfvyrpdqvsavdsyyyddgcepcgn<br>dtfnrepaivrffsrftevrefaivplhaapgdavaeidalydvyldvqekwgl<br>edvmimgdfnagcsyvrpsqwssirlwtsptfqwlipdsadttatpthcaydri<br>vvagmllrgavvpdsalpfnfqaayglsdqlaqaisdhypvevmlk* |
| 141 | hDNase1-3'A114F | dilkiaafniqtfgetkmsnatlvsyivqilsrydialvqevrdshltavgkll<br>dnlnqdapdtyhyvvseplgrnsykerylfvyrpdqvsavdsyyyddgcepcgn<br>dtfnrepfivrffsrftevrefaivplhaapgdavaeidalydvyldvqekwgl<br>edvmlmgdfnagcsyvrpsqwssirlwtsptfqwlipdsadttatpthcaydri<br>vvagmllrgavvpdsalpfnfqaayglsdqlaqaisdhypvevmlk* |
| 142 | hDNase1-5' -G105R; A114F | tglkiaafniqtfgetkmsnatlvsyivqilsrydialvqevrdshltavgkll<br>dnlnqdapdtyhyvvseplgrnsykerylfvyrpdqvsavdsyyyddgcepcrn<br>dtfnrepfivrffsrftevrefaivplhaapgdavaeidalydvyldvqekwgl<br>edvmlmgdfnagcsyvrpsqwssirlwtsptfqwlipdsadttatpthcaydri<br>vvagmllrgavvpdsalpfnfqaayglsdqlaqaisdhypvevmlkdle |
| 143 | hDNase1-5'-WT | tglkiaafniqtfgetkmsnatlvsyivqilsrydialvqevrdshltavgkll<br>dnlnqdapdtyhyvvseplgrnsykerylfvyrpdqvsavdsyyyddgcepcgn<br>dtfnrepaivrffsrftevrefaivplhaapgdavaeidalydvyldvqekwgl<br>edvmlmgdfnagcsyvrpsqwssirlwtsptfqwlipdsadttatpthcaydri<br>vvagmllrgavvpdsalpfnfqaayglsdqlaqaisdhypvevmlkdle |

TABLE 2-continued

| SEQ ID NO: | DESCRIPTION | SEQUENCE (NUCLEOTIDE SEQUENCES ARE 5'-3') |
|---|---|---|
| 144 | hDNase1-5'-A114F | tglkiaafniqtfgetkmsnatlvsyivqilsrydialvqevrdshltavgkll<br>dnlnqdapdtyhyvvseplgrnsykerylfvyrpdqvsavdsyyyddgcepcgn<br>dtfnrepfivrffsrftevrefaivplhaapgdavaeidalydvyldvqekwgl<br>edvmlmgdfnagcsyvrpsqwssirlwtsptfqwlipdsadttatpthcaydri<br>vvagmllrgavvpdsalpfnfqaayglsdqlaqaisdhypvevmlkdle |
| 145 | hIgG1WT | dlepkssdkthtcppcpapellggpsvflfppkpkdtlmisrtpevtcvvvdvs<br>hedpevkfnwyvdgvevhnaktkpreeqynstyrvvsvltvlhqdwlngkeykc<br>kvsnkalpapiektiskakgqprepqvytlppsrdeltknqvsltclvkgfyps<br>diavewesngqpennykttppvldsdgsfflyskitvdksrwqqgnvfscsvmh<br>ealhnhytqkslslspgk |
| 146 | hRNase-G88D-3' | vdgasspvnvsspsvqdipslgkesrakkfqrqhmdsdsspssstycnqmmrr<br>rnmtqgrckpvntfvheplvdvqnvcfqekvtckngqgncyksnssmhitdcrl<br>tndsrypncayrtspkerhiivacegspyvpvhfdasvedst* |
| 147 | human DNase1 + VK3LP | metpaqllflllwlpdttglkiaafniqtfgetkmsnatlvsyivqilsrydi<br>alvqevrdshltavgklldnlnqdapdtyhyvvseplgrnsykerylfvyrpdq<br>vsavdsyyyddgcepcgndtfnrepaivrffsrftevrefaivplhaapgdava<br>eidalydvyldvqekwgledvmlmgdfnagcsyvrpsqwssirlwtsptfqwli<br>pdsadttatpthcaydrivvagmllrgavvpdsalpfnfqaayglsdqlaqais<br>dhypvevmlk* |
| 148 | DNase1L3 | msrelapllllllsihsalamricsfnvrsfgeskqedknamdvivkvikrcdi<br>ilvmeikdsnnricpilmeklnrnsrrgitynyvissrlgrntykeqyaflyke<br>klvsvkrsyhyhdyqdgdadvfsrepfvvwfqsphtavkdfviiplhttpetsv<br>keidelvevytdvkhrwkaenfifmgdfnagcsyvpkkawknirlrtdprfvwl<br>igdqedttvkkstncaydrivlrgqeivssvvpksnsvfdfqkaykltee eald<br>vsdhfpvefklqssraftnskksvtlrkktkskrs* |
| 149 | human pancreatic ribo-nuclease | Mglekslvrllllvlillvlgwvqpslgkesrakkfqrqhmdsdsspssssstyc<br>nqmmrrrnmtqgrckpvntfvheplvdvqnvcfqekvtckngqgncyksnssmh<br>itdcrltngsrypncayrtspkerhiivacegspyvpvhfdatv* |
| 150 | huVK3LP + mrib1 + mIgG2A-C + 2S | metpaqllflllwlpdttgresaaqkfqrqhmdpdgssinsptycnqmmkrrd<br>mtngsckpvntfvhepladvqavcsqenvtcknrksncykssalhitdchlkg<br>nskypncdykttqyqkhiivacegnpyvpvhfdatvleprgltikpsppckcpa<br>pnllggssvfifppkikdvlmislspmvtcvvvdvseddpdvqiswfvnnvevh<br>taqtqthredynstlrvvsalpiqhqdwmsgkefkcsvnnkdlpasiertiskp<br>rgpvrapqvyvlpppaeemtkkefsltcmitgfIpaeiavdwtsngrteqnykn<br>tatvldsdgsyfmysklrvqkstwergslfacsvvheglhnhlttksfsrtp<br>gk* |
| 151 | huVK3LP-hRNaseWT-hIgGW-NLG-hDNase1-105-114 | metpaqllflllwlpdttgkesrakkfqrqhmdsdsspssstycnqmmrrrn<br>mtqgrckpvntfvheplvdvqnvcfqekvtckngqgncyksnssmhitdcrltn<br>gsrypncayrtspkerhiivacegspyvpvhfdasvedstdlepkssdkthtcp<br>pcpapellggpsvflfppkpkdtlmisrtpevtcvvvdvshedpevkfnwyvdg<br>vevhnaktkpreeqynstyrvvsvltvlhqdwlngkeykckvsnkalpapiekt<br>iskakgqprepqvytlppsrdeltknqvsltclvkgfypsdiavewesngqpen<br>nykttppvldsdgsfflyskitvdksrwqqgnvfscsvmheglhnhytqkslsl<br>spgkvdgasshvnvsspsvqdilkiaafniqtfgetkmsnatlvsyivqilsry<br>dialvqevrdshltavgklldnlnqdapdtyhyvvseplgrnsykerylfvyrp<br>dqvsavdsyyyddgcepcgndtfnrepaivrffsrftevrefaivplhaapgda<br>vaeidalydvyldvqekwgsedvmlmgdfnagcsyvrpsqwssirlwtsptfqw<br>lipdsadttatpthcaydrivvagmllrgavvpdsalpfnfqxayglsdqlaqa<br>isdhypvevmlk** |
| 152 | huVK3LP-hRNaseWT-hIgGWT-NLG-hDNase1-114F | metpaqllflllwlpdttgkesrakkfqrqhmdsdsspssstycnqmmrrrn<br>mtqgrckpvntfvheplvdvqnvcfqekvtckngqgncyksnssmhitdcrltn<br>gsrypncayrtspkerhiivacegspyvpvhfdasvedstdlepkssdkthtcp<br>pcpapellggpsvflfppkpkdtlmisrtpevtcvvvdvshedpevkfnwyvdg<br>vevhnaktkpreeqynstyrvvsvltvlhqdwlngkeykckvsnkalpapiekt<br>iskakgqprepqvytlppsrdeltknqvsltclvkgfypsdiavewesngqpen<br>nykttppvldsdgsfflyskitvdksrwqqgnvfscsvmheglhnhytqkslsl<br>spgkvdgasshvnvsspsvqdilkiaafniqtfgetkmsnatlvsyivqilsry<br>dialvqevrdshltavgklldnlnqdapdtyhyvvseplgrnsykerylfvyrp<br>dqvsavdsyyyddgcepcgndtfnrepfivrffsrftevrefaivplhaapgda<br>vaeidalydvyldvqekwgledvmlmgdfnagcsyvrpsqwssirlwtsptfqw<br>lipdsadttatpthcaydrivvagmllrgavvpdsalpfnfqaayglsdqlaqa<br>isdhypvevmlk* |

TABLE 2-continued

| SEQ ID NO: | DESCRIPTION | SEQUENCE (NUCLEOTIDE SEQUENCES ARE 5'-3') |
|---|---|---|
| 153 | huVK3LP-hRNaseWT-hIgGWT-NLG-hDNAse1-WT | metpaqllfllllwlpdttgkesrakkfqrqhmdsdsspsssstycnqmmrrrn mtqgrckpvntfvheplvdvqnvcfqekvtckngqgncyksnssmhitdcrltn gsrypncayrtspkerhiivacegspyvpvhfdasvedstdlepkssdkthtcp pcpapellggpsvflfppkpkdtlmisrtpevtcvvvdvshedpevkfnwyvdg vevhnaktkpreeqynstyrvvsvltvlhqdwlngkeykckvsnkalpapiekt iskakgqprepqvytlppsrdeltknqvsltclvkgfypsdiavewesngqpen nykttppvldsdgsfflyskltvdksrwqqgnvfscsvmheglhnhytqkslsl spgkvdgasshvnvsspsvqdilkiaafniqtfgetkmsnatlvsyivqilsry dialvqevrdshltavgklldnlnqdapdtyhyvvseplgrnsykerylfvyrp dqvsavdsyyyddgcepcgndtfnrepaivrffsrftevrefaivplhaapgda vaeidalydvyldvqekwgledvmlmgdfnagcsyvrpsqwssirlwtsptfqw lipdsadttatpthcaydrivvagmllrgavvpdsalpfnfqaayglsdqlaqa isdhypvevmlk* |
| 154 | hVK3LP-hDNase1 (WT)-hIgG1WT | metpaqllfllllwlpdttglkiaafniqtfgetkmsnatlvsyivqilsrydi alvqevrdshltavgklldnlnqdapdtyhyvvseplgrnsykerylfvyrpdq vsavdsyyyddgcepcgndtfnrepaivrffsrftevrefaivplhaapgdava eidalydvyldvqekwgledvmlmgdfnagcsyvrpsqwssirlwtsptfqwli pdsadttatpthcaydrivvagmllrgavvpdsalpfnfqaayglsdqlaqais dhypvevmlkdlepkssdkthtcppcpapellggpsvflfppkpkdtlmisrtp evtcvvvdvshedpevkfnwyvdgvevhnaktkpreeqynstyrvvsvltvlhq dwlngkeykckvsnkalpapiektiskakgqprepqvytlppsrdeltknqvsl tclvkgfypsdiavewesngqpennykttppvldsdgsfflyskitvdksrwqq gnvfscsvmhealhnhytqkslslspgk* |
| 155 | hVK3LP-hDNase1-A114F-hIgG1WT | metpaqllfllllwlpdttglkiaafniqtfgetkmsnatlvsyivqilsrydi alvqevrdshltavgklldnlnqdapdtyhyvvseplgrnsykerylfvyrpdq vsavdsyyyddgcepcgndtfnrepfivrffsrftevrefaivplhaapgdava eidalydvyldvqekwgledvmlmgdfnagcsyvrpsqwssirlwtsptfqwli pdsadttatpthcaydrivvagmllrgavvpdsalpfnfqaayglsdqlaqais dhypvevmlkdlepkssdkthtcppcpapellggpsvflfppkpkdtlmisrtp evtcvvvdvshedpevkfnwyvdgvevhnaktkpreeqynstyrvvsvltvlhq dwlngkeykckvsnkalpapiektiskakgqprepqvytlppsrdeltknqvsl tclvkgfypsdiavewesngqpennykttppvldsdgsfflyskitvdksrwqq gnvfscsvmhealhnhytqkslslspgk* |
| 156 | hVK3LP-hDNase1-G105R; A114F-(G4S)4-hIgG1 WT | metpaqllfllllwlpdttglkiaafniqtfgetkmsnatlvsyivqilsrydi alvqevrdshltavgklldnlnqdapdtyhyvvseplgrnsykerylfvyrpdq vsavdsyyyddgcepcrndtfnrepfivrffsrftevrefaivplhaapgdava eidalydvyldvqekwgledvmlmgdfnagcsyvrpsqwssirlwtsptfqwli pdsadttatpthcaydrivvagmllrgavvpdsalpfnfqaayglsdqlaqais dhypvevmlkdlsggggsggggsggggsggggstglepkssdkthtcppcpape llggpsvflfppkpkdtlmisrtpevtcvvvdvshedpevkfnwyvdgvevhna ktkpreeqynstyrvvsvltvlhqdwlngkeykckvsnkalpapiektiskakg qprepqvytlppsrdeltknqvsltclvkgfypsdiavewesngqpennykttp pvidsdgsfflyskltvdksrwqqgnvfscsvmhealhnhytqkslslspgk* |
| 157 | hVK3LP-hDNase1-G105R; A114F (G4s)5-hIgG1 WT | metpaqllfllllwlpdttglkiaafniqtfgetkmsnatlvsyivqilsrydi alvqevrdshltavgklldnlnqdapdtyhyvvseplgrnsykerylfvyrpdq vsavdsyyyddgcepcrndtfnrepfivrffsrftevrefaivplhaapgdava eidalydvyldvqekwgledvmlmgdfnagcsyvrpsqwssirlwtsptfqwli pdsadttatpthcaydrivvagmllrgavvpdsalpfnfqaayglsdqlaqais dhypvevmlkdlsggggsggggsggggsggggsggggstglepkssdkthtcpp cpapellggpsvflfppkpkdtlmisrtpevtcvvvdvshedpevkfnwyvdgv evhnaktkpreeqynstyrvvsvltvlhqdwlngkeykckvsnkalpapiekti skakgqprepqvytippsrdeltknqvsltcivkgfypsdiavewesngqpenn ykttppvldsdgsfflyskltvdksrwqqgnvfscsvmhealhnhytqkslsls pgk* |
| 158 | hVK3LP-hDNase1-G105R; A114F-(G4S)5-2-hIgG1 WT | metpaqllfllllwlpdttglkiaafniqtfgetkmsnatlvsyivqilsrydi alvqevrdshltavgklldnlnqdapdtyhyvvseplgrnsykerylfvyrpdq vsavdsyyyddgcepcrndtfnrepfivrffsrftevrefaivplhaapgdava eidalydvyldvqekwgledvmlmgdfnagcsyvrpsqwssirlwtsptfqwli pdsadttatpthcaydrivvagmllrgavvpdsalpfnfqaayglsdqlaqais dhypvevmlkdlsggggsggggsggggsggggsggggslepkssdkthtcppcp apellggpsvflfppkpkdtlmisrtpevtcvvvdvshedpevkfnwyvdgvev hnaktkpreeqynstyrvvsvltvlhqdwlngkeykckvsnkalpapiektisk akgqprepqvytlppsrdeltknqvsltclvkgfypsdiavewesngqpennyk ttppvldsdgsfflyskltvdksrwqqgnvfscsvmhealhnhytqkslslspg k* |
| 159 | hVK3LP-hDNase1-G105R; A114F-hIgG1 WT | metpaqllfllllwlpdttglkiaafniqtfgetkmsnatlvsyivqilsrydi alvqevrdshltavgklldnlnqdapdtyhyvvseplgrnsykerylfvyrpdq vsavdsyyyddgcepcrndtfnrepfivrffsrftevrefaivplhaapgdava eidalydvyldvqekwgledvmlmgdfnagcsyvrpsqwssirlwtsptfqwli pdsadttatpthcaydrivvagmllrgavvpdsalpfnfqaayglsdqlaqais |

TABLE 2-continued

| SEQ ID NO: | DESCRIPTION | SEQUENCE (NUCLEOTIDE SEQUENCES ARE 5'-3') |
|---|---|---|
| | | dhypvevmlkdlepkssdkthtcppcpapellggpsvflfppkpkdtlmisrtp<br>evtcvvvdvshedpevkfnwyvdgvevhnaktkpreeqynstyrvvsvltvlhq<br>dwlngkeykckvsnkalpapiektiskakgqprepqvytlppsrdeltknqvsl<br>tcivkgfypsdiavewesngqpennykttppvldsdgsfflyskitvdksrwqq<br>gnvfscsvmhealhnhytqkslslspgk* |
| 160 | hVK3LP-<br>hRNase1<br>(MT)-<br>hIgG1WT | metpaqllfllllwlpdttgkesrakkfqrqhmdsdsspsssstycnqmmrrrn<br>mtqgrckpvntfvheplvdvqnvcfqekvtckngqgncyksnssmhitdcrltn<br>dsrypncayrtspkerhiivacegspyvpvhfdasvedstdlepkssdkthtcp<br>pcpapellggpsvflfppkpkdtlmisrtpevtcvvvdvshedpevkfnwyvdg<br>vevhnaktkpreeqynstyrvvsvltvlhqdwlngkeykckvsnkalpapiekt<br>iskakgqprepqvytIppsrdeltknqvsltcivkgfypsdiavewesngqpen<br>nykttppvldsdgsfflyskltvdksrwqqgnvfscsvmhealhnhytqkslsl<br>spgk* |
| 161 | hVK3Lp-<br>hRNase1<br>(WT)-<br>(G4S)4lnk-<br>hIgG1WT | metpaqllfllllwlpdttgkesrakkfqrqhmdsdsspsssstycnqmmrrrn<br>mtqgrckpvntfvheplvdvqnvcfqekvtckngqgncyksnssmhitdcrltn<br>gsrypncayrtspkerhiivacegspyvpvhfdasvedstdlsggggsggggsg<br>gggsggggstglepkssdkthtcppcpapellggpsvflfppkpkdtlmisrtp<br>evtcvvvdvshedpevkfnwyvdgvevhnaktkpreeqynstyrvvsvltvlhq<br>dwlngkeykckvsnkalpapiektiskakgqprepqvytippsrdeltknqvsl<br>tcivkgfypsdiavewesngqpennykttppvldsdgsfflyskitvdksrwqq<br>gnvfscsvmhealhnhytqkslslspgk* |
| 162 | hVK3LP-<br>hRNase<br>(WT)-<br>(G4S)5-<br>2lnk-<br>hIgG1WT | metpaqllfllllwlpdttgkesrakkfqrqhmdsdsspsssstycnqmmrrrn<br>mtqgrckpvntfvheplvdvqnvcfqekvtckngqgncyksnssmhitdcrltn<br>gsrypncayrtspkerhiivacegspyvpvhfdasvedstdlsggggsggggsg<br>gggsggggsggggslepkssdkthtcppcpapellggpsvflfppkpkdtlmis<br>rtpevtcvvvdvshedpevkfnwyvdgvevhnaktkpreeqynstyrvvsvltv<br>ihqdwlngkeykckvsnkalpapiektiskakgqprepqvytlppsrdeltknq<br>vsltclvkgfypsdiavewesngqpennykttppvldsdgsfflyskitvdksr<br>wqqgnvfscsvmhealhnhytqkslslspgk* |
| 163 | hVK3LP-<br>hRNase<br>(WT)-<br>hIgG1 WT | metpaqllfllllwlpdttgkesrakkfqrqhmdsdsspsssstycnqmmrrrn<br>mtqgrckpvntfvheplvdvqnvcfqekvtckngqgncyksnssmhitdcrltn<br>gsrypncayrtspkerhiivacegspyvpvhfdasvedstdlepkssdkthtcp<br>pcpapellggpsvflfppkpkdtlmisrtpevtcvvvdvshedpevkfnwyvdg<br>vevhnaktkpreeqynstyrvvsvltvlhqdwlngkeykckvsnkalpapiekt<br>iskakgqprepqvytIppsrdeltknqvsltcivkgfypsdiavewesngqpen<br>nykttppvldsdgsfflyskltvdksrwqqgnvfscsvmhealhnhytqkslsl<br>spgk* |
| 164 | murine<br>Trex1<br>(FL)-<br>transcript<br>variant 1 | mgsqtlphghmqtlifidleatglpssrpevtelcllavhrralentsisqghp<br>ppvprpprvvdklslciapgkacspgaseitglskaelevqgrqrfddnlaill<br>rafiqrqpqpcclvahngdrydfpllqtelarlstpspldgtfcvdsiaalkal<br>eqasspsgngsrksyslgsiytrlywqaptdshtaegdvltllsicqwkpqall<br>qwvdeharpfstvkpmygtpattgttnlrphaatattplatangspsngrsrrp<br>kspppekvpeapsqegllaplslltlltlaiatlyglflaspgq* |
| 165 | mouse<br>Trex1-<br>minec | mgsqtlphghmqtlifidleatglpssrpevtelcllavhrralentsisqghp<br>ppvprpprvvdklslciapgkacspgaseitglskaelevqgrqrfddnlaill<br>rafIqrqpqpcclvahngdrydfpliqtelaristpspldgtfcvdsiaalkal<br>eqasspsgngsrksyslgsiytrlywqaptdshtaegdvltllsicqwkpqall<br>qwvdeharpfstvkpmygtpattgttdle |
| 166 | murine<br>Trex1-<br>(G4S)4-<br>mIgG2a-c | metpaqllfllllwlpdttgmgsqtlphghmqtlifidleatglpssrpevtel<br>cllavhrralentsisqghpppvprpprvvdklslciapgkacspgaseitgls<br>kaelevqgrqrfddnlaillraflqrqpqpcclvahngdrydfpllqtelaris<br>tpspldgtfcvdsiaalkaleqasspsgngsrksyslgsiytrlywqaptdsht<br>aegdvltllsicqwkpqallqwvdeharpfstvkpmygtpattgttdlsggggs<br>ggggsggggsggggsleprgptikpsppckcpapnllggssvfifppkikdvlm<br>islspmvtcvvvdvseddpdvqiswfvnnvevhtaqtqthredynstlrvvsal<br>piqhqdwmsgkefkcsvnnkdlpasiertiskprgpvrapqvyvlpppaeemtk<br>kefsltcmitgflpaeiavdwtsngrteqnyknatvldsdgsyfmysklrvqk<br>stwergsifacsvvheglhnhlttksfsrtpgk* |
| 167 | murine<br>Trex1-<br>(G4S)5-<br>mIgG2a-c | metpaqllfllllwlpdttgmgsqtlphghmqtlifldleatglpssrpevtel<br>cllavhrralentsisqghpppvprpprvvdklslciapgkacspgaseitgls<br>kaelevqgrqrfddnlaillrafIqrqpqpcclvahngdrydfplIqtelaris<br>tpspldgtfcvdsiaalkaleqasspsgngsrksyslgsiytrlywqaptdsht<br>aegdvltllsicqwkpqallqwvdeharpfstvkpmygtpattgttdlsggggs<br>ggggsggggsggggsggggsleprgptikpsppckcpapnllggssvfifppki<br>kdvlmislspmvtcvvvdvseddpdvqiswfvnnvevhtaqtqthredynstlr<br>vvsalpiqhqdwmsgkefkcsvnnkdlpasiertiskprgpvrapqvyvlpppa<br>eemtkkefsltcmitgfIpaeiavdwtsngrteqnyknatvldsdgsyfmysk<br>irvqkstwergslfacsvvheglhnhlttksfsrtpgk* |

TABLE 2-continued

| SEQ ID NO: | DESCRIPTION | SEQUENCE (NUCLEOTIDE SEQUENCES ARE 5'-3') |
|---|---|---|
| 168 | NLGlnk | vdgaaaspvnvsspsvqdi |
| 169 | Murine Trex-Trex1-(G4s)5-mIgG2a-c | metpaqllflllllwlpdttgmgsqtlphghmqtlifldleatglpssrpevtel<br>cllavhrralentsisqghpppvprpprvvdklslciapgkacspgaseitgls<br>kaelevqgrqrfddnlaillraflqrqpqpcclvahngdrydfpllqtelaris<br>tpspldgtfcvdsiaalkaleqasspsgngsrksyslgsiytrlywqaptdsht<br>aegdvltllsicqwkpqallqwvdeharpfstvkpmygtpattgttdlmgsqtl<br>phghmqtlifidleatglpssrpevtelcllavhrralentsisqghpppvprp<br>prvvdklslciapgkacspgaseitglskaelevqgrqrfddnlaillrafiqr<br>qpqpcclvahngdrydfpllqtelaristpspldgtfcvdsiaalkaleqassp<br>sgngsrksyslgsiytrlywqaptdshtaegdvltllsicqwkpqallqwvdeh<br>arpfstvkpmygtpattgttdlsggggsggggsggggsggggsggggsleprgp<br>tikpsppckcpapnllggssvfifppkikdvimisispmvtcvvvdvseddpdv<br>qiswfvnnvevhtaqtqthredynstlrvvsalpiqhqdwmsgkefkcsvnnkd<br>lpasiertiskprgpvrapqvyvlpppaeemtkkefsltcmitgflpaeiavdw<br>tsngrteqnykntatvldsdgsyfmysklrvqkstwergslfacsvvheglhnh<br>ittksfsrtpgk* |
| 170 | huVK3LP-huTREX1-72aa-(g4s)4-hIgG1 WT | metpaqllflllllwlpdttgmgpgarrqgrivqgrpemcfcppptplpplrilt<br>lgthtptpcsspgsaagtyptmgsqalppgpmqtliffdmeatglpfsqpkvte<br>lcllavhrcalespptsqgppptvppprvvdklslcvapgkacspaaseitgl<br>stavlaahgrqcfddnlanlllaflrrqpqpwclvahngdrydfpllqaelaml<br>gltsaldgafcvdsitalkalerasspsehgprksyslgsiytrlygqsppdsh<br>taegdvlallsicqwrpqallrwvdaharpfgtirpmygvtasartkdlsgggg<br>sggggsggggsggggslepkssdkthtcppcpapellggpsvflfppkpkdtlm<br>isrtpevtcvvvdvshedpevkfnwyvdgvevhnaktkpreeqynstyrvvsvl<br>tvlhqdwlngkeykckvsnkalpapiektiskakgqprepqvytlppsrdeltk<br>nqvsltclvkgfypsdiavewesngqpennykttppvldsdgsfflyskitvdk<br>srwqqgnvfscsvmhealhnhytqkslslspgk* |
| 171 | huVK3LP-huTREX1-72aa-(g4s)5-hIgG1 WT | metpaqllflllllwlpdttgmgpgarrqgrivqgrpemcfcppptplpplrilt<br>lgthtptpcsspgsaagtyptmgsqalppgpmqtliffdmeatglpfsqpkvte<br>lcllavhrcalespptsqgppptvppprvvdklslcvapgkacspaaseitgl<br>stavlaahgrqcfddnlanlllafirrqpqpwclvahngdrydfpllqaelaml<br>gltsaldgafcvdsitalkalerasspsehgprksyslgsiytrlygqsppdsh<br>taegdvlallsicqwrpqallrwvdaharpfgtirpmygvtasartkdlsgggg<br>sggggsggggsggggsggggslepkssdkthtcppcpapellggpsvflfppkp<br>kdtlmisrtpevtcvvvdvshedpevkfnwyvdgvevhnaktkpreeqynstyr<br>vvsvltvlhqdwlngkeykckvsnkalpapiektiskakgqprepqvytlppsr<br>deltknqvsltclvkgfypsdiavewesngqpennykttppvldsdgsfflysk<br>itvdksrwqqgnvfscsvmhealhnhytqkslslspgk* |
| 172 | huVK3LP-hDNase1-G105R; A114F-(G4S)4-hIgG1-WT-NLG-hRNase1-WT | gttaagcttgccaccatggaaaccccagcgcagcttctcttcctcctgctactc<br>tggctcccagataccaccggtctgaagatcgcagccttcaacatccagacattt<br>ggggagaccaagatgtccaatgccaccctcgtcagctacattgtgcagatcctg<br>agccgctatgacatcgccctggtccaggaggtcagagacagccacctgactgcc<br>gtggggaagctgctggacaacctcaatcaggatgcaccagacacctatcactac<br>gtggtcagtgagccactgggacggaacagctataaggagcgctacctgttcgtg<br>tacaggcctgaccaggtgtctgcggtggacagctactactacgatgatggctgc<br>gagccctgcaggaacgacaccttcaaccgagagccattcattgtcaggttcttc<br>tcccggttcacagaggtcagggagtttgccattgttcccctgcatgcggccccg<br>ggggacgcagtagccgagatcgacgctctctatgacgtctacctggatgtccaa<br>gagaaatggggcttggaggacgtcatgttgatgggcgacttcaatgcgggctgc<br>agctatgtgagaccctcccagtggtcatccatccgcctgtggacaagccccacc<br>ttccagtggctgatccccgacagcgctgacaccacagctacacccacgcactgt<br>gcctatgacaggatcgtggttgcagggatgctgctccgaggcgccgttgttccc<br>gactcggctcttccctttaacttccaggctgcctatggcctgagtgaccaactg<br>gcccaagccatcagtgaccactatccagtggaggtgatgctgaaagatctctcc<br>ggaggaggtggctcaggtggtggaggatctggaggaggtgggagtggtggaggt<br>ggttctaccggtctcgagcccaaatcttctgacaaaactcacacatgtccaccg<br>tgcccagcacctgaactcctggggggaccgtcagtcttcctcttccccccaaaa<br>cccaaggacaccctcatgatctcccggacccctgaggtcacatgcgtggtggtg<br>gacgtgagccacgaagaccctgaggtcaagttcaactggtacgtggacggcgtg<br>gaggtgcataatgccaagacaaagccgcgggaggagcagtacaacagcacgtac<br>cgtgtggtcagcgtcctcaccgtcctgcaccaggactggctgaatggcaaggag<br>tacaagtgcaaggtctccaacaaagccctcccagcccccatcgagaaaaccatc<br>tccaaagccaaagggcagccccgagaaccacaggtgtacaccctgcccccatcc<br>cgggatgagctgaccaagaaccaggtcagcctgacctgcctggtcaaaggcttc<br>tatcccagcgacatcgccgtggagtgggagagcaatgggcagccggagaacaac<br>tacaagaccacgcctcccgtgctggactccgacggctccttcttcctctacagc<br>aagctcaccgtggacaagagcaggtggcagcaggggaacgtcttctcatgctcc<br>gtgatgcatgaggctctgcacaaccactacacgcagaagagcctctctctgtct<br>ccgggtaaagtcgacggagctagcagccccgtgaacgtgagcagccccagcgtg<br>caggatatcccttccctgggcaaggaatcccgggccaagaaattccagcggcag<br>catatggactcagacagttcccccagcagcagctccacctactgtaaccaaatg<br>atgaggcgccggaatatgacacaggggcggtgcaaaccagtgaacacctttgtg<br>cacgagcccctggtagatgtccagaatgtctgtttccaggaaaaggtcacctgc |

TABLE 2-continued

| SEQ ID NO: | DESCRIPTION | SEQUENCE (NUCLEOTIDE SEQUENCES ARE 5'-3') |
|---|---|---|
| | | aagaacgggcagggcaactgctacaagagcaactccagcatgcacatcacagac<br>tgccgcctgacaaacggctccaggtaccccaactgtgcataccggaccagcccg<br>aaggagagacacatcattgtggcctgtgaagggagcccatatgtgccagtccac<br>tttgatgcttctgtggaggactctacctaataatctaga |
| 173 | huVK3LP-<br>hDNase1-<br>G105R;<br>A114F-<br>(G4S)4-<br>hIgG1-<br>WT-NLG-<br>hRNase1-<br>WT | metpaqllfllllwlpdttglkiaafniqtfgetkmsnatlvsyivqilsrydi<br>alvqevrdshltavgklldnlnqdapdtyhyvvseplgrnsykerylfvyrpdq<br>vsavdsyyyddgcepcrndtfnrepfivrffsrftevrefaivplhaapgdava<br>eidalydvyldvqekwgledvmlmgdfnagcsyvrpsqwssirlwtsptfqwli<br>pdsadttatpthcaydrivvagmllrgavvpdsalpfnfqaayglsdqlaqais<br>dhypvevmlkdlsggggsggggsggggsggggstglepkssdkthtcppcpape<br>llggpsvflfppkpkdtlmisrtpevtcvvvdvshedpevkfnwyvdgvevhna<br>ktkpreeqynstyrvvsvltvlhqdwlngkeykckvsnkalpapiektiskakg<br>qprepqvytlppsrdeltknqvsltclvkgfypsdiavewesngqpennykttp<br>pvldsdgsfflyskltvdksrwqqgnvfscsvmhealhnhytqkslslspgkvd<br>gasspvnvsspsvqdipslgkesrakkfqrqhmdsdsspssstycnqmmrrrn<br>mtqgrckpvntfvheplvdvqnvcfqekvtckngqgncyksnssmhitdcrltn<br>gsrypncayrtspkerhiivacegspyvpvhfdasvedst* |
| 174 | huVK3LP-<br>hRNAse-<br>G88D-<br>hIgG1-<br>P238S;<br>K322S;<br>P331S | gttaagcttgccaccatggaaaccccagcgcagcttctcttcctcctgctactc<br>tggctcccagataccaccggtccttccctgggcaaggaatcccgggccaagaaa<br>ttccagcggcagcatatggactcagacagttcccccagcagcagctccacctac<br>tgtaaccaaatgatgaggcgccggaatatgacacaggggcggtgcaaaccagtg<br>aacacctttgtgcacgagcccctggtagatgtccagaatgtctgtttccaggaa<br>aaggtcacctgcaagaacgggcagggcaactgctacaagagcaactccagcatg<br>cacatcacagactgccgcctgacaaacgactccaggtaccccaactgtgcatac<br>cggaccagcccgaaggagagacacatcattgtggcctgtgaagggagcccatat<br>gtgccagtccactttgatgcttctgtggaggactctacagatctcgagcccaaa<br>tcttctgacaaaactcacacatgtccaccgtgtccagcacctgaactcctgggt<br>ggatcgtcagtcttcctcttccccccaaaacccaaggacactctcatgatctcc<br>cggacccctgaggtcacgtgcgtggtggtggacgtgagccaggaagaccccgag<br>gtccagttcaactggtacgtggacggcatggaggtgcataatgccaagacaaag<br>ccacgggaggagcagttcaacagcacgttccgtgtggtcagcgtcctcaccgtc<br>gtgcaccaggactggctgaacggcaaggagtacaagtgcaaggtctccaacaaa<br>gccctcccagcctccatcgagaaaacaatctccaaaaccaaagggcagccccga<br>gaaccacaggtgtacaccctgcccccatcccgggaggagatgaccaagaaccag<br>gtcagcctgacctgcctggtcaaaggcttctatcccagcgacatcgccgtggag<br>tgggagagcaatgggcagccggagaacaactacaacaccacgcctcccgtgctg<br>gactccgacggctccttctccctctacagcaagctcaccgtggacaagagcagg<br>tggcagcaggggaacgtcttctcatgctccgtgatgcatgaggctctgcacaac<br>cactacacgcagaagagcctctctctgtctccgggtaaatgataatctaga |
| 175 | huVK3LP-<br>hRNAse-<br>G88D-<br>hIgG1-<br>P238S;<br>K322S;<br>P331S | metpaqllfllllwlpdttgpslgkesrakkfqrqhmdsdsspssstycnqmm<br>rrrnmtqgrckpvntfvheplvdvqnvcfqekvtckngqgncyksnssmhitdc<br>rltndsrypncayrtspkerhiivacegspyvpvhfdasvedstdlepkssdkt<br>htcppcpapellggssvfifppkpkdtlmisrtpevtcvvvdvsqedpevqfnw<br>yvdgmevhnaktkpreeqfnstfrvvsvltvvhqdwlngkeykckvsnkalpas<br>iektisktkgqprepqvytlppsreemtknqvsltclvkgfypsdiavewesng<br>qpennynttppvldsdgsfslyskltvdksrwqqgnvfscsvmhealhnhytqk<br>slslspgk* |
| 176 | huVK3LP-<br>hDNase1-<br>G105R;<br>A114F-<br>(G4S)5-<br>1-hIgG1-<br>WT-NLG-<br>hRNase1-<br>WT | gttaagcttgccaccatggaaaccccagcgcagcttctcttcctcctgctactc<br>tggctcccagataccaccggtctgaagatcgcagccttcaacatccagacattt<br>ggggagaccaagatgtccaatgccaccctcgtcagctacattgtgcagatcctg<br>agccgctatgacatcgccctggtccaggaggtcagagacagccacctgactgcc<br>gtggggaagctgctggacaacctcaatcaggatgcaccagacacctatcactac<br>gtggtcagtgagccactgggacggaacagctataaggagcgctacctgttcgtg<br>tacaggcctgaccaggtgtctgcggtggacagctactactacgatgatggctgc<br>gagccctgcaggaacgacaccttcaaccgagagccattcattgtcaggttcttc<br>tcccggttcacagaggtcagggagtttgccattgttcccctgcatgcggccccg<br>ggggacgcagtagccgagatcgacgctctctatgacgtctacctggatgtccaa<br>gagaaatggggcttggaggacgtcatgttgatgggcgacttcaatgcgggctgc<br>agctatgtgagaccctcccagtggtcatccatccgcctgtggacaagccccacc<br>ttccagtggctgatccccgacagcgctgacaccacagctacacccacgcactgt<br>gcctatgacaggatcgtggttgcagggatgctgctccgaggcgccgttgttccc<br>gactcggctcttccctttaacttccaggctgcctatggcctgagtgaccaactg<br>gcccaagccatcagtgaccactatccagtggaggtgatgctgaaagatctctcc<br>ggaggaggtggctcaggtggtggaggatctggaggaggtggctcaggtggtgga<br>ggatctggaggaggtgggagtaccggtctcgagcccaaatcttctgacaaaact<br>cacacatgtccaccgtgcccagcacctgaactcctgggggggaccgtcagtcttc<br>ctcttccccccaaaacccaaggacaccctcatgatctcccggacccctgaggtc<br>acatgcgtggtggtggacgtgagccacgaagaccctgaggtcaagttcaactgg<br>tacgtggacggcgtggaggtgcataatgccaagacaaagccgcgggaggagcag<br>tacaacagcacgtaccgtgtggtcagcgtcctcaccgtcctgcaccaggactgg<br>ctgaatggcaaggagtacaagtgcaaggtctccaacaaagccctcccagccccc<br>atcgagaaaaccatctccaaagccaaagggcagccccgagaaccacaggtgtac<br>accctgcccccatcccgggatgagctgaccaagaaccaggtcagcctgacctgc |

TABLE 2-continued

| SEQ ID NO: | DESCRIPTION | SEQUENCE (NUCLEOTIDE SEQUENCES ARE 5'-3') |
|---|---|---|
| | | ctggtcaaaggcttctatcccagcgacatcgccgtggagtgggagagcaatggg<br>cagccggagaacaactacaagaccacgcctcccgtgctggactccgacggctcc<br>ttcttcctctacagcaagctcaccgtggacaagagcaggtggcagcaggggaac<br>gtcttctcatgctccgtgatgcatgaggctctgcacaaccactacacgcagaag<br>agcctctctctgtctccgggtaaagtcgacggagctagcagccccgtgaacgtg<br>agcagccccagcgtgcaggatatcccttccctgggcaaggaatcccgggccaag<br>aaattccagcggcagcatatggactcagacagttcccccagcagcagctccacc<br>tactgtaaccaaatgatgaggcgccggaatatgacacaggggcggtgcaaacca<br>gtgaacacctttgtgcacgagcccctggtagatgtccagaatgtctgtttccag<br>gaaaaggtcacctgcaagaacgggcagggcaactgctacaagagcaactccagc<br>atgcacatcacagactgccgcctgacaaacggctccaggtaccccaactgtgca<br>taccggaccagcccgaaggagagacacatcattgtggcctgtgaagggagccca<br>tatgtgccagtccactttgatgcttctgtggaggactctacctaataatctaga |
| 177 | huVK3LP-<br>hDNase1-<br>G105R;<br>A114F-<br>(G4S)5-<br>1-hIgG1-<br>WT-NLG-<br>hRNase1-<br>WT | metpaqllfllllwlpdttglkiaafniqtfgetkmsnatlvsyivqilsrydi<br>alvqevrdshltavgklldnlnqdapdtyhyvvseplgrnsykerylfvyrpdq<br>vsavdsyyyddgcepcrndtfnrepfivrffsrftevrefaivplhaapgdava<br>eldalydvyldvqekwgledvmlmgdfnagcsyvrpsqwssirlwtsptfqwli<br>pdsadttatpthcaydrivvagmllrgavvpdsalpfnfqaayglsdqlaqais<br>dhypvevmlkdlsggggsggggsggggsggggsggggstglepkssdkthtcpp<br>cpapellggpsvflfppkpkdtlmisrtpevtcvvvdvshedpevkfnwyvdgv<br>evhnaktkpreeqynstyrvvsvltvlhqdwlngkeykckvsnkalpapiekti<br>skakgqprepqvytlppsrdeltknqvsltclvkgfypsdiavewesngqpenn<br>ykttppvldsdgsfflyskltvdksrwqqgnvfscsvmhealhnhytqkslsls<br>pgkvdgasspvnvsspsvqdipslgkesrakkfqrqhmdsdsspssstycnqm<br>mrrrnmtqgrckpvntfvheplvdvqnvcfqekvtckngqgncyksnssmhitd<br>crltngsrypncayrtspkerhiivacegspyvpvhfdasvedst* |
| 178 | huVK3LP-<br>hDNase1-<br>G105R;<br>A114F-<br>(G4S)5-<br>2-hIgG1-<br>WT-NLG-<br>hRNase1-<br>WT | gttaagcttgccaccatggaaaccccagcgcagcttctcttcctcctgctactc<br>tggctcccagataccaccggtctgaagatcgcagccttcaacatccagacattt<br>ggggagaccaagatgtccaatgccaccctcgtcagctacattgtgcagatcctg<br>agccgctatgacatcgccctggtccaggaggtcagagacagccacctgactgcc<br>gtggggaagctgctggacaacctcaatcaggatgcaccagacacctatcactac<br>gtggtcagtgagccactgggacggaacagctataaggagcgctacctgttcgtg<br>tacaggcctgaccaggtgtctgcggtggacagctactactacgatgatggctgc<br>gagccctgcaggaacgacaccttcaaccgagagccattcattgtcaggttcttc<br>tcccggttcacagaggtcagggagtttgccattgttcccctgcatgcggccccg<br>ggggacgcagtagccgagatcgacgctctctatgacgtctacctggatgtccaa<br>gagaaatggggcttggaggacgtcatgttgatgggcgacttcaatgcgggctgc<br>agctatgtgagaccctcccagtggtcatccatccgcctgtggacaagccccacc<br>ttccagtggctgatccccgacagcgctgacaccacagctacacccacgcactgt<br>gcctatgacaggatcgtggttgcagggatgctgctccgaggcgccgttgttccc<br>gactcggctcttccctttaacttccaggctgcctatggcctgagtgaccaactg<br>gcccaagccatcagtgaccactatccagtggaggtgatgctgaaagatctctcc<br>ggaggaggtggctcaggtggtggaggatctggaggaggtggctcaggtggtgga<br>ggatctggaggaggtgggagtctcgagcccaaatcttctgacaaaactcacaca<br>tgtccaccgtgcccagcacctgaactcctggggggaccgtcagtcttcctcttc<br>cccccaaaacccaaggacaccctcatgatctcccggacccctgaggtcacatgc<br>gtggtggtggacgtgagccacgaagaccctgaggtcaagttcaactggtacgtg<br>gacggcgtggaggtgcataatgccaagacaaagccgcgggaggagcagtacaac<br>agcacgtaccgtgtggtcagcgtcctcaccgtcctgcaccaggactggctgaat<br>ggcaaggagtacaagtgcaaggtctccaacaaagccctcccagcccccatcgag<br>aaaaccatctccaaagccaaagggcagccccgagaaccacaggtgtacaccctg<br>cccccatcccgggatgagctgaccaagaaccaggtcagcctgacctgcctggtc<br>aaaggcttctatcccagcgacatcgccgtggagtgggagagcaatgggcagccg<br>gagaacaactacaagaccacgcctcccgtgctggactccgacggctccttcttc<br>ctctacagcaagctcaccgtggacaagagcaggtggcagcaggggaacgtcttc<br>tcatgctccgtgatgcatgaggctctgcacaaccactacacgcagaagagcctc<br>tctctgtctccgggtaaagtcgacggagctagcagccccgtgaacgtgagcagc<br>cccagcgtgcaggatatcccttccctgggcaaggaatcccgggccaagaaattc<br>cagcggcagcatatggactcagacagttcccccagcagcagctccacctactgt<br>aaccaaatgatgaggcgccggaatatgacacaggggcggtgcaaaccagtgaac<br>acctttgtgcacgagcccctggtagatgtccagaatgtctgtttccaggaaaag<br>gtcacctgcaagaacgggcagggcaactgctacaagagcaactccagcatgcac<br>atcacagactgccgcctgacaaacggctccaggtaccccaactgtgcataccgg<br>accagcccgaaggagagacacatcattgtggcctgtgaagggagcccatatgtg<br>ccagtccactttgatgcttctgtggaggactctacctaataatctaga |
| 179 | huVK3LP-<br>hDNase1-<br>G105R;<br>A114F-<br>(G4S)5-<br>2-hIgG1-<br>WT-NLG-<br>hRNase1-<br>WT | metpaqllfllllwlpdttglkiaafniqtfgetkmsnatlvsyivqilsrydi<br>alvqevrdshltavgklldnlnqdapdtyhyvvseplgrnsykerylfvyrpdq<br>vsavdsyyyddgcepcrndtfnrepfivrffsrftevrefaivplhaapgdava<br>eidalydvyldvqekwgledvmlmgdfnagcsyvrpsqwssirlwtsptfqwli<br>pdsadttatpthcaydrivvagmllrgavvpdsalpfnfqaayglsdqlaqais<br>dhypvevmlkdlsggggsggggsggggsggggsggggslepkssdkthtcppcp<br>apellggpsvflfppkpkdtlmisrtpevtcvvvdvshedpevkfnwyvdgvev<br>hnaktkpreeqynstyrvvsvltvlhqdwlngkeykckvsnkalpapiektisk<br>akgqprepqvytlppsrdeltknqvsltclvkgfypsdiavewesngqpennyk |

TABLE 2-continued

| SEQ ID NO: | DESCRIPTION | SEQUENCE (NUCLEOTIDE SEQUENCES ARE 5'-3') |
|---|---|---|
| | | ttppvldsdgsfflyskltvdksrwqqgnvfscsvmhealhnhytqkslslspg<br>kvdgasspvnvsspsvqdipslgkesrakkfqrqhmdsdsspsssstycnqmmr<br>rrnmtqgrckpvntfvheplvdvqnvcfqekvtckngqgncyksnssmhitdcr<br>ltngsrypncayrtspkerhiivacegspyvpvhfdasvedst |
| 180 | huVK3LP-<br>hDNase1<br>G105R;<br>A114F-<br>hIgG1-<br>WT-NLG-<br>hRNasse1-<br>WT | gttaagcttgccaccatggaaaccccagcgcagcttctcttcctcctgctactc<br>tggctcccagataccaccggtctgaagatcgcagccttcaacatccagacattt<br>ggggagaccaagatgtccaatgccaccctcgtcagctacattgtgcagatcctg<br>agccgctatgacatcgccctggtccaggaggtcagagacagccacctgactgcc<br>gtggggaagctgctggacaacctcaatcaggatgcaccagacacctatcactac<br>gtggtcagtgagccactgggacggaacagctataaggagcgctacctgttcgtg<br>tacaggcctgaccaggtgtctgcggtggacagctactactacgatgatggctgc<br>gagccctgcaggaacgacaccttcaaccgagagccattcattgtcaggttcttc<br>tcccggttcacagaggtcagggagtttgccattgttcccctgcatgcggccccg<br>ggggacgcagtagccgagatcgacgctctctatgacgtctacctggatgtccaa<br>gagaaatggggcttggaggacgtcatgttgatgggcgacttcaatgcgggctgc<br>agctatgtgagaccctcccagtggtcatccatccgcctgtggacaagccccacc<br>ttccagtggctgatccccgacagcgctgacaccacagctacacccacgcactgt<br>gcctatgacaggatcgtggttgcagggatgctgctccgaggcgccgttgttccc<br>gactcggctcttccctttaacttccaggctgcctatggcctgagtgaccaactg<br>gcccaagccatcagtgaccactatccagtggaggtgatgctgaaagatctcgag<br>cccaaatcttctgacaaaactcacacatgtccaccgtgcccagcacctgaactc<br>ctggggggaccgtcagtcttcctcttccccccaaaacccaaggacaccctcatg<br>atctcccggacccctgaggtcacatgcgtggtggtggacgtgagccacgaagac<br>cctgaggtcaagttcaactggtacgtggacggcgtggaggtgcataatgccaag<br>acaaagccgcgggaggagcagtacaacagcacgtaccgtgtggtcagcgtcctc<br>accgtcctgcaccaggactggctgaatggcaaggagtacaagtgcaaggtctcc<br>aacaaagccctcccagcccccatcgagaaaaccatctccaaagccaaagggcag<br>ccccgagaaccacaggtgtacaccctgcccccatcccgggatgagctgaccaag<br>aaccaggtcagcctgacctgcctggtcaaaggcttctatcccagcgacatcgcc<br>gtggagtgggagagcaatgggcagccggagaacaactacaagaccacgcctccc<br>gtgctggactccgacggctccttcttcctctacagcaagctcaccgtggacaag<br>agcaggtggcagcaggggaacgtcttctcatgctccgtgatgcatgaggctctg<br>cacaaccactacacgcagaagagcctctctctgtctccgggtaaagtcgacgga<br>gctagcagccccgtgaacgtgagcagccccagcgtgcaggatatcccttccctg<br>ggcaaggaatcccgggccaagaaattccagcggcagcatatggactcagacagt<br>tcccccagcagcagctccacctactgtaaccaaatgatgaggcgccggaatatg<br>acacaggggcggtgcaaaccagtgaacacctttgtgcacgagcccctggtagat<br>gtccagaatgtctgtttccaggaaaaggtcacctgcaagaacgggcagggcaac<br>tgctacaagagcaactccagcatgcacatcacagactgccgcctgacaaacggc<br>tccaggtaccccaactgtgcataccggaccagcccgaaggagagacacatcatt<br>gtggcctgtgaagggagcccatatgtgccagtccactttgatgcttctgtggag<br>gactctacctaataatctaga |
| 181 | huVK3LP-<br>hDNase1<br>G105R;<br>A114F-<br>hIgG1-<br>WT-NLG-<br>hRNasse1-<br>WT | metpaqllfllllwlpdttglkiaafniqtfgetkmsnatlvsyivqilsrydi<br>alvqevrdshltavgklldnlnqdapdtyhyvvseplgrnsykerylfvyrpdq<br>vsavdsyyyddgcepcrndtfnrepfivrffsrftevrefaivplhaapgdava<br>eidalydvyldvqekwgledvmlmgdfnagcsyvrpsqwssirlwtsptfqwli<br>pdsadttatpthcaydrivvagmllrgavvpdsalpfnfqaayglsdqlaqais<br>dhypvevmlkdlepkssdkthtcppcpapellggpsvflfppkpkdtlmisrtp<br>evtcvvvdvshedpevkfnwyvdgvevhnaktkpreeqynstyrvvsvltvlhq<br>dwlngkeykckvsnkalpapiektiskakgqprepqvytlppsrdeltknqvsl<br>tclvkgfypsdiavewesngqpennykttppvldsdgsfflyskitvdksrwqq<br>gnvfscsvmhealhnhytqkslslspgkvdgasspvnvsspsvqdipslgkesr<br>akkfqrqhmdsdsspsssstycnqmmrrrnmtqgrckpvntfvheplvdvqnvc<br>fqekvtckngqgncyksnssmhitdcrltngsrypncayrtspkerhiivaceg<br>spyvpvhfdasvedst* |
| 182 | huVK3LP-<br>mDNase1L3-<br>mIgG2A-C<br>(mut) | gaccaagcttgccaccatggaaaccccagcgcagcttctcttcctcctgctact<br>ctggctcccagataccaccggtctaaggctctgctccttcaatgtgaggtcctt<br>tggagcgagcaagaaggaaaaccatgaagccatggatatcattgtgaagatcat<br>caaacgctgtgaccttatactgttgatggaaatcaaggacagcagcaacaacat<br>ctgtcccatgctgatggagaagctgaatggaaattcacgaagaagcacaacata<br>caactatgtgattagttctcgacttggaagaaacacgtacaaagagcagtatgc<br>cttcgtctacaaggagaagctggtgtctgtgaagacaaaataccactaccatga<br>ctatcaggatggagacacagacgtgttttccagggagccctttgtggtttggtt<br>ccattcccccttttactgctgtcaaggacttcgtgattgtccccttgcacacaac<br>tcccgagacctccgttaaagagatagatgagctggtcgatgtctacacggatgt<br>gagaagccagtggaagacagagaatttcatcttcatgggtgatttcaacgccgg<br>ctgtagctatgtccccaagaaggcctggcagaacattcgtttgaggacggaccc<br>caagtttgtttggctgattggggaccaagaggacactacggtcaagaagagtac<br>cagctgtgcctatgacaggattgtgctttgtggacaagagatagtcaactccgt<br>ggttccccgttccagtggcgtctttgactttcagaaagcttatgacttgtctga<br>agaggaggccctggatgtcagtgatcactttccagttgagtttaagctacagtc<br>ttcaagggccttcaccaacaacagaaaatctgtttctctcaaaaagagaaaaaa<br>aggcaatcgctcctcagatctcgagcccagaggtctcacaatcaagccctctcc<br>tccatgcaaatgcccagcacctaacctcttgggtggatcatccgtcttcatctt |

TABLE 2-continued

| SEQ ID NO: | DESCRIPTION | SEQUENCE (NUCLEOTIDE SEQUENCES ARE 5'-3') |
|---|---|---|
| | | ccctccaaagatcaaggatgtactcatgatctccctgagccccatggtcacatg<br>tgtggtggtggatgtgagcgaggatgacccagacgtccagatcagctggtttgt<br>gaacaacgtggaagtacacacagctcagacacaaacccatagagaggattacaa<br>cagtactctccgggtggtcagtgccctccccatccagcaccaggactggatgag<br>tggcaaggagttcaaatgctcggtcaacaacaaagacctcccagcgtccatcga<br>gagaaccatctcaaaacccagagggccagtaagagctccacaggtatatgtctt<br>gcctccaccagcagaagagatgactaagaaagagttcagtctgacctgcatgat<br>cacaggcttcttacctgccgaaattgctgtggactggaccagcaatgggcgtac<br>agagcaaaactacaagaacaccgcaacagtcctggactctgatggttcttactt<br>catgtacagcaagctcagagtacaaaagagcacttgggaaagaggaagtctttt<br>cgcctgctcagtggtccacgagggtctgcacaatcaccttacgactaagagctt<br>ctctcggactccgggtaaatgataatctagaa |
| 183 | huVK3LP-<br>mDNase1L3-<br>mIgG2A-C<br>(mut) | metpaqllfllllwlpdttglrlcsfnvrsfgaskkenheamdiivkiikrcdl<br>illmeikdssnnicpmlmeklngnsrrsttynyvissrlgrntykeqyafvyke<br>klvsvktkyhyhdyqdgdtdvfsrepfvvwfhspftavkdfvivplhttpetsv<br>keldelvdvytdvrsqwktenfifmgdfnagcsyvpkkawqnirlrtdpkfvwl<br>igdqedttvkkstscaydrivlcgqeivnsvvprssgvfdfqkaydlseeeald<br>vsdhfpvefklqssraftnnrksvslkkrkkgnrssdleprgltikpsppckcp<br>apnllggssvfifppkikdvimislspmvtcvvvdvseddpdvqiswfvnnvev<br>htaqtqthredynstlrvvsalpiqhqdwmsgkefkcsvnnkdlpasiertisk<br>prgpvrapqvyvlpppaeemtkkefsltcmitgfIpaeiavdwtsngrteqnyk<br>ntatvldsdgsyfmysklrvqkstwergslfacsvvheglhnhlttksfsrtpg<br>k* |
| 184 | mDNase1L3-<br>NL-<br>mIgG2A_C<br>(mut) | gagaccagcttgccccatgtccctgcacccagcttccccacgcctggcctccct<br>gctgctcttcatccttgccctccatgacaccctggccctaaggctctgctcctt<br>caatgtgaggtcctttggagcgagcaagaaggaaaaccatgaagccatggatat<br>cattgtgaagatcatcaaacgctgtgaccttatactgttgatggaaatcaagga<br>cagcagcaacaacatctgtcccatgctgatggagaagctgaatggaaattcacg<br>aagaagcacaacatacaactatgtgattagttctcgacttggaagaaacacgta<br>caaagagcagtatgccttcgtctacaaggagaagctggtgtctgtgaagacaaa<br>ataccactaccatgactatcaggatggagacacagacgtgttttccagggagcc<br>ctttgtggtttggttccattcccctttactgctgtcaaggacttcgtgattgt<br>ccccttgcacacaactcccgagacctccgttaaagagatagatgagctggtcga<br>tgtctacacggatgtgagaagccagtggaagacagagaatttcatcttcatggg<br>tgatttcaacgccggctgtagctatgtccccaagaaggcctggcagaacattcg<br>tttgaggacggaccccaagtttgtttggctgattggggaccaagaggacactac<br>ggtcaagaagagtaccagctgtgcctatgacaggattgtgctttgtggacaaga<br>gatagtcaactccgtggttccccgttccagtggcgtctttgactttcagaaagc<br>ttatgacttgtctgangaggangccctggatgtcagtgatcactttccagttga<br>gtttaagctacagtcttcaagggccttcaccaacaacagaaaatctgtttctct<br>caaaaagagaaaaaaaggcaatcgctcctcagatctcgagcccagaggtctcac<br>aatcaagccctctcctccatgcaaatgcccagcacctaacctcttgggtggatc<br>atccgtcttcatcttccctccaaagatcaaggatgtactcatgatctccctgag<br>ccccatggtcacatgtgtggtggtggatgtgagcgaggatgacccagacgtcca<br>gatcagctggtttgtgaacaacgtggaagtacacacagctcagacacaaaccca<br>tagagaggattacaacagtactctccgggtggtcagtgccctccccatccagca<br>ccaggactggatgagtggcaaggagttcaaatgctcggtcaacaacaaagacct<br>cccagcgtccatcgagagaaccatctcaaaacccagagggccagtaagagctcc<br>acaggtatatgtcttgcctccaccagcagaagagatgactaagaaagagttcag<br>tctgacctgcatgatcacaggcttcttacctgccgaaattgctgtggactggac<br>cagcaatgggcgtacagagcaaaactacaagaacaccgcaacagtcctggactc<br>tgatggttcttacttcatgtacagcaagctcagagtacaaaagagcacttggga<br>aagaggaagtcttttcgcctgctcagtggtccacgagggtctgcacaatcacct<br>tacgactaagagcttctctcggactccgggtaaatgataatctagaa |
| 185 | mDNase1L3-<br>NL-<br>mIgG2A_C<br>(mut) | mslhpasprlaslllfilalhdtlalrlcsfnvrsfgaskkenheamdiivkii<br>krcdlillmeikdssnnicpmlmeklngnsrrsttynyvissrlgrntykeqya<br>fvykeklvsvktkyhyhdyqdgdtdvfsrepfvvwfhspftavkdfvivplhtt<br>petsvkeidelvdvytdvrsqwktenfifmgdfnagcsyvpkkawqnirlrtdp<br>kfvwligdqedttvkkstscaydrivlcgqeivnsvvprssgvfdfqkaydlsx<br>exaldvsdhfpvefklqssraftnnrksvslkkrkkgnrssdleprgltikpsp<br>pckcpapnllggssvfifppkikdvlmislspmvtcvvvdvseddpdvqiswfv<br>nnvevhtaqtqthredynstlrvvsalpiqhqdwmsgkefkcsvnnkdlpasie<br>rtiskprgpvrapqvyvlpppaeemtkkefsltcmitgflpaeiavdwtsngrt<br>eqnykntatvldsdgsyfmysklrvqkstwergslfacsvvheglhnhlttksf<br>srtpgk* |
| 186 | huVK3LP-<br>hDNase1L3-<br>hIgG1WT-<br>NLG-<br>hRNase1-<br>WT | gttaagcttgccaccatggaaaccccagcgcagcttctcttcctcctgctactc<br>tggctcccagataccaccggtatgaggatctgctccttcaacgtcaggtccttt<br>ggggaaagcaagcaggaagacaagaatgccatggatgtcattgtgaaggtcatc<br>aaacgctgtgacatcatactcgtgatggaaatcaaggacagcaacaacaggatc<br>tgccccatactgatggagaagctgaacagaaattcaaggagaggcataacatac<br>aactatgtgattagctctcggcttggaagaaacacatataaagaacaatatgcc<br>tttctctacaaggaaaagctggtgtctgtgaagaggagttatcactaccatgac<br>tatcaggatggagacgcagatgtgttttccagggagccctttgtggtctggttc |

TABLE 2-continued

| SEQ ID NO: | DESCRIPTION | SEQUENCE (NUCLEOTIDE SEQUENCES ARE 5'-3') |
|---|---|---|
| | | caatctccccacactgctgtcaaagacttcgtgattatcccccctgcacaccacc<br>ccagagacatccgttaaggagatcgatgagttggttgaggtctacacggacgtg<br>aaacaccgctggaaggcggagaatttcattttcatgggtgacttcaatgccggc<br>tgcagctacgtccccaagaaggcctggaagaacatccgcttgaggactgacccc<br>aggtttgtttggctgatcggggaccaagaggacaccacggtgaagaagagcacc<br>aactgtgcatatgacaggattgtgcttagaggacaagaaatcgtcagttctgtt<br>gttcccaagtcaaacagtgtttttgacttccagaaagcttacaagctgactgaa<br>gaggaggccctggatgtcagcgaccactttccagttgaatttaaactacagtct<br>tcaagggccttcaccaacagcaaaaaatctgtcactctaaggaagaaaacaaag<br>agcaaacgctcagatctcgagcccaaatcttctgacaaaactcacacatgtcca<br>ccgtgcccagcacctgaactcctggggggaccgtcagtcttcctcttcccccca<br>aaacccaaggacaccctcatgatctcccggacccctgaggtcacatgcgtggtg<br>gtggacgtgagccacgaagaccctgaggtcaagttcaactggtacgtggacggc<br>gtggaggtgcataatgccaagacaaagccgcgggaggagcagtacaacagcacg<br>taccgtgtggtcagcgtcctcaccgtcctgcaccaggactggctgaatggcaag<br>gagtacaagtgcaaggtctccaacaaagccctcccagcccccatcgagaaaacc<br>atctccaaagccaaagggcagccccgagaaccacaggtgtacaccctgccccca<br>tcccgggatgagctgaccaagaaccaggtcagcctgacctgcctggtcaaaggc<br>ttctatcccagcgacatcgccgtggagtgggagagcaatgggcagccggagaac<br>aactacaagaccacgcctcccgtgctggactccgacggctccttcttcctctac<br>agcaagctcaccgtggacaagagcaggtggcagcaggggaacgtcttctcatgc<br>tccgtgatgcatgaggctctgcacaaccactacacgcagaagagcctctctctg<br>tctccgggtaaagtcgacggagctagcagccccgtgaacgtgagcagccccagc<br>gtgcaggatatcccttccctgggcaaggaatcccgggccaagaaattccagcgg<br>cagcatatggactcagacagttcccccagcagcagctccacctactgtaaccaa<br>atgatgaggcgccggaatatgacacaggggcggtgcaaaccagtgaacaccttt<br>gtgcacgagccccctggtagatgtccagaatgtctgtttccaggaaaaggtcacc<br>tgcaagaacgggcagggcaactgctacaagagcaactccagcatgcacatcaca<br>gactgccgcctgacaaacggctccaggtaccccaactgtgcataccggaccagc<br>ccgaaggagagacacatcattgtggcctgtgaagggagcccatatgtgccagtc<br>cactttgatgcttctgtggaggactctacctaataatctaga |
| 187 | huVK3LP-<br>hDNase1L3-<br>hIgG1-<br>WT-NLG-<br>hRNase1-<br>WT | metpaqllflllllwlpdttgmricsfnvrsfgeskqedknamdvivkvikrcdi<br>ilvmeikdsnnricpilmeklnrnsrrgitynyvissrlgrntykeqyaflyke<br>klvsvkrsyhyhdyqdgdadvfsrepfvvwfqsphtavkdfviiplhttpetsv<br>keidelvevytdvkhrwkaenfifmgdfnagcsyvpkkawknirlrtdprfvwl<br>lgdqedttvkkstncaydrivlrgqeivssvvpksnsvfdfqkaykltеееald<br>vsdhfpvefklqssraftnskksvtlrkkktkskrsdlepkssdkthtcppcpap<br>ellggpsvflfppkpkdtlmisrtpevtcvvvdvshedpevkfnwyvdgvevhn<br>aktkpreeqynstyrvvsvltvlhqdwlngkeykckvsnkalpapiektiskak<br>gqprepqvytlppsrdeltknqvsltclvkgfypsdiavewesngqpennyktt<br>ppvldsdgsfflyskltvdksrwqqgnvfscsvmhealhnhytqkslslspgkv<br>dgasspvnvsspsvqdipslgkesrakkfqrqhmdsdsspssssstycnqmmrrr<br>nmtqgrckpvntfvheplvdvqnvcfqekvtckngqgncyksnssmhitdcrlt<br>ngsrypncayrtspkerhiivacegspyvpvhfdasvedst* |
| 188 | huVK3LP-<br>hRNase1-<br>WT-<br>hIgG1-<br>WT-NLG-<br>hRNase1-<br>WT | aagcttgccgccatggaaaccccagcgcagcttctcttcctcctgctactctgg<br>ctcccagataccaccggtaaggaatcccgggccaagaaattccagcggcagcat<br>atggactcagacagttcccccagcagcagctccacctactgtaaccaaatgatg<br>aggcgccggaatatgacacaggggcggtgcaaaccagtgaacacctttgtgcac<br>gagccccctggtagatgtccagaatgtctgtttccaggaaaaggtcacctgcaag<br>aacgggcagggcaactgctacaagagcaactccagcatgcacatcacagactgc<br>cgcctgacaaacggctccaggtaccccaactgtgcataccggaccagcccgaag<br>gagagacacatcattgtggcctgtgaagggagcccatatgtgccagtccacttt<br>gatgcttctgtggaggactctacagatctcgagcccaaatcttctgacaaaact<br>cacacatgtccaccgtgcccagcacctgaactcctggggggaccgtcagtcttc<br>ctcttccccccaaaacccaaggacaccctcatgatctcccggacccctgaggtc<br>acatgcgtggtggtggacgtgagccacgaagaccctgaggtcaagttcaactgg<br>tacgtggacggcgtggaggtgcataatgccaagacaaagccgcgggaggagcag<br>tacaacagcacgtaccgtgtggtcagcgtcctcaccgtcctgcaccaggactgg<br>ctgaatggcaaggagtacaagtgcaaggtctccaacaaagccctcccagccccc<br>atcgagaaaaccatctccaaagccaaagggcagccccgagaaccacaggtgtac<br>accctgcccccatcccgggatgagctgaccaagaaccaggtcagcctgacctgc<br>ctggtcaaaggcttctatcccagcgacatcgccgtggagtgggagagcaatggg<br>cagccggagaacaactacaagaccacgcctcccgtgctggactccgacggctcc<br>ttcttcctctacagcaagctcaccgtggacaagagcaggtggcagcaggggaac<br>gtcttctcatgctccgtgatgcatgaggctctgcacaaccactacacgcagaag<br>agcctctctctgtctccgggtaaagtcgacggtgctagcagccatgtgaatgtg<br>agcagccctagcgtgcaggatatcccttccctgggcaaggaatcccgggccaag<br>aaattccagcggcagcatatggactcagacagttcccccagcagcagctccacc<br>tactgtaaccaaatgatgaggcgccggaatatgacacaggggcggtgcaaacca<br>gtgaacacctttgtgcacgagccccctggtagatgtccagaatgtctgtttccag<br>gaaaaggtcacctgcaagaacgggcagggcaactgctacaagagcaactccagc<br>atgcacatcacagactgccgcctgacaaacggctccaggtaccccaactgtgca<br>taccggaccagcccgaaggagagacacatcattgtggcctgtgaagggagccca<br>tatgtgccagtccactttgatgcttctgtggaggactctacctaataatctaga |

TABLE 2-continued

| SEQ ID NO: | DESCRIPTION | SEQUENCE (NUCLEOTIDE SEQUENCES ARE 5'-3') |
|---|---|---|
| 189 | huVK3LP-hRNase1-WT-hIgG1-WT-NLG-hRNase1-WT | metpaqllfllllwlpdttgkesrakkfqrqhmdsdsspssstycnqmmrrrn mtqgrckpvntfvheplvdvqnvcfqekvtckngqgncyksnssmhitdcrltn gsrypncayrtspkerhiivacegspyvpvhfdasvedstdlepkssdkthtcp pcpapellggpsvflfppkpkdtlmisrtpevtcvvvdvshedpevkfnwyvdg vevhnaktkpreeqynstyrvvsvltvlhqdwlngkeykckvsnkalpapiekt iskakgqprepqvytlppsrdeltknqvsltclvkgfypsdiavewesngqpen nykttppvldsdgsfflyskltvdksrwqqgnvfscsvmheglhnhytqkslsl spgkvdgasshvnvsspsvqdipslgkesrakkfqrqhmdsdsspssstycnq mmrrrnmtqgrckpvntfvheplvdvqnvcfqekvtckngqgncyksnssmhit dcrltngsrypncayrtspkerhiivacegspyvpvhfdasvedst* |
| 190 | huVK3LP-hRNase1-WT-(G4S)4-hIgG1-WT-NLG-hRNase1-WT | aagcttgccgccatggaaaccccagcgcagcttctcttcctcctgctactctgg ctcccagataccaccggtaaggaatcccgggccaagaaattccagcggcagcat atggactcagacagttcccccagcagcagctccacctactgtaaccaaatgatg aggcgccggaatatgacacaggggcggtgcaaaccagtgaacacctttgtgcac gagcccctggtagatgtccagaatgtctgtttccaggaaaaggtcacctgcaag aacgggcagggcaactgctacaagagcaactccagcatgcacatcacagactgc cgcctgacaaacggctccaggtaccccaactgtgcataccggaccagcccgaag gagagacacatcattgtggcctgtgaagggagcccatatgtgccagtccacttt gatgcttctgtggaggactctacagatctctccggaggaggtggctcaggtggt ggaggatctggaggaggtgggagtggtggaggtggttctaccggtctcgagccc aaatcttctgacaaaactcacacatgtccaccgtgcccagcacctgaactcctg gggggaccgtcagtcttcctcttccccccaaaacccaaggacaccctcatgatc tcccggacccctgaggtcacatgcgtggtggtggacgtgagccacgaagaccct gaggtcaagttcaactggtacgtggacggcgtggaggtgcataatgccaagaca aagccgcgggaggagcagtacaacagcacgtaccgtgtggtcagcgtcctcacc gtcctgcaccaggactggctgaatggcaaggagtacaagtgcaaggtctccaac aaagccctcccagcccccatcgagaaaaccatctccaaagccaaagggcagccc cgagaaccacaggtgtacaccctgcccccatcccgggatgagctgaccaagaac caggtcagcctgacctgcctggtcaaaggcttctatcccagcgacatcgccgtg gagtgggagagcaatgggcagccggagaacaactacaagaccacgcctcccgtg ctggactccgacggctccttcttcctctacagcaagctcaccgtggacaagagc aggtggcagcaggggaacgtcttctcatgctccgtgatgcatgagggtctgcac aaccactacacgcagaagagcctctctctgtctccgggtaaagtcgacggtgct agcagccatgtgaatgtgagcagccctagcgtgcaggatatcccttccctgggc aaggaatcccgggccaagaaattccagcggcagcatatggactcagacagttcc cccagcagcagctccacctactgtaaccaaatgatgaggcgccggaatatgaca caggggcggtgcaaaccagtgaacacctttgtgcacgagcccctggtagatgtc cagaatgtctgtttccaggaaaaggtcacctgcaagaacgggcagggcaactgc tacaagagcaactccagcatgcacatcacagactgccgcctgacaaacggctcc aggtaccccaactgtgcataccggaccagcccgaaggagagacacatcattgtg gcctgtgaagggagcccatatgtgccagtccactttgatgcttctgtggaggac tctacctaataatctaga |
| 191 | huVK3LP-hRNase1-WT-(G4S)4-hIgG1-WT-NLG-hRNase1-WT | metpaqllfllllwlpdttgkesrakkfqrqhmdsdsspssstycnqmmrrrn mtqgrckpvntfvheplvdvqnvcfqekvtckngqgncyksnssmhitdcrltn gsrypncayrtspkerhiivacegspyvpvhfdasvedstdlsggggsggggsg gggsggggstglepkssdkthtcppcpapellggpsvflfppkpkdtlmisrtp evtcvvvdvshedpevkfnwyvdgvevhnaktkpreeqynstyrvvsvltvlhq dwlngkeykckvsnkalpapiektiskakgqprepqvytlppsrdeltknqvsl tclvkgfypsdiavewesngqpennykttppvldsdgsfflyskitvdksrwqq gnvfscsvmheglhnhytqkslslspgkvdgasshvnvsspsvqdipslgkesr akkfqrqhmdsdsspssstycnqmmrrrnmtqgrckpvntfvheplvdvqnvc fqekvtckngqgncyksnssmhitdcrltngsrypncayrtspkerhiivaceg spyvpvhfdasvedst* |
| 192 | huVK3LP-hTREX1-72AA-(G4S)4-hIgG1-WT-NLG-hRNase1-WT | aagcttgccaccatggaaaccccagcgcagcttctcttcctcctgctactctgg ctcccagataccaccggtatgggccctggagctcgcagacagggcaggattgtg cagggaaggcctgagatgtgcttctgcccaccccctaccccactccctcccctt cggatcttaacactgggcactcacacacccaccccatgctcctctccaggctca gcagcaggtacgtacccaaccatgggctcgcaggccctgcccccggggcccatg cagaccctcatctttttcgacatggaggccactggcttgcccttctcccagccc aaggtcacggagctgtgcctgctggctgtccacagatgtgccctggagagcccc cccacctctcaggggccacctcccacagttcctccaccaccgcgtgtggtagac aagctctccctgtgtgtggctccggggaaggcctgcagccctgcagccagcgag atcacaggtctgagcacagctgtgctggcagcgcatgggcgtcaatgttttgat gacaacctggccaacctgctcctagccttcctgcggcgccagccacagccctgg tgcctggtggcacacaatggtgaccgctacgacttcccccctgctccaagcagag ctggctatgctgggcctcaccagtgctctggatggtgccttctgtgtggatagc atcactgcgctgaaggccctggagcgagcaagcagcccctcagaacacggccca aggaagagctacagcctaggcagcatctacactcgcctgtatgggcagtcccct ccagactcgcacacggctgagggtgatgtcctggccctgctcagcatctgtcag tggagaccacaggccctgctgcggtgggtggatgctcacgccaggcctttcggc accatcaggcccatgtatggggtcacagcctctgctaggaccaaagatctctcc ggaggaggtggctcaggtggtggaggatctggaggaggtgggagtggtggaggt ggttctaccggtctcgagcccaaatcttctgacaaaactcacacatgtccaccg tgcccagcacctgaactcctggggggaccgtcagtcttcctcttccccccaaaa |

TABLE 2-continued

| SEQ ID NO: | DESCRIPTION | SEQUENCE (NUCLEOTIDE SEQUENCES ARE 5'-3') |
|---|---|---|
| | | cccaaggacaccctcatgatctcccggacccctgaggtcacatgcgtggtggtg<br>gacgtgagccacgaagaccctgaggtcaagttcaactggtacgtggacggcgtg<br>gaggtgcataatgccaagacaaagccgcgggaggagcagtacaacagcacgtac<br>cgtgtggtcagcgtcctcaccgtcctgcaccaggactggctgaatggcaaggag<br>tacaagtgcaaggtctccaacaaagccctcccagcccccatcgagaaaaccatc<br>tccaaagccaaagggcagccccgagaaccacaggtgtacaccctgcccccatcc<br>cgggatgagctgaccaagaaccaggtcagcctgacctgcctggtcaaaggcttc<br>tatcccagcgacatcgccgtggagtgggagagcaatgggcagccggagaacaac<br>tacaagaccacgcctcccgtgctggactccgacggctccttcttcctctacagc<br>aagctcaccgtggacaagagcaggtggcagcaggggaacgtcttctcatgctcc<br>gtgatgcatgaggctctgcacaaccactacacgcagaagagcctctctctgtct<br>ccgggtaaagtcgacggagctagcagccccgtgaacgtgagcagccccagcgtg<br>caggatatcccttccctgggcaaggaatcccgggccaagaaattccagcggcag<br>catatggactcagacagttcccccagcagcagctccacctactgtaaccaaatg<br>atgaggcgccggaatatgacacaggggcggtgcaaaccagtgaacacctttgtg<br>cacgagcccctggtagatgtccagaatgtctgtttccaggaaaaggtcacctgc<br>aagaacgggcagggcaactgctacaagagcaactccagcatgcacatcacagac<br>tgccgcctgacaaacggctccaggtaccccaactgtgcataccggaccagcccg<br>aaggagagacacatcattgtggcctgtgaagggagcccatatgtgccagtccac<br>tttgatgcttctgtggaggactctacctaataatctaga |
| 193 | huVK3LP-<br>hTREX1-<br>72AA-<br>(G4S)4-<br>hIgG1-<br>WT-NLG-<br>hRNase1-<br>WT | metpaqllfllllwlpdttgmgpgarrqgrivqgrpemcfcppptplpplrilt<br>lgthtptpcsspgsaagtyptmgsqalppgpmqtliffdmeatglpfsqpkvte<br>lcllavhrcalespptsqgppptvppprvvdklslcvapgkacspaaseitgl<br>stavlaahgrqcfddnlanlllafirrqpqpwclvahngdrydfpllqaelaml<br>gltsaldgafcvdsitalkalerasspsehgprksyslgsiytrlygqsppdsh<br>taegdvlallsicqwrpqallrwvdaharpfgtirpmygvtasartkdlsgggg<br>sggggsggggsggggstglepkssdkthtcppcpapellggpsvflfppkpkdt<br>lmisrtpevtcvvvdvshedpevkfnwyvdgvevhnaktkpreeqynstyrvvs<br>vltvlhqdwlngkeykckvsnkalpapiektiskakgqprepqvytlppsrdel<br>tknqvsltclvkgfypsdiavewesngqpennykttppvldsdgsfflyskitv<br>dksrwqqgnvfscsvmhealhnhytqkslslspgkvdgasspvnvsspsvqdip<br>slgkesrakkfqrqhmdsdsspssstycnqmmrrrnmtqgrckpvntfvhepl<br>vdvqnvcfqekvtckngqgncyksnssmhitdcrltngsrypncayrtspkerh<br>iivacegspyvpvhfdasvedst* |
| 194 | huVK3LP-<br>hRNase1-<br>WT-<br>hIgG1-<br>WT-NLG-<br>hTREX1-<br>72AA | aagcttgccgccatggaaaccccagcgcagcttctcttcctcctgctactctgg<br>ctcccagataccaccggtaaggaatcccgggccaagaaattccagcggcagcat<br>atggactcagacagttcccccagcagcagctccacctactgtaaccaaatgatg<br>aggcgccggaatatgacacaggggcggtgcaaaccagtgaacacctttgtgcac<br>gagcccctggtagatgtccagaatgtctgtttccaggaaaaggtcacctgcaag<br>aacgggcagggcaactgctacaagagcaactccagcatgcacatcacagactgc<br>cgcctgacaaacggctccaggtaccccaactgtgcataccggaccagcccgaag<br>gagagacacatcattgtggcctgtgaagggagcccatatgtgccagtccacttt<br>gatgcttctgtggaggactctacagatctcgagcccaaatcttctgacaaaact<br>cacacatgtccaccgtgcccagcacctgaactcctggggggaccgtcagtcttc<br>ctcttccccccaaaacccaaggacaccctcatgatctcccggacccctgaggtc<br>acatgcgtggtggtggacgtgagccacgaagaccctgaggtcaagttcaactgg<br>tacgtggacggcgtggaggtgcataatgccaagacaaagccgcgggaggagcag<br>tacaacagcacgtaccgtgtggtcagcgtcctcaccgtcctgcaccaggactgg<br>ctgaatggcaaggagtacaagtgcaaggtctccaacaaagccctcccagccccc<br>atcgagaaaaccatctccaaagccaaagggcagccccgagaaccacaggtgtac<br>accctgcccccatcccgggatgagctgaccaagaaccaggtcagcctgacctgc<br>ctggtcaaaggcttctatcccagcgacatcgccgtggagtgggagagcaatggg<br>cagccggagaacaactacaagaccacgcctcccgtgctggactccgacggctcc<br>ttcttcctctacagcaagctcaccgtggacaagagcaggtggcagcaggggaac<br>gtcttctcatgctccgtgatgcatgagggtctgcacaaccactacacgcagaag<br>agcctctctctgtctccgggtaaagtcgacggtgctagcagccatgtgaatgtg<br>agcagccctagcgtgcaggatatcatgggccctggagctcgcagacagggcagg<br>attgtgcagggaaggcctgagatgtgcttctgcccacccccctaccccactccct<br>ccccttcggatcttaacactgggcactcacacacccaccccatgctcctctcca<br>ggctcagcagcaggtacgtacccaaccatgggctcgcaggccctgcccccgggg<br>cccatgcagaccctcatctttttcgacatggaggccactggcttgcccttctcc<br>cagcccaaggtcacggagctgtgcctgctggctgtccacagatgtgccctggag<br>agccccccacctctcaggggccacctcccacagttcctccaccaccgcgtgtg<br>gtagacaagctctccctgtgtgtggctccggggaaggcctgcagccctgcagcc<br>agegagatcacaggtctgagcacagctgtgctggcagcgcatgggcgtcaatgt<br>tttgatgacaacctggccaacctgctcctagccttcctgcggcgccagccacag<br>ccctggtgcctggtggcacacaatggtgaccgctacgacttcccccctgctccaa<br>gcagagctggctatgctgggcctcaccagtgctctggatggtgccttctgtgtg<br>gatagcatcactgcgctgaaggccctggagcgagcaagcagcccctcagaacac<br>ggcccaaggaagagctacagcctaggcagcatctacactcgcctgtatgggcag<br>tcccctccagactcgcacacggctgagggtgatgtcctggccctgctcagcatc<br>tgtcagtggagaccacaggccctgctgcggtgggtggatgctcacgccaggcct<br>ttcggcaccatcaggcccatgtatggggtcacagcctctgctaggaccaaatga<br>taatetaga |

TABLE 2-continued

| SEQ ID NO: | DESCRIPTION | SEQUENCE (NUCLEOTIDE SEQUENCES ARE 5'-3') |
|---|---|---|
| 195 | huVK3LP-hRNase1-WT-hIgG1-WT-NLG-hTREX1-72AA | metpaqllfllllwlpdttgkesrakkfqrqhmdsdsspssstycnqmmrrrn mtqgrckpvntfvheplvdvqnvcfqekvtckngqgncyksnssmhitdcrltn gsrypncayrtspkerhiivacegspyvpvhfdasvedstdlepkssdkthtcp pcpapellggpsvflfppkpkdtlmisrtpevtcvvvdvshedpevkfnwyvdg vevhnaktkpreeqynstyrvvsvltvlhqdwlngkeykckvsnkalpapiekt lskakgqprepqvytlppsrdeltknqvsltclvkgfypsdiavewesngqpen nykttppvldsdgsfflyskltvdksrwqqgnvfscsvmheglhnhytqkslsl spgkvdgasshvnvsspsvqdimgpgarrqgrivqgrpemcfcppptplpplri ltlgthtptpcsspgsaagtyptmgsqalppgpmqtliffdmeatglpfsqpkv telcllavhrcalespptsqgppptvppppprvvdklslcvapgkacspaaseit glstavlaahgrqcfddnlanlllafirrqpqpwclvahngdrydfpllqaela mlgltsaldgafcvdsitalkalerasspsehgprksyslgsiytrlygqsppd shtaegdvlallsicqwrpqallrwvdaharpfgtirpmygvtasartk* |
| 196 | huVK3LP-hDNase1L3-(G4S)4-hIgG1WT-NLG-hRNase1-WT | gttaagcttgccaccatggaaaccccagcgcagcttctcttcctcctgctactc tggctcccagataccaccggtatgaggatctgctccttcaacgtcaggtccttt ggggaaagcaagcaggaagacaagaatgccatggatgtcattgtgaaggtcatc aaacgctgtgacatcatactcgtgatggaaatcaaggacagcaacaacaggatc tgccccatactgatggagaagctgaacagaaattcaaggagaggcataacatac aactatgtgattagctctcggcttggaagaaacacatataaagaacaatatgcc tttctctacaaggaaaagctggtgtctgtgaagaggagttatcactaccatgac tatcaggatggagacgcagatgtgttttccagggagccctttgtggtctggttc caatctccccacactgctgtcaaagacttcgtgattatccccctgcacaccacc ccagagacatccgttaaggagatcgatgagttggttgaggtctacacggacgtg aaacaccgctggaaggcggagaatttcattttcatgggtgacttcaatgccggc tgcagctacgtccccaagaaggcctggaagaacatccgcttgaggactgacccc aggtttgtttggctgatcggggaccaagaggacaccacggtgaagaagagcacc aactgtgcatatgacaggattgtgcttagaggacaagaaatcgtcagttctgtt gttcccaagtcaaacagtgtttttgacttccagaaagcttacaagctgactgaa gaggaggccctggatgtcagcgaccactttccagttgaatttaaactacagtct tcaagggccttcaccaacagcaaaaaatctgtcactctaaggaagaaaacaaag agcaaacgctcagatctctccggaggaggtggctcaggtggtggaggatctgga ggaggtgggagtggtggaggtggttctaccggtctcgagcccaaatcttctgac aaaactcacacatgtccaccgtgcccagcacctgaactcctggggggaccgtca gtcttcctcttccccccaaaacccaaggacaccctcatgatctcccggacccct gaggtcacatgcgtggtggtggacgtgagccacgaagaccctgaggtcaagttc aactggtacgtggacggcgtggaggtgcataatgccaagacaaagccgcgggag gagcagtacaacagcacgtaccgtgtggtcagcgtcctcaccgtcctgcaccag gactggctgaatggcaaggagtacaagtgcaaggtctccaacaaagccctccca gcccccatcgagaaaaccatctccaaagccaaagggcagccccgagaaccacag gtgtacaccctgcccccatcccgggatgagctgaccaagaaccaggtcagcctg acctgcctggtcaaaggcttctatcccagcgacatcgccgtggagtgggagagc aatgggcagccggagaacaactacaagaccacgcctcccgtgctggactccgac ggctccttcttcctctacagcaagctcaccgtggacaagagcaggtggcagcag gggaacgtcttctcatgctccgtgatgcatgagggtctgcacaaccactacacg cagaagagcctctctctgtctccgggtaaagtcgacggtgctagcagccatgtg aatgtgagcagccctagcgtgcaggatatcccttccctgggcaaggaatcccgg gccaagaaattccagcggcagcatatggactcagacagttcccccagcagcagc tccacctactgtaaccaaatgatgaggcgccggaatatgacacaggggcggtgc aaaccagtgaacacctttgtgcacgagcccctggtagatgtccagaatgtctgt ttccaggaaaaggtcacctgcaagaacgggcagggcaactgctacaagagcaac tccagcatgcacatcacagactgccgcctgacaaacggctccaggtaccccaac tgtgcataccggaccagcccgaaggagagacacatcattgtggcctgtgaaggg agcccatatgtgccagtccactttgatgcttctgtggaggactctacctaataa tctaga |
| 197 | huVK3LP-hDNase1L3-(G4S)4-hIgG1WT-NLG-hRNase1-WT | metpaqllfllllwlpdttgmricsfnvrsfgeskqedknamdvivkvikrcdi llvmeikdsnnricpilmeklnrnsrrgitynyvissrlgrntykeqyaflyke klvsvkrsyhyhdyqdgdadvfsrepfvvwfqsphtavkdfviiplhttpetsv keidelvevytdvkhrwkaenfifmgdfnagcsyvpkkawknirlrtdprfvwl lgdqedttvkkstncaydrivlrgqeivssvvpksnsvfdfqkaykl teeeald vsdhfpvefklqssraftnskksvtlrkktkskrsdlsggggsggggsggggsg gggstglepkssdkthtcppcpapellggpsvflfppkpkdtlmisrtpevtcv vvdvshedpevkfnwyvdgvevhnaktkpreeqynstyrvvsvltvlhqdwlng keykckvsnkalpapiektiskakgqprepqvytlppsrdeltknqvsltclvk gfypsdiavewesngqpennykttppvldsdgsfflyskitvdksrwqqgnvfs csvmheglhnhytqkslslspgkvdgasshvnvsspsvqdipslgkesrakkfq rqhmdsdsspssstycnqmmrrrnmtqgrckpvntfvheplvdvqnvcfqekv tckngqgncyksnssmhitdcrltngsrypncayrtspkerhiivacegspyvp vhfdasvedst* |

TABLE 2-continued

| SEQ ID NO: | DESCRIPTION | SEQUENCE (NUCLEOTIDE SEQUENCES ARE 5'-3') |
|---|---|---|
| 198 | huVK3LP-<br>hRNase1-<br>WT-<br>(G4S)4-<br>hIgG1-<br>WT-NLG-<br>hDNase1L3 | gttaagcttgccaccatggaaaccccagcgcagcttctcttcctcctgctactc<br>tggctcccagataccaccggtaaggaatcccgggccaagaaattccagcggcag<br>catatggactcagacagttcccccagcagcagctccacctactgtaaccaaatg<br>atgaggcgccggaatatgacacaggggcggtgcaaaccagtgaacacctttgtg<br>cacgagcccctggtagatgtccagaatgtctgtttccaggaaaaggtcacctgc<br>aagaacgggcagggcaactgctacaagagcaactccagcatgcacatcacagac<br>tgccgcctgacaaacggctccaggtaccccaactgtgcataccggaccagcccg<br>aaggagagacacatcattgtggcctgtgaagggagcccatatgtgccagtccac<br>tttgatgcttctgtggaggactctacagatctctccggaggaggtggctcaggt<br>ggtggaggatctggaggaggtgggagtggtggaggtggttctaccggtctcgag<br>cccaaatcttctgacaaaactcacacatgtccaccgtgcccagcacctgaactc<br>ctggggggaccgtcagtcttcctcttccccccaaaacccaaggacaccctcatg<br>atctcccggacccctgaggtcacatgcgtggtggtggacgtgagccacgaagac<br>cctgaggtcaagttcaactggtacgtggacggcgtggaggtgcataatgccaag<br>acaaagccgcgggaggagcagtacaacagcacgtaccgtgtggtcagcgtcctc<br>accgtcctgcaccaggactggctgaatggcaaggagtacaagtgcaaggtctcc<br>aacaaagccctcccagcccccatcgagaaaaccatctccaaagccaaagggcag<br>ccccgagaaccacaggtgtacaccctgcccccatcccgggatgagctgaccaag<br>aaccaggtcagcctgacctgcctggtcaaaggcttctatcccagcgacatcgcc<br>gtggagtgggagagcaatgggcagccggagaacaactacaagaccacgcctccc<br>gtgctggactccgacggctccttcttcctctacagcaagctcaccgtggacaag<br>agcaggtggcagcaggggaacgtcttctcatgctccgtgatgcatgaggctctg<br>cacaaccactacacgcagaagagcctctctctgtctccgggtaaagtcgacggt<br>gctagcagccatgtgaatgtgagcagccctagcgtgcaggatatcatgaggatc<br>tgctccttcaacgtcaggtcctttggggaaagcaagcaggaagacaagaatgcc<br>atggatgtcattgtgaaggtcatcaaacgctgtgacatcatactcgtgatggaa<br>atcaaggacagcaacaacaggatctgccccatactgatggagaagctgaacaga<br>aattcaaggagaggcataacatacaactatgtgattagctctcggcttggaaga<br>aacacatataaagaacaatatgcctttctctacaaggaaaagctggtgtctgtg<br>aagaggagttatcactaccatgactatcaggatggagacgcagatgtgttttcc<br>agggagccctttgtggtctggttccaatctccccacactgctgtcaaagacttc<br>gtgattatccccctgcacaccaccccagagacatccgttaaggagatcgatgag<br>ttggttgaggtctacacggacgtgaaacaccgctggaaggcggagaatttcatt<br>ttcatgggtgacttcaatgccggctgcagctacgtccccaagaaggcctggaag<br>aacatccgcttgaggactgaccccaggtttgtttggctgatcggggaccaagag<br>gacaccacggtgaagaagagcaccaactgtgcatatgacaggattgtgcttaga<br>ggacaagaaatcgtcagttctgttgttcccaagtcaaacagtgtttttgacttc<br>cagaaagcttacaagctgactgaagaggaggccctggatgtcagcgaccacttt<br>ccagttgaatttaaactacagtcttcaagggccttcaccaacagcaaaaaatct<br>gtcactctaaggaagaaaacaaagagcaaacgctcctaatgatctaga |
| 199 | huVK3LP-<br>hRNase1-<br>WT-<br>(G4S)4-<br>hIgG1-<br>WT-NLG-<br>hDNase1L3 | metpaqllfllllwlpdttgkesrakkfqrqhmdsdsspssstycnqmmrrrn<br>mtqgrckpvntfvheplvdvqnvcfqekvtckngqgncyksnssmhitdcrltn<br>gsrypncayrtspkerhiivacegspyvpvhfdasvedstdlsggggsggggsg<br>gggsggggstglepkssdkthtcppcpapellggpsvflfppkpkdtlmisrtp<br>evtcvvvdvshedpevkfnwyvdgvevhnaktkpreeqynstyrvvsvltvlhq<br>dwlngkeykckvsnkalpapiektiskakgqprepqvytlppsrdeltknqvsl<br>tclvkgfypsdiavewesngqpennykttppvldsdgsfflyskitvdksrwqq<br>gnvfscsvmhealhnhytqkslslspgkvdgasshvnvsspsvqdimricsfnv<br>rsfgeskqedknamdvivkvikrcdiilvmeikdsnnricpilmeklnrnsrrg<br>itynyvissrlgrntykeqyaflykeklvsvkrsyhyhdyqdgdadvfsrepfv<br>vwfqsphtavkdfviiplhttpetsvkeidelvevytdvkhrwkaenfifmgdf<br>nagcsyvpkkawknirlrtdprfvwligdqedttvkkstncaydrivlrgqeiv<br>ssvvpksnsvfdfqkayklteeealdvsdhfpvefklqssraftnskksvtlrk<br>ktkskrs* |
| 200 | huVK3LP-<br>hDNase1-<br>G105R;<br>A114F-<br>(G4S)4-<br>hIgG1-<br>WT-NLG-<br>hTREX1-<br>72AA | gttaagcttgccaccatggaaaccccagcgcagcttctcttcctcctgctactc<br>tggctcccagataccaccggtctgaagatcgcagccttcaacatccagacattt<br>ggggagaccaagatgtccaatgccaccctcgtcagctacattgtgcagatcctg<br>agccgctatgacatcgccctggtccaggaggtcagagacagccacctgactgcc<br>gtggggaagctgctggacaacctcaatcaggatgcaccagacacctatcactac<br>gtggtcagtgagccactgggacggaacagctataaggagcgctacctgttcgtg<br>tacaggcctgaccaggtgtctgcggtggacagctactactacgatgatggctgc<br>gagccctgcaggaacgacaccttcaaccgagagccattcattgtcaggttcttc<br>tcccggttcacagaggtcagggagtttgccattgttcccctgcatgcggccccg<br>ggggacgcagtagccgagatcgacgctctctatgacgtctacctggatgtccaa<br>gagaaatggggcttggaggacgtcatgttgatgggcgacttcaatgcgggctgc<br>agctatgtgagaccctcccagtggtcatccatccgcctgtggacaagccccacc<br>ttccagtggctgatccccgacagcgctgacaccacagctacacccacgcactgt<br>gcctatgacaggatcgtggttgcagggatgctgctccgaggcgccgttgttccc<br>gactcggctcttccctttaacttccaggctgcctatggcctgagtgaccaactg<br>gcccaagccatcagtgaccactatccagtggaggtgatgctgaaagatctctcc<br>ggaggaggtggctcaggtggtggaggatctggaggaggtgggagtggtggaggt<br>ggttctaccggtctcgagcccaaatcttctgacaaaactcacacatgtccaccg<br>tgcccagcacctgaactcctggggggaccgtcagtcttcctcttccccccaaaa<br>cccaaggacaccctcatgatctcccggacccctgaggtcacatgcgtggtggtg |

TABLE 2-continued

| SEQ ID NO: | DESCRIPTION | SEQUENCE (NUCLEOTIDE SEQUENCES ARE 5'-3') |
|---|---|---|
| | | gacgtgagccacgaagaccctgaggtcaagttcaactggtacgtggacggcgtg<br>gaggtgcataatgccaagacaaagccgcgggaggagcagtacaacagcacgtac<br>cgtgtggtcagcgtcctcaccgtcctgcaccaggactggctgaatggcaaggag<br>tacaagtgcaaggtctccaacaaagccctcccagcccccatcgagaaaaccatc<br>tccaaagccaaagggcagccccgagaaccacaggtgtacaccctgcccccatcc<br>cgggatgagctgaccaagaaccaggtcagcctgacctgcctggtcaaaggcttc<br>tatcccagcgacatcgccgtggagtgggagagcaatgggcagccggagaacaac<br>tacaagaccacgcctcccgtgctggactccgacggctccttcttcctctacagc<br>aagctcaccgtggacaagagcaggtggcagcaggggaacgtcttctcatgctcc<br>gtgatgcatgaggctctgcacaaccactacacgcagaagagcctctctctgtct<br>ccgggtaaagtcgacggtgctagcagccatgtgaatgtgagcagccctagcgtg<br>caggatatcatgggccctggagctcgcagacagggcaggattgtgcagggaagg<br>cctgagatgtgcttctgcccacccccctaccccactccctccccttcggatctta<br>acactgggcactcacacacccaccccatgctcctctccaggctcagcagcaggt<br>acgtacccaaccatgggctcgcaggccctgcccccggggcccatgcagaccctc<br>atctttttcgacatggaggccactggcttgcccttctcccagcccaaggtcacg<br>gagctgtgcctgctggctgtccacagatgtgccctggagagcccccccacctct<br>caggggccacctcccacagttcctccaccaccgcgtgtggtagacaagctctcc<br>ctgtgtgtggctccggggaaggcctgcagccctgcagccagcgagatcacaggt<br>ctgagcacagctgtgctggcagcgcatgggcgtcaatgttttgatgacaacctg<br>gccaacctgctcctagccttcctgcggcgccagccacagccctggtgcctggtg<br>gcacacaatggtgaccgctacgacttcccccctgctccaagcagagctggctatg<br>ctgggcctcaccagtgctctggatggtgccttctgtgtggatagcatcactgcg<br>ctgaaggccctggagcgagcaagcagcccctcagaacacggcccaaggaagagc<br>tacagcctaggcagcatctacactcgcctgtatgggcagtcccctccagactcg<br>cacacggctgagggtgatgtcctggccctgctcagcatctgtcagtggagacca<br>caggccctgctgcggtgggtggatgctcacgccaggcctttcggcaccatcagg<br>cccatgtatggggtcacagcctctgctaggaccaaatgataatctaga |
| 201 | huVK3LP-<br>hDNase1-<br>G105R;<br>A114F-<br>(G4S)4-<br>hIgG1-<br>WT-NLG-<br>hTREX1-<br>72AA | metpaqllfllllwlpdttglkiaafniqtfgetkmsnatlvsyivqilsrydi<br>alvqevrdshltavgklldnlnqdapdtyhyvvseplgrnsykerylfvyrpdq<br>vsavdsyyyddgcepcrndtfnrepfivrffsrftevrefaivplhaapgdava<br>eidalydvyldvqekwgledvmlmgdfnagcsyvrpsqwssirlwtsptfqwli<br>pdsadttatpthcaydrivvagmllrgavvpdsalpfnfqaayglsdqlaqais<br>dhypvevmlkdlsggggsggggsggggsggggstglepkssdkthtcppcpape<br>llggpsvflfppkpkdtlmisrtpevtcvvvdvshedpevkfnwyvdgvevhna<br>ktkpreeqynstyrvvsvltvlhqdwlngkeykckvsnkalpapiektiskakg<br>qprepqvytlppsrdeltknqvsltclvkgfypsdiavewesngqpennykttp<br>pvidsdgsfflyskltvdksrwqqgnvfscsvmhealhnhytqkslslspgkvd<br>gasshvnvsspsvqdimgpgarrqgrivqgrpemcfcppptplpplriltlgth<br>tptpcsspgsaagtyptmgsqalppgpmqtliffdmeatgipfsqpkvtelcll<br>avhrcalespptsqgppptvppppprvvdklslcvapgkacspaaseitglstav<br>laahgrqcfddnlanlllafIrrqpqpwclvahngdrydfpllqaelamlglts<br>aldgafcvdsitalkalerasspsehgprksyslgsiytrlygqsppdshtaeg<br>dvlallsicqwrpqallrwvdaharpfgtirpmygvtasartk* |
| 202 | huVK3LP-<br>hTREX1-<br>72AA<br>(G4S)4-<br>hIgG1-<br>WT-NLG-<br>hDNase1-<br>G105R;<br>A114F | aagcttgccaccatggaaaccccagcgcagcttctcttcctcctgctactctgg<br>ctcccagataccaccggtatgggccctggagctcgcagacagggcaggattgtg<br>cagggaaggcctgagatgtgcttctgcccacccccctaccccactccctcccctt<br>cggatcttaacactgggcactcacacacccaccccatgctcctctccaggctca<br>gcagcaggtacgtacccaaccatgggctcgcaggccctgcccccggggcccatg<br>cagaccctcatctttttcgacatggaggccactggcttgcccttctcccagccc<br>aaggtcacggagctgtgcctgctggctgtccacagatgtgccctggagagcccc<br>cccacctctcaggggccacctcccacagttcctccaccaccgcgtgtggtagac<br>aagctctccctgtgtgtggctccggggaaggcctgcagccctgcagccagcgag<br>atcacaggtctgagcacagctgtgctggcagcgcatgggcgtcaatgttttgat<br>gacaacctggccaacctgctcctagccttcctgcggcgccagccacagccctgg<br>tgcctggtggcacacaatggtgaccgctacgacttcccccctgctccaagcagag<br>ctggctatgctgggcctcaccagtgctctggatggtgccttctgtgtggatagc<br>atcactgcgctgaaggccctggagcgagcaagcagcccctcagaacacggccca<br>aggaagagctacagcctaggcagcatctacactcgcctgtatgggcagtcccct<br>ccagactcgcacacggctgagggtgatgtcctggccctgctcagcatctgtcag<br>tggagaccacaggccctgctgcggtgggtggatgctcacgccaggcctttcggc<br>accatcaggcccatgtatggggtcacagcctctgctaggaccaaagatctctcc<br>ggaggaggtggctcaggtggtggaggatctggaggaggtgggagtggtggaggt<br>ggttctaccggtctcgagcccaaatcttctgacaaaactcacacatgtccaccg<br>tgcccagcacctgaactcctggggggaccgtcagtcttcctcttccccccaaaa<br>cccaaggacaccctcatgatctcccggacccctgaggtcacatgcgtggtggtg<br>gacgtgagccacgaagaccctgaggtcaagttcaactggtacgtggacggcgtg<br>gaggtgcataatgccaagacaaagccgcgggaggagcagtacaacagcacgtac<br>cgtgtggtcagcgtcctcaccgtcctgcaccaggactggctgaatggcaaggag<br>tacaagtgcaaggtctccaacaaagccctcccagcccccatcgagaaaaccatc<br>tccaaagccaaagggcagccccgagaaccacaggtgtacaccctgcccccatcc<br>cgggatgagctgaccaagaaccaggtcagcctgacctgcctggtcaaaggcttc<br>tatcccagcgacatcgccgtggagtgggagagcaatgggcagccggagaacaac<br>tacaagaccacgcctcccgtgctggactccgacggctccttcttcctctacagc<br>aagctcaccgtggacaagagcaggtggcagcaggggaacgtcttctcatgctcc |

TABLE 2-continued

| SEQ ID NO: | DESCRIPTION | SEQUENCE (NUCLEOTIDE SEQUENCES ARE 5'-3') |
|---|---|---|
| | | gtgatgcatgaggctctgcacaaccactacacgcagaagagcctctctctgtct<br>ccgggtaaagtcgacggtgctagcagccatgtgaatgtgagcagccctagcgtg<br>caggatatcctgaagatcgcagccttcaacatccagacatttggggagaccaag<br>atgtccaatgccaccctcgtcagctacattgtgcagatcctgagccgctatgac<br>atcgccctggtccaggaggtcagagacagccacctgactgccgtggggaagctg<br>ctggacaacctcaatcaggatgcaccagacacctatcactacgtggtcagtgag<br>ccactgggacggaacagctataaggagcgctacctgttcgtgtacaggcctgac<br>caggtgtctgcggtggacagctactactacgatgatggctgcgagccctgcggg<br>aacgacaccttcaaccgagagccagccattgtcaggttcttctcccggttcaca<br>gaggtcagggagtttgccattgttcccctgcatgcggcccgggggacgcagta<br>gccgagatcgacgctctctatgacgtctacctggatgtccaagagaaatggggc<br>tcggaggacgtcatgttgatgggcgacttcaatgcgggctgcagctatgtgaga<br>ccctcccagtggtcatccatccgcctgtggacaagccccaccttccagtggctg<br>atccccgacagcgctgacaccacagctacacccacgcactgtgcctatgacagg<br>atcgtggttgcagggatgctgctccgaggcgccgttgttcccgactcggctctt<br>ccctttaacttccagnctgcctatggcctgagtgaccaactggcccaagccatc<br>agtgaccactatccagtggaggtgatgctgaagtgataatctaga |
| 203 | huVK3LP-<br>hTREX1-<br>72AA<br>(G4S)4-<br>hIgG1-<br>WT-NLG-<br>hDNase1-<br>G105R;<br>A114F | metpaqllfllllwlpdttgmgpgarrqgrivqgrpemcfcppptplpplrilt<br>lgthtptpcsspgsaagtyptmgsqalppgpmqtliffdmeatglpfsqpkvte<br>lcllavhrcalespptsqgppptvppprvvdklslcvapgkacspaaseitgl<br>stavlaahgrqcfddnlanlllaflrrqpqpwclvahngdrydfpllqaelaml<br>gltsaldgafcvdsitalkalerasspsehgprksyslgsiytrlygqsppdsh<br>taegdvlallsicqwrpqallrwvdaharpfgtirpmygvtasartkdlsgggg<br>sggggsggggsggggstglepkssdkthtcppcpapellggpsvflfppkpkdt<br>lmisrtpevtcvvvdvshedpevkfnwyvdgvevhnaktkpreeqynstyrvvs<br>vltvlhqdwlngkeykckvsnkalpapiektiskakgqprepqvytlppsrdel<br>tknqvsltclvkgfypsdiavewesngqpennykttppvldsdgsfflyskltv<br>dksrwqqgnvfscsvmhealhnhytqkslslspgkvdgasshvnvsspsvqdil<br>kiaafniqtfgetkmsnatlvsyivqilsrydialvqevrdshltavgklldnl<br>nqdapdtyhyvvseplgrnsykerylfvyrpdqvsavdsyyyddgcepcgndtf<br>nrepaivrffsrftevrefaivplhaapgdavaeidalydvyldvqekwgsedv<br>mlmgdfnagcsyvrpsqwssirlwtsptfqwlipdsadttatpthcaydrivva<br>gmllrgavvpdsalpfnfqxayglsdqlaqaisdhypvevmlk* |
| 204 | huVK3LP-<br>hRNase1-<br>WT-<br>(G4S)4-<br>hIgG1-<br>WT-NLG-<br>hTREX1-<br>72AA | gttaagcttgccaccatggaaaccccagcgcagcttctcttcctcctgctactc<br>tggctcccagataccaccggtaaggaatcccgggccaagaaattccagcggcag<br>catatggactcagacagttcccccagcagcagctccacctactgtaaccaaatg<br>atgaggcgccggaatatgacacaggggcggtgcaaaccagtgaacacctttgtg<br>cacgagcccctggtagatgtccagaatgtctgtttccaggaaaaggtcacctgc<br>aagaacgggcagggcaactgctacaagagcaactccagcatgcacatcacagac<br>tgccgcctgacaaacggctccaggtaccccaactgtgcataccggaccagcccg<br>aaggagagacacatcattgtggcctgtgaagggagcccatatgtgccagtccac<br>tttgatgcttctgtggaggactctacagatctctccggaggaggtggctcaggt<br>ggtggaggatctggaggaggtgggagtggtggaggtggttctaccggtctcgag<br>cccaaatcttctgacaaaactcacacatgtccaccgtgcccagcacctgaactc<br>ctggggggaccgtcagtcttcctcttccccccaaaacccaaggacaccctcatg<br>atctcccggacccctgaggtcacatgcgtggtggtggacgtgagccacgaagac<br>cctgaggtcaagttcaactggtacgtggacggcgtggaggtgcataatgccaag<br>acaaagccgcgggaggagcagtacaacagcacgtaccgtgtggtcagcgtcctc<br>accgtcctgcaccaggactggctgaatggcaaggagtacaagtgcaaggtctcc<br>aacaaagccctcccagcccccatcgagaaaaccatctccaaagccaaagggcag<br>ccccgagaaccacaggtgtacaccctgcccccatcccgggatgagctgaccaag<br>aaccaggtcagcctgacctgcctggtcaaaggcttctatcccagcgacatcgcc<br>gtggagtgggagagcaatgggcagccggagaacaactacaagaccacgcctccc<br>gtgctggactccgacggctccttcttcctctacagcaagctcaccgtggacaag<br>agcaggtggcagcaggggaacgtcttctcatgctccgtgatgcatgaggctctg<br>cacaaccactacacgcagaagagcctctctctgtctccgggtaaagtcgacggt<br>gctagcagccatgtgaatgtgagcagccctagcgtgcaggatatcatgggccct<br>ggagctcgcagacagggcaggattgtgcagggaaggcctgagatgtgcttctgc<br>ccacccccctaccccactccctccccttcggatcttaacactgggcactcacaca<br>cccaccccatgctcctctccaggctcagcagcaggtacgtacccaaccatgggc<br>tcgcaggccctgcccccggggcccatgcagaccctcatctttttcgacatggag<br>gccactggcttgcccttctcccagcccaaggtcacggagctgtgcctgctggct<br>gtccacagatgtgccctggagagccccccacctctcaggggccacctcccaca<br>gttcctccaccaccgcgtgtggtagacaagctctccctgtgtgtggctccgggg<br>aaggcctgcagccctgcagccagcgagatcacaggtctgagcacagctgtgctg<br>gcagcgcatgggcgtcaatgttttgatgacaacctggccaacctgctcctagcc<br>ttcctgcggcgccagccacagccctggtgcctggtggcacacaatggtgaccgc<br>tacgacttcccccctgctccaagcagagctggctatgctgggcctcaccagtgct<br>ctggatggtgccttctgtgtggatagcatcactgcgctgaaggccctggagcga<br>gcaagcagcccctcagaacacggcccaaggaagagctacagcctaggcagcatc<br>tacactcgcctgtatgggcagtcccctccagactcgcacacggctgagggtgat<br>gtcctggccctgctcagcatctgtcagtggagaccacaggccctgctgcggtgg<br>gtggatgctcacgccaggcctttcggcaccatcaggcccatgtatggggtcaca<br>gcctctgctaggaccaaatgataatctaga |

TABLE 2-continued

| SEQ ID NO: | DESCRIPTION | SEQUENCE (NUCLEOTIDE SEQUENCES ARE 5'-3') |
|---|---|---|
| 205 | huVK3LP-hRNase1-WT-(G4S)4-hIgG1-WT-NLG-hTREX1-72AA | metpaqllfllllwlpdttgkesrakkfqrqhmdsdsspssstycnqmmrrrn<br>mtqgrckpvntfvheplvdvqnvcfqekvtckngqgncyksnssmhitdcrltn<br>gsrypncayrtspkerhiivacegspyvpvhfdasvedstdlsggggsggggsg<br>gggsggggstglepkssdkthtcppcpapellggpsvflfppkpkdtlmisrtp<br>evtcvvvdvshedpevkfnwyvdgvevhnaktkpreeqynstyrvvsvltvlhq<br>dwlngkeykckvsnkalpapiektiskakgqprepqvytlppsrdeltknqvsl<br>tcivkgfypsdiavewesngqpennykttppvldsdgsfflyskitvdksrwqq<br>gnvfscsvmhealhnhytqkslslspgkvdgasshvnvsspsvqdimgpgarrq<br>grivqgrpemcfcppptplpplriltlgthtptpcsspgsaagtyptmgsqalp<br>pgpmqtliffdmeatglpfsqpkvtelcllavhrcalespptsqgppptvpppp<br>rvvdklslcvapgkacspaaseitglstavlaahgrqcfddnlanlllafirrq<br>pqpwclvahngdrydfpllqaelamlgltsaldgafcvdsitalkalerassps<br>ehgprksyslgsiytrlygqsppdshtaegdvlallsicqwrpqallrwvdaha<br>rpfgtirpmygvtasartk* |
| 206 | huVK3LP-hDNase1L3-hIgG1-WT-NLG-hTREX1-72AA | gttaagcttgccaccatggaaaccccagcgcagcttctcttcctcctgctactc<br>tggctcccagataccaccggtatgaggatctgctccttcaacgtcaggtccttt<br>ggggaaagcaagcaggaagacaagaatgccatggatgtcattgtgaaggtcatc<br>aaacgctgtgacatcatactcgtgatggaaatcaaggacagcaacaacaggatc<br>tgccccatactgatggagaagctgaacagaaattcaaggagaggcataacatac<br>aactatgtgattagctctcggcttggaagaaacacatataaagaacaatatgcc<br>tttctctacaaggaaaagctggtgtctgtgaagaggagttatcactaccatgac<br>tatcaggatggagacgcagatgtgttttccagggagccctttgtggtctggttc<br>caatctccccacactgctgtcaaagacttcgtgattatccccctgcacaccacc<br>ccagagacatccgttaaggagatcgatgagttggttgaggtctacacggacgtg<br>aaacaccgctggaaggcggagaatttcattttcatgggtgacttcaatgccggc<br>tgcagctacgtccccaagaaggcctggaagaacatccgcttgaggactgacccc<br>aggtttgtttggctgatcggggaccaagaggacaccacggtgaagaagagcacc<br>aactgtgcatatgacaggattgtgcttagaggacaagaaatcgtcagttctgtt<br>gttcccaagtcaaacagtgtttttgacttccagaaagcttacaagctgactgaa<br>gaggaggccctggatgtcagcgaccactttccagttgaatttaaactacagtct<br>tcaagggccttcaccaacagcaaaaaatctgtcactctaaggaagaaaacaaag<br>agcaaacgctcagatctcgagcccaaatcttctgacaaaactcacacatgtcca<br>ccgtgcccagcacctgaactcctggggggaccgtcagtcttcctcttcccccca<br>aaacccaaggacaccctcatgatctcccggacccctgaggtcacatgcgtggtg<br>gtggacgtgagccacgaagaccctgaggtcaagttcaactggtacgtggacggc<br>gtggaggtgcataatgccaagacaaagccgcgggaggagcagtacaacagcacg<br>taccgtgtggtcagcgtcctcaccgtcctgcaccaggactggctgaatggcaag<br>gagtacaagtgcaaggtctccaacaaagccctcccagcccccatcgagaaaacc<br>atctccaaagccaaagggcagccccgagaaccacaggtgtacaccctgcccca<br>tcccgggatgagctgaccaagaaccaggtcagcctgacctgcctggtcaaaggc<br>ttctatcccagcgacatcgccgtggagtgggagagcaatgggcagccggagaac<br>aactacaagaccacgcctcccgtgctggactccgacggctccttcttcctctac<br>agcaagctcaccgtggacaagagcaggtggcagcaggggaacgtcttctcatgc<br>tccgtgatgcatgaggctctgcacaaccactacacgcagaagagcctctctctg<br>tctccgggtaaagtcgacggagctagcagccccgtgaacgtgagcagccccagc<br>gtgcaggatatcatgggccctggagctcgcagacagggcaggattgtgcaggga<br>aggcctgagatgtgcttctgcccacccctaccccactccctccccttcggatc<br>ttaacactgggcactcacacacccaccccatgctcctctccaggctcagcagca<br>ggtacgtacccaaccatgggctcgcaggccctgcccccggggcccatgcagacc<br>ctcatctttttcgacatggaggccactggcttgcccttctcccagcccaaggtc<br>acggagctgtgcctgctggctgtccacagatgtgccctggagagcccccccacc<br>tctcaggggccacctcccacagttcctccaccaccgcgtgtggtagacaagctc<br>tccctgtgtgtggctccggggaaggcctgcagccctgcagccagcgagatcaca<br>ggtctgagcacagctgtgctggcagcgcatgggcgtcaatgttttgatgacaac<br>ctggccaacctgctcctagccttcctgcggcgccagccacagccctggtgcctg<br>gtggcacacaatggtgaccgctacgacttcccccctgctccaagcagagctggct<br>atgctgggcctcaccagtgctctggatggtgccttctgtgtggatagcatcact<br>gcgctgaaggccctggagcgagcaagcagcccctcagaacacggcccaaggaag<br>agctacagcctaggcagcatctacactcgcctgtatgggcagtcccctccagac<br>tcgcacacggctgagggtgatgtcctggccctgctcagcatctgtcagtggaga<br>ccacaggccctgctgcggtgggtggatgctcacgccaggcctttcggcaccatc<br>aggcccatgtatggggtcacagcctctgctaggaccaaatgataatctaga |
| 207 | huVK3LP-hDNase1L3-hIgG1-WT-NLG-hTREX1-72AA | metpaqllfllllwlpdttgmricsfnvrsfgeskqedknamdvivkvikrcdi<br>ilvmeikdsnnricpilmeklnrnsrrgitynyvissrlgrntykeqyaflyke<br>klvsvkrsyhyhdyqdgdadvfsrepfvvwfqsphtavkdfviiplhttpetsv<br>keidelvevytdvkhrwkaenfifmgdfnagcsyvpkkawknirlrtdprfvwl<br>igdqedttvkkstncaydrivlrgqeivssvvpksnsvfdfqkaykltteeeald<br>vsdhfpvefklqssraftnskksvtlrkktkskrsdlepkssdkthtcppcpap<br>ellggpsvflfppkpkdtlmisrtpevtcvvvdvshedpevkfnwyvdgvevhn<br>aktkpreeqynstyrvvsvltvlhqdwlngkeykckvsnkalpapiektiskak<br>gqprepqvytlppsrdeltknqvsltclvkgfypsdiavewesngqpennyktt<br>ppvldsdgsfflyskltvdksrwqqgnvfscsvmhealhnhytqkslslspgkv<br>dgasspvnvsspsvqdimgpgarrqgrivqgrpemcfcppptplpplriltlgt<br>htptpcsspgsaagtyptmgsqalppgpmqtliffdmeatglpfsqpkvtelcl<br>lavhrcalespptsqgppptvppprvvdklslcvapgkacspaaseitglsta |

TABLE 2-continued

| SEQ ID NO: | DESCRIP-TION | SEQUENCE (NUCLEOTIDE SEQUENCES ARE 5'-3') |
|---|---|---|
| | | vlaahgrqcfddnlanlllafIrrqpqpwclvahngdrydfpllqaelamlglt saldgafcvdsitalkalerasspsehgprksyslgsiytrlygqsppdshtae gdvlallsicqwrpqallrwvdaharpfgtirpmygvtasartk* |

The invention claimed is:

1. A method for treating lupus nephritis in a subject in need thereof, comprising administering to the subject a composition comprising:

a polypeptide comprising human RNase 1 operatively coupled with or without a linker to the N-terminus of an Fc domain, and DNase operatively coupled with or without a linker to the C-terminus of the Fc domain, wherein the Fc domain is a human immunoglobulin Fc domain or a mutant human immunoglobulin Fc domain, and wherein the human immunoglobulin Fc domain or mutant human immunoglobulin Fc domain comprises at least one hinge region; and a pharmaceutically acceptable carrier, such that treatment occurs.

2. The method of claim 1, wherein the Fc domain is a mutant human IgG1 Fc domain comprising one or more of the mutations selected from P238S, P331S, K322S, N297S, wherein numbering is according to the EU index.

3. The method of claim 1, wherein the Fc domain comprises a mutant human IgG1 Fc domain comprising a substitution of one or more of three hinge region cysteine residues with serine.

4. The method of claim 1, wherein the human RNase 1 comprises the amino acid sequence set forth in SEQ ID NO:149, with or without a leader sequence.

5. The method of claim 1, wherein the Fc domain comprises a human IgG1 Fc domain.

6. The method of claim 1, wherein the Fc domain is a mutant Fc domain that has reduced binding to Fc receptors on human cells.

7. The method of claim 1, wherein the Fc domain comprises the amino acid sequence set forth in SEQ ID NO:145.

8. The method of claim 1, wherein the DNase comprises:

(a) the amino acid sequence set forth in SEQ ID NO: 143; or (b) a G105R mutation as set forth in SEQ ID NO: 142; or (c) mutations G105R and A114F as set forth in SEQ ID NO: 139.

9. The method of claim 1, wherein the polypeptide comprises a first linker domain, a second linker domain, or both, wherein when the polypeptide comprises a first linker domain, the human RNase 1 is operatively coupled to the Fc domain by the first linker domain, and when the polypeptide comprises a second linker domain, the DNase is operatively coupled to the Fc domain by the second linker domain.

10. The method of claim 9, wherein the first linker domain, the second linker domain, or both, comprise a gly/ser peptide.

11. The method of claim 9, wherein the first linker domain, the second linker domain, or both, comprise an NLG peptide comprising the amino acid sequence set forth in SEQ ID NO: 168.

12. The method of claim 1, wherein the polypeptide comprises a dimeric polypeptide.

13. The method of claim 1, wherein the composition is formulated for intravenous administration.

14. A method for treating lupus nephritis in a subject in need thereof, comprising administering to the subject a composition comprising:

(a) a polypeptide comprising the amino acid sequence set forth in SEQ ID NO: 151, SEQ ID NO: 152, or SEQ ID NO: 153, with or without a leader sequence; or (b) a polypeptide comprising the amino acid sequence set forth in SEQ ID NO: 151, SEQ ID NO: 152, or SEQ ID NO: 153, with or without a leader sequence and comprising one or more Fc mutations selected from P238S, P331S, K322S, and N297S, numbering according to EU index; and a pharmaceutical carrier, such that treatment occurs.

15. The method of claim 14, wherein the Fc domain comprises a mutant human IgG1 Fc domain comprising a substitution of one or more of three hinge region cysteine residues with serine.

16. The method of claim 14, wherein the polypeptide comprises a dimeric polypeptide.

17. The method of claim 14, wherein the composition is formulated for intravenous administration.

18. A method for treating lupus nephritis in a subject in need thereof, comprising administering to the subject a composition comprising:

a polypeptide comprising human RNase 1 operatively linked with or without a linker to the N-terminus of a mutant human IgG1 Fc domain, and DNase operatively linked with or without a linker to the C-terminus of the mutant Fc domain, wherein the human RNase 1 comprises the amino acid sequence set forth in SEQ ID NO: 149, with or without a leader sequence, and wherein the DNase comprises the amino acid sequence set forth in SEQ ID NO: 139, and wherein the mutant human IgG1 Fc domain comprises at least one hinge region; and a pharmaceutically acceptable carrier, such that treatment occurs.

19. The method of claim 18, wherein the mutant Fc domain comprises one or more of the mutations selected from P238S, P331S, K322S, and N297S, numbering is according to the EU index.

20. The method of claim 19, wherein the mutant Fc domain comprises a substitution of one or more of three hinge region cysteine residues with serine.

21. The method of claim 18, wherein the polypeptide comprises a dimeric polypeptide.

22. The method of claim 18, wherein the composition is formulated for intravenous administration.

* * * * *

SEQUENCE LISTING

<160> NUMBER OF SEQ ID NOS: 225

<210> SEQ ID NO 1
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
gttaagcttg ccaccatggg tctggagaag tccctcattc tg 42

<210> SEQ ID NO 2
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
gataccaccg gtagggaatc tgcagcacag aagtttcag 39

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
ggctcgagca cagtagcatc aaagtggact ggtacgtagg 40

<210> SEQ ID NO 4
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 4
aaatctagac ctcaaccagg tagggaatct gcagcacaga agtttcag 48

<210> SEQ ID NO 5
<211> LENGTH: 43
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 5
tctagactat cacacagtag catcaaagtg gactggtacg tag 43

```
<210> SEQ ID NO 6
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

tgtccaccgt gtccagcacc tgaactcctg ggtggatcgt cagtcttcc                49


<210> SEQ ID NO 7
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

agatctcgag cccaaatctt ctgacaaaac tcacacatgt ccaccgtgt                49


<210> SEQ ID NO 8
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

tctagattat catttacccg gagacagaga gaggctcttc tgcgtgtagt g             51


<210> SEQ ID NO 9
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

cctccatgca aatgcccagc acctaacctc ttgggtggat catccgtctt catcttcc      58


<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

gaagatctcg agcccagagg tcccacaatc aagccctctc ctcca                    45


<210> SEQ ID NO 11
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

gtttctagat tatcatttac ccggagtccg agagaagctc ttagtcgt                 48
```

<210> SEQ ID NO 12
<211> LENGTH: 49
<212> TYPE: DNA
<213> ORGANISM: Artificial Sequence
<220> FEATURE:
<223> OTHER INFORMATION: Description of Artificial Sequence: Synthetic
primer

<400> SEQUENCE: 12
agatctcgag cccaaatctt ctgacaaaac tcacacatgt ccaccgtgt 49

<210> SEQ ID NO 13
<211> LENGTH: 39
<212> TYPE: DNA
<213> ORGANISM: Artificial Sequence
<220> FEATURE:
<223> OTHER INFORMATION: Description of Artificial Sequence: Synthetic
primer

<400> SEQUENCE: 13
gttttctcga tggaggctgg gagggctttg ttggagacc 39

<210> SEQ ID NO 14
<211> LENGTH: 48
<212> TYPE: DNA
<213> ORGANISM: Artificial Sequence
<220> FEATURE:
<223> OTHER INFORMATION: Description of Artificial Sequence: Synthetic
primer

<400> SEQUENCE: 14
aaggtctcca acaaagccct cccagcctcc atcgagaaaa caatctcc 48

<210> SEQ ID NO 15
<211> LENGTH: 51
<212> TYPE: DNA
<213> ORGANISM: Artificial Sequence
<220> FEATURE:
<223> OTHER INFORMATION: Description of Artificial Sequence: Synthetic
primer

<400> SEQUENCE: 15
tctagattat catttacccg gagacagaga gaggctcttc tgcgtgtagt g 51

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 16
accggtaagg aatcccgggc caagaaattc c 31

<210> SEQ ID NO 17
<211> LENGTH: 40
<212> TYPE: DNA
<213> ORGANISM: Artificial Sequence
<220> FEATURE:
<223> OTHER INFORMATION: Description of Artificial Sequence: Synthetic
primer

<400> SEQUENCE: 17
ctcgagatct gtagagtcct ccacagaagc atcaaagtgg 40

<210> SEQ ID NO 18

<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
agactgccgc ctgacaaacg actccaggta ccc 33

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
gggtacctgg agtcgtttgt caggcggcag tct 33

<210> SEQ ID NO 20
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
accggtatgg gctcacagac cctgccccat ggtcaca 37

<210> SEQ ID NO 21
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
ctcgagatct gttgttccag tggtagccgg agtgccgtac atg 43

<210> SEQ ID NO 22
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
gttaagcttg ccaccatgtc cctgcaccca gcttccccac gcctg 45

<210> SEQ ID NO 23
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
ctcgagatct gaggagcgat tgccttttt tctctttttg agag 44

<210> SEQ ID NO 24
<211> LENGTH: 42

<212> TYPE: DNA
<213> ORGANISM: Artificial Sequence
<220> FEATURE:
<223> OTHER INFORMATION: Description of Artificial Sequence: Synthetic
primer

<400> SEQUENCE: 24
accggtctaa ggctctgctc cttcaatgtg aggtcctttg ga 42

<210> SEQ ID NO 25
<211> LENGTH: 44
<212> TYPE: DNA
<213> ORGANISM: Artificial Sequence
<220> FEATURE:
<223> OTHER INFORMATION: Description of Artificial Sequence: Synthetic
primer

<400> SEQUENCE: 25
ctcgagatct gaggagcgat tgcctttttt tctctttttg agag 44

<210> SEQ ID NO 26
<211> LENGTH: 36
<212> TYPE: DNA
<213> ORGANISM: Artificial Sequence
<220> FEATURE:
<223> OTHER INFORMATION: Description of Artificial Sequence: Synthetic
primer

<400> SEQUENCE: 26
gttaccggtc tgaagatcgc agccttcaac atccag 36

<210> SEQ ID NO 27
<211> LENGTH: 39
<212> TYPE: DNA
<213> ORGANISM: Artificial Sequence
<220> FEATURE:
<223> OTHER INFORMATION: Description of Artificial Sequence: Synthetic
primer

<400> SEQUENCE: 27
gttctcgaga tctttcagca tcacctccac tggatagtg 39

<210> SEQ ID NO 28
<211> LENGTH: 36
<212> TYPE: DNA
<213> ORGANISM: Artificial Sequence
<220> FEATURE:
<223> OTHER INFORMATION: Description of Artificial Sequence: Synthetic
primer

<400> SEQUENCE: 28
gttgatatcc tgaagatcgc agccttcaac atccag 36

<210> SEQ ID NO 29
<211> LENGTH: 42
<212> TYPE: DNA
<213> ORGANISM: Artificial Sequence
<220> FEATURE:
<223> OTHER INFORMATION: Description of Artificial Sequence: Synthetic
primer

<400> SEQUENCE: 29
gtttctagat tatcacttca gcatcacctc cactggatag tg 42

<210> SEQ ID NO 30
<211> LENGTH: 49
<212> TYPE: DNA

<213> ORGANISM: Artificial Sequence
<220> FEATURE:
<223> OTHER INFORMATION: Description of Artificial Sequence: Synthetic primer

<400> SEQUENCE: 30
tgtccaccgt gtccagcacc tgaactcctg ggtggatcgt cagtcttcc 49

<210> SEQ ID NO 31
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
agatctcgag cccaaatctt ctgacaaaac tcacacatgt ccaccgtgt 49

<210> SEQ ID NO 32
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
gaagatctcg agcccaaatc ttctgacaaa actcacacat gt 42

<210> SEQ ID NO 33
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
gttagatctc gagcccaaat cttctgacaa aactcacaca tct 43

<210> SEQ ID NO 34
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
tctagattat catttacccg gagacagaga gaggctcttc tgcgtgtagt g 51

<210> SEQ ID NO 35
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
aaggtctcca acaaagccct cccagcctcc atcgagaaaa caatctcc 48

<210> SEQ ID NO 36
<211> LENGTH: 39
<212> TYPE: DNA
<213> ORGANISM: Artificial Sequence
<220> FEATURE:
<223> OTHER INFORMATION: Description of Artificial Sequence: Synthetic
primer

<400> SEQUENCE: 36
gttttctcga tggaggctgg gagggctttg ttggagacc 39

<210> SEQ ID NO 37
<211> LENGTH: 43
<212> TYPE: DNA
<213> ORGANISM: Artificial Sequence
<220> FEATURE:
<223> OTHER INFORMATION: Description of Artificial Sequence: Synthetic
primer

<400> SEQUENCE: 37
aagcttgcca ccatggctct ggagaagtct cttgtccggc tcc 43

<210> SEQ ID NO 38
<211> LENGTH: 40
<212> TYPE: DNA
<213> ORGANISM: Artificial Sequence
<220> FEATURE:
<223> OTHER INFORMATION: Description of Artificial Sequence: Synthetic
primer

<400> SEQUENCE: 38
ctcgagatct gtagagtcct ccacagaagc atcaaagtgg 40

<210> SEQ ID NO 39
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 39
accggtaagg aatcccgggc caagaaattc c 31

<210> SEQ ID NO 40
<211> LENGTH: 45
<212> TYPE: DNA
<213> ORGANISM: Artificial Sequence
<220> FEATURE:
<223> OTHER INFORMATION: Description of Artificial Sequence: Synthetic
primer

<400> SEQUENCE: 40
gatatccctt ccctgggcaa ggaatcccgg gccaagaaat tccag 45

<210> SEQ ID NO 41
<211> LENGTH: 45
<212> TYPE: DNA
<213> ORGANISM: Artificial Sequence
<220> FEATURE:
<223> OTHER INFORMATION: Description of Artificial Sequence: Synthetic
primer

<400> SEQUENCE: 41
gtttctagat tattaggtag agtcctccac agaagcatca aagtg 45

<210> SEQ ID NO 42
<211> LENGTH: 45
<212> TYPE: DNA
<213> ORGANISM: Artificial Sequence
<220> FEATURE:

<223> OTHER INFORMATION: Description of Artificial Sequence: Synthetic primer

<400> SEQUENCE: 42
ggtaagcttg ccaccatgtc acgggagctg gccccactgc tgctt 45

<210> SEQ ID NO 43
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
ctcgagatct gaggagcgtt tgctctttgt tttcttcctt ag 42

<210> SEQ ID NO 44
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
accggtatga ggatctgctc cttcaacgtc aggtcctttg g 41

<210> SEQ ID NO 45
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
gttaccggtc tgaagatcgc agccttcaac atccag 36

<210> SEQ ID NO 46
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
gttctcgaga tctttcagca tcacctccac tggatagtg 39

<210> SEQ ID NO 47
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
gttgatatcc tgaagatcgc agccttcaac atccag 36

<210> SEQ ID NO 48
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
gtttctagat tatcacttca gcatcacctc cactggatag tg 42

<210> SEQ ID NO 49
<211> LENGTH: 60
<212> TYPE: DNA
<213> ORGANISM: Artificial Sequence
<220> FEATURE:
<223> OTHER INFORMATION: Description of Artificial Sequence: Synthetic
primer

<400> SEQUENCE: 49
gatggctgcg agccctgcag gaacgacacc ttcaaccgag agccattcat tgtcaggttc 60

<210> SEQ ID NO 50
<211> LENGTH: 60
<212> TYPE: DNA
<213> ORGANISM: Artificial Sequence
<220> FEATURE:
<223> OTHER INFORMATION: Description of Artificial Sequence: Synthetic
primer

<400> SEQUENCE: 50
gaacctgaca atgaatggct ctcggttgaa ggtgtcgttc ctgcagggct cgcagccatc 60

<210> SEQ ID NO 51
<211> LENGTH: 39
<212> TYPE: DNA
<213> ORGANISM: Artificial Sequence
<220> FEATURE:
<223> OTHER INFORMATION: Description of Artificial Sequence: Synthetic
primer

<400> SEQUENCE: 51
ggagaagaac ctgacaatga atggctctcg gttgaaggt 39

<210> SEQ ID NO 52
<211> LENGTH: 39
<212> TYPE: DNA
<213> ORGANISM: Artificial Sequence
<220> FEATURE:
<223> OTHER INFORMATION: Description of Artificial Sequence: Synthetic
primer

<400> SEQUENCE: 52
accttcaacc gagagccatt cattgtcagg ttcttctcc 39

<210> SEQ ID NO 53
<211> LENGTH: 35
<212> TYPE: DNA
<213> ORGANISM: Artificial Sequence
<220> FEATURE:
<223> OTHER INFORMATION: Description of Artificial Sequence: Synthetic
primer

<400> SEQUENCE: 53
accggtatgg gccctggagc tcgcagacag ggcag 35

<210> SEQ ID NO 54
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 54
ctcgagatct ttggtcctag cagaggctgt gacc 34

<210> SEQ ID NO 55
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
accggtctcg agatgggccc tggagctcgc agacagg 37

<210> SEQ ID NO 56
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 56
ctcgagtttg gtcctagcag aggctgtgac c 31

<210> SEQ ID NO 57
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 57
accggtatgg gctcacagac cctgccccat ggtcaca 37

<210> SEQ ID NO 58
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 58
ctcgagatct gttgttccag tggtagccgg agtgccgtac atg 43

<210> SEQ ID NO 59
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 59
gttaagcttg ccaccatgtc cctgcaccca gcttccccac gcctg 45

<210> SEQ ID NO 60
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 60
ctcgagatct gaggagcgat tgcctttttt tctcttttttg agag 44

<210> SEQ ID NO 61
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 61
gttaagcttg ccaccatggg tctggagaag tccctcattc tg 42

<210> SEQ ID NO 62
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 62
ggctcgagca cagtagcatc aaagtggact ggtacgtagg 40

<210> SEQ ID NO 63
<211> LENGTH: 58
<212> TYPE: DNA
<213> ORGANISM: Artificial Sequence
<220> FEATURE:
<223> OTHER INFORMATION: Description of Artificial Sequence: Synthetic primer

<400> SEQUENCE: 63
cctccatgca aatgcccagc acctaacctc ttgggtggat catccgtctt catcttcc 58

<210> SEQ ID NO 64
<211> LENGTH: 53
<212> TYPE: DNA
<213> ORGANISM: Artificial Sequence
<220> FEATURE:
<223> OTHER INFORMATION: Description of Artificial Sequence: Synthetic primer

<400> SEQUENCE: 64
agatctcgag cccagaggtc ccacaatcaa gccctctcct ccatgcaaat gcc 53

<210> SEQ ID NO 65
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 65
gaagatctcg agcccagagg tcccacaatc aagccctctc ctcca 45

<210> SEQ ID NO 66
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 66
atcaagccct ctcctccatc taaatcccca gcacctaac 39

<210> SEQ ID NO 67
<211> LENGTH: 57
<212> TYPE: DNA
<213> ORGANISM: Artificial Sequence
<220> FEATURE:
<223> OTHER INFORMATION: Description of Artificial Sequence: Synthetic primer

<400> SEQUENCE: 67
agtggcaagg agttcaaatg ctcggtcaag aagaaagacc tcccagcgtc catcgag 57

<210> SEQ ID NO 68
<211> LENGTH: 55
<212> TYPE: DNA
<213> ORGANISM: Artificial Sequence
<220> FEATURE:
<223> OTHER INFORMATION: Description of Artificial Sequence: Synthetic primer

<400> SEQUENCE: 68
ggttctctcg atggacgctg ggaggtcttt gttgttgacc gagcatttga actcc 55

<210> SEQ ID NO 69
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 69
gtttctagat tatcatttac ccggagtccg agagaagctc ttagtcgt 48

<210> SEQ ID NO 70
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 70
gctagctccg tcgactttac ccggagacag agagagg 37

<210> SEQ ID NO 71
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 71
gactggctga atggcaagga gtacaagtgc tcggtctcca acaaagccct c 51

<210> SEQ ID NO 72
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 72
gagggctttg ttggagaccg agcacttgta agacttgcca ttcagccagt c 51

<210> SEQ ID NO 73
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 73
ccgcgggagg agcagtacag cagcacgtac cgtgtggtca gcgtc 45

<210> SEQ ID NO 74
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 74
gacgctgacc acacggtacg tgctgctgta ctgctcctcc cgcgg 45

<210> SEQ ID NO 75
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 75
gatatctcta gatttacccg gagtccgaga gaagctctta gtcgt 45

<210> SEQ ID NO 76
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 76
gatatctccg gagtcgactt tacccggagt ccgagagaag ctcttag 47

<210> SEQ ID NO 77
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 77
cacaaaccca tagagaggat tacagcagta ctctccgggt ggtc 44

<210> SEQ ID NO 78
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 78
gaccacccgg agagtactgc tgtaatcctc tctatgggtt tgag 44

<210> SEQ ID NO 79

<400> SEQUENCE: 79

000

<210> SEQ ID NO 80
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 80
gatatcaccg gtagaaccac ctccaccact cccacctcct ccagtgcctc c 51

<210> SEQ ID NO 81
<211> LENGTH: 50
<212> TYPE: DNA
<213> ORGANISM: Artificial Sequence
<220> FEATURE:
<223> OTHER INFORMATION: Description of Artificial Sequence: Synthetic primer

<400> SEQUENCE: 81
gtcgactccg gaggaggtgg ctcaggtggt ggaggcagtg gaggaggtgg 50

<210> SEQ ID NO 82
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 82
aaagtcgacg gagctagcag ccccgtgaac gtgagcagcc ccagcgtg 48

<210> SEQ ID NO 83
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 83
cccatgatat cctgcacgct ggggctgctc 30

<210> SEQ ID NO 84
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 84
accggtatga ggatctgctc cttcaacgtc aggtcctttg g 41

<210> SEQ ID NO 85
<211> LENGTH: 42
<212> TYPE: DNA
<213> ORGANISM: Artificial Sequence
<220> FEATURE:

<223> OTHER INFORMATION: Description of Artificial Sequence: Synthetic primer

<400> SEQUENCE: 85
agatctttat caggagcgtt tgctctttgt tttcttcctt ag 42

<210> SEQ ID NO 86
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 86
tctagattat caggagcgat tgcctttttt tctcttttg agag 44

<210> SEQ ID NO 87
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 87
accggtctaa ggctctgctc cttcaatgtg aggtcctttg ga 42

<210> SEQ ID NO 88
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 88
gataccaccg gtagggaatc tgcagcacag aagtttcag 39

<210> SEQ ID NO 89
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 89
aaatctagac ctcaaccagg tagggaatct gcagcacaga agtttcag 48

<210> SEQ ID NO 90
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 90
tctagactat cacacagtag catcaaagtg gactggtacg ta 42

<210> SEQ ID NO 91
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 91
agactgccgc ctgacaaacg actccaggta ccc 33

<210> SEQ ID NO 92
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 92
gggtacctgg agtcgtttgt caggcggcag tct 33

<210> SEQ ID NO 93
<211> LENGTH: 52
<212> TYPE: DNA
<213> ORGANISM: Artificial Sequence
<220> FEATURE:
<223> OTHER INFORMATION: Description of Artificial Sequence: Synthetic
primer

<400> SEQUENCE: 93
ggctcaggtg gtggaggatc tggaggaggt ggctcaggtg gtggaggatc tg 52

<210> SEQ ID NO 94
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 94
gttagatctc tccggaggag gtggctcagg tggtggagga tctgga 46

<210> SEQ ID NO 95
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 95
ctcgagactc ccacctcctc cagatcctcc accacctgag ccacct 46

<210> SEQ ID NO 96
<211> LENGTH: 50
<212> TYPE: DNA
<213> ORGANISM: Artificial Sequence
<220> FEATURE:
<223> OTHER INFORMATION: Description of Artificial Sequence: Synthetic
primer

<400> SEQUENCE: 96
aaagatctct ccggaggagg tggctcaggt ggtggaggat ctggaggagg 50

<210> SEQ ID NO 97
<211> LENGTH: 50
<212> TYPE: DNA
<213> ORGANISM: Artificial Sequence
<220> FEATURE:
<223> OTHER INFORMATION: Description of Artificial Sequence: Synthetic
primer

<400> SEQUENCE: 97
ctcgagaccg gtagaaccac ctccaccact cccacctcct ccagatcctc 50

<210> SEQ ID NO 98
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 98
gttagatctc tccggaggag gtggctca 28

<210> SEQ ID NO 99
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 99
accggtctcg agactcccac ctcctccaga tc 32

<210> SEQ ID NO 100
<211> LENGTH: 82
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 100
agatctctcc ggaggaggtg gctcaggtgg tggaggatct ggaggaggtg ggagtggtgg 60
aggtggttct accggtctcg ag 82

<210> SEQ ID NO 101
<211> LENGTH: 97
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 101
agatctctcc ggaggaggtg gctcaggtgg tggaggatct ggaggaggtg gctcaggtgg 60
tggaggatct ggaggaggtg ggagtaccgg tctcgag 97

<210> SEQ ID NO 102
<211> LENGTH: 91
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 102
agatctctcc ggaggaggtg gctcaggtgg tggaggatct ggaggaggtg gctcaggtgg 60
tggaggatct ggaggaggtg ggagtctcga g 91

<210> SEQ ID NO 103
<211> LENGTH: 462

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 103
gtcgacggag ctagcagccc cgtgaacgtg agcagcccca gcgtgcagga tatcccttcc 60
ctgggcaagg aatcccgggc caagaaattc cagcggcagc atatggactc agacagttcc 120
cccagcagca gctccaccta ctgtaaccaa atgatgaggc gccggaatat gacacagggg 180
cggtgcaaac cagtgaacac ctttgtgcac gagcccctgg tagatgtcca gaatgtctgt 240
ttccaggaaa aggtcacctg caagaacggg cagggcaact gctacaagag caactccagc 300
atgcacatca cagactgccg cctgacaaac gactccaggt accccaactg tgcataccgg 360
accagcccga aggagagaca catcattgtg gcctgtgaag ggagcccata tgtgccagtc 420
cactttgatg cttctgtgga ggactctacc taataatcta ga 462

<210> SEQ ID NO 104
<211> LENGTH: 798
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 104
gatatcctga agatcgcagc cttcaacatc cagacatttg gggagaccaa gatgtccaat 60
gccaccctcg tcagctacat tgtgcagatc ctgagccgct atgacatcgc cctggtccag 120
gaggtcagag acagccacct gactgccgtg gggaagctgc tggacaacct caatcaggat 180
gcaccagaca cctatcacta cgtggtcagt gagccactgg gacggaacag ctataaggag 240
cgctacctgt tcgtgtacag gcctgaccag gtgtctgcgg tggacagcta ctactacgat 300
gatggctgcg agccctgcag gaacgacacc ttcaaccgag agccattcat tgtcaggttc 360
ttctcccggt tcacagaggt cagggagttt gccattgttc ccctgcatgc ggccccgggg 420
gacgcagtag ccgagatcga cgctctctat gacgtctacc tggatgtcca agagaaatgg 480
ggcttggagg acgtcatgtt gatgggcgac ttcaatgcgg gctgcagcta tgtgagaccc 540
tcccagtggt catccatccg cctgtggaca agccccacct tccagtggct gatccccgac 600
agcgctgaca ccacagctac acccacgcac tgtgcctatg acaggatcgt ggttgcaggg 660
atgctgctcc gaggcgccgt tgttcccgac tcggctcttc cctttaactt ccaggctgcc 720
tatggcctga gtgaccaact ggcccaagcc atcagtgacc actatccagt ggaggtgatg 780
ctgaagtgat aatctaga 798

<210> SEQ ID NO 105
<211> LENGTH: 798
<212> TYPE: DNA
<213> ORGANISM: Homo sapiens

<400> SEQUENCE: 105
gatatcctga agatcgcagc cttcaacatc cagacatttg gggagaccaa gatgtccaat 60
gccaccctcg tcagctacat tgtgcagatc ctgagccgct atgacatcgc cctggtccag 120
gaggtcagag acagccacct gactgccgtg gggaagctgc tggacaacct caatcaggat 180
gcaccagaca cctatcacta cgtggtcagt gagccactgg gacggaacag ctataaggag 240
cgctacctgt tcgtgtacag gcctgaccag gtgtctgcgg tggacagcta ctactacgat 300
gatggctgcg agccctgcgg gaacgacacc ttcaaccgag agccagccat tgtcaggttc 360
ttctcccggt tcacagaggt cagggagttt gccattgttc ccctgcatgc ggccccgggg 420
gacgcagtag ccgagatcga cgctctctat gacgtctacc tggatgtcca agagaaatgg 480
ggcttggagg acgtcatgtt gatgggcgac ttcaatgcgg gctgcagcta tgtgagaccc 540
tcccagtggt catccatccg cctgtggaca agccccacct tccagtggct gatccccgac 600
agcgctgaca ccacagctac acccacgcac tgtgcctatg acaggatcgt ggttgcaggg 660
atgctgctcc gaggcgccgt tgttcccgac tcggctcttc cctttaactt ccaggctgcc 720
tatggcctga gtgaccaact ggcccaagcc atcagtgacc actatccagt ggaggtgatg 780
ctgaaatgat aatctaga 798

<210> SEQ ID NO 106
<211> LENGTH: 798
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 106
gatatcctga agatcgcagc cttcaacatc cagacatttg gggagaccaa gatgtccaat 60
gccaccctcg tcagctacat tgtgcagatc ctgagccgct atgacatcgc cctggtccag 120
gaggtcagag acagccacct gactgccgtg gggaagctgc tggacaacct caatcaggat 180
gcaccagaca cctatcacta cgtggtcagt gagccactgg gacggaacag ctataaggag 240
cgctacctgt tcgtgtacag gcctgaccag gtgtctgcgg tggacagcta ctactacgat 300
gatggctgcg agccctgcgg gaacgacacc ttcaaccgag agccattcat tgtcaggttc 360
ttctcccggt tcacagaggt cagggagttt gccattgttc ccctgcatgc ggccccgggg 420
gacgcagtag ccgagatcga cgctctctat gacgtctacc tggatgtcca agagaaatgg 480
ggcttagagg acgtcatgtt gatgggcgac ttcaatgcgg gctgcagcta tgtgagaccc 540
tcccagtggt catccatccg cctgtggaca agccccacct tccagtggct gatccccgac 600
agcgctgaca ccacagctac acccacgcac tgtgcctatg acaggatcgt ggttgcaggg 660
atgctgctcc gaggcgccgt tgttcccgac tcggctcttc cctttaactt ccaggctgcc 720
tatggcctga gtgaccaact ggcccaagcc atcagtgacc actatccagt ggaggtgatg 780
ctgaagtgat aatctaga 798

<210> SEQ ID NO 107
<211> LENGTH: 795
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 107
accggtctga agatcgcagc cttcaacatc cagacatttg gggagaccaa gatgtccaat 60
gccaccctcg tcagctacat tgtgcagatc ctgagccgct atgacatcgc cctggtccag 120
gaggtcagag acagccacct gactgccgtg gggaagctgc tggacaacct caatcaggat 180
gcaccagaca cctatcacta cgtggtcagt gagccactgg gacggaacag ctataaggag 240
cgctacctgt tcgtgtacag gcctgaccag gtgtctgcgg tggacagcta ctactacgat 300
gatggctgcg agccctgcag gaacgacacc ttcaaccgag agccattcat tgtcaggttc 360
ttctcccggt tcacagaggt cagggagttt gccattgttc ccctgcatgc ggccccgggg 420
gacgcagtag ccgagatcga cgctctctat gacgtctacc tggatgtcca agagaaatgg 480
ggcttggagg acgtcatgtt gatgggcgac ttcaatgcgg gctgcagcta tgtgagaccc 540
tcccagtggt catccatccg cctgtggaca agccccacct tccagtggct gatccccgac 600
agcgctgaca ccacagctac acccacgcac tgtgcctatg acaggatcgt ggttgcaggg 660
atgctgctcc gaggcgccgt tgttcccgac tcggctcttc cctttaactt ccaggctgcc 720
tatggcctga gtgaccaact ggcccaagcc atcagtgacc actatccagt ggaggtgatg 780
ctgaaagatc tcgag 795

<210> SEQ ID NO 108
<211> LENGTH: 795
<212> TYPE: DNA
<213> ORGANISM: Homo sapiens

<400> SEQUENCE: 108
accggtctga agatcgcagc cttcaacatc cagacatttg gggagaccaa gatgtccaat 60
gccaccctcg tcagctacat tgtgcagatc ctgagccgct atgacatcgc cctggtccag 120
gaggtcagag acagccacct gactgccgtg gggaagctgc tggacaacct caatcaggat 180
gcaccagaca cctatcacta cgtggtcagt gagccactgg gacggaacag ctataaggag 240
cgctacctgt tcgtgtacag gcctgaccag gtgtctgcgg tggacagcta ctactacgat 300
gatggctgcg agccctgcgg gaacgacacc ttcaaccgag agccagccat tgtcaggttc 360
ttctcccggt tcacagaggt cagggagttt gccattgttc ccctgcatgc ggccccgggg 420
gacgcagtag ccgagatcga cgctctctat gacgtctacc tggatgtcca agagaaatgg 480
ggcttggagg acgtcatgtt gatgggcgac ttcaatgcgg gctgcagcta tgtgagaccc 540
tcccagtggt catccatccg cctgtggaca agccccacct tccagtggct gatccccgac 600
agcgctgaca ccacagctac acccacgcac tgtgcctatg acaggatcgt ggttgcaggg 660
atgctgctcc gaggcgccgt tgttcccgac tcggctcttc cctttaactt ccaggctgcc 720
tatggcctga gtgaccaact ggcccaagcc atcagtgacc actatccagt ggaggtgatg 780
ctgaaagatc tcgag 795

<210> SEQ ID NO 109
<211> LENGTH: 795
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109
accggtctga agatcgcagc cttcaacatc cagacatttg gggagaccaa gatgtccaat 60
gccaccctcg tcagctacat tgtgcagatc ctgagccgct atgacatcgc cctggtccag 120
gaggtcagag acagccacct gactgccgtg gggaagctgc tggacaacct caatcaggat 180
gcaccagaca cctatcacta cgtggtcagt gagccactgg gacggaacag ctataaggag 240
cgctacctgt tcgtgtacag gcctgaccag gtgtctgcgg tggacagcta ctactacgat 300
gatggctgcg agccctgcgg gaacgacacc ttcaaccgag agccattcat tgtcaggttc 360
ttctcccggt tcacagaggt cagggagttt gccattgttc ccctgcatgc ggccccgggg 420

```
gacgcagtag ccgagatcga cgctctctat gacgtctacc tggatgtcca agagaaatgg    480

ggcttagagg acgtcatgtt gatgggcgac ttcaatgcgg gctgcagcta tgtgagaccc    540

tcccagtggt catccatccg cctgtggaca agccccacct tccagtggct gatccccgac    600

agcgctgaca ccacagctac acccacgcac tgtgcctatg acaggatcgt ggttgcaggg    660

atgctgctcc gaggcgccgt tgttcccgac tcggctcttc cctttaactt ccaggctgcc    720

tatggcctga gtgaccaact ggcccaagcc atcagtgacc actatccagt ggaggtgatg    780

ctgaaagatc tcgag                                                     795
```

<210> SEQ ID NO 110
<211> LENGTH: 715
<212> TYPE: DNA
<213> ORGANISM: Homo sapiens

<400> SEQUENCE: 110

```
agatctcgag cccaaatctt ctgacaaaac tcacacatgt ccaccgtgcc cagcacctga     60

actcctgggg ggaccgtcag tcttcctctt ccccccaaaa cccaaggaca ccctcatgat    120

ctcccggacc cctgaggtca catgcgtggt ggtggacgtg agccacgaag accctgaggt    180

caagttcaac tggtacgtgg acggcgtgga ggtgcataat gccaagacaa agccgcggga    240

ggagcagtac aacagcacgt accgtgtggt cagcgtcctc accgtcctgc accaggactg    300

gctgaatggc aaggagtaca agtgcaaggt ctccaacaaa gccctcccag cccccatcga    360

gaaaaccatc tccaaagcca aagggcagcc ccgagaacca caggtgtaca ccctgccccc    420

atcccgggat gagctgacca agaaccaggt cagcctgacc tgcctggtca aaggcttcta    480

tcccagcgac atcgccgtgg agtgggagag caatgggcag ccggagaaca actacaagac    540

cacgcctccc gtgctggact ccgacggctc cttcttcctc tacagcaagc tcaccgtgga    600

caagagcagg tggcagcagg ggaacgtctt ctcatgctcc gtgatgcatg aggctctgca    660

caaccactac acgcagaaga gcctctctct gtctccgggt aaatgataat ctaga         715
```

<210> SEQ ID NO 111
<211> LENGTH: 858
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 111

```
gttaagcttg ccaccatgga aaccccagcg cagcttctct tcctcctgct actctggctc     60

ccagatacca ccggtctgaa gatcgcagcc ttcaacatcc agacatttgg ggagaccaag    120

atgtccaatg ccaccctcgt cagctacatt gtgcagatcc tgagccgcta tgacatcgcc    180

ctggtccagg aggtcagaga cagccacctg actgccgtgg ggaagctgct ggacaacctc    240

aatcaggatg caccagacac ctatcactac gtggtcagtg agccactggg acggaacagc    300

tataaggagc gctacctgtt cgtgtacagg cctgaccagg tgtctgcggt ggacagctac    360

tactacgatg atggctgcga gccctgcggg aacgacacct tcaaccgaga gccagccatt    420

gtcaggttct tctcccggtt cacagaggtc agggagtttg ccattgttcc cctgcatgcg    480

gccccggggg acgcagtagc cgagatcgac gctctctatg acgtctacct ggatgtccaa    540

gagaaatggg gcttggagga cgtcatgttg atgggcgact tcaatgcggg ctgcagctat    600

gtgagaccct cccagtggtc atccatccgc ctgtggacaa gccccacctt ccagtggctg    660
```

atccccgaca gcgctgacac cacagctaca cccacgcact gtgcctatga caggatcgtg 720
gttgcaggga tgctgctccg aggcgccgtt gttcccgact cggctcttcc ctttaacttc 780
caggctgcct atggcctgag tgaccaactg gcccaagcca tcagtgacca ctatccagtg 840
gaggtgatgc tgaagtga 858

<210> SEQ ID NO 112
<211> LENGTH: 918
<212> TYPE: DNA
<213> ORGANISM: Homo sapiens

<400> SEQUENCE: 112
atgtcacggg agctggcccc actgctgctt ctcctcctct ccatccacag cgccctggcc 60
atgaggatct gctccttcaa cgtcaggtcc tttggggaaa gcaagcagga agacaagaat 120
gccatggatg tcattgtgaa ggtcatcaaa cgctgtgaca tcatactcgt gatggaaatc 180
aaggacagca acaacaggat ctgccccata ctgatggaga agctgaacag aaattcaagg 240
agaggcataa catacaacta tgtgattagc tctcggcttg gaagaaacac atataaagaa 300
caatatgcct ttctctacaa ggaaaagctg gtgtctgtga agaggagtta tcactaccat 360
gactatcagg atggagacgc agatgtgttt tccagggagc cctttgtggt ctggttccaa 420
tctccccaca ctgctgtcaa agacttcgtg attatccccc tgcacaccac cccagagaca 480
tccgttaagg agatcgatga gttggttgag gtctacacgg acgtgaaaca ccgctggaag 540
gcggagaatt tcattttcat gggtgacttc aatgccggct gcagctacgt ccccaagaag 600
gcctggaaga acatccgctt gaggactgac cccaggtttg tttggctgat cggggaccaa 660
gaggacacca cggtgaagaa gagcaccaac tgtgcatatg acaggattgt gcttagagga 720
caagaaatcg tcagttctgt tgttcccaag tcaaacagtg tttttgactt ccagaaagct 780
tacaagctga ctgaagagga ggccctggat gtcagcgacc actttccagt tgaatttaaa 840
ctacagtctt caagggcctt caccaacagc aaaaaatctg tcactctaag gaagaaaaca 900
aagagcaaac gctcctag 918

<210> SEQ ID NO 113
<211> LENGTH: 459
<212> TYPE: DNA
<213> ORGANISM: Homo sapiens

<400> SEQUENCE: 113
atgggtctgg agaagtctct tgtccggctc cttctgcttg tcctgatact gctggtgctg 60
ggctgggtcc agccttccct gggcaaggaa tcccgggcca agaaattcca gcggcagcat 120
atggactcag acagttcccc cagcagcagc tccacctact gtaaccaaat gatgaggcgc 180
cggaatatga cacaggggcg gtgcaaacca gtgaacacct ttgtgcacga gcccctggta 240
gatgtccaga atgtctgttt ccaggaaaag gtcacctgca agaacgggca gggcaactgc 300
tacaagagca actccagcat gcacatcaca gactgccgcc tgacaaacgg ctccaggtac 360
cccaactgtg cataccggac cagcccgaag gagagacaca tcattgtggc ctgtgaaggg 420
agcccatatg tgccagtcca ctttgatgct actgtgtag 459

<210> SEQ ID NO 114
<211> LENGTH: 1162
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 114
gttaagcttg ccaccatgga aaccccagcg cagcttctct tcctcctgct actctggctc 60
ccagatacca ccggtaggga atctgcagca cagaagtttc agcggcagca catggatcca 120
gatggttcct ccatcaacag ccccacctac tgcaaccaaa tgatgaaacg ccgggatatg 180
acaaatgggt catgcaagcc cgtgaacacc ttcgtgcatg agcccttggc agatgtccag 240
gccgtctgct cccaggaaaa tgtcacctgc aagaacagga agagcaactg ctacaagagc 300
agctctgccc tgcacatcac tgactgccac ctgaagggca actccaagta tcccaactgt 360
gactacaaga ccactcaata ccagaagcac atcattgtgg cctgtgaagg gaacccctac 420
gtaccagtcc actttgatgc tactgtgctc gagcccagag gtctcacaat caagccctct 480
cctccatgca aatgcccagc acctaacctc ttgggtggat catccgtctt catcttccct 540
ccaaagatca aggatgtact catgatctcc ctgagcccca tggtcacatg tgtggtggtg 600
gatgtgagcg aggatgaccc agacgtccag atcagctggt ttgtgaacaa cgtggaagta 660
cacacagctc agacacaaac ccatagagag gattacaaca gtactctccg ggtggtcagt 720
gccctcccca tccagcacca ggactggatg agtggcaagg agttcaaatg ctcggtcaac 780
aacaaagacc tcccagcgtc catcgagaga accatctcaa aacccagagg gccagtaaga 840
gctccacagg tatatgtctt gcctccacca gcagaagaga tgactaagaa agagttcagt 900
ctgacctgca tgatcacagg cttcttacct gccgaaattg ctgtggactg gaccagcaat 960
gggcgtacag agcaaaacta caagaacacc gcaacagtcc tggactctga tggttcttac 1020
ttcatgtaca gcaagctcag agtacaaaag agcacttggg aaagaggaag tcttttcgcc 1080
tgctcagtgg tccacgaggg tctgcacaat caccttacga ctaagagctt ctctcggact 1140
ccgggtaaat gataatctag aa 1162

<210> SEQ ID NO 115
<211> LENGTH: 2004
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1921)..(1921)
<223> OTHER INFORMATION: a, c, t, g, unknown or other

<400> SEQUENCE: 115
aagcttgccg ccatggaaac cccagcgcag cttctcttcc tcctgctact ctggctccca 60
gataccaccg gtaaggaatc ccgggccaag aaattccagc ggcagcatat ggactcagac 120
agttccccca gcagcagctc cacctactgt aaccaaatga tgaggcgccg gaatatgaca 180
caggggcggt gcaaaccagt gaacaccttt gtgcacgagc ccctggtaga tgtccagaat 240
gtctgtttcc aggaaaaggt cacctgcaag aacgggcagg gcaactgcta caagagcaac 300
tccagcatgc acatcacaga ctgccgcctg acaaacggct ccaggtaccc caactgtgca 360
taccggacca gcccgaagga gagacacatc attgtggcct gtgaagggag cccatatgtg 420
ccagtccact ttgatgcttc tgtggaggac tctacagatc tcgagcccaa atcttctgac 480
aaaactcaca catgtccacc gtgcccagca cctgaactcc tggggggacc gtcagtcttc 540
ctcttccccc caaaacccaa ggacaccctc atgatctccc ggacccctga ggtcacatgc 600
gtggtggtgg acgtgagcca cgaagaccct gaggtcaagt tcaactggta cgtggacggc 660
gtggaggtgc ataatgccaa gacaaagccg cgggaggagc agtacaacag cacgtaccgt 720
gtggtcagcg tcctcaccgt cctgcaccag gactggctga atggcaagga gtacaagtgc 780
aaggtctcca acaaagccct cccagccccc atcgagaaaa ccatctccaa agccaaaggg 840
cagccccgag aaccacaggt gtacaccctg cccccatccc gggatgagct gaccaagaac 900
caggtcagcc tgacctgcct ggtcaaaggc ttctatccca gcgacatcgc cgtggagtgg 960
gagagcaatg ggcagccgga gaacaactac aagaccacgc ctcccgtgct ggactccgac 1020
ggctccttct tcctctacag caagctcacc gtggacaaga gcaggtggca gcaggggaac 1080
gtcttctcat gctccgtgat gcatgagggt ctgcacaacc actacacgca gaagagcctc 1140
tctctgtctc cgggtaaagt cgacggtgct agcagccatg tgaatgtgag cagccctagc 1200
gtgcaggata tcctgaagat cgcagccttc aacatccaga catttgggga gaccaagatg 1260
tccaatgcca ccctcgtcag ctacattgtg cagatcctga gccgctatga catcgccctg 1320
gtccaggagg tcagagacag ccacctgact gccgtgggga agctgctgga caacctcaat 1380
caggatgcac cagacaccta tcactacgtg gtcagtgagc cactgggacg gaacagctat 1440
aaggagcgct acctgttcgt gtacaggcct gaccaggtgt ctgcggtgga cagctactac 1500
tacgatgatg gctgcgagcc ctgcgggaac gacaccttca accgagagcc agccattgtc 1560
aggttcttct cccggttcac agaggtcagg gagtttgcca ttgttcccct gcatgcggcc 1620
ccgggggacg cagtagccga gatcgacgct ctctatgacg tctacctgga tgtccaagag 1680
aaatggggct cggaggacgt catgttgatg ggcgacttca atgcgggctg cagctatgtg 1740
agaccctccc agtggtcatc catccgcctg tggacaagcc ccaccttcca gtggctgatc 1800
cccgacagcg ctgacaccac agctacaccc acgcactgtg cctatgacag gatcgtggtt 1860
gcagggatgc tgctccgagg cgccgttgtt cccgactcgg ctcttccctt taacttccag 1920
nctgcctatg gcctgagtga ccaactggcc caagccatca gtgaccacta tccagtggag 1980
gtgatgctga agtgataatc taga 2004

<210> SEQ ID NO 116
<211> LENGTH: 2004
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 116
aagcttgccg ccatggaaac cccagcgcag cttctcttcc tcctgctact ctggctccca 60
gataccaccg gtaaggaatc ccgggccaag aaattccagc ggcagcatat ggactcagac 120
agttccccca gcagcagctc cacctactgt aaccaaatga tgaggcgccg gaatatgaca 180
caggggcggt gcaaaccagt gaacaccttt gtgcacgagc ccctggtaga tgtccagaat 240
gtctgtttcc aggaaaaggt cacctgcaag aacgggcagg gcaactgcta caagagcaac 300
tccagcatgc acatcacaga ctgccgcctg acaaacggct ccaggtaccc caactgtgca 360
taccggacca gcccgaagga gagacacatc attgtggcct gtgaagggag cccatatgtg 420
ccagtccact ttgatgcttc tgtggaggac tctacagatc tcgagcccaa atcttctgac 480
aaaactcaca catgtccacc gtgcccagca cctgaactcc tgggggggacc gtcagtcttc 540 ctcttccccc caaaacccaa ggacaccctc atgatctccc ggacccctga ggtcacatgc 600

```
gtggtggtgg acgtgagcca cgaagaccct gaggtcaagt tcaactggta cgtggacggc    660

gtggaggtgc ataatgccaa gacaaagccg cgggaggagc agtacaacag cacgtaccgt    720

gtggtcagcg tcctcaccgt cctgcaccag gactggctga atggcaagga gtacaagtgc    780

aaggtctcca acaaagccct cccagccccc atcgagaaaa ccatctccaa agccaaaggg    840

cagccccgag aaccacaggt gtacaccctg cccccatccc gggatgagct gaccaagaac    900

caggtcagcc tgacctgcct ggtcaaaggc ttctatccca gcgacatcgc cgtggagtgg    960

gagagcaatg ggcagccgga gaacaactac aagaccacgc ctcccgtgct ggactccgac   1020

ggctccttct tcctctacag caagctcacc gtggacaaga gcaggtggca gcaggggaac   1080

gtcttctcat gctccgtgat gcatgagggt ctgcacaacc actacacgca gaagagcctc   1140

tctctgtctc cgggtaaagt cgacggtgct agcagccatg tgaatgtgag cagccctagc   1200

gtgcaggata tcctgaagat cgcagccttc aacatccaga catttgggga gaccaagatg   1260

tccaatgcca ccctcgtcag ctacattgtg cagatcctga gccgctatga catcgccctg   1320

gtccaggagg tcagagacag ccacctgact gccgtgggga agctgctgga caacctcaat   1380

caggatgcac cagacaccta tcactacgtg gtcagtgagc cactgggacg gaacagctat   1440

aaggagcgct acctgttcgt gtacaggcct gaccaggtgt ctgcggtgga cagctactac   1500

tacgatgatg gctgcgagcc ctgcgggaac gacaccttca accgagagcc attcattgtc   1560

aggttcttct cccggttcac agaggtcagg gagtttgcca ttgttcccct gcatgcggcc   1620

ccgggggacg cagtagccga gatcgacgct ctctatgacg tctacctgga tgtccaagag   1680

aaatggggct tagaggacgt catgttgatg ggcgacttca atgcgggctg cagctatgtg   1740

agaccctccc agtggtcatc catccgcctg tggacaagcc ccaccttcca gtggctgatc   1800

cccgacagcg ctgacaccac agctacaccc acgcactgtg cctatgacag gatcgtggtt   1860

gcagggatgc tgctccgagg cgccgttgtt cccgactcgg ctcttccctt taacttccag   1920

gctgcctatg gcctgagtga ccaactggcc caagccatca gtgaccacta tccagtggag   1980

gtgatgctga agtgataatc taga                                          2004
```

<210> SEQ ID NO 117
<211> LENGTH: 2004
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 117

```
aagcttgccg ccatggaaac ccagcgcgag cttctcttcc tcctgctact ctggctccca     60

gataccaccg gtaaggaatc ccgggccaag aaattccagc ggcagcatat ggactcagac    120

agttccccca gcagcagctc cacctactgt aaccaaatga tgaggcgccg gaatatgaca    180

caggggcggt gcaaaccagt gaacaccttt gtgcacgagc ccctggtaga tgtccagaat    240

gtctgtttcc aggaaaaggt cacctgcaag aacgggcagg gcaactgcta caagagcaac    300

tccagcatgc acatcacaga ctgccgcctg acaaacggct ccaggtaccc caactgtgca    360

taccggacca gcccgaagga gagacacatc attgtggcct gtgaagggag cccatatgtg    420

ccagtccact ttgatgcttc tgtggaggac tctacagatc tcgagcccaa atcttctgac    480

aaaactcaca catgtccacc gtgcccagca cctgaactcc tgggggggacc gtcagtcttc    540

ctcttccccc caaaacccaa ggacaccctc atgatctccc ggacccctga ggtcacatgc    600
```

gtggtggtgg acgtgagcca cgaagaccct gaggtcaagt tcaactggta cgtggacggc 660
gtggaggtgc ataatgccaa gacaaagccg cgggaggagc agtacaacag cacgtaccgt 720
gtggtcagcg tcctcaccgt cctgcaccag gactggctga atggcaagga gtacaagtgc 780
aaggtctcca acaaagccct cccagccccc atcgagaaaa ccatctccaa agccaaaggg 840
cagccccgag aaccacaggt gtacaccctg cccccatccc gggatgagct gaccaagaac 900
caggtcagcc tgacctgcct ggtcaaaggc ttctatccca gcgacatcgc cgtggagtgg 960
gagagcaatg ggcagccgga gaacaactac aagaccacgc ctcccgtgct ggactccgac 1020
ggctccttct tcctctacag caagctcacc gtggacaaga gcaggtggca gcaggggaac 1080
gtcttctcat gctccgtgat gcatgagggt ctgcacaacc actacacgca gaagagcctc 1140
tctctgtctc cgggtaaagt cgacggtgct agcagccatg tgaatgtgag cagccctagc 1200
gtgcaggata tcctgaagat cgcagccttc aacatccaga catttgggga gaccaagatg 1260
tccaatgcca ccctcgtcag ctacattgtg cagatcctga gccgctatga catcgccctg 1320
gtccaggagg tcagagacag ccacctgact gccgtgggga agctgctgga caacctcaat 1380
caggatgcac cagacaccta tcactacgtg gtcagtgagc cactgggacg gaacagctat 1440
aaggagcgct acctgttcgt gtacaggcct gaccaggtgt ctgcggtgga cagctactac 1500
tacgatgatg gctgcgagcc ctgcgggaac gacaccttca accgagagcc agccattgtc 1560
aggttcttct cccggttcac agaggtcagg gagtttgcca ttgttcccct gcatgcggcc 1620
ccgggggacg cagtagccga gatcgacgct ctctatgacg tctacctgga tgtccaagag 1680
aaatggggct tggaggacgt catgttgatg ggcgacttca atgcgggctg cagctatgtg 1740
agaccctccc agtggtcatc catccgcctg tggacaagcc ccaccttcca gtggctgatc 1800
cccgacagcg ctgacaccac agctacaccc acgcactgtg cctatgacag gatcgtggtt 1860
gcagggatgc tgctccgagg cgccgttgtt cccgactcgg ctcttccctt taacttccag 1920
gctgcctatg gcctgagtga ccaactggcc caagccatca gtgaccacta tccagtggag 1980
gtgatgctga aatgataatc taga 2004

<210> SEQ ID NO 118
<211> LENGTH: 1569
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 118
gttaagcttg ccaccatgga aaccccagcg cagcttctct tcctcctgct actctggctc 60
ccagatacca ccggtctgaa gatcgcagcc ttcaacatcc agacatttgg ggagaccaag 120
atgtccaatg ccaccctcgt cagctacatt gtgcagatcc tgagccgcta tgacatcgcc 180
ctggtccagg aggtcagaga cagccacctg actgccgtgg ggaagctgct ggacaacctc 240
aatcaggatg caccagacac ctatcactac gtggtcagtg agccactggg acggaacagc 300
tataaggagc gctacctgtt cgtgtacagg cctgaccagg tgtctgcggt ggacagctac 360
tactacgatg atggctgcga gccctgcggg aacgacacct tcaaccgaga gccagccatt 420
gtcaggttct tctcccggtt cacagaggtc agggagtttg ccattgttcc cctgcatgcg 480
gccccggggg acgcagtagc cgagatcgac gctctctatg acgtctacct ggatgtccaa 540
gagaaatggg gcttggagga cgtcatgttg atgggcgact tcaatgcggg ctgcagctat 600
gtgagaccct cccagtggtc atccatccgc ctgtggacaa gccccacctt ccagtggctg 660
atccccgaca gcgctgacac cacagctaca cccacgcact gtgcctatga caggatcgtg 720
gttgcaggga tgctgctccg aggcgccgtt gttcccgact cggctcttcc ctttaacttc 780
caggctgcct atggcctgag tgaccaactg gcccaagcca tcagtgacca ctatccagtg 840
gaggtgatgc tgaaagatct cgagcccaaa tcttctgaca aaactcacac atgtccaccg 900
tgcccagcac ctgaactcct ggggggaccg tcagtcttcc tcttcccccc aaaacccaag 960
gacaccctca tgatctcccg gacccctgag gtcacatgcg tggtggtgga cgtgagccac 1020
gaagaccctg aggtcaagtt caactggtac gtggacggcg tggaggtgca taatgccaag 1080
acaaagccgc gggaggagca gtacaacagc acgtaccgtg tggtcagcgt cctcaccgtc 1140
ctgcaccagg actggctgaa tggcaaggag tacaagtgca aggtctccaa caaagccctc 1200
ccagccccca tcgagaaaac catctccaaa gccaaagggc agccccgaga accacaggtg 1260
tacaccctgc ccccatcccg ggatgagctg accaagaacc aggtcagcct gacctgcctg 1320
gtcaaaggct tctatcccag cgacatcgcc gtggagtggg agagcaatgg gcagccggag 1380
aacaactaca agaccacgcc tcccgtgctg gactccgacg gctccttctt cctctacagc 1440
aagctcaccg tggacaagag caggtggcag caggggaacg tcttctcatg ctccgtgatg 1500
catgaggctc tgcacaacca ctacacgcag aagagcctct ctctgtctcc gggtaaatga 1560
taatctaga 1569

<210> SEQ ID NO 119
<211> LENGTH: 1569
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 119
gttaagcttg ccaccatgga aaccccagcg cagcttctct tcctcctgct actctggctc 60
ccagatacca ccggtctgaa gatcgcagcc ttcaacatcc agacatttgg ggagaccaag 120
atgtccaatg ccaccctcgt cagctacatt gtgcagatcc tgagccgcta tgacatcgcc 180
ctggtccagg aggtcagaga cagccacctg actgccgtgg ggaagctgct ggacaacctc 240
aatcaggatg caccagacac ctatcactac gtggtcagtg agccactggg acggaacagc 300
tataaggagc gctacctgtt cgtgtacagg cctgaccagg tgtctgcggt ggacagctac 360
tactacgatg atggctgcga gccctgcggg aacgacacct tcaaccgaga gccattcatt 420
gtcaggttct tctcccggtt cacagaggtc agggagtttg ccattgttcc cctgcatgcg 480
gccccggggg acgcagtagc cgagatcgac gctctctatg acgtctacct ggatgtccaa 540
gagaaatggg gcttagagga cgtcatgttg atgggcgact tcaatgcggg ctgcagctat 600
gtgagaccct cccagtggtc atccatccgc ctgtggacaa gccccacctt ccagtggctg 660
atccccgaca gcgctgacac cacagctaca cccacgcact gtgcctatga caggatcgtg 720
gttgcaggga tgctgctccg aggcgccgtt gttcccgact cggctcttcc ctttaacttc 780
caggctgcct atggcctgag tgaccaactg gcccaagcca tcagtgacca ctatccagtg 840
gaggtgatgc tgaaagatct cgagcccaaa tcttctgaca aaactcacac atgtccaccg 900
tgcccagcac ctgaactcct ggggggaccg tcagtcttcc tcttcccccc aaaacccaag 960
gacaccctca tgatctcccg gacccctgag gtcacatgcg tggtggtgga cgtgagccac 1020
gaagaccctg aggtcaagtt caactggtac gtggacggcg tggaggtgca taatgccaag 1080
acaaagccgc gggaggagca gtacaacagc acgtaccgtg tggtcagcgt cctcaccgtc 1140
ctgcaccagg actggctgaa tggcaaggag tacaagtgca aggtctccaa caaagccctc 1200
ccagccccca tcgagaaaac catctccaaa gccaaagggc agccccgaga accacaggtg 1260
tacaccctgc ccccatcccg ggatgagctg accaagaacc aggtcagcct gacctgcctg 1320
gtcaaaggct tctatcccag cgacatcgcc gtggagtggg agagcaatgg gcagccggag 1380
aacaactaca agaccacgcc tcccgtgctg gactccgacg gctccttctt cctctacagc 1440
aagctcaccg tggacaagag caggtggcag caggggaacg tcttctcatg ctccgtgatg 1500
catgaggctc tgcacaacca ctacacgcag aagagcctct ctctgtctcc gggtaaatga 1560
taatctaga 1569

<210> SEQ ID NO 120
<211> LENGTH: 1641
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 120
gttaagcttg ccaccatgga aaccccagcg cagcttctct tcctcctgct actctggctc 60
ccagatacca ccggtctgaa gatcgcagcc ttcaacatcc agacatttgg ggagaccaag 120
atgtccaatg ccaccctcgt cagctacatt gtgcagatcc tgagccgcta tgacatcgcc 180
ctggtccagg aggtcagaga cagccacctg actgccgtgg ggaagctgct ggacaacctc 240
aatcaggatg caccagacac ctatcactac gtggtcagtg agccactggg acggaacagc 300
tataaggagc gctacctgtt cgtgtacagg cctgaccagg tgtctgcggt ggacagctac 360
tactacgatg atggctgcga gccctgcagg aacgacacct tcaaccgaga gccattcatt 420
gtcaggttct tctcccggtt cacagaggtc agggagtttg ccattgttcc cctgcatgcg 480
gccccggggg acgcagtagc cgagatcgac gctctctatg acgtctacct ggatgtccaa 540
gagaaatggg gcttggagga cgtcatgttg atgggcgact tcaatgcggg ctgcagctat 600
gtgagaccct cccagtggtc atccatccgc ctgtggacaa gccccacctt ccagtggctg 660
atccccgaca gcgctgacac cacagctaca cccacgcact gtgcctatga caggatcgtg 720
gttgcaggga tgctgctccg aggcgccgtt gttcccgact cggctcttcc ctttaacttc 780
caggctgcct atggcctgag tgaccaactg gcccaagcca tcagtgacca ctatccagtg 840
gaggtgatgc tgaaagatct ctccggagga ggtggctcag gtggtggagg atctggagga 900
ggtgggagtg gtggaggtgg ttctaccggt ctcgagccca aatcttctga caaaactcac 960
acatgtccac cgtgcccagc acctgaactc ctggggggac cgtcagtctt cctcttcccc 1020
ccaaaaccca aggacaccct catgatctcc cggacccctg aggtcacatg cgtggtggtg 1080
gacgtgagcc acgaagaccc tgaggtcaag ttcaactggt acgtggacgg cgtggaggtg 1140
cataatgcca agacaaagcc gcgggaggag cagtacaaca gcacgtaccg tgtggtcagc 1200
gtcctcaccg tcctgcacca ggactggctg aatggcaagg agtacaagtg caaggtctcc 1260
aacaaagccc tcccagcccc catcgagaaa accatctcca aagccaaagg gcagccccga 1320
gaaccacagg tgtacaccct gcccccatcc cgggatgagc tgaccaagaa ccaggtcagc 1380
ctgacctgcc tggtcaaagg cttctatccc agcgacatcg ccgtggagtg ggagagcaat 1440
gggcagccgg agaacaacta caagaccacg cctcccgtgc tggactccga cggctccttc 1500
ttcctctaca gcaagctcac cgtggacaag agcaggtggc agcaggggaa cgtcttctca 1560
tgctccgtga tgcatgaggc tctgcacaac cactacacgc agaagagcct ctctctgtct 1620
ccgggtaaat gataatctag a 1641

<210> SEQ ID NO 121
<211> LENGTH: 1656
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 121
gttaagcttg ccaccatgga aaccccagcg cagcttctct tcctcctgct actctggctc 60
ccagatacca ccggtctgaa gatcgcagcc ttcaacatcc agacatttgg ggagaccaag 120
atgtccaatg ccaccctcgt cagctacatt gtgcagatcc tgagccgcta tgacatcgcc 180
ctggtccagg aggtcagaga cagccacctg actgccgtgg ggaagctgct ggacaacctc 240
aatcaggatg caccagacac ctatcactac gtggtcagtg agccactggg acggaacagc 300
tataaggagc gctacctgtt cgtgtacagg cctgaccagg tgtctgcggt ggacagctac 360
tactacgatg atggctgcga gccctgcagg aacgacacct tcaaccgaga gccattcatt 420
gtcaggttct tctcccggtt cacagaggtc agggagtttg ccattgttcc cctgcatgcg 480
gccccggggg acgcagtagc cgagatcgac gctctctatg acgtctacct ggatgtccaa 540
gagaaatggg gcttggagga cgtcatgttg atgggcgact tcaatgcggg ctgcagctat 600
gtgagaccct cccagtggtc atccatccgc ctgtggacaa gccccacctt ccagtggctg 660
atccccgaca gcgctgacac cacagctaca cccacgcact gtgcctatga caggatcgtg 720
gttgcaggga tgctgctccg aggcgccgtt gttcccgact cggctcttcc ctttaacttc 780
caggctgcct atggcctgag tgaccaactg gcccaagcca tcagtgacca ctatccagtg 840
gaggtgatgc tgaaagatct ctccggagga ggtggctcag gtggtggagg atctggagga 900
ggtggctcag gtggtggagg atctggagga ggtgggagta ccggtctcga gcccaaatct 960
tctgacaaaa ctcacacatg tccaccgtgc ccagcacctg aactcctggg gggaccgtca 1020
gtcttcctct tccccccaaa acccaaggac accctcatga tctcccggac ccctgaggtc 1080
acatgcgtgg tggtggacgt gagccacgaa gaccctgagg tcaagttcaa ctggtacgtg 1140
gacggcgtgg aggtgcataa tgccaagaca aagccgcggg aggagcagta caacagcacg 1200
taccgtgtgg tcagcgtcct caccgtcctg caccaggact ggctgaatgg caaggagtac 1260
aagtgcaagg tctccaacaa agccctccca gcccccatcg agaaaaccat ctccaaagcc 1320
aaagggcagc cccgagaacc acaggtgtac accctgcccc catcccggga tgagctgacc 1380
aagaaccagg tcagcctgac ctgcctggtc aaaggcttct atcccagcga catcgccgtg 1440
gagtgggaga gcaatgggca gccggagaac aactacaaga ccacgcctcc cgtgctggac 1500
tccgacggct ccttcttcct ctacagcaag ctcaccgtgg acaagagcag gtggcagcag 1560
gggaacgtct tctcatgctc cgtgatgcat gaggctctgc acaaccacta cacgcagaag 1620
agcctctctc tgtctccggg taaatgataa tctaga 1656

<210> SEQ ID NO 122
<211> LENGTH: 1650

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 122

```
gttaagcttg ccaccatgga aaccccagcg cagcttctct tcctcctgct actctggctc     60
ccagatacca ccggtctgaa gatcgcagcc ttcaacatcc agacatttgg ggagaccaag    120
atgtccaatg ccaccctcgt cagctacatt gtgcagatcc tgagccgcta tgacatcgcc    180
ctggtccagg aggtcagaga cagccacctg actgccgtgg ggaagctgct ggacaacctc    240
aatcaggatg caccagacac ctatcactac gtggtcagtg agccactggg acggaacagc    300
tataaggagc gctacctgtt cgtgtacagg cctgaccagg tgtctgcggt ggacagctac    360
tactacgatg atggctgcga gccctgcagg aacgacacct tcaaccgaga gccattcatt    420
gtcaggttct tctcccggtt cacagaggtc agggagtttg ccattgttcc cctgcatgcg    480
gccccggggg acgcagtagc cgagatcgac gctctctatg acgtctacct ggatgtccaa    540
gagaaatggg gcttggagga cgtcatgttg atgggcgact tcaatgcggg ctgcagctat    600
gtgagaccct cccagtggtc atccatccgc ctgtggacaa gccccacctt ccagtggctg    660
atccccgaca gcgctgacac cacagctaca cccacgcact gtgcctatga caggatcgtg    720
gttgcaggga tgctgctccg aggcgccgtt gttcccgact cggctcttcc ctttaacttc    780
caggctgcct atggcctgag tgaccaactg gcccaagcca tcagtgacca ctatccagtg    840
gaggtgatgc tgaaagatct ctccggagga ggtggctcag gtggtggagg atctggagga    900
ggtggctcag gtggtggagg atctggagga ggtgggagtc tcgagcccaa atcttctgac    960
aaaactcaca catgtccacc gtgcccagca cctgaactcc tgggggggacc gtcagtcttc   1020
ctcttccccc caaaacccaa ggacaccctc atgatctccc ggacccctga ggtcacatgc   1080
gtggtggtgg acgtgagcca cgaagaccct gaggtcaagt tcaactggta cgtggacggc   1140
gtggaggtgc ataatgccaa gacaaagccg cgggaggagc agtacaacag cacgtaccgt   1200
gtggtcagcg tcctcaccgt cctgcaccag gactggctga atggcaagga gtacaagtgc   1260
aaggtctcca acaaagccct cccagccccc atcgagaaaa ccatctccaa agccaaaggg   1320
cagccccgag aaccacaggt gtacaccctg cccccatccc gggatgagct gaccaagaac   1380
caggtcagcc tgacctgcct ggtcaaaggc ttctatccca gcgacatcgc cgtggagtgg   1440
gagagcaatg ggcagccgga gaacaactac aagaccacgc ctcccgtgct ggactccgac   1500
ggctccttct tcctctacag caagctcacc gtggacaaga gcaggtggca gcaggggaac   1560
gtcttctcat gctccgtgat gcatgaggct ctgcacaacc actacacgca gaagagcctc   1620
tctctgtctc cgggtaaatg ataatctaga                                     1650
```

<210> SEQ ID NO 123
<211> LENGTH: 1569
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 123

```
gttaagcttg ccaccatgga aaccccagcg cagcttctct tcctcctgct actctggctc     60
ccagatacca ccggtctgaa gatcgcagcc ttcaacatcc agacatttgg ggagaccaag    120
```

```
atgtccaatg ccaccctcgt cagctacatt gtgcagatcc tgagccgcta tgacatcgcc    180

ctggtccagg aggtcagaga cagccacctg actgccgtgg ggaagctgct ggacaacctc    240

aatcaggatg caccagacac ctatcactac gtggtcagtg agccactggg acggaacagc    300

tataaggagc gctacctgtt cgtgtacagg cctgaccagg tgtctgcggt ggacagctac    360

tactacgatg atggctgcga gccctgcagg aacgacacct tcaaccgaga gccattcatt    420

gtcaggttct tctcccggtt cacagaggtc agggagtttg ccattgttcc cctgcatgcg    480

gccccggggg acgcagtagc cgagatcgac gctctctatg acgtctacct ggatgtccaa    540

gagaaatggg gcttggagga cgtcatgttg atgggcgact tcaatgcggg ctgcagctat    600

gtgagaccct cccagtggtc atccatccgc ctgtggacaa gccccacctt ccagtggctg    660

atccccgaca gcgctgacac cacagctaca cccacgcact gtgcctatga caggatcgtg    720

gttgcaggga tgctgctccg aggcgccgtt gttcccgact cggctcttcc ctttaacttc    780

caggctgcct atggcctgag tgaccaactg gcccaagcca tcagtgacca ctatccagtg    840

gaggtgatgc tgaaagatct cgagcccaaa tcttctgaca aaactcacac atgtccaccg    900

tgcccagcac ctgaactcct ggggggaccg tcagtcttcc tcttcccccc aaaacccaag    960

gacaccctca tgatctcccg gacccctgag gtcacatgcg tggtggtgga cgtgagccac   1020

gaagaccctg aggtcaagtt caactggtac gtggacggcg tggaggtgca taatgccaag   1080

acaaagccgc gggaggagca gtacaacagc acgtaccgtg tggtcagcgt cctcaccgtc   1140

ctgcaccagg actggctgaa tggcaaggag tacaagtgca aggtctccaa caaagccctc   1200

ccagccccca tcgagaaaac catctccaaa gccaaagggc agccccgaga accacaggtg   1260

tacaccctgc ccccatcccg ggatgagctg accaagaacc aggtcagcct gacctgcctg   1320

gtcaaaggct tctatcccag cgacatcgcc gtggagtggg agagcaatgg gcagccggag   1380

aacaactaca agaccacgcc tcccgtgctg gactccgacg gctccttctt cctctacagc   1440

aagctcaccg tggacaagag caggtggcag caggggaacg tcttctcatg ctccgtgatg   1500

catgaggctc tgcacaacca ctacacgcag aagagcctct ctctgtctcc gggtaaatga   1560

taatctaga                                                           1569
```

```
<210> SEQ ID NO 124
<211> LENGTH: 1173
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 124

gttaagcttg ccaccatgga aaccccagcg cagcttctct tcctcctgct actctggctc     60

ccagatacca ccggtaagga atcccgggcc aagaaattcc agcggcagca tatggactca    120

gacagttccc ccagcagcag ctccacctac tgtaaccaaa tgatgaggcg ccggaatatg    180

acacaggggc ggtgcaaacc agtgaacacc tttgtgcacg agcccctggt agatgtccag    240

aatgtctgtt tccaggaaaa ggtcacctgc aagaacgggc agggcaactg ctacaagagc    300

aactccagca tgcacatcac agactgccgc ctgacaaacg actccaggta ccccaactgt    360

gcataccgga ccagcccgaa ggagagacac atcattgtgg cctgtgaagg gagcccatat    420

gtgccagtcc actttgatgc ttctgtggag gactctacag atctcgagcc caaatcttct    480

gacaaaactc acacatgtcc accgtgccca gcacctgaac tcctgggggg accgtcagtc    540
```

```
ttcctcttcc ccccaaaacc caaggacacc ctcatgatct cccggacccc tgaggtcaca    600

tgcgtggtgg tggacgtgag ccacgaagac cctgaggtca agttcaactg gtacgtggac    660

ggcgtggagg tgcataatgc caagacaaag ccgcgggagg agcagtacaa cagcacgtac    720

cgtgtggtca gcgtcctcac cgtcctgcac caggactggc tgaatggcaa ggagtacaag    780

tgcaaggtct ccaacaaagc cctcccagcc cccatcgaga aaaccatctc caaagccaaa    840

gggcagcccc gagaaccaca ggtgtacacc ctgcccccat cccgggatga gctgaccaag    900

aaccaggtca gcctgacctg cctggtcaaa ggcttctatc ccagcgacat cgccgtggag    960

tgggagagca atgggcagcc ggagaacaac tacaagacca cgcctcccgt gctggactcc   1020

gacggctcct tcttcctcta cagcaagctc accgtggaca agagcaggtg gcagcagggg   1080

aacgtcttct catgctccgt gatgcatgag gctctgcaca accactacac gcagaagagc   1140

ctctctctgt ctccgggtaa atgataatct aga                                1173
```

<210> SEQ ID NO 125
<211> LENGTH: 1245
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 125

```
gttaagcttg ccaccatgga aaccccagcg cagcttctct tcctcctgct actctggctc     60

ccagatacca ccggtaagga atcccgggcc aagaaattcc agcggcagca tatggactca    120

gacagttccc ccagcagcag ctccacctac tgtaaccaaa tgatgaggcg ccggaatatg    180

acacaggggc ggtgcaaacc agtgaacacc tttgtgcacg agcccctggt agatgtccag    240

aatgtctgtt tccaggaaaa ggtcacctgc aagaacgggc agggcaactg ctacaagagc    300

aactccagca tgcacatcac agactgccgc ctgacaaacg gctccaggta ccccaactgt    360

gcataccgga ccagcccgaa ggagagacac atcattgtgg cctgtgaagg gagcccatat    420

gtgccagtcc actttgatgc ttctgtggag gactctacag atctctccgg aggaggtggc    480

tcaggtggtg gaggatctgg aggaggtggg agtggtggag gtggttctac cggtctcgag    540

cccaaatctt ctgacaaaac tcacacatgt ccaccgtgcc cagcacctga actcctgggg    600

ggaccgtcag tcttcctctt ccccccaaaa cccaaggaca ccctcatgat ctcccggacc    660

cctgaggtca catgcgtggt ggtggacgtg agccacgaag accctgaggt caagttcaac    720

tggtacgtgg acggcgtgga ggtgcataat gccaagacaa agccgcggga ggagcagtac    780

aacagcacgt accgtgtggt cagcgtcctc accgtcctgc accaggactg gctgaatggc    840

aaggagtaca agtgcaaggt ctccaacaaa gccctcccag cccccatcga gaaaaccatc    900

tccaaagcca aagggcagcc ccgagaacca caggtgtaca ccctgccccc atcccgggat    960

gagctgacca agaaccaggt cagcctgacc tgcctggtca aaggcttcta tcccagcgac   1020

atcgccgtgg agtgggagag caatgggcag ccggagaaca actacaagac cacgcctccc   1080

gtgctggact ccgacggctc cttcttcctc tacagcaagc tcaccgtgga caagagcagg   1140

tggcagcagg ggaacgtctt ctcatgctcc gtgatgcatg aggctctgca caaccactac   1200

acgcagaaga gcctctctct gtctccgggt aaatgataat ctaga                   1245
```

<210> SEQ ID NO 126
<211> LENGTH: 1254
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 126
gttaagcttg ccaccatgga aaccccagcg cagcttctct tcctcctgct actctggctc 60
ccagatacca ccggtaagga atcccgggcc aagaaattcc agcggcagca tatggactca 120
gacagttccc ccagcagcag ctccacctac tgtaaccaaa tgatgaggcg ccggaatatg 180
acacaggggc ggtgcaaacc agtgaacacc tttgtgcacg agcccctggt agatgtccag 240
aatgtctgtt tccaggaaaa ggtcacctgc aagaacgggc agggcaactg ctacaagagc 300
aactccagca tgcacatcac agactgccgc ctgacaaacg gctccaggta ccccaactgt 360
gcataccgga ccagcccgaa ggagagacac atcattgtgg cctgtgaagg gagcccatat 420
gtgccagtcc actttgatgc ttctgtggag gactctacag atctctccgg aggaggtggc 480
tcaggtggtg gaggatctgg aggaggtggc tcaggtggtg gaggatctgg aggaggtggg 540
agtctcgagc ccaaatcttc tgacaaaact cacacatgtc caccgtgccc agcacctgaa 600
ctcctggggg gaccgtcagt cttcctcttc cccccaaaac ccaaggacac cctcatgatc 660
tcccggaccc ctgaggtcac atgcgtggtg gtggacgtga gccacgaaga ccctgaggtc 720
aagttcaact ggtacgtgga cggcgtggag gtgcataatg ccaagacaaa gccgcgggag 780
gagcagtaca acagcacgta ccgtgtggtc agcgtcctca ccgtcctgca ccaggactgg 840
ctgaatggca aggagtacaa gtgcaaggtc tccaacaaag ccctcccagc ccccatcgag 900
aaaaccatct ccaaagccaa agggcagccc cgagaaccac aggtgtacac cctgccccca 960
tcccgggatg agctgaccaa gaaccaggtc agcctgacct gcctggtcaa aggcttctat 1020
cccagcgaca tcgccgtgga gtgggagagc aatgggcagc cggagaacaa ctacaagacc 1080
acgcctcccg tgctggactc cgacggctcc ttcttcctct acagcaagct caccgtggac 1140
aagagcaggt ggcagcaggg gaacgtcttc tcatgctccg tgatgcatga ggctctgcac 1200
aaccactaca cgcagaagag cctctctctg tctccgggta aatgataatc taga 1254

<210> SEQ ID NO 127
<211> LENGTH: 1173
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 127
gttaagcttg ccaccatgga aaccccagcg cagcttctct tcctcctgct actctggctc 60
ccagatacca ccggtaagga atcccgggcc aagaaattcc agcggcagca tatggactca 120
gacagttccc ccagcagcag ctccacctac tgtaaccaaa tgatgaggcg ccggaatatg 180
acacaggggc ggtgcaaacc agtgaacacc tttgtgcacg agcccctggt agatgtccag 240
aatgtctgtt tccaggaaaa ggtcacctgc aagaacgggc agggcaactg ctacaagagc 300
aactccagca tgcacatcac agactgccgc ctgacaaacg gctccaggta ccccaactgt 360
gcataccgga ccagcccgaa ggagagacac atcattgtgg cctgtgaagg gagcccatat 420
gtgccagtcc actttgatgc ttctgtggag gactctacag atctcgagcc caaatcttct 480
gacaaaactc acacatgtcc accgtgccca gcacctgaac tcctgggggg accgtcagtc 540
ttcctcttcc ccccaaaacc caaggacacc ctcatgatct cccggacccc tgaggtcaca 600

```
tgcgtggtgg tggacgtgag ccacgaagac cctgaggtca agttcaactg gtacgtggac    660

ggcgtggagg tgcataatgc caagacaaag ccgcgggagg agcagtacaa cagcacgtac    720

cgtgtggtca gcgtcctcac cgtcctgcac caggactggc tgaatggcaa ggagtacaag    780

tgcaaggtct ccaacaaagc cctcccagcc cccatcgaga aaaccatctc caaagccaaa    840

gggcagcccc gagaaccaca ggtgtacacc ctgcccccat cccgggatga gctgaccaag    900

aaccaggtca gcctgacctg cctggtcaaa ggcttctatc ccagcgacat cgccgtggag    960

tgggagagca atgggcagcc ggagaacaac tacaagacca cgcctcccgt gctggactcc   1020

gacggctcct tcttcctcta cagcaagctc accgtggaca agagcaggtg gcagcagggg   1080

aacgtcttct catgctccgt gatgcatgag gctctgcaca accactacac gcagaagagc   1140

ctctctctgt ctccgggtaa atgataatct aga                                1173
```

<210> SEQ ID NO 128
<211> LENGTH: 945
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 128

```
atgggctcac agaccctgcc ccatggtcac atgcagaccc tcatcttctt agacctggaa     60

gccactggcc tgccttcgtc tcggcccgaa gtcacagagc tgtgcctgct ggctgtccac    120

agacgtgctc tggagaacac ttccatttct cagggacatc cacctccagt gcccagaccg    180

ccccgtgtgg tggacaagct ctctctgtgc attgctccag ggaaagcctg tagccctggg    240

gccagtgaga tcacaggtct gagcaaagct gagctggaag tacaggggcg tcaacgcttc    300

gatgacaacc tggccatcct gctccgagcc ttcctgcagc gccagccaca gccttgctgc    360

cttgtggcac acaacggtga ccgctatgac tttcctctgc tccagacaga gcttgctagg    420

ctgagcactc ccagtcccct agatggtacc ttctgtgtgg acagcatcgc tgccctaaag    480

gccttggaac aagctagcag cccctcaggg aatggttcga ggaaaagcta cagcctgggc    540

agcatctaca cccgcctgta ctggcaagca ccgacagact cacatactgc tgaaggtgat    600

gttctaaccc tgctcagcat ctgtcagtgg aagccacagg ccctactgca gtgggtggac    660

gaacatgccc ggccctttag caccgtcaag cccatgtacg gcactccggc taccactgga    720

acaaccaacc taaggccaca tgctgccaca gctactacac ccctggccac agccaatgga    780

agtcccagca atggcaggag caggcgacct aagagtcctc ctccagagaa ggtcccagaa    840

gccccatcac aggaggggct gctggcccca ctgagcctgc tgaccctcct gaccttggca    900

atagccactc tgtatggact cttcctggcc tcacctgggc agtaa                    945
```

<210> SEQ ID NO 129
<211> LENGTH: 735
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 129

```
atgggctcac agaccctgcc ccatggtcac atgcagaccc tcatcttctt agacctggaa     60

gccactggcc tgccttcgtc tcggcccgaa gtcacagagc tgtgcctgct ggctgtccac    120
```

-continued agacgtgctc tggagaacac ttccatttct cagggacatc cacctccagt gcccagaccg 180
ccccgtgtgg tggacaagct ctctctgtgc attgctccag ggaaagcctg tagccctggg 240
gccagtgaga tcacaggtct gagcaaagct gagctggaag tacaggggcg tcaacgcttc 300
gatgacaacc tggccatcct gctccgagcc ttcctgcagc gccagccaca gccttgctgc 360
cttgtggcac acaacggtga ccgctatgac tttcctctgc tccagacaga gcttgctagg 420
ctgagcactc ccagtcccct agatggtacc ttctgtgtgg acagcatcgc tgccctaaag 480
gccttggaac aagctagcag cccctcaggg aatggttcga ggaaaagcta cagcctgggc 540
agcatctaca cccgcctgta ctggcaagca ccgacagact cacatactgc tgaaggtgat 600
gttctaaccc tgctcagcat ctgtcagtgg aagccacagg ccctactgca gtgggtggac 660
gaacatgccc ggccctttag caccgtcaag cccatgtacg gcactccggc taccactgga 720
acaacagatc tcgag 735

<210> SEQ ID NO 130
<211> LENGTH: 1593
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 130
aagcttgcca ccatggaaac cccagcgcag cttctcttcc tcctgctact ctggctccca 60
gataccaccg gtatgggctc acagaccctg ccccatggtc acatgcagac cctcatcttc 120
ttagacctgg aagccactgg cctgccttcg tctcggcccg aagtcacaga gctgtgcctg 180
ctggctgtcc acagacgtgc tctggagaac acttccattt ctcagggaca tccacctcca 240
gtgcccagac cgccccgtgt ggtggacaag ctctctctgt gcattgctcc agggaaagcc 300
tgtagccctg gggccagtga gatcacaggt ctgagcaaag ctgagctgga agtacagggg 360
cgtcaacgct tcgatgacaa cctggccatc ctgctccgag ccttcctgca gcgccagcca 420
cagccttgct gccttgtggc acacaacggt gaccgctatg actttcctct gctccagaca 480
gagcttgcta ggctgagcac tcccagtccc ctagatggta ccttctgtgt ggacagcatc 540
gctgccctaa aggccttgga acaagctagc agcccctcag ggaatggttc gaggaaaagc 600
tacagcctgg gcagcatcta cacccgcctg tactggcaag caccgacaga ctcacatact 660
gctgaaggtg atgttctaac cctgctcagc atctgtcagt ggaagccaca ggccctactg 720
cagtgggtgg acgaacatgc ccggcccttt agcaccgtca agcccatgta cggcactccg 780
gctaccactg gaacaacaga tctctccgga ggaggtggct caggtggtgg aggatctgga 840
ggaggtggct cagggagtgg tggaggtggt tctaccggtc tcgagcccag aggtcccaca 900
atcaagccct ctcctccatg caaatgccca gcacctaacc tcttgggtgg atcatccgtc 960
ttcatcttcc ctccaaagat caaggatgta ctcatgatct ccctgagccc catggtcaca 1020
tgtgtggtgg tggatgtgag cgaggatgac ccagacgtcc agatcagctg gtttgtgaac 1080
aacgtggaag tacacacagc tcagacacaa acccatagag aggattacaa cagtactctc 1140
cgggtggtca gtgccctccc catccagcac caggactgga tgagtggcaa ggagttcaaa 1200
tgctcggtca acaacaaaga cctcccagcg tccatcgaga gaaccatctc aaaacccaga 1260
gggccagtaa gagctccaca ggtatatgtc ttgcctccac cagcagaaga gatgactaag 1320
aaagagttca gtctgacctg catgatcaca ggcttcttac ctgccgaaat tgctgtggac 1380

```
tggaccagca atgggcgtac agagcaaaac tacaagaaca ccgcaacagt cctggactct   1440

gatggttctt acttcatgta cagcaagctc agagtacaaa agagcacttg ggaaagagga   1500

agtcttttcg cctgctcagt ggtccacgag ggtctgcaca atcaccttac gactaagagc   1560

ttctctcgga ctccgggtaa atgataatct aga                                1593
```

<210> SEQ ID NO 131
<211> LENGTH: 1596
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 131

```
aagcttgcca ccatggaaac cccagcgcag cttctcttcc tcctgctact ctggctccca     60

gataccaccg gtatgggctc acagaccctg ccccatggtc acatgcagac cctcatcttc    120

ttagacctgg aagccactgg cctgccttcg tctcggcccg aagtcacaga gctgtgcctg    180

ctggctgtcc acagacgtgc tctggagaac acttccattt ctcagggaca tccacctcca    240

gtgcccagac cgccccgtgt ggtggacaag ctctctctgt gcattgctcc agggaaagcc    300

tgtagccctg gggccagtga gatcacaggt ctgagcaaag ctgagctgga agtacagggg    360

cgtcaacgct tcgatgacaa cctggccatc ctgctccgag ccttcctgca gcgccagcca    420

cagccttgct gccttgtggc acacaacggt gaccgctatg actttcctct gctccagaca    480

gagcttgcta ggctgagcac tcccagtccc ctagatggta ccttctgtgt ggacagcatc    540

gctgccctaa aggccttgga acaagctagc agcccctcag ggaatggttc gaggaaaagc    600

tacagcctgg gcagcatcta cacccgcctg tactggcaag caccgacaga ctcacatact    660

gctgaaggtg atgttctaac cctgctcagc atctgtcagt ggaagccaca ggccctactg    720

cagtgggtgg acgaacatgc ccggcccttt agcaccgtca agcccatgta cggcactccg    780

gctaccactg gaacaacaga tctctccgga ggaggtggct caggtggtgg aggatctgga    840

ggaggtggct caggtggtgg aggatctgga ggaggtggga gtctcgagcc cagaggtccc    900

acaatcaagc cctctcctcc atgcaaatgc ccagcaccta acctcttggg tggatcatcc    960

gtcttcatct tccctccaaa gatcaaggat gtactcatga tctccctgag ccccatggtc   1020

acatgtgtgg tggtggatgt gagcgaggat gacccagacg tccagatcag ctggtttgtg   1080

aacaacgtgg aagtacacac agctcagaca caaacccata gagaggatta caacagtact   1140

ctccgggtgg tcagtgccct ccccatccag caccaggact ggatgagtgg caaggagttc   1200

aaatgctcgg tcaacaacaa agacctccca gcgtccatcg agagaaccat ctcaaaaccc   1260

agagggccag taagagctcc acaggtatat gtcttgcctc caccagcaga agagatgact   1320

aagaaagagt tcagtctgac ctgcatgatc acaggcttct tacctgccga aattgctgtg   1380

gactggacca gcaatgggcg tacagagcaa aactacaaga acaccgcaac agtcctggac   1440

tctgatggtt cttacttcat gtacagcaag ctcagagtac aaaagagcac ttgggaaaga   1500

ggaagtcttt tcgcctgctc agtggtccac gagggtctgc acaatcacct tacgactaag   1560

agcttctctc ggactccggg taaatgataa tctaga                             1596
```

<210> SEQ ID NO 132
<211> LENGTH: 57
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 132
gtcgacggcg cggccgccag ccccgtgaac gtgagcagcc ccagcgtgca ggatatc        57

<210> SEQ ID NO 133
<211> LENGTH: 2328
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 133
aagcttgcca ccatggaaac cccagcgcag cttctcttcc tcctgctact ctggctccca     60
gataccaccg gtatgggctc acagaccctg ccccatggtc acatgcagac cctcatcttc    120
ttagacctgg aagccactgg cctgccttcg tctcggcccg aagtcacaga gctgtgcctg    180
ctggctgtcc acagacgtgc tctggagaac acttccattt ctcagggaca tccacctcca    240
gtgcccagac cgccccgtgt ggtggacaag ctctctctgt gcattgctcc agggaaagcc    300
tgtagccctg ggccagtgta gatcacaggt ctgagcaaag ctgagctgga agtacagggg    360
cgtcaacgct tcgatgacaa cctggccatc ctgctccgag ccttcctgca gcgccagcca    420
cagccttgct gccttgtggc acacaacggt gaccgctatg actttcctct gctccagaca    480
gagcttgcta ggctgagcac tcccagtccc ctagatggta ccttctgtgt ggacagcatc    540
gctgccctaa aggccttgga acaagctagc agcccctcag ggaatggttc gaggaaaagc    600
tacagcctgg gcagcatcta cacccgcctg tactggcaag caccgacaga ctcacatact    660
gctgaaggtg atgttctaac cctgctcagc atctgtcagt ggaagccaca ggccctactg    720
cagtgggtgg acgaacatgc ccggcccttt agcaccgtca agcccatgta cggcactccg    780
gctaccactg gaacaacaga tctcatgggc tcacagaccc tgccccatgg tcacatgcag    840
accctcatct tcttagacct ggaagccact ggcctgcctt cgtctcggcc cgaagtcaca    900
gagctgtgcc tgctggctgt ccacagacgt gctctggaga acacttccat ttctcaggga    960
catccacctc cagtgcccag accgccccgt gtggtggaca agctctctct gtgcattgct   1020
ccagggaaag cctgtagccc tggggccagt gagatcacag gtctgagcaa agctgagctg   1080
gaagtacagg ggcgtcaacg cttcgatgac aacctggcca tcctgctccg agccttcctg   1140
cagcgccagc cacagccttg ctgccttgtg gcacacaacg gtgaccgcta tgactttcct   1200
ctgctccaga cagagcttgc taggctgagc actcccagtc ccctagatgg taccttctgt   1260
gtggacagca tcgctgccct aaaggccttg gaacaagcta gcagcccctc agggaatggt   1320
tcgaggaaaa gctacagcct gggcagcatc tacacccgcc tgtactggca agcaccgaca   1380
gactcacata ctgctgaagg tgatgttcta accctgctca gcatctgtca gtggaagcca   1440
caggccctac tgcagtgggt ggacgaacat gcccggccct ttagcaccgt caagcccatg   1500
tacggcactc cggctaccac tggaacaaca gatctctccg gaggaggtgg ctcaggtggt   1560
ggaggatctg gaggaggtgg ctcaggtggt ggaggatctg gaggaggtgg gagtctcgag   1620
cccagaggtc ccacaatcaa gccctctcct ccatgcaaat gcccagcacc taacctcttg   1680
ggtggatcat ccgtcttcat cttccctcca aagatcaagg atgtactcat gatctccctg   1740
agccccatgg tcacatgtgt ggtggtggat gtgagcgagg atgacccaga cgtccagatc   1800
agctggtttg tgaacaacgt ggaagtacac acagctcaga cacaaaccca tagagaggat   1860

```
tacaacagta ctctccgggt ggtcagtgcc ctccccatcc agcaccagga ctggatgagt   1920

ggcaaggagt tcaaatgctc ggtcaacaac aaagacctcc cagcgtccat cgagagaacc   1980

atctcaaaac ccagagggcc agtaagagct ccacaggtat atgtcttgcc tccaccagca   2040

gaagagatga ctaagaaaga gttcagtctg acctgcatga tcacaggctt cttacctgcc   2100

gaaattgctg tggactggac cagcaatggg cgtacagagc aaaactacaa gaacaccgca   2160

acagtcctgg actctgatgg ttcttacttc atgtacagca agctcagagt acaaaagagc   2220

acttgggaaa gaggaagtct tttcgcctgc tcagtggtcc acgagggtct gcacaatcac   2280

cttacgacta agagcttctc tcggactccg ggtaaatgat aatctaga                2328
```

<210> SEQ ID NO 134
<211> LENGTH: 1749
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 134

```
aagcttgcca ccatggaaac cccagcgcag cttctcttcc tcctgctact ctggctccca     60

gataccaccg gtatgggccc tggagctcgc agacagggca ggattgtgca gggaaggcct    120

gagatgtgct tctgcccacc ccctacccca ctccctcccc ttcggatctt aacactgggc    180

actcacacac ccaccccatg ctcctctcca ggctcagcag caggtacgta cccaaccatg    240

ggctcgcagg ccctgccccc ggggcccatg cagaccctca tctttttcga catggaggcc    300

actggcttgc ccttctccca gcccaaggtc acggagctgt gcctgctggc tgtccacaga    360

tgtgccctgg agagcccccc cacctctcag ggccacctc ccacagttcc tccaccaccg    420

cgtgtggtag acaagctctc cctgtgtgtg gctccgggga aggcctgcag ccctgcagcc    480

agcgagatca caggtctgag cacagctgtg ctggcagcgc atgggcgtca atgttttgat    540

gacaacctgg ccaacctgct cctagccttc ctgcggcgcc agccacagcc ctggtgcctg    600

gtggcacaca atggtgaccg ctacgacttc cccctgctcc aagcagagct ggctatgctg    660

ggcctcacca gtgctctgga tggtgccttc tgtgtggata gcatcactgc gctgaaggcc    720

ctggagcgag caagcagccc ctcagaacac ggcccaagga agagctacag cctaggcagc    780

atctacactc gcctgtatgg gcagtcccct ccagactcgc acacggctga gggtgatgtc    840

ctggccctgc tcagcatctg tcagtggaga ccacaggccc tgctgcggtg ggtggatgct    900

cacgccaggc ctttcggcac catcaggccc atgtatgggg tcacagcctc tgctaggacc    960

aaagatctct ccggaggagg tggctcaggt ggtggaggat ctggaggagg tgggagtggt   1020

ggaggtggtt ctaccggtct cgagcccaaa tcttctgaca aaactcacac atgtccaccg   1080

tgcccagcac ctgaactcct ggggggaccg tcagtcttcc tcttcccccc aaaacccaag   1140

gacaccctca tgatctcccg gacccctgag gtcacatgcg tggtggtgga cgtgagccac   1200

gaagaccctg aggtcaagtt caactggtac gtggacggcg tggaggtgca taatgccaag   1260

acaaagccgc gggaggagca gtacaacagc acgtaccgtg tggtcagcgt cctcaccgtc   1320

ctgcaccagg actggctgaa tggcaaggag tacaagtgca aggtctccaa caaagccctc   1380

ccagccccca tcgagaaaac catctccaaa gccaaagggc agccccgaga accacaggtg   1440

tacaccctgc ccccatcccg ggatgagctg accaagaacc aggtcagcct gacctgcctg   1500

gtcaaaggct tctatcccag cgacatcgcc gtggagtggg agagcaatgg gcagccggag   1560
```

aacaactaca agaccacgcc tcccgtgctg gactccgacg gctccttctt cctctacagc 1620
aagctcaccg tggacaagag caggtggcag caggggaacg tcttctcatg ctccgtgatg 1680
catgaggctc tgcacaacca ctacacgcag aagagcctct ctctgtctcc gggtaaatga 1740
taatctaga 1749

<210> SEQ ID NO 135
<211> LENGTH: 1758
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 135
aagcttgcca ccatggaaac cccagcgcag cttctcttcc tcctgctact ctggctccca 60
gataccaccg gtatgggccc tggagctcgc agacagggca ggattgtgca gggaaggcct 120
gagatgtgct tctgcccacc ccctacccca ctccctcccc ttcggatctt aacactgggc 180
actcacacac ccaccccatg ctcctctcca ggctcagcag caggtacgta cccaaccatg 240
ggctcgcagg ccctgccccc ggggcccatg cagaccctca tctttttcga catggaggcc 300
actggcttgc ccttctccca gcccaaggtc acggagctgt gcctgctggc tgtccacaga 360
tgtgccctgg agagcccccc cacctctcag ggccacctcc ccacagttcc tccaccaccg 420
cgtgtggtag acaagctctc cctgtgtgtg gctccgggga aggcctgcag ccctgcagcc 480
agcgagatca caggtctgag cacagctgtg ctggcagcgc atgggcgtca atgttttgat 540
gacaacctgg ccaacctgct cctagccttc ctgcggcgcc agccacagcc ctggtgcctg 600
gtggcacaca atggtgaccg ctacgacttc cccctgctcc aagcagagct ggctatgctg 660
ggcctcacca gtgctctgga tggtgccttc tgtgtggata gcatcactgc gctgaaggcc 720
ctggagcgag caagcagccc ctcagaacac ggcccaagga agagctacag cctaggcagc 780
atctacactc gcctgtatgg gcagtcccct ccagactcgc acacggctga gggtgatgtc 840
ctggccctgc tcagcatctg tcagtggaga ccacaggccc tgctgcggtg ggtggatgct 900
cacgccaggc ctttcggcac catcaggccc atgtatgggg tcacagcctc tgctaggacc 960
aaagatctct ccggaggagg tggctcaggt ggtggaggat ctggaggagg tggctcaggt 1020
ggtggaggat ctggaggagg tgggagtctc gagcccaaat cttctgacaa aactcacaca 1080
tgtccaccgt gcccagcacc tgaactcctg gggggaccgt cagtcttcct cttcccccca 1140
aaacccaagg acaccctcat gatctcccgg acccctgagg tcacatgcgt ggtggtggac 1200
gtgagccacg aagaccctga ggtcaagttc aactggtacg tggacggcgt ggaggtgcat 1260
aatgccaaga caaagccgcg ggaggagcag tacaacagca cgtaccgtgt ggtcagcgtc 1320
ctcaccgtcc tgcaccagga ctggctgaat ggcaaggagt acaagtgcaa ggtctccaac 1380
aaagccctcc cagcccccat cgagaaaacc atctccaaag ccaaagggca gccccgagaa 1440
ccacaggtgt acaccctgcc cccatcccgg gatgagctga ccaagaacca ggtcagcctg 1500
acctgcctgg tcaaaggctt ctatcccagc gacatcgccg tggagtggga gagcaatggg 1560
cagccggaga acaactacaa gaccacgcct cccgtgctgg actccgacgg ctccttcttc 1620
ctctacagca agctcaccgt ggacaagagc aggtggcagc aggggaacgt cttctcatgc 1680
tccgtgatgc atgaggctct gcacaaccac tacacgcaga agagcctctc tctgtctccg 1740
ggtaaatgat aatctaga 1758

```
<210> SEQ ID NO 136
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gly Gly Gly Gly Ser Gly Gly Gly Gly Ser Gly Gly Gly Gly Ser Gly
1               5                   10                  15

Gly Gly Gly Ser
            20


<210> SEQ ID NO 137
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25


<210> SEQ ID NO 138
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25


<210> SEQ ID NO 139
<211> LENGTH: 260
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Leu Lys Ile Ala Ala Phe Asn Ile Gln Thr Phe Gly Glu Thr Lys Met
1               5                   10                  15

Ser Asn Ala Thr Leu Val Ser Tyr Ile Val Gln Ile Leu Ser Arg Tyr
            20                  25                  30

Asp Ile Ala Leu Val Gln Glu Val Arg Asp Ser His Leu Thr Ala Val
        35                  40                  45

Gly Lys Leu Leu Asp Asn Leu Asn Gln Asp Ala Pro Asp Thr Tyr His
    50                  55                  60

Tyr Val Val Ser Glu Pro Leu Gly Arg Asn Ser Tyr Lys Glu Arg Tyr
65                  70                  75                  80

Leu Phe Val Tyr Arg Pro Asp Gln Val Ser Ala Val Asp Ser Tyr Tyr
```

```
                85                  90                  95

Tyr Asp Asp Gly Cys Glu Pro Cys Arg Asn Asp Thr Phe Asn Arg Glu
            100                 105                 110

Pro Phe Ile Val Arg Phe Phe Ser Arg Phe Thr Glu Val Arg Glu Phe
        115                 120                 125

Ala Ile Val Pro Leu His Ala Ala Pro Gly Asp Ala Val Ala Glu Ile
    130                 135                 140

Asp Ala Leu Tyr Asp Val Tyr Leu Asp Val Gln Glu Lys Trp Gly Leu
145                 150                 155                 160

Glu Asp Val Met Leu Met Gly Asp Phe Asn Ala Gly Cys Ser Tyr Val
                165                 170                 175

Arg Pro Ser Gln Trp Ser Ser Ile Arg Leu Trp Thr Ser Pro Thr Phe
            180                 185                 190

Gln Trp Leu Ile Pro Asp Ser Ala Asp Thr Thr Ala Thr Pro Thr His
        195                 200                 205

Cys Ala Tyr Asp Arg Ile Val Val Ala Gly Met Leu Leu Arg Gly Ala
    210                 215                 220

Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu
                245                 250                 255

Val Met Leu Lys
            260


<210> SEQ ID NO 140
<211> LENGTH: 260
<212> TYPE: PRT
<213> ORGANISM: Homo sapiens

<400> SEQUENCE: 140

Leu Lys Ile Ala Ala Phe Asn Ile Gln Thr Phe Gly Glu Thr Lys Met
1               5                   10                  15

Ser Asn Ala Thr Leu Val Ser Tyr Ile Val Gln Ile Leu Ser Arg Tyr
            20                  25                  30

Asp Ile Ala Leu Val Gln Glu Val Arg Asp Ser His Leu Thr Ala Val
        35                  40                  45

Gly Lys Leu Leu Asp Asn Leu Asn Gln Asp Ala Pro Asp Thr Tyr His
    50                  55                  60

Tyr Val Val Ser Glu Pro Leu Gly Arg Asn Ser Tyr Lys Glu Arg Tyr
65                  70                  75                  80

Leu Phe Val Tyr Arg Pro Asp Gln Val Ser Ala Val Asp Ser Tyr Tyr
                85                  90                  95

Tyr Asp Asp Gly Cys Glu Pro Cys Gly Asn Asp Thr Phe Asn Arg Glu
            100                 105                 110

Pro Ala Ile Val Arg Phe Phe Ser Arg Phe Thr Glu Val Arg Glu Phe
        115                 120                 125

Ala Ile Val Pro Leu His Ala Ala Pro Gly Asp Ala Val Ala Glu Ile
    130                 135                 140

Asp Ala Leu Tyr Asp Val Tyr Leu Asp Val Gln Glu Lys Trp Gly Leu
145                 150                 155                 160

Glu Asp Val Met Leu Met Gly Asp Phe Asn Ala Gly Cys Ser Tyr Val
                165                 170                 175

Arg Pro Ser Gln Trp Ser Ser Ile Arg Leu Trp Thr Ser Pro Thr Phe
            180                 185                 190
```

```
Gln Trp Leu Ile Pro Asp Ser Ala Asp Thr Thr Ala Thr Pro Thr His
        195                 200                 205

Cys Ala Tyr Asp Arg Ile Val Val Ala Gly Met Leu Leu Arg Gly Ala
    210                 215                 220

Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu
                245                 250                 255

Val Met Leu Lys
            260


<210> SEQ ID NO 141
<211> LENGTH: 260
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Leu Lys Ile Ala Ala Phe Asn Ile Gln Thr Phe Gly Glu Thr Lys Met
1               5                   10                  15

Ser Asn Ala Thr Leu Val Ser Tyr Ile Val Gln Ile Leu Ser Arg Tyr
            20                  25                  30

Asp Ile Ala Leu Val Gln Glu Val Arg Asp Ser His Leu Thr Ala Val
        35                  40                  45

Gly Lys Leu Leu Asp Asn Leu Asn Gln Asp Ala Pro Asp Thr Tyr His
    50                  55                  60

Tyr Val Val Ser Glu Pro Leu Gly Arg Asn Ser Tyr Lys Glu Arg Tyr
65                  70                  75                  80

Leu Phe Val Tyr Arg Pro Asp Gln Val Ser Ala Val Asp Ser Tyr Tyr
                85                  90                  95

Tyr Asp Asp Gly Cys Glu Pro Cys Gly Asn Asp Thr Phe Asn Arg Glu
            100                 105                 110

Pro Phe Ile Val Arg Phe Phe Ser Arg Phe Thr Glu Val Arg Glu Phe
        115                 120                 125

Ala Ile Val Pro Leu His Ala Ala Pro Gly Asp Ala Val Ala Glu Ile
    130                 135                 140

Asp Ala Leu Tyr Asp Val Tyr Leu Asp Val Gln Glu Lys Trp Gly Leu
145                 150                 155                 160

Glu Asp Val Met Leu Met Gly Asp Phe Asn Ala Gly Cys Ser Tyr Val
                165                 170                 175

Arg Pro Ser Gln Trp Ser Ser Ile Arg Leu Trp Thr Ser Pro Thr Phe
            180                 185                 190

Gln Trp Leu Ile Pro Asp Ser Ala Asp Thr Thr Ala Thr Pro Thr His
        195                 200                 205

Cys Ala Tyr Asp Arg Ile Val Val Ala Gly Met Leu Leu Arg Gly Ala
    210                 215                 220

Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu
                245                 250                 255

Val Met Leu Lys
            260


<210> SEQ ID NO 142
```

<211> LENGTH: 260
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 142

Leu Lys Ile Ala Ala Phe Asn Ile Gln Thr Phe Gly Glu Thr Lys Met
1 5 10 15

Ser Asn Ala Thr Leu Val Ser Tyr Ile Val Gln Ile Leu Ser Arg Tyr
20 25 30

Asp Ile Ala Leu Val Gln Glu Val Arg Asp Ser His Leu Thr Ala Val
35 40 45

Gly Lys Leu Leu Asp Asn Leu Asn Gln Asp Ala Pro Asp Thr Tyr His
50 55 60

Tyr Val Val Ser Glu Pro Leu Gly Arg Asn Ser Tyr Lys Glu Arg Tyr
65 70 75 80

Leu Phe Val Tyr Arg Pro Asp Gln Val Ser Ala Val Asp Ser Tyr Tyr
85 90 95

Tyr Asp Asp Gly Cys Glu Pro Cys Arg Asn Asp Thr Phe Asn Arg Glu
100 105 110

Pro Ala Ile Val Arg Phe Phe Ser Arg Phe Thr Glu Val Arg Glu Phe
115 120 125

Ala Ile Val Pro Leu His Ala Ala Pro Gly Asp Ala Val Ala Glu Ile
130 135 140

Asp Ala Leu Tyr Asp Val Tyr Leu Asp Val Gln Glu Lys Trp Gly Leu
145 150 155 160

Glu Asp Val Met Leu Met Gly Asp Phe Asn Ala Gly Cys Ser Tyr Val
165 170 175

Arg Pro Ser Gln Trp Ser Ser Ile Arg Leu Trp Thr Ser Pro Thr Phe
180 185 190

Gln Trp Leu Ile Pro Asp Ser Ala Asp Thr Thr Ala Thr Pro Thr His
195 200 205

Cys Ala Tyr Asp Arg Ile Val Val Ala Gly Met Leu Leu Arg Gly Ala
210 215 220

Val Val Pro Asp Ser Ala Leu Pro Phe Asn Phe Gln Ala Ala Tyr Gly
225 230 235 240

Leu Ser Asp Gln Leu Ala Gln Ala Ile Ser Asp His Tyr Pro Val Glu
245 250 255

Val Met Leu Lys
260

<210> SEQ ID NO 143
<211> LENGTH: 260
<212> TYPE: PRT
<213> ORGANISM: Homo sapiens

<400> SEQUENCE: 143

Leu Lys Ile Ala Ala Phe Asn Ile Gln Thr Phe Gly Glu Thr Lys Met
1 5 10 15

Ser Asn Ala Thr Leu Val Ser Tyr Ile Val Gln Ile Leu Ser Arg Tyr
20 25 30

Asp Ile Ala Leu Val Gln Glu Val Arg Asp Ser His Leu Thr Ala Val
35 40 45

Gly Lys Leu Leu Asp Asn Leu Asn Gln Asp Ala Pro Asp Thr Tyr His
50 55 60

Tyr Val Val Ser Glu Pro Leu Gly Arg Asn Ser Tyr Lys Glu Arg Tyr
65 70 75 80

Leu Phe Val Tyr Arg Pro Asp Gln Val Ser Ala Val Asp Ser Tyr Tyr
85 90 95

Tyr Asp Asp Gly Cys Glu Pro Cys Gly Asn Asp Thr Phe Asn Arg Glu
100 105 110

Pro Ala Ile Val Arg Phe Phe Ser Arg Phe Thr Glu Val Arg Glu Phe
115 120 125

Ala Ile Val Pro Leu His Ala Ala Pro Gly Asp Ala Val Ala Glu Ile
130 135 140

Asp Ala Leu Tyr Asp Val Tyr Leu Asp Val Gln Glu Lys Trp Gly Leu
145 150 155 160

Glu Asp Val Met Leu Met Gly Asp Phe Asn Ala Gly Cys Ser Tyr Val
165 170 175

Arg Pro Ser Gln Trp Ser Ser Ile Arg Leu Trp Thr Ser Pro Thr Phe
180 185 190

Gln Trp Leu Ile Pro Asp Ser Ala Asp Thr Thr Ala Thr Pro Thr His
195 200 205

Cys Ala Tyr Asp Arg Ile Val Val Ala Gly Met Leu Leu Arg Gly Ala
210 215 220

Val Val Pro Asp Ser Ala Leu Pro Phe Asn Phe Gln Ala Ala Tyr Gly
225 230 235 240

Leu Ser Asp Gln Leu Ala Gln Ala Ile Ser Asp His Tyr Pro Val Glu
245 250 255

Val Met Leu Lys
260

<210> SEQ ID NO 144
<211> LENGTH: 260
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 144

Leu Lys Ile Ala Ala Phe Asn Ile Gln Thr Phe Gly Glu Thr Lys Met
1 5 10 15

Ser Asn Ala Thr Leu Val Ser Tyr Ile Val Gln Ile Leu Ser Arg Tyr
20 25 30

Asp Ile Ala Leu Val Gln Glu Val Arg Asp Ser His Leu Thr Ala Val
35 40 45

Gly Lys Leu Leu Asp Asn Leu Asn Gln Asp Ala Pro Asp Thr Tyr His
50 55 60

Tyr Val Val Ser Glu Pro Leu Gly Arg Asn Ser Tyr Lys Glu Arg Tyr
65 70 75 80

Leu Phe Val Tyr Arg Pro Asp Gln Val Ser Ala Val Asp Ser Tyr Tyr
85 90 95

Tyr Asp Asp Gly Cys Glu Pro Cys Gly Asn Asp Thr Phe Asn Arg Glu
100 105 110

Pro Phe Ile Val Arg Phe Phe Ser Arg Phe Thr Glu Val Arg Glu Phe
115 120 125

Ala Ile Val Pro Leu His Ala Ala Pro Gly Asp Ala Val Ala Glu Ile
130 135 140

Asp Ala Leu Tyr Asp Val Tyr Leu Asp Val Gln Glu Lys Trp Gly Leu

```
145                 150                 155                 160

Glu Asp Val Met Leu Met Gly Asp Phe Asn Ala Gly Cys Ser Tyr Val
                165                 170                 175

Arg Pro Ser Gln Trp Ser Ser Ile Arg Leu Trp Thr Ser Pro Thr Phe
            180                 185                 190

Gln Trp Leu Ile Pro Asp Ser Ala Asp Thr Thr Ala Thr Pro Thr His
        195                 200                 205

Cys Ala Tyr Asp Arg Ile Val Val Ala Gly Met Leu Leu Arg Gly Ala
    210                 215                 220

Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu
                245                 250                 255

Val Met Leu Lys
            260
```

<210> SEQ ID NO 145
<211> LENGTH: 233
<212> TYPE: PRT
<213> ORGANISM: Homo sapiens

<400> SEQUENCE: 145

```
Leu Glu Pro Lys Ser Ser Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230
```

<210> SEQ ID NO 146
<211> LENGTH: 128

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 146

```
Lys Glu Ser Arg Ala Lys Lys Phe Gln Arg Gln His Met Asp Ser Asp
1               5                   10                  15

Ser Ser Pro Ser Ser Ser Ser Thr Tyr Cys Asn Gln Met Met Arg Arg
            20                  25                  30

Arg Asn Met Thr Gln Gly Arg Cys Lys Pro Val Asn Thr Phe Val His
        35                  40                  45

Glu Pro Leu Val Asp Val Gln Asn Val Cys Phe Gln Glu Lys Val Thr
    50                  55                  60

Cys Lys Asn Gly Gln Gly Asn Cys Tyr Lys Ser Asn Ser Ser Met His
65                  70                  75                  80

Ile Thr Asp Cys Arg Leu Thr Asn Asp Ser Arg Tyr Pro Asn Cys Ala
                85                  90                  95

Tyr Arg Thr Ser Pro Lys Glu Arg His Ile Ile Val Ala Cys Glu Gly
            100                 105                 110

Ser Pro Tyr Val Pro Val His Phe Asp Ala Ser Val Glu Asp Ser Thr
        115                 120                 125
```

<210> SEQ ID NO 147
<211> LENGTH: 280
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 147

```
Met Glu Thr Pro Ala Gln Leu Leu Phe Leu Leu Leu Leu Trp Leu Pro
1               5                   10                  15

Asp Thr Thr Gly Leu Lys Ile Ala Ala Phe Asn Ile Gln Thr Phe Gly
            20                  25                  30

Glu Thr Lys Met Ser Asn Ala Thr Leu Val Ser Tyr Ile Val Gln Ile
        35                  40                  45

Leu Ser Arg Tyr Asp Ile Ala Leu Val Gln Glu Val Arg Asp Ser His
    50                  55                  60

Leu Thr Ala Val Gly Lys Leu Leu Asp Asn Leu Asn Gln Asp Ala Pro
65                  70                  75                  80

Asp Thr Tyr His Tyr Val Val Ser Glu Pro Leu Gly Arg Asn Ser Tyr
                85                  90                  95

Lys Glu Arg Tyr Leu Phe Val Tyr Arg Pro Asp Gln Val Ser Ala Val
            100                 105                 110

Asp Ser Tyr Tyr Tyr Asp Asp Gly Cys Glu Pro Cys Gly Asn Asp Thr
        115                 120                 125

Phe Asn Arg Glu Pro Ala Ile Val Arg Phe Phe Ser Arg Phe Thr Glu
    130                 135                 140

Val Arg Glu Phe Ala Ile Val Pro Leu His Ala Ala Pro Gly Asp Ala
145                 150                 155                 160

Val Ala Glu Ile Asp Ala Leu Tyr Asp Val Tyr Leu Asp Val Gln Glu
                165                 170                 175

Lys Trp Gly Leu Glu Asp Val Met Leu Met Gly Asp Phe Asn Ala Gly
            180                 185                 190
```

```
Cys Ser Tyr Val Arg Pro Ser Gln Trp Ser Ser Ile Arg Leu Trp Thr
        195                 200                 205

Ser Pro Thr Phe Gln Trp Leu Ile Pro Asp Ser Ala Asp Thr Thr Ala
    210                 215                 220

Thr Pro Thr His Cys Ala Tyr Asp Arg Ile Val Val Ala Gly Met Leu
225                 230                 235                 240

Leu Arg Gly Ala Val Val Pro Asp Ser Ala Leu Pro Phe Asn Phe Gln
                245                 250                 255

Ala Ala Tyr Gly Leu Ser Asp Gln Leu Ala Gln Ala Ile Ser Asp His
            260                 265                 270

Tyr Pro Val Glu Val Met Leu Lys
        275                 280


<210> SEQ ID NO 148
<211> LENGTH: 305
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Met Ser Arg Glu Leu Ala Pro Leu Leu Leu Leu Leu Leu Ser Ile His
1               5                   10                  15

Ser Ala Leu Ala Met Arg Ile Cys Ser Phe Asn Val Arg Ser Phe Gly
            20                  25                  30

Glu Ser Lys Gln Glu Asp Lys Asn Ala Met Asp Val Ile Val Lys Val
        35                  40                  45

Ile Lys Arg Cys Asp Ile Ile Leu Val Met Glu Ile Lys Asp Ser Asn
    50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
        115                 120                 125

Val Phe Ser Arg Glu Pro Phe Val Val Trp Phe Gln Ser Pro His Thr
    130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
            180                 185                 190

Gly Cys Ser Tyr Val Pro Lys Lys Ala Trp Lys Asn Ile Arg Leu Arg
        195                 200                 205

Thr Asp Pro Arg Phe Val Trp Leu Ile Gly Asp Gln Glu Asp Thr Thr
    210                 215                 220

Val Lys Lys Ser Thr Asn Cys Ala Tyr Asp Arg Ile Val Leu Arg Gly
225                 230                 235                 240

Gln Glu Ile Val Ser Ser Val Val Pro Lys Ser Asn Ser Val Phe Asp
                245                 250                 255

Phe Gln Lys Ala Tyr Lys Leu Thr Glu Glu Glu Ala Leu Asp Val Ser
            260                 265                 270
```

Asp His Phe Pro Val Glu Phe Lys Leu Gln Ser Ser Arg Ala Phe Thr
275 280 285

Asn Ser Lys Lys Ser Val Thr Leu Arg Lys Lys Thr Lys Ser Lys Arg
290 295 300

Ser
305

<210> SEQ ID NO 149
<211> LENGTH: 156
<212> TYPE: PRT
<213> ORGANISM: Homo sapiens

<400> SEQUENCE: 149

Met Gly Leu Glu Lys Ser Leu Val Arg Leu Leu Leu Leu Val Leu Ile
1 5 10 15

Leu Leu Val Leu Gly Trp Val Gln Pro Ser Leu Gly Lys Glu Ser Arg
20 25 30

Ala Lys Lys Phe Gln Arg Gln His Met Asp Ser Asp Ser Ser Pro Ser
35 40 45

Ser Ser Ser Thr Tyr Cys Asn Gln Met Met Arg Arg Arg Asn Met Thr
50 55 60

Gln Gly Arg Cys Lys Pro Val Asn Thr Phe Val His Glu Pro Leu Val
65 70 75 80

Asp Val Gln Asn Val Cys Phe Gln Glu Lys Val Thr Cys Lys Asn Gly
85 90 95

Gln Gly Asn Cys Tyr Lys Ser Asn Ser Ser Met His Ile Thr Asp Cys
100 105 110

Arg Leu Thr Asn Gly Ser Arg Tyr Pro Asn Cys Ala Tyr Arg Thr Ser
115 120 125

Pro Lys Glu Arg His Ile Ile Val Ala Cys Glu Gly Ser Pro Tyr Val
130 135 140

Pro Val His Phe Asp Ala Ser Val Glu Asp Ser Thr
145 150 155

<210> SEQ ID NO 150
<211> LENGTH: 378
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 150

Met Glu Thr Pro Ala Gln Leu Leu Phe Leu Leu Leu Leu Trp Leu Pro
1 5 10 15

Asp Thr Thr Gly Arg Glu Ser Ala Ala Gln Lys Phe Gln Arg Gln His
20 25 30

Met Asp Pro Asp Gly Ser Ser Ile Asn Ser Pro Thr Tyr Cys Asn Gln
35 40 45

Met Met Lys Arg Arg Asp Met Thr Asn Gly Ser Cys Lys Pro Val Asn
50 55 60

Thr Phe Val His Glu Pro Leu Ala Asp Val Gln Ala Val Cys Ser Gln
65 70 75 80

Glu Asn Val Thr Cys Lys Asn Arg Lys Ser Asn Cys Tyr Lys Ser Ser
85 90 95

Ser Ala Leu His Ile Thr Asp Cys His Leu Lys Gly Asn Ser Lys Tyr
100 105 110

Pro Asn Cys Asp Tyr Lys Thr Thr Gln Tyr Gln Lys His Ile Ile Val
115 120 125

Ala Cys Glu Gly Asn Pro Tyr Val Pro Val His Phe Asp Ala Thr Val
130 135 140

Leu Glu Pro Arg Gly Leu Thr Ile Lys Pro Ser Pro Pro Cys Lys Cys
145 150 155 160

Pro Ala Pro Asn Leu Leu Gly Gly Ser Ser Val Phe Ile Phe Pro Pro
165 170 175

Lys Ile Lys Asp Val Leu Met Ile Ser Leu Ser Pro Met Val Thr Cys
180 185 190

Val Val Val Asp Val Ser Glu Asp Asp Pro Asp Val Gln Ile Ser Trp
195 200 205

Phe Val Asn Asn Val Glu Val His Thr Ala Gln Thr Gln Thr His Arg
210 215 220

Glu Asp Tyr Asn Ser Thr Leu Arg Val Val Ser Ala Leu Pro Ile Gln
225 230 235 240

His Gln Asp Trp Met Ser Gly Lys Glu Phe Lys Cys Ser Val Asn Asn
245 250 255

Lys Asp Leu Pro Ala Ser Ile Glu Arg Thr Ile Ser Lys Pro Arg Gly
260 265 270

Pro Val Arg Ala Pro Gln Val Tyr Val Leu Pro Pro Pro Ala Glu Glu
275 280 285

Met Thr Lys Lys Glu Phe Ser Leu Thr Cys Met Ile Thr Gly Phe Leu
290 295 300

Pro Ala Glu Ile Ala Val Asp Trp Thr Ser Asn Gly Arg Thr Glu Gln
305 310 315 320

Asn Tyr Lys Asn Thr Ala Thr Val Leu Asp Ser Asp Gly Ser Tyr Phe
325 330 335

Met Tyr Ser Lys Leu Arg Val Gln Lys Ser Thr Trp Glu Arg Gly Ser
340 345 350

Leu Phe Ala Cys Ser Val Val His Glu Gly Leu His Asn His Leu Thr
355 360 365

Thr Lys Ser Phe Ser Arg Thr Pro Gly Lys
370 375

<210> SEQ ID NO 151
<211> LENGTH: 659
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 151

Met Glu Thr Pro Ala Gln Leu Leu Phe Leu Leu Leu Leu Trp Leu Pro
1 5 10 15

Asp Thr Thr Gly Lys Glu Ser Arg Ala Lys Lys Phe Gln Arg Gln His
20 25 30

Met Asp Ser Asp Ser Ser Pro Ser Ser Ser Ser Thr Tyr Cys Asn Gln
35 40 45

Met Met Arg Arg Arg Asn Met Thr Gln Gly Arg Cys Lys Pro Val Asn
50 55 60

Thr Phe Val His Glu Pro Leu Val Asp Val Gln Asn Val Cys Phe Gln
65 70 75 80

Glu Lys Val Thr Cys Lys Asn Gly Gln Gly Asn Cys Tyr Lys Ser Asn

```
                85                  90                  95

Ser Ser Met His Ile Thr Asp Cys Arg Leu Thr Asn Gly Ser Arg Tyr
            100                 105                 110

Pro Asn Cys Ala Tyr Arg Thr Ser Pro Lys Glu Arg His Ile Ile Val
        115                 120                 125

Ala Cys Glu Gly Ser Pro Tyr Val Pro Val His Phe Asp Ala Ser Val
    130                 135                 140

Glu Asp Ser Thr Leu Glu Pro Lys Ser Ser Asp Lys Thr His Thr Cys
145                 150                 155                 160

Pro Pro Cys Pro Ala Pro Glu Leu Leu Gly Gly Pro Ser Val Phe Leu
                165                 170                 175

Phe Pro Pro Lys Pro Lys Asp Thr Leu Met Ile Ser Arg Thr Pro Glu
            180                 185                 190

Val Thr Cys Val Val Val Asp Val Ser His Glu Asp Pro Glu Val Lys
        195                 200                 205

Phe Asn Trp Tyr Val Asp Gly Val Glu Val His Asn Ala Lys Thr Lys
    210                 215                 220

Pro Arg Glu Glu Gln Tyr Asn Ser Thr Tyr Arg Val Val Ser Val Leu
225                 230                 235                 240

Thr Val Leu His Gln Asp Trp Leu Asn Gly Lys Glu Tyr Lys Cys Lys
                245                 250                 255

Val Ser Asn Lys Ala Leu Pro Ala Pro Ile Glu Lys Thr Ile Ser Lys
            260                 265                 270

Ala Lys Gly Gln Pro Arg Glu Pro Gln Val Tyr Thr Leu Pro Pro Ser
        275                 280                 285

Arg Asp Glu Leu Thr Lys Asn Gln Val Ser Leu Thr Cys Leu Val Lys
    290                 295                 300

Gly Phe Tyr Pro Ser Asp Ile Ala Val Glu Trp Glu Ser Asn Gly Gln
305                 310                 315                 320

Pro Glu Asn Asn Tyr Lys Thr Thr Pro Pro Val Leu Asp Ser Asp Gly
                325                 330                 335

Ser Phe Phe Leu Tyr Ser Lys Leu Thr Val Asp Lys Ser Arg Trp Gln
            340                 345                 350

Gln Gly Asn Val Phe Ser Cys Ser Val Met His Glu Gly Leu His Asn
        355                 360                 365

His Tyr Thr Gln Lys Ser Leu Ser Leu Ser Pro Gly Lys Val Asp Gly
    370                 375                 380

Ala Ser Ser Pro Val Asn Val Ser Ser Pro Ser Val Gln Asp Ile Leu
385                 390                 395                 400

Lys Ile Ala Ala Phe Asn Ile Gln Thr Phe Gly Glu Thr Lys Met Ser
                405                 410                 415

Asn Ala Thr Leu Val Ser Tyr Ile Val Gln Ile Leu Ser Arg Tyr Asp
            420                 425                 430

Ile Ala Leu Val Gln Glu Val Arg Asp Ser His Leu Thr Ala Val Gly
        435                 440                 445

Lys Leu Leu Asp Asn Leu Asn Gln Asp Ala Pro Asp Thr Tyr His Tyr
    450                 455                 460

Val Val Ser Glu Pro Leu Gly Arg Asn Ser Tyr Lys Glu Arg Tyr Leu
465                 470                 475                 480

Phe Val Tyr Arg Pro Asp Gln Val Ser Ala Val Asp Ser Tyr Tyr Tyr
                485                 490                 495

Asp Asp Gly Cys Glu Pro Cys Arg Asn Asp Thr Phe Asn Arg Glu Pro
            500                 505                 510
```

Phe Ile Val Arg Phe Phe Ser Arg Phe Thr Glu Val Arg Glu Phe Ala
515 520 525

Ile Val Pro Leu His Ala Ala Pro Gly Asp Ala Val Ala Glu Ile Asp
530 535 540

Ala Leu Tyr Asp Val Tyr Leu Asp Val Gln Glu Lys Trp Gly Ser Glu
545 550 555 560

Asp Val Met Leu Met Gly Asp Phe Asn Ala Gly Cys Ser Tyr Val Arg
565 570 575

Pro Ser Gln Trp Ser Ser Ile Arg Leu Trp Thr Ser Pro Thr Phe Gln
580 585 590

Trp Leu Ile Pro Asp Ser Ala Asp Thr Thr Ala Thr Pro Thr His Cys
595 600 605

Ala Tyr Asp Arg Ile Val Val Ala Gly Met Leu Leu Arg Gly Ala Val
610 615 620

Val Pro Asp Ser Ala Leu Pro Phe Asn Phe Gln Ala Ala Tyr Gly Leu
625 630 635 640

Ser Asp Gln Leu Ala Gln Ala Ile Ser Asp His Tyr Pro Val Glu Val
645 650 655

Met Leu Lys

<210> SEQ ID NO 152
<211> LENGTH: 659
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 152

Met Glu Thr Pro Ala Gln Leu Leu Phe Leu Leu Leu Leu Trp Leu Pro
1 5 10 15

Asp Thr Thr Gly Lys Glu Ser Arg Ala Lys Lys Phe Gln Arg Gln His
20 25 30

Met Asp Ser Asp Ser Ser Pro Ser Ser Ser Ser Thr Tyr Cys Asn Gln
35 40 45

Met Met Arg Arg Arg Asn Met Thr Gln Gly Arg Cys Lys Pro Val Asn
50 55 60

Thr Phe Val His Glu Pro Leu Val Asp Val Gln Asn Val Cys Phe Gln
65 70 75 80

Glu Lys Val Thr Cys Lys Asn Gly Gln Gly Asn Cys Tyr Lys Ser Asn
85 90 95

Ser Ser Met His Ile Thr Asp Cys Arg Leu Thr Asn Gly Ser Arg Tyr
100 105 110

Pro Asn Cys Ala Tyr Arg Thr Ser Pro Lys Glu Arg His Ile Ile Val
115 120 125

Ala Cys Glu Gly Ser Pro Tyr Val Pro Val His Phe Asp Ala Ser Val
130 135 140

Glu Asp Ser Thr Leu Glu Pro Lys Ser Ser Asp Lys Thr His Thr Cys
145 150 155 160

Pro Pro Cys Pro Ala Pro Glu Leu Leu Gly Gly Pro Ser Val Phe Leu
165 170 175

Phe Pro Pro Lys Pro Lys Asp Thr Leu Met Ile Ser Arg Thr Pro Glu
180 185 190

Val Thr Cys Val Val Val Asp Val Ser His Glu Asp Pro Glu Val Lys
195 200 205

```
Phe Asn Trp Tyr Val Asp Gly Val Glu Val His Asn Ala Lys Thr Lys
    210                 215                 220

Pro Arg Glu Glu Gln Tyr Asn Ser Thr Tyr Arg Val Val Ser Val Leu
225                 230                 235                 240

Thr Val Leu His Gln Asp Trp Leu Asn Gly Lys Glu Tyr Lys Cys Lys
                245                 250                 255

Val Ser Asn Lys Ala Leu Pro Ala Pro Ile Glu Lys Thr Ile Ser Lys
            260                 265                 270

Ala Lys Gly Gln Pro Arg Glu Pro Gln Val Tyr Thr Leu Pro Pro Ser
        275                 280                 285

Arg Asp Glu Leu Thr Lys Asn Gln Val Ser Leu Thr Cys Leu Val Lys
    290                 295                 300

Gly Phe Tyr Pro Ser Asp Ile Ala Val Glu Trp Glu Ser Asn Gly Gln
305                 310                 315                 320

Pro Glu Asn Asn Tyr Lys Thr Thr Pro Pro Val Leu Asp Ser Asp Gly
                325                 330                 335

Ser Phe Phe Leu Tyr Ser Lys Leu Thr Val Asp Lys Ser Arg Trp Gln
            340                 345                 350

Gln Gly Asn Val Phe Ser Cys Ser Val Met His Glu Gly Leu His Asn
        355                 360                 365

His Tyr Thr Gln Lys Ser Leu Ser Leu Ser Pro Gly Lys Val Asp Gly
    370                 375                 380

Ala Ser Ser Pro Val Asn Val Ser Ser Pro Ser Val Gln Asp Ile Leu
385                 390                 395                 400

Lys Ile Ala Ala Phe Asn Ile Gln Thr Phe Gly Glu Thr Lys Met Ser
                405                 410                 415

Asn Ala Thr Leu Val Ser Tyr Ile Val Gln Ile Leu Ser Arg Tyr Asp
            420                 425                 430

Ile Ala Leu Val Gln Glu Val Arg Asp Ser His Leu Thr Ala Val Gly
        435                 440                 445

Lys Leu Leu Asp Asn Leu Asn Gln Asp Ala Pro Asp Thr Tyr His Tyr
    450                 455                 460

Val Val Ser Glu Pro Leu Gly Arg Asn Ser Tyr Lys Glu Arg Tyr Leu
465                 470                 475                 480

Phe Val Tyr Arg Pro Asp Gln Val Ser Ala Val Asp Ser Tyr Tyr Tyr
                485                 490                 495

Asp Asp Gly Cys Glu Pro Cys Gly Asn Asp Thr Phe Asn Arg Glu Pro
            500                 505                 510

Phe Ile Val Arg Phe Phe Ser Arg Phe Thr Glu Val Arg Glu Phe Ala
        515                 520                 525

Ile Val Pro Leu His Ala Ala Pro Gly Asp Ala Val Ala Glu Ile Asp
    530                 535                 540

Ala Leu Tyr Asp Val Tyr Leu Asp Val Gln Glu Lys Trp Gly Leu Glu
545                 550                 555                 560

Asp Val Met Leu Met Gly Asp Phe Asn Ala Gly Cys Ser Tyr Val Arg
                565                 570                 575

Pro Ser Gln Trp Ser Ser Ile Arg Leu Trp Thr Ser Pro Thr Phe Gln
            580                 585                 590

Trp Leu Ile Pro Asp Ser Ala Asp Thr Thr Ala Thr Pro Thr His Cys
        595                 600                 605

Ala Tyr Asp Arg Ile Val Val Ala Gly Met Leu Leu Arg Gly Ala Val
    610                 615                 620
```

Val Pro Asp Ser Ala Leu Pro Phe Asn Phe Gln Ala Ala Tyr Gly Leu
625 630 635 640

Ser Asp Gln Leu Ala Gln Ala Ile Ser Asp His Tyr Pro Val Glu Val
645 650 655

Met Leu Lys

<210> SEQ ID NO 153
<211> LENGTH: 659
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 153

Met Glu Thr Pro Ala Gln Leu Leu Phe Leu Leu Leu Leu Trp Leu Pro
1 5 10 15

Asp Thr Thr Gly Lys Glu Ser Arg Ala Lys Lys Phe Gln Arg Gln His
20 25 30

Met Asp Ser Asp Ser Ser Pro Ser Ser Ser Ser Thr Tyr Cys Asn Gln
35 40 45

Met Met Arg Arg Arg Asn Met Thr Gln Gly Arg Cys Lys Pro Val Asn
50 55 60

Thr Phe Val His Glu Pro Leu Val Asp Val Gln Asn Val Cys Phe Gln
65 70 75 80

Glu Lys Val Thr Cys Lys Asn Gly Gln Gly Asn Cys Tyr Lys Ser Asn
85 90 95

Ser Ser Met His Ile Thr Asp Cys Arg Leu Thr Asn Gly Ser Arg Tyr
100 105 110

Pro Asn Cys Ala Tyr Arg Thr Ser Pro Lys Glu Arg His Ile Ile Val
115 120 125

Ala Cys Glu Gly Ser Pro Tyr Val Pro Val His Phe Asp Ala Ser Val
130 135 140

Glu Asp Ser Thr Leu Glu Pro Lys Ser Ser Asp Lys Thr His Thr Cys
145 150 155 160

Pro Pro Cys Pro Ala Pro Glu Leu Leu Gly Gly Pro Ser Val Phe Leu
165 170 175

Phe Pro Pro Lys Pro Lys Asp Thr Leu Met Ile Ser Arg Thr Pro Glu
180 185 190

Val Thr Cys Val Val Val Asp Val Ser His Glu Asp Pro Glu Val Lys
195 200 205

Phe Asn Trp Tyr Val Asp Gly Val Glu Val His Asn Ala Lys Thr Lys
210 215 220

Pro Arg Glu Glu Gln Tyr Asn Ser Thr Tyr Arg Val Val Ser Val Leu
225 230 235 240

Thr Val Leu His Gln Asp Trp Leu Asn Gly Lys Glu Tyr Lys Cys Lys
245 250 255

Val Ser Asn Lys Ala Leu Pro Ala Pro Ile Glu Lys Thr Ile Ser Lys
260 265 270

Ala Lys Gly Gln Pro Arg Glu Pro Gln Val Tyr Thr Leu Pro Pro Ser
275 280 285

Arg Asp Glu Leu Thr Lys Asn Gln Val Ser Leu Thr Cys Leu Val Lys
290 295 300

Gly Phe Tyr Pro Ser Asp Ile Ala Val Glu Trp Glu Ser Asn Gly Gln
305 310 315 320

Pro Glu Asn Asn Tyr Lys Thr Thr Pro Pro Val Leu Asp Ser Asp Gly
325 330 335

Ser Phe Phe Leu Tyr Ser Lys Leu Thr Val Asp Lys Ser Arg Trp Gln
340 345 350

Gln Gly Asn Val Phe Ser Cys Ser Val Met His Glu Gly Leu His Asn
355 360 365

His Tyr Thr Gln Lys Ser Leu Ser Leu Ser Pro Gly Lys Val Asp Gly
370 375 380

Ala Ser Ser Pro Val Asn Val Ser Ser Pro Ser Val Gln Asp Ile Leu
385 390 395 400

Lys Ile Ala Ala Phe Asn Ile Gln Thr Phe Gly Glu Thr Lys Met Ser
405 410 415

Asn Ala Thr Leu Val Ser Tyr Ile Val Gln Ile Leu Ser Arg Tyr Asp
420 425 430

Ile Ala Leu Val Gln Glu Val Arg Asp Ser His Leu Thr Ala Val Gly
435 440 445

Lys Leu Leu Asp Asn Leu Asn Gln Asp Ala Pro Asp Thr Tyr His Tyr
450 455 460

Val Val Ser Glu Pro Leu Gly Arg Asn Ser Tyr Lys Glu Arg Tyr Leu
465 470 475 480

Phe Val Tyr Arg Pro Asp Gln Val Ser Ala Val Asp Ser Tyr Tyr Tyr
485 490 495

Asp Asp Gly Cys Glu Pro Cys Gly Asn Asp Thr Phe Asn Arg Glu Pro
500 505 510

Ala Ile Val Arg Phe Phe Ser Arg Phe Thr Glu Val Arg Glu Phe Ala
515 520 525

Ile Val Pro Leu His Ala Ala Pro Gly Asp Ala Val Ala Glu Ile Asp
530 535 540

Ala Leu Tyr Asp Val Tyr Leu Asp Val Gln Glu Lys Trp Gly Leu Glu
545 550 555 560

Asp Val Met Leu Met Gly Asp Phe Asn Ala Gly Cys Ser Tyr Val Arg
565 570 575

Pro Ser Gln Trp Ser Ser Ile Arg Leu Trp Thr Ser Pro Thr Phe Gln
580 585 590

Trp Leu Ile Pro Asp Ser Ala Asp Thr Thr Ala Thr Pro Thr His Cys
595 600 605

Ala Tyr Asp Arg Ile Val Val Ala Gly Met Leu Leu Arg Gly Ala Val
610 615 620

Val Pro Asp Ser Ala Leu Pro Phe Asn Phe Gln Ala Ala Tyr Gly Leu
625 630 635 640

Ser Asp Gln Leu Ala Gln Ala Ile Ser Asp His Tyr Pro Val Glu Val
645 650 655

Met Leu Lys

<210> SEQ ID NO 154
<211> LENGTH: 513
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 154

Met Glu Thr Pro Ala Gln Leu Leu Phe Leu Leu Leu Leu Trp Leu Pro
1 5 10 15

```
Asp Thr Thr Gly Leu Lys Ile Ala Ala Phe Asn Ile Gln Thr Phe Gly
            20                  25                  30

Glu Thr Lys Met Ser Asn Ala Thr Leu Val Ser Tyr Ile Val Gln Ile
        35                  40                  45

Leu Ser Arg Tyr Asp Ile Ala Leu Val Gln Glu Val Arg Asp Ser His
    50                  55                  60

Leu Thr Ala Val Gly Lys Leu Leu Asp Asn Leu Asn Gln Asp Ala Pro
65                  70                  75                  80

Asp Thr Tyr His Tyr Val Val Ser Glu Pro Leu Gly Arg Asn Ser Tyr
                85                  90                  95

Lys Glu Arg Tyr Leu Phe Val Tyr Arg Pro Asp Gln Val Ser Ala Val
            100                 105                 110

Asp Ser Tyr Tyr Tyr Asp Asp Gly Cys Glu Pro Cys Gly Asn Asp Thr
        115                 120                 125

Phe Asn Arg Glu Pro Ala Ile Val Arg Phe Phe Ser Arg Phe Thr Glu
    130                 135                 140

Val Arg Glu Phe Ala Ile Val Pro Leu His Ala Ala Pro Gly Asp Ala
145                 150                 155                 160

Val Ala Glu Ile Asp Ala Leu Tyr Asp Val Tyr Leu Asp Val Gln Glu
                165                 170                 175

Lys Trp Gly Leu Glu Asp Val Met Leu Met Gly Asp Phe Asn Ala Gly
            180                 185                 190

Cys Ser Tyr Val Arg Pro Ser Gln Trp Ser Ser Ile Arg Leu Trp Thr
        195                 200                 205

Ser Pro Thr Phe Gln Trp Leu Ile Pro Asp Ser Ala Asp Thr Thr Ala
    210                 215                 220

Thr Pro Thr His Cys Ala Tyr Asp Arg Ile Val Val Ala Gly Met Leu
225                 230                 235                 240

Leu Arg Gly Ala Val Val Pro Asp Ser Ala Leu Pro Phe Asn Phe Gln
                245                 250                 255

Ala Ala Tyr Gly Leu Ser Asp Gln Leu Ala Gln Ala Ile Ser Asp His
            260                 265                 270

Tyr Pro Val Glu Val Met Leu Lys Leu Glu Pro Lys Ser Ser Asp Lys
        275                 280                 285

Thr His Thr Cys Pro Pro Cys Pro Ala Pro Glu Leu Leu Gly Gly Pro
    290                 295                 300

Ser Val Phe Leu Phe Pro Pro Lys Pro Lys Asp Thr Leu Met Ile Ser
305                 310                 315                 320

Arg Thr Pro Glu Val Thr Cys Val Val Val Asp Val Ser His Glu Asp
                325                 330                 335

Pro Glu Val Lys Phe Asn Trp Tyr Val Asp Gly Val Glu Val His Asn
            340                 345                 350

Ala Lys Thr Lys Pro Arg Glu Glu Gln Tyr Asn Ser Thr Tyr Arg Val
        355                 360                 365

Val Ser Val Leu Thr Val Leu His Gln Asp Trp Leu Asn Gly Lys Glu
    370                 375                 380

Tyr Lys Cys Lys Val Ser Asn Lys Ala Leu Pro Ala Pro Ile Glu Lys
385                 390                 395                 400

Thr Ile Ser Lys Ala Lys Gly Gln Pro Arg Glu Pro Gln Val Tyr Thr
                405                 410                 415

Leu Pro Pro Ser Arg Asp Glu Leu Thr Lys Asn Gln Val Ser Leu Thr
            420                 425                 430

Cys Leu Val Lys Gly Phe Tyr Pro Ser Asp Ile Ala Val Glu Trp Glu
```

```
        435                 440                 445

Ser Asn Gly Gln Pro Glu Asn Asn Tyr Lys Thr Thr Pro Pro Val Leu
    450                 455                 460

Asp Ser Asp Gly Ser Phe Phe Leu Tyr Ser Lys Leu Thr Val Asp Lys
465                 470                 475                 480

Ser Arg Trp Gln Gln Gly Asn Val Phe Ser Cys Ser Val Met His Glu
                485                 490                 495

Ala Leu His Asn His Tyr Thr Gln Lys Ser Leu Ser Leu Ser Pro Gly
            500                 505                 510

Lys


<210> SEQ ID NO 155
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Met Glu Thr Pro Ala Gln Leu Leu Phe Leu Leu Leu Leu Trp Leu Pro
1               5                   10                  15

Asp Thr Thr Gly Leu Lys Ile Ala Ala Phe Asn Ile Gln Thr Phe Gly
            20                  25                  30

Glu Thr Lys Met Ser Asn Ala Thr Leu Val Ser Tyr Ile Val Gln Ile
        35                  40                  45

Leu Ser Arg Tyr Asp Ile Ala Leu Val Gln Glu Val Arg Asp Ser His
    50                  55                  60

Leu Thr Ala Val Gly Lys Leu Leu Asp Asn Leu Asn Gln Asp Ala Pro
65                  70                  75                  80

Asp Thr Tyr His Tyr Val Val Ser Glu Pro Leu Gly Arg Asn Ser Tyr
                85                  90                  95

Lys Glu Arg Tyr Leu Phe Val Tyr Arg Pro Asp Gln Val Ser Ala Val
            100                 105                 110

Asp Ser Tyr Tyr Tyr Asp Asp Gly Cys Glu Pro Cys Gly Asn Asp Thr
        115                 120                 125

Phe Asn Arg Glu Pro Phe Ile Val Arg Phe Phe Ser Arg Phe Thr Glu
    130                 135                 140

Val Arg Glu Phe Ala Ile Val Pro Leu His Ala Ala Pro Gly Asp Ala
145                 150                 155                 160

Val Ala Glu Ile Asp Ala Leu Tyr Asp Val Tyr Leu Asp Val Gln Glu
                165                 170                 175

Lys Trp Gly Leu Glu Asp Val Met Leu Met Gly Asp Phe Asn Ala Gly
            180                 185                 190

Cys Ser Tyr Val Arg Pro Ser Gln Trp Ser Ser Ile Arg Leu Trp Thr
        195                 200                 205

Ser Pro Thr Phe Gln Trp Leu Ile Pro Asp Ser Ala Asp Thr Thr Ala
    210                 215                 220

Thr Pro Thr His Cys Ala Tyr Asp Arg Ile Val Val Ala Gly Met Leu
225                 230                 235                 240

Leu Arg Gly Ala Val Val Pro Asp Ser Ala Leu Pro Phe Asn Phe Gln
                245                 250                 255

Ala Ala Tyr Gly Leu Ser Asp Gln Leu Ala Gln Ala Ile Ser Asp His
            260                 265                 270

Tyr Pro Val Glu Val Met Leu Lys Leu Glu Pro Lys Ser Ser Asp Lys
```

```
        275                 280                 285

Thr His Thr Cys Pro Pro Cys Pro Ala Pro Glu Leu Leu Gly Gly Pro
    290                 295                 300

Ser Val Phe Leu Phe Pro Pro Lys Pro Lys Asp Thr Leu Met Ile Ser
305                 310                 315                 320

Arg Thr Pro Glu Val Thr Cys Val Val Val Asp Val Ser His Glu Asp
                325                 330                 335

Pro Glu Val Lys Phe Asn Trp Tyr Val Asp Gly Val Glu Val His Asn
            340                 345                 350

Ala Lys Thr Lys Pro Arg Glu Glu Gln Tyr Asn Ser Thr Tyr Arg Val
        355                 360                 365

Val Ser Val Leu Thr Val Leu His Gln Asp Trp Leu Asn Gly Lys Glu
    370                 375                 380

Tyr Lys Cys Lys Val Ser Asn Lys Ala Leu Pro Ala Pro Ile Glu Lys
385                 390                 395                 400

Thr Ile Ser Lys Ala Lys Gly Gln Pro Arg Glu Pro Gln Val Tyr Thr
                405                 410                 415

Leu Pro Pro Ser Arg Asp Glu Leu Thr Lys Asn Gln Val Ser Leu Thr
            420                 425                 430

Cys Leu Val Lys Gly Phe Tyr Pro Ser Asp Ile Ala Val Glu Trp Glu
        435                 440                 445

Ser Asn Gly Gln Pro Glu Asn Asn Tyr Lys Thr Thr Pro Pro Val Leu
    450                 455                 460

Asp Ser Asp Gly Ser Phe Phe Leu Tyr Ser Lys Leu Thr Val Asp Lys
465                 470                 475                 480

Ser Arg Trp Gln Gln Gly Asn Val Phe Ser Cys Ser Val Met His Glu
                485                 490                 495

Ala Leu His Asn His Tyr Thr Gln Lys Ser Leu Ser Leu Ser Pro Gly
            500                 505                 510

Lys


<210> SEQ ID NO 156
<211> LENGTH: 533
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Met Glu Thr Pro Ala Gln Leu Leu Phe Leu Leu Leu Leu Trp Leu Pro
1               5                   10                  15

Asp Thr Thr Gly Leu Lys Ile Ala Ala Phe Asn Ile Gln Thr Phe Gly
            20                  25                  30

Glu Thr Lys Met Ser Asn Ala Thr Leu Val Ser Tyr Ile Val Gln Ile
        35                  40                  45

Leu Ser Arg Tyr Asp Ile Ala Leu Val Gln Glu Val Arg Asp Ser His
    50                  55                  60

Leu Thr Ala Val Gly Lys Leu Leu Asp Asn Leu Asn Gln Asp Ala Pro
65                  70                  75                  80

Asp Thr Tyr His Tyr Val Val Ser Glu Pro Leu Gly Arg Asn Ser Tyr
                85                  90                  95

Lys Glu Arg Tyr Leu Phe Val Tyr Arg Pro Asp Gln Val Ser Ala Val
            100                 105                 110

Asp Ser Tyr Tyr Tyr Asp Asp Gly Cys Glu Pro Cys Arg Asn Asp Thr
```

```
        115                 120                 125

Phe Asn Arg Glu Pro Phe Ile Val Arg Phe Phe Ser Arg Phe Thr Glu
    130                 135                 140

Val Arg Glu Phe Ala Ile Val Pro Leu His Ala Ala Pro Gly Asp Ala
145                 150                 155                 160

Val Ala Glu Ile Asp Ala Leu Tyr Asp Val Tyr Leu Asp Val Gln Glu
                165                 170                 175

Lys Trp Gly Leu Glu Asp Val Met Leu Met Gly Asp Phe Asn Ala Gly
            180                 185                 190

Cys Ser Tyr Val Arg Pro Ser Gln Trp Ser Ser Ile Arg Leu Trp Thr
        195                 200                 205

Ser Pro Thr Phe Gln Trp Leu Ile Pro Asp Ser Ala Asp Thr Thr Ala
    210                 215                 220

Thr Pro Thr His Cys Ala Tyr Asp Arg Ile Val Val Ala Gly Met Leu
225                 230                 235                 240

Leu Arg Gly Ala Val Val Pro Asp Ser Ala Leu Pro Phe Asn Phe Gln
                245                 250                 255

Ala Ala Tyr Gly Leu Ser Asp Gln Leu Ala Gln Ala Ile Ser Asp His
            260                 265                 270

Tyr Pro Val Glu Val Met Leu Lys Gly Gly Gly Gly Ser Gly Gly Gly
        275                 280                 285

Gly Ser Gly Gly Gly Gly Ser Gly Gly Gly Gly Ser Leu Glu Pro Lys
    290                 295                 300

Ser Ser Asp Lys Thr His Thr Cys Pro Pro Cys Pro Ala Pro Glu Leu
305                 310                 315                 320

Leu Gly Gly Pro Ser Val Phe Leu Phe Pro Pro Lys Pro Lys Asp Thr
                325                 330                 335

Leu Met Ile Ser Arg Thr Pro Glu Val Thr Cys Val Val Val Asp Val
            340                 345                 350

Ser His Glu Asp Pro Glu Val Lys Phe Asn Trp Tyr Val Asp Gly Val
        355                 360                 365

Glu Val His Asn Ala Lys Thr Lys Pro Arg Glu Glu Gln Tyr Asn Ser
    370                 375                 380

Thr Tyr Arg Val Val Ser Val Leu Thr Val Leu His Gln Asp Trp Leu
385                 390                 395                 400

Asn Gly Lys Glu Tyr Lys Cys Lys Val Ser Asn Lys Ala Leu Pro Ala
                405                 410                 415

Pro Ile Glu Lys Thr Ile Ser Lys Ala Lys Gly Gln Pro Arg Glu Pro
            420                 425                 430

Gln Val Tyr Thr Leu Pro Pro Ser Arg Asp Glu Leu Thr Lys Asn Gln
        435                 440                 445

Val Ser Leu Thr Cys Leu Val Lys Gly Phe Tyr Pro Ser Asp Ile Ala
    450                 455                 460

Val Glu Trp Glu Ser Asn Gly Gln Pro Glu Asn Asn Tyr Lys Thr Thr
465                 470                 475                 480

Pro Pro Val Leu Asp Ser Asp Gly Ser Phe Phe Leu Tyr Ser Lys Leu
                485                 490                 495

Thr Val Asp Lys Ser Arg Trp Gln Gln Gly Asn Val Phe Ser Cys Ser
            500                 505                 510

Val Met His Glu Ala Leu His Asn His Tyr Thr Gln Lys Ser Leu Ser
        515                 520                 525

Leu Ser Pro Gly Lys
    530
```

<210> SEQ ID NO 157
<211> LENGTH: 538
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 157

Met Glu Thr Pro Ala Gln Leu Leu Phe Leu Leu Leu Leu Trp Leu Pro
1               5                   10                  15

Asp Thr Thr Gly Leu Lys Ile Ala Ala Phe Asn Ile Gln Thr Phe Gly
            20                  25                  30

Glu Thr Lys Met Ser Asn Ala Thr Leu Val Ser Tyr Ile Val Gln Ile
        35                  40                  45

Leu Ser Arg Tyr Asp Ile Ala Leu Val Gln Glu Val Arg Asp Ser His
    50                  55                  60

Leu Thr Ala Val Gly Lys Leu Leu Asp Asn Leu Asn Gln Asp Ala Pro
65                  70                  75                  80

Asp Thr Tyr His Tyr Val Val Ser Glu Pro Leu Gly Arg Asn Ser Tyr
                85                  90                  95

Lys Glu Arg Tyr Leu Phe Val Tyr Arg Pro Asp Gln Val Ser Ala Val
            100                 105                 110

Asp Ser Tyr Tyr Tyr Asp Asp Gly Cys Glu Pro Cys Arg Asn Asp Thr
        115                 120                 125

Phe Asn Arg Glu Pro Phe Ile Val Arg Phe Phe Ser Arg Phe Thr Glu
    130                 135                 140

Val Arg Glu Phe Ala Ile Val Pro Leu His Ala Ala Pro Gly Asp Ala
145                 150                 155                 160

Val Ala Glu Ile Asp Ala Leu Tyr Asp Val Tyr Leu Asp Val Gln Glu
                165                 170                 175

Lys Trp Gly Leu Glu Asp Val Met Leu Met Gly Asp Phe Asn Ala Gly
            180                 185                 190

Cys Ser Tyr Val Arg Pro Ser Gln Trp Ser Ser Ile Arg Leu Trp Thr
        195                 200                 205

Ser Pro Thr Phe Gln Trp Leu Ile Pro Asp Ser Ala Asp Thr Thr Ala
    210                 215                 220

Thr Pro Thr His Cys Ala Tyr Asp Arg Ile Val Val Ala Gly Met Leu
225                 230                 235                 240

Leu Arg Gly Ala Val Val Pro Asp Ser Ala Leu Pro Phe Asn Phe Gln
                245                 250                 255

Ala Ala Tyr Gly Leu Ser Asp Gln Leu Ala Gln Ala Ile Ser Asp His
            260                 265                 270

Tyr Pro Val Glu Val Met Leu Lys Gly Gly Gly Gly Ser Gly Gly Gly
        275                 280                 285

Gly Ser Gly Gly Gly Gly Ser Gly Gly Gly Gly Ser Gly Gly Gly Gly
    290                 295                 300

Ser Leu Glu Pro Lys Ser Ser Asp Lys Thr His Thr Cys Pro Pro Cys
305                 310                 315                 320

Pro Ala Pro Glu Leu Leu Gly Gly Pro Ser Val Phe Leu Phe Pro Pro
                325                 330                 335

Lys Pro Lys Asp Thr Leu Met Ile Ser Arg Thr Pro Glu Val Thr Cys
            340                 345                 350

Val Val Val Asp Val Ser His Glu Asp Pro Glu Val Lys Phe Asn Trp

```
        355                 360                 365

Tyr Val Asp Gly Val Glu Val His Asn Ala Lys Thr Lys Pro Arg Glu
    370                 375                 380

Glu Gln Tyr Asn Ser Thr Tyr Arg Val Val Ser Val Leu Thr Val Leu
385                 390                 395                 400

His Gln Asp Trp Leu Asn Gly Lys Glu Tyr Lys Cys Lys Val Ser Asn
                405                 410                 415

Lys Ala Leu Pro Ala Pro Ile Glu Lys Thr Ile Ser Lys Ala Lys Gly
            420                 425                 430

Gln Pro Arg Glu Pro Gln Val Tyr Thr Leu Pro Pro Ser Arg Asp Glu
        435                 440                 445

Leu Thr Lys Asn Gln Val Ser Leu Thr Cys Leu Val Lys Gly Phe Tyr
    450                 455                 460

Pro Ser Asp Ile Ala Val Glu Trp Glu Ser Asn Gly Gln Pro Glu Asn
465                 470                 475                 480

Asn Tyr Lys Thr Thr Pro Pro Val Leu Asp Ser Asp Gly Ser Phe Phe
                485                 490                 495

Leu Tyr Ser Lys Leu Thr Val Asp Lys Ser Arg Trp Gln Gln Gly Asn
            500                 505                 510

Val Phe Ser Cys Ser Val Met His Glu Ala Leu His Asn His Tyr Thr
        515                 520                 525

Gln Lys Ser Leu Ser Leu Ser Pro Gly Lys
    530                 535


<210> SEQ ID NO 158
<211> LENGTH: 538
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Met Glu Thr Pro Ala Gln Leu Leu Phe Leu Leu Leu Leu Trp Leu Pro
1               5                   10                  15

Asp Thr Thr Gly Leu Lys Ile Ala Ala Phe Asn Ile Gln Thr Phe Gly
            20                  25                  30

Glu Thr Lys Met Ser Asn Ala Thr Leu Val Ser Tyr Ile Val Gln Ile
        35                  40                  45

Leu Ser Arg Tyr Asp Ile Ala Leu Val Gln Glu Val Arg Asp Ser His
    50                  55                  60

Leu Thr Ala Val Gly Lys Leu Leu Asp Asn Leu Asn Gln Asp Ala Pro
65                  70                  75                  80

Asp Thr Tyr His Tyr Val Val Ser Glu Pro Leu Gly Arg Asn Ser Tyr
                85                  90                  95

Lys Glu Arg Tyr Leu Phe Val Tyr Arg Pro Asp Gln Val Ser Ala Val
            100                 105                 110

Asp Ser Tyr Tyr Tyr Asp Asp Gly Cys Glu Pro Cys Arg Asn Asp Thr
        115                 120                 125

Phe Asn Arg Glu Pro Phe Ile Val Arg Phe Phe Ser Arg Phe Thr Glu
    130                 135                 140

Val Arg Glu Phe Ala Ile Val Pro Leu His Ala Ala Pro Gly Asp Ala
145                 150                 155                 160

Val Ala Glu Ile Asp Ala Leu Tyr Asp Val Tyr Leu Asp Val Gln Glu
                165                 170                 175
```

```
Lys Trp Gly Leu Glu Asp Val Met Leu Met Gly Asp Phe Asn Ala Gly
            180                 185                 190

Cys Ser Tyr Val Arg Pro Ser Gln Trp Ser Ser Ile Arg Leu Trp Thr
        195                 200                 205

Ser Pro Thr Phe Gln Trp Leu Ile Pro Asp Ser Ala Asp Thr Thr Ala
    210                 215                 220

Thr Pro Thr His Cys Ala Tyr Asp Arg Ile Val Val Ala Gly Met Leu
225                 230                 235                 240

Leu Arg Gly Ala Val Val Pro Asp Ser Ala Leu Pro Phe Asn Phe Gln
                245                 250                 255

Ala Ala Tyr Gly Leu Ser Asp Gln Leu Ala Gln Ala Ile Ser Asp His
            260                 265                 270

Tyr Pro Val Glu Val Met Leu Lys Gly Gly Gly Gly Ser Gly Gly Gly
        275                 280                 285

Gly Ser Gly Gly Gly Gly Ser Gly Gly Gly Gly Ser Gly Gly Gly Gly
    290                 295                 300

Ser Leu Glu Pro Lys Ser Ser Asp Lys Thr His Thr Cys Pro Pro Cys
305                 310                 315                 320

Pro Ala Pro Glu Leu Leu Gly Gly Pro Ser Val Phe Leu Phe Pro Pro
                325                 330                 335

Lys Pro Lys Asp Thr Leu Met Ile Ser Arg Thr Pro Glu Val Thr Cys
            340                 345                 350

Val Val Val Asp Val Ser His Glu Asp Pro Glu Val Lys Phe Asn Trp
        355                 360                 365

Tyr Val Asp Gly Val Glu Val His Asn Ala Lys Thr Lys Pro Arg Glu
    370                 375                 380

Glu Gln Tyr Asn Ser Thr Tyr Arg Val Val Ser Val Leu Thr Val Leu
385                 390                 395                 400

His Gln Asp Trp Leu Asn Gly Lys Glu Tyr Lys Cys Lys Val Ser Asn
                405                 410                 415

Lys Ala Leu Pro Ala Pro Ile Glu Lys Thr Ile Ser Lys Ala Lys Gly
            420                 425                 430

Gln Pro Arg Glu Pro Gln Val Tyr Thr Leu Pro Pro Ser Arg Asp Glu
        435                 440                 445

Leu Thr Lys Asn Gln Val Ser Leu Thr Cys Leu Val Lys Gly Phe Tyr
    450                 455                 460

Pro Ser Asp Ile Ala Val Glu Trp Glu Ser Asn Gly Gln Pro Glu Asn
465                 470                 475                 480

Asn Tyr Lys Thr Thr Pro Pro Val Leu Asp Ser Asp Gly Ser Phe Phe
                485                 490                 495

Leu Tyr Ser Lys Leu Thr Val Asp Lys Ser Arg Trp Gln Gln Gly Asn
            500                 505                 510

Val Phe Ser Cys Ser Val Met His Glu Ala Leu His Asn His Tyr Thr
        515                 520                 525

Gln Lys Ser Leu Ser Leu Ser Pro Gly Lys
    530                 535
```

<210> SEQ ID NO 159
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

-continued

```
Met Glu Thr Pro Ala Gln Leu Leu Phe Leu Leu Leu Leu Trp Leu Pro
1               5                   10                  15

Asp Thr Thr Gly Leu Lys Ile Ala Ala Phe Asn Ile Gln Thr Phe Gly
            20                  25                  30

Glu Thr Lys Met Ser Asn Ala Thr Leu Val Ser Tyr Ile Val Gln Ile
        35                  40                  45

Leu Ser Arg Tyr Asp Ile Ala Leu Val Gln Glu Val Arg Asp Ser His
    50                  55                  60

Leu Thr Ala Val Gly Lys Leu Leu Asp Asn Leu Asn Gln Asp Ala Pro
65                  70                  75                  80

Asp Thr Tyr His Tyr Val Val Ser Glu Pro Leu Gly Arg Asn Ser Tyr
                85                  90                  95

Lys Glu Arg Tyr Leu Phe Val Tyr Arg Pro Asp Gln Val Ser Ala Val
            100                 105                 110

Asp Ser Tyr Tyr Tyr Asp Asp Gly Cys Glu Pro Cys Arg Asn Asp Thr
        115                 120                 125

Phe Asn Arg Glu Pro Phe Ile Val Arg Phe Phe Ser Arg Phe Thr Glu
    130                 135                 140

Val Arg Glu Phe Ala Ile Val Pro Leu His Ala Ala Pro Gly Asp Ala
145                 150                 155                 160

Val Ala Glu Ile Asp Ala Leu Tyr Asp Val Tyr Leu Asp Val Gln Glu
                165                 170                 175

Lys Trp Gly Leu Glu Asp Val Met Leu Met Gly Asp Phe Asn Ala Gly
            180                 185                 190

Cys Ser Tyr Val Arg Pro Ser Gln Trp Ser Ser Ile Arg Leu Trp Thr
        195                 200                 205

Ser Pro Thr Phe Gln Trp Leu Ile Pro Asp Ser Ala Asp Thr Thr Ala
    210                 215                 220

Thr Pro Thr His Cys Ala Tyr Asp Arg Ile Val Val Ala Gly Met Leu
225                 230                 235                 240

Leu Arg Gly Ala Val Val Pro Asp Ser Ala Leu Pro Phe Asn Phe Gln
                245                 250                 255

Ala Ala Tyr Gly Leu Ser Asp Gln Leu Ala Gln Ala Ile Ser Asp His
            260                 265                 270

Tyr Pro Val Glu Val Met Leu Lys Leu Glu Pro Lys Ser Ser Asp Lys
        275                 280                 285

Thr His Thr Cys Pro Pro Cys Pro Ala Pro Glu Leu Leu Gly Gly Pro
    290                 295                 300

Ser Val Phe Leu Phe Pro Pro Lys Pro Lys Asp Thr Leu Met Ile Ser
305                 310                 315                 320

Arg Thr Pro Glu Val Thr Cys Val Val Val Asp Val Ser His Glu Asp
                325                 330                 335

Pro Glu Val Lys Phe Asn Trp Tyr Val Asp Gly Val Glu Val His Asn
            340                 345                 350

Ala Lys Thr Lys Pro Arg Glu Glu Gln Tyr Asn Ser Thr Tyr Arg Val
        355                 360                 365

Val Ser Val Leu Thr Val Leu His Gln Asp Trp Leu Asn Gly Lys Glu
    370                 375                 380

Tyr Lys Cys Lys Val Ser Asn Lys Ala Leu Pro Ala Pro Ile Glu Lys
385                 390                 395                 400

Thr Ile Ser Lys Ala Lys Gly Gln Pro Arg Glu Pro Gln Val Tyr Thr
                405                 410                 415
```

```
Leu Pro Pro Ser Arg Asp Glu Leu Thr Lys Asn Gln Val Ser Leu Thr
            420                 425                 430

Cys Leu Val Lys Gly Phe Tyr Pro Ser Asp Ile Ala Val Glu Trp Glu
        435                 440                 445

Ser Asn Gly Gln Pro Glu Asn Asn Tyr Lys Thr Thr Pro Pro Val Leu
    450                 455                 460

Asp Ser Asp Gly Ser Phe Phe Leu Tyr Ser Lys Leu Thr Val Asp Lys
465                 470                 475                 480

Ser Arg Trp Gln Gln Gly Asn Val Phe Ser Cys Ser Val Met His Glu
                485                 490                 495

Ala Leu His Asn His Tyr Thr Gln Lys Ser Leu Ser Leu Ser Pro Gly
            500                 505                 510

Lys


<210> SEQ ID NO 160
<211> LENGTH: 381
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Met Glu Thr Pro Ala Gln Leu Leu Phe Leu Leu Leu Leu Trp Leu Pro
1               5                   10                  15

Asp Thr Thr Gly Lys Glu Ser Arg Ala Lys Lys Phe Gln Arg Gln His
            20                  25                  30

Met Asp Ser Asp Ser Ser Pro Ser Ser Ser Ser Thr Tyr Cys Asn Gln
        35                  40                  45

Met Met Arg Arg Arg Asn Met Thr Gln Gly Arg Cys Lys Pro Val Asn
    50                  55                  60

Thr Phe Val His Glu Pro Leu Val Asp Val Gln Asn Val Cys Phe Gln
65                  70                  75                  80

Glu Lys Val Thr Cys Lys Asn Gly Gln Gly Asn Cys Tyr Lys Ser Asn
                85                  90                  95

Ser Ser Met His Ile Thr Asp Cys Arg Leu Thr Asn Asp Ser Arg Tyr
            100                 105                 110

Pro Asn Cys Ala Tyr Arg Thr Ser Pro Lys Glu Arg His Ile Ile Val
        115                 120                 125

Ala Cys Glu Gly Ser Pro Tyr Val Pro Val His Phe Asp Ala Ser Val
    130                 135                 140

Glu Asp Ser Thr Leu Glu Pro Lys Ser Ser Asp Lys Thr His Thr Cys
145                 150                 155                 160

Pro Pro Cys Pro Ala Pro Glu Leu Leu Gly Gly Pro Ser Val Phe Leu
                165                 170                 175

Phe Pro Pro Lys Pro Lys Asp Thr Leu Met Ile Ser Arg Thr Pro Glu
            180                 185                 190

Val Thr Cys Val Val Val Asp Val Ser His Glu Asp Pro Glu Val Lys
        195                 200                 205

Phe Asn Trp Tyr Val Asp Gly Val Glu Val His Asn Ala Lys Thr Lys
    210                 215                 220

Pro Arg Glu Glu Gln Tyr Asn Ser Thr Tyr Arg Val Val Ser Val Leu
225                 230                 235                 240

Thr Val Leu His Gln Asp Trp Leu Asn Gly Lys Glu Tyr Lys Cys Lys
                245                 250                 255
```

```
Val Ser Asn Lys Ala Leu Pro Ala Pro Ile Glu Lys Thr Ile Ser Lys
            260                 265                 270

Ala Lys Gly Gln Pro Arg Glu Pro Gln Val Tyr Thr Leu Pro Pro Ser
        275                 280                 285

Arg Asp Glu Leu Thr Lys Asn Gln Val Ser Leu Thr Cys Leu Val Lys
    290                 295                 300

Gly Phe Tyr Pro Ser Asp Ile Ala Val Glu Trp Glu Ser Asn Gly Gln
305                 310                 315                 320

Pro Glu Asn Asn Tyr Lys Thr Thr Pro Pro Val Leu Asp Ser Asp Gly
                325                 330                 335

Ser Phe Phe Leu Tyr Ser Lys Leu Thr Val Asp Lys Ser Arg Trp Gln
            340                 345                 350

Gln Gly Asn Val Phe Ser Cys Ser Val Met His Glu Ala Leu His Asn
        355                 360                 365

His Tyr Thr Gln Lys Ser Leu Ser Leu Ser Pro Gly Lys
    370                 375                 380


<210> SEQ ID NO 161
<211> LENGTH: 401
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Met Glu Thr Pro Ala Gln Leu Leu Phe Leu Leu Leu Leu Trp Leu Pro
1               5                   10                  15

Asp Thr Thr Gly Lys Glu Ser Arg Ala Lys Lys Phe Gln Arg Gln His
            20                  25                  30

Met Asp Ser Asp Ser Ser Pro Ser Ser Ser Ser Thr Tyr Cys Asn Gln
        35                  40                  45

Met Met Arg Arg Arg Asn Met Thr Gln Gly Arg Cys Lys Pro Val Asn
    50                  55                  60

Thr Phe Val His Glu Pro Leu Val Asp Val Gln Asn Val Cys Phe Gln
65                  70                  75                  80

Glu Lys Val Thr Cys Lys Asn Gly Gln Gly Asn Cys Tyr Lys Ser Asn
                85                  90                  95

Ser Ser Met His Ile Thr Asp Cys Arg Leu Thr Asn Gly Ser Arg Tyr
            100                 105                 110

Pro Asn Cys Ala Tyr Arg Thr Ser Pro Lys Glu Arg His Ile Ile Val
        115                 120                 125

Ala Cys Glu Gly Ser Pro Tyr Val Pro Val His Phe Asp Ala Ser Val
    130                 135                 140

Glu Asp Ser Thr Gly Gly Gly Gly Ser Gly Gly Gly Gly Ser Gly Gly
145                 150                 155                 160

Gly Gly Ser Gly Gly Gly Gly Ser Leu Glu Pro Lys Ser Ser Asp Lys
                165                 170                 175

Thr His Thr Cys Pro Pro Cys Pro Ala Pro Glu Leu Leu Gly Gly Pro
            180                 185                 190

Ser Val Phe Leu Phe Pro Pro Lys Pro Lys Asp Thr Leu Met Ile Ser
        195                 200                 205

Arg Thr Pro Glu Val Thr Cys Val Val Val Asp Val Ser His Glu Asp
    210                 215                 220

Pro Glu Val Lys Phe Asn Trp Tyr Val Asp Gly Val Glu Val His Asn
225                 230                 235                 240
```

```
Ala Lys Thr Lys Pro Arg Glu Glu Gln Tyr Asn Ser Thr Tyr Arg Val
                245                 250                 255

Val Ser Val Leu Thr Val Leu His Gln Asp Trp Leu Asn Gly Lys Glu
            260                 265                 270

Tyr Lys Cys Lys Val Ser Asn Lys Ala Leu Pro Ala Pro Ile Glu Lys
        275                 280                 285

Thr Ile Ser Lys Ala Lys Gly Gln Pro Arg Glu Pro Gln Val Tyr Thr
    290                 295                 300

Leu Pro Pro Ser Arg Asp Glu Leu Thr Lys Asn Gln Val Ser Leu Thr
305                 310                 315                 320

Cys Leu Val Lys Gly Phe Tyr Pro Ser Asp Ile Ala Val Glu Trp Glu
                325                 330                 335

Ser Asn Gly Gln Pro Glu Asn Asn Tyr Lys Thr Thr Pro Pro Val Leu
            340                 345                 350

Asp Ser Asp Gly Ser Phe Phe Leu Tyr Ser Lys Leu Thr Val Asp Lys
        355                 360                 365

Ser Arg Trp Gln Gln Gly Asn Val Phe Ser Cys Ser Val Met His Glu
    370                 375                 380

Ala Leu His Asn His Tyr Thr Gln Lys Ser Leu Ser Leu Ser Pro Gly
385                 390                 395                 400

Lys


<210> SEQ ID NO 162
<211> LENGTH: 406
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Met Glu Thr Pro Ala Gln Leu Leu Phe Leu Leu Leu Leu Trp Leu Pro
1               5                   10                  15

Asp Thr Thr Gly Lys Glu Ser Arg Ala Lys Lys Phe Gln Arg Gln His
            20                  25                  30

Met Asp Ser Asp Ser Ser Pro Ser Ser Ser Ser Thr Tyr Cys Asn Gln
        35                  40                  45

Met Met Arg Arg Arg Asn Met Thr Gln Gly Arg Cys Lys Pro Val Asn
    50                  55                  60

Thr Phe Val His Glu Pro Leu Val Asp Val Gln Asn Val Cys Phe Gln
65                  70                  75                  80

Glu Lys Val Thr Cys Lys Asn Gly Gln Gly Asn Cys Tyr Lys Ser Asn
                85                  90                  95

Ser Ser Met His Ile Thr Asp Cys Arg Leu Thr Asn Gly Ser Arg Tyr
            100                 105                 110

Pro Asn Cys Ala Tyr Arg Thr Ser Pro Lys Glu Arg His Ile Ile Val
        115                 120                 125

Ala Cys Glu Gly Ser Pro Tyr Val Pro Val His Phe Asp Ala Ser Val
    130                 135                 140

Glu Asp Ser Thr Gly Gly Gly Gly Ser Gly Gly Gly Gly Ser Gly Gly
145                 150                 155                 160

Gly Gly Ser Gly Gly Gly Gly Ser Gly Gly Gly Gly Ser Leu Glu Pro
                165                 170                 175

Lys Ser Ser Asp Lys Thr His Thr Cys Pro Pro Cys Pro Ala Pro Glu
            180                 185                 190
```

Leu Leu Gly Gly Pro Ser Val Phe Leu Phe Pro Pro Lys Pro Lys Asp
195 200 205

Thr Leu Met Ile Ser Arg Thr Pro Glu Val Thr Cys Val Val Val Asp
210 215 220

Val Ser His Glu Asp Pro Glu Val Lys Phe Asn Trp Tyr Val Asp Gly
225 230 235 240

Val Glu Val His Asn Ala Lys Thr Lys Pro Arg Glu Glu Gln Tyr Asn
245 250 255

Ser Thr Tyr Arg Val Val Ser Val Leu Thr Val Leu His Gln Asp Trp
260 265 270

Leu Asn Gly Lys Glu Tyr Lys Cys Lys Val Ser Asn Lys Ala Leu Pro
275 280 285

Ala Pro Ile Glu Lys Thr Ile Ser Lys Ala Lys Gly Gln Pro Arg Glu
290 295 300

Pro Gln Val Tyr Thr Leu Pro Pro Ser Arg Asp Glu Leu Thr Lys Asn
305 310 315 320

Gln Val Ser Leu Thr Cys Leu Val Lys Gly Phe Tyr Pro Ser Asp Ile
325 330 335

Ala Val Glu Trp Glu Ser Asn Gly Gln Pro Glu Asn Asn Tyr Lys Thr
340 345 350

Thr Pro Pro Val Leu Asp Ser Asp Gly Ser Phe Phe Leu Tyr Ser Lys
355 360 365

Leu Thr Val Asp Lys Ser Arg Trp Gln Gln Gly Asn Val Phe Ser Cys
370 375 380

Ser Val Met His Glu Ala Leu His Asn His Tyr Thr Gln Lys Ser Leu
385 390 395 400

Ser Leu Ser Pro Gly Lys
405

<210> SEQ ID NO 163
<211> LENGTH: 381
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 163

Met Glu Thr Pro Ala Gln Leu Leu Phe Leu Leu Leu Leu Trp Leu Pro
1 5 10 15

Asp Thr Thr Gly Lys Glu Ser Arg Ala Lys Lys Phe Gln Arg Gln His
20 25 30

Met Asp Ser Asp Ser Ser Pro Ser Ser Ser Ser Thr Tyr Cys Asn Gln
35 40 45

Met Met Arg Arg Arg Asn Met Thr Gln Gly Arg Cys Lys Pro Val Asn
50 55 60

Thr Phe Val His Glu Pro Leu Val Asp Val Gln Asn Val Cys Phe Gln
65 70 75 80

Glu Lys Val Thr Cys Lys Asn Gly Gln Gly Asn Cys Tyr Lys Ser Asn
85 90 95

Ser Ser Met His Ile Thr Asp Cys Arg Leu Thr Asn Gly Ser Arg Tyr
100 105 110

Pro Asn Cys Ala Tyr Arg Thr Ser Pro Lys Glu Arg His Ile Ile Val
115 120 125

Ala Cys Glu Gly Ser Pro Tyr Val Pro Val His Phe Asp Ala Ser Val

```
    130                 135                 140

Glu Asp Ser Thr Leu Glu Pro Lys Ser Ser Asp Lys Thr His Thr Cys
145                 150                 155                 160

Pro Pro Cys Pro Ala Pro Glu Leu Leu Gly Gly Pro Ser Val Phe Leu
                165                 170                 175

Phe Pro Pro Lys Pro Lys Asp Thr Leu Met Ile Ser Arg Thr Pro Glu
            180                 185                 190

Val Thr Cys Val Val Val Asp Val Ser His Glu Asp Pro Glu Val Lys
        195                 200                 205

Phe Asn Trp Tyr Val Asp Gly Val Glu Val His Asn Ala Lys Thr Lys
    210                 215                 220

Pro Arg Glu Glu Gln Tyr Asn Ser Thr Tyr Arg Val Val Ser Val Leu
225                 230                 235                 240

Thr Val Leu His Gln Asp Trp Leu Asn Gly Lys Glu Tyr Lys Cys Lys
                245                 250                 255

Val Ser Asn Lys Ala Leu Pro Ala Pro Ile Glu Lys Thr Ile Ser Lys
            260                 265                 270

Ala Lys Gly Gln Pro Arg Glu Pro Gln Val Tyr Thr Leu Pro Pro Ser
        275                 280                 285

Arg Asp Glu Leu Thr Lys Asn Gln Val Ser Leu Thr Cys Leu Val Lys
    290                 295                 300

Gly Phe Tyr Pro Ser Asp Ile Ala Val Glu Trp Glu Ser Asn Gly Gln
305                 310                 315                 320

Pro Glu Asn Asn Tyr Lys Thr Thr Pro Pro Val Leu Asp Ser Asp Gly
                325                 330                 335

Ser Phe Phe Leu Tyr Ser Lys Leu Thr Val Asp Lys Ser Arg Trp Gln
            340                 345                 350

Gln Gly Asn Val Phe Ser Cys Ser Val Met His Glu Ala Leu His Asn
        355                 360                 365

His Tyr Thr Gln Lys Ser Leu Ser Leu Ser Pro Gly Lys
    370                 375                 380


<210> SEQ ID NO 164
<211> LENGTH: 314
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Met Gly Ser Gln Thr Leu Pro His Gly His Met Gln Thr Leu Ile Phe
1               5                   10                  15

Leu Asp Leu Glu Ala Thr Gly Leu Pro Ser Ser Arg Pro Glu Val Thr
            20                  25                  30

Glu Leu Cys Leu Leu Ala Val His Arg Arg Ala Leu Glu Asn Thr Ser
        35                  40                  45

Ile Ser Gln Gly His Pro Pro Pro Val Pro Arg Pro Pro Arg Val Val
    50                  55                  60

Asp Lys Leu Ser Leu Cys Ile Ala Pro Gly Lys Ala Cys Ser Pro Gly
65                  70                  75                  80

Ala Ser Glu Ile Thr Gly Leu Ser Lys Ala Glu Leu Glu Val Gln Gly
                85                  90                  95

Arg Gln Arg Phe Asp Asp Asn Leu Ala Ile Leu Leu Arg Ala Phe Leu
            100                 105                 110
```

```
Gln Arg Gln Pro Gln Pro Cys Cys Leu Val Ala His Asn Gly Asp Arg
        115                 120                 125

Tyr Asp Phe Pro Leu Leu Gln Thr Glu Leu Ala Arg Leu Ser Thr Pro
    130                 135                 140

Ser Pro Leu Asp Gly Thr Phe Cys Val Asp Ser Ile Ala Ala Leu Lys
145                 150                 155                 160

Ala Leu Glu Gln Ala Ser Ser Pro Ser Gly Asn Gly Ser Arg Lys Ser
                165                 170                 175

Tyr Ser Leu Gly Ser Ile Tyr Thr Arg Leu Tyr Trp Gln Ala Pro Thr
            180                 185                 190

Asp Ser His Thr Ala Glu Gly Asp Val Leu Thr Leu Leu Ser Ile Cys
        195                 200                 205

Gln Trp Lys Pro Gln Ala Leu Leu Gln Trp Val Asp Glu His Ala Arg
    210                 215                 220

Pro Phe Ser Thr Val Lys Pro Met Tyr Gly Thr Pro Ala Thr Thr Gly
225                 230                 235                 240

Thr Thr Asn Leu Arg Pro His Ala Ala Thr Ala Thr Thr Pro Leu Ala
                245                 250                 255

Thr Ala Asn Gly Ser Pro Ser Asn Gly Arg Ser Arg Arg Pro Lys Ser
            260                 265                 270

Pro Pro Pro Glu Lys Val Pro Glu Ala Pro Ser Gln Glu Gly Leu Leu
        275                 280                 285

Ala Pro Leu Ser Leu Leu Thr Leu Leu Thr Leu Ala Ile Ala Thr Leu
    290                 295                 300

Tyr Gly Leu Phe Leu Ala Ser Pro Gly Gln
305                 310
```

<210> SEQ ID NO 165
<211> LENGTH: 245
<212> TYPE: PRT
<213> ORGANISM: Mus sp.

<400> SEQUENCE: 165

```
Met Gly Ser Gln Thr Leu Pro His Gly His Met Gln Thr Leu Ile Phe
1               5                   10                  15

Leu Asp Leu Glu Ala Thr Gly Leu Pro Ser Ser Arg Pro Glu Val Thr
            20                  25                  30

Glu Leu Cys Leu Leu Ala Val His Arg Arg Ala Leu Glu Asn Thr Ser
        35                  40                  45

Ile Ser Gln Gly His Pro Pro Pro Val Pro Arg Pro Pro Arg Val Val
    50                  55                  60

Asp Lys Leu Ser Leu Cys Ile Ala Pro Gly Lys Ala Cys Ser Pro Gly
65                  70                  75                  80

Ala Ser Glu Ile Thr Gly Leu Ser Lys Ala Glu Leu Glu Val Gln Gly
                85                  90                  95

Arg Gln Arg Phe Asp Asp Asn Leu Ala Ile Leu Leu Arg Ala Phe Leu
            100                 105                 110

Gln Arg Gln Pro Gln Pro Cys Cys Leu Val Ala His Asn Gly Asp Arg
        115                 120                 125

Tyr Asp Phe Pro Leu Leu Gln Thr Glu Leu Ala Arg Leu Ser Thr Pro
    130                 135                 140

Ser Pro Leu Asp Gly Thr Phe Cys Val Asp Ser Ile Ala Ala Leu Lys
145                 150                 155                 160

Ala Leu Glu Gln Ala Ser Ser Pro Ser Gly Asn Gly Ser Arg Lys Ser
                165                 170                 175
```

```
Tyr Ser Leu Gly Ser Ile Tyr Thr Arg Leu Tyr Trp Gln Ala Pro Thr
            180                 185                 190

Asp Ser His Thr Ala Glu Gly Asp Val Leu Thr Leu Leu Ser Ile Cys
        195                 200                 205

Gln Trp Lys Pro Gln Ala Leu Leu Gln Trp Val Asp Glu His Ala Arg
    210                 215                 220

Pro Phe Ser Thr Val Lys Pro Met Tyr Gly Thr Pro Ala Thr Thr Gly
225                 230                 235                 240

Thr Thr Asp Leu Glu
                245


<210> SEQ ID NO 166
<211> LENGTH: 516
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Met Glu Thr Pro Ala Gln Leu Leu Phe Leu Leu Leu Leu Trp Leu Pro
1               5                   10                  15

Asp Thr Thr Gly Met Gly Ser Gln Thr Leu Pro His Gly His Met Gln
            20                  25                  30

Thr Leu Ile Phe Leu Asp Leu Glu Ala Thr Gly Leu Pro Ser Ser Arg
        35                  40                  45

Pro Glu Val Thr Glu Leu Cys Leu Leu Ala Val His Arg Arg Ala Leu
    50                  55                  60

Glu Asn Thr Ser Ile Ser Gln Gly His Pro Pro Pro Val Pro Arg Pro
65                  70                  75                  80

Pro Arg Val Val Asp Lys Leu Ser Leu Cys Ile Ala Pro Gly Lys Ala
                85                  90                  95

Cys Ser Pro Gly Ala Ser Glu Ile Thr Gly Leu Ser Lys Ala Glu Leu
            100                 105                 110

Glu Val Gln Gly Arg Gln Arg Phe Asp Asp Asn Leu Ala Ile Leu Leu
        115                 120                 125

Arg Ala Phe Leu Gln Arg Gln Pro Gln Pro Cys Cys Leu Val Ala His
    130                 135                 140

Asn Gly Asp Arg Tyr Asp Phe Pro Leu Leu Gln Thr Glu Leu Ala Arg
145                 150                 155                 160

Leu Ser Thr Pro Ser Pro Leu Asp Gly Thr Phe Cys Val Asp Ser Ile
                165                 170                 175

Ala Ala Leu Lys Ala Leu Glu Gln Ala Ser Ser Pro Ser Gly Asn Gly
            180                 185                 190

Ser Arg Lys Ser Tyr Ser Leu Gly Ser Ile Tyr Thr Arg Leu Tyr Trp
        195                 200                 205

Gln Ala Pro Thr Asp Ser His Thr Ala Glu Gly Asp Val Leu Thr Leu
    210                 215                 220

Leu Ser Ile Cys Gln Trp Lys Pro Gln Ala Leu Leu Gln Trp Val Asp
225                 230                 235                 240

Glu His Ala Arg Pro Phe Ser Thr Val Lys Pro Met Tyr Gly Thr Pro
                245                 250                 255

Ala Thr Thr Gly Thr Thr Gly Gly Gly Gly Ser Gly Gly Gly Gly Ser
            260                 265                 270

Gly Gly Gly Gly Ser Gly Gly Gly Gly Ser Leu Glu Pro Arg Gly Pro
```

```
        275                 280                 285

Thr Ile Lys Pro Ser Pro Pro Cys Lys Cys Pro Ala Pro Asn Leu Leu
    290                 295                 300

Gly Gly Ser Ser Val Phe Ile Phe Pro Pro Lys Ile Lys Asp Val Leu
305                 310                 315                 320

Met Ile Ser Leu Ser Pro Met Val Thr Cys Val Val Val Asp Val Ser
                325                 330                 335

Glu Asp Asp Pro Asp Val Gln Ile Ser Trp Phe Val Asn Asn Val Glu
            340                 345                 350

Val His Thr Ala Gln Thr Gln Thr His Arg Glu Asp Tyr Asn Ser Thr
        355                 360                 365

Leu Arg Val Val Ser Ala Leu Pro Ile Gln His Gln Asp Trp Met Ser
    370                 375                 380

Gly Lys Glu Phe Lys Cys Ser Val Asn Asn Lys Asp Leu Pro Ala Ser
385                 390                 395                 400

Ile Glu Arg Thr Ile Ser Lys Pro Arg Gly Pro Val Arg Ala Pro Gln
                405                 410                 415

Val Tyr Val Leu Pro Pro Pro Ala Glu Glu Met Thr Lys Lys Glu Phe
            420                 425                 430

Ser Leu Thr Cys Met Ile Thr Gly Phe Leu Pro Ala Glu Ile Ala Val
        435                 440                 445

Asp Trp Thr Ser Asn Gly Arg Thr Glu Gln Asn Tyr Lys Asn Thr Ala
    450                 455                 460

Thr Val Leu Asp Ser Asp Gly Ser Tyr Phe Met Tyr Ser Lys Leu Arg
465                 470                 475                 480

Val Gln Lys Ser Thr Trp Glu Arg Gly Ser Leu Phe Ala Cys Ser Val
                485                 490                 495

Val His Glu Gly Leu His Asn His Leu Thr Thr Lys Ser Phe Ser Arg
            500                 505                 510

Thr Pro Gly Lys
        515


<210> SEQ ID NO 167
<211> LENGTH: 521
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Met Glu Thr Pro Ala Gln Leu Leu Phe Leu Leu Leu Leu Trp Leu Pro
1               5                   10                  15

Asp Thr Thr Gly Met Gly Ser Gln Thr Leu Pro His Gly His Met Gln
            20                  25                  30

Thr Leu Ile Phe Leu Asp Leu Glu Ala Thr Gly Leu Pro Ser Ser Arg
        35                  40                  45

Pro Glu Val Thr Glu Leu Cys Leu Leu Ala Val His Arg Arg Ala Leu
    50                  55                  60

Glu Asn Thr Ser Ile Ser Gln Gly His Pro Pro Pro Val Pro Arg Pro
65                  70                  75                  80

Pro Arg Val Val Asp Lys Leu Ser Leu Cys Ile Ala Pro Gly Lys Ala
                85                  90                  95

Cys Ser Pro Gly Ala Ser Glu Ile Thr Gly Leu Ser Lys Ala Glu Leu
            100                 105                 110
```

```
Glu Val Gln Gly Arg Gln Arg Phe Asp Asp Asn Leu Ala Ile Leu Leu
        115                 120                 125

Arg Ala Phe Leu Gln Arg Gln Pro Gln Pro Cys Cys Leu Val Ala His
    130                 135                 140

Asn Gly Asp Arg Tyr Asp Phe Pro Leu Leu Gln Thr Glu Leu Ala Arg
145                 150                 155                 160

Leu Ser Thr Pro Ser Pro Leu Asp Gly Thr Phe Cys Val Asp Ser Ile
                165                 170                 175

Ala Ala Leu Lys Ala Leu Glu Gln Ala Ser Ser Pro Ser Gly Asn Gly
            180                 185                 190

Ser Arg Lys Ser Tyr Ser Leu Gly Ser Ile Tyr Thr Arg Leu Tyr Trp
        195                 200                 205

Gln Ala Pro Thr Asp Ser His Thr Ala Glu Gly Asp Val Leu Thr Leu
    210                 215                 220

Leu Ser Ile Cys Gln Trp Lys Pro Gln Ala Leu Leu Gln Trp Val Asp
225                 230                 235                 240

Glu His Ala Arg Pro Phe Ser Thr Val Lys Pro Met Tyr Gly Thr Pro
                245                 250                 255

Ala Thr Thr Gly Thr Thr Gly Gly Gly Gly Ser Gly Gly Gly Gly Ser
            260                 265                 270

Gly Gly Gly Gly Ser Gly Gly Gly Gly Ser Gly Gly Gly Gly Ser Leu
        275                 280                 285

Glu Pro Arg Gly Pro Thr Ile Lys Pro Ser Pro Pro Cys Lys Cys Pro
    290                 295                 300

Ala Pro Asn Leu Leu Gly Gly Ser Ser Val Phe Ile Phe Pro Pro Lys
305                 310                 315                 320

Ile Lys Asp Val Leu Met Ile Ser Leu Ser Pro Met Val Thr Cys Val
                325                 330                 335

Val Val Asp Val Ser Glu Asp Asp Pro Asp Val Gln Ile Ser Trp Phe
            340                 345                 350

Val Asn Asn Val Glu Val His Thr Ala Gln Thr Gln Thr His Arg Glu
        355                 360                 365

Asp Tyr Asn Ser Thr Leu Arg Val Val Ser Ala Leu Pro Ile Gln His
    370                 375                 380

Gln Asp Trp Met Ser Gly Lys Glu Phe Lys Cys Ser Val Asn Asn Lys
385                 390                 395                 400

Asp Leu Pro Ala Ser Ile Glu Arg Thr Ile Ser Lys Pro Arg Gly Pro
                405                 410                 415

Val Arg Ala Pro Gln Val Tyr Val Leu Pro Pro Pro Ala Glu Glu Met
            420                 425                 430

Thr Lys Lys Glu Phe Ser Leu Thr Cys Met Ile Thr Gly Phe Leu Pro
        435                 440                 445

Ala Glu Ile Ala Val Asp Trp Thr Ser Asn Gly Arg Thr Glu Gln Asn
    450                 455                 460

Tyr Lys Asn Thr Ala Thr Val Leu Asp Ser Asp Gly Ser Tyr Phe Met
465                 470                 475                 480

Tyr Ser Lys Leu Arg Val Gln Lys Ser Thr Trp Glu Arg Gly Ser Leu
                485                 490                 495

Phe Ala Cys Ser Val Val His Glu Gly Leu His Asn His Leu Thr Thr
            500                 505                 510

Lys Ser Phe Ser Arg Thr Pro Gly Lys
        515                 520
```

<210> SEQ ID NO 168
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 168

Val Asp Gly Ala Ser Ser Pro Val Asn Val Ser Ser Pro Ser Val Gln
1 5 10 15

Asp Ile

<210> SEQ ID NO 169
<211> LENGTH: 763
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 169

Met Glu Thr Pro Ala Gln Leu Leu Phe Leu Leu Leu Leu Trp Leu Pro
1 5 10 15

Asp Thr Thr Gly Met Gly Ser Gln Thr Leu Pro His Gly His Met Gln
20 25 30

Thr Leu Ile Phe Leu Asp Leu Glu Ala Thr Gly Leu Pro Ser Ser Arg
35 40 45

Pro Glu Val Thr Glu Leu Cys Leu Leu Ala Val His Arg Arg Ala Leu
50 55 60

Glu Asn Thr Ser Ile Ser Gln Gly His Pro Pro Pro Val Pro Arg Pro
65 70 75 80

Pro Arg Val Val Asp Lys Leu Ser Leu Cys Ile Ala Pro Gly Lys Ala
85 90 95

Cys Ser Pro Gly Ala Ser Glu Ile Thr Gly Leu Ser Lys Ala Glu Leu
100 105 110

Glu Val Gln Gly Arg Gln Arg Phe Asp Asp Asn Leu Ala Ile Leu Leu
115 120 125

Arg Ala Phe Leu Gln Arg Gln Pro Gln Pro Cys Cys Leu Val Ala His
130 135 140

Asn Gly Asp Arg Tyr Asp Phe Pro Leu Leu Gln Thr Glu Leu Ala Arg
145 150 155 160

Leu Ser Thr Pro Ser Pro Leu Asp Gly Thr Phe Cys Val Asp Ser Ile
165 170 175

Ala Ala Leu Lys Ala Leu Glu Gln Ala Ser Ser Pro Ser Gly Asn Gly
180 185 190

Ser Arg Lys Ser Tyr Ser Leu Gly Ser Ile Tyr Thr Arg Leu Tyr Trp
195 200 205

Gln Ala Pro Thr Asp Ser His Thr Ala Glu Gly Asp Val Leu Thr Leu
210 215 220

Leu Ser Ile Cys Gln Trp Lys Pro Gln Ala Leu Leu Gln Trp Val Asp
225 230 235 240

Glu His Ala Arg Pro Phe Ser Thr Val Lys Pro Met Tyr Gly Thr Pro
245 250 255

Ala Thr Thr Gly Thr Thr Met Gly Ser Gln Thr Leu Pro His Gly His
260 265 270

Met Gln Thr Leu Ile Phe Leu Asp Leu Glu Ala Thr Gly Leu Pro Ser
275 280 285

```
Ser Arg Pro Glu Val Thr Glu Leu Cys Leu Leu Ala Val His Arg Arg
    290                 295                 300

Ala Leu Glu Asn Thr Ser Ile Ser Gln Gly His Pro Pro Pro Val Pro
305                 310                 315                 320

Arg Pro Pro Arg Val Val Asp Lys Leu Ser Leu Cys Ile Ala Pro Gly
                325                 330                 335

Lys Ala Cys Ser Pro Gly Ala Ser Glu Ile Thr Gly Leu Ser Lys Ala
            340                 345                 350

Glu Leu Glu Val Gln Gly Arg Gln Arg Phe Asp Asp Asn Leu Ala Ile
        355                 360                 365

Leu Leu Arg Ala Phe Leu Gln Arg Gln Pro Gln Pro Cys Cys Leu Val
    370                 375                 380

Ala His Asn Gly Asp Arg Tyr Asp Phe Pro Leu Leu Gln Thr Glu Leu
385                 390                 395                 400

Ala Arg Leu Ser Thr Pro Ser Pro Leu Asp Gly Thr Phe Cys Val Asp
                405                 410                 415

Ser Ile Ala Ala Leu Lys Ala Leu Glu Gln Ala Ser Ser Pro Ser Gly
            420                 425                 430

Asn Gly Ser Arg Lys Ser Tyr Ser Leu Gly Ser Ile Tyr Thr Arg Leu
        435                 440                 445

Tyr Trp Gln Ala Pro Thr Asp Ser His Thr Ala Glu Gly Asp Val Leu
    450                 455                 460

Thr Leu Leu Ser Ile Cys Gln Trp Lys Pro Gln Ala Leu Leu Gln Trp
465                 470                 475                 480

Val Asp Glu His Ala Arg Pro Phe Ser Thr Val Lys Pro Met Tyr Gly
                485                 490                 495

Thr Pro Ala Thr Thr Gly Thr Thr Gly Gly Gly Gly Ser Gly Gly Gly
            500                 505                 510

Gly Ser Gly Gly Gly Gly Ser Gly Gly Gly Gly Ser Gly Gly Gly Gly
        515                 520                 525

Ser Leu Glu Pro Arg Gly Pro Thr Ile Lys Pro Ser Pro Pro Cys Lys
    530                 535                 540

Cys Pro Ala Pro Asn Leu Leu Gly Gly Ser Ser Val Phe Ile Phe Pro
545                 550                 555                 560

Pro Lys Ile Lys Asp Val Leu Met Ile Ser Leu Ser Pro Met Val Thr
                565                 570                 575

Cys Val Val Val Asp Val Ser Glu Asp Asp Pro Asp Val Gln Ile Ser
            580                 585                 590

Trp Phe Val Asn Asn Val Glu Val His Thr Ala Gln Thr Gln Thr His
        595                 600                 605

Arg Glu Asp Tyr Asn Ser Thr Leu Arg Val Val Ser Ala Leu Pro Ile
    610                 615                 620

Gln His Gln Asp Trp Met Ser Gly Lys Glu Phe Lys Cys Ser Val Asn
625                 630                 635                 640

Asn Lys Asp Leu Pro Ala Ser Ile Glu Arg Thr Ile Ser Lys Pro Arg
                645                 650                 655

Gly Pro Val Arg Ala Pro Gln Val Tyr Val Leu Pro Pro Pro Ala Glu
            660                 665                 670

Glu Met Thr Lys Lys Glu Phe Ser Leu Thr Cys Met Ile Thr Gly Phe
        675                 680                 685

Leu Pro Ala Glu Ile Ala Val Asp Trp Thr Ser Asn Gly Arg Thr Glu
    690                 695                 700
```

Gln Asn Tyr Lys Asn Thr Ala Thr Val Leu Asp Ser Asp Gly Ser Tyr
705 710 715 720

Phe Met Tyr Ser Lys Leu Arg Val Gln Lys Ser Thr Trp Glu Arg Gly
725 730 735

Ser Leu Phe Ala Cys Ser Val Val His Glu Gly Leu His Asn His Leu
740 745 750

Thr Thr Lys Ser Phe Ser Arg Thr Pro Gly Lys
755 760

<210> SEQ ID NO 170
<211> LENGTH: 570
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 170

Met Glu Thr Pro Ala Gln Leu Leu Phe Leu Leu Leu Leu Trp Leu Pro
1 5 10 15

Asp Thr Thr Gly Met Gly Pro Gly Ala Arg Arg Gln Gly Arg Ile Val
20 25 30

Gln Gly Arg Pro Glu Met Cys Phe Cys Pro Pro Pro Thr Pro Leu Pro
35 40 45

Pro Leu Arg Ile Leu Thr Leu Gly Thr His Thr Pro Thr Pro Cys Ser
50 55 60

Ser Pro Gly Ser Ala Ala Gly Thr Tyr Pro Thr Met Gly Ser Gln Ala
65 70 75 80

Leu Pro Pro Gly Pro Met Gln Thr Leu Ile Phe Phe Asp Met Glu Ala
85 90 95

Thr Gly Leu Pro Phe Ser Gln Pro Lys Val Thr Glu Leu Cys Leu Leu
100 105 110

Ala Val His Arg Cys Ala Leu Glu Ser Pro Pro Thr Ser Gln Gly Pro
115 120 125

Pro Pro Thr Val Pro Pro Pro Pro Arg Val Val Asp Lys Leu Ser Leu
130 135 140

Cys Val Ala Pro Gly Lys Ala Cys Ser Pro Ala Ala Ser Glu Ile Thr
145 150 155 160

Gly Leu Ser Thr Ala Val Leu Ala Ala His Gly Arg Gln Cys Phe Asp
165 170 175

Asp Asn Leu Ala Asn Leu Leu Leu Ala Phe Leu Arg Arg Gln Pro Gln
180 185 190

Pro Trp Cys Leu Val Ala His Asn Gly Asp Arg Tyr Asp Phe Pro Leu
195 200 205

Leu Gln Ala Glu Leu Ala Met Leu Gly Leu Thr Ser Ala Leu Asp Gly
210 215 220

Ala Phe Cys Val Asp Ser Ile Thr Ala Leu Lys Ala Leu Glu Arg Ala
225 230 235 240

Ser Ser Pro Ser Glu His Gly Pro Arg Lys Ser Tyr Ser Leu Gly Ser
245 250 255

Ile Tyr Thr Arg Leu Tyr Gly Gln Ser Pro Pro Asp Ser His Thr Ala
260 265 270

Glu Gly Asp Val Leu Ala Leu Leu Ser Ile Cys Gln Trp Arg Pro Gln
275 280 285

Ala Leu Leu Arg Trp Val Asp Ala His Ala Arg Pro Phe Gly Thr Ile
290 295 300

Arg Pro Met Tyr Gly Val Thr Ala Ser Ala Arg Thr Lys Gly Gly Gly
305 310 315 320

Gly Ser Gly Gly Gly Gly Ser Gly Gly Gly Gly Ser Gly Gly Gly Gly
325 330 335

Ser Leu Glu Pro Lys Ser Ser Asp Lys Thr His Thr Cys Pro Pro Cys
340 345 350

Pro Ala Pro Glu Leu Leu Gly Gly Pro Ser Val Phe Leu Phe Pro Pro
355 360 365

Lys Pro Lys Asp Thr Leu Met Ile Ser Arg Thr Pro Glu Val Thr Cys
370 375 380

Val Val Val Asp Val Ser His Glu Asp Pro Glu Val Lys Phe Asn Trp
385 390 395 400

Tyr Val Asp Gly Val Glu Val His Asn Ala Lys Thr Lys Pro Arg Glu
405 410 415

Glu Gln Tyr Asn Ser Thr Tyr Arg Val Val Ser Val Leu Thr Val Leu
420 425 430

His Gln Asp Trp Leu Asn Gly Lys Glu Tyr Lys Cys Lys Val Ser Asn
435 440 445

Lys Ala Leu Pro Ala Pro Ile Glu Lys Thr Ile Ser Lys Ala Lys Gly
450 455 460

Gln Pro Arg Glu Pro Gln Val Tyr Thr Leu Pro Pro Ser Arg Asp Glu
465 470 475 480

Leu Thr Lys Asn Gln Val Ser Leu Thr Cys Leu Val Lys Gly Phe Tyr
485 490 495

Pro Ser Asp Ile Ala Val Glu Trp Glu Ser Asn Gly Gln Pro Glu Asn
500 505 510

Asn Tyr Lys Thr Thr Pro Pro Val Leu Asp Ser Asp Gly Ser Phe Phe
515 520 525

Leu Tyr Ser Lys Leu Thr Val Asp Lys Ser Arg Trp Gln Gln Gly Asn
530 535 540

Val Phe Ser Cys Ser Val Met His Glu Ala Leu His Asn His Tyr Thr
545 550 555 560

Gln Lys Ser Leu Ser Leu Ser Pro Gly Lys
565 570

<210> SEQ ID NO 171
<211> LENGTH: 575
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 171

Met Glu Thr Pro Ala Gln Leu Leu Phe Leu Leu Leu Leu Trp Leu Pro
1 5 10 15

Asp Thr Thr Gly Met Gly Pro Gly Ala Arg Arg Gln Gly Arg Ile Val
20 25 30

Gln Gly Arg Pro Glu Met Cys Phe Cys Pro Pro Pro Thr Pro Leu Pro
35 40 45

Pro Leu Arg Ile Leu Thr Leu Gly Thr His Thr Pro Thr Pro Cys Ser
50 55 60

Ser Pro Gly Ser Ala Ala Gly Thr Tyr Pro Thr Met Gly Ser Gln Ala
65 70 75 80

Leu Pro Pro Gly Pro Met Gln Thr Leu Ile Phe Phe Asp Met Glu Ala

```
                85                  90                  95

Thr Gly Leu Pro Phe Ser Gln Pro Lys Val Thr Glu Leu Cys Leu Leu
            100                 105                 110

Ala Val His Arg Cys Ala Leu Glu Ser Pro Pro Thr Ser Gln Gly Pro
        115                 120                 125

Pro Pro Thr Val Pro Pro Pro Pro Arg Val Val Asp Lys Leu Ser Leu
    130                 135                 140

Cys Val Ala Pro Gly Lys Ala Cys Ser Pro Ala Ala Ser Glu Ile Thr
145                 150                 155                 160

Gly Leu Ser Thr Ala Val Leu Ala Ala His Gly Arg Gln Cys Phe Asp
                165                 170                 175

Asp Asn Leu Ala Asn Leu Leu Leu Ala Phe Leu Arg Arg Gln Pro Gln
            180                 185                 190

Pro Trp Cys Leu Val Ala His Asn Gly Asp Arg Tyr Asp Phe Pro Leu
        195                 200                 205

Leu Gln Ala Glu Leu Ala Met Leu Gly Leu Thr Ser Ala Leu Asp Gly
    210                 215                 220

Ala Phe Cys Val Asp Ser Ile Thr Ala Leu Lys Ala Leu Glu Arg Ala
225                 230                 235                 240

Ser Ser Pro Ser Glu His Gly Pro Arg Lys Ser Tyr Ser Leu Gly Ser
                245                 250                 255

Ile Tyr Thr Arg Leu Tyr Gly Gln Ser Pro Pro Asp Ser His Thr Ala
            260                 265                 270

Glu Gly Asp Val Leu Ala Leu Leu Ser Ile Cys Gln Trp Arg Pro Gln
        275                 280                 285

Ala Leu Leu Arg Trp Val Asp Ala His Ala Arg Pro Phe Gly Thr Ile
    290                 295                 300

Arg Pro Met Tyr Gly Val Thr Ala Ser Ala Arg Thr Lys Gly Gly Gly
305                 310                 315                 320

Gly Ser Gly Gly Gly Gly Ser Gly Gly Gly Gly Ser Gly Gly Gly Gly
                325                 330                 335

Ser Gly Gly Gly Gly Ser Leu Glu Pro Lys Ser Ser Asp Lys Thr His
            340                 345                 350

Thr Cys Pro Pro Cys Pro Ala Pro Glu Leu Leu Gly Gly Pro Ser Val
        355                 360                 365

Phe Leu Phe Pro Pro Lys Pro Lys Asp Thr Leu Met Ile Ser Arg Thr
    370                 375                 380

Pro Glu Val Thr Cys Val Val Val Asp Val Ser His Glu Asp Pro Glu
385                 390                 395                 400

Val Lys Phe Asn Trp Tyr Val Asp Gly Val Glu Val His Asn Ala Lys
                405                 410                 415

Thr Lys Pro Arg Glu Glu Gln Tyr Asn Ser Thr Tyr Arg Val Val Ser
            420                 425                 430

Val Leu Thr Val Leu His Gln Asp Trp Leu Asn Gly Lys Glu Tyr Lys
        435                 440                 445

Cys Lys Val Ser Asn Lys Ala Leu Pro Ala Pro Ile Glu Lys Thr Ile
    450                 455                 460

Ser Lys Ala Lys Gly Gln Pro Arg Glu Pro Gln Val Tyr Thr Leu Pro
465                 470                 475                 480

Pro Ser Arg Asp Glu Leu Thr Lys Asn Gln Val Ser Leu Thr Cys Leu
                485                 490                 495

Val Lys Gly Phe Tyr Pro Ser Asp Ile Ala Val Glu Trp Glu Ser Asn
            500                 505                 510
```

```
Gly Gln Pro Glu Asn Asn Tyr Lys Thr Thr Pro Pro Val Leu Asp Ser
        515                 520                 525

Asp Gly Ser Phe Phe Leu Tyr Ser Lys Leu Thr Val Asp Lys Ser Arg
    530                 535                 540

Trp Gln Gln Gly Asn Val Phe Ser Cys Ser Val Met His Glu Ala Leu
545                 550                 555                 560

His Asn His Tyr Thr Gln Lys Ser Leu Ser Leu Ser Pro Gly Lys
                565                 570                 575
```

<210> SEQ ID NO 172
<211> LENGTH: 2091
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 172

```
gttaagcttg ccaccatgga aaccccagcg cagcttctct tcctcctgct actctggctc     60

ccagatacca ccggtctgaa gatcgcagcc ttcaacatcc agacatttgg ggagaccaag    120

atgtccaatg ccaccctcgt cagctacatt gtgcagatcc tgagccgcta tgacatcgcc    180

ctggtccagg aggtcagaga cagccacctg actgccgtgg ggaagctgct ggacaacctc    240

aatcaggatg caccagacac ctatcactac gtggtcagtg agccactggg acggaacagc    300

tataaggagc gctacctgtt cgtgtacagg cctgaccagg tgtctgcggt ggacagctac    360

tactacgatg atggctgcga gccctgcagg aacgacacct tcaaccgaga gccattcatt    420

gtcaggttct tctcccggtt cacagaggtc agggagtttg ccattgttcc cctgcatgcg    480

gccccggggg acgcagtagc cgagatcgac gctctctatg acgtctacct ggatgtccaa    540

gagaaatggg gcttggagga cgtcatgttg atgggcgact tcaatgcggg ctgcagctat    600

gtgagaccct cccagtggtc atccatccgc ctgtggacaa gccccacctt ccagtggctg    660

atccccgaca gcgctgacac cacagctaca cccacgcact gtgcctatga caggatcgtg    720

gttgcaggga tgctgctccg aggcgccgtt gttcccgact cggctcttcc ctttaacttc    780

caggctgcct atggcctgag tgaccaactg gcccaagcca tcagtgacca ctatccagtg    840

gaggtgatgc tgaaagatct ctccggagga ggtggctcag gtggtggagg atctggagga    900

ggtgggagtg gtggaggtgg ttctaccggt ctcgagccca aatcttctga caaaactcac    960

acatgtccac cgtgcccagc acctgaactc ctggggggac cgtcagtctt cctcttcccc   1020

ccaaaaccca aggacaccct catgatctcc cggacccctg aggtcacatg cgtggtggtg   1080

gacgtgagcc acgaagaccc tgaggtcaag ttcaactggt acgtggacgg cgtggaggtg   1140

cataatgcca agacaaagcc gcgggaggag cagtacaaca gcacgtaccg tgtggtcagc   1200

gtcctcaccg tcctgcacca ggactggctg aatggcaagg agtacaagtg caaggtctcc   1260

aacaaagccc tcccagcccc catcgagaaa accatctcca aagccaaagg gcagccccga   1320

gaaccacagg tgtacaccct gcccccatcc cgggatgagc tgaccaagaa ccaggtcagc   1380

ctgacctgcc tggtcaaagg cttctatccc agcgacatcg ccgtggagtg ggagagcaat   1440

gggcagccgg agaacaacta caagaccacg cctcccgtgc tggactccga cggctccttc   1500

ttcctctaca gcaagctcac cgtggacaag agcaggtggc agcaggggaa cgtcttctca   1560

tgctccgtga tgcatgaggc tctgcacaac cactacacgc agaagagcct ctctctgtct   1620

ccgggtaaag tcgacggagc tagcagcccc gtgaacgtga gcagccccag cgtgcaggat   1680
```

```
atcccttccc tgggcaagga atcccgggcc aagaaattcc agcggcagca tatggactca   1740

gacagttccc ccagcagcag ctccacctac tgtaaccaaa tgatgaggcg ccggaatatg   1800

acacaggggc ggtgcaaacc agtgaacacc tttgtgcacg agcccctggt agatgtccag   1860

aatgtctgtt tccaggaaaa ggtcacctgc aagaacgggc agggcaactg ctacaagagc   1920

aactccagca tgcacatcac agactgccgc ctgacaaacg gctccaggta ccccaactgt   1980

gcataccgga ccagcccgaa ggagagacac atcattgtgg cctgtgaagg gagcccatat   2040

gtgccagtcc actttgatgc ttctgtggag gactctacct aataatctag a            2091


<210> SEQ ID NO 173
<211> LENGTH: 679
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Met Glu Thr Pro Ala Gln Leu Leu Phe Leu Leu Leu Leu Trp Leu Pro
1               5                   10                  15

Asp Thr Thr Gly Leu Lys Ile Ala Ala Phe Asn Ile Gln Thr Phe Gly
            20                  25                  30

Glu Thr Lys Met Ser Asn Ala Thr Leu Val Ser Tyr Ile Val Gln Ile
        35                  40                  45

Leu Ser Arg Tyr Asp Ile Ala Leu Val Gln Glu Val Arg Asp Ser His
    50                  55                  60

Leu Thr Ala Val Gly Lys Leu Leu Asp Asn Leu Asn Gln Asp Ala Pro
65                  70                  75                  80

Asp Thr Tyr His Tyr Val Val Ser Glu Pro Leu Gly Arg Asn Ser Tyr
                85                  90                  95

Lys Glu Arg Tyr Leu Phe Val Tyr Arg Pro Asp Gln Val Ser Ala Val
            100                 105                 110

Asp Ser Tyr Tyr Tyr Asp Asp Gly Cys Glu Pro Cys Arg Asn Asp Thr
        115                 120                 125

Phe Asn Arg Glu Pro Phe Ile Val Arg Phe Phe Ser Arg Phe Thr Glu
    130                 135                 140

Val Arg Glu Phe Ala Ile Val Pro Leu His Ala Ala Pro Gly Asp Ala
145                 150                 155                 160

Val Ala Glu Ile Asp Ala Leu Tyr Asp Val Tyr Leu Asp Val Gln Glu
                165                 170                 175

Lys Trp Gly Leu Glu Asp Val Met Leu Met Gly Asp Phe Asn Ala Gly
            180                 185                 190

Cys Ser Tyr Val Arg Pro Ser Gln Trp Ser Ser Ile Arg Leu Trp Thr
        195                 200                 205

Ser Pro Thr Phe Gln Trp Leu Ile Pro Asp Ser Ala Asp Thr Thr Ala
    210                 215                 220

Thr Pro Thr His Cys Ala Tyr Asp Arg Ile Val Val Ala Gly Met Leu
225                 230                 235                 240

Leu Arg Gly Ala Val Val Pro Asp Ser Ala Leu Pro Phe Asn Phe Gln
                245                 250                 255

Ala Ala Tyr Gly Leu Ser Asp Gln Leu Ala Gln Ala Ile Ser Asp His
            260                 265                 270

Tyr Pro Val Glu Val Met Leu Lys Gly Gly Gly Gly Ser Gly Gly Gly
        275                 280                 285
```

```
Gly Ser Gly Gly Gly Gly Ser Gly Gly Gly Gly Ser Leu Glu Pro Lys
    290                 295                 300

Ser Ser Asp Lys Thr His Thr Cys Pro Pro Cys Pro Ala Pro Glu Leu
305                 310                 315                 320

Leu Gly Gly Pro Ser Val Phe Leu Phe Pro Pro Lys Pro Lys Asp Thr
                325                 330                 335

Leu Met Ile Ser Arg Thr Pro Glu Val Thr Cys Val Val Val Asp Val
            340                 345                 350

Ser His Glu Asp Pro Glu Val Lys Phe Asn Trp Tyr Val Asp Gly Val
        355                 360                 365

Glu Val His Asn Ala Lys Thr Lys Pro Arg Glu Glu Gln Tyr Asn Ser
    370                 375                 380

Thr Tyr Arg Val Val Ser Val Leu Thr Val Leu His Gln Asp Trp Leu
385                 390                 395                 400

Asn Gly Lys Glu Tyr Lys Cys Lys Val Ser Asn Lys Ala Leu Pro Ala
                405                 410                 415

Pro Ile Glu Lys Thr Ile Ser Lys Ala Lys Gly Gln Pro Arg Glu Pro
            420                 425                 430

Gln Val Tyr Thr Leu Pro Pro Ser Arg Asp Glu Leu Thr Lys Asn Gln
        435                 440                 445

Val Ser Leu Thr Cys Leu Val Lys Gly Phe Tyr Pro Ser Asp Ile Ala
    450                 455                 460

Val Glu Trp Glu Ser Asn Gly Gln Pro Glu Asn Asn Tyr Lys Thr Thr
465                 470                 475                 480

Pro Pro Val Leu Asp Ser Asp Gly Ser Phe Phe Leu Tyr Ser Lys Leu
                485                 490                 495

Thr Val Asp Lys Ser Arg Trp Gln Gln Gly Asn Val Phe Ser Cys Ser
            500                 505                 510

Val Met His Glu Ala Leu His Asn His Tyr Thr Gln Lys Ser Leu Ser
        515                 520                 525

Leu Ser Pro Gly Lys Val Asp Gly Ala Ser Ser Pro Val Asn Val Ser
    530                 535                 540

Ser Pro Ser Val Gln Asp Ile Lys Glu Ser Arg Ala Lys Lys Phe Gln
545                 550                 555                 560

Arg Gln His Met Asp Ser Asp Ser Ser Pro Ser Ser Ser Ser Thr Tyr
                565                 570                 575

Cys Asn Gln Met Met Arg Arg Arg Asn Met Thr Gln Gly Arg Cys Lys
            580                 585                 590

Pro Val Asn Thr Phe Val His Glu Pro Leu Val Asp Val Gln Asn Val
        595                 600                 605

Cys Phe Gln Glu Lys Val Thr Cys Lys Asn Gly Gln Gly Asn Cys Tyr
    610                 615                 620

Lys Ser Asn Ser Ser Met His Ile Thr Asp Cys Arg Leu Thr Asn Gly
625                 630                 635                 640

Ser Arg Tyr Pro Asn Cys Ala Tyr Arg Thr Ser Pro Lys Glu Arg His
                645                 650                 655

Ile Ile Val Ala Cys Glu Gly Ser Pro Tyr Val Pro Val His Phe Asp
            660                 665                 670

Ala Ser Val Glu Asp Ser Thr
        675
```

<210> SEQ ID NO 174
<211> LENGTH: 1185

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 174

```
gttaagcttg ccaccatgga aaccccagcg cagcttctct tcctcctgct actctggctc     60
ccagatacca ccggtccttc cctgggcaag gaatcccggg ccaagaaatt ccagcggcag    120
catatggact cagacagttc ccccagcagc agctccacct actgtaacca aatgatgagg    180
cgccggaata tgacacaggg gcggtgcaaa ccagtgaaca cctttgtgca cgagcccctg    240
gtagatgtcc agaatgtctg tttccaggaa aaggtcacct gcaagaacgg gcagggcaac    300
tgctacaaga gcaactccag catgcacatc acagactgcc gcctgacaaa cgactccagg    360
taccccaact gtgcataccg gaccagcccg aaggagagac acatcattgt ggcctgtgaa    420
gggagcccat atgtgccagt ccactttgat gcttctgtgg aggactctac agatctcgag    480
cccaaatctt ctgacaaaac tcacacatgt ccaccgtgtc cagcacctga actcctgggt    540
ggatcgtcag tcttcctctt ccccccaaaa cccaaggaca ctctcatgat ctcccggacc    600
cctgaggtca cgtgcgtggt ggtggacgtg agccaggaag accccgaggt ccagttcaac    660
tggtacgtgg acggcatgga ggtgcataat gccaagacaa agccacggga ggagcagttc    720
aacagcacgt tccgtgtggt cagcgtcctc accgtcgtgc accaggactg gctgaacggc    780
aaggagtaca agtgcaaggt ctccaacaaa gccctcccag cctccatcga gaaaacaatc    840
tccaaaacca aagggcagcc ccgagaacca caggtgtaca ccctgccccc atcccgggag    900
gagatgacca agaaccaggt cagcctgacc tgcctggtca aaggcttcta tcccagcgac    960
atcgccgtgg agtgggagag caatgggcag ccggagaaca actacaacac cacgcctccc   1020
gtgctggact ccgacggctc cttctccctc tacagcaagc tcaccgtgga caagagcagg   1080
tggcagcagg ggaacgtctt ctcatgctcc gtgatgcatg aggctctgca caaccactac   1140
acgcagaaga gcctctctct gtctccgggt aaatgataat ctaga                   1185
```

<210> SEQ ID NO 175
<211> LENGTH: 381
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 175

```
Met Glu Thr Pro Ala Gln Leu Leu Phe Leu Leu Leu Leu Trp Leu Pro
1               5                   10                  15

Asp Thr Thr Gly Lys Glu Ser Arg Ala Lys Lys Phe Gln Arg Gln His
            20                  25                  30

Met Asp Ser Asp Ser Ser Pro Ser Ser Ser Ser Thr Tyr Cys Asn Gln
        35                  40                  45

Met Met Arg Arg Arg Asn Met Thr Gln Gly Arg Cys Lys Pro Val Asn
    50                  55                  60

Thr Phe Val His Glu Pro Leu Val Asp Val Gln Asn Val Cys Phe Gln
65                  70                  75                  80

Glu Lys Val Thr Cys Lys Asn Gly Gln Gly Asn Cys Tyr Lys Ser Asn
                85                  90                  95

Ser Ser Met His Ile Thr Asp Cys Arg Leu Thr Asn Asp Ser Arg Tyr
            100                 105                 110
```

```
Pro Asn Cys Ala Tyr Arg Thr Ser Pro Lys Glu Arg His Ile Ile Val
        115                 120                 125

Ala Cys Glu Gly Ser Pro Tyr Val Pro Val His Phe Asp Ala Ser Val
    130                 135                 140

Glu Asp Ser Thr Leu Glu Pro Lys Ser Ser Asp Lys Thr His Thr Cys
145                 150                 155                 160

Pro Pro Cys Pro Ala Pro Glu Leu Leu Gly Gly Ser Ser Val Phe Leu
                165                 170                 175

Phe Pro Pro Lys Pro Lys Asp Thr Leu Met Ile Ser Arg Thr Pro Glu
            180                 185                 190

Val Thr Cys Val Val Val Asp Val Ser Gln Glu Asp Pro Glu Val Gln
        195                 200                 205

Phe Asn Trp Tyr Val Asp Gly Met Glu Val His Asn Ala Lys Thr Lys
    210                 215                 220

Pro Arg Glu Glu Gln Phe Asn Ser Thr Phe Arg Val Val Ser Val Leu
225                 230                 235                 240

Thr Val Val His Gln Asp Trp Leu Asn Gly Lys Glu Tyr Lys Cys Lys
                245                 250                 255

Val Ser Asn Lys Ala Leu Pro Ala Ser Ile Glu Lys Thr Ile Ser Lys
            260                 265                 270

Thr Lys Gly Gln Pro Arg Glu Pro Gln Val Tyr Thr Leu Pro Pro Ser
        275                 280                 285

Arg Glu Glu Met Thr Lys Asn Gln Val Ser Leu Thr Cys Leu Val Lys
    290                 295                 300

Gly Phe Tyr Pro Ser Asp Ile Ala Val Glu Trp Glu Ser Asn Gly Gln
305                 310                 315                 320

Pro Glu Asn Asn Tyr Asn Thr Thr Pro Pro Val Leu Asp Ser Asp Gly
                325                 330                 335

Ser Phe Ser Leu Tyr Ser Lys Leu Thr Val Asp Lys Ser Arg Trp Gln
            340                 345                 350

Gln Gly Asn Val Phe Ser Cys Ser Val Met His Glu Ala Leu His Asn
        355                 360                 365

His Tyr Thr Gln Lys Ser Leu Ser Leu Ser Pro Gly Lys
    370                 375                 380
```

<210> SEQ ID NO 176
<211> LENGTH: 2106
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 176

```
gttaagcttg ccaccatgga aaccccagcg cagcttctct tcctcctgct actctggctc     60

ccagatacca ccggtctgaa gatcgcagcc ttcaacatcc agacatttgg ggagaccaag    120

atgtccaatg ccaccctcgt cagctacatt gtgcagatcc tgagccgcta tgacatcgcc    180

ctggtccagg aggtcagaga cagccacctg actgccgtgg ggaagctgct ggacaacctc    240

aatcaggatg caccagacac ctatcactac gtggtcagtg agccactggg acggaacagc    300

tataaggagc gctacctgtt cgtgtacagg cctgaccagg tgtctgcggt ggacagctac    360

tactacgatg atggctgcga gccctgcagg aacgacacct tcaaccgaga gccattcatt    420

gtcaggttct tctcccggtt cacagaggtc agggagtttg ccattgttcc cctgcatgcg    480
```

```
gccccggggg acgcagtagc cgagatcgac gctctctatg acgtctacct ggatgtccaa    540

gagaaatggg gcttggagga cgtcatgttg atgggcgact tcaatgcggg ctgcagctat    600

gtgagaccct cccagtggtc atccatccgc ctgtggacaa gccccacctt ccagtggctg    660

atccccgaca gcgctgacac cacagctaca cccacgcact gtgcctatga caggatcgtg    720

gttgcaggga tgctgctccg aggcgccgtt gttcccgact cggctcttcc ctttaacttc    780

caggctgcct atggcctgag tgaccaactg gcccaagcca tcagtgacca ctatccagtg    840

gaggtgatgc tgaaagatct ctccggagga ggtggctcag gtggtggagg atctggagga    900

ggtggctcag gtggtggagg atctggagga ggtgggagta ccggtctcga gcccaaatct    960

tctgacaaaa ctcacacatg tccaccgtgc ccagcacctg aactcctggg gggaccgtca   1020

gtcttcctct tccccccaaa acccaaggac accctcatga tctcccggac ccctgaggtc   1080

acatgcgtgg tggtggacgt gagccacgaa gaccctgagg tcaagttcaa ctggtacgtg   1140

gacggcgtgg aggtgcataa tgccaagaca aagccgcggg aggagcagta caacagcacg   1200

taccgtgtgg tcagcgtcct caccgtcctg caccaggact ggctgaatgg caaggagtac   1260

aagtgcaagg tctccaacaa agccctccca gcccccatcg agaaaaccat ctccaaagcc   1320

aaagggcagc cccgagaacc acaggtgtac accctgcccc catcccggga tgagctgacc   1380

aagaaccagg tcagcctgac ctgcctggtc aaaggcttct atcccagcga catcgccgtg   1440

gagtgggaga gcaatgggca gccggagaac aactacaaga ccacgcctcc cgtgctggac   1500

tccgacggct ccttcttcct ctacagcaag ctcaccgtgg acaagagcag gtggcagcag   1560

gggaacgtct tctcatgctc cgtgatgcat gaggctctgc acaaccacta cacgcagaag   1620

agcctctctc tgtctccggg taaagtcgac ggagctagca gccccgtgaa cgtgagcagc   1680

cccagcgtgc aggatatccc ttccctgggc aaggaatccc gggccaagaa attccagcgg   1740

cagcatatgg actcagacag ttcccccagc agcagctcca cctactgtaa ccaaatgatg   1800

aggcgccgga atatgacaca ggggcggtgc aaaccagtga acacctttgt gcacgagccc   1860

ctggtagatg tccagaatgt ctgtttccag gaaaaggtca cctgcaagaa cgggcagggc   1920

aactgctaca agagcaactc cagcatgcac atcacagact gccgcctgac aaacggctcc   1980

aggtacccca actgtgcata ccggaccagc ccgaaggaga gacacatcat tgtggcctgt   2040

gaagggagcc catatgtgcc agtccacttt gatgcttctg tggaggactc tacctaataa   2100

tctaga                                                              2106
```

<210> SEQ ID NO 177
<211> LENGTH: 684
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

```
Met Glu Thr Pro Ala Gln Leu Leu Phe Leu Leu Leu Leu Trp Leu Pro
1               5                   10                  15

Asp Thr Thr Gly Leu Lys Ile Ala Ala Phe Asn Ile Gln Thr Phe Gly
            20                  25                  30

Glu Thr Lys Met Ser Asn Ala Thr Leu Val Ser Tyr Ile Val Gln Ile
        35                  40                  45

Leu Ser Arg Tyr Asp Ile Ala Leu Val Gln Glu Val Arg Asp Ser His
    50                  55                  60
```

```
Leu Thr Ala Val Gly Lys Leu Leu Asp Asn Leu Asn Gln Asp Ala Pro
65                  70                  75                  80

Asp Thr Tyr His Tyr Val Val Ser Glu Pro Leu Gly Arg Asn Ser Tyr
                85                  90                  95

Lys Glu Arg Tyr Leu Phe Val Tyr Arg Pro Asp Gln Val Ser Ala Val
            100                 105                 110

Asp Ser Tyr Tyr Tyr Asp Asp Gly Cys Glu Pro Cys Arg Asn Asp Thr
        115                 120                 125

Phe Asn Arg Glu Pro Phe Ile Val Arg Phe Phe Ser Arg Phe Thr Glu
    130                 135                 140

Val Arg Glu Phe Ala Ile Val Pro Leu His Ala Ala Pro Gly Asp Ala
145                 150                 155                 160

Val Ala Glu Ile Asp Ala Leu Tyr Asp Val Tyr Leu Asp Val Gln Glu
                165                 170                 175

Lys Trp Gly Leu Glu Asp Val Met Leu Met Gly Asp Phe Asn Ala Gly
            180                 185                 190

Cys Ser Tyr Val Arg Pro Ser Gln Trp Ser Ser Ile Arg Leu Trp Thr
        195                 200                 205

Ser Pro Thr Phe Gln Trp Leu Ile Pro Asp Ser Ala Asp Thr Thr Ala
    210                 215                 220

Thr Pro Thr His Cys Ala Tyr Asp Arg Ile Val Val Ala Gly Met Leu
225                 230                 235                 240

Leu Arg Gly Ala Val Val Pro Asp Ser Ala Leu Pro Phe Asn Phe Gln
                245                 250                 255

Ala Ala Tyr Gly Leu Ser Asp Gln Leu Ala Gln Ala Ile Ser Asp His
            260                 265                 270

Tyr Pro Val Glu Val Met Leu Lys Gly Gly Gly Gly Ser Gly Gly Gly
        275                 280                 285

Gly Ser Gly Gly Gly Gly Ser Gly Gly Gly Gly Ser Gly Gly Gly Gly
    290                 295                 300

Ser Leu Glu Pro Lys Ser Ser Asp Lys Thr His Thr Cys Pro Pro Cys
305                 310                 315                 320

Pro Ala Pro Glu Leu Leu Gly Gly Pro Ser Val Phe Leu Phe Pro Pro
                325                 330                 335

Lys Pro Lys Asp Thr Leu Met Ile Ser Arg Thr Pro Glu Val Thr Cys
            340                 345                 350

Val Val Val Asp Val Ser His Glu Asp Pro Glu Val Lys Phe Asn Trp
        355                 360                 365

Tyr Val Asp Gly Val Glu Val His Asn Ala Lys Thr Lys Pro Arg Glu
    370                 375                 380

Glu Gln Tyr Asn Ser Thr Tyr Arg Val Val Ser Val Leu Thr Val Leu
385                 390                 395                 400

His Gln Asp Trp Leu Asn Gly Lys Glu Tyr Lys Cys Lys Val Ser Asn
                405                 410                 415

Lys Ala Leu Pro Ala Pro Ile Glu Lys Thr Ile Ser Lys Ala Lys Gly
            420                 425                 430

Gln Pro Arg Glu Pro Gln Val Tyr Thr Leu Pro Pro Ser Arg Asp Glu
        435                 440                 445

Leu Thr Lys Asn Gln Val Ser Leu Thr Cys Leu Val Lys Gly Phe Tyr
    450                 455                 460

Pro Ser Asp Ile Ala Val Glu Trp Glu Ser Asn Gly Gln Pro Glu Asn
465                 470                 475                 480

Asn Tyr Lys Thr Thr Pro Pro Val Leu Asp Ser Asp Gly Ser Phe Phe
```

```
                485                 490                 495

Leu Tyr Ser Lys Leu Thr Val Asp Lys Ser Arg Trp Gln Gln Gly Asn
            500                 505                 510

Val Phe Ser Cys Ser Val Met His Glu Ala Leu His Asn His Tyr Thr
        515                 520                 525

Gln Lys Ser Leu Ser Leu Ser Pro Gly Lys Val Asp Gly Ala Ser Ser
    530                 535                 540

Pro Val Asn Val Ser Ser Pro Ser Val Gln Asp Ile Lys Glu Ser Arg
545                 550                 555                 560

Ala Lys Lys Phe Gln Arg Gln His Met Asp Ser Asp Ser Ser Pro Ser
                565                 570                 575

Ser Ser Ser Thr Tyr Cys Asn Gln Met Met Arg Arg Arg Asn Met Thr
            580                 585                 590

Gln Gly Arg Cys Lys Pro Val Asn Thr Phe Val His Glu Pro Leu Val
        595                 600                 605

Asp Val Gln Asn Val Cys Phe Gln Glu Lys Val Thr Cys Lys Asn Gly
    610                 615                 620

Gln Gly Asn Cys Tyr Lys Ser Asn Ser Ser Met His Ile Thr Asp Cys
625                 630                 635                 640

Arg Leu Thr Asn Gly Ser Arg Tyr Pro Asn Cys Ala Tyr Arg Thr Ser
                645                 650                 655

Pro Lys Glu Arg His Ile Ile Val Ala Cys Glu Gly Ser Pro Tyr Val
            660                 665                 670

Pro Val His Phe Asp Ala Ser Val Glu Asp Ser Thr
        675                 680


<210> SEQ ID NO 178
<211> LENGTH: 2100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 178

gttaagcttg ccaccatgga aaccccagcg cagcttctct tcctcctgct actctggctc     60

ccagatacca ccggtctgaa gatcgcagcc ttcaacatcc agacatttgg ggagaccaag    120

atgtccaatg ccaccctcgt cagctacatt gtgcagatcc tgagccgcta tgacatcgcc    180

ctggtccagg aggtcagaga cagccacctg actgccgtgg ggaagctgct ggacaacctc    240

aatcaggatg caccagacac ctatcactac gtggtcagtg agccactggg acggaacagc    300

tataaggagc gctacctgtt cgtgtacagg cctgaccagg tgtctgcggt ggacagctac    360

tactacgatg atggctgcga gccctgcagg aacgacacct tcaaccgaga gccattcatt    420

gtcaggttct tctcccggtt cacagaggtc agggagtttg ccattgttcc cctgcatgcg    480

gccccggggg acgcagtagc cgagatcgac gctctctatg acgtctacct ggatgtccaa    540

gagaaatggg gcttggagga cgtcatgttg atgggcgact tcaatgcggg ctgcagctat    600

gtgagaccct cccagtggtc atccatccgc ctgtggacaa gccccacctt ccagtggctg    660

atccccgaca gcgctgacac cacagctaca cccacgcact gtgcctatga caggatcgtg    720

gttgcaggga tgctgctccg aggcgccgtt gttcccgact cggctcttcc ctttaacttc    780

caggctgcct atggcctgag tgaccaactg gcccaagcca tcagtgacca ctatccagtg    840

gaggtgatgc tgaaagatct ctccggagga ggtggctcag gtggtggagg atctggagga    900
```

ggtggctcag gtggtggagg atctggagga ggtgggagtc tcgagcccaa atcttctgac 960
aaaactcaca catgtccacc gtgcccagca cctgaactcc tggggggacc gtcagtcttc 1020
ctcttccccc caaaacccaa ggacaccctc atgatctccc ggacccctga ggtcacatgc 1080
gtggtggtgg acgtgagcca cgaagaccct gaggtcaagt tcaactggta cgtggacggc 1140
gtggaggtgc ataatgccaa gacaaagccg cgggaggagc agtacaacag cacgtaccgt 1200
gtggtcagcg tcctcaccgt cctgcaccag gactggctga atggcaagga gtacaagtgc 1260
aaggtctcca acaaagccct cccagccccc atcgagaaaa ccatctccaa agccaaaggg 1320
cagccccgag aaccacaggt gtacaccctg cccccatccc gggatgagct gaccaagaac 1380
caggtcagcc tgacctgcct ggtcaaaggc ttctatccca gcgacatcgc cgtggagtgg 1440
gagagcaatg ggcagccgga gaacaactac aagaccacgc ctcccgtgct ggactccgac 1500
ggctccttct tcctctacag caagctcacc gtggacaaga gcaggtggca gcaggggaac 1560
gtcttctcat gctccgtgat gcatgaggct ctgcacaacc actacacgca gaagagcctc 1620
tctctgtctc cgggtaaagt cgacggagct agcagccccg tgaacgtgag cagccccagc 1680
gtgcaggata tcccttccct gggcaaggaa tcccgggcca agaaattcca gcggcagcat 1740
atggactcag acagttcccc cagcagcagc tccacctact gtaaccaaat gatgaggcgc 1800
cggaatatga cacaggggcg gtgcaaacca gtgaacacct ttgtgcacga gcccctggta 1860
gatgtccaga atgtctgttt ccaggaaaag gtcacctgca agaacgggca gggcaactgc 1920
tacaagagca actccagcat gcacatcaca gactgccgcc tgacaaacgg ctccaggtac 1980
cccaactgtg cataccggac cagcccgaag gagagacaca tcattgtggc ctgtgaaggg 2040
agcccatatg tgccagtcca ctttgatgct tctgtggagg actctaccta ataatctaga 2100

<210> SEQ ID NO 179
<211> LENGTH: 684
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 179

Met Glu Thr Pro Ala Gln Leu Leu Phe Leu Leu Leu Leu Trp Leu Pro
1               5                   10                  15

Asp Thr Thr Gly Leu Lys Ile Ala Ala Phe Asn Ile Gln Thr Phe Gly
            20                  25                  30

Glu Thr Lys Met Ser Asn Ala Thr Leu Val Ser Tyr Ile Val Gln Ile
        35                  40                  45

Leu Ser Arg Tyr Asp Ile Ala Leu Val Gln Glu Val Arg Asp Ser His
    50                  55                  60

Leu Thr Ala Val Gly Lys Leu Leu Asp Asn Leu Asn Gln Asp Ala Pro
65                  70                  75                  80

Asp Thr Tyr His Tyr Val Val Ser Glu Pro Leu Gly Arg Asn Ser Tyr
                85                  90                  95

Lys Glu Arg Tyr Leu Phe Val Tyr Arg Pro Asp Gln Val Ser Ala Val
            100                 105                 110

Asp Ser Tyr Tyr Tyr Asp Asp Gly Cys Glu Pro Cys Arg Asn Asp Thr
        115                 120                 125

Phe Asn Arg Glu Pro Phe Ile Val Arg Phe Phe Ser Arg Phe Thr Glu
    130                 135                 140

Val Arg Glu Phe Ala Ile Val Pro Leu His Ala Ala Pro Gly Asp Ala

-continued

```
145                 150                 155                 160

Val Ala Glu Ile Asp Ala Leu Tyr Asp Val Tyr Leu Asp Val Gln Glu
                165                 170                 175

Lys Trp Gly Leu Glu Asp Val Met Leu Met Gly Asp Phe Asn Ala Gly
            180                 185                 190

Cys Ser Tyr Val Arg Pro Ser Gln Trp Ser Ser Ile Arg Leu Trp Thr
        195                 200                 205

Ser Pro Thr Phe Gln Trp Leu Ile Pro Asp Ser Ala Asp Thr Thr Ala
    210                 215                 220

Thr Pro Thr His Cys Ala Tyr Asp Arg Ile Val Val Ala Gly Met Leu
225                 230                 235                 240

Leu Arg Gly Ala Val Val Pro Asp Ser Ala Leu Pro Phe Asn Phe Gln
                245                 250                 255

Ala Ala Tyr Gly Leu Ser Asp Gln Leu Ala Gln Ala Ile Ser Asp His
            260                 265                 270

Tyr Pro Val Glu Val Met Leu Lys Gly Gly Gly Gly Ser Gly Gly Gly
        275                 280                 285

Gly Ser Gly Gly Gly Gly Ser Gly Gly Gly Gly Ser Gly Gly Gly Gly
    290                 295                 300

Ser Leu Glu Pro Lys Ser Ser Asp Lys Thr His Thr Cys Pro Pro Cys
305                 310                 315                 320

Pro Ala Pro Glu Leu Leu Gly Gly Pro Ser Val Phe Leu Phe Pro Pro
                325                 330                 335

Lys Pro Lys Asp Thr Leu Met Ile Ser Arg Thr Pro Glu Val Thr Cys
            340                 345                 350

Val Val Val Asp Val Ser His Glu Asp Pro Glu Val Lys Phe Asn Trp
        355                 360                 365

Tyr Val Asp Gly Val Glu Val His Asn Ala Lys Thr Lys Pro Arg Glu
    370                 375                 380

Glu Gln Tyr Asn Ser Thr Tyr Arg Val Val Ser Val Leu Thr Val Leu
385                 390                 395                 400

His Gln Asp Trp Leu Asn Gly Lys Glu Tyr Lys Cys Lys Val Ser Asn
                405                 410                 415

Lys Ala Leu Pro Ala Pro Ile Glu Lys Thr Ile Ser Lys Ala Lys Gly
            420                 425                 430

Gln Pro Arg Glu Pro Gln Val Tyr Thr Leu Pro Pro Ser Arg Asp Glu
        435                 440                 445

Leu Thr Lys Asn Gln Val Ser Leu Thr Cys Leu Val Lys Gly Phe Tyr
    450                 455                 460

Pro Ser Asp Ile Ala Val Glu Trp Glu Ser Asn Gly Gln Pro Glu Asn
465                 470                 475                 480

Asn Tyr Lys Thr Thr Pro Pro Val Leu Asp Ser Asp Gly Ser Phe Phe
                485                 490                 495

Leu Tyr Ser Lys Leu Thr Val Asp Lys Ser Arg Trp Gln Gln Gly Asn
            500                 505                 510

Val Phe Ser Cys Ser Val Met His Glu Ala Leu His Asn His Tyr Thr
        515                 520                 525

Gln Lys Ser Leu Ser Leu Ser Pro Gly Lys Val Asp Gly Ala Ser Ser
    530                 535                 540

Pro Val Asn Val Ser Ser Pro Ser Val Gln Asp Ile Lys Glu Ser Arg
545                 550                 555                 560

Ala Lys Lys Phe Gln Arg Gln His Met Asp Ser Asp Ser Ser Pro Ser
                565                 570                 575
```

```
Ser Ser Ser Thr Tyr Cys Asn Gln Met Met Arg Arg Arg Asn Met Thr
            580                 585                 590

Gln Gly Arg Cys Lys Pro Val Asn Thr Phe Val His Glu Pro Leu Val
        595                 600                 605

Asp Val Gln Asn Val Cys Phe Gln Glu Lys Val Thr Cys Lys Asn Gly
    610                 615                 620

Gln Gly Asn Cys Tyr Lys Ser Asn Ser Ser Met His Ile Thr Asp Cys
625                 630                 635                 640

Arg Leu Thr Asn Gly Ser Arg Tyr Pro Asn Cys Ala Tyr Arg Thr Ser
                645                 650                 655

Pro Lys Glu Arg His Ile Ile Val Ala Cys Glu Gly Ser Pro Tyr Val
            660                 665                 670

Pro Val His Phe Asp Ala Ser Val Glu Asp Ser Thr
        675                 680


<210> SEQ ID NO 180
<211> LENGTH: 2019
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 180

gttaagcttg ccaccatgga aaccccagcg cagcttctct tcctcctgct actctggctc     60

ccagatacca ccggtctgaa gatcgcagcc ttcaacatcc agacatttgg ggagaccaag    120

atgtccaatg ccaccctcgt cagctacatt gtgcagatcc tgagccgcta tgacatcgcc    180

ctggtccagg aggtcagaga cagccacctg actgccgtgg ggaagctgct ggacaacctc    240

aatcaggatg caccagacac ctatcactac gtggtcagtg agccactggg acggaacagc    300

tataaggagc gctacctgtt cgtgtacagg cctgaccagg tgtctgcggt ggacagctac    360

tactacgatg atggctgcga gccctgcagg aacgacacct tcaaccgaga gccattcatt    420

gtcaggttct tctcccggtt cacagaggtc agggagtttg ccattgttcc cctgcatgcg    480

gccccggggg acgcagtagc cgagatcgac gctctctatg acgtctacct ggatgtccaa    540

gagaaatggg gcttggagga cgtcatgttg atgggcgact tcaatgcggg ctgcagctat    600

gtgagaccct cccagtggtc atccatccgc ctgtggacaa gccccacctt ccagtggctg    660

atccccgaca gcgctgacac cacagctaca cccacgcact gtgcctatga caggatcgtg    720

gttgcaggga tgctgctccg aggcgccgtt gttcccgact cggctcttcc ctttaacttc    780

caggctgcct atggcctgag tgaccaactg gcccaagcca tcagtgacca ctatccagtg    840

gaggtgatgc tgaaagatct cgagcccaaa tcttctgaca aaactcacac atgtccaccg    900

tgcccagcac ctgaactcct ggggggaccg tcagtcttcc tcttcccccc aaaacccaag    960

gacaccctca tgatctcccg gacccctgag gtcacatgcg tggtggtgga cgtgagccac   1020

gaagaccctg aggtcaagtt caactggtac gtggacggcg tggaggtgca taatgccaag   1080

acaaagccgc gggaggagca gtacaacagc acgtaccgtg tggtcagcgt cctcaccgtc   1140

ctgcaccagg actggctgaa tggcaaggag tacaagtgca aggtctccaa caaagccctc   1200

ccagccccca tcgagaaaac catctccaaa gccaaagggc agccccgaga accacaggtg   1260

tacaccctgc ccccatcccg ggatgagctg accaagaacc aggtcagcct gacctgcctg   1320

gtcaaaggct tctatcccag cgacatcgcc gtggagtggg agagcaatgg gcagccggag   1380
```

```
aacaactaca agaccacgcc tcccgtgctg gactccgacg gctccttctt cctctacagc   1440

aagctcaccg tggacaagag caggtggcag caggggaacg tcttctcatg ctccgtgatg   1500

catgaggctc tgcacaacca ctacacgcag aagagcctct ctctgtctcc gggtaaagtc   1560

gacggagcta gcagccccgt gaacgtgagc agccccagcg tgcaggatat cccttccctg   1620

ggcaaggaat cccgggccaa gaaattccag cggcagcata tggactcaga cagttccccc   1680

agcagcagct ccacctactg taaccaaatg atgaggcgcc ggaatatgac acaggggcgg   1740

tgcaaaccag tgaacacctt tgtgcacgag cccctggtag atgtccagaa tgtctgtttc   1800

caggaaaagg tcacctgcaa gaacgggcag ggcaactgct acaagagcaa ctccagcatg   1860

cacatcacag actgccgcct gacaaacggc tccaggtacc ccaactgtgc ataccggacc   1920

agcccgaagg agagacacat cattgtggcc tgtgaaggga gcccatatgt gccagtccac   1980

tttgatgctt ctgtggagga ctctacctaa taatctaga                          2019


<210> SEQ ID NO 181
<211> LENGTH: 659
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Met Glu Thr Pro Ala Gln Leu Leu Phe Leu Leu Leu Leu Trp Leu Pro
1               5                   10                  15

Asp Thr Thr Gly Leu Lys Ile Ala Ala Phe Asn Ile Gln Thr Phe Gly
            20                  25                  30

Glu Thr Lys Met Ser Asn Ala Thr Leu Val Ser Tyr Ile Val Gln Ile
        35                  40                  45

Leu Ser Arg Tyr Asp Ile Ala Leu Val Gln Glu Val Arg Asp Ser His
    50                  55                  60

Leu Thr Ala Val Gly Lys Leu Leu Asp Asn Leu Asn Gln Asp Ala Pro
65                  70                  75                  80

Asp Thr Tyr His Tyr Val Val Ser Glu Pro Leu Gly Arg Asn Ser Tyr
                85                  90                  95

Lys Glu Arg Tyr Leu Phe Val Tyr Arg Pro Asp Gln Val Ser Ala Val
            100                 105                 110

Asp Ser Tyr Tyr Tyr Asp Asp Gly Cys Glu Pro Cys Arg Asn Asp Thr
        115                 120                 125

Phe Asn Arg Glu Pro Phe Ile Val Arg Phe Phe Ser Arg Phe Thr Glu
    130                 135                 140

Val Arg Glu Phe Ala Ile Val Pro Leu His Ala Ala Pro Gly Asp Ala
145                 150                 155                 160

Val Ala Glu Ile Asp Ala Leu Tyr Asp Val Tyr Leu Asp Val Gln Glu
                165                 170                 175

Lys Trp Gly Leu Glu Asp Val Met Leu Met Gly Asp Phe Asn Ala Gly
            180                 185                 190

Cys Ser Tyr Val Arg Pro Ser Gln Trp Ser Ser Ile Arg Leu Trp Thr
        195                 200                 205

Ser Pro Thr Phe Gln Trp Leu Ile Pro Asp Ser Ala Asp Thr Thr Ala
    210                 215                 220

Thr Pro Thr His Cys Ala Tyr Asp Arg Ile Val Val Ala Gly Met Leu
225                 230                 235                 240

Leu Arg Gly Ala Val Val Pro Asp Ser Ala Leu Pro Phe Asn Phe Gln
```

```
                245                 250                 255

Ala Ala Tyr Gly Leu Ser Asp Gln Leu Ala Gln Ala Ile Ser Asp His
            260                 265                 270

Tyr Pro Val Glu Val Met Leu Lys Leu Glu Pro Lys Ser Ser Asp Lys
        275                 280                 285

Thr His Thr Cys Pro Pro Cys Pro Ala Pro Glu Leu Leu Gly Gly Pro
    290                 295                 300

Ser Val Phe Leu Phe Pro Pro Lys Pro Lys Asp Thr Leu Met Ile Ser
305                 310                 315                 320

Arg Thr Pro Glu Val Thr Cys Val Val Val Asp Val Ser His Glu Asp
                325                 330                 335

Pro Glu Val Lys Phe Asn Trp Tyr Val Asp Gly Val Glu Val His Asn
            340                 345                 350

Ala Lys Thr Lys Pro Arg Glu Glu Gln Tyr Asn Ser Thr Tyr Arg Val
        355                 360                 365

Val Ser Val Leu Thr Val Leu His Gln Asp Trp Leu Asn Gly Lys Glu
    370                 375                 380

Tyr Lys Cys Lys Val Ser Asn Lys Ala Leu Pro Ala Pro Ile Glu Lys
385                 390                 395                 400

Thr Ile Ser Lys Ala Lys Gly Gln Pro Arg Glu Pro Gln Val Tyr Thr
                405                 410                 415

Leu Pro Pro Ser Arg Asp Glu Leu Thr Lys Asn Gln Val Ser Leu Thr
            420                 425                 430

Cys Leu Val Lys Gly Phe Tyr Pro Ser Asp Ile Ala Val Glu Trp Glu
        435                 440                 445

Ser Asn Gly Gln Pro Glu Asn Asn Tyr Lys Thr Thr Pro Pro Val Leu
    450                 455                 460

Asp Ser Asp Gly Ser Phe Phe Leu Tyr Ser Lys Leu Thr Val Asp Lys
465                 470                 475                 480

Ser Arg Trp Gln Gln Gly Asn Val Phe Ser Cys Ser Val Met His Glu
                485                 490                 495

Ala Leu His Asn His Tyr Thr Gln Lys Ser Leu Ser Leu Ser Pro Gly
            500                 505                 510

Lys Val Asp Gly Ala Ser Ser Pro Val Asn Val Ser Ser Pro Ser Val
        515                 520                 525

Gln Asp Ile Lys Glu Ser Arg Ala Lys Lys Phe Gln Arg Gln His Met
    530                 535                 540

Asp Ser Asp Ser Ser Pro Ser Ser Ser Ser Thr Tyr Cys Asn Gln Met
545                 550                 555                 560

Met Arg Arg Arg Asn Met Thr Gln Gly Arg Cys Lys Pro Val Asn Thr
                565                 570                 575

Phe Val His Glu Pro Leu Val Asp Val Gln Asn Val Cys Phe Gln Glu
            580                 585                 590

Lys Val Thr Cys Lys Asn Gly Gln Gly Asn Cys Tyr Lys Ser Asn Ser
        595                 600                 605

Ser Met His Ile Thr Asp Cys Arg Leu Thr Asn Gly Ser Arg Tyr Pro
    610                 615                 620

Asn Cys Ala Tyr Arg Thr Ser Pro Lys Glu Arg His Ile Ile Val Ala
625                 630                 635                 640

Cys Glu Gly Ser Pro Tyr Val Pro Val His Phe Asp Ala Ser Val Glu
                645                 650                 655

Asp Ser Thr
```

<210> SEQ ID NO 182
<211> LENGTH: 1652
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 182
gaccaagctt gccaccatgg aaaccccagc gcagcttctc ttcctcctgc tactctggct 60
cccagatacc accggtctaa ggctctgctc cttcaatgtg aggtcctttg gagcgagcaa 120
gaaggaaaac catgaagcca tggatatcat tgtgaagatc atcaaacgct gtgaccttat 180
actgttgatg gaaatcaagg acagcagcaa caacatctgt cccatgctga tggagaagct 240
gaatggaaat tcacgaagaa gcacaacata caactatgtg attagttctc gacttggaag 300
aaacacgtac aaagagcagt atgccttcgt ctacaaggag aagctggtgt ctgtgaagac 360
aaaataccac taccatgact atcaggatgg agacacagac gtgttttcca gggagccctt 420
tgtggtttgg ttccattccc cctttactgc tgtcaaggac ttcgtgattg tccccttgca 480
cacaactccc gagacctccg ttaaagagat agatgagctg gtcgatgtct acacggatgt 540
gagaagccag tggaagacag agaatttcat cttcatgggt gatttcaacg ccggctgtag 600
ctatgtcccc aagaaggcct ggcagaacat tcgtttgagg acggacccca agtttgtttg 660
gctgattggg gaccaagagg acactacggt caagaagagt accagctgtg cctatgacag 720
gattgtgctt tgtggacaag agatagtcaa ctccgtggtt ccccgttcca gtggcgtctt 780
tgactttcag aaagcttatg acttgtctga agaggaggcc ctggatgtca gtgatcactt 840
tccagttgag tttaagctac agtcttcaag ggccttcacc aacaacagaa aatctgtttc 900
tctcaaaaag agaaaaaaag gcaatcgctc ctcagatctc gagcccagag gtctcacaat 960
caagccctct cctccatgca aatgcccagc acctaacctc ttgggtggat catccgtctt 1020
catcttccct ccaaagatca aggatgtact catgatctcc ctgagcccca tggtcacatg 1080
tgtggtggtg gatgtgagcg aggatgaccc agacgtccag atcagctggt ttgtgaacaa 1140
cgtggaagta cacacagctc agacacaaac ccatagagag gattacaaca gtactctccg 1200
ggtggtcagt gccctcccca tccagcacca ggactggatg agtggcaagg agttcaaatg 1260
ctcggtcaac aacaaagacc tcccagcgtc catcgagaga accatctcaa aacccagagg 1320
gccagtaaga gctccacagg tatatgtctt gcctccacca gcagaagaga tgactaagaa 1380
agagttcagt ctgacctgca tgatcacagg cttcttacct gccgaaattg ctgtggactg 1440
gaccagcaat gggcgtacag agcaaaacta caagaacacc gcaacagtcc tggactctga 1500
tggttcttac ttcatgtaca gcaagctcag agtacaaaag agcacttggg aaagaggaag 1560
tcttttcgcc tgctcagtgg tccacgaggg tctgcacaat caccttacga ctaagagctt 1620
ctctcggact ccgggtaaat gataatctag aa 1652

<210> SEQ ID NO 183
<211> LENGTH: 541
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 183

Met Glu Thr Pro Ala Gln Leu Leu Phe Leu Leu Leu Leu Trp Leu Pro

```
1               5                   10                  15

Asp Thr Thr Gly Leu Arg Leu Cys Ser Phe Asn Val Arg Ser Phe Gly
            20                  25                  30

Ala Ser Lys Lys Glu Asn His Glu Ala Met Asp Ile Ile Val Lys Ile
        35                  40                  45

Ile Lys Arg Cys Asp Leu Ile Leu Leu Met Glu Ile Lys Asp Ser Ser
    50                  55                  60

Asn Asn Ile Cys Pro Met Leu Met Glu Lys Leu Asn Gly Asn Ser Arg
65                  70                  75                  80

Arg Ser Thr Thr Tyr Asn Tyr Val Ile Ser Ser Arg Leu Gly Arg Asn
                85                  90                  95

Thr Tyr Lys Glu Gln Tyr Ala Phe Val Tyr Lys Glu Lys Leu Val Ser
            100                 105                 110

Val Lys Thr Lys Tyr His Tyr His Asp Tyr Gln Asp Gly Asp Thr Asp
        115                 120                 125

Val Phe Ser Arg Glu Pro Phe Val Val Trp Phe His Ser Pro Phe Thr
    130                 135                 140

Ala Val Lys Asp Phe Val Ile Val Pro Leu His Thr Thr Pro Glu Thr
145                 150                 155                 160

Ser Val Lys Glu Ile Asp Glu Leu Val Asp Val Tyr Thr Asp Val Arg
                165                 170                 175

Ser Gln Trp Lys Thr Glu Asn Phe Ile Phe Met Gly Asp Phe Asn Ala
            180                 185                 190

Gly Cys Ser Tyr Val Pro Lys Lys Ala Trp Gln Asn Ile Arg Leu Arg
        195                 200                 205

Thr Asp Pro Lys Phe Val Trp Leu Ile Gly Asp Gln Glu Asp Thr Thr
    210                 215                 220

Val Lys Lys Ser Thr Ser Cys Ala Tyr Asp Arg Ile Val Leu Cys Gly
225                 230                 235                 240

Gln Glu Ile Val Asn Ser Val Val Pro Arg Ser Ser Gly Val Phe Asp
                245                 250                 255

Phe Gln Lys Ala Tyr Asp Leu Ser Glu Glu Glu Ala Leu Asp Val Ser
            260                 265                 270

Asp His Phe Pro Val Glu Phe Lys Leu Gln Ser Ser Arg Ala Phe Thr
        275                 280                 285

Asn Asn Arg Lys Ser Val Ser Leu Lys Lys Arg Lys Lys Gly Asn Arg
    290                 295                 300

Ser Ser Asp Leu Glu Pro Arg Gly Leu Thr Ile Lys Pro Ser Pro Pro
305                 310                 315                 320

Cys Lys Cys Pro Ala Pro Asn Leu Leu Gly Gly Ser Ser Val Phe Ile
                325                 330                 335

Phe Pro Pro Lys Ile Lys Asp Val Leu Met Ile Ser Leu Ser Pro Met
            340                 345                 350

Val Thr Cys Val Val Val Asp Val Ser Glu Asp Asp Pro Asp Val Gln
        355                 360                 365

Ile Ser Trp Phe Val Asn Asn Val Glu Val His Thr Ala Gln Thr Gln
    370                 375                 380

Thr His Arg Glu Asp Tyr Asn Ser Thr Leu Arg Val Val Ser Ala Leu
385                 390                 395                 400

Pro Ile Gln His Gln Asp Trp Met Ser Gly Lys Glu Phe Lys Cys Ser
                405                 410                 415

Val Asn Asn Lys Asp Leu Pro Ala Ser Ile Glu Arg Thr Ile Ser Lys
            420                 425                 430
```

```
Pro Arg Gly Pro Val Arg Ala Pro Gln Val Tyr Val Leu Pro Pro Pro
        435                 440                 445

Ala Glu Glu Met Thr Lys Lys Glu Phe Ser Leu Thr Cys Met Ile Thr
    450                 455                 460

Gly Phe Leu Pro Ala Glu Ile Ala Val Asp Trp Thr Ser Asn Gly Arg
465                 470                 475                 480

Thr Glu Gln Asn Tyr Lys Asn Thr Ala Thr Val Leu Asp Ser Asp Gly
                485                 490                 495

Ser Tyr Phe Met Tyr Ser Lys Leu Arg Val Gln Lys Ser Thr Trp Glu
            500                 505                 510

Arg Gly Ser Leu Phe Ala Cys Ser Val Val His Glu Gly Leu His Asn
        515                 520                 525

His Leu Thr Thr Lys Ser Phe Ser Arg Thr Pro Gly Lys
    530                 535                 540


<210> SEQ ID NO 184
<211> LENGTH: 1667
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (826)..(826)
<223> OTHER INFORMATION: a, c, t, g, unknown or other
<220> FEATURE:
<221> NAME/KEY: modified_base
<222> LOCATION: (832)..(832)
<223> OTHER INFORMATION: a, c, t, g, unknown or other

<400> SEQUENCE: 184

gagaccagct tgccccatgt ccctgcaccc agcttcccca cgcctggcct ccctgctgct     60

cttcatcctt gccctccatg acaccctggc cctaaggctc tgctccttca atgtgaggtc    120

ctttggagcg agcaagaagg aaaaccatga agccatggat atcattgtga agatcatcaa    180

acgctgtgac cttatactgt tgatggaaat caaggacagc agcaacaaca tctgtcccat    240

gctgatggag aagctgaatg gaaattcacg aagaagcaca acatacaact atgtgattag    300

ttctcgactt ggaagaaaca cgtacaaaga gcagtatgcc ttcgtctaca aggagaagct    360

ggtgtctgtg aagacaaaat accactacca tgactatcag gatggagaca cagacgtgtt    420

ttccagggag ccctttgtgg tttggttcca ttccccttt actgctgtca aggacttcgt    480

gattgtcccc ttgcacacaa ctcccgagac ctccgttaaa gagatagatg agctggtcga    540

tgtctacacg gatgtgagaa gccagtggaa gacagagaat ttcatcttca tgggtgattt    600

caacgccggc tgtagctatg tccccaagaa ggcctggcag aacattcgtt tgaggacgga    660

ccccaagttt gtttggctga ttggggacca agaggacact acggtcaaga agagtaccag    720

ctgtgcctat gacaggattg tgctttgtgg acaagagata gtcaactccg tggttccccg    780

ttccagtggc gtctttgact ttcagaaagc ttatgacttg tctgangagg angccctgga    840

tgtcagtgat cactttccag ttgagtttaa gctacagtct tcaagggcct tcaccaacaa    900

cagaaaatct gtttctctca aaaagagaaa aaaaggcaat cgctcctcag atctcgagcc    960

cagaggtctc acaatcaagc cctctcctcc atgcaaatgc ccagcaccta acctcttggg   1020

tggatcatcc gtcttcatct tccctccaaa gatcaaggat gtactcatga tctccctgag   1080

ccccatggtc acatgtgtgg tggtggatgt gagcgaggat gacccagacg tccagatcag   1140
```

```
ctggtttgtg aacaacgtgg aagtacacac agctcagaca caaacccata gagaggatta   1200

caacagtact ctccgggtgg tcagtgccct ccccatccag caccaggact ggatgagtgg   1260

caaggagttc aaatgctcgg tcaacaacaa agacctccca gcgtccatcg agagaaccat   1320

ctcaaaaccc agagggccag taagagctcc acaggtatat gtcttgcctc caccagcaga   1380

agagatgact aagaaagagt tcagtctgac ctgcatgatc acaggcttct tacctgccga   1440

aattgctgtg gactggacca gcaatgggcg tacagagcaa aactacaaga acaccgcaac   1500

agtcctggac tctgatggtt cttacttcat gtacagcaag ctcagagtac aaaagagcac   1560

ttgggaaaga ggaagtcttt tcgcctgctc agtggtccac gagggtctgc acaatcacct   1620

tacgactaag agcttctctc ggactccggg taaatgataa tctagaa                 1667
```

```
<210> SEQ ID NO 185
<211> LENGTH: 546
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (270)..(270)
<223> OTHER INFORMATION: Any amino acid
<220> FEATURE:
<221> NAME/KEY: MOD_RES
<222> LOCATION: (272)..(272)
<223> OTHER INFORMATION: Any amino acid

<400> SEQUENCE: 185

Met Ser Leu His Pro Ala Ser Pro Arg Leu Ala Ser Leu Leu Leu Phe
1               5                   10                  15

Ile Leu Ala Leu His Asp Thr Leu Ala Leu Arg Leu Cys Ser Phe Asn
            20                  25                  30

Val Arg Ser Phe Gly Ala Ser Lys Lys Glu Asn His Glu Ala Met Asp
        35                  40                  45

Ile Ile Val Lys Ile Ile Lys Arg Cys Asp Leu Ile Leu Leu Met Glu
    50                  55                  60

Ile Lys Asp Ser Ser Asn Asn Ile Cys Pro Met Leu Met Glu Lys Leu
65                  70                  75                  80

Asn Gly Asn Ser Arg Arg Ser Thr Thr Tyr Asn Tyr Val Ile Ser Ser
                85                  90                  95

Arg Leu Gly Arg Asn Thr Tyr Lys Glu Gln Tyr Ala Phe Val Tyr Lys
            100                 105                 110

Glu Lys Leu Val Ser Val Lys Thr Lys Tyr His Tyr His Asp Tyr Gln
        115                 120                 125

Asp Gly Asp Thr Asp Val Phe Ser Arg Glu Pro Phe Val Val Trp Phe
    130                 135                 140

His Ser Pro Phe Thr Ala Val Lys Asp Phe Val Ile Val Pro Leu His
145                 150                 155                 160

Thr Thr Pro Glu Thr Ser Val Lys Glu Ile Asp Glu Leu Val Asp Val
                165                 170                 175

Tyr Thr Asp Val Arg Ser Gln Trp Lys Thr Glu Asn Phe Ile Phe Met
            180                 185                 190

Gly Asp Phe Asn Ala Gly Cys Ser Tyr Val Pro Lys Lys Ala Trp Gln
        195                 200                 205

Asn Ile Arg Leu Arg Thr Asp Pro Lys Phe Val Trp Leu Ile Gly Asp
    210                 215                 220
```

```
Gln Glu Asp Thr Thr Val Lys Lys Ser Thr Ser Cys Ala Tyr Asp Arg
225                 230                 235                 240

Ile Val Leu Cys Gly Gln Glu Ile Val Asn Ser Val Val Pro Arg Ser
                245                 250                 255

Ser Gly Val Phe Asp Phe Gln Lys Ala Tyr Asp Leu Ser Xaa Glu Xaa
            260                 265                 270

Ala Leu Asp Val Ser Asp His Phe Pro Val Glu Phe Lys Leu Gln Ser
        275                 280                 285

Ser Arg Ala Phe Thr Asn Asn Arg Lys Ser Val Ser Leu Lys Lys Arg
    290                 295                 300

Lys Lys Gly Asn Arg Ser Ser Asp Leu Glu Pro Arg Gly Leu Thr Ile
305                 310                 315                 320

Lys Pro Ser Pro Pro Cys Lys Cys Pro Ala Pro Asn Leu Leu Gly Gly
                325                 330                 335

Ser Ser Val Phe Ile Phe Pro Pro Lys Ile Lys Asp Val Leu Met Ile
            340                 345                 350

Ser Leu Ser Pro Met Val Thr Cys Val Val Val Asp Val Ser Glu Asp
        355                 360                 365

Asp Pro Asp Val Gln Ile Ser Trp Phe Val Asn Asn Val Glu Val His
    370                 375                 380

Thr Ala Gln Thr Gln Thr His Arg Glu Asp Tyr Asn Ser Thr Leu Arg
385                 390                 395                 400

Val Val Ser Ala Leu Pro Ile Gln His Gln Asp Trp Met Ser Gly Lys
                405                 410                 415

Glu Phe Lys Cys Ser Val Asn Asn Lys Asp Leu Pro Ala Ser Ile Glu
            420                 425                 430

Arg Thr Ile Ser Lys Pro Arg Gly Pro Val Arg Ala Pro Gln Val Tyr
        435                 440                 445

Val Leu Pro Pro Pro Ala Glu Glu Met Thr Lys Lys Glu Phe Ser Leu
    450                 455                 460

Thr Cys Met Ile Thr Gly Phe Leu Pro Ala Glu Ile Ala Val Asp Trp
465                 470                 475                 480

Thr Ser Asn Gly Arg Thr Glu Gln Asn Tyr Lys Asn Thr Ala Thr Val
                485                 490                 495

Leu Asp Ser Asp Gly Ser Tyr Phe Met Tyr Ser Lys Leu Arg Val Gln
            500                 505                 510

Lys Ser Thr Trp Glu Arg Gly Ser Leu Phe Ala Cys Ser Val Val His
        515                 520                 525

Glu Gly Leu His Asn His Leu Thr Thr Lys Ser Phe Ser Arg Thr Pro
    530                 535                 540

Gly Lys
545
```

<210> SEQ ID NO 186
<211> LENGTH: 2094
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 186

```
gttaagcttg ccaccatgga aaccccagcg cagcttctct tcctcctgct actctggctc     60

ccagatacca ccggtatgag gatctgctcc ttcaacgtca ggtcctttgg ggaaagcaag    120

caggaagaca agaatgccat ggatgtcatt gtgaaggtca tcaaacgctg tgacatcata    180
```

```
ctcgtgatgg aaatcaagga cagcaacaac aggatctgcc ccatactgat ggagaagctg    240
aacagaaatt caaggagagg cataacatac aactatgtga ttagctctcg gcttggaaga    300
aacacatata aagaacaata tgcctttctc tacaaggaaa agctggtgtc tgtgaagagg    360
agttatcact accatgacta tcaggatgga gacgcagatg tgttttccag ggagcccttt    420
gtggtctggt tccaatctcc ccacactgct gtcaaagact tcgtgattat ccccctgcac    480
accaccccag agacatccgt taaggagatc gatgagttgg ttgaggtcta cacggacgtg    540
aaacaccgct ggaaggcgga gaatttcatt ttcatgggtg acttcaatgc cggctgcagc    600
tacgtcccca agaaggcctg gaagaacatc cgcttgagga ctgaccccag gtttgtttgg    660
ctgatcgggg accaagagga caccacggtg aagaagagca ccaactgtgc atatgacagg    720
attgtgctta gaggacaaga aatcgtcagt tctgttgttc ccaagtcaaa cagtgttttt    780
gacttccaga aagcttacaa gctgactgaa gaggaggccc tggatgtcag cgaccacttt    840
ccagttgaat ttaaactaca gtcttcaagg gccttcacca acagcaaaaa atctgtcact    900
ctaaggaaga aaacaaagag caaacgctca gatctcgagc ccaaatcttc tgacaaaact    960
cacacatgtc caccgtgccc agcacctgaa ctcctggggg gaccgtcagt cttcctcttc   1020
cccccaaaac ccaaggacac cctcatgatc tcccggaccc ctgaggtcac atgcgtggtg   1080
gtggacgtga gccacgaaga ccctgaggtc aagttcaact ggtacgtgga cggcgtggag   1140
gtgcataatg ccaagacaaa gccgcgggag gagcagtaca acagcacgta ccgtgtggtc   1200
agcgtcctca ccgtcctgca ccaggactgg ctgaatggca aggagtacaa gtgcaaggtc   1260
tccaacaaag ccctcccagc ccccatcgag aaaaccatct ccaaagccaa agggcagccc   1320
cgagaaccac aggtgtacac cctgccccca tcccgggatg agctgaccaa gaaccaggtc   1380
agcctgacct gcctggtcaa aggcttctat cccagcgaca tcgccgtgga gtgggagagc   1440
aatgggcagc cggagaacaa ctacaagacc acgcctcccg tgctggactc cgacggctcc   1500
ttcttcctct acagcaagct caccgtggac aagagcaggt ggcagcaggg gaacgtcttc   1560
tcatgctccg tgatgcatga ggctctgcac aaccactaca cgcagaagag cctctctctg   1620
tctccgggta aagtcgacgg agctagcagc cccgtgaacg tgagcagccc cagcgtgcag   1680
gatatccctt ccctgggcaa ggaatcccgg gccaagaaat tccagcggca gcatatggac   1740
tcagacagtt cccccagcag cagctccacc tactgtaacc aaatgatgag gcgccggaat   1800
atgacacagg ggcggtgcaa accagtgaac acctttgtgc acgagcccct ggtagatgtc   1860
cagaatgtct gtttccagga aaaggtcacc tgcaagaacg ggcagggcaa ctgctacaag   1920
agcaactcca gcatgcacat cacagactgc cgcctgacaa acggctccag gtaccccaac   1980
tgtgcatacc ggaccagccc gaaggagaga cacatcattg tggcctgtga agggagccca   2040
tatgtgccag tccactttga tgcttctgtg gaggactcta cctaataatc taga         2094
```

```
<210> SEQ ID NO 187
<211> LENGTH: 684
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Met Glu Thr Pro Ala Gln Leu Leu Phe Leu Leu Leu Leu Trp Leu Pro
1               5                   10                  15
```

```
Asp Thr Thr Gly Met Arg Ile Cys Ser Phe Asn Val Arg Ser Phe Gly
            20                  25                  30

Glu Ser Lys Gln Glu Asp Lys Asn Ala Met Asp Val Ile Val Lys Val
        35                  40                  45

Ile Lys Arg Cys Asp Ile Ile Leu Val Met Glu Ile Lys Asp Ser Asn
    50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
        115                 120                 125

Val Phe Ser Arg Glu Pro Phe Val Val Trp Phe Gln Ser Pro His Thr
    130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
            180                 185                 190

Gly Cys Ser Tyr Val Pro Lys Lys Ala Trp Lys Asn Ile Arg Leu Arg
        195                 200                 205

Thr Asp Pro Arg Phe Val Trp Leu Ile Gly Asp Gln Glu Asp Thr Thr
    210                 215                 220

Val Lys Lys Ser Thr Asn Cys Ala Tyr Asp Arg Ile Val Leu Arg Gly
225                 230                 235                 240

Gln Glu Ile Val Ser Ser Val Val Pro Lys Ser Asn Ser Val Phe Asp
                245                 250                 255

Phe Gln Lys Ala Tyr Lys Leu Thr Glu Glu Glu Ala Leu Asp Val Ser
            260                 265                 270

Asp His Phe Pro Val Glu Phe Lys Leu Gln Ser Ser Arg Ala Phe Thr
        275                 280                 285

Asn Ser Lys Lys Ser Val Thr Leu Arg Lys Lys Thr Lys Ser Lys Arg
    290                 295                 300

Ser Leu Glu Pro Lys Ser Ser Asp Lys Thr His Thr Cys Pro Pro Cys
305                 310                 315                 320

Pro Ala Pro Glu Leu Leu Gly Gly Pro Ser Val Phe Leu Phe Pro Pro
                325                 330                 335

Lys Pro Lys Asp Thr Leu Met Ile Ser Arg Thr Pro Glu Val Thr Cys
            340                 345                 350

Val Val Val Asp Val Ser His Glu Asp Pro Glu Val Lys Phe Asn Trp
        355                 360                 365

Tyr Val Asp Gly Val Glu Val His Asn Ala Lys Thr Lys Pro Arg Glu
    370                 375                 380

Glu Gln Tyr Asn Ser Thr Tyr Arg Val Val Ser Val Leu Thr Val Leu
385                 390                 395                 400

His Gln Asp Trp Leu Asn Gly Lys Glu Tyr Lys Cys Lys Val Ser Asn
                405                 410                 415

Lys Ala Leu Pro Ala Pro Ile Glu Lys Thr Ile Ser Lys Ala Lys Gly
            420                 425                 430

Gln Pro Arg Glu Pro Gln Val Tyr Thr Leu Pro Pro Ser Arg Asp Glu
```

435 440 445

Leu Thr Lys Asn Gln Val Ser Leu Thr Cys Leu Val Lys Gly Phe Tyr
450 455 460

Pro Ser Asp Ile Ala Val Glu Trp Glu Ser Asn Gly Gln Pro Glu Asn
465 470 475 480

Asn Tyr Lys Thr Thr Pro Pro Val Leu Asp Ser Asp Gly Ser Phe Phe
485 490 495

Leu Tyr Ser Lys Leu Thr Val Asp Lys Ser Arg Trp Gln Gln Gly Asn
500 505 510

Val Phe Ser Cys Ser Val Met His Glu Ala Leu His Asn His Tyr Thr
515 520 525

Gln Lys Ser Leu Ser Leu Ser Pro Gly Lys Val Asp Gly Ala Ser Ser
530 535 540

Pro Val Asn Val Ser Ser Pro Ser Val Gln Asp Ile Lys Glu Ser Arg
545 550 555 560

Ala Lys Lys Phe Gln Arg Gln His Met Asp Ser Asp Ser Ser Pro Ser
565 570 575

Ser Ser Ser Thr Tyr Cys Asn Gln Met Met Arg Arg Arg Asn Met Thr
580 585 590

Gln Gly Arg Cys Lys Pro Val Asn Thr Phe Val His Glu Pro Leu Val
595 600 605

Asp Val Gln Asn Val Cys Phe Gln Glu Lys Val Thr Cys Lys Asn Gly
610 615 620

Gln Gly Asn Cys Tyr Lys Ser Asn Ser Ser Met His Ile Thr Asp Cys
625 630 635 640

Arg Leu Thr Asn Gly Ser Arg Tyr Pro Asn Cys Ala Tyr Arg Thr Ser
645 650 655

Pro Lys Glu Arg His Ile Ile Val Ala Cys Glu Gly Ser Pro Tyr Val
660 665 670

Pro Val His Phe Asp Ala Ser Val Glu Asp Ser Thr
675 680

<210> SEQ ID NO 188
<211> LENGTH: 1620
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 188
aagcttgccg ccatggaaac cccagcgcag cttctcttcc tcctgctact ctggctccca 60
gataccaccg gtaaggaatc ccgggccaag aaattccagc ggcagcatat ggactcagac 120
agttccccca gcagcagctc cacctactgt aaccaaatga tgaggcgccg gaatatgaca 180
caggggcggt gcaaaccagt gaacaccttt gtgcacgagc cctggtaga tgtccagaat 240 gtctgtttcc aggaaaaggt cacctgcaag aacgggcagg gcaactgcta caagagcaac 300
tccagcatgc acatcacaga ctgccgcctg acaaacggct ccaggtaccc caactgtgca 360
taccggacca gcccgaagga gagacacatc attgtggcct gtgaagggag cccatatgtg 420
ccagtccact ttgatgcttc tgtggaggac tctacagatc tcgagcccaa atcttctgac 480
aaaactcaca catgtccacc gtgcccagca cctgaactcc tggggggacc gtcagtcttc 540
ctcttccccc caaaacccaa ggacaccctc atgatctccc ggacccctga ggtcacatgc 600
gtggtggtgg acgtgagcca cgaagaccct gaggtcaagt tcaactggta cgtggacggc 660

```
gtggaggtgc ataatgccaa gacaaagccg cgggaggagc agtacaacag cacgtaccgt    720

gtggtcagcg tcctcaccgt cctgcaccag gactggctga atggcaagga gtacaagtgc    780

aaggtctcca acaaagccct cccagccccc atcgagaaaa ccatctccaa agccaaaggg    840

cagccccgag aaccacaggt gtacaccctg cccccatccc gggatgagct gaccaagaac    900

caggtcagcc tgacctgcct ggtcaaaggc ttctatccca gcgacatcgc cgtggagtgg    960

gagagcaatg ggcagccgga gaacaactac aagaccacgc ctcccgtgct ggactccgac   1020

ggctccttct tcctctacag caagctcacc gtggacaaga gcaggtggca gcaggggaac   1080

gtcttctcat gctccgtgat gcatgagggt ctgcacaacc actacacgca gaagagcctc   1140

tctctgtctc cgggtaaagt cgacggtgct agcagccatg tgaatgtgag cagccctagc   1200

gtgcaggata tcccttccct gggcaaggaa tcccgggcca agaaattcca gcggcagcat   1260

atggactcag acagttcccc cagcagcagc tccacctact gtaaccaaat gatgaggcgc   1320

cggaatatga cacaggggcg gtgcaaacca gtgaacacct ttgtgcacga gcccctggta   1380

gatgtccaga atgtctgttt ccaggaaaag gtcacctgca agaacgggca gggcaactgc   1440

tacaagagca actccagcat gcacatcaca gactgccgcc tgacaaacgg ctccaggtac   1500

cccaactgtg cataccggac cagcccgaag gagagacaca tcattgtggc ctgtgaaggg   1560

agcccatatg tgccagtcca ctttgatgct tctgtggagg actctaccta ataatctaga   1620
```

```
<210> SEQ ID NO 189
<211> LENGTH: 527
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Met Glu Thr Pro Ala Gln Leu Leu Phe Leu Leu Leu Leu Trp Leu Pro
1               5                   10                  15

Asp Thr Thr Gly Lys Glu Ser Arg Ala Lys Lys Phe Gln Arg Gln His
            20                  25                  30

Met Asp Ser Asp Ser Ser Pro Ser Ser Ser Ser Thr Tyr Cys Asn Gln
        35                  40                  45

Met Met Arg Arg Arg Asn Met Thr Gln Gly Arg Cys Lys Pro Val Asn
    50                  55                  60

Thr Phe Val His Glu Pro Leu Val Asp Val Gln Asn Val Cys Phe Gln
65                  70                  75                  80

Glu Lys Val Thr Cys Lys Asn Gly Gln Gly Asn Cys Tyr Lys Ser Asn
                85                  90                  95

Ser Ser Met His Ile Thr Asp Cys Arg Leu Thr Asn Gly Ser Arg Tyr
            100                 105                 110

Pro Asn Cys Ala Tyr Arg Thr Ser Pro Lys Glu Arg His Ile Ile Val
        115                 120                 125

Ala Cys Glu Gly Ser Pro Tyr Val Pro Val His Phe Asp Ala Ser Val
    130                 135                 140

Glu Asp Ser Thr Leu Glu Pro Lys Ser Ser Asp Lys Thr His Thr Cys
145                 150                 155                 160

Pro Pro Cys Pro Ala Pro Glu Leu Leu Gly Gly Pro Ser Val Phe Leu
                165                 170                 175

Phe Pro Pro Lys Pro Lys Asp Thr Leu Met Ile Ser Arg Thr Pro Glu
            180                 185                 190
```

Val Thr Cys Val Val Val Asp Val Ser His Glu Asp Pro Glu Val Lys
195 200 205

Phe Asn Trp Tyr Val Asp Gly Val Glu Val His Asn Ala Lys Thr Lys
210 215 220

Pro Arg Glu Glu Gln Tyr Asn Ser Thr Tyr Arg Val Val Ser Val Leu
225 230 235 240

Thr Val Leu His Gln Asp Trp Leu Asn Gly Lys Glu Tyr Lys Cys Lys
245 250 255

Val Ser Asn Lys Ala Leu Pro Ala Pro Ile Glu Lys Thr Ile Ser Lys
260 265 270

Ala Lys Gly Gln Pro Arg Glu Pro Gln Val Tyr Thr Leu Pro Pro Ser
275 280 285

Arg Asp Glu Leu Thr Lys Asn Gln Val Ser Leu Thr Cys Leu Val Lys
290 295 300

Gly Phe Tyr Pro Ser Asp Ile Ala Val Glu Trp Glu Ser Asn Gly Gln
305 310 315 320

Pro Glu Asn Asn Tyr Lys Thr Thr Pro Pro Val Leu Asp Ser Asp Gly
325 330 335

Ser Phe Phe Leu Tyr Ser Lys Leu Thr Val Asp Lys Ser Arg Trp Gln
340 345 350

Gln Gly Asn Val Phe Ser Cys Ser Val Met His Glu Gly Leu His Asn
355 360 365

His Tyr Thr Gln Lys Ser Leu Ser Leu Ser Pro Gly Lys Val Asp Gly
370 375 380

Ala Ser Ser His Val Asn Val Ser Ser Pro Ser Val Gln Asp Ile Lys
385 390 395 400

Glu Ser Arg Ala Lys Lys Phe Gln Arg Gln His Met Asp Ser Asp Ser
405 410 415

Ser Pro Ser Ser Ser Ser Thr Tyr Cys Asn Gln Met Met Arg Arg Arg
420 425 430

Asn Met Thr Gln Gly Arg Cys Lys Pro Val Asn Thr Phe Val His Glu
435 440 445

Pro Leu Val Asp Val Gln Asn Val Cys Phe Gln Glu Lys Val Thr Cys
450 455 460

Lys Asn Gly Gln Gly Asn Cys Tyr Lys Ser Asn Ser Ser Met His Ile
465 470 475 480

Thr Asp Cys Arg Leu Thr Asn Gly Ser Arg Tyr Pro Asn Cys Ala Tyr
485 490 495

Arg Thr Ser Pro Lys Glu Arg His Ile Ile Val Ala Cys Glu Gly Ser
500 505 510

Pro Tyr Val Pro Val His Phe Asp Ala Ser Val Glu Asp Ser Thr
515 520 525

<210> SEQ ID NO 190
<211> LENGTH: 1692
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 190
aagcttgccg ccatggaaac cccagcgcag cttctcttcc tcctgctact ctggctccca 60
gataccaccg gtaaggaatc ccgggccaag aaattccagc ggcagcatat ggactcagac 120

```
agttccccca gcagcagctc cacctactgt aaccaaatga tgaggcgccg gaatatgaca    180

caggggcggt gcaaaccagt gaacaccttt gtgcacgagc cctggtaga tgtccagaat    240

gtctgtttcc aggaaaaggt cacctgcaag aacgggcagg gcaactgcta caagagcaac    300

tccagcatgc acatcacaga ctgccgcctg acaaacggct ccaggtaccc caactgtgca    360

taccggacca gcccgaagga gagacacatc attgtggcct gtgaagggag cccatatgtg    420

ccagtccact ttgatgcttc tgtggaggac tctacagatc tctccggagg aggtggctca    480

ggtggtggag gatctggagg aggtgggagt ggtggaggtg gttctaccgg tctcgagccc    540

aaatcttctg acaaaactca cacatgtcca ccgtgcccag cacctgaact cctgggggga    600

ccgtcagtct tcctcttccc cccaaaaccc aaggacaccc tcatgatctc ccggacccct    660

gaggtcacat gcgtggtggt ggacgtgagc cacgaagacc ctgaggtcaa gttcaactgg    720

tacgtggacg gcgtggaggt gcataatgcc aagacaaagc cgcgggagga gcagtacaac    780

agcacgtacc gtgtggtcag cgtcctcacc gtcctgcacc aggactggct gaatggcaag    840

gagtacaagt gcaaggtctc caacaaagcc ctcccagccc ccatcgagaa aaccatctcc    900

aaagccaaag ggcagccccg agaaccacag gtgtacaccc tgcccccatc ccgggatgag    960

ctgaccaaga accaggtcag cctgacctgc ctggtcaaag gcttctatcc cagcgacatc   1020

gccgtggagt gggagagcaa tgggcagccg gagaacaact acaagaccac gcctcccgtg   1080

ctggactccg acggctcctt cttcctctac agcaagctca ccgtggacaa gagcaggtgg   1140

cagcagggga acgtcttctc atgctccgtg atgcatgagg gtctgcacaa ccactacacg   1200

cagaagagcc tctctctgtc tccgggtaaa gtcgacggtg ctagcagcca tgtgaatgtg   1260

agcagcccta gcgtgcagga tatcccttcc ctgggcaagg aatcccgggc caagaaattc   1320

cagcggcagc atatggactc agacagttcc cccagcagca gctccaccta ctgtaaccaa   1380

atgatgaggc gccggaatat gacacagggg cggtgcaaac cagtgaacac ctttgtgcac   1440

gagcccctgg tagatgtcca gaatgtctgt ttccaggaaa aggtcacctg caagaacggg   1500

cagggcaact gctacaagag caactccagc atgcacatca cagactgccg cctgacaaac   1560

ggctccaggt accccaactg tgcataccgg accagcccga aggagagaca catcattgtg   1620

gcctgtgaag ggagcccata tgtgccagtc cactttgatg cttctgtgga ggactctacc   1680

taataatcta ga                                                        1692
```

<210> SEQ ID NO 191
<211> LENGTH: 547
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 191

```
Met Glu Thr Pro Ala Gln Leu Leu Phe Leu Leu Leu Leu Trp Leu Pro
1               5                   10                  15

Asp Thr Thr Gly Lys Glu Ser Arg Ala Lys Lys Phe Gln Arg Gln His
            20                  25                  30

Met Asp Ser Asp Ser Ser Pro Ser Ser Ser Ser Thr Tyr Cys Asn Gln
        35                  40                  45

Met Met Arg Arg Arg Asn Met Thr Gln Gly Arg Cys Lys Pro Val Asn
    50                  55                  60

Thr Phe Val His Glu Pro Leu Val Asp Val Gln Asn Val Cys Phe Gln
65                  70                  75                  80
```

-continued

Glu Lys Val Thr Cys Lys Asn Gly Gln Gly Asn Cys Tyr Lys Ser Asn
85 90 95

Ser Ser Met His Ile Thr Asp Cys Arg Leu Thr Asn Gly Ser Arg Tyr
100 105 110

Pro Asn Cys Ala Tyr Arg Thr Ser Pro Lys Glu Arg His Ile Ile Val
115 120 125

Ala Cys Glu Gly Ser Pro Tyr Val Pro Val His Phe Asp Ala Ser Val
130 135 140

Glu Asp Ser Thr Gly Gly Gly Gly Ser Gly Gly Gly Gly Ser Gly Gly
145 150 155 160

Gly Gly Ser Gly Gly Gly Gly Ser Leu Glu Pro Lys Ser Ser Asp Lys
165 170 175

Thr His Thr Cys Pro Pro Cys Pro Ala Pro Glu Leu Leu Gly Gly Pro
180 185 190

Ser Val Phe Leu Phe Pro Pro Lys Pro Lys Asp Thr Leu Met Ile Ser
195 200 205

Arg Thr Pro Glu Val Thr Cys Val Val Val Asp Val Ser His Glu Asp
210 215 220

Pro Glu Val Lys Phe Asn Trp Tyr Val Asp Gly Val Glu Val His Asn
225 230 235 240

Ala Lys Thr Lys Pro Arg Glu Glu Gln Tyr Asn Ser Thr Tyr Arg Val
245 250 255

Val Ser Val Leu Thr Val Leu His Gln Asp Trp Leu Asn Gly Lys Glu
260 265 270

Tyr Lys Cys Lys Val Ser Asn Lys Ala Leu Pro Ala Pro Ile Glu Lys
275 280 285

Thr Ile Ser Lys Ala Lys Gly Gln Pro Arg Glu Pro Gln Val Tyr Thr
290 295 300

Leu Pro Pro Ser Arg Asp Glu Leu Thr Lys Asn Gln Val Ser Leu Thr
305 310 315 320

Cys Leu Val Lys Gly Phe Tyr Pro Ser Asp Ile Ala Val Glu Trp Glu
325 330 335

Ser Asn Gly Gln Pro Glu Asn Asn Tyr Lys Thr Thr Pro Pro Val Leu
340 345 350

Asp Ser Asp Gly Ser Phe Phe Leu Tyr Ser Lys Leu Thr Val Asp Lys
355 360 365

Ser Arg Trp Gln Gln Gly Asn Val Phe Ser Cys Ser Val Met His Glu
370 375 380

Gly Leu His Asn His Tyr Thr Gln Lys Ser Leu Ser Leu Ser Pro Gly
385 390 395 400

Lys Val Asp Gly Ala Ser Ser His Val Asn Val Ser Ser Pro Ser Val
405 410 415

Gln Asp Ile Lys Glu Ser Arg Ala Lys Lys Phe Gln Arg Gln His Met
420 425 430

Asp Ser Asp Ser Ser Pro Ser Ser Ser Ser Thr Tyr Cys Asn Gln Met
435 440 445

Met Arg Arg Arg Asn Met Thr Gln Gly Arg Cys Lys Pro Val Asn Thr
450 455 460

Phe Val His Glu Pro Leu Val Asp Val Gln Asn Val Cys Phe Gln Glu
465 470 475 480

Lys Val Thr Cys Lys Asn Gly Gln Gly Asn Cys Tyr Lys Ser Asn Ser
485 490 495

Ser Met His Ile Thr Asp Cys Arg Leu Thr Asn Gly Ser Arg Tyr Pro
500 505 510

Asn Cys Ala Tyr Arg Thr Ser Pro Lys Glu Arg His Ile Ile Val Ala
515 520 525

Cys Glu Gly Ser Pro Tyr Val Pro Val His Phe Asp Ala Ser Val Glu
530 535 540

Asp Ser Thr
545

<210> SEQ ID NO 192
<211> LENGTH: 2199
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 192
aagcttgcca ccatggaaac cccagcgcag cttctcttcc tcctgctact ctggctccca 60
gataccaccg gtatgggccc tggagctcgc agacagggca ggattgtgca gggaaggcct 120
gagatgtgct tctgcccacc ccctacccca ctccctcccc ttcggatctt aacactgggc 180
actcacacac ccaccccatg ctcctctcca ggctcagcag caggtacgta cccaaccatg 240
ggctcgcagg ccctgccccc ggggcccatg cagaccctca tctttttcga catggaggcc 300
actggcttgc ccttctccca gcccaaggtc acggagctgt gcctgctggc tgtccacaga 360
tgtgccctgg agagcccccc cacctctcag gggccacctc ccacagttcc tccaccaccg 420
cgtgtggtag acaagctctc cctgtgtgtg gctccgggga aggcctgcag ccctgcagcc 480
agcgagatca caggtctgag cacagctgtg ctggcagcgc atgggcgtca atgttttgat 540
gacaacctgg ccaacctgct cctagccttc ctgcggcgcc agccacagcc ctggtgcctg 600
gtggcacaca atggtgaccg ctacgacttc cccctgctcc aagcagagct ggctatgctg 660
ggcctcacca gtgctctgga tggtgccttc tgtgtggata gcatcactgc gctgaaggcc 720
ctggagcgag caagcagccc ctcagaacac ggcccaagga agagctacag cctaggcagc 780
atctacactc gcctgtatgg gcagtcccct ccagactcgc acacggctga gggtgatgtc 840
ctggccctgc tcagcatctg tcagtggaga ccacaggccc tgctgcggtg ggtggatgct 900
cacgccaggc ctttcggcac catcaggccc atgtatgggg tcacagcctc tgctaggacc 960
aaagatctct ccggaggagg tggctcaggt ggtggaggat ctggaggagg tgggagtggt 1020
ggaggtggtt ctaccggtct cgagcccaaa tcttctgaca aaactcacac atgtccaccg 1080
tgcccagcac ctgaactcct ggggggaccg tcagtcttcc tcttcccccc aaaacccaag 1140
gacaccctca tgatctcccg gacccctgag gtcacatgcg tggtggtgga cgtgagccac 1200
gaagaccctg aggtcaagtt caactggtac gtggacggcg tggaggtgca taatgccaag 1260
acaaagccgc gggaggagca gtacaacagc acgtaccgtg tggtcagcgt cctcaccgtc 1320
ctgcaccagg actggctgaa tggcaaggag tacaagtgca aggtctccaa caaagccctc 1380 ccagcccccca tcgagaaaac catctccaaa gccaaagggc agccccgaga accacaggtg 1440
tacaccctgc ccccatcccg ggatgagctg accaagaacc aggtcagcct gacctgcctg 1500
gtcaaaggct tctatcccag cgacatcgcc gtggagtggg agagcaatgg gcagccggag 1560
aacaactaca agaccacgcc tcccgtgctg gactccgacg gctccttctt cctctacagc 1620
aagctcaccg tggacaagag caggtggcag caggggaacg tcttctcatg ctccgtgatg 1680

```
catgaggctc tgcacaacca ctacacgcag aagagcctct ctctgtctcc gggtaaagtc   1740

gacggagcta gcagccccgt gaacgtgagc agccccagcg tgcaggatat cccttccctg   1800

ggcaaggaat cccgggccaa gaaattccag cggcagcata tggactcaga cagttccccc   1860

agcagcagct ccacctactg taaccaaatg atgaggcgcc ggaatatgac acaggggcgg   1920

tgcaaaccag tgaacacctt tgtgcacgag cccctggtag atgtccagaa tgtctgtttc   1980

caggaaaagg tcacctgcaa gaacgggcag ggcaactgct acaagagcaa ctccagcatg   2040

cacatcacag actgccgcct gacaaacggc tccaggtacc ccaactgtgc ataccggacc   2100

agcccgaagg agagacacat cattgtggcc tgtgaaggga gcccatatgt gccagtccac   2160

tttgatgctt ctgtggagga ctctacctaa taatctaga                          2199
```

<210> SEQ ID NO 193
<211> LENGTH: 716
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 193

```
Met Glu Thr Pro Ala Gln Leu Leu Phe Leu Leu Leu Leu Trp Leu Pro
1               5                   10                  15

Asp Thr Thr Gly Met Gly Pro Gly Ala Arg Arg Gln Gly Arg Ile Val
            20                  25                  30

Gln Gly Arg Pro Glu Met Cys Phe Cys Pro Pro Pro Thr Pro Leu Pro
        35                  40                  45

Pro Leu Arg Ile Leu Thr Leu Gly Thr His Thr Pro Thr Pro Cys Ser
    50                  55                  60

Ser Pro Gly Ser Ala Ala Gly Thr Tyr Pro Thr Met Gly Ser Gln Ala
65                  70                  75                  80

Leu Pro Pro Gly Pro Met Gln Thr Leu Ile Phe Phe Asp Met Glu Ala
                85                  90                  95

Thr Gly Leu Pro Phe Ser Gln Pro Lys Val Thr Glu Leu Cys Leu Leu
            100                 105                 110

Ala Val His Arg Cys Ala Leu Glu Ser Pro Pro Thr Ser Gln Gly Pro
        115                 120                 125

Pro Pro Thr Val Pro Pro Pro Pro Arg Val Val Asp Lys Leu Ser Leu
    130                 135                 140

Cys Val Ala Pro Gly Lys Ala Cys Ser Pro Ala Ala Ser Glu Ile Thr
145                 150                 155                 160

Gly Leu Ser Thr Ala Val Leu Ala Ala His Gly Arg Gln Cys Phe Asp
                165                 170                 175

Asp Asn Leu Ala Asn Leu Leu Leu Ala Phe Leu Arg Arg Gln Pro Gln
            180                 185                 190

Pro Trp Cys Leu Val Ala His Asn Gly Asp Arg Tyr Asp Phe Pro Leu
        195                 200                 205

Leu Gln Ala Glu Leu Ala Met Leu Gly Leu Thr Ser Ala Leu Asp Gly
    210                 215                 220

Ala Phe Cys Val Asp Ser Ile Thr Ala Leu Lys Ala Leu Glu Arg Ala
225                 230                 235                 240

Ser Ser Pro Ser Glu His Gly Pro Arg Lys Ser Tyr Ser Leu Gly Ser
                245                 250                 255

Ile Tyr Thr Arg Leu Tyr Gly Gln Ser Pro Pro Asp Ser His Thr Ala
            260                 265                 270
```

```
Glu Gly Asp Val Leu Ala Leu Leu Ser Ile Cys Gln Trp Arg Pro Gln
        275                 280                 285

Ala Leu Leu Arg Trp Val Asp Ala His Ala Arg Pro Phe Gly Thr Ile
    290                 295                 300

Arg Pro Met Tyr Gly Val Thr Ala Ser Ala Arg Thr Lys Gly Gly Gly
305                 310                 315                 320

Gly Ser Gly Gly Gly Gly Ser Gly Gly Gly Gly Ser Gly Gly Gly Gly
                325                 330                 335

Ser Leu Glu Pro Lys Ser Ser Asp Lys Thr His Thr Cys Pro Pro Cys
            340                 345                 350

Pro Ala Pro Glu Leu Leu Gly Gly Pro Ser Val Phe Leu Phe Pro Pro
        355                 360                 365

Lys Pro Lys Asp Thr Leu Met Ile Ser Arg Thr Pro Glu Val Thr Cys
    370                 375                 380

Val Val Val Asp Val Ser His Glu Asp Pro Glu Val Lys Phe Asn Trp
385                 390                 395                 400

Tyr Val Asp Gly Val Glu Val His Asn Ala Lys Thr Lys Pro Arg Glu
                405                 410                 415

Glu Gln Tyr Asn Ser Thr Tyr Arg Val Val Ser Val Leu Thr Val Leu
            420                 425                 430

His Gln Asp Trp Leu Asn Gly Lys Glu Tyr Lys Cys Lys Val Ser Asn
        435                 440                 445

Lys Ala Leu Pro Ala Pro Ile Glu Lys Thr Ile Ser Lys Ala Lys Gly
    450                 455                 460

Gln Pro Arg Glu Pro Gln Val Tyr Thr Leu Pro Pro Ser Arg Asp Glu
465                 470                 475                 480

Leu Thr Lys Asn Gln Val Ser Leu Thr Cys Leu Val Lys Gly Phe Tyr
                485                 490                 495

Pro Ser Asp Ile Ala Val Glu Trp Glu Ser Asn Gly Gln Pro Glu Asn
            500                 505                 510

Asn Tyr Lys Thr Thr Pro Pro Val Leu Asp Ser Asp Gly Ser Phe Phe
        515                 520                 525

Leu Tyr Ser Lys Leu Thr Val Asp Lys Ser Arg Trp Gln Gln Gly Asn
    530                 535                 540

Val Phe Ser Cys Ser Val Met His Glu Ala Leu His Asn His Tyr Thr
545                 550                 555                 560

Gln Lys Ser Leu Ser Leu Ser Pro Gly Lys Val Asp Gly Ala Ser Ser
                565                 570                 575

Pro Val Asn Val Ser Ser Pro Ser Val Gln Asp Ile Lys Glu Ser Arg
            580                 585                 590

Ala Lys Lys Phe Gln Arg Gln His Met Asp Ser Asp Ser Ser Pro Ser
        595                 600                 605

Ser Ser Ser Thr Tyr Cys Asn Gln Met Met Arg Arg Arg Asn Met Thr
    610                 615                 620

Gln Gly Arg Cys Lys Pro Val Asn Thr Phe Val His Glu Pro Leu Val
625                 630                 635                 640

Asp Val Gln Asn Val Cys Phe Gln Glu Lys Val Thr Cys Lys Asn Gly
                645                 650                 655

Gln Gly Asn Cys Tyr Lys Ser Asn Ser Ser Met His Ile Thr Asp Cys
            660                 665                 670

Arg Leu Thr Asn Gly Ser Arg Tyr Pro Asn Cys Ala Tyr Arg Thr Ser
        675                 680                 685
```

```
Pro Lys Glu Arg His Ile Ile Val Ala Cys Glu Gly Ser Pro Tyr Val
    690                 695                 700

Pro Val His Phe Asp Ala Ser Val Glu Asp Ser Thr
705                 710                 715


<210> SEQ ID NO 194
<211> LENGTH: 2115
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 194

aagcttgccg ccatggaaac cccagcgcag cttctcttcc tcctgctact ctggctccca     60

gataccaccg gtaaggaatc ccgggccaag aaattccagc ggcagcatat ggactcagac    120

agttccccca gcagcagctc cacctactgt aaccaaatga tgaggcgccg gaatatgaca    180

caggggcggt gcaaaccagt gaacaccttt gtgcacgagc cctggtaga tgtccagaat     240

gtctgtttcc aggaaaaggt cacctgcaag aacgggcagg gcaactgcta caagagcaac    300

tccagcatgc acatcacaga ctgccgcctg acaaacggct ccaggtaccc caactgtgca    360

taccggacca gcccgaagga gagacacatc attgtggcct gtgaagggag cccatatgtg    420

ccagtccact ttgatgcttc tgtggaggac tctacagatc tcgagcccaa atcttctgac    480

aaaactcaca catgtccacc gtgcccagca cctgaactcc tgggggggacc gtcagtcttc   540

ctcttccccc caaaacccaa ggacaccctc atgatctccc ggacccctga ggtcacatgc    600

gtggtggtgg acgtgagcca cgaagaccct gaggtcaagt tcaactggta cgtggacggc    660

gtggaggtgc ataatgccaa gacaaagccg cgggaggagc agtacaacag cacgtaccgt    720

gtggtcagcg tcctcaccgt cctgcaccag gactggctga atggcaagga gtacaagtgc    780

aaggtctcca acaaagccct cccagccccc atcgagaaaa ccatctccaa agccaaaggg    840

cagccccgag aaccacaggt gtacaccctg cccccatccc gggatgagct gaccaagaac    900

caggtcagcc tgacctgcct ggtcaaaggc ttctatccca gcgacatcgc cgtggagtgg    960

gagagcaatg ggcagccgga gaacaactac aagaccacgc ctcccgtgct ggactccgac   1020

ggctccttct tcctctacag caagctcacc gtggacaaga gcaggtggca gcaggggaac   1080

gtcttctcat gctccgtgat gcatgagggt ctgcacaacc actacacgca gaagagcctc   1140

tctctgtctc cgggtaaagt cgacggtgct agcagccatg tgaatgtgag cagccctagc   1200

gtgcaggata tcatgggccc tggagctcgc agacagggca ggattgtgca gggaaggcct   1260

gagatgtgct tctgcccacc ccctacccca ctccctcccc ttcggatctt aacactgggc   1320

actcacacac ccaccccatg ctcctctcca ggctcagcag caggtacgta cccaaccatg   1380

ggctcgcagg ccctgccccc ggggcccatg cagaccctca tctttttcga catggaggcc   1440

actggcttgc ccttctccca gcccaaggtc acggagctgt gcctgctggc tgtccacaga   1500

tgtgccctgg agagcccccc cacctctcag ggccacctc ccacagttcc tccaccaccg    1560

cgtgtggtag acaagctctc cctgtgtgtg gctccgggga aggcctgcag ccctgcagcc   1620

agcgagatca caggtctgag cacagctgtg ctggcagcgc atgggcgtca atgttttgat   1680

gacaacctgg ccaacctgct cctagccttc ctgcggcgcc agccacagcc ctggtgcctg   1740

gtggcacaca atggtgaccg ctacgacttc cccctgctcc aagcagagct ggctatgctg   1800

ggcctcacca gtgctctgga tggtgccttc tgtgtggata gcatcactgc gctgaaggcc   1860
```

```
ctggagcgag caagcagccc ctcagaacac ggcccaagga agagctacag cctaggcagc   1920

atctacactc gcctgtatgg gcagtcccct ccagactcgc acacggctga gggtgatgtc   1980

ctggccctgc tcagcatctg tcagtggaga ccacaggccc tgctgcggtg ggtggatgct   2040

cacgccaggc ctttcggcac catcaggccc atgtatgggg tcacagcctc tgctaggacc   2100

aaatgataat ctaga                                                    2115


<210> SEQ ID NO 195
<211> LENGTH: 696
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Met Glu Thr Pro Ala Gln Leu Leu Phe Leu Leu Leu Leu Trp Leu Pro
1               5                   10                  15

Asp Thr Thr Gly Lys Glu Ser Arg Ala Lys Lys Phe Gln Arg Gln His
            20                  25                  30

Met Asp Ser Asp Ser Ser Pro Ser Ser Ser Ser Thr Tyr Cys Asn Gln
        35                  40                  45

Met Met Arg Arg Arg Asn Met Thr Gln Gly Arg Cys Lys Pro Val Asn
    50                  55                  60

Thr Phe Val His Glu Pro Leu Val Asp Val Gln Asn Val Cys Phe Gln
65                  70                  75                  80

Glu Lys Val Thr Cys Lys Asn Gly Gln Gly Asn Cys Tyr Lys Ser Asn
                85                  90                  95

Ser Ser Met His Ile Thr Asp Cys Arg Leu Thr Asn Gly Ser Arg Tyr
            100                 105                 110

Pro Asn Cys Ala Tyr Arg Thr Ser Pro Lys Glu Arg His Ile Ile Val
        115                 120                 125

Ala Cys Glu Gly Ser Pro Tyr Val Pro Val His Phe Asp Ala Ser Val
    130                 135                 140

Glu Asp Ser Thr Leu Glu Pro Lys Ser Ser Asp Lys Thr His Thr Cys
145                 150                 155                 160

Pro Pro Cys Pro Ala Pro Glu Leu Leu Gly Gly Pro Ser Val Phe Leu
                165                 170                 175

Phe Pro Pro Lys Pro Lys Asp Thr Leu Met Ile Ser Arg Thr Pro Glu
            180                 185                 190

Val Thr Cys Val Val Val Asp Val Ser His Glu Asp Pro Glu Val Lys
        195                 200                 205

Phe Asn Trp Tyr Val Asp Gly Val Glu Val His Asn Ala Lys Thr Lys
    210                 215                 220

Pro Arg Glu Glu Gln Tyr Asn Ser Thr Tyr Arg Val Val Ser Val Leu
225                 230                 235                 240

Thr Val Leu His Gln Asp Trp Leu Asn Gly Lys Glu Tyr Lys Cys Lys
                245                 250                 255

Val Ser Asn Lys Ala Leu Pro Ala Pro Ile Glu Lys Thr Ile Ser Lys
            260                 265                 270

Ala Lys Gly Gln Pro Arg Glu Pro Gln Val Tyr Thr Leu Pro Pro Ser
        275                 280                 285

Arg Asp Glu Leu Thr Lys Asn Gln Val Ser Leu Thr Cys Leu Val Lys
    290                 295                 300

Gly Phe Tyr Pro Ser Asp Ile Ala Val Glu Trp Glu Ser Asn Gly Gln
```

```
305                 310                 315                 320

Pro Glu Asn Asn Tyr Lys Thr Thr Pro Pro Val Leu Asp Ser Asp Gly
                325                 330                 335

Ser Phe Phe Leu Tyr Ser Lys Leu Thr Val Asp Lys Ser Arg Trp Gln
            340                 345                 350

Gln Gly Asn Val Phe Ser Cys Ser Val Met His Glu Gly Leu His Asn
        355                 360                 365

His Tyr Thr Gln Lys Ser Leu Ser Leu Ser Pro Gly Lys Val Asp Gly
    370                 375                 380

Ala Ser Ser His Val Asn Val Ser Ser Pro Ser Val Gln Asp Ile Met
385                 390                 395                 400

Gly Pro Gly Ala Arg Arg Gln Gly Arg Ile Val Gln Gly Arg Pro Glu
                405                 410                 415

Met Cys Phe Cys Pro Pro Pro Thr Pro Leu Pro Pro Leu Arg Ile Leu
            420                 425                 430

Thr Leu Gly Thr His Thr Pro Thr Pro Cys Ser Ser Pro Gly Ser Ala
        435                 440                 445

Ala Gly Thr Tyr Pro Thr Met Gly Ser Gln Ala Leu Pro Pro Gly Pro
    450                 455                 460

Met Gln Thr Leu Ile Phe Phe Asp Met Glu Ala Thr Gly Leu Pro Phe
465                 470                 475                 480

Ser Gln Pro Lys Val Thr Glu Leu Cys Leu Leu Ala Val His Arg Cys
                485                 490                 495

Ala Leu Glu Ser Pro Pro Thr Ser Gln Gly Pro Pro Pro Thr Val Pro
            500                 505                 510

Pro Pro Pro Arg Val Val Asp Lys Leu Ser Leu Cys Val Ala Pro Gly
        515                 520                 525

Lys Ala Cys Ser Pro Ala Ala Ser Glu Ile Thr Gly Leu Ser Thr Ala
    530                 535                 540

Val Leu Ala Ala His Gly Arg Gln Cys Phe Asp Asp Asn Leu Ala Asn
545                 550                 555                 560

Leu Leu Leu Ala Phe Leu Arg Arg Gln Pro Gln Pro Trp Cys Leu Val
                565                 570                 575

Ala His Asn Gly Asp Arg Tyr Asp Phe Pro Leu Leu Gln Ala Glu Leu
            580                 585                 590

Ala Met Leu Gly Leu Thr Ser Ala Leu Asp Gly Ala Phe Cys Val Asp
        595                 600                 605

Ser Ile Thr Ala Leu Lys Ala Leu Glu Arg Ala Ser Ser Pro Ser Glu
    610                 615                 620

His Gly Pro Arg Lys Ser Tyr Ser Leu Gly Ser Ile Tyr Thr Arg Leu
625                 630                 635                 640

Tyr Gly Gln Ser Pro Pro Asp Ser His Thr Ala Glu Gly Asp Val Leu
                645                 650                 655

Ala Leu Leu Ser Ile Cys Gln Trp Arg Pro Gln Ala Leu Leu Arg Trp
            660                 665                 670

Val Asp Ala His Ala Arg Pro Phe Gly Thr Ile Arg Pro Met Tyr Gly
        675                 680                 685

Val Thr Ala Ser Ala Arg Thr Lys
    690                 695
```

<210> SEQ ID NO 196
<211> LENGTH: 2166
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 196
gttaagcttg ccaccatgga aaccccagcg cagcttctct tcctcctgct actctggctc 60
ccagatacca ccggtatgag gatctgctcc ttcaacgtca ggtcctttgg ggaaagcaag 120
caggaagaca agaatgccat ggatgtcatt gtgaaggtca tcaaacgctg tgacatcata 180
ctcgtgatgg aaatcaagga cagcaacaac aggatctgcc ccatactgat ggagaagctg 240
aacagaaatt caaggagagg cataacatac aactatgtga ttagctctcg gcttggaaga 300
aacacatata aagaacaata tgcctttctc tacaaggaaa agctggtgtc tgtgaagagg 360
agttatcact accatgacta tcaggatgga gacgcagatg tgttttccag ggagcccttt 420
gtggtctggt tccaatctcc ccacactgct gtcaaagact tcgtgattat ccccctgcac 480
accaccccag agacatccgt taaggagatc gatgagttgg ttgaggtcta cacggacgtg 540
aaacaccgct ggaaggcgga gaatttcatt ttcatgggtg acttcaatgc cggctgcagc 600
tacgtcccca agaaggcctg gaagaacatc cgcttgagga ctgaccccag gtttgtttgg 660
ctgatcgggg accaagagga caccacggtg aagaagagca ccaactgtgc atatgacagg 720
attgtgctta gaggacaaga aatcgtcagt tctgttgttc ccaagtcaaa cagtgttttt 780
gacttccaga aagcttacaa gctgactgaa gaggaggccc tggatgtcag cgaccacttt 840
ccagttgaat ttaaactaca gtcttcaagg gccttcacca acagcaaaaa atctgtcact 900
ctaaggaaga aaacaaagag caaacgctca gatctctccg gaggaggtgg ctcaggtggt 960
ggaggatctg gaggaggtgg gagtggtgga ggtggttcta ccggtctcga gcccaaatct 1020
tctgacaaaa ctcacacatg tccaccgtgc ccagcacctg aactcctggg gggaccgtca 1080
gtcttcctct tccccccaaa acccaaggac accctcatga tctcccggac ccctgaggtc 1140
acatgcgtgg tggtggacgt gagccacgaa gaccctgagg tcaagttcaa ctggtacgtg 1200
gacggcgtgg aggtgcataa tgccaagaca aagccgcggg aggagcagta caacagcacg 1260
taccgtgtgg tcagcgtcct caccgtcctg caccaggact ggctgaatgg caaggagtac 1320
aagtgcaagg tctccaacaa agccctccca gcccccatcg agaaaaccat ctccaaagcc 1380
aaagggcagc cccgagaacc acaggtgtac accctgcccc catcccggga tgagctgacc 1440
aagaaccagg tcagcctgac ctgcctggtc aaaggcttct atcccagcga catcgccgtg 1500
gagtgggaga gcaatgggca gccggagaac aactacaaga ccacgcctcc cgtgctggac 1560
tccgacggct ccttcttcct ctacagcaag ctcaccgtgg acaagagcag gtggcagcag 1620
gggaacgtct tctcatgctc cgtgatgcat gagggtctgc acaaccacta cacgcagaag 1680
agcctctctc tgtctccggg taaagtcgac ggtgctagca gccatgtgaa tgtgagcagc 1740
cctagcgtgc aggatatccc ttccctgggc aaggaatccc gggccaagaa attccagcgg 1800
cagcatatgg actcagacag ttcccccagc agcagctcca cctactgtaa ccaaatgatg 1860
aggcgccgga atatgacaca ggggcggtgc aaaccagtga acacctttgt gcacgagccc 1920
ctggtagatg tccagaatgt ctgtttccag gaaaaggtca cctgcaagaa cgggcagggc 1980
aactgctaca agagcaactc cagcatgcac atcacagact gccgcctgac aaacggctcc 2040
aggtacccca actgtgcata ccggaccagc ccgaaggaga gacacatcat tgtggcctgt 2100
gaagggagcc catatgtgcc agtccacttt gatgcttctg tggaggactc tacctaataa 2160
tctaga 2166

<210> SEQ ID NO 197
<211> LENGTH: 704
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 197

Met Glu Thr Pro Ala Gln Leu Leu Phe Leu Leu Leu Leu Trp Leu Pro
1 5 10 15

Asp Thr Thr Gly Met Arg Ile Cys Ser Phe Asn Val Arg Ser Phe Gly
20 25 30

Glu Ser Lys Gln Glu Asp Lys Asn Ala Met Asp Val Ile Val Lys Val
35 40 45

Ile Lys Arg Cys Asp Ile Ile Leu Val Met Glu Ile Lys Asp Ser Asn
50 55 60

Asn Arg Ile Cys Pro Ile Leu Met Glu Lys Leu Asn Arg Asn Ser Arg
65 70 75 80

Arg Gly Ile Thr Tyr Asn Tyr Val Ile Ser Ser Arg Leu Gly Arg Asn
85 90 95

Thr Tyr Lys Glu Gln Tyr Ala Phe Leu Tyr Lys Glu Lys Leu Val Ser
100 105 110

Val Lys Arg Ser Tyr His Tyr His Asp Tyr Gln Asp Gly Asp Ala Asp
115 120 125

Val Phe Ser Arg Glu Pro Phe Val Val Trp Phe Gln Ser Pro His Thr
130 135 140

Ala Val Lys Asp Phe Val Ile Ile Pro Leu His Thr Thr Pro Glu Thr
145 150 155 160

Ser Val Lys Glu Ile Asp Glu Leu Val Glu Val Tyr Thr Asp Val Lys
165 170 175

His Arg Trp Lys Ala Glu Asn Phe Ile Phe Met Gly Asp Phe Asn Ala
180 185 190

Gly Cys Ser Tyr Val Pro Lys Lys Ala Trp Lys Asn Ile Arg Leu Arg
195 200 205

Thr Asp Pro Arg Phe Val Trp Leu Ile Gly Asp Gln Glu Asp Thr Thr
210 215 220

Val Lys Lys Ser Thr Asn Cys Ala Tyr Asp Arg Ile Val Leu Arg Gly
225 230 235 240

Gln Glu Ile Val Ser Ser Val Val Pro Lys Ser Asn Ser Val Phe Asp
245 250 255

Phe Gln Lys Ala Tyr Lys Leu Thr Glu Glu Glu Ala Leu Asp Val Ser
260 265 270

Asp His Phe Pro Val Glu Phe Lys Leu Gln Ser Ser Arg Ala Phe Thr
275 280 285

Asn Ser Lys Lys Ser Val Thr Leu Arg Lys Lys Thr Lys Ser Lys Arg
290 295 300

Ser Gly Gly Gly Gly Ser Gly Gly Gly Gly Ser Gly Gly Gly Gly Ser
305 310 315 320

Gly Gly Gly Gly Ser Leu Glu Pro Lys Ser Ser Asp Lys Thr His Thr
325 330 335

Cys Pro Pro Cys Pro Ala Pro Glu Leu Leu Gly Gly Pro Ser Val Phe
340 345 350

Leu Phe Pro Pro Lys Pro Lys Asp Thr Leu Met Ile Ser Arg Thr Pro

```
        355                 360                 365

Glu Val Thr Cys Val Val Val Asp Val Ser His Glu Asp Pro Glu Val
    370                 375                 380

Lys Phe Asn Trp Tyr Val Asp Gly Val Glu Val His Asn Ala Lys Thr
385                 390                 395                 400

Lys Pro Arg Glu Glu Gln Tyr Asn Ser Thr Tyr Arg Val Val Ser Val
                405                 410                 415

Leu Thr Val Leu His Gln Asp Trp Leu Asn Gly Lys Glu Tyr Lys Cys
            420                 425                 430

Lys Val Ser Asn Lys Ala Leu Pro Ala Pro Ile Glu Lys Thr Ile Ser
        435                 440                 445

Lys Ala Lys Gly Gln Pro Arg Glu Pro Gln Val Tyr Thr Leu Pro Pro
    450                 455                 460

Ser Arg Asp Glu Leu Thr Lys Asn Gln Val Ser Leu Thr Cys Leu Val
465                 470                 475                 480

Lys Gly Phe Tyr Pro Ser Asp Ile Ala Val Glu Trp Glu Ser Asn Gly
                485                 490                 495

Gln Pro Glu Asn Asn Tyr Lys Thr Thr Pro Pro Val Leu Asp Ser Asp
            500                 505                 510

Gly Ser Phe Phe Leu Tyr Ser Lys Leu Thr Val Asp Lys Ser Arg Trp
        515                 520                 525

Gln Gln Gly Asn Val Phe Ser Cys Ser Val Met His Glu Gly Leu His
    530                 535                 540

Asn His Tyr Thr Gln Lys Ser Leu Ser Leu Ser Pro Gly Lys Val Asp
545                 550                 555                 560

Gly Ala Ser Ser His Val Asn Val Ser Ser Pro Ser Val Gln Asp Ile
                565                 570                 575

Lys Glu Ser Arg Ala Lys Lys Phe Gln Arg Gln His Met Asp Ser Asp
            580                 585                 590

Ser Ser Pro Ser Ser Ser Ser Thr Tyr Cys Asn Gln Met Met Arg Arg
        595                 600                 605

Arg Asn Met Thr Gln Gly Arg Cys Lys Pro Val Asn Thr Phe Val His
    610                 615                 620

Glu Pro Leu Val Asp Val Gln Asn Val Cys Phe Gln Glu Lys Val Thr
625                 630                 635                 640

Cys Lys Asn Gly Gln Gly Asn Cys Tyr Lys Ser Asn Ser Ser Met His
                645                 650                 655

Ile Thr Asp Cys Arg Leu Thr Asn Gly Ser Arg Tyr Pro Asn Cys Ala
            660                 665                 670

Tyr Arg Thr Ser Pro Lys Glu Arg His Ile Ile Val Ala Cys Glu Gly
        675                 680                 685

Ser Pro Tyr Val Pro Val His Phe Asp Ala Ser Val Glu Asp Ser Thr
    690                 695                 700
```

<210> SEQ ID NO 198
<211> LENGTH: 2154
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 198

```
gttaagcttg ccaccatgga aaccccagcg cagcttctct tcctcctgct actctggctc      60

ccagatacca ccggtaagga atcccgggcc aagaaattcc agcggcagca tatggactca     120
```

```
gacagttccc ccagcagcag ctccacctac tgtaaccaaa tgatgaggcg ccggaatatg    180
acacaggggc ggtgcaaacc agtgaacacc tttgtgcacg agcccctggt agatgtccag    240
aatgtctgtt tccaggaaaa ggtcacctgc aagaacgggc agggcaactg ctacaagagc    300
aactccagca tgcacatcac agactgccgc ctgacaaacg gctccaggta ccccaactgt    360
gcataccgga ccagcccgaa ggagagacac atcattgtgg cctgtgaagg gagcccatat    420
gtgccagtcc actttgatgc ttctgtggag gactctacag atctctccgg aggaggtggc    480
tcaggtggtg gaggatctgg aggaggtggg agtggtggag gtggttctac cggtctcgag    540
cccaaatctt ctgacaaaac tcacacatgt ccaccgtgcc cagcacctga actcctgggg    600
ggaccgtcag tcttcctctt ccccccaaaa cccaaggaca ccctcatgat ctcccggacc    660
cctgaggtca catgcgtggt ggtggacgtg agccacgaag accctgaggt caagttcaac    720
tggtacgtgg acggcgtgga ggtgcataat gccaagacaa agccgcggga ggagcagtac    780
aacagcacgt accgtgtggt cagcgtcctc accgtcctgc accaggactg gctgaatggc    840
aaggagtaca agtgcaaggt ctccaacaaa gccctcccag cccccatcga gaaaaccatc    900
tccaaagcca aagggcagcc ccgagaacca caggtgtaca ccctgccccc atcccgggat    960
gagctgacca agaaccaggt cagcctgacc tgcctggtca aaggcttcta tcccagcgac   1020
atcgccgtgg agtgggagag caatgggcag ccggagaaca actacaagac cacgcctccc   1080
gtgctggact ccgacggctc cttcttcctc tacagcaagc tcaccgtgga caagagcagg   1140
tggcagcagg ggaacgtctt ctcatgctcc gtgatgcatg aggctctgca caaccactac   1200
acgcagaaga gcctctctct gtctccgggt aaagtcgacg gtgctagcag ccatgtgaat   1260
gtgagcagcc ctagcgtgca ggatatcatg aggatctgct ccttcaacgt caggtccttt   1320
ggggaaagca agcaggaaga caagaatgcc atggatgtca ttgtgaaggt catcaaacgc   1380
tgtgacatca tactcgtgat ggaaatcaag gacagcaaca acaggatctg ccccatactg   1440
atggagaagc tgaacagaaa ttcaaggaga ggcataacat acaactatgt gattagctct   1500
cggcttggaa gaaacacata taaagaacaa tatgcctttc tctacaagga aaagctggtg   1560
tctgtgaaga ggagttatca ctaccatgac tatcaggatg gagacgcaga tgtgttttcc   1620
agggagccct ttgtggtctg gttccaatct ccccacactg ctgtcaaaga cttcgtgatt   1680
atccccctgc acaccacccc agagacatcc gttaaggaga tcgatgagtt ggttgaggtc   1740
tacacggacg tgaaacaccg ctggaaggcg gagaatttca ttttcatggg tgacttcaat   1800
gccggctgca gctacgtccc caagaaggcc tggaagaaca tccgcttgag gactgacccc   1860
aggtttgttt ggctgatcgg ggaccaagag gacaccacgg tgaagaagag caccaactgt   1920
gcatatgaca ggattgtgct tagaggacaa gaaatcgtca gttctgttgt tcccaagtca   1980
aacagtgttt ttgacttcca gaaagcttac aagctgactg aagaggaggc cctggatgtc   2040
agcgaccact ttccagttga atttaaacta cagtcttcaa gggccttcac caacagcaaa   2100
aaatctgtca ctctaaggaa gaaaacaaag agcaaacgct cctaatgatc taga         2154
```

<210> SEQ ID NO 199
<211> LENGTH: 704
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 199

```
Met Glu Thr Pro Ala Gln Leu Leu Phe Leu Leu Leu Leu Trp Leu Pro
1               5                   10                  15

Asp Thr Thr Gly Lys Glu Ser Arg Ala Lys Lys Phe Gln Arg Gln His
            20                  25                  30

Met Asp Ser Asp Ser Ser Pro Ser Ser Ser Ser Thr Tyr Cys Asn Gln
        35                  40                  45

Met Met Arg Arg Arg Asn Met Thr Gln Gly Arg Cys Lys Pro Val Asn
    50                  55                  60

Thr Phe Val His Glu Pro Leu Val Asp Val Gln Asn Val Cys Phe Gln
65                  70                  75                  80

Glu Lys Val Thr Cys Lys Asn Gly Gln Gly Asn Cys Tyr Lys Ser Asn
                85                  90                  95

Ser Ser Met His Ile Thr Asp Cys Arg Leu Thr Asn Gly Ser Arg Tyr
            100                 105                 110

Pro Asn Cys Ala Tyr Arg Thr Ser Pro Lys Glu Arg His Ile Ile Val
        115                 120                 125

Ala Cys Glu Gly Ser Pro Tyr Val Pro Val His Phe Asp Ala Ser Val
    130                 135                 140

Glu Asp Ser Thr Gly Gly Gly Gly Ser Gly Gly Gly Gly Ser Gly Gly
145                 150                 155                 160

Gly Gly Ser Gly Gly Gly Gly Ser Leu Glu Pro Lys Ser Ser Asp Lys
                165                 170                 175

Thr His Thr Cys Pro Pro Cys Pro Ala Pro Glu Leu Leu Gly Gly Pro
            180                 185                 190

Ser Val Phe Leu Phe Pro Pro Lys Pro Lys Asp Thr Leu Met Ile Ser
        195                 200                 205

Arg Thr Pro Glu Val Thr Cys Val Val Val Asp Val Ser His Glu Asp
    210                 215                 220

Pro Glu Val Lys Phe Asn Trp Tyr Val Asp Gly Val Glu Val His Asn
225                 230                 235                 240

Ala Lys Thr Lys Pro Arg Glu Glu Gln Tyr Asn Ser Thr Tyr Arg Val
                245                 250                 255

Val Ser Val Leu Thr Val Leu His Gln Asp Trp Leu Asn Gly Lys Glu
            260                 265                 270

Tyr Lys Cys Lys Val Ser Asn Lys Ala Leu Pro Ala Pro Ile Glu Lys
        275                 280                 285

Thr Ile Ser Lys Ala Lys Gly Gln Pro Arg Glu Pro Gln Val Tyr Thr
    290                 295                 300

Leu Pro Pro Ser Arg Asp Glu Leu Thr Lys Asn Gln Val Ser Leu Thr
305                 310                 315                 320

Cys Leu Val Lys Gly Phe Tyr Pro Ser Asp Ile Ala Val Glu Trp Glu
                325                 330                 335

Ser Asn Gly Gln Pro Glu Asn Asn Tyr Lys Thr Thr Pro Pro Val Leu
            340                 345                 350

Asp Ser Asp Gly Ser Phe Phe Leu Tyr Ser Lys Leu Thr Val Asp Lys
        355                 360                 365

Ser Arg Trp Gln Gln Gly Asn Val Phe Ser Cys Ser Val Met His Glu
    370                 375                 380

Ala Leu His Asn His Tyr Thr Gln Lys Ser Leu Ser Leu Ser Pro Gly
385                 390                 395                 400

Lys Val Asp Gly Ala Ser Ser His Val Asn Val Ser Ser Pro Ser Val
                405                 410                 415
```

```
Gln Asp Ile Met Arg Ile Cys Ser Phe Asn Val Arg Ser Phe Gly Glu
            420                 425                 430

Ser Lys Gln Glu Asp Lys Asn Ala Met Asp Val Ile Val Lys Val Ile
        435                 440                 445

Lys Arg Cys Asp Ile Ile Leu Val Met Glu Ile Lys Asp Ser Asn Asn
    450                 455                 460

Arg Ile Cys Pro Ile Leu Met Glu Lys Leu Asn Arg Asn Ser Arg Arg
465                 470                 475                 480

Gly Ile Thr Tyr Asn Tyr Val Ile Ser Ser Arg Leu Gly Arg Asn Thr
                485                 490                 495

Tyr Lys Glu Gln Tyr Ala Phe Leu Tyr Lys Glu Lys Leu Val Ser Val
            500                 505                 510

Lys Arg Ser Tyr His Tyr His Asp Tyr Gln Asp Gly Asp Ala Asp Val
        515                 520                 525

Phe Ser Arg Glu Pro Phe Val Val Trp Phe Gln Ser Pro His Thr Ala
    530                 535                 540

Val Lys Asp Phe Val Ile Ile Pro Leu His Thr Thr Pro Glu Thr Ser
545                 550                 555                 560

Val Lys Glu Ile Asp Glu Leu Val Glu Val Tyr Thr Asp Val Lys His
                565                 570                 575

Arg Trp Lys Ala Glu Asn Phe Ile Phe Met Gly Asp Phe Asn Ala Gly
            580                 585                 590

Cys Ser Tyr Val Pro Lys Lys Ala Trp Lys Asn Ile Arg Leu Arg Thr
        595                 600                 605

Asp Pro Arg Phe Val Trp Leu Ile Gly Asp Gln Glu Asp Thr Thr Val
    610                 615                 620

Lys Lys Ser Thr Asn Cys Ala Tyr Asp Arg Ile Val Leu Arg Gly Gln
625                 630                 635                 640

Glu Ile Val Ser Ser Val Val Pro Lys Ser Asn Ser Val Phe Asp Phe
                645                 650                 655

Gln Lys Ala Tyr Lys Leu Thr Glu Glu Glu Ala Leu Asp Val Ser Asp
            660                 665                 670

His Phe Pro Val Glu Phe Lys Leu Gln Ser Ser Arg Ala Phe Thr Asn
        675                 680                 685

Ser Lys Lys Ser Val Thr Leu Arg Lys Lys Thr Lys Ser Lys Arg Ser
    690                 695                 700
```

<210> SEQ ID NO 200
<211> LENGTH: 2586
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 200

```
gttaagcttg ccaccatgga aaccccagcg cagcttctct tcctcctgct actctggctc     60

ccagatacca ccggtctgaa gatcgcagcc ttcaacatcc agacatttgg ggagaccaag    120

atgtccaatg ccaccctcgt cagctacatt gtgcagatcc tgagccgcta tgacatcgcc    180

ctggtccagg aggtcagaga cagccacctg actgccgtgg ggaagctgct ggacaacctc    240

aatcaggatg caccagacac ctatcactac gtggtcagtg agccactggg acggaacagc    300

tataaggagc gctacctgtt cgtgtacagg cctgaccagg tgtctgcggt ggacagctac    360

tactacgatg atggctgcga gccctgcagg aacgacacct tcaaccgaga gccattcatt    420
```

```
gtcaggttct tctcccggtt cacagaggtc agggagtttg ccattgttcc cctgcatgcg    480
gccccggggg acgcagtagc cgagatcgac gctctctatg acgtctacct ggatgtccaa    540
gagaaatggg gcttggagga cgtcatgttg atgggcgact tcaatgcggg ctgcagctat    600
gtgagaccct cccagtggtc atccatccgc ctgtggacaa gccccacctt ccagtggctg    660
atccccgaca gcgctgacac cacagctaca cccacgcact gtgcctatga caggatcgtg    720
gttgcaggga tgctgctccg aggcgccgtt gttcccgact cggctcttcc ctttaacttc    780
caggctgcct atggcctgag tgaccaactg gcccaagcca tcagtgacca ctatccagtg    840
gaggtgatgc tgaaagatct ctccggagga ggtggctcag gtggtggagg atctggagga    900
ggtgggagtg gtggaggtgg ttctaccggt ctcgagccca aatcttctga caaaactcac    960
acatgtccac cgtgcccagc acctgaactc ctggggggac cgtcagtctt cctcttcccc   1020
ccaaaaccca aggacaccct catgatctcc cggacccctg aggtcacatg cgtggtggtg   1080
gacgtgagcc acgaagaccc tgaggtcaag ttcaactggt acgtggacgg cgtggaggtg   1140
cataatgcca agacaaagcc gcgggaggag cagtacaaca gcacgtaccg tgtggtcagc   1200
gtcctcaccg tcctgcacca ggactggctg aatggcaagg agtacaagtg caaggtctcc   1260
aacaaagccc tcccagcccc catcgagaaa accatctcca aagccaaagg gcagccccga   1320
gaaccacagg tgtacaccct gcccccatcc cgggatgagc tgaccaagaa ccaggtcagc   1380
ctgacctgcc tggtcaaagg cttctatccc agcgacatcg ccgtggagtg ggagagcaat   1440
gggcagccgg agaacaacta caagaccacg cctcccgtgc tggactccga cggctccttc   1500
ttcctctaca gcaagctcac cgtggacaag agcaggtggc agcaggggaa cgtcttctca   1560
tgctccgtga tgcatgaggc tctgcacaac cactacacgc agaagagcct ctctctgtct   1620
ccgggtaaag tcgacggtgc tagcagccat gtgaatgtga gcagccctag cgtgcaggat   1680
atcatgggcc ctggagctcg cagacagggc aggattgtgc agggaaggcc tgagatgtgc   1740
ttctgcccac cccctacccc actccctccc cttcggatct taacactggg cactcacaca   1800
cccaccccat gctcctctcc aggctcagca gcaggtacgt acccaaccat gggctcgcag   1860
gccctgcccc cggggcccat gcagaccctc atctttttcg acatggaggc cactggcttg   1920
cccttctccc agcccaaggt cacggagctg tgcctgctgg ctgtccacag atgtgccctg   1980
gagagccccc ccacctctca ggggccacct cccacagttc ctccaccacc gcgtgtggta   2040
gacaagctct ccctgtgtgt ggctccgggg aaggcctgca gccctgcagc cagcgagatc   2100
acaggtctga gcacagctgt gctggcagcg catgggcgtc aatgttttga tgacaacctg   2160
gccaacctgc tcctagcctt cctgcggcgc cagccacagc cctggtgcct ggtggcacac   2220
aatggtgacc gctacgactt cccccctgctc caagcagagc tggctatgct gggcctcacc   2280
agtgctctgg atggtgcctt ctgtgtggat agcatcactg cgctgaaggc cctggagcga   2340
gcaagcagcc cctcagaaca cggcccaagg aagagctaca gcctaggcag catctacact   2400
cgcctgtatg ggcagtcccc tccagactcg cacacggctg agggtgatgt cctggccctg   2460
ctcagcatct gtcagtggag accacaggcc ctgctgcggt gggtggatgc tcacgccagg   2520
cctttcggca ccatcaggcc catgtatggg gtcacagcct ctgctaggac caaatgataa   2580
tctaga                                                               2586
```

<210> SEQ ID NO 201
<211> LENGTH: 848
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 201

```
Met Glu Thr Pro Ala Gln Leu Leu Phe Leu Leu Leu Leu Trp Leu Pro
1               5                   10                  15

Asp Thr Thr Gly Leu Lys Ile Ala Ala Phe Asn Ile Gln Thr Phe Gly
            20                  25                  30

Glu Thr Lys Met Ser Asn Ala Thr Leu Val Ser Tyr Ile Val Gln Ile
        35                  40                  45

Leu Ser Arg Tyr Asp Ile Ala Leu Val Gln Glu Val Arg Asp Ser His
    50                  55                  60

Leu Thr Ala Val Gly Lys Leu Leu Asp Asn Leu Asn Gln Asp Ala Pro
65                  70                  75                  80

Asp Thr Tyr His Tyr Val Val Ser Glu Pro Leu Gly Arg Asn Ser Tyr
                85                  90                  95

Lys Glu Arg Tyr Leu Phe Val Tyr Arg Pro Asp Gln Val Ser Ala Val
            100                 105                 110

Asp Ser Tyr Tyr Tyr Asp Asp Gly Cys Glu Pro Cys Arg Asn Asp Thr
        115                 120                 125

Phe Asn Arg Glu Pro Phe Ile Val Arg Phe Phe Ser Arg Phe Thr Glu
    130                 135                 140

Val Arg Glu Phe Ala Ile Val Pro Leu His Ala Ala Pro Gly Asp Ala
145                 150                 155                 160

Val Ala Glu Ile Asp Ala Leu Tyr Asp Val Tyr Leu Asp Val Gln Glu
                165                 170                 175

Lys Trp Gly Leu Glu Asp Val Met Leu Met Gly Asp Phe Asn Ala Gly
            180                 185                 190

Cys Ser Tyr Val Arg Pro Ser Gln Trp Ser Ser Ile Arg Leu Trp Thr
        195                 200                 205

Ser Pro Thr Phe Gln Trp Leu Ile Pro Asp Ser Ala Asp Thr Thr Ala
    210                 215                 220

Thr Pro Thr His Cys Ala Tyr Asp Arg Ile Val Val Ala Gly Met Leu
225                 230                 235                 240

Leu Arg Gly Ala Val Val Pro Asp Ser Ala Leu Pro Phe Asn Phe Gln
                245                 250                 255

Ala Ala Tyr Gly Leu Ser Asp Gln Leu Ala Gln Ala Ile Ser Asp His
            260                 265                 270

Tyr Pro Val Glu Val Met Leu Lys Gly Gly Gly Gly Ser Gly Gly Gly
        275                 280                 285

Gly Ser Gly Gly Gly Gly Ser Gly Gly Gly Gly Ser Leu Glu Pro Lys
    290                 295                 300

Ser Ser Asp Lys Thr His Thr Cys Pro Pro Cys Pro Ala Pro Glu Leu
305                 310                 315                 320

Leu Gly Gly Pro Ser Val Phe Leu Phe Pro Pro Lys Pro Lys Asp Thr
                325                 330                 335

Leu Met Ile Ser Arg Thr Pro Glu Val Thr Cys Val Val Val Asp Val
            340                 345                 350

Ser His Glu Asp Pro Glu Val Lys Phe Asn Trp Tyr Val Asp Gly Val
        355                 360                 365

Glu Val His Asn Ala Lys Thr Lys Pro Arg Glu Glu Gln Tyr Asn Ser
    370                 375                 380

Thr Tyr Arg Val Val Ser Val Leu Thr Val Leu His Gln Asp Trp Leu
```

```
385                 390                 395                 400

Asn Gly Lys Glu Tyr Lys Cys Lys Val Ser Asn Lys Ala Leu Pro Ala
                405                 410                 415

Pro Ile Glu Lys Thr Ile Ser Lys Ala Lys Gly Gln Pro Arg Glu Pro
            420                 425                 430

Gln Val Tyr Thr Leu Pro Pro Ser Arg Asp Glu Leu Thr Lys Asn Gln
        435                 440                 445

Val Ser Leu Thr Cys Leu Val Lys Gly Phe Tyr Pro Ser Asp Ile Ala
    450                 455                 460

Val Glu Trp Glu Ser Asn Gly Gln Pro Glu Asn Asn Tyr Lys Thr Thr
465                 470                 475                 480

Pro Pro Val Leu Asp Ser Asp Gly Ser Phe Phe Leu Tyr Ser Lys Leu
                485                 490                 495

Thr Val Asp Lys Ser Arg Trp Gln Gln Gly Asn Val Phe Ser Cys Ser
            500                 505                 510

Val Met His Glu Ala Leu His Asn His Tyr Thr Gln Lys Ser Leu Ser
        515                 520                 525

Leu Ser Pro Gly Lys Val Asp Gly Ala Ser Ser His Val Asn Val Ser
    530                 535                 540

Ser Pro Ser Val Gln Asp Ile Met Gly Pro Gly Ala Arg Arg Gln Gly
545                 550                 555                 560

Arg Ile Val Gln Gly Arg Pro Glu Met Cys Phe Cys Pro Pro Pro Thr
                565                 570                 575

Pro Leu Pro Pro Leu Arg Ile Leu Thr Leu Gly Thr His Thr Pro Thr
            580                 585                 590

Pro Cys Ser Ser Pro Gly Ser Ala Ala Gly Thr Tyr Pro Thr Met Gly
        595                 600                 605

Ser Gln Ala Leu Pro Pro Gly Pro Met Gln Thr Leu Ile Phe Phe Asp
    610                 615                 620

Met Glu Ala Thr Gly Leu Pro Phe Ser Gln Pro Lys Val Thr Glu Leu
625                 630                 635                 640

Cys Leu Leu Ala Val His Arg Cys Ala Leu Glu Ser Pro Pro Thr Ser
                645                 650                 655

Gln Gly Pro Pro Pro Thr Val Pro Pro Pro Pro Arg Val Val Asp Lys
            660                 665                 670

Leu Ser Leu Cys Val Ala Pro Gly Lys Ala Cys Ser Pro Ala Ala Ser
        675                 680                 685

Glu Ile Thr Gly Leu Ser Thr Ala Val Leu Ala Ala His Gly Arg Gln
    690                 695                 700

Cys Phe Asp Asp Asn Leu Ala Asn Leu Leu Leu Ala Phe Leu Arg Arg
705                 710                 715                 720

Gln Pro Gln Pro Trp Cys Leu Val Ala His Asn Gly Asp Arg Tyr Asp
                725                 730                 735

Phe Pro Leu Leu Gln Ala Glu Leu Ala Met Leu Gly Leu Thr Ser Ala
            740                 745                 750

Leu Asp Gly Ala Phe Cys Val Asp Ser Ile Thr Ala Leu Lys Ala Leu
        755                 760                 765

Glu Arg Ala Ser Ser Pro Ser Glu His Gly Pro Arg Lys Ser Tyr Ser
    770                 775                 780

Leu Gly Ser Ile Tyr Thr Arg Leu Tyr Gly Gln Ser Pro Pro Asp Ser
785                 790                 795                 800

His Thr Ala Glu Gly Asp Val Leu Ala Leu Leu Ser Ile Cys Gln Trp
                805                 810                 815
```

Arg Pro Gln Ala Leu Leu Arg Trp Val Asp Ala His Ala Arg Pro Phe
820 825 830

Gly Thr Ile Arg Pro Met Tyr Gly Val Thr Ala Ser Ala Arg Thr Lys
835 840 845

<210> SEQ ID NO 202
<211> LENGTH: 2583
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (2500)..(2500)
<223> OTHER INFORMATION: a, c, t, g, unknown or other

<400> SEQUENCE: 202
aagcttgcca ccatggaaac cccagcgcag cttctcttcc tcctgctact ctggctccca 60
gataccaccg gtatgggccc tggagctcgc agacagggca ggattgtgca gggaaggcct 120
gagatgtgct tctgcccacc ccctacccca ctccctcccc ttcggatctt aacactgggc 180
actcacacac ccaccccatg ctcctctcca ggctcagcag caggtacgta cccaaccatg 240
ggctcgcagg ccctgccccc ggggcccatg cagaccctca tctttttcga catggaggcc 300
actggcttgc ccttctccca gcccaaggtc acggagctgt gcctgctggc tgtccacaga 360
tgtgccctgg agagcccccc cacctctcag gggccacctc ccacagttcc tccaccaccg 420
cgtgtggtag acaagctctc cctgtgtgtg gctccgggga aggcctgcag ccctgcagcc 480
agcgagatca caggtctgag cacagctgtg ctggcagcgc atgggcgtca atgttttgat 540
gacaacctgg ccaacctgct cctagccttc ctgcggcgcc agccacagcc ctggtgcctg 600
gtggcacaca atggtgaccg ctacgacttc cccctgctcc aagcagagct ggctatgctg 660
ggcctcacca gtgctctgga tggtgccttc tgtgtggata gcatcactgc gctgaaggcc 720
ctggagcgag caagcagccc ctcagaacac ggcccaagga agagctacag cctaggcagc 780
atctacactc gcctgtatgg gcagtcccct ccagactcgc acacggctga gggtgatgtc 840
ctggccctgc tcagcatctg tcagtggaga ccacaggccc tgctgcggtg ggtggatgct 900
cacgccaggc ctttcggcac catcaggccc atgtatgggg tcacagcctc tgctaggacc 960
aaagatctct ccggaggagg tggctcaggt ggtggaggat ctggaggagg tgggagtggt 1020
ggaggtggtt ctaccggtct cgagcccaaa tcttctgaca aaactcacac atgtccaccg 1080
tgcccagcac ctgaactcct ggggggaccg tcagtcttcc tcttcccccc aaaacccaag 1140
gacaccctca tgatctcccg gacccctgag gtcacatgcg tggtggtgga cgtgagccac 1200
gaagaccctg aggtcaagtt caactggtac gtggacggcg tggaggtgca taatgccaag 1260
acaaagccgc gggaggagca gtacaacagc acgtaccgtg tggtcagcgt cctcaccgtc 1320
ctgcaccagg actggctgaa tggcaaggag tacaagtgca aggtctccaa caaagccctc 1380
ccagccccca tcgagaaaac catctccaaa gccaaagggc agccccgaga accacaggtg 1440
tacaccctgc ccccatcccg ggatgagctg accaagaacc aggtcagcct gacctgcctg 1500
gtcaaaggct tctatcccag cgacatcgcc gtggagtggg agagcaatgg gcagccggag 1560
aacaactaca agaccacgcc tcccgtgctg gactccgacg gctccttctt cctctacagc 1620
aagctcaccg tggacaagag caggtggcag caggggaacg tcttctcatg ctccgtgatg 1680
catgaggctc tgcacaacca ctacacgcag aagagcctct ctctgtctcc gggtaaagtc 1740

```
gacggtgcta gcagccatgt gaatgtgagc agccctagcg tgcaggatat cctgaagatc   1800

gcagccttca acatccagac atttggggag accaagatgt ccaatgccac cctcgtcagc   1860

tacattgtgc agatcctgag ccgctatgac atcgccctgg tccaggaggt cagagacagc   1920

cacctgactg ccgtggggaa gctgctggac aacctcaatc aggatgcacc agacacctat   1980

cactacgtgg tcagtgagcc actgggacgg aacagctata aggagcgcta cctgttcgtg   2040

tacaggcctg accaggtgtc tgcggtggac agctactact acgatgatgg ctgcgagccc   2100

tgcgggaacg acaccttcaa ccgagagcca gccattgtca ggttcttctc ccggttcaca   2160

gaggtcaggg agtttgccat tgttcccctg catgcggccc cgggggacgc agtagccgag   2220

atcgacgctc tctatgacgt ctacctggat gtccaagaga aatggggctc ggaggacgtc   2280

atgttgatgg gcgacttcaa tgcgggctgc agctatgtga gaccctccca gtggtcatcc   2340

atccgcctgt ggacaagccc caccttccag tggctgatcc ccgacagcgc tgacaccaca   2400

gctacaccca cgcactgtgc ctatgacagg atcgtggttg cagggatgct gctccgaggc   2460

gccgttgttc ccgactcggc tcttcccttt aacttccagn ctgcctatgg cctgagtgac   2520

caactggccc aagccatcag tgaccactat ccagtggagg tgatgctgaa gtgataatct   2580

aga                                                                 2583
```

```
<210> SEQ ID NO 203
<211> LENGTH: 848
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (825)..(825)
<223> OTHER INFORMATION: Any amino acid

<400> SEQUENCE: 203

Met Glu Thr Pro Ala Gln Leu Leu Phe Leu Leu Leu Leu Trp Leu Pro
1               5                   10                  15

Asp Thr Thr Gly Met Gly Pro Gly Ala Arg Arg Gln Gly Arg Ile Val
            20                  25                  30

Gln Gly Arg Pro Glu Met Cys Phe Cys Pro Pro Pro Thr Pro Leu Pro
        35                  40                  45

Pro Leu Arg Ile Leu Thr Leu Gly Thr His Thr Pro Thr Pro Cys Ser
    50                  55                  60

Ser Pro Gly Ser Ala Ala Gly Thr Tyr Pro Thr Met Gly Ser Gln Ala
65                  70                  75                  80

Leu Pro Pro Gly Pro Met Gln Thr Leu Ile Phe Phe Asp Met Glu Ala
                85                  90                  95

Thr Gly Leu Pro Phe Ser Gln Pro Lys Val Thr Glu Leu Cys Leu Leu
            100                 105                 110

Ala Val His Arg Cys Ala Leu Glu Ser Pro Pro Thr Ser Gln Gly Pro
        115                 120                 125

Pro Pro Thr Val Pro Pro Pro Pro Arg Val Val Asp Lys Leu Ser Leu
    130                 135                 140

Cys Val Ala Pro Gly Lys Ala Cys Ser Pro Ala Ala Ser Glu Ile Thr
145                 150                 155                 160

Gly Leu Ser Thr Ala Val Leu Ala Ala His Gly Arg Gln Cys Phe Asp
                165                 170                 175
```

```
Asp Asn Leu Ala Asn Leu Leu Leu Ala Phe Leu Arg Arg Gln Pro Gln
            180                 185                 190

Pro Trp Cys Leu Val Ala His Asn Gly Asp Arg Tyr Asp Phe Pro Leu
        195                 200                 205

Leu Gln Ala Glu Leu Ala Met Leu Gly Leu Thr Ser Ala Leu Asp Gly
    210                 215                 220

Ala Phe Cys Val Asp Ser Ile Thr Ala Leu Lys Ala Leu Glu Arg Ala
225                 230                 235                 240

Ser Ser Pro Ser Glu His Gly Pro Arg Lys Ser Tyr Ser Leu Gly Ser
                245                 250                 255

Ile Tyr Thr Arg Leu Tyr Gly Gln Ser Pro Pro Asp Ser His Thr Ala
            260                 265                 270

Glu Gly Asp Val Leu Ala Leu Leu Ser Ile Cys Gln Trp Arg Pro Gln
        275                 280                 285

Ala Leu Leu Arg Trp Val Asp Ala His Ala Arg Pro Phe Gly Thr Ile
    290                 295                 300

Arg Pro Met Tyr Gly Val Thr Ala Ser Ala Arg Thr Lys Gly Gly Gly
305                 310                 315                 320

Gly Ser Gly Gly Gly Gly Ser Gly Gly Gly Gly Ser Gly Gly Gly Gly
                325                 330                 335

Ser Leu Glu Pro Lys Ser Ser Asp Lys Thr His Thr Cys Pro Pro Cys
            340                 345                 350

Pro Ala Pro Glu Leu Leu Gly Gly Pro Ser Val Phe Leu Phe Pro Pro
        355                 360                 365

Lys Pro Lys Asp Thr Leu Met Ile Ser Arg Thr Pro Glu Val Thr Cys
    370                 375                 380

Val Val Val Asp Val Ser His Glu Asp Pro Glu Val Lys Phe Asn Trp
385                 390                 395                 400

Tyr Val Asp Gly Val Glu Val His Asn Ala Lys Thr Lys Pro Arg Glu
                405                 410                 415

Glu Gln Tyr Asn Ser Thr Tyr Arg Val Val Ser Val Leu Thr Val Leu
            420                 425                 430

His Gln Asp Trp Leu Asn Gly Lys Glu Tyr Lys Cys Lys Val Ser Asn
        435                 440                 445

Lys Ala Leu Pro Ala Pro Ile Glu Lys Thr Ile Ser Lys Ala Lys Gly
    450                 455                 460

Gln Pro Arg Glu Pro Gln Val Tyr Thr Leu Pro Pro Ser Arg Asp Glu
465                 470                 475                 480

Leu Thr Lys Asn Gln Val Ser Leu Thr Cys Leu Val Lys Gly Phe Tyr
                485                 490                 495

Pro Ser Asp Ile Ala Val Glu Trp Glu Ser Asn Gly Gln Pro Glu Asn
            500                 505                 510

Asn Tyr Lys Thr Thr Pro Pro Val Leu Asp Ser Asp Gly Ser Phe Phe
        515                 520                 525

Leu Tyr Ser Lys Leu Thr Val Asp Lys Ser Arg Trp Gln Gln Gly Asn
    530                 535                 540

Val Phe Ser Cys Ser Val Met His Glu Ala Leu His Asn His Tyr Thr
545                 550                 555                 560

Gln Lys Ser Leu Ser Leu Ser Pro Gly Lys Val Asp Gly Ala Ser Ser
                565                 570                 575

His Val Asn Val Ser Ser Pro Ser Val Gln Asp Ile Leu Lys Ile Ala
            580                 585                 590

Ala Phe Asn Ile Gln Thr Phe Gly Glu Thr Lys Met Ser Asn Ala Thr
```

```
        595                 600                 605

Leu Val Ser Tyr Ile Val Gln Ile Leu Ser Arg Tyr Asp Ile Ala Leu
    610                 615                 620

Val Gln Glu Val Arg Asp Ser His Leu Thr Ala Val Gly Lys Leu Leu
625                 630                 635                 640

Asp Asn Leu Asn Gln Asp Ala Pro Asp Thr Tyr His Tyr Val Val Ser
                645                 650                 655

Glu Pro Leu Gly Arg Asn Ser Tyr Lys Glu Arg Tyr Leu Phe Val Tyr
            660                 665                 670

Arg Pro Asp Gln Val Ser Ala Val Asp Ser Tyr Tyr Tyr Asp Asp Gly
        675                 680                 685

Cys Glu Pro Cys Gly Asn Asp Thr Phe Asn Arg Glu Pro Ala Ile Val
    690                 695                 700

Arg Phe Phe Ser Arg Phe Thr Glu Val Arg Glu Phe Ala Ile Val Pro
705                 710                 715                 720

Leu His Ala Ala Pro Gly Asp Ala Val Ala Glu Ile Asp Ala Leu Tyr
                725                 730                 735

Asp Val Tyr Leu Asp Val Gln Glu Lys Trp Gly Ser Glu Asp Val Met
            740                 745                 750

Leu Met Gly Asp Phe Asn Ala Gly Cys Ser Tyr Val Arg Pro Ser Gln
        755                 760                 765

Trp Ser Ser Ile Arg Leu Trp Thr Ser Pro Thr Phe Gln Trp Leu Ile
    770                 775                 780

Pro Asp Ser Ala Asp Thr Thr Ala Thr Pro Thr His Cys Ala Tyr Asp
785                 790                 795                 800

Arg Ile Val Val Ala Gly Met Leu Leu Arg Gly Ala Val Val Pro Asp
                805                 810                 815

Ser Ala Leu Pro Phe Asn Phe Gln Xaa Ala Tyr Gly Leu Ser Asp Gln
            820                 825                 830

Leu Ala Gln Ala Ile Ser Asp His Tyr Pro Val Glu Val Met Leu Lys
        835                 840                 845
```

<210> SEQ ID NO 204
<211> LENGTH: 2190
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 204

```
gttaagcttg ccaccatgga aaccccagcg cagcttctct tcctcctgct actctggctc     60

ccagatacca ccggtaagga atcccgggcc aagaaattcc agcggcagca tatggactca    120

gacagttccc ccagcagcag ctccacctac tgtaaccaaa tgatgaggcg ccggaatatg    180

acacaggggc ggtgcaaacc agtgaacacc tttgtgcacg agcccctggt agatgtccag    240

aatgtctgtt tccaggaaaa ggtcacctgc aagaacgggc agggcaactg ctacaagagc    300

aactccagca tgcacatcac agactgccgc ctgacaaacg gctccaggta ccccaactgt    360

gcataccgga ccagcccgaa ggagagacac atcattgtgg cctgtgaagg gagcccatat    420

gtgccagtcc actttgatgc ttctgtggag gactctacag atctctccgg aggaggtggc    480

tcaggtggtg gaggatctgg aggaggtggg agtggtggag gtggttctac cggtctcgag    540

cccaaatctt ctgacaaaac tcacacatgt ccaccgtgcc cagcacctga actcctgggg    600

ggaccgtcag tcttcctctt ccccccaaaa cccaaggaca ccctcatgat ctcccggacc    660
```

```
cctgaggtca catgcgtggt ggtggacgtg agccacgaag accctgaggt caagttcaac    720

tggtacgtgg acggcgtgga ggtgcataat gccaagacaa agccgcggga ggagcagtac    780

aacagcacgt accgtgtggt cagcgtcctc accgtcctgc accaggactg gctgaatggc    840

aaggagtaca agtgcaaggt ctccaacaaa gccctcccag cccccatcga gaaaaccatc    900

tccaaagcca aagggcagcc ccgagaacca caggtgtaca ccctgccccc atcccgggat    960

gagctgacca agaaccaggt cagcctgacc tgcctggtca aaggcttcta tcccagcgac   1020

atcgccgtgg agtgggagag caatgggcag ccggagaaca actacaagac cacgcctccc   1080

gtgctggact ccgacggctc cttcttcctc tacagcaagc tcaccgtgga caagagcagg   1140

tggcagcagg ggaacgtctt ctcatgctcc gtgatgcatg aggctctgca caaccactac   1200

acgcagaaga gcctctctct gtctccgggt aaagtcgacg gtgctagcag ccatgtgaat   1260

gtgagcagcc ctagcgtgca ggatatcatg ggccctggag ctcgcagaca gggcaggatt   1320

gtgcagggaa ggcctgagat gtgcttctgc ccacccccta ccccactccc tccccttcgg   1380

atcttaacac tgggcactca cacacccacc ccatgctcct ctccaggctc agcagcaggt   1440

acgtacccaa ccatgggctc gcaggccctg cccccggggc ccatgcagac cctcatcttt   1500

ttcgacatgg aggccactgg cttgcccttc tcccagccca aggtcacgga gctgtgcctg   1560

ctggctgtcc acagatgtgc cctggagagc ccccccacct ctcaggggcc acctcccaca   1620

gttcctccac caccgcgtgt ggtagacaag ctctccctgt gtgtggctcc ggggaaggcc   1680

tgcagccctg cagccagcga gatcacaggt ctgagcacag ctgtgctggc agcgcatggg   1740

cgtcaatgtt ttgatgacaa cctggccaac ctgctcctag ccttcctgcg gcgccagcca   1800

cagccctggt gcctggtggc acacaatggt gaccgctacg acttccccct gctccaagca   1860

gagctggcta tgctgggcct caccagtgct ctggatggtg ccttctgtgt ggatagcatc   1920

actgcgctga aggccctgga gcgagcaagc agcccctcag aacacggccc aaggaagagc   1980

tacagcctag gcagcatcta cactcgcctg tatgggcagt cccctccaga ctcgcacacg   2040

gctgagggtg atgtcctggc cctgctcagc atctgtcagt ggagaccaca ggccctgctg   2100

cggtgggtgg atgctcacgc caggcctttc ggcaccatca ggcccatgta tggggtcaca   2160

gcctctgcta ggaccaaatg ataatctaga                                    2190
```

<210> SEQ ID NO 205
<211> LENGTH: 716
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 205

```
Met Glu Thr Pro Ala Gln Leu Leu Phe Leu Leu Leu Leu Trp Leu Pro
1               5                   10                  15

Asp Thr Thr Gly Lys Glu Ser Arg Ala Lys Lys Phe Gln Arg Gln His
            20                  25                  30

Met Asp Ser Asp Ser Ser Pro Ser Ser Ser Ser Thr Tyr Cys Asn Gln
        35                  40                  45

Met Met Arg Arg Arg Asn Met Thr Gln Gly Arg Cys Lys Pro Val Asn
    50                  55                  60

Thr Phe Val His Glu Pro Leu Val Asp Val Gln Asn Val Cys Phe Gln
65                  70                  75                  80
```

```
Glu Lys Val Thr Cys Lys Asn Gly Gln Gly Asn Cys Tyr Lys Ser Asn
                85                  90                  95

Ser Ser Met His Ile Thr Asp Cys Arg Leu Thr Asn Gly Ser Arg Tyr
            100                 105                 110

Pro Asn Cys Ala Tyr Arg Thr Ser Pro Lys Glu Arg His Ile Ile Val
        115                 120                 125

Ala Cys Glu Gly Ser Pro Tyr Val Pro Val His Phe Asp Ala Ser Val
    130                 135                 140

Glu Asp Ser Thr Gly Gly Gly Gly Ser Gly Gly Gly Gly Ser Gly Gly
145                 150                 155                 160

Gly Gly Ser Gly Gly Gly Gly Ser Leu Glu Pro Lys Ser Ser Asp Lys
                165                 170                 175

Thr His Thr Cys Pro Pro Cys Pro Ala Pro Glu Leu Leu Gly Gly Pro
            180                 185                 190

Ser Val Phe Leu Phe Pro Pro Lys Pro Lys Asp Thr Leu Met Ile Ser
        195                 200                 205

Arg Thr Pro Glu Val Thr Cys Val Val Val Asp Val Ser His Glu Asp
    210                 215                 220

Pro Glu Val Lys Phe Asn Trp Tyr Val Asp Gly Val Glu Val His Asn
225                 230                 235                 240

Ala Lys Thr Lys Pro Arg Glu Glu Gln Tyr Asn Ser Thr Tyr Arg Val
                245                 250                 255

Val Ser Val Leu Thr Val Leu His Gln Asp Trp Leu Asn Gly Lys Glu
            260                 265                 270

Tyr Lys Cys Lys Val Ser Asn Lys Ala Leu Pro Ala Pro Ile Glu Lys
        275                 280                 285

Thr Ile Ser Lys Ala Lys Gly Gln Pro Arg Glu Pro Gln Val Tyr Thr
    290                 295                 300

Leu Pro Pro Ser Arg Asp Glu Leu Thr Lys Asn Gln Val Ser Leu Thr
305                 310                 315                 320

Cys Leu Val Lys Gly Phe Tyr Pro Ser Asp Ile Ala Val Glu Trp Glu
                325                 330                 335

Ser Asn Gly Gln Pro Glu Asn Asn Tyr Lys Thr Thr Pro Pro Val Leu
            340                 345                 350

Asp Ser Asp Gly Ser Phe Phe Leu Tyr Ser Lys Leu Thr Val Asp Lys
        355                 360                 365

Ser Arg Trp Gln Gln Gly Asn Val Phe Ser Cys Ser Val Met His Glu
    370                 375                 380

Ala Leu His Asn His Tyr Thr Gln Lys Ser Leu Ser Leu Ser Pro Gly
385                 390                 395                 400

Lys Val Asp Gly Ala Ser Ser His Val Asn Val Ser Ser Pro Ser Val
                405                 410                 415

Gln Asp Ile Met Gly Pro Gly Ala Arg Arg Gln Gly Arg Ile Val Gln
            420                 425                 430

Gly Arg Pro Glu Met Cys Phe Cys Pro Pro Pro Thr Pro Leu Pro Pro
        435                 440                 445

Leu Arg Ile Leu Thr Leu Gly Thr His Thr Pro Thr Pro Cys Ser Ser
    450                 455                 460

Pro Gly Ser Ala Ala Gly Thr Tyr Pro Thr Met Gly Ser Gln Ala Leu
465                 470                 475                 480

Pro Pro Gly Pro Met Gln Thr Leu Ile Phe Phe Asp Met Glu Ala Thr
                485                 490                 495

Gly Leu Pro Phe Ser Gln Pro Lys Val Thr Glu Leu Cys Leu Leu Ala
```

```
            500                 505                 510

Val His Arg Cys Ala Leu Glu Ser Pro Pro Thr Ser Gln Gly Pro Pro
        515                 520                 525

Pro Thr Val Pro Pro Pro Pro Arg Val Val Asp Lys Leu Ser Leu Cys
    530                 535                 540

Val Ala Pro Gly Lys Ala Cys Ser Pro Ala Ala Ser Glu Ile Thr Gly
545                 550                 555                 560

Leu Ser Thr Ala Val Leu Ala Ala His Gly Arg Gln Cys Phe Asp Asp
                565                 570                 575

Asn Leu Ala Asn Leu Leu Leu Ala Phe Leu Arg Arg Gln Pro Gln Pro
            580                 585                 590

Trp Cys Leu Val Ala His Asn Gly Asp Arg Tyr Asp Phe Pro Leu Leu
        595                 600                 605

Gln Ala Glu Leu Ala Met Leu Gly Leu Thr Ser Ala Leu Asp Gly Ala
    610                 615                 620

Phe Cys Val Asp Ser Ile Thr Ala Leu Lys Ala Leu Glu Arg Ala Ser
625                 630                 635                 640

Ser Pro Ser Glu His Gly Pro Arg Lys Ser Tyr Ser Leu Gly Ser Ile
                645                 650                 655

Tyr Thr Arg Leu Tyr Gly Gln Ser Pro Pro Asp Ser His Thr Ala Glu
            660                 665                 670

Gly Asp Val Leu Ala Leu Leu Ser Ile Cys Gln Trp Arg Pro Gln Ala
        675                 680                 685

Leu Leu Arg Trp Val Asp Ala His Ala Arg Pro Phe Gly Thr Ile Arg
    690                 695                 700

Pro Met Tyr Gly Val Thr Ala Ser Ala Arg Thr Lys
705                 710                 715
```

<210> SEQ ID NO 206
<211> LENGTH: 2589
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 206

```
gttaagcttg ccaccatgga aaccccagcg cagcttctct tcctcctgct actctggctc      60

ccagatacca ccggtatgag gatctgctcc ttcaacgtca ggtcctttgg ggaaagcaag     120

caggaagaca agaatgccat ggatgtcatt gtgaaggtca tcaaacgctg tgacatcata     180

ctcgtgatgg aaatcaagga cagcaacaac aggatctgcc ccatactgat ggagaagctg     240

aacagaaatt caaggagagg cataacatac aactatgtga ttagctctcg gcttggaaga     300

aacacatata aagaacaata tgcctttctc tacaaggaaa agctggtgtc tgtgaagagg     360

agttatcact accatgacta tcaggatgga gacgcagatg tgttttccag ggagcccttt     420

gtggtctggt tccaatctcc ccacactgct gtcaaagact tcgtgattat ccccctgcac     480

accaccccag agacatccgt taaggagatc gatgagttgg ttgaggtcta cacggacgtg     540

aaacaccgct ggaaggcgga gaatttcatt ttcatgggtg acttcaatgc cggctgcagc     600

tacgtcccca agaaggcctg gaagaacatc cgcttgagga ctgaccccag gtttgtttgg     660

ctgatcgggg accaagagga caccacggtg aagaagagca ccaactgtgc atatgacagg     720

attgtgctta gaggacaaga aatcgtcagt tctgttgttc ccaagtcaaa cagtgttttt     780

gacttccaga aagcttacaa gctgactgaa gaggaggccc tggatgtcag cgaccacttt     840
```

```
ccagttgaat ttaaactaca gtcttcaagg gccttcacca acagcaaaaa atctgtcact    900

ctaaggaaga aaacaaagag caaacgctca gatctcgagc ccaaatcttc tgacaaaact    960

cacacatgtc caccgtgccc agcacctgaa ctcctggggg gaccgtcagt cttcctcttc   1020

cccccaaaac ccaaggacac cctcatgatc tcccggaccc ctgaggtcac atgcgtggtg   1080

gtggacgtga gccacgaaga ccctgaggtc aagttcaact ggtacgtgga cggcgtggag   1140

gtgcataatg ccaagacaaa gccgcgggag gagcagtaca acagcacgta ccgtgtggtc   1200

agcgtcctca ccgtcctgca ccaggactgg ctgaatggca aggagtacaa gtgcaaggtc   1260

tccaacaaag ccctcccagc ccccatcgag aaaaccatct ccaaagccaa agggcagccc   1320

cgagaaccac aggtgtacac cctgccccca tcccgggatg agctgaccaa gaaccaggtc   1380

agcctgacct gcctggtcaa aggcttctat cccagcgaca tcgccgtgga gtgggagagc   1440

aatgggcagc cggagaacaa ctacaagacc acgcctcccg tgctggactc cgacggctcc   1500

ttcttcctct acagcaagct caccgtggac aagagcaggt ggcagcaggg gaacgtcttc   1560

tcatgctccg tgatgcatga ggctctgcac aaccactaca cgcagaagag cctctctctg   1620

tctccgggta aagtcgacgg agctagcagc cccgtgaacg tgagcagccc cagcgtgcag   1680

gatatcatgg gccctggagc tcgcagacag ggcaggattg tgcagggaag gcctgagatg   1740

tgcttctgcc caccccctac cccactccct ccccttcgga tcttaacact gggcactcac   1800

acacccaccc catgctcctc tccaggctca gcagcaggta cgtacccaac catgggctcg   1860

caggccctgc ccccggggcc catgcagacc ctcatctttt tcgacatgga ggccactggc   1920

ttgcccttct cccagcccaa ggtcacggag ctgtgcctgc tggctgtcca cagatgtgcc   1980

ctggagagcc cccccacctc tcaggggcca cctcccacag ttcctccacc accgcgtgtg   2040

gtagacaagc tctccctgtg tgtggctccg gggaaggcct gcagccctgc agccagcgag   2100

atcacaggtc tgagcacagc tgtgctggca gcgcatgggc gtcaatgttt tgatgacaac   2160

ctggccaacc tgctcctagc cttcctgcgg cgccagccac agccctggtg cctggtggca   2220

cacaatggtg accgctacga cttcccccctg ctccaagcag agctggctat gctgggcctc  2280

accagtgctc tggatggtgc cttctgtgtg gatagcatca ctgcgctgaa ggccctggag   2340

cgagcaagca gcccctcaga acacggccca aggaagagct acagcctagg cagcatctac   2400

actcgcctgt atgggcagtc ccctccagac tcgcacacgg ctgagggtga tgtcctggcc   2460

ctgctcagca tctgtcagtg gagaccacag gccctgctgc ggtgggtgga tgctcacgcc   2520

aggcctttcg gcaccatcag gcccatgtat ggggtcacag cctctgctag gaccaaatga   2580

taatctaga                                                          2589
```

```
<210> SEQ ID NO 207
<211> LENGTH: 854
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Met Glu Thr Pro Ala Gln Leu Leu Phe Leu Leu Leu Leu Trp Leu Pro
1               5                   10                  15

Asp Thr Thr Gly Met Arg Ile Cys Ser Phe Asn Val Arg Ser Phe Gly
            20                  25                  30

Glu Ser Lys Gln Glu Asp Lys Asn Ala Met Asp Val Ile Val Lys Val
```

```
        35                  40                  45

Ile Lys Arg Cys Asp Ile Ile Leu Val Met Glu Ile Lys Asp Ser Asn
    50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
        115                 120                 125

Val Phe Ser Arg Glu Pro Phe Val Val Trp Phe Gln Ser Pro His Thr
    130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
            180                 185                 190

Gly Cys Ser Tyr Val Pro Lys Lys Ala Trp Lys Asn Ile Arg Leu Arg
        195                 200                 205

Thr Asp Pro Arg Phe Val Trp Leu Ile Gly Asp Gln Glu Asp Thr Thr
    210                 215                 220

Val Lys Lys Ser Thr Asn Cys Ala Tyr Asp Arg Ile Val Leu Arg Gly
225                 230                 235                 240

Gln Glu Ile Val Ser Ser Val Val Pro Lys Ser Asn Ser Val Phe Asp
                245                 250                 255

Phe Gln Lys Ala Tyr Lys Leu Thr Glu Glu Glu Ala Leu Asp Val Ser
            260                 265                 270

Asp His Phe Pro Val Glu Phe Lys Leu Gln Ser Ser Arg Ala Phe Thr
        275                 280                 285

Asn Ser Lys Lys Ser Val Thr Leu Arg Lys Lys Thr Lys Ser Lys Arg
    290                 295                 300

Ser Asp Leu Glu Pro Lys Ser Ser Asp Lys Thr His Thr Cys Pro Pro
305                 310                 315                 320

Cys Pro Ala Pro Glu Leu Leu Gly Gly Pro Ser Val Phe Leu Phe Pro
                325                 330                 335

Pro Lys Pro Lys Asp Thr Leu Met Ile Ser Arg Thr Pro Glu Val Thr
            340                 345                 350

Cys Val Val Val Asp Val Ser His Glu Asp Pro Glu Val Lys Phe Asn
        355                 360                 365

Trp Tyr Val Asp Gly Val Glu Val His Asn Ala Lys Thr Lys Pro Arg
    370                 375                 380

Glu Glu Gln Tyr Asn Ser Thr Tyr Arg Val Val Ser Val Leu Thr Val
385                 390                 395                 400

Leu His Gln Asp Trp Leu Asn Gly Lys Glu Tyr Lys Cys Lys Val Ser
                405                 410                 415

Asn Lys Ala Leu Pro Ala Pro Ile Glu Lys Thr Ile Ser Lys Ala Lys
            420                 425                 430

Gly Gln Pro Arg Glu Pro Gln Val Tyr Thr Leu Pro Pro Ser Arg Asp
        435                 440                 445

Glu Leu Thr Lys Asn Gln Val Ser Leu Thr Cys Leu Val Lys Gly Phe
    450                 455                 460
```

```
Tyr Pro Ser Asp Ile Ala Val Glu Trp Glu Ser Asn Gly Gln Pro Glu
465                 470                 475                 480

Asn Asn Tyr Lys Thr Thr Pro Pro Val Leu Asp Ser Asp Gly Ser Phe
                485                 490                 495

Phe Leu Tyr Ser Lys Leu Thr Val Asp Lys Ser Arg Trp Gln Gln Gly
            500                 505                 510

Asn Val Phe Ser Cys Ser Val Met His Glu Ala Leu His Asn His Tyr
        515                 520                 525

Thr Gln Lys Ser Leu Ser Leu Ser Pro Gly Lys Val Asp Gly Ala Ser
    530                 535                 540

Ser Pro Val Asn Val Ser Ser Pro Ser Val Gln Asp Ile Met Gly Pro
545                 550                 555                 560

Gly Ala Arg Arg Gln Gly Arg Ile Val Gln Gly Arg Pro Glu Met Cys
                565                 570                 575

Phe Cys Pro Pro Pro Thr Pro Leu Pro Pro Leu Arg Ile Leu Thr Leu
            580                 585                 590

Gly Thr His Thr Pro Thr Pro Cys Ser Ser Pro Gly Ser Ala Ala Gly
        595                 600                 605

Thr Tyr Pro Thr Met Gly Ser Gln Ala Leu Pro Pro Gly Pro Met Gln
    610                 615                 620

Thr Leu Ile Phe Phe Asp Met Glu Ala Thr Gly Leu Pro Phe Ser Gln
625                 630                 635                 640

Pro Lys Val Thr Glu Leu Cys Leu Leu Ala Val His Arg Cys Ala Leu
                645                 650                 655

Glu Ser Pro Pro Thr Ser Gln Gly Pro Pro Pro Thr Val Pro Pro Pro
            660                 665                 670

Pro Arg Val Val Asp Lys Leu Ser Leu Cys Val Ala Pro Gly Lys Ala
        675                 680                 685

Cys Ser Pro Ala Ala Ser Glu Ile Thr Gly Leu Ser Thr Ala Val Leu
    690                 695                 700

Ala Ala His Gly Arg Gln Cys Phe Asp Asp Asn Leu Ala Asn Leu Leu
705                 710                 715                 720

Leu Ala Phe Leu Arg Arg Gln Pro Gln Pro Trp Cys Leu Val Ala His
                725                 730                 735

Asn Gly Asp Arg Tyr Asp Phe Pro Leu Leu Gln Ala Glu Leu Ala Met
            740                 745                 750

Leu Gly Leu Thr Ser Ala Leu Asp Gly Ala Phe Cys Val Asp Ser Ile
        755                 760                 765

Thr Ala Leu Lys Ala Leu Glu Arg Ala Ser Ser Pro Ser Glu His Gly
    770                 775                 780

Pro Arg Lys Ser Tyr Ser Leu Gly Ser Ile Tyr Thr Arg Leu Tyr Gly
785                 790                 795                 800

Gln Ser Pro Pro Asp Ser His Thr Ala Glu Gly Asp Val Leu Ala Leu
                805                 810                 815

Leu Ser Ile Cys Gln Trp Arg Pro Gln Ala Leu Leu Arg Trp Val Asp
            820                 825                 830

Ala His Ala Arg Pro Phe Gly Thr Ile Arg Pro Met Tyr Gly Val Thr
        835                 840                 845

Ala Ser Ala Arg Thr Lys
    850
```

<210> SEQ ID NO 208
<211> LENGTH: 25

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(25)
<223> OTHER INFORMATION: This sequence may encompass 0 to 5 "GGGGS"
      repeating units

<400> SEQUENCE: 208

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25


<210> SEQ ID NO 209
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25


<210> SEQ ID NO 210
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(50)
<223> OTHER INFORMATION: This sequence may encompass 1 to 10 "GGGGS"
      repeating units

<400> SEQUENCE: 210

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50


<210> SEQ ID NO 211
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Gly Gly Gly Gly Ser Gly Gly Gly Gly Ser Gly Gly Gly Gly Ser
1               5                   10                  15
```

<210> SEQ ID NO 212
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 212

```
Gly Gly Gly Gly Ser Gly Gly Gly Gly Ser Gly Gly Gly Gly Ser Gly
1               5                   10                  15

Gly Gly Gly Ser
            20
```

<210> SEQ ID NO 213
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 213

```
Gly Gly Gly Gly Ser
1               5
```

<210> SEQ ID NO 214
<211> LENGTH: 51
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: misc_feature
<222> LOCATION: (2)..(51)
<223> OTHER INFORMATION: This region may encompass 1 to 10 “GGGGS” repeating units

<400> SEQUENCE: 214

```
Ser Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser Gly
            20                  25                  30

Gly Gly Gly Ser Gly Gly Gly Gly Ser Gly Gly Gly Gly Ser Gly Gly
        35                  40                  45

Gly Gly Ser
    50
```

<210> SEQ ID NO 215
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 215

```
Ser Gly Gly Gly Gly Ser Gly Gly Gly Gly Ser Gly Gly Gly Gly Ser
1               5                   10                  15
```

<210> SEQ ID NO 216
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 216

Ser Gly Gly Gly Gly Ser Gly Gly Gly Gly Ser Gly Gly Gly Gly Ser
1 5 10 15

Gly Gly Gly Gly Ser
20

<210> SEQ ID NO 217
<211> LENGTH: 31
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: misc_feature
<222> LOCATION: (2)..(31)
<223> OTHER INFORMATION: This region may encompass 1 to 6 “GGGGS”
repeating units

<400> SEQUENCE: 217

Ser Gly Gly Gly Gly Ser Gly Gly Gly Gly Ser Gly Gly Gly Gly Ser
1 5 10 15

Gly Gly Gly Gly Ser Gly Gly Gly Gly Ser Gly Gly Gly Gly Ser
20 25 30

<210> SEQ ID NO 218
<211> LENGTH: 25
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: misc_feature
<222> LOCATION: (1)..(25)
<223> OTHER INFORMATION: This sequence may encompass 3 to 5 “GGGGS”
repeating units

<400> SEQUENCE: 218

Gly Gly Gly Gly Ser Gly Gly Gly Gly Ser Gly Gly Gly Gly Ser Gly
1 5 10 15

Gly Gly Gly Ser Gly Gly Gly Gly Ser
20 25

<210> SEQ ID NO 219
<211> LENGTH: 25
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: misc_feature
<222> LOCATION: (1)..(25)
<223> OTHER INFORMATION: This sequence may encompass 1 to 5 “GGGGS”
repeating units

<400> SEQUENCE: 219

Gly Gly Gly Gly Ser Gly Gly Gly Gly Ser Gly Gly Gly Gly Ser Gly
1 5 10 15

Gly Gly Gly Ser Gly Gly Gly Gly Ser
20 25

<210> SEQ ID NO 220
<211> LENGTH: 18

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(18)
<223> OTHER INFORMATION: This sequence may encompass 1 to 12 repeating
      "t" nucleotides

<400> SEQUENCE: 220

tttttttttt tttttttt                                                 18


<210> SEQ ID NO 221
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Gly Gly Gly Gly Gly
1               5


<210> SEQ ID NO 222
<211> LENGTH: 1177
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (16)..(1164)

<400> SEQUENCE: 222

gttaagcttg ccacc atg ggt ctg gag aag tcc ctc att ctg ttt cca ttg      51
                 Met Gly Leu Glu Lys Ser Leu Ile Leu Phe Pro Leu
                 1               5                   10

ttt ttc ctg ctg ctt gga tgg gtc cag cct tcc ccg ggc agg gaa tct       99
Phe Phe Leu Leu Leu Gly Trp Val Gln Pro Ser Pro Gly Arg Glu Ser
        15                  20                  25

gca gca cag aag ttt cag cgg cag cac atg gat cca gat ggt tcc tcc      147
Ala Ala Gln Lys Phe Gln Arg Gln His Met Asp Pro Asp Gly Ser Ser
    30                  35                  40

atc aac agc ccc acc tac tgc aac caa atg atg aaa cgc cgg gat atg      195
Ile Asn Ser Pro Thr Tyr Cys Asn Gln Met Met Lys Arg Arg Asp Met
45                  50                  55                  60

aca aat ggg tca tgc aag ccc gtg aac acc ttc gtg cat gag ccc ttg      243
Thr Asn Gly Ser Cys Lys Pro Val Asn Thr Phe Val His Glu Pro Leu
                65                  70                  75

gca gat gtc cag gcc gtc tgc tcc cag gaa aat gtc acc tgc aag aac      291
Ala Asp Val Gln Ala Val Cys Ser Gln Glu Asn Val Thr Cys Lys Asn
            80                  85                  90

agg aag agc aac tgc tac aag agc agc tct gcc ctg cac atc act gac      339
Arg Lys Ser Asn Cys Tyr Lys Ser Ser Ser Ala Leu His Ile Thr Asp
        95                  100                 105

tgc cac ctg aag ggc aac tcc aag tat ccc aac tgt gac tac aag acc      387
Cys His Leu Lys Gly Asn Ser Lys Tyr Pro Asn Cys Asp Tyr Lys Thr
    110                 115                 120

act caa tac cag aag cac atc att gtg gcc tgt gaa ggg aac ccc tac      435
Thr Gln Tyr Gln Lys His Ile Ile Val Ala Cys Glu Gly Asn Pro Tyr
125                 130                 135                 140
```

```
gta cca gtc cac ttt gat gct act gtg ctc gag ccc aga ggt ctc aca      483
Val Pro Val His Phe Asp Ala Thr Val Leu Glu Pro Arg Gly Leu Thr
                145                 150                 155

atc aag ccc tct cct cca tgc aaa tgc cca gca cct aac ctc ttg ggt      531
Ile Lys Pro Ser Pro Pro Cys Lys Cys Pro Ala Pro Asn Leu Leu Gly
            160                 165                 170

gga tca tcc gtc ttc atc ttc cct cca aag atc aag gat gta ctc atg      579
Gly Ser Ser Val Phe Ile Phe Pro Pro Lys Ile Lys Asp Val Leu Met
        175                 180                 185

atc tcc ctg agc ccc atg gtc aca tgt gtg gtg gtg gat gtg agc gag      627
Ile Ser Leu Ser Pro Met Val Thr Cys Val Val Val Asp Val Ser Glu
    190                 195                 200

gat gac cca gac gtc cag atc agc tgg ttt gtg aac aac gtg gaa gta      675
Asp Asp Pro Asp Val Gln Ile Ser Trp Phe Val Asn Asn Val Glu Val
205                 210                 215                 220

cac aca gct cag aca caa acc cat aga gag gat tac aac agt act ctc      723
His Thr Ala Gln Thr Gln Thr His Arg Glu Asp Tyr Asn Ser Thr Leu
                225                 230                 235

cgg gtg gtc agt gcc ctc ccc atc cag cac cag gac tgg atg agt ggc      771
Arg Val Val Ser Ala Leu Pro Ile Gln His Gln Asp Trp Met Ser Gly
            240                 245                 250

aag gag ttc aaa tgc tcg gtc aac aac aaa gac ctc cca gcg tcc atc      819
Lys Glu Phe Lys Cys Ser Val Asn Asn Lys Asp Leu Pro Ala Ser Ile
        255                 260                 265

gag aga acc atc tca aaa ccc aga ggg cca gta aga gct cca cag gta      867
Glu Arg Thr Ile Ser Lys Pro Arg Gly Pro Val Arg Ala Pro Gln Val
    270                 275                 280

tat gtc ttg cct cca cca gca gaa gag atg act aag aaa gag ttc agt      915
Tyr Val Leu Pro Pro Pro Ala Glu Glu Met Thr Lys Lys Glu Phe Ser
285                 290                 295                 300

ctg acc tgc atg atc aca ggc ttc tta cct gcc gaa att gct gtg gac      963
Leu Thr Cys Met Ile Thr Gly Phe Leu Pro Ala Glu Ile Ala Val Asp
                305                 310                 315

tgg acc agc aat ggg cgt aca gag caa aac tac aag aac acc gca aca     1011
Trp Thr Ser Asn Gly Arg Thr Glu Gln Asn Tyr Lys Asn Thr Ala Thr
            320                 325                 330

gtc ctg gac tct gat ggt tct tac ttc atg tac agc aag ctc aga gta     1059
Val Leu Asp Ser Asp Gly Ser Tyr Phe Met Tyr Ser Lys Leu Arg Val
        335                 340                 345

caa aag agc act tgg gaa aga gga agt ctt ttc gcc tgc tca gtg gtc     1107
Gln Lys Ser Thr Trp Glu Arg Gly Ser Leu Phe Ala Cys Ser Val Val
    350                 355                 360

cac gag ggt ctg cac aat cac ctt acg act aag agc ttc tct cgg act     1155
His Glu Gly Leu His Asn His Leu Thr Thr Lys Ser Phe Ser Arg Thr
365                 370                 375                 380

ccg ggt aaa tgataatcta gaa                                          1177
Pro Gly Lys
```

<210> SEQ ID NO 223
<211> LENGTH: 383
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 223

```
Met Gly Leu Glu Lys Ser Leu Ile Leu Phe Pro Leu Phe Phe Leu Leu
1               5                   10                  15

Leu Gly Trp Val Gln Pro Ser Pro Gly Arg Glu Ser Ala Ala Gln Lys
            20                  25                  30
```

```
Phe Gln Arg Gln His Met Asp Pro Asp Gly Ser Ser Ile Asn Ser Pro
        35                  40                  45

Thr Tyr Cys Asn Gln Met Met Lys Arg Arg Asp Met Thr Asn Gly Ser
    50                  55                  60

Cys Lys Pro Val Asn Thr Phe Val His Glu Pro Leu Ala Asp Val Gln
65                  70                  75                  80

Ala Val Cys Ser Gln Glu Asn Val Thr Cys Lys Asn Arg Lys Ser Asn
                85                  90                  95

Cys Tyr Lys Ser Ser Ser Ala Leu His Ile Thr Asp Cys His Leu Lys
            100                 105                 110

Gly Asn Ser Lys Tyr Pro Asn Cys Asp Tyr Lys Thr Thr Gln Tyr Gln
        115                 120                 125

Lys His Ile Ile Val Ala Cys Glu Gly Asn Pro Tyr Val Pro Val His
    130                 135                 140

Phe Asp Ala Thr Val Leu Glu Pro Arg Gly Leu Thr Ile Lys Pro Ser
145                 150                 155                 160

Pro Pro Cys Lys Cys Pro Ala Pro Asn Leu Leu Gly Gly Ser Ser Val
                165                 170                 175

Phe Ile Phe Pro Pro Lys Ile Lys Asp Val Leu Met Ile Ser Leu Ser
            180                 185                 190

Pro Met Val Thr Cys Val Val Val Asp Val Ser Glu Asp Asp Pro Asp
        195                 200                 205

Val Gln Ile Ser Trp Phe Val Asn Asn Val Glu Val His Thr Ala Gln
    210                 215                 220

Thr Gln Thr His Arg Glu Asp Tyr Asn Ser Thr Leu Arg Val Val Ser
225                 230                 235                 240

Ala Leu Pro Ile Gln His Gln Asp Trp Met Ser Gly Lys Glu Phe Lys
                245                 250                 255

Cys Ser Val Asn Asn Lys Asp Leu Pro Ala Ser Ile Glu Arg Thr Ile
            260                 265                 270

Ser Lys Pro Arg Gly Pro Val Arg Ala Pro Gln Val Tyr Val Leu Pro
        275                 280                 285

Pro Pro Ala Glu Glu Met Thr Lys Lys Glu Phe Ser Leu Thr Cys Met
    290                 295                 300

Ile Thr Gly Phe Leu Pro Ala Glu Ile Ala Val Asp Trp Thr Ser Asn
305                 310                 315                 320

Gly Arg Thr Glu Gln Asn Tyr Lys Asn Thr Ala Thr Val Leu Asp Ser
                325                 330                 335

Asp Gly Ser Tyr Phe Met Tyr Ser Lys Leu Arg Val Gln Lys Ser Thr
            340                 345                 350

Trp Glu Arg Gly Ser Leu Phe Ala Cys Ser Val Val His Glu Gly Leu
        355                 360                 365

His Asn His Leu Thr Thr Lys Ser Phe Ser Arg Thr Pro Gly Lys
    370                 375                 380


<210> SEQ ID NO 224
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Met Gly Leu Glu Lys Ser Leu Val Arg Leu Leu Leu Leu Val Leu Ile
```

-continued

```
1               5                   10                  15

Leu Leu Val Leu Gly Trp Val Gln Pro Ser Leu Gly
            20                  25


<210> SEQ ID NO 225
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Met Glu Thr Pro Ala Gln Leu Leu Phe Leu Leu Leu Leu Trp Leu Pro
1               5                   10                  15

Asp Thr Thr Gly
            20
```